(12) United States Patent
Deloughery et al.

(10) Patent No.: US 12,077,775 B2
(45) Date of Patent: Sep. 3, 2024

(54) EFFECTOR PROTEINS AND METHODS OF USE

(71) Applicant: Mammoth Biosciences, Inc., Brisbane, CA (US)

(72) Inventors: Aaron Deloughery, San Francisco, CA (US); Matan Drory Retwitzer, Foster City, CA (US); Lucas Benjamin Harrington, San Francisco, CA (US); Wiputra Jaya Hartono, San Francisco, CA (US); Alexander Richard Neckelmann, San Francisco, CA (US); David Paez-Espino, Concord, CA (US); Benjamin Julius Rauch, San Francisco, CA (US); Clarissa Oriel Rhines, San Mateo, CA (US); Stepan Tymoshenko, Sacramento, CA (US); Fnu Yunanda, Daly City, CA (US); William Douglass Wright, Fairfield, CA (US)

(73) Assignee: Mammoth Biosciences, Inc., Brisbane, CA (US)

( * ) Notice: Subject to any disclaimer, the term of this patent is extended or adjusted under 35 U.S.C. 154(b) by 73 days.

(21) Appl. No.: 18/333,467

(22) Filed: Jun. 12, 2023

(65) Prior Publication Data
US 2023/0323406 A1    Oct. 12, 2023

Related U.S. Application Data

(63) Continuation of application No. PCT/US2023/061022, filed on Jan. 20, 2023.
(Continued)

(51) Int. Cl.
*C12N 9/22* (2006.01)
*C12N 15/00* (2006.01)
(Continued)

(52) U.S. Cl.
CPC ............ *C12N 15/907* (2013.01); *C12N 9/22* (2013.01); *C12N 15/11* (2013.01); *C12N 15/86* (2013.01); *C12N 2750/14143* (2013.01)

(58) Field of Classification Search
None
See application file for complete search history.

(56) References Cited

U.S. PATENT DOCUMENTS 10,889,808 B2 *   1/2021   Carter .................... C12N 15/85
10,975,392 B2     4/2021   Tsai et al.
(Continued)

FOREIGN PATENT DOCUMENTS

WO   WO 2010/075303 A1   7/2010
WO   WO 2012/068627 A1   5/2012
(Continued)

OTHER PUBLICATIONS

Bhattacharya et al. Insights into the Mechanism of CRISPR/Cas9-Based Genome Editing from Molecular Dynamics Simulations (ACS Omega, 2023, 8:1817-1837) (Year: 2023).*
(Continued)

*Primary Examiner* — Arthur S Leonard
(74) *Attorney, Agent, or Firm* — Greenberg Traurig, LLP

(57) ABSTRACT

Provided herein are compositions, systems, and methods comprising effector proteins and uses thereof. These effector proteins are shown to be active with guide RNAs and may be characterized as CRISPR-associated (Cas) proteins. Various compositions, systems, and methods of the present disclosure leverage the activities of these effector proteins for the modification, detection, and engineering of nucleic acids.

30 Claims, 52 Drawing Sheets
Specification includes a Sequence Listing.

Related U.S. Application Data

(60) Provisional application No. 63/386,144, filed on Dec. 5, 2022, provisional application No. 63/381,282, filed on Oct. 27, 2022, provisional application No. 63/371,502, filed on Aug. 15, 2022, provisional application No. 63/346,244, filed on May 26, 2022, provisional application No. 63/334,663, filed on Apr. 25, 2022, provisional application No. 63/301,963, filed on Jan. 21, 2022.

(51) Int. Cl.
    *C12N 15/11*     (2006.01)
    *C12N 15/86*     (2006.01)
    *C12N 15/90*     (2006.01)

(56) References Cited

U.S. PATENT DOCUMENTS

| | | |
|---|---|---|
| 2020/0190494 A1 | 6/2020 | Hou et al. |
| 2021/0198330 A1 | 7/2021 | Liu et al. |
| 2023/0227857 A1* | 7/2023 | Thomas ............... C12N 15/90 435/462 |
| 2023/0257739 A1 | 8/2023 | Deloughery et al. |

FOREIGN PATENT DOCUMENTS

| | | |
|---|---|---|
| WO | WO 2017/070632 A2 | 4/2017 |
| WO | WO 2018/027078 A1 | 2/2018 |
| WO | WO 2019/226953 A1 | 5/2019 |
| WO | WO 2020/123887 A2 | 6/2020 |
| WO | WO 2021/041945 A2 | 3/2021 |
| WO | WO 2021/050571 A1 | 3/2021 |
| WO | WO 2021/062227 A2 | 4/2021 |
| WO | WO 2021/087246 A1 | 5/2021 |
| WO | WO 2021/163587 A1 | 8/2021 |
| WO | WO 2021/216868 A1 | 10/2021 |
| WO | WO 2022/240858 A1 | 11/2022 |
| WO | WO 2022/241059 A2 | 11/2022 |
| WO | WO 2023/028444 A1 | 3/2023 |

OTHER PUBLICATIONS

Altschul et al., "Gapped BLAST and PSI-BLAST: a new generation of protein database search programs," *Nucleic Acids Res.*, 25(17):3389-3402 (1997).
Benskey et al., "Basic Concepts in Viral Vector-Mediated Gene Therapy," *Methods Mol. Biol.*, 1937:3-26 (2019).
Chang et al., "The distribution of different classes of nuclear localization signals (NLSs) in diverse organisms and the utilization of the minor NLS-binding site inplantnuclear import factor importin-α," *Plant Signal Behav.*, 8(10):e25976 (2013).
Chen et al., "Programmable C:G to G:C genome editing with CRISPR-Cas9-directed base excision repair proteins," *Nat. Commun.*, 12:1384 (2021).
Chu et al., "Rationally Designed Base Editors for Precise Editing of the Sickle Cell Disease Mutation," *CRISPR J.*, 4(2):169-177 (2021).
Devereux et al., "A comprehensive set of sequence analysis programs for the VAX," *Nucleic Acids Res.*, 11;12(1 Pt 1):387-395 (1984).
Dong et al., "Genome-Wide Off-Target Analysis in CRISPR-Cas9 Modified Mice and Their Offspring", G3, 9(11): 3645-3651 (2019).
Gaudelli et al., "Programmable base editing of A•T to G•C in genomic DNA without DNA cleavage," *Nature*, 551:464-471 (2017).
Henikoff et al., "Amino acid substitution matrices from protein blocks," *Proc. Natl. Acad. Sci. USA*, 89:10915-10919 (1992).
Ingusci et al., "Gene Therapy Tools for Brain Diseases," *Front. Pharmacol.*, 10:724 (2019).
Kim et al., "Enhancement of target specificity of CRISPR-Cas 12a by using a chimeric DNA-RNA guide," *Nucleic Acids Res.*, 48(15):8601-8616 (2020).

Koblan et al., "Efficient C•G-to-G•C base editors developed using CRISPRi screens, target-library analysis, and machine learning," *Nat. Biotechnol.*, 1-16 (2021).
Koblan et al., "Improving cytidine and adenine base editors by expression optimization and ancestral reconstruction," *Nat. Biotechnol.*, 36:843-846 (2018).
Komor et al., "Improved base excision repair inhibition and bacteriophage Mu Gam protein yields C:G-to-T:A base editors with higher efficiency and product purity," *Sci. Adv.*, 3(8): eaao4774 (2017).
Komor et al., "Programmable editing of a target base in genomic DNA without double-stranded DNA cleavage," *Nature*, 533:420-424 (2016).
Kulemzin et al., "Design and analysis of stably integrated reporters for inducible transgene expression in human T cells and CAR NK-cell lines," *BMC Med. Genomics*, 12:44 (2019).
Kulkarni et al., "Lipid Nanoparticles Enabling Gene Therapies: From Concepts to Clinical Utility," *Nucl. Acid Ther.*, 28(3): 146-157 (2018).
Kurt et al., "CRISPR C-to-G base editors for inducing targeted DNA transversions in human cells," *Nat. Biotechnol.*, 39:41-46 (2021).
Ma et al., "A CRISPR-Based Screen Identifies Genes Essential for West-Nile-Virus-Induced Cell Death," *Cell Rep.*, 12(4):673-683 (2015).
Myers et al., "Optimal alignments in linear space," *Comput. Appl. Biosci.*, 4(1): 11-17 (1988).
Naso et al., "Adeno-Associated Virus (AAV) as a Vector for Gene Therapy," *BioDrugs*, 31(4):317-334 (2017).
O'Hare et al., "Transformation of mouse fibroblasts to methotrexate resistance by a recombinant plasmid expressing a prokaryotic dihydrofolate reductase," *Proc. Natl. Acad. Sci. USA*, 78(3): 1527-1531 (1981).
Panyam et al., "Biodegradable nanoparticles for drug and gene delivery to cells and tissue," *Adv. Drug Deliv. Rev.*, 64 (Supp):61-71 (2012).
Pearson et al., "Improved tools for biological sequence comparison," *Proc. Natl. Acad. Sci. USA*, 85(8):2444-2448 (1988).
Pearson, "Rapid and sensitive sequence comparison with FASTP and FASTA," *Methods Enzymol.*, 183:63-98 (1990).
Rees et al., "Base editing: precision chemistry on the genome and transcriptome of living cells," *Nat. Rev. Genet.*, 19(12): 770-788 (2018).
Sinha et al., "A systematic genome-wide mapping of oncogenic mutation selection during CRISPR-Cas9 genome editing," *Nature Comm.*, 12:6512 (2021).
Smith et al., "Production of human beta interferon in insect cells infected with a baculovirus expression vector," *Mol. Cell. Biol.*, 3(12):2156-2165 (1983).
Sundaresan et al., "RNA-Independent DNA Cleavage Activities of Cas9 and Cas12a," *Cell Rep.*, 21(13):3728-3739 (2017).
Takebe et al., "SR alpha promoter: an efficient and versatile mammalian cDNA expression system composed of the simian virus 40 early promoter and the R-U5 segment of human T-cell leukemia virus type 1 long terminal repeat," *Mol. Cell. Biol.*, 8(1):466-472 (1988).
Tran et al., "Engineering domain-inlaid SaCas9 adenine base editors with reduced RNA off-targets and increased on-target DNA editing," *Nat. Commun.*, 11:4871 (2020).
Tuladhar et al., "CRISPR-Cas9-based mutagenesis frequently provokes on-target mRNA misregulation," *Nat. Commun.*, 10:4056 (2019).
Urabe et al., "Insect cells as a factory to produce adeno-associated virus type 2 vectors," *Hum. Gene. Ther.*, 13(16): 1935-1943 (2002).
Wang et al., "Specificity profiling of CRISPR system reveals greatly enhanced off-target gene editing," *Scientific Reports*, 10:2269 (2020).
Wildin et al., "Functional dissection of the murine lck distal promoter," *J. Immunol.*, 155(3): 1286-1295 (1995).
Winter et al., "Genome-wide CRISPR screen reveals novel host factors required for *Staphylococcus aureus* α-hemolysin-mediated toxicity," *Sci. Rep.*, 6:24242 (2016).
Zhao et al., "Glycosylase base editors enable C-to-A and C-to-G base changes," *Nat. Biotechnol.*, 39:35-40 (2021).

(56) References Cited

OTHER PUBLICATIONS

GenBank Association No. RKJ68762.1, "transposase, [*Roseburia* sp. 1XD42-69]," Oct. 4, 2018.
Ran et al., "In vivo genome editing using *Staphylococcus aureus* Cas9," *Nature*, 520(7546): 186-191 (2015).
Xu et al., "Engineered miniature CRISPR-Cas system for mammalian genome regulation and editing," *Mol Cell.*, 81:1-13 (2021).
Karvelis et al., "PAM recognition by miniature CRISPR-Cas 12f nucleases triggers programmable double-stranded DNA target cleavage," *Nucleic Acids Research*, vol. 48, Issue 9, 5016-5023 (2020).
"COG0675—Transposase," www.ncbi.nlm.nih.gov/Structure/cdd/cddsrv.cgi?uid=COG0675/. Accessed Dec. 12, 2023.
Moon et al., "Recent advances in the CRISPR genome editing tool set," *Exp Mol Med*, 51, 1-11 (2019).
Written Opinion mailed on Jul. 31, 2023 for PCT Application No. PCT/US2023/061022, 9 pages.
"pfam01385—OrfB_IS605," www.ebi.ac.uk/interpro/entry/pfam/PF01385/. Accessed Dec. 12, 2023.
"pfam07282—OrfB_Zn_ribbon," www.ebi.ac.uk/interpro/entry/pfam/PF07282/. Accessed Dec. 12, 2023.
Ilmberge et al., "A Comparative Metagenome Survey of the Fecal Microbiota of a Breast- and a Plant-Fed Asian Elephant Reveals an Unexpectedly High Diversity of Glycoside Hydrolase Family Enzymes," *PLoS One*, 9(9): e106707 (2014).
Genome ID No. EMG_100164656 [online], Joint Genome Institute, Release date Jun. 17, 2023 [retrieved on Dec. 11, 2023]. Retrieved from the Internet: <URL: [https://img.jgi.doe.gov/cgi-bin/m/main.cgi?section=MetaGeneDetail&page=metaGeneDetail&data_type=assembled&tax on_oid=3300001598&gene_oid=EMG_10016-4656] >.
International Search Report mailed on Jul. 31, 2023 for PCT Application No. PCT/US2023/061022, 5 pages.
Xu et al., "Engineered miniature CRISPR-Cas system for mammalian genome regulation and editing," *Molecular Cell*, vol. 81, Issue 20, 4333-4345.e4 (2021).

\* cited by examiner

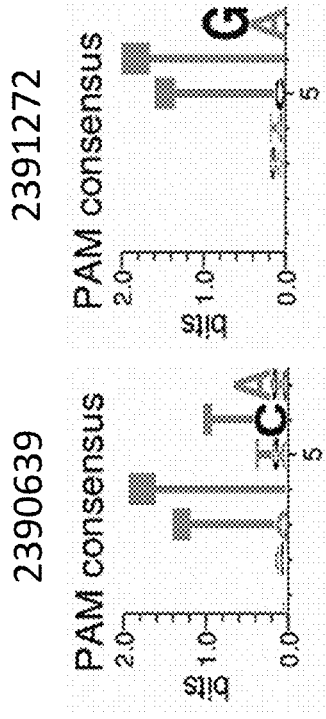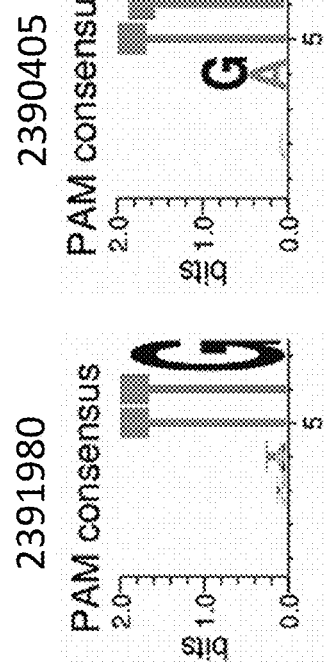
FIG. 38A  FIG. 38B  FIG. 38C  FIG. 38D
FIG. 38E  FIG. 38F  FIG. 38G  FIG. 38H

EFFECTOR PROTEINS AND METHODS OF USE

CROSS-REFERENCED APPLICATIONS

This application is a continuation of International Patent Application No. PCT/US23/61022, filed Jan. 20, 2023, which claims the benefit of priority to U.S. Provisional Application No. 63/301,963, filed on Jan. 21, 2022, U.S. Provisional Application No. 63/334,663, filed on Apr. 25, 2022, U.S. Provisional Application No. 63/346,244, filed on May 26, 2022, U.S. Provisional Application No. 63/371,502, filed on Aug. 15, 2022, U.S. Provisional Application No. 63/381,282, filed on Oct. 27, 2022, and U.S. Provisional Application No. 63/386,144, filed on Dec. 5, 2022, the entire contents of each of which are incorporated herein by reference.

INCORPORATION BY REFERENCE OF SEQUENCE LISTING

The instant application contains a Sequence Listing, which has been submitted via Patent Center. The Sequence Listing titled 203477-752302_US_SL.xml, which was created on Jun. 12, 2023 and is 1,449,494 bytes in size, is hereby incorporated by reference in its entirety.

FIELD

The present disclosure relates generally to polypeptides, such as effector proteins, compositions of such polypeptides and guide nucleic acids, systems, and methods of using such polypeptides and compositions, including detecting and modifying target nucleic acids.

BACKGROUND

Programmable nucleases are proteins that bind and cleave nucleic acids in a sequence-specific manner. A programmable nuclease may bind a target region of a nucleic acid and cleave the nucleic acid within the target region or at a position adjacent to the target region. In some instances, a programmable nuclease is activated when it binds a target region of a nucleic acid to cleave regions of the nucleic acid that are near, but not adjacent to the target region. A programmable nuclease, such as a CRISPR-associated (Cas) protein, may be coupled to a guide nucleic acid that imparts activity or sequence selectivity to the programmable nuclease. In general, guide nucleic acids comprise a CRISPR RNA (crRNA) that is at least partially complementary to a target nucleic acid. In some embodiments, guide nucleic acids comprise a trans activating crRNA (tracrRNA), at least a portion of which interacts with the programmable nuclease. In some embodiments, guide nucleic acids comprise a repeat region or a handle region, wherein, in some aspects, at least a portion of which interacts with the programmable nuclease, wherein in some aspects a handle region comprises at least a portion of a repeat region. In some embodiments, a tracrRNA or intermediary RNA is provided separately from the guide nucleic acid. The tracrRNA, repeat region, handle region, or any combination thereof may hybridize to a portion of the guide nucleic acid that does not hybridize to the target nucleic acid.

Programmable nucleases may cleave nucleic acids, including single stranded RNA (ssRNA), double stranded DNA (dsDNA), and single-stranded DNA (ssDNA). Programmable nucleases may provide cis cleavage activity, trans cleavage activity, nickase activity, or a combination thereof. Cis cleavage activity is cleavage of a target nucleic acid that is hybridized to a guide RNA (a dual nucleic acid system or sgRNA), wherein cleavage occurs within or directly adjacent to the region of the target nucleic acid that is hybridized to guide RNA. Trans cleavage activity (also referred to as transcollateral cleavage) comprises cleavage of ssDNA or ssRNA that is near, but not hybridized to the guide RNA. Trans cleavage activity is triggered by the hybridization of guide RNA to the target nucleic acid. Nickase activity is the selective cleavage of one strand of a dsDNA molecule. While certain programmable nucleases may be used to edit and detect nucleic acid molecules in a sequence specific manner, challenging biological sample conditions (e.g., high viscosity, metal chelating) may limit their accuracy and effectiveness. There is thus a need for systems and methods that employ programmable nucleases having specificity and efficiency across a wide range of sample conditions.

SUMMARY

The present disclosure provides compositions, systems, and methods comprising effector protein and uses thereof. In general, the effector proteins are DNA modifying, are dual-guided (require a crRNA and tracrRNA sequence for activity) and are short (less than 700 linked amino acids in length). Thus, they are referred to herein as D2S effector proteins. Compositions, systems and methods disclosed herein leverage the nucleic acid modifying activities (e.g., cis cleavage activity and transcollateral cleavage activity) of these D2S effector proteins for the modification, detection and engineering of target nucleic acids.

I. Certain Embodiments

Provided herein are systems comprising an effector protein or a nucleic acid encoding the effector protein, and an engineered guide nucleic acid or a nucleic acid encoding the engineered guide nucleic acid, wherein the effector protein comprises an amino acid sequence that is at least 65%, at least 70%, at least 75%, at least 80%, at least 85%, at least 90%, at least 95%, at least 98%, at least 99% or 100% identical to any one of the sequences recited in TABLE 1. In some embodiments, the effector protein comprises an amino acid sequence that is at least 65%, at least 70%, at least 75%, at least 80%, at least 85%, at least 90%, at least 95%, at least 98%, at least 99% or 100% identical to SEQ ID NO: 37, wherein each recitation of X within SEQ ID NO: 37 is independently any amino acid residue. In some embodiments, the effector protein comprises an amino acid sequence that is at least 65%, at least 70%, at least 75%, at least 80%, at least 85%, at least 90%, at least 95%, at least 98%, at least 99% or 100% identical to any one of SEQ ID NO: 60-69, wherein each recitation of X within any one of SEQ ID NO: 60-69 is independently selected from any amino acid residue. In some embodiments, the length of the effector protein is about 350 to about 450 linked amino acids, about 380 to about 430 linked amino acids, or about 395 to about 410 linked amino acids. In some embodiments, the amino acid sequence of the effector protein comprises one or more amino acid alterations relative to a sequence selected from TABLE 1. In some embodiments, the one or more amino acid alterations comprises: (a) 1 to 5, 1 to 10, or 1 to 20 non-conservative amino acid substitutions; (b) 1 to 5, 1 to 10, or 1 to 20 conservative amino acid substitutions; or (c) a combination thereof. In some embodiments, the effector protein comprises one or more amino acid substitutions relative to SEQ ID NO: 1, wherein the one or more amino acid substitutions comprises K58W, I80K, N193K, S209F, A218K, E225K, N286K, M295W, M298L, A306K, and Y315M. In some embodiments, the effector protein comprises one or more amino acid substitutions relative to SEQ ID NO: 1, wherein the one or more amino acid substitutions comprises D237A, D418A, D418N, E335A, and E335Q. In some embodiments, one, two, three, four, five, six, seven, eight, nine, or ten amino acids of the effector protein are substituted with a positively charged amino acid residue relative to a sequence recited in TABLE 1. In some embodiments, one or more positively charged amino acid residues are independently selected from arginine, lysine and histidine. In some embodiments, the positively charged amino acid residue is arginine. In some embodiments, the effector protein comprises one or more amino acid substitutions relative to SEQ ID NO: 1, wherein the one or more amino acid substitutions comprises I80R, T84R, K105R, G210R, C202R, A218R, D220R, E225R, C246R, and Q360R. In some embodiments, the one or more amino acid alterations are in one or more domain comprising a REC domain, RuvC-I domain, or a RuvC-II domain. In some embodiments, the engineered guide nucleic acid is a single guide RNA (sgRNA). In some embodiments, the engineered guide nucleic acid comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46.

Provided herein are systems comprising an effector protein or a nucleic acid encoding the effector protein, wherein the effector protein comprises an amino acid sequence that is at least 90%, at least 95%, at least 98%, or at least 99% identical to SEQ ID NO: 1, wherein the amino acid sequence comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions. In some embodiments, the effector protein comprises one or more amino acid substitutions relative to SEQ ID NO: 1, wherein the one or more amino acid substitutions are selected from D220R, N286K, E225K, I80K, S209F, Y315M, N193K, M298L, M295W, A306K, A218K, and K58W. In some embodiments, the effector protein comprises a non-conservative amino acid substitution of D220R. In some embodiments, the effector protein comprises an amino acid substitution selected from E335Q and D237A. In some embodiments, the systems described here further comprises an engineered guide nucleic acid or a nucleic acid encoding the engineered guide nucleic acid.

Provided herein are systems comprising an effector protein or a nucleic acid encoding the effector protein, wherein the effector protein comprises an amino acid sequence that is at least 75%, at least 80%, at least 85%, at least 90%, at least 95%, at least 98%, at least 99% or 100% similar to SEQ ID NO: 1; and an engineered guide nucleic acid or a nucleic acid encoding the engineered guide nucleic acid. In some embodiments, the engineered guide nucleic acid comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the engineered guide nucleic acid comprises: (a) a nucleotide sequence that is at least 75%, at least 80%, at least 85%, at least 90%, at least 95%, at least 98%, at least 99% or 100% identical to SEQ ID NO: 72; (b) a nucleotide sequence that is at least 75%, at least 80%, at least 85%, at least 90%, at least 95%, at least 98%, at least 99% or 100% identical to SEQ ID NO: 22; or (c) a combination thereof.

Provided herein are systems described herein, wherein the effector protein is fused to a fusion partner. In some embodiments, the fusion partner comprises a protein selected from a polymerase, deaminase, a reverse transcriptase, a transcriptional repressor, and a transcriptional activator. In some embodiments, the fusion partner comprises an amino acid sequence that is at least 70%, at least 75%, at least 80%, at least 85%, at least 90%, at least 95%, or 100% identical to one or more amino acid sequences recited in TABLE 2 and TABLE 2.1. In some embodiments, a complex formed by the effector protein and the engineered guide nucleic acid recognizes any one of the PAM sequences recited in TABLE 10, TABLE 36, TABLE 37, TABLE 38, TABLE 42, and TABLE 43 within a target nucleic acid, wherein each N is selected from any nucleotide; wherein each V is selected from adenine, cytosine and guanine; and wherein each R is selected from adenine and guanine. In some embodiments, the complex recognizes a protospacer adjacent motif (PAM) sequence of 5'-NNTN-3' (SEQ ID NO: 946), wherein each N is selected from any nucleotide. In some embodiments, the systems described herein comprise a lipid nanoparticle. In some embodiments, the nucleic acid encoding the effector protein is a messenger RNA. In some embodiments, the effector protein is capable of forming a complex with a guide nucleic acid, and wherein the complex is capable of binding a target nucleic acid. In some embodiments, the effector protein or nucleic acid encoding the effector protein, and the engineered guide nucleic acid or a nucleic acid encoding the engineered guide nucleic acid are in separate compositions. In some embodiments, the effector protein or nucleic acid encoding the effector protein, and the engineered guide nucleic acid or a nucleic acid encoding the engineered guide nucleic acid are in a single composition. In some embodiments, the systems described herein comprise at least one detection reagent for detecting a target nucleic acid, wherein the at least one detection reagent is selected from a reporter nucleic acid, a detection moiety, amplification reagent, and a combination thereof, optionally wherein the reporter nucleic acid comprises a fluorophore, a quencher, or a combination thereof.

Provided herein are compositions comprising the systems described herein or a component thereof.

Provided herein are pharmaceutical compositions comprising the systems described herein or a component thereof, and a pharmaceutically acceptable excipient.

Provided herein are methods of editing a target nucleic acid comprising contacting the target nucleic acid with the systems described here, the composition described herein, or the pharmaceutical composition described herein. In some embodiments, the methods comprise contacting the target nucleic acid with the effector protein or nucleic acid encoding the effector protein, and the engineered guide nucleic acid or a nucleic acid encoding the engineered guide nucleic acid sequentially. In some embodiments, the methods comprise contacting the target nucleic acid with the effector protein or nucleic acid encoding the effector protein, and the engineered guide nucleic acid or a nucleic acid encoding the engineered guide nucleic acid simultaneously. In some embodiments, the methods comprise modifying at least one nucleotide of a target sequence of the target nucleic acid, wherein the target sequence is adjacent to a PAM sequence of 5'-NNTN-3' (SEQ ID NO: 946), wherein each N is selected from any nucleotide. In some embodiments, the target nucleic acid comprises double stranded DNA (dsDNA), and modifying comprises cleaving at least one strand of the dsDNA. In some embodiments, modifying comprises modifying at least one nucleobase of the target nucleic acid. In some embodiments, the methods comprise contacting a cell comprising the target nucleic acid with the system or the composition.

Provided herein are methods of detecting a target nucleic acid in a sample comprising: (a) contacting the sample with the systems described herein; and (b) detecting the detectable signal.

Provided herein is a cell comprising the systems described herein or the composition described herein. Provided herein is a cell modified by the systems described herein, the composition described herein, or the pharmaceutical composition described herein. In some embodiments, the cell is a eukaryotic cell. In some embodiments, the cell is a mammalian cell. In some embodiments, the cell is a human cell. In some embodiments, the cell is a liver cell. In some embodiments, the cell is a stem cell.

Provided herein are expression vectors comprising a nucleic acid encoding an effector protein, wherein the effector protein comprises an amino acid sequence that is at least 75%, at least 80%, at least 85%, at least 90%, at least 95%, at least 98%, at least 99% or 100% identical to any one of the sequences recited in TABLE 1. In some embodiments, the effector protein comprises an amino acid sequence that is at least 90%, at least 95%, at least 98%, or at least 99% identical to SEQ ID NO: 1, wherein the amino acid sequence comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions. In some embodiments, the effector protein comprises one or more amino acid substitutions relative to SEQ ID NO: 1, wherein the one or more amino acid substitutions are selected from D220R, N286K, E225K, I80K, S209F, Y315M, N193K, M298L, M295W, A306K, A218K, and K58W. In some embodiments, the effector protein comprises an amino acid substitution relative to SEQ ID NO: 1, wherein the amino acid substitution is D220R. In some embodiments, the effector protein comprises an amino acid substitution relative to SEQ ID NO: 1, wherein the amino acid substitution is selected from E335Q and D237A. In some embodiments, the effector protein comprises an amino acid sequence that is at least 75%, at least 80%, at least 85%, at least 90%, at least 95%, at least 98%, at least 99% or 100% similar to SEQ ID NO: 1. In some embodiments, the expression vectors described herein comprise an engineered guide nucleic acid or a nucleic acid encoding the engineered guide nucleic acid. In some embodiments, the engineered guide nucleic acid comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35 and TABLE 45. In some embodiments, the engineered guide nucleic acid comprises: (a) a nucleotide sequence that is at least 75%, at least 80%, at least 85%, at least 90%, at least 95%, at least 98%, at least 99% or 100% identical to SEQ ID NO: 72; (b) a nucleotide sequence that is at least 75%, at least 80%, at least 85%, at least 90%, at least 95%, at least 98%, at least 99% or 100% identical to SEQ ID NO: 22; or (c) a combination thereof. In some embodiments, the expression vectors described herein comprise a donor nucleic acid.

Provided herein are expression vectors comprising: (a) a first nucleotide sequence encoding an effector protein, wherein the effector protein comprises an amino acid sequence that is at least 75%, at least 80%, at least 85%, at least 90%, at least 95%, at least 98%, at least 99% or 100% identical to SEQ ID NO: 1, optionally wherein the amino acid sequence comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions; and (b) a second nucleotide sequence encoding an engineered guide nucleic acid. In some embodiments, the effector protein is a fusion protein. In some embodiments, the expression vectors described herein comprise a donor nucleic acid. In some embodiments, the effector protein comprises an amino acid substitution relative to SEQ ID NO: 1, wherein the amino acid substitution is selected from D220R, N286K, E225K, I80K, S209F, Y315M, N193K, M298L, M295W, A306K, A218K and K58W, E335Q and D237A. In some embodiments, the expression vector is a viral vector, optionally wherein the viral vector is an adeno-associated viral (AAV) vector, optionally wherein the AAV vector is a self-complementary AAV vector.

Provided herein are methods of modifying a target nucleic acid comprising contacting a cell with the expression vectors described herein, optionally comprising transducing a cell by contacting the cell with a virus containing the viral vector described herein.

Provided herein are methods of treating a disease comprising administering to a subject in need thereof the pharmaceutical composition described herein.

Provided herein are methods of treating a disease comprising administering to a subject in need thereof the cell described herein.

Provided herein are methods of treating a disease comprising administering to a subject in need thereof the expression vector.

Provided herein are effector proteins comprising an amino acid sequence that is at least 60%, at least 65%, at least 70%, at least 75%, at least 80%, at least 85%, at least 90%, at least 95%, at least 98%, or at least 99% identical to SEQ ID NO: 1, wherein the amino acid sequence comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions, optionally wherein the effector protein comprises one or more amino acid substitutions selected from D220R, N286K, E225K, I80K, S209F, Y315M, N193K, M298L, M295W, A306K, A218K, K58W, E335Q, and D237A.

Provided herein are nucleic acids encoding effector proteins, wherein the effector protein comprises an amino acid sequence that is at least 60%, at least 65%, at least 70%, at least 75%, at least 80%, at least 85%, at least 90%, at least 95%, at least 98%, or at least 99% identical to SEQ ID NO: 1, wherein the amino acid sequence comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions, optionally wherein the effector protein comprises one or more amino acid substitutions selected from D220R, N286K, E225K, I80K, S209F, Y315M, N193K, M298L, M295W, A306K, A218K, K58W, E335Q, and D237A.

In some embodiments are compositions comprising an effector protein or a nucleic acid encoding the effector protein, and an engineered guide nucleic acid or a nucleic acid encoding the engineered guide nucleic acid, wherein the effector protein comprises an amino acid sequence that is at least 75%, at least 80%, at least 85%, at least 90%, at least 95%, at least 98%, at least 99% or 100% identical to any one of the sequences recited in TABLE 1. In some embodiments, the effector protein comprises an amino acid sequence that is at least 75%, at least 80%, at least 85%, at least 90%, at least 95%, at least 98%, at least 99% or 100% identical to SEQ ID NO: 37. In some embodiments, the effector protein comprises an amino acid sequence that is at least 75%, at least 80%, at least 85%, at least 90%, at least 95%, at least 98%, at least 99% or 100% identical to any one of SEQ ID NO: 60-69, wherein each recitation of X within any one of SEQ ID NO: 60-69 is independently selected from any amino acid residue. In some embodiments, the effector protein is at least 350 linked amino acid residues. In some embodiments, the effector protein is about 350 to about 450 linked amino acid residues. In some embodiments, the effector protein is about 380 to about 430 linked amino acid residues. In some embodiments, the effector protein is about 395 to about 410 linked amino acid residues.

In some embodiments are compositions comprising an effector protein or a nucleic acid encoding the effector protein, and an engineered guide nucleic acid or a nucleic acid encoding the engineered guide nucleic acid, wherein the effector protein comprises an amino acid sequence that is at least 75%, at least 80%, at least 85%, at least 90%, at least 95%, at least 98%, at least 99% or 100% identical to any one of the sequences recited in TABLE 1. In some embodiments are compositions comprising an effector protein, or a nucleic acid encoding the effector protein, and an engineered guide nucleic acid, wherein the effector protein comprises an amino acid sequence that is at least 75%, at least 80%, at least 85%, at least 90%, at least 95%, at least 98%, at least 99% or 100% identical to SEQ ID NO: 1. In some embodiments are compositions comprising an effector protein, or a nucleic acid encoding the effector protein, and an engineered guide nucleic acid, wherein the effector protein comprises an amino acid sequence that is at least 75%, at least 80%, at least 85%, at least 90%, at least 95%, at least 98%, at least 99% or 100% identical to SEQ ID NO: 2. In some embodiments, are compositions comprising an effector protein, or a nucleic acid encoding the effector protein, and an engineered guide nucleic acid, wherein the effector protein comprises an amino acid sequence that is at least 75%, at least 80%, at least 85%, at least 90%, at least 95%, at least 98%, at least 99% or 100% identical to SEQ ID NO: 37. In some embodiments are compositions comprising an effector protein, or a nucleic acid encoding the effector protein, and an engineered guide nucleic acid, wherein the effector protein comprises an amino acid sequence that is at least 75%, at least 80%, at least 85%, at least 90%, at least 95%, at least 98%, at least 99% or 100% identical to any one of SEQ ID NO: 60-69, wherein each recitation of X within any one of SEQ ID NO: 60-69 is independently selected from any amino acid residue.

In some embodiments are compositions described herein, wherein the amino acid sequence of the effector protein comprises one or more amino acid alterations relative to a sequence selected from TABLE 1. In some embodiments, the one or more amino acid alterations comprises: a) up to 1%, 2%, 3%, 4%, or 5%1 to 5, 1 to 10, or 1 to 20 non-conservative substitutions; b) 1 to 5, 1 to 10, or 1 to 20 conservative substitutions; or c) a combination thereof. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine. In some embodiments, the effector protein comprises one or more alterations relative to SEQ ID NO: 1, wherein the one or more alterations comprises K58W, I80R, T84R, K105R, N193K, G210R, C202R, S209F, A218K, A218R, D220R, E225K, E225R, C246R, N286K, M295W, M298L, A306K, Y315M, and Q360R. In some embodiments, the amino acid sequence of the effector protein comprises one or more amino acid alterations in one or more domain comprising a REC domain, RuvC-I domain, or a RuvC-II domain.

In some embodiments, the effector protein of the compositions described herein comprise a nuclear localization signal. In some embodiments, the effector protein is a fusion protein comprising a fusion partner. In some embodiments, the fusion partner comprises one or more amino acid sequences recited in TABLE 2 and TABLE 2.1.

In some embodiments, the engineered guide nucleic acid is a single guide RNA (sgRNA). In some embodiments, the sgRNA comprises a handle sequence. In some embodiments, the handle sequence comprises a repeat sequence. In some embodiments, the sgRNA comprises a handle sequence, a linker, or a repeat sequence. In some embodiments, the handle sequence comprises a handle sequence of any one of those sequences identified in TABLE 4. In some embodiments, the sgRNA comprises a linker. In some embodiments, the linker comprises a linker of any one of those sequences identified in TABLE 4. In some embodiments, the sgRNA comprises a repeat. In some embodiments, the repeat sequence comprises a repeat sequence of any one of those sequence identified in TABLE 3. In some embodiments, the sgRNA comprises a handle sequence of any one of those sequences identified in TABLE 4. In some embodiments, the handle comprises a portion of the nucleotide sequence of SEQ ID NO: 22. In some embodiments, the handle comprises the nucleotide sequence of SEQ ID NO: 70. In some embodiments, the handle comprises the nucleotide sequence of SEQ ID NO: 32. In some embodiments, the handle comprises the nucleotide sequence of SEQ ID NO: 73. In some embodiments, the handle comprises the nucleotide sequence of SEQ ID NO: 35. In some embodiments, the handle comprises a portion of the nucleotide sequence of SEQ ID NO: 25. In some embodiments, the handle comprises the nucleotide sequence of SEQ ID NO: 36. In some embodiments, the handle comprises a portion of the nucleotide sequence of SEQ ID NO: 26. In some embodiments, the sgRNA comprises a handle sequence, a linker, or a repeat sequence.

In some embodiments are compositions comprising an effector protein, or a nucleic acid encoding the effector protein, and an engineered guide nucleic acid, wherein the effector protein comprises an amino acid sequence that is at least 75%%, at least 80%, at least 85%, at least 90%, at least 95%, at least 98%, at least 99% or 100% identical to any one of SEQ ID NOs: 1-2, or 37, and wherein the engineered guide nucleic acid comprises: (i) a portion of a crRNA comprising a nucleobase sequence that is at least 75%, at least 80%, at least 85%, at least 90%, at least 95%, or 100% identical to an equal length portion of any one of SEQ ID NOs: 17-21; (ii) a portion of a tracrRNA sequence comprising a nucleobase sequence that is at least 75%, at least 80%, at least 85%, at least 90%, at least 95%, or 100% identical to an equal length portion of any one of SEQ ID NOs: 22-26, (iii) or a combination thereof.

In some embodiments, the compositions disclosed herein comprise an engineered guide nucleic acid wherein the guide nucleic acid comprises: (i) a portion of a crRNA comprising a nucleobase sequence that is at least 75%, at least 80%, at least 85%, at least 90%, at least 95%, or 100% identical to an equal length portion of SEQ ID NO: 17; and (ii) a portion of a tracrRNA sequence comprising a nucleobase sequence that is at least 75%, at least 80%, at least 85%, at least 90%, at least 95%, or 100% identical to an equal length portion of SEQ ID NO: 22.

In some embodiments, the compositions disclosed herein comprise an engineered guide nucleic acid wherein the guide nucleic acid comprises: (i) a portion of a crRNA comprising a nucleobase sequence that is at least 75%, at least 80%, at least 85%, at least 90%, at least 95%, or 100% identical to an equal length portion of SEQ ID NO: 17; and (ii) a portion of a tracrRNA sequence comprising a nucleobase sequence that is at least 75%, at least 80%, at least 85%, at least 90%, at least 95%, or 100% identical to the nucleotide sequence of an equal length portion of SEQ ID NO: 23.

In some embodiments, the compositions disclosed herein comprise an engineered guide nucleic acid wherein the guide nucleic acid comprises: (i) a portion of a crRNA comprising a nucleobase sequence that is at least 75%, at least 80%, at least 85%, at least 90%, at least 95%, or 100% identical to the nucleotide sequence of an equal length portion of SEQ ID NO: 19; and (ii) a portion of a tracrRNA sequence comprising a nucleobase sequence that is at least 75%, at least 80%, at least 85%, at least 90%, at least 95%, or 100% identical to the nucleotide sequence of an equal length portion of SEQ ID NO: 24.

In some embodiments, the compositions disclosed herein comprise an engineered guide nucleic acid wherein the guide nucleic acid comprises: (i) a portion of a crRNA comprising a nucleobase sequence that is at least 75%, at least 80%, at least 85%, at least 90%, at least 95%, or 100% identical to an equal length portion of SEQ ID NO: 20; and (ii) a portion of a tracrRNA sequence comprising a nucleobase sequence that is at least 75%, at least 80%, at least 85%, at least 90%, at least 95%, or 100% identical to an equal length portion of any one of SEQ ID NO: 25.

In some embodiments, the compositions disclosed herein comprise an engineered guide nucleic acid wherein the guide nucleic acid comprises: (i) a portion of a crRNA comprising a nucleobase sequence that is at least 75%, at least 80%, at least 85%, at least 90%, at least 95%, or 100% identical to an equal length portion of SEQ ID NO: 21; and (ii) a portion of a tracrRNA sequence comprising a nucleobase sequence that is at least 75%, at least 80%, at least 85%, at least 90%, at least 95%, or 100% identical to an equal length portion of SEQ ID NO: 26.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to any one of SEQ ID NO: 42-59.

In some embodiments, the compositions disclosed herein comprise an engineered guide nucleic acid wherein the guide nucleic acid comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to any one of SEQ ID NO: 27-30.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to any one of SEQ ID NO: 31-36.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to SEQ ID NO: 70.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to an equal length portion of any one of SEQ ID NO: 22, SEQ ID NO: 25, and SEQ ID NO: 26.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to any one of SEQ ID NO: 70, SEQ ID NO: 32, SEQ ID NO: 73, SEQ ID NO: 35, SEQ ID NO: 36.

In some embodiments, the compositions disclosed herein comprise an engineered guide nucleic acid wherein the guide nucleic acid comprises a nucleobase sequence that is at least 75%, at least 80%, at least 85%, at least 90%, at least 95%, or 100% identical to any one of SEQ ID NO: 125-257 or SEQ ID NO: 260-279.

In some embodiments, the compositions disclosed herein comprise an effector protein and an engineered guide nucleic acid, wherein the effector protein comprises a portion of SEQ ID NO: 37, wherein each recitation of X within SEQ ID NO: 37 is independently any amino acid residue, and wherein the portion is about 30, about 40, about 50, about 60, about 70, about 80, about 90, or about 100 continuous amino acids.

In some embodiments, the compositions described herein comprise a portion of a crRNA and a portion of a tracrRNA sequence, wherein the crRNA and the tracrRNA sequence are linked in a single guide RNA.

In some embodiments, a complex formed by the effector protein and the engineered guide nucleic acid of the compositions described herein recognizes any one of PAM sequences recited in TABLE 10, TABLE 36, TABLE 37, TABLE 38, TABLE 42, and TABLE 43 within a target nucleic acid, wherein each N is selected from any nucleotide; wherein each R is selected from adenine and guanine, and wherein each V is selected from adenine, cytosine or guanine. In some embodiments, the complex recognizes a PAM sequence of 5'-NNTN-3' (SEQ ID NO: 946), wherein each N is selected from any nucleotide. In some embodiments, the guide nucleic acid comprises a spacer sequence, wherein the first nucleotide from the 5' end of the spacer sequence is a nucleotide selected from A, T or G. In some embodiments, the spacer sequence is 20 nucleotides in length. In some embodiments, at least two nucleotides of the first three nucleotides from the 5' end of the spacer sequence are nucleotides selected from A and T.

In some embodiments are pharmaceutical compositions comprising a composition described herein and a pharmaceutically acceptable excipient. In some embodiments are systems comprising a composition described herein. In some embodiments, the system comprises at least one detection reagent for detecting a target nucleic acid. In some embodiments, the at least one detection reagent is selected from a reporter nucleic acid, a detection moiety, an additional effector protein, or a combination thereof, optionally wherein the reporter nucleic acid comprises a fluorophore, a quencher, or a combination thereof. In some embodiments, the system comprises at least one amplification reagent for amplifying a target nucleic acid. In some embodiments, the at least one amplification reagent is selected from the group consisting of a primer, an activator, a dNTP, an rNTP, and combinations thereof.

In some embodiments are methods of modifying a target nucleic acid in a sample, comprising contacting the sample with a composition or system described herein thereby generating a modification of the target nucleic acid; and optionally detecting the modification. In some embodiments are methods of detecting a target nucleic acid in a sample, comprising the steps of (a) contacting the sample with a composition described herein; and a reporter nucleic acid comprising a detectable moiety that produces a detectable signal in the presence of the target nucleic acid and the composition of system, and (b) detecting the detectable signal. In some embodiments, the target nucleic acid comprises a PAM sequence of any one of the sequences recited in TABLE 10, TABLE 36, TABLE 37, TABLE 38, TABLE 42, and TABLE 43, wherein each N is selected from any nucleotide; wherein each V is selected from adenine, cytosine or guanine; and wherein each R is selected from adenine and guanine. In some embodiments, the target nucleic acid comprises a PAM sequence of NNTN (SEQ ID NO: 946), wherein each N is selected from any nucleotide.

In some embodiments, the effector protein comprises an amino acid sequence that is at least 75%, at least 80%, at least 85%, at least 90%, at least 95%, at least 98%, at least 99% or 100% identical to SEQ ID NO: 1; a portion of the crRNA comprises a nucleobase sequence that is at least 75%, at least 80%, at least 85%, at least 90%, at least 95%, or 100% identical to an equal length portion of SEQ ID NO: 17; and a portion of the tracrRNA sequence comprises a nucleobase sequence that is at least 75%, at least 80%, at least 85%, at least 90%, at least 95%, or 100% identical to an equal length portion of SEQ ID NO: 22. In some embodiments, the effector protein comprises an amino acid sequence that is at least 75%, at least 80%, at least 85%, at least 90%, at least 95%, at least 98%, at least 99% or 100% identical to SEQ ID NO: 1; a portion of the crRNA comprises a nucleobase sequence that is at least 75%, at least 80%, at least 85%, at least 90%, at least 95%, or 100% identical to an equal length portion of SEQ ID NO: 17; and a portion of the tracrRNA sequence comprises a nucleobase sequence that is at least 75%, at least 80%, at least 85%, at least 90%, at least 95%, or 100% identical to an equal length portion of SEQ ID NO: 23. In some embodiments, the target nucleic acid has a PAM sequence of NNTN (SEQ ID NO: 946), wherein each N is selected from any nucleotide.

In some embodiments, the effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 19; and a portion of the tracrRNA sequence comprises a nucleobase sequence that is at least 75%, at least 80%, at least 85%, at least 90%, at least 95%, or 100% identical to an equal length portion of SEQ ID NO: 24. In some embodiments, the effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 20; and a portion of the tracrRNA sequence comprises a nucleobase sequence that is at least 75%, at least 80%, at least 85%, at least 90%, at least 95%, or 100% identical to an equal length portion of SEQ ID NO: 25. In some embodiments, effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 21; and a portion of the tracrRNA sequence comprises a nucleobase sequence that is at least 75%, at least 80%, at least 85%, at least 90%, at least 95%, or 100% identical to an equal length portion of SEQ ID NO: 26. In some embodiments, the effector protein comprises an amino acid sequence that is at least 75%, at least 80%, at least 85%, at least 90%, at least 95%, at least 98%, at least 99% or 100% identical to SEQ ID NO: 27. In some embodiments, the target nucleic acid has a PAM sequence of NNTN (SEQ ID NO: 946), wherein each N is selected from any nucleotide, wherein each N is selected from any nucleotide; and wherein each R is selected from adenine and guanine.

In some embodiments, the effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 19; and a portion of the tracrRNA sequence comprises a nucleobase sequence that is at least 75%, at least 80%, at least 85%, at least 90%, at least 95%, or 100% identical to an equal length portion of SEQ ID NO: 24. In some embodiments, the effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 20; and a portion of the tracrRNA sequence comprises a nucleobase sequence that is at least 75%, at least 80%, at least 85%, at least 90%, at least 95%, or 100% identical to an equal length portion of SEQ ID NO: 25. In some embodiments, the effector protein comprises an amino acid sequence that is at least 75%, at least 80%, at least 85%, at least 90%, at least 95%, at least 98%, at least 99% or 100% identical to SEQ ID NO: 2; a portion of the crRNA comprises a nucleobase sequence that is at least 75%, at least 80%, at least 85%, at least 90%, at least 95%, or 100% identical to an equal length portion of SEQ ID NO: 21; and a portion of the tracrRNA sequence comprises a nucleobase sequence that is at least 75%, at least 80%, at least 85%, at least 90%, at least 95%, or 100% identical to an equal length portion of SEQ ID NO: 26. In some embodiments, the effector protein comprises an amino acid sequence that is at least 75%, at least 80%, at least 85%, at least 90%, at least 95%, at least 98%, at least 99% or 100% identical to SEQ ID NO: 1; and the sgRNA comprises a nucleobase sequence that is at least 75%, at least 80%, at least 85%, at least 90%, at least 95%, or 100% identical to SEQ ID NO: 27. In some embodiments, the effector protein comprises an amino acid sequence that is at least 75%, at least 80%, at least 85%, at least 90%, at least 95%, at least 98%, at least 99% or 100% identical to SEQ ID NO: 2; and the sgRNA comprises a nucleobase sequence that is at least 75%, at least 80%, at least 85%, at least 90%, at least 95%, or 100% identical to SEQ ID NO: 28. In some embodiments, the effector protein comprises an amino acid sequence that is at least 75%, at least 80%, at least 85%, at least 90%, at least 95%, at least 98%, at least 99% or 100% identical to SEQ ID NO: 2; and the sgRNA comprises a nucleobase sequence that is at least 75%, at least 80%, at least 85%, at least 90%, at least 95%, or 100% identical to SEQ ID NO: 29. In some embodiments, the effector protein comprises an amino acid sequence that is at least 75%, at least 80%, at least 85%, at least 90%, at least 95%, at least 98%, at least 99% or 100% identical to SEQ ID NO: 2; and the sgRNA comprises a nucleobase sequence that is at least 75%, at least 80%, at least 85%, at least 90%, at least 95%, or 100% identical to SEQ ID NO: 30. In some embodiments, the effector protein comprises an amino acid sequence that is at least 75%, at least 80%, at least 85%, at least 90%, at least 95%, at least 98%, at least 99% or 100% identical to SEQ ID NO: 1; and the sgRNA comprises a nucleobase sequence that is at least 75%, at least 80%, at least 85%, at least 90%, at least 95%, or 100% identical to SEQ ID NO: 70. In some embodiments, the effector protein comprises an amino acid sequence that is at least 75%, at least 80%, at least 85%, at least 90%, at least 95%, at least 98%, at least 99% or 100% identical to SEQ ID NO: 2; and the sgRNA comprises a nucleobase sequence that is at least 75%, at least 80%, at least 85%, at least 90%, at least 95%, or 100% identical to of any one of SEQ ID NO: 32, 35, 70, and 36. In some embodiments, the target nucleic acid has a PAM sequence of NNTN (SEQ ID NO: 946), wherein each N is selected from any nucleotide.

In some embodiments, a method of detecting a target nucleic acid described herein comprises a complex formed by the effector protein and the engineered guide nucleic acid of the compositions described herein that recognizes any one of PAM sequences recited in TABLE 43, wherein each N is selected from any nucleotide; wherein each V is selected from adenine, cytosine and guanine; and wherein each R is selected from adenine and guanine. In some embodiments, the complex recognizes any one of PAM sequences recited in TABLE 43, wherein each N is selected from any nucleotide; wherein each V is selected from adenine, cytosine and guanine; and wherein each R is selected from adenine and guanine. In some embodiments, the guide nucleic acid comprises a spacer sequence, wherein the first nucleotide from the 5' end of the spacer sequence is a nucleotide selected from A, T or G. In some embodiments, the spacer sequence is 20 nucleotides in length. In some embodiments, at least two nucleotides of the first three nucleotides from the 5' end of the spacer sequence are nucleotides selected from A and T. In some embodiments, the reporter nucleic acid comprises a fluorophore, a quencher, or a combination thereof, and wherein the detecting comprises detecting a fluorescent signal. In some embodiments, the methods described herein further comprise reverse transcribing the target nucleic acid, amplifying the target nucleic acid, in vitro transcribing the target nucleic acid, or any combination thereof. In some embodiments, the methods described herein further comprise reverse transcribing the target nucleic acid and/or amplifying the target nucleic acid before contacting the sample with the composition. In some embodiments, the methods described herein further comprise reverse transcribing the target nucleic acid and/or amplifying the target nucleic acid after contacting the sample with the composition. In some embodiments, amplifying comprises isothermal amplification. In some embodiments, the target nucleic acid is from a pathogen. In some embodiments, the pathogen is a virus. In some embodiments, the virus is a SARS-CoV-2 virus or a variant thereof, an influenza A virus, an influenza B virus, a human papillomavirus, a herpes simplex virus, or a combination thereof. In some embodiments, the pathogen is a bacterium. In some embodiments, the bacterium is *Chlamydia trachomatis*. In some embodiments, the target nucleic acid is RNA. In some embodiments, the target nucleic acid is DNA.

In some embodiments are methods of modifying a target nucleic acid, the methods comprising: contacting the target nucleic acid with the compositions described herein, thereby modifying the target nucleic acid. In some embodiments are methods of modifying a target nucleic acid, the methods comprising: contacting a system described herein with the target nucleic acid, thereby modifying the target nucleic acid. In some embodiments, modifying the target nucleic acid comprises cleaving the target nucleic acid, deleting a nucleotide of the target nucleic acid, inserting a nucleotide into the target nucleic acid, substituting a nucleotide of the target nucleic acid with a donor nucleotide or an additional nucleotide, or any combination thereof. In some embodiments, the methods described herein further comprise contacting the target nucleic acid with a donor nucleic acid. In some embodiments, the target nucleic acid comprises a mutation associated with a disease. In some embodiments, the disease is suspected to cause, at least in part, a cancer, an inherited disorder, an ophthalmological disorder, or a combination thereof. In some embodiments, the disease is cancer, an ophthalmological disease, a neurological disorder, a blood disorder, or a metabolic disorder. In some embodiments, the neurological disorder is Duchenne muscular dystrophy, myotonic dystrophy Type 1, or cystic fibrosis. In some embodiments, the neurological disorder is a neurodegenerative disease. In some embodiments, the target nucleic acid is encoded by a gene selected from TABLE 8. In some embodiments, the gene is PCSK9. In some embodiments, the gene is TRAC, B2M, PD1, or a combination thereof. In some embodiments, contacting occurs in vitro. In some embodiments, contacting occurs in vivo. In some embodiments, contacting occurs ex vivo.

In some embodiments, a cell comprises a composition described herein. In some embodiments, a cell is produced by a method described herein. In some embodiments, a cell is modified by a method described herein. In some embodiments, the cell is a eukaryotic cell. In some embodiments, the cell is a mammalian cell. In some embodiments, the cell is a T cell, optionally wherein the T cell is a natural killer T cell (NKT). In some embodiments, the cell is an induced pluripotent stem cell (iPSC). In some embodiments is a population of cells of any of the cells described herein.

In some embodiments are methods of producing a protein, the methods comprising: (i) contacting a cell comprising a target nucleic acid to a composition described herein, thereby editing the target nucleic acid to produce a modified cell comprising a modified nucleic acid; and (ii) producing a protein from the cell that is encoded, transcriptionally affected, or translationally affected by the modified nucleic acid. In some embodiments, contacting the cell occurs with a DNA donor template. In some embodiments, the cell is a cancer cell, an animal cell, an HEK293T cell, or an immune cell. In some embodiments, the cell is a Chinese hamster ovary cell.

In some embodiments are methods of treating a disease comprising administering to a subject in need thereof a composition described herein, a pharmaceutical composition described herein, or a cell described herein. In some embodiments, the compositions described herein are for use in therapy. In some embodiments, the compositions described herein are for use in treating a disease or condition described herein. Also provided is the use of the compositions described herein in the manufacture of a medicament. Also provided is the use of the compositions described herein in the manufacture of a medicament for therapeutic and/or prophylactic treatment of a disease or condition described herein.

In some embodiments, the effector proteins described herein are for use in therapy. In some embodiments, the effector proteins described herein are for use in treating a disease or condition described herein. Also provided is the use of the effector proteins described herein in the manufacture of a medicament. Also provided is the use of the effector proteins described herein in the manufacture of a medicament for therapeutic and/or prophylactic treatment of a disease or condition described herein.

In some embodiments, the guide nucleic acids described herein are for use in therapy. In some embodiments, the guide nucleic acids described herein are for use in treating a disease or condition described herein. Also provided is the use of the guide nucleic acids described herein in the manufacture of a medicament. Also provided is the use of the guide nucleic acids described herein in the manufacture of a medicament for therapeutic and/or prophylactic treatment of a disease or condition described herein.

In some embodiments are methods of editing a target nucleic acid in a mammalian cell comprising contacting the mammalian cell with a composition comprising an effector protein and a guide nucleic acid, wherein the effector protein comprises an amino acid sequence that is at least 75%, at least 80%, at least 85%, at least 90%, at least 95%, at least 98%, at least 99% or 100% identical to any one of the sequences recited in TABLE 1. In some embodiments, the effector protein is a fusion protein comprising a fusion partner. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine.

In some embodiments are methods of editing a target nucleic acid in a mammalian cell comprising contacting the mammalian cell with a composition comprising an effector protein and a guide nucleic acid, wherein the effector protein comprises an amino acid sequence that is at least 75%, at least 80%, at least 85%, at least 90%, at least 95%, at least 98%, at least 99% or 100% identical to SEQ ID NO: 1. In some embodiments, the guide nucleic acid comprises a sequence that is at least 75%, at least 80%, at least 85%, at least 90%, at least 95%, at least 98%, at least 99% or 100% identical to SEQ ID NO: 27. In some embodiments, the guide nucleic acid comprises a sequence that is at least 75%, at least 80%, at least 85%, at least 90%, at least 95%, at least 98%, at least 99% or 100% identical to any one of SEQ ID NO: 22, SEQ ID NO: 25, and SEQ ID NO: 26. In some embodiments, the guide nucleic acid comprises a sequence that is at least 75%, at least 80%, at least 85%, at least 90%, at least 95%, at least 98%, at least 99% or 100% identical to any one of SEQ ID NO: 70, SEQ ID NO: 32, SEQ ID NO: 73, SEQ ID NO: 35, and SEQ ID NO: 36. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to any one of SEQ ID NO: 22, SEQ ID NO: 25, and SEQ ID NO: 26. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to any one of SEQ ID NO: 70, SEQ ID NO: 32, SEQ ID NO: 73, SEQ ID NO: 35, and SEQ ID NO: 36. In some embodiments, the effector protein is a fusion protein comprising a fusion partner. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine.

In some embodiments are methods of editing a target nucleic acid in a mammalian cell comprising contacting the mammalian cell with a composition comprising an effector protein and a guide nucleic acid, wherein the effector protein comprises an amino acid sequence that is at least 75%, at least 80%, at least 85%, at least 90%, at least 95%, at least 98%, at least 99% or 100% identical to SEQ ID NO: 1. In some embodiments, the guide nucleic acid comprises a sequence that is at least 75%, at least 80%, at least 85%, at least 90%, at least 95%, at least 98%, at least 99% or 100% identical to SEQ ID NO: 27. In some embodiments, the guide nucleic acid comprises a sequence that is at least 75%, at least 80%, at least 85%, at least 90%, at least 95%, at least 98%, at least 99% or 100% identical to SEQ ID NO: 70. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to SEQ ID NO: 70. In some embodiments, the effector protein is a fusion protein comprising a fusion partner. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine.

In some embodiments, a mammalian cell or a population of mammalian cells is produced by a method described herein. In some embodiments, a mammalian cell or a population of mammalian cells is modified by a method described herein.

In some embodiments are methods of editing a target nucleic acid in a mammalian cell comprising contacting the mammalian cell with a composition comprising an effector protein and a guide nucleic acid, wherein the effector protein comprises an amino acid sequence that is at least 75%, at least 80%, at least 85%, at least 90%, at least 95%, at least 98%, at least 99% or 100% identical to SEQ ID NO: 2. In some embodiments, the guide nucleic acid comprises a sequence that is at least 75%, at least 80%, at least 85%, at least 90%, at least 95%, at least 98%, at least 99% or 100% identical to SEQ ID NO: 28. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to SEQ ID NO: 28. In some embodiments, the guide nucleic acid comprises a sequence that is at least 75%, at least 80%, at least 85%, at least 90%, at least 95%, at least 98%, at least 99% or 100% identical to SEQ ID NO: 29. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to SEQ ID NO: 29. In some embodiments, the guide nucleic acid comprises a sequence that is at least 75%, at least 80%, at least 85%, at least 90%, at least 95%, at least 98%, at least 99% or 100% identical to SEQ ID NO: 30. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to SEQ ID NO: 30. In some embodiments, the guide nucleic acid comprises a sequence that is at least 75%, at least 80%, at least 85%, at least 90%, at least 95%, at least 98%, at least 99% or 100% identical to any one of SEQ ID NO: 22, SEQ ID NO: 25, and SEQ ID NO: 26. In some embodiments, the guide nucleic acid comprises a sequence that is at least 75%, at least 80%, at least 85%, at least 90%, at least 95%, at least 98%, at least 99% or 100% identical to any one of SEQ ID NO: 70, SEQ ID NO: 32, SEQ ID NO: 73, SEQ ID NO: 35, and SEQ ID NO: 36. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to any one of SEQ ID NO: 22, SEQ ID NO: 25, and SEQ ID NO: 26. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to any one of SEQ ID NO: 70, SEQ ID NO: 32, SEQ ID NO: 73, SEQ ID NO: 35, and SEQ ID NO: 36. In some embodiments, the guide nucleic acid comprises a sequence that is at least 75%, at least 80%, at least 85%, at least 90%, at least 95%, at least 98%, at least 99% or 100% identical to SEQ ID NO: 70. In some embodiments, the guide nucleic acid comprises at least about 40, at least about 50, at least about 60, or at least about 70 contiguous nucleotides that are at least 75%, at least 80%, at least 85%, at least 90%, at least 95%, at least 98%, at least 99% or 100% identical to SEQ ID NO: 70. In some embodiments, the effector protein is a fusion protein comprising a fusion partner. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine.

In some embodiments, provided herein is a system comprising: a) a polypeptide comprising an amino acid sequence at least 90% identical to any one of the sequences recited in TABLE 1, or a nucleic acid encoding the polypeptide; b) a first guide nucleic acid comprising a first spacer sequence complementary to a first target sequence of a target nucleic acid; c) a second guide nucleic acid comprising a second spacer sequence complementary to a second target sequence of the target nucleic acid, wherein the first target sequence and the second target sequence are different. In some embodiments, provided herein is a system comprising: a) a polypeptide comprising an amino acid sequence at least 90% identical to SEQ ID NO: 1, or a nucleic acid encoding the polypeptide; b) a first guide nucleic acid comprising a first spacer sequence complementary to a first target sequence of a target nucleic acid; c) a second guide nucleic acid comprising a second spacer sequence complementary to a second target sequence of the target nucleic acid, wherein the first target sequence and the second target sequence are different. In some embodiments, the effector protein comprises one or more mutations of K58W, I80R, T84R, K105R, N193K, G210R, C202R, S209F, A218K, A218R, D220R, E225K, E225R, C246R, N286K, M295W, M298L, A306K, Y315M, and Q360R relative to SEQ ID NO: 1. In some embodiments, provided herein is a method of excising a portion of a target nucleic acid comprising contacting the target nucleic acid with the system described herein. In some embodiments, the portion of the target nucleic acid is at least about 50 nucleotides, at least about 100 nucleotides, at least about 150 nucleotides, at least about 200 nucleotides, at least about 250 nucleotides, at least about 300 nucleotides, at least about 350 nucleotides, at least about 400 nucleotides, at least about 450 nucleotides, at least about 500 nucleotides, at least about 550 nucleotides, at least about 600 nucleotides, at least about 650 nucleotides, at least about 700 nucleotides, at least about 750 nucleotides, at least about 800 nucleotides, at least about 850 nucleotides, at least about 900 nucleotides, at least about 950 nucleotides, or at least about 1000 nucleotides. In some embodiments, the system provided herein, or the method provided herein includes wherein the portion of the target nucleic acid spans and intron-exon junction of a gene.

Some embodiments are viral vectors. In some embodiments, the viral vector comprises an effector protein. In some embodiments, the effector protein comprises an amino acid sequence that is at least 75%, at least 80%, at least 85%, at least 90%, at least 95%, at least 98%, at least 99% or 100% identical to any one of the sequences recited in TABLE 1. In some embodiments, the effector protein comprises an amino acid sequence that is at least 75%, at least 80%, at least 85%, at least 90%, at least 95%, at least 98%, at least 99% or 100% identical to any one of SEQ ID NO: 60-69, wherein each recitation of X within any one of SEQ ID NO: 60-69 is independently selected from any amino acid residue. In some embodiments, the length of the effector protein is at least 350 linked amino acid residues. In some embodiments, the length of the effector protein is about 350 to about 450 linked amino acids, about 380 to about 430 linked amino acids, or about 395 to about 410 linked amino acids. In some embodiments, the amino acid sequence of the effector protein comprises one or more amino acid alteration. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine. In some embodiments, the one or more amino acid alterations are in one or more domain comprising a REC domain, RuvC-I domain, or a RuvC-II domain. In some embodiments, wherein the effector protein comprises one or more alterations relative to SEQ ID NO: 1, wherein the one or more alterations comprises K58W, I80R, T84R, K105R, N193K, G210R, C202R, S209F, A218K, A218R, D220R, E225K, E225R, C246R, N286K, M295W, M298L, A306K, Y315M, and Q360R. In some embodiments, the effector protein is a fusion protein comprising a fusion partner. In some embodiments, the fusion partner comprises one or more amino acid sequences recited in TABLE 2 and TABLE 2.1. In some embodiments, the viral vector further comprises an engineered guide nucleic acid or a nucleic acid encoding the engineered guide nucleic acid. In some embodiments, the engineered guide nucleic acid comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the guide nucleic acid comprises a spacer sequence, wherein the first nucleotide from the 5' end of the spacer sequence is a nucleotide selected from A, T or G. In some embodiments, the spacer sequence is 20 nucleotides in length. In some embodiments, at least two nucleotides of the first three nucleotides from the 5' end of the spacer sequence are nucleotides selected from A and T. In some embodiments, a complex formed by the effector protein and the engineered guide nucleic acid recognizes any one of the PAM sequences recited in TABLE 10, TABLE 36, TABLE 37, TABLE 38, TABLE 42, and TABLE 43 within a target nucleic acid, wherein each N is selected from any nucleotide; wherein each V is selected from adenine, cytosine or guanine; and wherein each R is selected from adenine and guanine. In some embodiments, a complex formed by the effector protein and the engineered guide nucleic acid recognizes a PAM sequence of 5'-NNTN-3' (SEQ ID NO: 964) wherein each N is selected from any nucleotide. In some embodiments, the viral vector is an AAV vector. In some embodiments, the viral vector is a scAAV vector.

Some embodiments are methods of transducing a cell. In some embodiments, the method comprises contacting the cell with a virus containing any one of the viral vectors described herein. In some embodiments, the cell is a eukaryotic cell. In some embodiments, the cell is a mammalian cell. In some embodiments, the cell is a T cell. In some embodiments, the T cell is a natural killer T cell (NKT). In some embodiments, the cell is an induced pluripotent stem cell (iPSC).

Some embodiments are systems for modifying target nucleic acids. In some embodiments, the systems comprise at least two components each individually comprising one of the following: (i) an effector protein or a nucleic acid encoding the effector protein, wherein the effector protein comprises an amino acid sequence that is at least 75%, at least 80%, at least 85%, at least 90%, at least 95%, at least 98%, at least 99%, or 100% identical to any one of the sequences recited in TABLE 1; and (ii) a guide nucleic acid or a nucleic acid encoding the guide nucleic acid, wherein at least a portion of the guide nucleic acid is complementary to a target sequence of a target nucleic acid. In some embodiments, the length of the effector protein is about 350 to about 450 linked amino acids, about 380 to about 430 linked amino acids, or about 395 to about 410 linked amino acids. In some embodiments, the amino acid sequence of the effector protein comprises one or more amino acid alterations relative to a sequence selected from TABLE 1. In some embodiments, the one or more amino acid alterations comprises: a) 1 to 5, 1 to 10, or 1 to 20 non-conservative substitutions; b) 1 to 5, 1 to 10, or 1 to 20 conservative substitutions; or c) a combination thereof. In some embodiments, the effector protein comprises a substitution of at least one, at least two, at least three, at least four, at least five, at least six, at least seven, at least eight, at least nine, or at least ten amino acids with positively charged amino acid residues. In some embodiments, the positively charged amino acid residues are independently selected from arginine, lysine and histidine. In some embodiments, the positively charged amino acid residue is arginine. In some embodiments, the one or more amino acid alterations are in one or more domain comprising a REC domain, RuvC-I domain, or a RuvC-II domain. In some embodiments, the effector protein comprises one or more alterations relative to SEQ ID NO: 1, wherein the one or more alterations comprises K58W, I80R, T84R, K105R, N193K, G210R, C202R, S209F, A218K, A218R, D220R, E225K, E225R, C246R, N286K, M295W, M298L, A306K, Y315M, and Q360R. In some embodiments, the guide RNA sequence comprises a nucleotide sequence that is at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the engineered guide nucleic acid is a single guide RNA (sgRNA). In some embodiments, the sgRNA comprises a handle sequence. In some embodiments, the handle sequence comprises a repeat sequence. In some embodiments, the sgRNA comprises a handle sequence, a linker, or a repeat sequence. In some embodiments, the handle sequence comprises a nucleotide sequence that is at least 75%, at least 80%, at least 85%, at least 90%, at least 95%, or 100% identical to any one of the sequences recited in TABLE 4. In some embodiments, the effector protein is a fusion protein comprising a fusion partner. In some embodiments, the fusion partner comprises one or more amino acid sequences recited in TABLE 2 and TABLE 2.1. In some embodiments, a complex formed by the effector protein and the engineered guide nucleic acid recognizes any one of the PAM sequences recited in TABLE 10, TABLE 36, TABLE 37, TABLE 38, TABLE 42, and TABLE 43 within a target nucleic acid, wherein each N is selected from any nucleotide; wherein each V is selected from adenine, cytosine and guanine; and wherein each R is selected from adenine and guanine. In some embodiments, the complex recognizes a PAM sequence of 5'-NNTN-3' (SEQ ID NO: 946), wherein each N is selected from any nucleotide. In some embodiments, the guide nucleic acid comprises a spacer sequence, wherein the first nucleotide from the 5' end of the spacer sequence is a nucleotide selected from A, T or G. In some embodiments, the spacer sequence is 20 nucleotides in length. In some embodiments, at least two nucleotides of the first three nucleotides from the 5' end of the spacer sequence are nucleotides selected from A and T.

INCORPORATION BY REFERENCE

All publications, patents, and patent applications mentioned in this specification are herein incorporated by reference to the same extent as if each individual publication, patent, or patent application was specifically and individually indicated to be incorporated by reference.

BRIEF DESCRIPTION OF THE DRAWINGS

FIG. 7A and FIG. 7B are ssAAV constructs, whereas FIG. 7C is an scAAV construct. Included in FIGS. 7A-7C are the following abbreviations representing elements of the AAV construct: ITR=Inverted terminal repeat; gRNA=guide RNA; UTR=untranslated region; WPRE=Woodchuck Hepatitis Virus (WHV) posttranscriptional regulatory element; and hGH Poly A=human growth hormone polyadenylation signal.

FIG. 9 show FACS results of B2M editing in primary T cells at day 3 post electroporation for the percent of B2M negative cells with different amounts of Cas 265466 and different amounts of guide constructs.

FIG. 26A shows results of indel precision of wildtype CasM.265466 protein a dose ratio of 1:10 (15 ng of effector protein: 150 ng of guide RNA). FIG. 26B shows results of indel precision of sbcB-CasM.265466 fusion protein a dose ratio of 1:10 (15 ng of effector protein: 150 ng of guide RNA).

FIG. 27A shows results of indel precision of wildtype CasM.265466 protein a dose ratio of 1:1 (150 ng of effector protein: 150 ng of guide RNA). FIG. 27B shows results of indel precision of sbcB-CasM.265466 fusion protein a dose ratio of 1:1 (150 ng of effector protein: 150 ng of guide RNA).

FIG. 28A shows results of indel potency and indel precision of wildtype CasM.265466 protein a dose ratio of 1:1 (150 ng of effector protein: 150 ng of guide RNA). FIG. 28B shows results of indel potency and indel precision of sbcB-CasM.265466 fusion protein a dose ratio of 1:1 (150 ng of effector protein: 150 ng of guide RNA).

FIG. 29A shows results of indel precision of sbcB-CasM.265466-recJ fusion protein at a dose ratio of 1:1 (150 ng of effector protein: 150 ng of guide RNA). FIG. 29B shows results of indel potency and indel precision of sbcB-CasM.265466-recJ fusion protein at a dose ratio of 1:1 (150 ng of effector protein: 150 ng of guide RNA).

FIG. 30A shows % indel mutations generated in the PCSK9 gene in mice liver post AAV8 vector injection. FIG. 30B shows serum PCSK9 protein concentration in mice post AAV8 vector injection.

FIG. 33A shows performance of CasM.286672 (SEQ ID NO: 895). FIG. 33B shows performance of CasM.2391980 (SEQ ID NO: 913). FIG. 33C shows performance of CasM.275447 (SEQ ID NO: 889). FIG. 33D shows performance of CasM.2391641 (SEQ ID NO: 906). FIG. 33E shows performance of CasM.2340775 (SEQ ID NO: 892). FIG. 33F shows performance of CasM.2390160 (SEQ ID NO: 910).

FIG. 34A shows performance of CasM.2728047 (SEQ ID NO: 871). FIG. 34B shows performance of CasM.2728226 (SEQ ID NO: 884).

FIG. 35A shows performance of CasM.2391980 (SEQ ID NO: 913). FIG. 35B shows performance of CasM.286672 (SEQ ID NO: 895). FIG. 35C shows performance of CasM.2390160 (SEQ ID NO: 910).

FIGS. 38A-38H show exemplary results of cis cleavage PAM sequence enrichment assays. FIG. 38A shows the WebLogo of cis cleavage PAM sequence enrichment with 2390639 (SEQ ID NO: 921) effector protein. FIG. 38B shows the WebLogo of cis cleavage PAM sequence enrichment with 2391272 (SEQ ID NO: 918) effector protein. FIG. 38C shows the WebLogo of cis cleavage PAM sequence enrichment with 2391641 (SEQ ID NO: 906) effector protein. FIG. 38D shows the WebLogo of cis cleavage PAM sequence enrichment with 2390160 (SEQ ID NO: 910) effector protein. FIG. 38E shows the WebLogo of cis cleavage PAM sequence enrichment with 2391980 (SEQ ID NO: 913) effector protein.

FIG. 38F shows the WebLogo of cis cleavage PAM sequence enrichment with 2390405 (SEQ ID NO: 909) effector protein. FIG. 38G shows the WebLogo of cis cleavage PAM sequence enrichment with 2390685 (SEQ ID NO: 922) effector protein. FIG. 38H shows the WebLogo of cis cleavage PAM sequence enrichment with 2390217 (SEQ ID NO: 919) effector protein.

DETAILED DESCRIPTION

Figure 1:
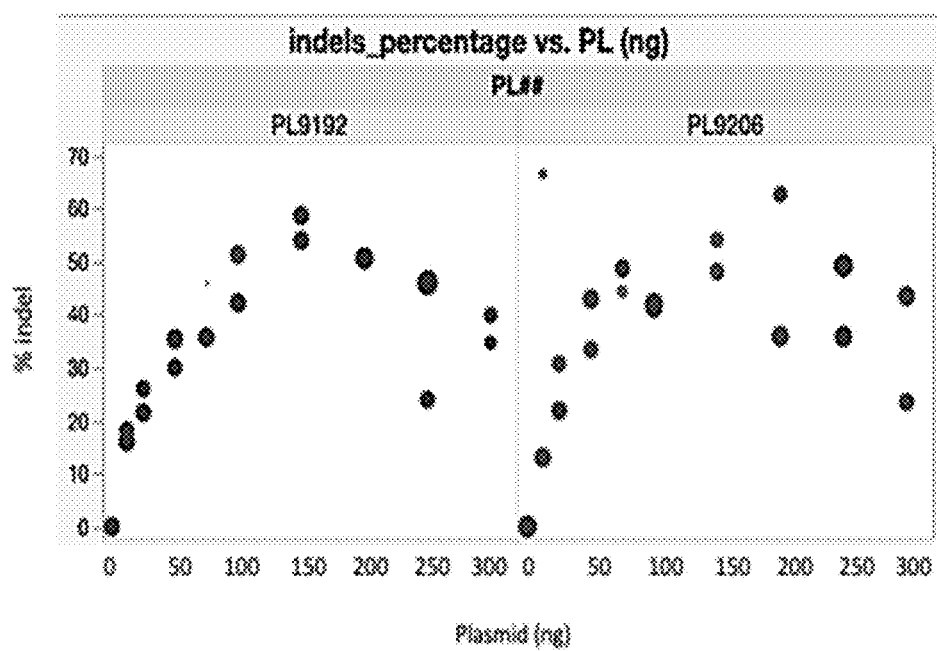
FIG. 1 is a graphical representation illustrating percentage indel occurrence generated with CasM.265466 (SEQ ID NO: 1) and two different guide RNAs, corresponding to composition 10 (PL9192) and composition 20 (PL9206) as described in Example 5.
Figure 2:
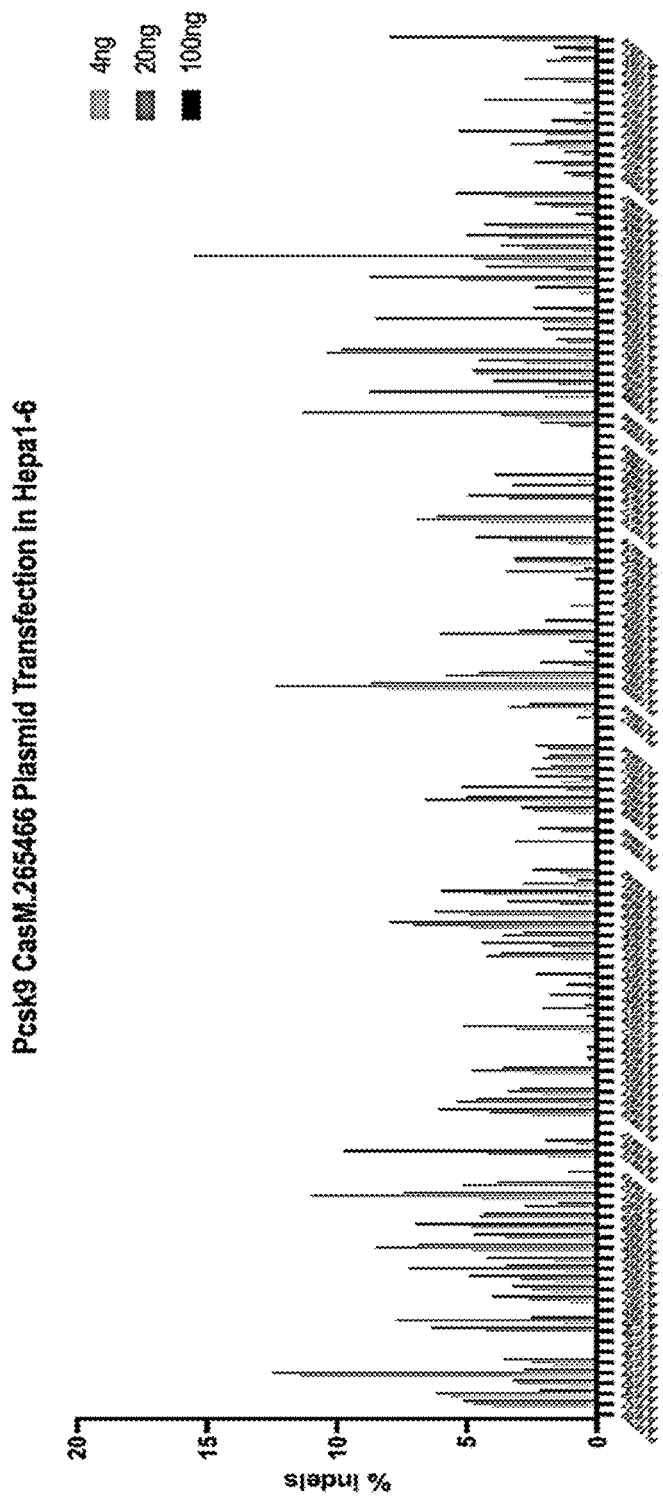
FIG. 2 is a graphical representation illustrating percentage indel occurrence in Pcsk9 generated with CasM.265466 (SEQ ID NO: 1) with various guide RNAs, corresponding to Composition Nos.: 28-160 as described in TABLE 3.3 and Example 8. For each guide RNA, three columns are plotted which shows % indel at 4 ng, 20 ng, and 100 ng (from left to right), respectively.

It is to be understood that both the foregoing general description and the following detailed description are exemplary and explanatory only and are not restrictive of the disclosure. Herein, the use of the singular includes the plural unless specifically stated otherwise.

The section headings used herein are for organizational purposes only and are not to be construed as limiting the subject matter described. All documents, or portions of documents, cited in this application, including, but not limited to, patents, patent applications, articles, books, and treatises, are hereby expressly incorporated by reference in their entirety for any purpose.

II. Definitions

Unless otherwise indicated, all technical terms used herein have the same meaning as commonly understood by one of ordinary skill in the art to which this invention belongs. Unless otherwise indicated or obvious from context, the following terms have the following meanings:

As used in the specification and claims, the singular forms "a", "an", and "the" include plural references unless the context clearly dictates otherwise. For example, the term "a sample" includes a plurality of samples, including mixtures thereof.

Unless specifically stated or obvious from context, as used herein, the term "about" in reference to a number or range of numbers is understood to mean the stated number and numbers+/−10% thereof, or 10% below the lower listed limit and 10% above the higher listed limit for the values listed for a range.

The term, "alteration" as used herein can refer to the insertion, deletion, or substitution of an amino acid in an amino acid sequence at a position identified relative to a reference or parent sequence.

As used herein, the term "comprising" and its grammatical equivalents specifies the presence of stated features, integers, steps, operations, elements, and/or components, but do not preclude the presence or addition of one or more other features, integers, steps, operations, elements, components, and/or groups thereof.

As used herein, the term "and/or" includes any and all combinations of one or more of the associated listed items.

The terms, "amplification" and "amplifying," or grammatical equivalents thereof, as used herein, refers to a process by which a nucleic acid molecule is enzymatically copied to generate a plurality of nucleic acid molecules containing the same sequence as the original nucleic acid molecule or a distinguishable portion thereof.

The term, "base editing enzyme," as used herein, refers to a protein, polypeptide or fragment thereof that is capable of catalyzing the chemical modification of a nucleobase of a deoxyribonucleotide or a ribonucleotide. Such a base editing enzyme, for example, is capable of catalyzing a reaction that modifies a nucleobase that is present in a nucleic acid molecule, such as DNA or RNA (single stranded or double stranded). Non-limiting examples of the type of modification that a base editing enzyme is capable of catalyzing includes converting an existing nucleobase to a different nucleobase, such as converting a cytosine to a guanine or thymine or converting an adenine to a guanine, hydrolytic deamination of an adenine or adenosine, or methylation of cytosine (e.g., CpG, CpA, CpT or CpC). A base editing enzyme itself may or may not bind to the nucleic acid molecule containing the nucleobase.

The term, "base editor," as used herein, refers to a fusion protein comprising abase editing enzyme fused to an effector protein. The base editor is functional when the effector protein is coupled to a guide nucleic acid. The guide nucleic acid imparts sequence specific activity to the base editor. By way of non-limiting example, the effector protein may comprise a catalytically inactive effector protein. Also, by way of non-limiting example, the base editing enzyme may comprise deaminase activity. Additional base editors are described herein.

The term, "catalytically inactive effector protein," as used herein, refers to an effector protein that is modified relative to a naturally-occurring effector protein to have a reduced or eliminated catalytic activity relative to that of the naturally-occurring effector protein, but retains its ability to interact with a guide nucleic acid. The catalytic activity that is reduced or eliminated is often a nuclease activity. The naturally-occurring effector protein may be a wildtype protein. In some instances, the catalytically inactive effector protein is referred to as a catalytically inactive variant of an effector protein, e.g., a Cas effector protein. Catalytically inactive effector proteins may also be referred to as "nuclease-dead" proteins or "dCas" proteins.

The term, "cis cleavage," as used herein, refers to cleavage (hydrolysis of a phosphodiester bond) of a target nucleic acid by an effector protein complexed with a guide nucleic acid refers to cleavage of a target nucleic acid that is hybridized to a guide nucleic acid, wherein cleavage occurs within or directly adjacent to the region of the target nucleic acid that is hybridized to the guide nucleic acid.

The terms, "complementary" and "complementarity," as used herein, with reference to a nucleic acid molecule or nucleotide sequence, refer to the characteristic of a polynucleotide having nucleotides that base pair with their Watson-Crick counterparts (C with G; or A with T) in a reference nucleic acid. For example, when every nucleotide in a polynucleotide forms a base pair with a reference nucleic acid, that polynucleotide is said to be 100% complementary to the reference nucleic acid. In a double stranded DNA or RNA sequence, the upper (sense) strand sequence is in general, understood as going in the direction from its 5'- to 3'-end, and the complementary sequence is thus understood as the sequence of the lower (antisense) strand in the same direction as the upper strand. Following the same logic, the reverse sequence is understood as the sequence of the upper strand in the direction from its 3'- to its 5'-end, while the 'reverse complement' sequence or the 'reverse complementary' sequence is understood as the sequence of the lower strand in the direction of its 5'- to its 3'-end. Each nucleotide in a double stranded DNA or RNA molecule that is paired with its Watson-Crick counterpart called its complementary nucleotide.

The term, "cleavage assay," as used herein, refers to an assay designed to visualize, quantitate or identify cleavage of a nucleic acid. In some embodiments, the cleavage activity may be cis cleavage activity. In some embodiments, the cleavage activity may be trans cleavage activity.

The terms, "cleave," "cleaving," and "cleavage," as used herein, with reference to a nucleic acid molecule or nuclease activity of an effector protein, refer to the hydrolysis of a phosphodiester bond of a nucleic acid molecule that results in breakage of that bond. The result of this breakage can be a nick (hydrolysis of a single phosphodiester bond on one side of a double-stranded molecule), single strand break (hydrolysis of a single phosphodiester bond on a single-stranded molecule) or double strand break (hydrolysis of two phosphodiester bonds on both sides of a double-stranded molecule) depending upon whether the nucleic acid molecule is single-stranded (e.g., ssDNA or ssRNA) or double-stranded (e.g., dsDNA) and the type of nuclease activity being catalyzed by the effector protein.

The term, "clustered regularly interspaced short palindromic repeats (CRISPR)," as used herein, refers to a segment of DNA found in the genomes of certain prokaryotic organisms, including some bacteria and archaea, that includes repeated short sequences of nucleotides interspersed at regular intervals between unique sequences of nucleotides derived from the DNA of a pathogen (e.g., virus) that had previously infected the organism and that functions to protect the organism against future infections by the same pathogen.

The term, "CRISPR RNA" or "crRNA," as used herein, refer to a type of guide nucleic acid, wherein the nucleic acid is RNA comprising a first sequence, often referred to herein as a spacer sequence, that hybridizes to a target sequence of a target nucleic acid, and a second sequence that is capable of connecting crRNA to an effector protein by either a) hybridizes to a portion of a tracrRNA sequence or b) is capable of being non-covalently bound by an effector protein. In some instances, the crRNA is covalently linked to an additional nucleic acid (e.g., a tracrRNA sequence) that interacts with the effector protein. In a dual nucleic acid system, where a crRNA and a tracrRNA sequence form a complex with an effector protein, crRNA includes the first sequence that hybridizes to the target sequence of the target nucleic acid and the second sequence hybridizes to a portion of the tracrRNA sequence.

The terms, "determining," "measuring," "evaluating," "assessing," "assaying," and "analyzing" are often used interchangeably herein to refer to forms of measurement. The terms include determining if an element is present or not (for example, detection). These terms can include quantitative, qualitative or quantitative and qualitative determinations. Assessing can be relative or absolute. "Detecting the presence of" can include determining the amount of something present in addition to determining whether it is present or absent depending on the context.

A "genetic disease", as used herein, refers to a disease caused by one or more mutations in the DNA of an organism. In some instances, a disease is referred to as a "disorder." Mutations may be due to several different cellular mechanisms, including, but not limited to, an error in DNA replication, recombination, or repair, or due to environmental factors. Mutations may be encoded in the sequence of a target nucleic acid from the germline of an organism. A genetic disease may comprise a single mutation, multiple mutations, or a chromosomal aberration.

The term, "detectable signal," as used herein, refers to a signal that can be detected using optical, fluorescent, chemiluminescent, electrochemical and other detection methods known in the art.

The term, "donor nucleic acid," as used herein, refers to a nucleic acid that is incorporated into a target nucleic acid or target sequence.

The term, "donor nucleotide," as used herein, refers to a single nucleotide that is incorporated into a target nucleic acid. A nucleotide is typically inserted at a site of cleavage by an effector protein.

The term, "effector protein," as used herein, refers to a protein, polypeptide, or peptide that non-covalently binds to a guide nucleic acid to form a complex that contacts a target nucleic acid, wherein at least a portion of the guide nucleic acid hybridizes to a target sequence of the target nucleic acid. A complex between an effector protein and a guide nucleic acid can include multiple effector proteins or a single effector protein. In some instances, the effector protein modifies the target nucleic acid when the complex contacts the target nucleic acid. In some instances, the effector protein does not modify the target nucleic acid, but it is fused to a fusion partner protein that modifies the target nucleic acid when the complex contacts the target nucleic acid. A non-limiting example of an effector protein modifying a target nucleic acid is cleaving of a phosphodiester bond of the target nucleic acid. Additional examples of modifications an effector protein can make to target nucleic acids are described herein and throughout.

The term, "functional fragment," as used herein, refers to a fragment of a protein that retains some function relative to the entire protein. Non-limiting examples of functions are nucleic acid binding, protein binding, nuclease activity, nickase activity, deaminase activity, demethylase activity, or acetylation activity.

The terms, "fusion effector protein," "fusion protein," and "fusion polypeptide," as used herein, refer to a protein comprising at least two heterologous polypeptides. Often a fusion effector protein comprises an effector protein and a fusion partner protein. In general, the fusion partner protein is not an effector protein. Examples of fusion partner proteins are provided herein.

The term, "fusion partner protein" or "fusion partner," as used herein, refer to a protein, polypeptide or peptide that is fused to an effector protein. The fusion partner generally imparts some function to the fusion protein that is not provided by the effector protein. The fusion partner may provide a detectable signal. The fusion partner may modify a target nucleic acid, including changing a nucleobase of the target nucleic acid and making a chemical modification to one or more nucleotides of the target nucleic acid. The fusion partner may be capable of modulating the expression of a target nucleic acid. The fusion partner may inhibit, reduce, activate or increase expression of a target nucleic acid via additional proteins or nucleic acid modifications to the target sequence.

The term, "heterologous," as used herein, means a nucleotide or polypeptide sequence that is not found in a native nucleic acid or protein, respectively. In some instances, fusion proteins comprise an effector protein and a fusion partner protein, wherein the fusion partner protein is heterologous to an effector protein. These fusion proteins may be referred to as a "heterologous protein." A protein that is heterologous to the effector protein is a protein that is not covalently linked via an amide bond to the effector protein in nature. In some instances, a heterologous protein is not encoded by a species that encodes the effector protein. In some instances, the heterologous protein exhibits an activity (e.g., enzymatic activity) when it is fused to the effector protein. In some instances, the heterologous protein exhibits increased or reduced activity (e.g., enzymatic activity) when it is fused to the effector protein, relative to when it is not fused to the effector protein. In some instances, the heterologous protein exhibits an activity (e.g., enzymatic activity) that it does not exhibit when it is fused to the effector protein. A guide nucleic acid may comprise a first sequence and a second sequence, wherein the first sequence and the second sequence are not found covalently linked via a phosphodiester bond in nature. Thus, the first sequence is considered to be heterologous with the second sequence, and the guide nucleic acid may be referred to as a heterologous guide nucleic acid.

The term, "in vitro," as used herein, is used to describe an event that takes places contained in a container for holding laboratory reagent such that it is separated from the biological source from which the material is obtained. In vitro assays can encompass cell-based assays in which living or dead cells are employed. In vitro assays can also encompass a cell-free assay in which no intact cells are employed. The term "in vivo" is used to describe an event that takes place in a subject's body. The term "ex vivo" is used to describe an event that takes place outside of a subject's body. An ex vivo assay is not performed on a subject. Rather, it is performed upon a sample separate from a subject. An example of an ex vivo assay performed on a sample is an "in vitro" assay.

The term, "functional domain," as used herein, refers to a region of one or more amino acids in a protein that is required for an activity of the protein, or the full extent of that activity, as measured in an in vitro assay. Activities include, but are not limited to nucleic acid binding, nucleic acid modification, nucleic acid cleavage, protein binding. The absence of the functional domain, including mutations of the functional domain, would abolish or reduce activity.

The term, "guide nucleic acid," as used herein, refers to a nucleic acid comprising: a first nucleotide sequence that hybridizes to a target nucleic acid; and a second nucleotide sequence that is capable of connecting an effector protein to the nucleic acid by either a) hybridizing to a portion of an additional nucleic acid that is bound by an effector protein (e.g., a tracrRNA sequence) or b) being non-covalently bound by an effector protein. The first sequence may be referred to herein as a spacer sequence. In some instances, the second sequence may be referred to herein as a repeat sequence. In some instances, the second sequence may be referred to herein as a handle sequence. In some instances, the handle sequence may comprise a portion of, or all of a repeat sequence. In some instances, the first sequence is located 5' of the second nucleotide sequence. In some instances, the first sequence is located 3' of the second nucleotide sequence. In preferred embodiments, the first sequence is located 3' of the second nucleotide sequence. In a single guide nucleic acid system, also referred to as a single guide RNA (sgRNA), the second sequence may be a handle sequence. Guide nucleic acids, when complexed with an effector protein, may bring the effector protein into proximity of a target nucleic acid. Sufficient conditions for hybridization of a guide nucleic acid to a target nucleic acid and/or for binding of a guide nucleic acid to an effector protein include in vivo physiological conditions of a desired cell type or in vitro conditions sufficient for assaying catalytic activity of a protein, polypeptide or peptide described herein, such as the nuclease activity of an effector protein. Guide nucleic acids may comprise DNA, RNA, or a combination thereof (e.g., RNA with a thymine base). Guide nucleic acids may include a chemically modified nucleobase or modified phosphate backbone. Additional chemical modifications included in the guide nucleic acids may be a phosphorothioate linkage in addition to sugar and base modifications. For example, a modified phosphate backbone may comprise a phosphorothioate linkage between two nucleotides of the guide nucleic acid. Guide nucleic acids may be referred to herein as a guide RNA (gRNA). However, a guide RNA is not limited to ribonucleotides, but may comprise deoxyribonucleotides and other chemically modified nucleotides. A guide nucleic acid may comprise a CRISPR RNA (crRNA), a short-complementarity untranslated RNA (scoutRNA), an associated trans activating RNA sequence (tracrRNA sequence) or a combination thereof. The combination of a crRNA with a tracrRNA sequence may be referred to herein as a single guide RNA (sgRNA), wherein the crRNA and the tracrRNA sequence are covalently linked. In some instances, the crRNA and tracrRNA sequence are linked by a phosphodiester bond. In some instances, the crRNA and tracrRNA sequence are linked by one or more linked nucleotides. A guide nucleic acid may comprise a naturally occurring guide nucleic acid. A guide nucleic acid may comprise a non-naturally occurring guide nucleic acid, including a guide nucleic acid that is designed to contain a chemical or biochemical modification.

The term, "handle sequence," as used herein, in the context of a sgRNA refers to a portion of the sgRNA that is capable of being non-covalently bound by an effector protein. The nucleotide sequence of a handle sequence may contain or be derived from a tracrRNA sequence. For example, in some aspects, a handle sequence can include a portion of a tracrRNA sequence that is capable of being non-covalently bound by an effector protein, but does not include all or a part of the portion of a tracrRNA sequence that hybridizes to a portion of a crRNA as found in a dual nucleic acid system. In some aspects, a handle sequence can include a portion of a tracrRNA sequence as well as a portion of a repeat sequence, which can optionally be connected by a linker. In some aspects, a handle sequence in the context of a sgRNA can also be described as the portion of the sgRNA that does not hybridize to a target sequence in a target nucleic acid (e.g., a spacer sequence).

The term, "linked amino acids" as used herein, refers to at least two amino acids linked by an amide bond. The term, "linked amino acids" includes amino acids that are linked by a peptide bond.

The term, "linker," as used herein, refers to a bond or molecule that links a first polypeptide to a second polypeptide or a first nucleic acid to a second nucleic acid. A "peptide linker" comprises at least two amino acids linked by an amide bond.

The term, "modified target nucleic acid," as used herein, refers to a target nucleic acid, wherein the target nucleic acid has undergone a modification, for example, after contact with an effector protein. In some embodiments, the modification is an alteration in the sequence of the target nucleic acid. In some embodiments, the modified target nucleic acid comprises an insertion, deletion, or replacement of one or more nucleotides compared to the unmodified target nucleic acid.

The term, "mutation associated with a disease," as used herein, refers to the co-occurrence of a mutation and the phenotype of a disease. The mutation may occur in a gene, wherein transcription or translation products from the gene occur at a significantly abnormal level or in an abnormal form in a cell or subject harboring the mutation as compared to a non-disease control subject not having the mutation.

The terms, "non-naturally occurring" and "engineered," as used herein, are used interchangeably and indicate the involvement of the hand of man. The terms, when referring to a nucleic acid, nucleotide, protein, polypeptide, peptide or amino acid, refer to a nucleic acid, nucleotide, protein, polypeptide, peptide or amino acid that is at least substantially free from at least one other feature with which it is naturally associated in nature and as found in nature, and/or contains a modification (e.g., chemical modification, nucleotide sequence, or amino acid sequence) that is not present in the naturally occurring nucleic acid, nucleotide, protein, polypeptide, peptide, or amino acid. The terms, when referring to a composition or system described herein, refer to a composition or system having at least one component that is not naturally associated with the other components of the composition or system. By way of a non-limiting example, a composition may include an effector protein and a guide nucleic acid that do not naturally occur together. Conversely, and as a non-limiting further clarifying example, an effector protein or guide nucleic acid that is "natural," "naturally-occurring," or "found in nature" includes an effector protein and a guide nucleic acid from a cell or organism that have not been genetically modified by the hand of man.

The term, "nucleic acid expression vector," as used herein, refers to a plasmid that can be used to express a nucleic acid of interest.

The term, "nuclear localization signal," as used herein, refers to an entity (e.g., peptide) that facilitates localization of a nucleic acid, protein, or small molecule to the nucleus, when present in a cell that contains a nuclear compartment.

The term, "nuclease activity," as used herein, refers to the enzymatic activity of an enzyme which allows the enzyme to cleave the phosphodiester bonds between the nucleotide subunits of nucleic acids; the term "endonuclease activity" refers to the enzymatic activity of an enzyme which allows the enzyme to cleave the phosphodiester bond within a polynucleotide chain. An enzyme with nuclease activity may be referred to as a "nuclease."

"Percent identity," "% identity," and "% identical" refers to the extent to which two sequences (nucleotide or amino acid) have the same residue at the same positions in an alignment. For example, "an amino acid sequence is X % identical to SEQ ID NO: Y" can refer to % identity of the amino acid sequence to SEQ ID NO: Y and is elaborated as X % of residues in the amino acid sequence are identical to the residues of sequence disclosed in SEQ ID NO: Y. Generally, computer programs can be employed for such calculations. Illustrative programs that compare and align pairs of sequences, include ALIGN (Myers and Miller, Comput Appl Biosci. 1988 March; 4(1):11-7), FASTA (Pearson and Lipman, Proc Natl Acad Sci USA. 1988 April; 85(8):2444-8; Pearson, Methods Enzymol. 1990; 183:63-98) and gapped BLAST (Altschul et al., Nucleic Acids Res. 1997 Sep. 1; 25(17):3389-40), BLASTP, BLASTN, or GCG (Devereux et al., Nucleic Acids Res. 1984 Jan. 11; 12(1 Pt 1):387-95).

The term, "% similarity," as used herein, in the context of an amino acid sequence, refers to a value that is calculated by dividing a similarity score by the length of the alignment. The similarity of two amino acid sequences can be calculated by using a BLOSUM62 similarity matrix (Henikoff and Henikoff, *Proc. Natl. Acad. Sci. USA.*, 89:10915-10919 (1992)) that is transformed so that any value ≥1 is replaced with +1 and any value ≤0 is replaced with 0. For example, an Ile (I) to Leu (L) substitution is scored at +2.0 by the BLOSUM62 similarity matrix, which in the transformed matrix is scored at +1. This transformation allows the calculation of percent similarity, rather than a similarity score. Alternately, when comparing two full protein sequences, the proteins can be aligned using pairwise MUSCLE alignment. Then, the % similarity can be scored at each residue and divided by the length of the alignment. For determining % similarity over a protein domain or motif, a multilevel consensus sequence (or PROSITE motif sequence) can be used to identify how strongly each domain or motif is conserved. In calculating the similarity of a domain or motif, the second and third levels of the multi-level sequence are treated as equivalent to the top level. Additionally, if a substitution could be treated as conservative with any of the amino acids in that position of the multilevel consensus sequence, +1 point is assigned. For example, given the multilevel consensus sequence: RLG and YCK, the test sequence QIQ would receive three points. This is because in the transformed BLOSUM62 matrix, each combination is scored as: Q-R: +1; Q-Y: +0; I-L: +1; I-C: +0; Q-G: +0; Q-K: +1 For each position, the highest score is used when calculating similarity. The % similarity can also be calculated using commercially available programs, such as the Geneious Prime software given the parameters matrix=BLOSUM62 and threshold ≥1.

The term, "pharmaceutically acceptable excipient, carrier or diluent," as used herein, refers to any substance formulated alongside the active ingredient of a pharmaceutical composition that allows the active ingredient to retain biological activity and is non-reactive with the subject's immune system. Such a substance can be included for the purpose of long-term stabilization, bulking up solid formulations that contain potent active ingredients in small amounts, or to confer a therapeutic enhancement on the active ingredient in the final dosage form, such as facilitating absorption, reducing viscosity, or enhancing solubility. The selection of appropriate substance can depend upon the route of administration and the dosage form, as well as the active ingredient and other factors. Compositions having such substances can be formulated by well-known conventional methods (see, e.g., Remington's Pharmaceutical Sciences, 18th edition, A. Gennaro, ed., Mack Publishing Co., Easton, Pa., 1990; and Remington, The Science and Practice of Pharmacy 23rd Ed. Mack Publishing, 2020).

The term, "protospacer adjacent motif (PAM)," as used herein, refers to a nucleotide sequence found in a target nucleic acid that directs an effector protein to modify the target nucleic acid at a specific location. A PAM sequence may be required for a complex having an effector protein and a guide nucleic acid to hybridize to and modify the target nucleic acid. However, a given effector protein may not require a PAM sequence being present in a target nucleic acid for the effector protein to modify the target nucleic acid.

The term, "recombinant," as used herein, as applied to proteins, polypeptides, peptides and nucleic acids, refers to proteins, polypeptides, peptides and nucleic acids that are products of various combinations of cloning, restriction, and/or ligation steps resulting in a construct having a structural coding or non-coding sequence distinguishable from endogenous nucleic acids found in natural systems. Generally, DNA sequences encoding the structural coding sequence can be assembled from cDNA fragments and short oligonucleotide linkers, or from a series of synthetic oligonucleotides, to provide a synthetic nucleic acid which is capable of being expressed from a recombinant transcriptional unit contained in a cell or in a cell-free transcription and translation system. Such sequences can be provided in the form of an open reading frame uninterrupted by internal non translated sequences, or introns, which are typically present in eukaryotic genes. Genomic DNA comprising the relevant sequences can also be used in the formation of a recombinant gene or transcriptional unit. Sequences of non-translated DNA may be present 5' or 3' from the open reading frame, where such sequences do not interfere with manipulation or expression of the coding regions and may act to modulate production of a desired product by various mechanisms. Thus, for example, the term "recombinant polynucleotide" or "recombinant nucleic acid" refers to one which is not naturally occurring, e.g., is made by the artificial combination of two otherwise separated segments of sequence through human intervention. This artificial combination is often accomplished by either chemical synthesis means, or by the artificial manipulation of isolated segments of nucleic acids, e.g., by genetic engineering techniques. Such is usually done to replace a codon with a redundant codon encoding the same or a conservative amino acid, while typically introducing or removing a sequence recognition site. Alternatively, it is performed to join together nucleic acid segments of desired functions to generate a desired combination of functions. Similarly, the term "recombinant polypeptide" or "recombinant protein" refers to one which is not naturally occurring, e.g., is made by the artificial combination of two otherwise separated segments of amino sequences through human intervention. Thus, for example, a polypeptide that includes a heterologous amino acid sequence is a recombinant polypeptide.

In some embodiments, the term "region" as used herein may be used to describe a portion of or all of a corresponding sequence, for example, a spacer region is understood to comprise a portion of or all of a spacer sequence.

The terms, "reporter" and reporter nucleic acid" are used interchangeably herein to refer to a non-target nucleic acid molecule that can provide a detectable signal upon cleavage by an effector protein. Examples of detectable signals and detectable moieties that generate detectable signals are provided herein.

The term, "sample," as used herein, generally refers to something comprising a target nucleic acid. In some instances, the sample is a biological sample, such as a biological fluid or tissue sample. In some instances, the sample is an environmental sample. The sample may be a biological sample or environmental sample that is modified or manipulated. By way of non-limiting example, samples may be modified or manipulated with purification techniques, heat, nucleic acid amplification, salts and buffers.

The term, "subject," as used herein, refers to a biological entity containing expressed genetic materials. The biological entity can be a plant, animal, or microorganism, including, for example, bacteria, viruses, fungi, and protozoa. The subject can be tissues, cells and their progeny of a biological entity obtained in vivo or cultured in vitro. The subject can be a mammal. The mammal can be a human. The subject may be diagnosed or suspected of being at high risk for a disease. In some instances, the subject is not necessarily diagnosed or suspected of being at high risk for the disease.

A "syndrome", as used herein, refers to a group of symptoms which, taken together, characterize a condition.

The term, "target nucleic acid," as used herein, refers to a nucleic acid that is selected as the nucleic acid for modification, binding, hybridization or any other activity of or interaction with a nucleic acid, protein, polypeptide, or peptide described herein. A target nucleic acid may comprise RNA, DNA, or a combination thereof. A target nucleic acid may be single-stranded (e.g., single-stranded RNA or single-stranded DNA) or double-stranded (e.g., double-stranded DNA). The target nucleic acid may be from any organism, including, but not limited to, a bacterium, a virus, a parasite, a protozoon, a fungus, a mammal, a plant, and an insect. As another non-limiting example, the target nucleic acid may be responsible for a disease, contain a mutation (e.g., single strand polymorphism, point mutation, insertion, or deletion), be contained in an amplicon, or be uniquely identifiable from the surrounding nucleic acids (e.g., contain a unique sequence of nucleotides).

The term, "target sequence," as used herein, when used in reference to a target nucleic acid, refers to a sequence of nucleotides found within a target nucleic acid. Such a sequence of nucleotides can, for example, hybridize to an equal length portion of a guide nucleic acid. Hybridization of the guide nucleic acid to the target sequence may bring an effector protein into contact with the target nucleic acid.

The term, "trans cleavage," is used herein, in reference to cleavage (hydrolysis of a phosphodiester bond) of one or more nucleic acids by an effector protein that is complexed with a guide nucleic acid and a target nucleic acid. The one or more nucleic acids may include the target nucleic acid as well as non-target nucleic acids. Trans cleavage may occur near, but not within or directly adjacent to, the region of the target nucleic acid that is hybridized to the guide nucleic acid. Trans cleavage activity may be triggered by the hybridization of the guide nucleic acid to the target nucleic acid.

The term, "trans activating RNA (tracrRNA)," as used herein, refers to a nucleic acid that comprises a first sequence that is capable of being non-covalently bound by an effector protein. TracrRNAs may comprise a second sequence that hybridizes to a portion of a crRNA, which may be referred to as a repeat hybridization sequence. A tracrRNA may include deoxyribonucleosides, ribonucleosides, chemically modified nucleosides, or any combination thereof. A tracrRNA may be separate from, but form a complex with, a guide nucleic acid and an effector protein. The tracrRNA may be attached (e.g., covalently) by an artificial linker to a guide nucleic acid. A tracrRNA may include a nucleotide sequence that hybridizes with a portion of a guide nucleic acid. A tracrRNA may also form a secondary structure (e.g., one or more hairpin loops) that facilitates the binding of an effector protein to a guide nucleic acid and/or modification activity of an effector protein on a target nucleic acid. A tracrRNA may include a repeat hybridization region and a hairpin region. The repeat hybridization region may hybridize to all or part of the repeat sequence of a guide nucleic acid. The repeat hybridization region may be positioned 3' of the hairpin region. The hairpin region may include a first sequence, a second sequence that is reverse complementary to the first sequence, and a stem-loop linking the first sequence and the second sequence.

The term, "transcriptional activator," as used herein, refers to a polypeptide or a fragment thereof that can activate or increase transcription of a target nucleic acid molecule.

The term, "transcriptional repressor," as used herein, refers to a polypeptide or a fragment thereof that is capable of arresting, preventing, or reducing transcription of a target nucleic acid.

The terms, "treatment" or "treating," as used herein, are used in reference to a pharmaceutical or other intervention regimen for obtaining beneficial or desired results in the recipient. Beneficial or desired results include but are not limited to a therapeutic benefit and/or a prophylactic benefit. A therapeutic benefit may refer to eradication or amelioration of symptoms or of an underlying disorder being treated. Also, a therapeutic benefit can be achieved with the eradication or amelioration of one or more of the physiological symptoms associated with the underlying disorder such that an improvement is observed in the subject, notwithstanding that the subject may still be afflicted with the underlying disorder. A prophylactic effect includes delaying, preventing, or eliminating the appearance of a disease or condition, delaying, or eliminating the onset of symptoms of a disease or condition, slowing, halting, or reversing the progression of a disease or condition, or any combination thereof. For prophylactic benefit, a subject at risk of developing a particular disease, or to a subject reporting one or more of the physiological symptoms of a disease may undergo treatment, even though a diagnosis of this disease may not have been made.

The term, "variant," when used in reference to any amino acid or nucleic acid described herein refers to a sequence having a variation or alteration at an amino acid position or nucleic acid position as compared to a parent sequence. The parent sequence can be, for example, an unmodified, wild-type sequence, a homolog thereof or a modified variant of, for example, a wild-type sequence or homolog thereof.

The term, "viral vector," as used herein, refers to a nucleic acid to be delivered into a host cell via a recombinantly produced virus or viral particle. The nucleic acid may be single-stranded or double stranded, linear or circular, segmented or non-segmented. The nucleic acid may comprise DNA, RNA, or a combination thereof. Non-limiting examples of viruses or viral particles that can deliver a viral vector include retroviruses (e.g., lentiviruses and γ-retroviruses), adenoviruses, arenaviruses, alphaviruses, adeno-associated viruses (AAVs), baculoviruses, vaccinia viruses, herpes simplex viruses and poxviruses. A viral vector delivered by such viruses or viral particles may be referred to by the type of virus to deliver the viral vector (e.g., an AAV viral vector is a viral vector that is to be delivered by an adeno-associated virus). A viral vector referred to by the type of virus to be delivered by the viral vector can contain viral elements (e.g., nucleotide sequences) necessary for packaging of the viral vector into the virus or viral particle, replicating the virus, or other desired viral activities. A virus containing a viral vector may be replication competent, replication deficient or replication defective.

The term, "T cell," as used herein, refers to a type of lymphocyte that matures in the thymus. T cells play an important role in cell-mediated immunity and are distinguished from other lymphocytes, such as B cells, by the presence of a T-cell receptor on the cell surface. A T cell includes all types of immune cells expressing CD3, including: naïve T cells (cells that have not encountered their cognate antigens), T-helper cells ($CD4^+$ cells), cytotoxic T-cells ($CD8^+$ cells), natural killer T-cells, primary T-cells, T-regulatory cells (T-reg), and gamma-delta T cells. Non-limiting exemplary sources for commercially available T cell lines include the American Type Culture Collection (ATCC), and the German Collection of Microorganisms and Cell Cultures.

The term, "cancer," as used herein, refers to a disease state characterized by the presence in a subject of cells demonstrating abnormal uncontrolled replication. The term cancer may be used interchangeably with the terms "carcino-," "onco-," and "tumor." Non-limiting examples of cancers include: acute lymphoblastic leukemia; acute lymphoblastic lymphoma; acute lymphocytic leukemia; acute myelogenous leukemia; acute myeloid leukemia (adult/childhood); adrenocortical carcinoma; AIDS-related cancers; AIDS-related lymphoma; anal cancer; appendix cancer; astrocytoma; atypical teratoid/rhabdoid tumor; basal-cell carcinoma; bile duct cancer, extrahepatic (cholangiocarcinoma); bladder cancer; bone osteosarcoma/malignant fibrous histiocytoma; brain cancer (adult/childhood); brain tumor, cerebellar astrocytoma (adult/childhood); brain tumor, cerebral astrocytoma/malignant glioma brain tumor; brain tumor, ependymoma; brain tumor, medulloblastoma; brain tumor, supratentorial primitive neuroectodermal tumors; brain tumor, visual pathway and hypothalamic glioma; brainstem glioma; breast cancer; bronchial adenomas/carcinoids; bronchial tumor; Burkitt lymphoma; cancer of childhood; carcinoid gastrointestinal tumor; carcinoid tumor; carcinoma of adult, unknown primary site; carcinoma of unknown primary; central nervous system embryonal tumor; central nervous system lymphoma, primary; cervical cancer; childhood adrenocortical carcinoma; childhood cancers; childhood cerebral astrocytoma; chordoma, childhood; chronic lymphocytic leukemia; chronic myelogenous leukemia; chronic myeloid leukemia; chronic myeloproliferative disorders; colon cancer; colorectal cancer; craniopharyngioma; cutaneous T-cell lymphoma; desmoplastic small round cell tumor; emphysema; endometrial cancer; ependymoblastoma; ependymoma; esophageal cancer; Ewing sarcoma in the Ewing family of tumors; extracranial germ cell tumor; extragonadal germ cell tumor; extrahepatic bile duct cancer; gallbladder cancer; gastric (stomach) cancer; gastric carcinoid; gastrointestinal carcinoid tumor; gastrointestinal stromal tumor; germ cell tumor: extracranial, extragonadal, or ovarian gestational trophoblastic tumor; gestational trophoblastic tumor, unknown primary site; glioma; glioma of the brain stem; glioma, childhood visual pathway and hypothalamic; hairy cell leukemia; head and neck cancer; heart cancer; hepatocellular (liver) cancer; Hodgkin's lymphoma; hypopharyngeal cancer; hypothalamic and visual pathway glioma; intraocular melanoma; islet cell carcinoma (endocrine pancreas); Kaposi Sarcoma; kidney cancer (renal cell cancer); Langerhans cell histiocytosis; laryngeal cancer; lip and oral cavity cancer; liposarcoma; liver cancer (primary); lung cancer, non-small cell; lung cancer, small cell; lymphoma, primary central nervous system; macroglobulinemia, Waldenström; male breast cancer; malignant fibrous histiocytoma of bone/osteosarcoma; medulloblastoma; medulloepithelioma; melanoma; melanoma, intraocular (eye); Merkel cell cancer; Merkel cell skin carcinoma; mesothelioma; mesothelioma, adult malignant; metastatic squamous neck cancer with occult primary; mouth cancer; multiple endocrine neoplasia syndrome; multiple myeloma/plasma cell neoplasm; mycosis fungoides, myelodysplastic syndromes; myelodysplastic/myeloproliferative diseases; myelogenous leukemia, chronic; myeloid leukemia, adult acute; myeloid leukemia, childhood acute; myeloma, multiple (cancer of the bone-marrow); myeloproliferative disorders, chronic; nasal cavity and paranasal sinus cancer; nasopharyngeal carcinoma; neuroblastoma, non-small cell lung cancer; non-Hodgkin's lymphoma; oligodendroglioma; oral cancer; oral cavity cancer; oropharyngeal cancer; osteosarcoma/malignant fibrous histiocytoma of bone; ovarian cancer; ovarian epithelial cancer (surface epithelial-stromal tumor); ovarian germ cell tumor; ovarian low malignant potential tumor; pancreatic cancer; pancreatic cancer, islet cell; papillomatosis; paranasal sinus and nasal cavity cancer; parathyroid cancer; penile cancer; pharyngeal cancer; pheochromocytoma; pineal astrocytoma; pineal germinoma; pineal parenchymal tumors of intermediate differentiation; pineoblastoma and supratentorial primitive neuroectodermal tumors; pituitary tumor; pituitary adenoma; plasma cell neoplasia/multiple myeloma; pleuropulmonary blastoma; primary central nervous system lymphoma; prostate cancer; rectal cancer; renal cell carcinoma (kidney cancer); renal pelvis and ureter, transitional cell cancer; NUT midline carcinoma; retinoblastoma; rhabdomyosarcoma, childhood; salivary gland cancer; sarcoma, Ewing family of tumors; Sézary syndrome; skin cancer (melanoma); skin cancer (non-melanoma); small cell lung cancer; small intestine cancer soft tissue sarcoma; soft tissue sarcoma; spinal cord tumor; squamous cell carcinoma; squamous neck cancer with occult primary, metastatic; stomach (gastric) cancer; supratentorial primitive neuroectodermal tumor; T-cell lymphoma, cutaneous (Mycosis Fungoides and Sézary syndrome); testicular cancer; throat cancer; thymoma; thymoma and thymic carcinoma; thyroid cancer; thyroid cancer, childhood; transitional cell cancer of the renal pelvis and ureter; urethral cancer; uterine cancer, endometrial; uterine sarcoma; vaginal cancer; vulvar cancer; and Wilms Tumor.

A person of ordinary skill in the art would appreciate that referring to a nucleotide(s), and/or nucleoside(s), in the context of a nucleic acid molecule having multiple residues, is interchangeable and describe the sugar and base of the residue contained in the nucleic acid molecule. Similarly, a skilled artisan would understand that linked nucleotides and/or linked nucleosides, as used in the context of a nucleic acid having multiple linked residues, are interchangeable and describe linked sugars and bases of residues contained in a nucleic acid molecule. When referring to a nucleobase, or linked nucleobase, as used in the context of a nucleic acid molecule, it is understood as describing the base of the residue contained in the nucleic acid molecule, for example, the base of a nucleotide, nucleosides, or linked nucleotides or linked nucleosides.

III. Introduction

Disclosed herein are non-naturally occurring compositions and systems comprising an effector protein (e.g., a D2S effector protein) and an engineered guide nucleic acid, which may simply be referred to herein as a guide nucleic acid. In general, an engineered effector protein and an engineered guide nucleic acid refer to an effector protein and a guide nucleic acid, respectively, that are not found in nature. In some embodiments, systems and compositions comprise at least one non-naturally occurring component. For example, compositions and systems may comprise a guide nucleic acid, wherein the sequence of the guide nucleic acid is different or modified from that of a naturally-occurring guide nucleic acid. In some embodiments, compositions and systems comprise at least two components that do not naturally occur together. For example, compositions and systems may comprise a guide nucleic acid comprising a repeat region and a spacer region which do not naturally occur together. Also, by way of example, composition and systems may comprise a guide nucleic acid and an effector protein that do not naturally occur together. Conversely, and for clarity, a D2S effector protein or guide nucleic acid that is "natural," "naturally-occurring," or "found in nature" includes D2S effector proteins and guide nucleic acids from cells or organisms that have not been genetically modified by a human or machine.

In general, guide nucleic acids in nature comprise a CRISPR RNA (crRNA) that is at least partially complementary to a target nucleic acid. In some embodiments, guide nucleic acids disclosed herein comprise a non-natural nucleotide sequence. In some embodiments, the non-natural sequence is a nucleotide sequence that is not found in nature. The non-natural sequence may comprise a portion of a naturally-occurring sequence, wherein the portion of the naturally-occurring sequence is not present in nature, absent the remainder of the naturally-occurring sequence. In some embodiments, the guide nucleic acid comprises two naturally-occurring sequences arranged in an order or proximity that is not observed in nature. In some embodiments, compositions and systems comprise a ribonucleotide complex comprising an effector protein (e.g., a D2S effector protein) and a guide nucleic acid that do not occur together in nature. Engineered guide nucleic acids may comprise a first sequence and a second sequence that do not occur naturally together. For example, an engineered guide nucleic acid may comprise a sequence of a naturally-occurring repeat region and a spacer region that is complementary to a naturally-occurring eukaryotic sequence. The engineered guide nucleic acid may comprise a sequence of a repeat region that occurs naturally in an organism and a spacer region that does not occur naturally in that organism. An engineered guide nucleic acid may comprise a first sequence that occurs in a first organism and a second sequence that occurs in a second organism, wherein the first organism and the second organism are different. The guide nucleic acid may comprise a third sequence located at a 3' or 5' end of the guide nucleic acid, or between the first and second sequences of the guide nucleic acid. For example, a guide nucleic acid may comprise a spacer sequence and an engineered handle sequence coupled by a linker sequence, wherein the engineered handle sequence comprises only a portion of a native repeat sequence and/or only a portion of a native trans activating crRNA (tracrRNA) sequence. In some embodiments, the portion of tracrRNA sequence interacts with the effector protein. In some instances, the portion of the repeat sequence is less than about 30, less than about 25, less than about 20, less than about 15 or less than about 10 nucleotides. In some instances, the portion of the tracrRNA sequence is less than about 100, less than about 95, less than about 90, less than about 85, less than about 80, less than about 75, less than about 70, less than about 65, less than about 60, less than about 55, less than about 50, less than about 45, less than about 40, less than about 35, less than about 30, less than about 25, less than about 20, less than about 15 or less than about 10 nucleotides. In some embodiments, the guide nucleic acid comprises two heterologous sequences arranged in an order or proximity that is not observed in nature. Therefore, compositions described herein are not naturally occurring. As another example, an engineered guide nucleic acid may comprise a naturally occurring CRISPR RNA (crRNA) and at least a portion of trans activating crRNA (tracrRNA) sequence coupled by a linker sequence.

In some embodiments, compositions and systems described herein comprise an engineered effector protein that is similar to a naturally occurring D2S effector protein. The engineered effector protein may lack a portion of the naturally occurring D2S effector protein. The D2S effector protein may comprise a mutation relative to the naturally-occurring D2S effector protein, wherein the mutation is not found in nature. The D2S effector protein may also comprise at least one additional amino acid relative to the naturally-occurring D2S effector protein. For example, the D2S effector protein may comprise an addition of a nuclear localization signal relative to the natural occurring D2S effector protein. In some embodiments, the nucleotide sequence encoding the effector protein is codon optimized (e.g., for expression in a eukaryotic cell) relative to the naturally occurring sequence. In some embodiments, the nucleotide sequence encoding the effector protein is codon optimized, preferably for expression in a eukaryotic cell.

IV. Effector Proteins

An effector protein (e.g., a D2S effector protein) may be brought into proximity of a target nucleic acid in the presence of a guide nucleic acid when the guide nucleic acid includes a nucleotide sequence that is complementary with a target sequence in the target nucleic acid and/or hybridizes to the target sequence in the target nucleic acid. The ability of an effector protein to modify a target nucleic acid may be dependent upon the effector protein being bound to a guide nucleic acid and the guide nucleic acid being hybridized to a target nucleic acid. An effector protein (e.g., a D2S effector protein) may also recognize a protospacer adjacent motif (PAM) sequence present in the target nucleic acid, which may direct the modification activity of the effector protein. An effector protein (e.g., a D2S effector protein) may modify a nucleic acid by cis cleavage or trans cleavage. The modification of the target nucleic acid generated by an effector protein may, as a non-limiting example, result in modulation of the expression of the nucleic acid (e.g., increasing or decreasing expression of the nucleic acid) or modulation of the activity of a translation product of the target nucleic acid (e.g., inactivation of a protein binding to an RNA molecule or hybridization).

An effector protein (e.g., a D2S effector protein) may be a CRISPR-associated ("Cas") protein. An effector protein (e.g., a D2S effector protein) may function as a single protein, including a single protein that is capable of binding to a guide nucleic acid and modifying a target nucleic acid. Alternatively, an effector protein (e.g., a D2S effector protein) may function as part of a multiprotein complex, including, for example, a complex having two or more effector proteins, including two or more of the same effector proteins (e.g., dimer or multimer). An effector protein (e.g., a D2S effector protein), when functioning in a multiprotein complex, may have only one functional activity (e.g., binding to a guide nucleic acid), while other effector proteins present in the multiprotein complex are capable of the other functional activity (e.g., modifying a target nucleic acid). An effector protein (e.g., a D2S effector protein) may be a modified effector protein having reduced modification activity (e.g., a catalytically defective effector protein) or no modification activity (e.g., a catalytically inactive effector protein). Accordingly, an effector protein (e.g., a D2S effector protein) as used herein encompasses a modified or programmable nuclease that does not have nuclease activity.

In some embodiments, effector proteins disclosed herein (e.g., D2S effector proteins) may function as an endonuclease that catalyzes cleavage at a specific position (e.g., at a specific nucleotide within a nucleic acid sequence) in a target nucleic acid. The target nucleic acid may be single stranded RNA (ssRNA), double stranded DNA (dsDNA) or single-stranded DNA (ssDNA). In some embodiments, the target nucleic acid is single-stranded DNA. In some embodiments, the target nucleic acid is single-stranded RNA. The effector proteins may provide cis cleavage activity, trans cleavage activity, nickase activity, or a combination thereof. Cis cleavage activity may comprise cleavage of a target nucleic acid that is hybridized to a guide RNA (e.g., a dual nucleic acid system or a sgRNA), wherein cleavage occurs within or directly adjacent to the region of the target nucleic acid that is hybridized to guide RNA. Trans cleavage activity (also referred to as transcollateral cleavage) may comprise cleavage of ssDNA or ssRNA that is near, but not hybridized to the guide RNA. Trans cleavage activity may be triggered by the hybridization of guide RNA to the target nucleic acid. Nickase activity may comprise a selective cleavage of one strand of a dsDNA. While certain effector proteins may be used to edit and detect nucleic acids in a sequence specific manner, challenging biological sample conditions (e.g., high viscosity, metal chelating) may limit their accuracy and effectiveness. There is thus a need for systems and methods that employ effector proteins having specificity and efficiency across a wide range of sample conditions.

An effector protein (e.g., a D2S effector protein) may be small, which may be beneficial for nucleic acid detection or editing (for example, the effector protein may be less likely to adsorb to a surface or another biological species due to its small size). The smaller nature of these effector proteins may allow for them to be more easily packaged and delivered with higher efficiency in the context of genome editing and more readily incorporated as a reagent in an assay. In some embodiments, the length of the effector protein is at least 400 linked amino acid residues. In some embodiments, the length of the effector protein is less than 500 linked amino acid residues. In some embodiments, the length of the effector protein is about 350 to about 500 linked amino acid residues. In some embodiments, the length of the effector protein is about 350 to about 500, about 350 to about 450, about 360 to about 440, about 380 to about 430, about 390 to about 420, about 400 to about 410, about 420 to about 450, about 430 to about 450 or about 440 to 455 linked amino acids.

Provided herein, in some embodiments, are compositions that comprise one or more D2S effector proteins. TABLE 1 provides illustrative amino acid sequences of D2S effector proteins. In some embodiments, the amino acid sequence of the D2S effector protein is at least 65%, at least 70%, at least 75%, at least 80%, at least 85%, at least 90%, at least 95%, at least 97%, or at least 98%, at least 99%, or 100% identical to any one of the sequences recited in TABLE 1. In some embodiments, the amino acid sequence of the D2S effector protein is at least 80%, at least 85%, at least 90%, at least 95%, at least 97%, or at least 98%, or at least 99% similar to any one of the sequences recited in TABLE 1.

In some embodiments, compositions comprise an effector protein (e.g., a D2S effector protein) and an engineered guide nucleic acid, wherein the effector protein comprises an amino acid sequence that is at least 65%, at least 70%, at least 75%, at least 80%, at least 85%, at least 90%, at least 95%, at least 98%, at least 99%, or 100% identical to any one of the sequences recited in TABLE 1. In some embodiments, the effector protein comprises an amino acid sequence that is at least 65%, at least 70%, at least 75%, at least 80%, at least 85%, at least 90%, at least 95%, at least 97%, or at least 98%, at least 99%, or 100% identical to any one of the sequences recited in TABLE 1. In some embodiments, the effector protein comprises an amino acid sequence that is at least 80%, at least 85%, at least 90%, at least 95%, at least 97%, or at least 98%, or at least 99% similar to any one of the sequences recited in TABLE 1. In some embodiments, compositions comprise an effector protein (e.g., a D2S effector protein) and an engineered guide nucleic acid, wherein the amino acid sequence of the effector protein comprises at least about 200, at least about 220, at least about 240, at least about 260, at least about 280, at least about 300, at least about 320, at least about 340, at least about 360, at least about 380, or at least about 400 contiguous amino acids of any one of the sequences recited in TABLE 1.

In some embodiments, the compositions comprise an effector protein (e.g., a D2S effector protein) having a portion of an effector protein described herein (e.g., SEQ ID NOs: 1-2, or 37). In some embodiments, the portion of the effector protein comprises about 30 continuous amino acids, about 40 continuous amino acids, about 50 continuous amino acids, about 60 continuous amino acids, about 70 continuous amino acids, about 80 continuous amino acids, about 90 continuous amino acids, or about 100 continuous amino acids.

In some embodiments, the compositions comprise an effector protein (e.g., a D2S effector protein) having a portion of an effector protein of SEQ ID NO: 37, wherein the amino acid sequence of the effector protein comprises:

VGBKEEXDRVYXYJRDGIXXQNXAMNXYMSXLYX-A (SEQ ID NO: 60), SKXDRKELNXLYXRIXTSXKGS-AYXTDIZFPXGLXXTSXL (SEQ ID NO: 61), KDGLMY-GRVSLPTYRXBNPL (SEQ ID NO: 62), GLYHXYXSHT-EFLXXLYXXD (SEQ ID NO: 63), IKFANBITFQXXFG (SEQ ID NO: 64), FEEYYXVCXSSIZXS (SEQ ID NO: 65), ELDEBXXVGVDLGI (SEQ ID NO: 66), VDFAX-KXKAKYINXEBLXG (SEQ ID NO: 67), NWSYYZL-QQYITYKAXXYGIEVRK (SEQ ID NO: 68), or NADFN-AXRNIAMSTEFXSGKKTKKQKKEQHE (SEQ ID NO: 69), wherein each recitation of X within SEQ ID NO: 60-69 can be independently any amino acid. In some embodiments B is Asp. In some embodiments, B is Asn. In some embodiments, J is Ile. In some embodiments, J is Leu.

In some embodiments, the compositions comprise an effector protein (e.g., a D2S effector protein), wherein the amino acid sequence of the effector protein comprises about 110 amino acids, about 120 amino acids, about 140 amino acids, about 160 amino acids, about 180 amino acids, about 200 amino acids, about 220 amino acids, about 240 amino acids, about 260 amino acids, about 280 amino acids, about 300 amino acids, about 320 amino acids, about 340 amino acids, about 360 amino acids, about 380 amino acids, about 400 amino acids, about 420 amino acids, about 440 amino acids, or about 460 amino acids of any one of sequences recited in TABLE 1 in continuous amino acid residues.

In some embodiments, other than a truncation of the first 10 amino acids, 20 amino acids, 30 amino acids, 40 amino acids, 50 amino acids, 60 amino acids, 70 amino acids, 80 amino acids, 90 amino acids, or 100 amino acids, and/or a truncation of the last 10 amino acids, 20 amino acids, 30 amino acids, 40 amino acids, 50 amino acids, 60 amino acids, 70 amino acids, 80 amino acids, 90 amino acids, or 100 amino acids, the amino acid sequence of an effector protein provided herein (e.g., a D2S effector protein) comprises any one of the sequences of TABLE 1.

In some embodiments, effector proteins described herein (e.g., a D2S effector protein) comprise one or more functional domains. Effector protein functional domains can include a protospacer adjacent motif (PAM)-interacting domain, an oligonucleotide-interacting domain, one or more recognition domains, a non-target strand interacting domain, and a RuvC domain. A PAM interacting domain can be a target strand PAM interacting domain (TPID) or a non-target strand PAM interacting domain (NTPID). In some embodiments, a PAM interacting domain, such as a TPID or a NTPID, on an effector protein describes a region of an effector protein that interacts with target nucleic acid.

Effector proteins of the present disclosure, dimers thereof, and multimeric complexes thereof may cleave or nick a target nucleic acid within or near a protospacer adjacent motif (PAM) sequence of the target nucleic acid. In some embodiments, cleavage occurs within 1, 2, 3, 4, 5, 6, 7, 8, 9 or 10 nucleosides of a 5' or 3' terminus of a PAM sequence. A target nucleic acid may comprise a PAM sequence adjacent to a sequence that is complementary to a guide nucleic acid spacer region. In some embodiments, the effector protein recognizes a PAM motif, wherein any suitable PAM sequence may be targeted. A person of ordinary skill in the art would understand that a suitable PAM sequence allows for effector protein recognition without substantially compromising effector protein activity. In some embodiments, the effector protein recognizes a PAM motif as shown in TABLE 10, TABLE 36, TABLE 37, TABLE 38, TABLE 42 and TABLE 43, wherein each N is any nucleotide, wherein each R is adenine or guanine, and wherein each V is adenine, cytosine or guanine. In some embodiments, a composition comprising an effector protein (e.g., a D2S effector protein) recognizes a PAM sequence comprising any of the following nucleotide sequence motifs as shown in TABLE 10, TABLE 36, TABLE 37, TABLE 38, TABLE 42 and TABLE 43 wherein each N is any nucleotide, wherein each R is adenine or guanine, and wherein each V is adenine, cytosine or guanine. In some embodiments, the effector protein recognizes a PAM sequence represented by 5'-NNTN-3' (SEQ ID NO: 946) wherein each N is selected from any nucleotide. In some embodiments, the effector protein recognizes a PAM sequence represented by 5'-NNTNTR-3' (SEQ ID NO: 3) where each N is selected from any nucleotide and each R is selected from adenine or guanine. In some embodiments, the effector protein recognizes a PAM sequence represented by 5'-TNTR-3' (SEQ ID NO: 4) where N is any nucleotide and R is adenine or guanine. In some embodiments, 5'-NNTNTR-3' (SEQ ID NO: 3) and 5'-TNTR-3' (SEQ ID NO: 4) are examples of a flexible PAM sequence of 5'-NNTN-3' (SEQ ID NO: 946).

In some embodiments, the D2S effector proteins comprise a RuvC domain (e.g., a partial RuvC domain). In some embodiments, the RuvC domain may be defined by a single, contiguous sequence, or a set of partial RuvC domains that are not contiguous with respect to the primary amino acid sequence of the protein. A D2S effector protein of the present disclosure may include multiple partial RuvC domains, which may combine to generate a RuvC domain with substrate binding or catalytic activity. For example, a D2S effector protein may include 3 partial RuvC domains (RuvC-I, RuvC-II, and RuvC-III, also referred to herein as subdomains) that are not contiguous with respect to the primary amino acid sequence of the D2S effector protein, but form a RuvC domain once the protein is produced and folds. In some embodiments, a partial RuvC domain is a RuvC subdomain. In many embodiments, D2S effector proteins comprise a recognition domain (e.g., a REC domain) with a binding affinity for a guide nucleic acid or for a guide nucleic acid-target nucleic acid heteroduplex. An effector protein may comprise a zinc finger domain. In some embodiments, the effector protein does not comprise an HNH domain.

In some embodiments, the amino acid sequence of the D2S effector protein comprises an alteration. In some embodiments, the amino acid sequence of the D2S effector protein comprises one or more alterations. In some embodiments, the one or more amino acid alteration can be an insertion, deletion, or substitution. In some embodiments, the one or more amino acid alteration can be a substitution. In some embodiments, the one or more amino acid alteration can be a conservative or non-conservative amino acid substitution. In some embodiments, the D2S effector protein comprises an arginine substitution. In some embodiments, the D2S effector protein provided herein comprises: 1 conservative amino acid substitution, 2 conservative amino acid substitutions, 3 conservative amino acid substitutions, 4 conservative amino acid substitutions, 5 conservative amino acid substitutions, 6 conservative amino acid substitutions, 7 conservative amino acid substitutions, 8 conservative amino acid substitutions, 9 conservative amino acid substitutions, 10 conservative amino acid substitutions or more relative to any one of the sequences of TABLE 1. In some embodiments, an effector protein provided herein comprises: 1 non-conservative amino acid substitution, 2 non-conservative amino acid substitutions, 3 non-conservative amino acid substitutions, 4 non-conservative amino acid substitutions, 5 non-conservative amino acid substitutions, 6 non-conservative amino acid substitutions, 7 non-conservative amino acid substitutions, 8 non-conservative amino acid substitutions, 9 non-conservative amino acid substitutions, 10 non-conservative amino acid substitutions or more relative to any one of the sequences recited in TABLE 1.

In some embodiments, SEQ ID NO: 37 may be referred to as a "consensus sequence" possessing a percent homology with respect to two or more effector proteins. In some embodiments the compositions comprise an effector protein comprising a portion of SEQ ID NO: 37. In some embodiments, the portion of SEQ ID NO: 37 is in the RuvC domain. In some embodiments, the portion of SEQ ID NO: 37 is in the RuvC-I domain. In some embodiments, the portion of SEQ ID NO: 37 is in the RuvC-II domain.

For the purpose of amino acid position numbering, in some embodiments, SEQ ID NO: 1 can be used as the reference sequence. Therefore, for example, mention of amino acid position 278 in reference to SEQ ID NO: 1, but in the context of a variant sequence, the corresponding amino acid position for variant creation may have the same or different position number. In some embodiments, the original amino acid and its position on the SEQ ID NO: 1 reference template will precisely correlate with the amino acid and position on the variant sequence. In other embodiments, the original amino acid and its position on the SEQ ID NO: 1 reference template will correlate with the original amino acid, but its position on the variant will not be in the corresponding template position. However, the corresponding amino acid on the variant can be a predetermined distance from the position on the template, such as within 10, 9, 8, 7, 6, 5, 4, 3, 2, or 1 amino acid positions from the reference template position. In other embodiments, the original amino acid on the SEQ ID NO: 1 reference template will not precisely correlate with the amino acid on the variant. However, one can understand what the corresponding amino acid on the variant sequence is based on the general location of the amino acid on the template and the sequence of amino acids in the vicinity of the variant amino acid.

In some embodiments, the D2S effector protein comprises one or more amino acid alteration in a domain of the D2S effector protein, wherein the D2S effector protein comprises a RuvC domain, a REC domain, or a zinc finger domain, or any combination thereof. In some embodiments, the RuvC domain comprises RuvC-I, RuvC-II, RuvC-III subdomains, or any combination thereof. In some embodiments, the D2S effector protein comprises one or more amino acid alteration in a RuvC subdomain, or the REC domain. In some embodiments, the D2S effector protein comprises one or more amino acid alteration in the RuvC-I subdomain, the RuvC-II subdomain, or the REC domain. In some embodiments, the D2S effector protein comprises one or more amino acid alteration in the RuvC-I subdomain. In some embodiments, the D2S effector protein comprises one or more amino acid alteration in the RuvC-II subdomain. In some embodiments, the D2S effector protein comprises one or more amino acid alteration in the REC domain. In some embodiments, the D2S effector protein comprises one or more amino acid alteration in a domain of SEQ ID NO: 1. In some embodiments, the D2S effector protein comprises one or more amino acid alteration in the RuvC-I subdomain, the RuvC-II subdomain, or the REC domain of SEQ ID NO: 1. In some embodiments, the D2S effector protein comprises one or more amino acid alteration in a domain of SEQ ID NO: 2. In some embodiments, the D2S effector protein comprises one or more amino acid alteration in the RuvC-I subdomain, the RuvC-II subdomain, or the REC domain of SEQ ID NO: 2.

In some embodiments, the amino acid sequence of the D2S effector protein comprises two, three, four, five, six, seven, eight, nine, ten or more alterations. In some embodiments, the amino acid sequence of the D2S effector protein is at least 65%, at least 70%, at least 75%, at least 80%, at least 85%, at least 90%, at least 95%, at least 97%, or at least 98%, at least 99%, or 100% identical to any one of the sequences recited in TABLE 1, wherein the amino acid sequence of the D2S effector protein can further comprise one or more amino acid alteration. In some embodiments, the amino acid sequence of the D2S effector comprises one or more amino acid alteration in any one of the sequences recited in TABLE 1. In some embodiments, the amino acid sequence of the D2S effector comprises one or more amino acid alterations at an amino acid residue identified as "X" in SEQ ID NO: 37. In some embodiments, the alteration of one or more residues to an effector protein of SEQ ID NO: 1 comprises an alteration at an amino acid residue identified as "X" in SEQ ID NO: 37, or a domain within SEQ ID NO: 37. In some embodiments, the alteration of one or more residues to an effector protein of SEQ ID NO: 2 comprises an alteration at an amino acid residue identified as "X" in SEQ ID NO: 37, or a domain within SEQ ID NO: 37.

In some embodiments, the effector protein comprises an amino acid sequence of SEQ ID NO: 37, wherein one to fifteen, one to twelve, one to ten, one to eight, one to five, one to three, three to fifteen, three to twelve, three to ten, three to eight, three to five, five to fifteen, five to twelve, five to ten, five to eight, eight to fifteen, eight to twelve, eight to ten, ten to fifteen, ten to twelve, or twelve to fifteen of the residues designated by X are independently any naturally occurring amino acid residues that are not identical to the corresponding amino acid residues of SEQ ID NO: 1 or SEQ ID NO: 2, and wherein the remaining residues designated by X are similar or identical to the corresponding amino acid residues of SEQ ID NO: 1 or SEQ ID NO: 2. In some embodiments, the effector protein comprise an amino acid sequence of SEQ ID NO: 37, wherein at least one, at least two, at least three, at least four, at least five, at least six, at least seven, at least eight, at least nine, or at least ten of the residues represented by X are any of the naturally occurring amino acids that are not similar to corresponding amino acid residues of SEQ ID NO: 1, and wherein the remaining X residues are amino acids that are similar to the corresponding amino acid residues of SEQ ID NO: 1 (e.g., T84R, T84K, T84H). In some embodiments, the effector protein comprises an amino acid sequence of SEQ ID NO: 37, wherein at least one, at least two, at least three, at least four, at least five, at least six, at least seven, at least eight, at least nine, or at least ten of the residues represented by X are any of the naturally occurring amino acids that are not similar to corresponding amino acid residues of SEQ ID NO: 2, and wherein the remaining X residues are amino acids that are similar to the corresponding amino acid residues of SEQ ID NO: 2.

In some embodiments, to provide a D2S effector protein variant, a D2S effector protein disclosed herein is selected as a template or parent sequence. Variants can be created by introducing one or more amino acid alteration (e.g., a substitution) into the template or parent sequence. The variants can be screened to identify those that have increased activity and/or specificity for their substrates. For example, a D2S effector protein variant is screened to identify those alterations leading to increased activity or specificity for the parent D2S effector protein's substrate or substrates. In some embodiments, a variant D2S effector protein has an increased nuclease activity as compared to the nuclease activity of the corresponding any one of the parent sequences recited in TABLE 1. In some embodiments, a variant D2S effector protein has a nuclease activity that is at least 0.25 fold, at least 0.5 fold, at least 0.75 fold, at least 1 fold, at least 1.25 fold, 1.5 fold, at least 2 fold, at least 5 fold, at least 10 fold, at least 25 fold, or 0.25-25 fold as compared to the nuclease activity of any one of the corresponding parent sequences recited in TABLE 1.

In some embodiments, the effector proteins function as an endonuclease that catalyzes cleavage within a target nucleic acid. In some embodiments, the effector proteins are capable of catalyzing non-sequence-specific cleavage of a single stranded nucleic acid. In some embodiments, the effector proteins (e.g., the effector proteins having SEQ ID NOs: 1-2, or 37) are activated to perform trans cleavage activity after binding of a guide nucleic acid with a target nucleic acid. This trans cleavage activity may also be referred to as "collateral" or "transcollateral" cleavage. Trans cleavage activity may be non-specific cleavage of nearby single-stranded nucleic acid by the activated effector protein, such as trans cleavage of detector nucleic acids with a detection moiety.

Engineered Proteins

In some embodiments, effector proteins disclosed herein (e.g., a D2S effector protein) are engineered proteins. Engineered proteins are not identical to a naturally-occurring protein. Engineered proteins may provide enhanced nuclease or nickase activity as compared to a naturally occurring nuclease or nickase. In some embodiments, an engineered protein may comprise a modified form of a naturally-occurring protein, which in some cases may be a WT effector protein.

An engineered protein may comprise a modified form of a wildtype counterpart protein (e.g., a D2S effector protein). The modified form of the wildtype counterpart may comprise an amino acid change (e.g., deletion, insertion, or substitution) that reduces the nucleic acid-cleaving activity of the effector protein relative to the wildtype counterpart. For example, a nuclease domain (e.g., RuvC domain) of a D2S effector protein may be deleted or mutated relative to a wildtype counterpart D2S effector protein so that it is no longer functional or comprises reduced nuclease activity. The modified form of the effector protein may have less than 90%, less than 80%, less than 70%, less than 60%, less than 50%, less than 40%, less than 30%, less than 20%, less than 10%, less than 5%, or less than 1% of the nucleic acid-cleaving activity of the wild-type counterpart. Engineered proteins may have no substantial nucleic acid-cleaving activity. Engineered proteins may be enzymatically inactive or "dead," that is it may bind to a nucleic acid but not cleave it. An enzymatically inactive protein may comprise an enzymatically inactive domain (e.g. inactive nuclease domain). Enzymatically inactive may refer to an activity less than 1%, less than 2%, less than 3%, less than 4%, less than 5%, less than 6%, less than 7%, less than 8%, less than 9%, or less than 10% activity compared to the wild-type counterpart. A dead protein may associate with a guide nucleic acid to activate or repress transcription of a target nucleic acid sequence. In some embodiments, the enzymatically inactive protein is fused with a protein comprising recombinase activity.

Alternatively, in some embodiments, the modified form of the wildtype counterpart may comprise an amino acid change (e.g., deletion, insertion, or substitution) that increases the nucleic acid-cleaving activity of the effector protein relative to the wildtype counterpart. The modified form of the effector protein may have a 1%, 5%, 10%, 20%, 30%, 40%, 50%, 60%, 70%, 80%, 90%, 100%, 120%, 140%, 160%, 180%, 200%, or more of the nucleic acid-cleaving activity of the wild-type counterpart. In some embodiments, the modified form of the wildtype counterpart may have a 1%, 5%, 10%, 20%, 30%, 40%, 50%, 60%, 70%, 80%, 90%, 100%, 120%, 140%, 160%, 180%, 200%, or more binding affinity for a guide nucleic acid or for a guide nucleic acid-target nucleic acid heteroduplex relative to the wild-type counterpart.

In some embodiments, the modified effector proteins described herein have improved binding affinity to the guide nucleic acids relative to the corresponding wildtype effector protein. In some embodiments, the modified effector proteins described herein have improved catalytic activity relative to the wildtype corresponding effector protein. Methods for determining an effector protein's binding affinity for nucleic acid as well as catalytic activity are well known in the art, which can be used for assaying the binding affinity and catalytic activity of an effector proteins, including methods described herein in the Examples. For example, when an effector protein comprises the amino acid sequence of SEQ ID NO: 37, which identifies conserved amino acid residues relative to SEQ ID NO: 1 and SEQ ID NO: 2, the effector protein may comprise one or more conserved amino acid substitutions for improving binding affinity, catalytic activity, or combination thereof, which can be assayed with such method. Similarly, in some embodiments, the effector protein described herein may comprise one or more non-conserved amino acid substitutions for improving binding affinity, catalytic activity, or combination thereof, which can also be assayed with such method.

In some embodiments, effector proteins provided herein are a variant of a reference polypeptide, wherein the reference polypeptide has any one of the amino acid sequences recited in TABLE 1. In some embodiments, the effector protein comprises one or more amino acid alterations relative to the reference polypeptide. In some embodiments, the effector proteins described herein comprises at least one, at least two, at least three, at least four, at least five, at least six, at least seven, at least eight, at least nine, or at least ten amino acid alterations relative to the reference polypeptide. In some embodiments, the effector proteins described herein comprises one, two, three, four, five, six, seven, eight, nine, or ten amino acid alterations relative to the reference polypeptide. In some embodiments, the one or more amino acid alterations comprises substitutions, deletions, insertions, or any combination thereof. In some embodiments, the one or more amino acid alterations comprises one or more conservative or non-conservative amino acid substitutions. In some embodiments, the effector protein comprises 1, 2, 3, 4 or 5 non-conservative amino acid substitutions relative to the reference polypeptide. In some embodiments, the effector protein comprises less than 2, less than 3, less than 4, less than 5, less than 6, less than 7, less than 8, less than 9, less than 10, less than 11, or less than 12 non-conservative substitutions relative to the reference polypeptide. In some embodiments, the effector protein comprises 1 to 5, 1 to 10, 1 to 20, 1 to 25, 5 to 10, 5 to 15, 5 to 20, 5 to 25, 10 to 15, 10 to 20, 10 to 25, 15 to 20, 15 to 25, or 20 to 25 non-conservative amino acid substitutions relative to the reference polypeptide. In some embodiments, the effector protein comprises not more than 1, 2, 3, 4, 5, 10, 15 or 20 amino acid substitutions that are non-conservative substitutions relative to the reference polypeptide. In some embodiments, the effector protein comprises at least 1, 2, 3, 4, 5, 8, 10, 12, 15, 18, 20 or 25 conservative substitutions relative to the reference polypeptide. In some embodiments, the effector protein comprises at less than 10, less than 15, less than 20, less than 25, or less than 30 conservative substitutions relative to the reference polypeptide. In some embodiments, the effector protein comprises 1 to 5, 1 to 10, 1 to 20, 1 to 25, 5 to 10, 5 to 15, 5 to 20, 5 to 25, 10 to 15, 10 to 20, 10 to 25, 15 to 20, 15 to 25, or 20 to 25 conservative amino acid substitutions relative to the reference polypeptide. In some embodiments, the effector protein comprises not more than 1, 2, 3, 4, 5, 10, 15 or 20 amino acid substitutions that are conservative substitutions relative to the reference polypeptide. In some embodiments, the conservative substitution (a type of alteration) comprises: (1) substitution of an acidic (positively charged) amino acid (e.g., Lys (K), Arg (R), or His (H)) of the reference polypeptide with another acidic amino acid; (2) substitution of a basic (negatively charged) amino acid (e.g., Asp (D), Glu (E), Asn (N), or Gln (Q)) of the reference polypeptide with another basic amino acid; (3) substitution of an aliphatic amino acid (e.g., Gly (G), Ala (A), Val (V), Leu (L), or Ile (I)) of the reference polypeptide with another aliphatic amino acid; (4) substitution of an aromatic amino acid (e.g., Phe (F), Tyr (Y), or Trp (W)) of the reference polypeptide with another aromatic amino acid; (5) or combinations thereof. In some embodiments, the non-conservative substitution (a type of alteration) comprises: (1) substitution of a positively charged amino acid of the reference polypeptide with a non-positively charged amino acid; (2) substitution of a negatively charged amino acid of the reference polypeptide with a non-negatively charged amino acid; (3) substitution of an aliphatic amino acid of the reference polypeptide with a non-aliphatic amino acid; (4) substitution of an aromatic amino acid of the reference polypeptide with a non-aromatic amino acid; (5) or combinations thereof. In some embodiments, the reference polypeptide has an amino acid sequence of SEQ ID NO: 1, and the effector protein comprises one or more amino acid alterations as described herein. In some embodiments, the effector protein comprises an amino acid sequence that is at least 75%, at least 80%, at least 85%, at least 90%, at least 95%, at least 98%, at least 99% or less than 100% identical to SEQ ID NO: 1, wherein the amino acid sequence also comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions. In some embodiments, the effector protein comprises an amino acid sequence that is at least 75%, at least 80%, at least 85%, at least 90%, at least 95%, at least 98%, at least 99% or 100% similar to SEQ ID NO: 1, wherein the amino acid sequence also comprises at least one amino acid substitution relative to SEQ ID NO: 1, wherein not more than 1, 2, 3, 4, 5, 10, 15 or 20 amino acid substitutions are non-conservative substitutions relative to SEQ ID NO: 1, and any remaining amino acid substitutions relative to SEQ ID NO: 1 are conservative amino acid substitutions. In some embodiments, the one or more alterations comprises substitution of one more amino acids with a basic (positively charged) amino acids (e.g., Lys (K), Arg (R), or His (H)). In some embodiments, the effector proteins described herein comprises a substitution of at least one, at least two, at least three, at least four, at least five, at least six, at least seven, at least eight, at least nine, or at least ten amino acids with positively charged amino acids. In some embodiments, the effector proteins described herein comprises a substitution of one, two, three, four, five, six, seven, eight, nine, or ten amino acids with positively charged amino acids. In some embodiments, the reference polypeptide has an amino acid sequence of SEQ ID NO: 1, and the effector protein comprises one or more amino acid alterations at K58, I80, T84, K105, N193, C202, S209, G210, A218, D220, E225, C246, N286, M295, M298, A306, Y315 and Q360. In some embodiments, the reference polypeptide has an amino acid sequence of SEQ ID NO: 1, and the effector protein comprises one or more amino acid alterations (e.g., substitutions) comprising I80R, T84R, K105R, C202R, G210R, A218R, D220R, E225R, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, Q360H, K58W, S209F, M295W, M298L, and Y315M. In some embodiments, the reference polypeptide has an amino acid sequence of SEQ ID NO: 1, and the effector protein comprises one or more amino acid alterations comprising K58W, I80R, T84R, K105R, N193K, C202R, S209F, G210R, A218K, A218R, D220R, E225K, E225R, C246R, N286K, M295W, M298L, A306K, Y315M, and Q360R.

In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises one or more alterations at K58, I80, T84, K105, N193, C202, S209, G210, A218, D220, E225, C246, N286, M295, M298, A306, Y315 and Q360. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, and wherein the effector protein also comprises one or more alterations at K58, I80, T84, K105, N193, C202, S209, G210, A218, D220, E225, C246, N286, M295, M298, A306, Y315 and Q360. In some embodiments, the one or more alterations comprises one or more substitutions selected from I80R, T84R, K105R, C202R, G210R, A218R, D220R, E225R, C246R, and Q360R. In some embodiments, the one or more alterations comprises one or more substitutions selected from I80K, T84K, C202K, G210K, A218K, D220K, E225K, C246K, and Q360K. In some embodiments, the one or more alterations comprises one or more substitutions selected from I80H, T84H, K105H, G210H, C202H, A218H, D220H, E225H, C246H, and Q360H. In some embodiments, the one or more alterations comprises one or more substitutions selected from K58W, I80K, N193K, S209F, A218R, E225K, N286K, M295W, M298L, A306K, and Y315M.

In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises A306K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises A306K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises N286K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises N286K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises E225K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises E225K substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises D220R substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises D220R substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises G210R substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises G210R substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein also comprises C202R substitution. In some embodiments, the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, and wherein the effector protein also comprises C202R substitution.

In some embodiments, engineered protein described herein may show an improved activity (e.g., nucleic acid binding activity, enhanced nuclease activity, enhanced potency of nuclease activity, enhanced precision of nuclease activity) relative to the wildtype counterpart. Precision of nuclease activity may be assessed by measuring the number of nucleotides that are deleted in a target nucleic acid, e.g., by sequencing. Nuclease activity is more precise if it deletes fewer nucleotides around a target site as compared to nuclease activity that is less precise and deletes more nucleotides around a target site. See, e.g., Example 32 provided herein. In some embodiments, introduction of a positive charge within a DNA binding region of the effector protein may strengthen the interaction between the effector protein and the negatively charged DNA backbone. In some embodiments, an engineered effector protein comprises addition of one or more positively charged amino acids, substitution of one or more amino acids with positively charged amino acids, deletion of one or more negatively charged amino acids, or combinations thereof. In some embodiments, the positively charged amino acid residues are independently selected from arginine, lysine and histidine. In some embodiments, the positively charged amino acid residue is arginine. In some embodiments, the introduction of the positive charge enhances nuclease activity relative to the counterpart wildtype protein. In some embodiments, the introduction of the positive charge enhances potency of the effector protein.

V. Fusion Proteins

In some embodiments, an effector protein is a fusion protein, wherein the fusion protein comprises a D2S effector protein and at least one fusion partner protein. In some embodiments, an effector protein is fused to one or more fusion partner proteins. In some embodiments, the D2S effector protein comprises an amino acid sequence that is at least 70%, at least 75%, at least 80%, at least 85%, at least 90%, at least 95%, or 100% identical to any one of the sequences recited in TABLE 1. In some embodiments the amino acid of the D2S effector protein is at least 70%, at least 75%, at least 80%, at least 85%, at least 90%, at least 95%, or 100% identical to any one of the sequences recited in TABLE 1. Unless otherwise indicated, reference to effector proteins throughout the present disclosure include fusion proteins thereof.

A fusion partner protein is also simply referred to herein as a fusion partner. In some embodiments, the fusion partner comprises a heterologous peptide or heterologous polypeptides. In some embodiments, the fusion partner comprises a protein selected from a polymerase, deaminase, a reverse transcriptase, a transcriptional repressor, and a transcriptional activator. In some embodiments, the fusion partner promotes the formation of a multimeric complex of the D2S effector protein. In some embodiments, the fusion partner inhibits the formation of a multimeric complex of the D2S effector protein.

In some embodiments, a fusion partner may be located at or near the amino terminus (N-terminus) of the D2S effector proteins disclosed herein. In some embodiments, a fusion partner may be located at or near the carboxy terminus (C-terminus) of the D2S effector proteins disclosed herein. In some embodiments, a fusion partner is located internally in D2S effector proteins described herein (i.e., is not at the N- or C-terminus of a D2S effector protein described herein) at a suitable insertion site. In some embodiments, a vector encodes the D2S effector proteins described herein, wherein the vector or vector systems disclosed herein comprises one or more fusion partners, such as about or more than about 1, 2, 3, 4, 5, 6, 7, 8, 9, 10, or more fusion partners. In some embodiments, D2S effector proteins described herein comprise 1, 2, 3, 4, 5, 6, 7, 8, 9, 10, or more fusion partners at or near the N-terminus, 1, 2, 3, 4, 5, 6, 7, 8, 9, 10, or more fusion partners at or near the C-terminus, or a combination of these (e.g. one or more fusion partners at the amino-terminus and one or more fusion partners at the carboxy terminus). When more than one fusion partner is present, each may be selected independently of the others, such that a single fusion partner may be present in more than one copy and/or in combination with one or more other fusion partners present in one or more copies. In some embodiments, a fusion partner is considered near the N- or C-terminus when the nearest amino acid of the fusion partner is within about 1, 2, 3, 4, 5, 10, 15, 20, 25, 30, 40, 50, or more amino acids along the polypeptide chain from the N- or C-terminus.

In some embodiments, the fusion partner modulates transcription (e.g., inhibits transcription, increases transcription) of a target nucleic acid. In some embodiments, the fusion partner is a protein (or a domain from a protein) that inhibits transcription, also referred to as a transcriptional repressor. Transcriptional repressors may inhibit transcription via recruitment of transcription inhibitor proteins, modification of target DNA such as methylation, recruitment of a DNA modifier, modulation of histones associated with target DNA, recruitment of a histone modifier such as those that modify acetylation and/or methylation of histones, or a combination thereof. In some embodiments, the fusion partner is a protein (or a domain from a protein) that increases transcription, also referred to as a transcription activator. Transcriptional activators may promote transcription via recruitment of transcription activator proteins, modification of target DNA such as demethylation, recruitment of a DNA modifier, modulation of histones associated with target DNA, recruitment of a histone modifier such as those that modify acetylation and/or methylation of histones, or a combination thereof. In some embodiments, the fusion partner is a reverse transcriptase. In some embodiments, the fusion partner is a base editor. In general, a base editor comprises a deaminase that when fused with a D2S protein changes a nucleobase to a different nucleobase, e.g., cytosine to thymine or guanine to adenine. In some embodiments, the base editor comprises a deaminase.

In some embodiments, fusion partners provide enzymatic activity that modifies a target nucleic acid. Such enzymatic activities include, but are not limited to, nuclease activity, methyltransferase activity, demethylase activity, DNA repair activity, DNA damage activity, deamination activity, dismutase activity, alkylation activity, depurination activity, oxidation activity, pyrimidine dimer forming activity, integrase activity, transposase activity, recombinase activity, polymerase activity, ligase activity, helicase activity, photolyase activity, and glycosylase activity.

In some embodiments, a fusion partner comprises one or more subcellular localization signals. In some embodiments, the subcellular localization signal can be a nuclear localization signal (NLS) for targeting the effector protein (e.g., a D2S effector protein) to the nucleus. In some embodiments, the subcellular localization signal is a nuclear export signal (NES), a sequence to keep an effector protein (e.g., a D2S effector protein) retained in the cytoplasm, a mitochondrial localization signal for targeting to the mitochondria, a chloroplast localization signal for targeting to a chloroplast, an ER retention signal, and the like. In some embodiments, an effector protein (e.g., a D2S effector protein) described herein is not modified with a subcellular localization signal so that the polypeptide is not targeted to the nucleus, which can be advantageous depending on the circumstance (e.g., when the target nucleic acid is an RNA that is present in the cytosol).

In some embodiments, the fusion partner is a nuclear localization signal (NLS). In some embodiments, a NLS comprises any one of the amino acid sequences recited in TABLE 2.

In some embodiments, the fusion partner is a chloroplast transit peptide (CTP), also referred to as a plastid transit peptide. In some embodiments, this targets the fusion protein to a chloroplast. Chromosomal transgenes from bacterial sources must have a sequence encoding a CTP sequence fused to a sequence encoding an expressed protein if the expressed protein is to be compartmentalized in the plant plastid (e.g. chloroplast). The CTP is removed in a processing step during translocation into the plastid. Accordingly, localization of an exogenous protein to a chloroplast is often accomplished by means of operably linking a polynucleotide sequence encoding a CTP sequence to the 5' region of a polynucleotide encoding the exogenous protein. In some embodiments, the CTP is located at the N-terminus of the fusion protein. Processing efficiency may, however, be affected by the amino acid sequence of the CTP and nearby sequences at the amino terminus ($NH_2$ terminus) of the peptide.

In some embodiments, the fusion partner is an endosomal escape peptide. An endosomal escape peptide is an agent that quickly disrupts the endosome in order to minimize the amount of time that a delivered molecule, such an effector protein (e.g., a D2S effector protein), spends in the endosome-like environment, and to avoid getting trapped in the endosomal vesicles and degraded in the lysosomal compartment. In some embodiments, an endosomal escape protein comprises the amino acid sequence GLFXALLXLLXSLWXLLLXA (SEQ ID NO: 5), wherein each X is independently selected from lysine, histidine, and arginine. In some embodiments, an endosomal escape protein comprises the amino acid sequence GLFHALLHLLHSLWHLLLHA (SEQ ID NO: 6). In some embodiments, the amino acid sequence of the endosomal escape protein is SEQ ID NO: 5 or SEQ ID NO: 6.

In some embodiments, the fusion partner is a nuclear localization signal (NLS). In some cases, said NLS may have a sequence of KRPAATKKAGQAKKKKEF (SEQ ID NO: 1107). The NLS can be selected to match the cell type of interest, for example several NLSs are known to be functional in different types of eukaryotic cell e.g. in mammalian cells. Suitable NLSs include the SV40 large T antigen NLS (PKKKRKV, SEQ ID NO: 1108) and the c-Myc NLS (PAAKRVKLD, SEQ ID NO: 1109). In some embodiments, an NLS may be the SV40 large T antigen NLS or the c-Myc NLS. NLSs that are functional in plant cells are described in Chang et al., (Plant Signal Behav. 2013 October; 8(10):e25976). In some embodiments, an NLS sequence can be selected from the following consensus sequences: KR(K/R)R (SEQ ID NO: 863), K(K/R)RK (SEQ ID NO: 1106); (P/R)XXKR(^DE)(K/R) (SEQ ID NO: 864); KRX(W/F/Y)XXAF (SEQ ID NO: 865); (R/P)XXKR(K/R) (^DE) (SEQ ID NO: 866); LGKR(K/R)(W/F/Y) (SEQ ID NO: 867); KRX10-12K(KR)(KR) (SEQ ID NO: 868) or KRX10-12K(KR)X(K/R) (SEQ ID NO: 1105).

In some embodiments, the nucleoplasmin NLS (KR-PAATKKAGQAKKKKEF (SEQ ID NO: 1107)) is linked or fused to the C-terminus of the effector protein. In some embodiments, the SV40 NLS (PKKKRKVGIHGVPAA) (SEQ ID NO: 1110) is linked or fused to the N-terminus of the effector protein. In preferred embodiments, the nucleoplasmin NLS (SEQ ID NO: 1107) is linked or fused to the C-terminus of the effector protein and the SV40 NLS (SEQ ID NO: 1110) is linked or fused to the N-terminus of the effector protein.

Further suitable fusion partners include, but are not limited to, proteins (or fragments/domains thereof) that are boundary elements (e.g., CTCF), proteins and fragments thereof that provide periphery recruitment (e.g., Lamin A, Lamin B, etc.), protein docking elements (e.g., FKBP/FRB, Pil1/Aby1, etc.). In some embodiments, the fusion partner is a cell penetrating peptide (CPP), also known as a Protein Transduction Domain (PTD). A CPP or PTD is a polypeptide, polynucleotide, carbohydrate, or organic or inorganic compound that facilitates traversing a lipid bilayer, micelle, cell membrane, organelle membrane, or vesicle membrane.

In some embodiments, the fusion partner is a protein tag. In some embodiments, the protein tag is referred to as purification tag or a fluorescent protein. The protein tag may be detectable for use in detection of the effector protein and/or purification of the effector protein. Accordingly, in some embodiments, compositions, systems and methods comprise a protein tag or use thereof. Any suitable protein tag may be used depending on the purpose of its use. Non-limiting examples of protein tags include a fluorescent protein, a histidine tag, e.g., a 6×His tag; a hemagglutinin (HA) tag; a FLAG tag; a Myc tag; and maltose binding protein (MBP). In some instances, the protein tag is a portion of MBP that can be detected and/or purified. Non-limiting examples of fluorescent proteins include green fluorescent protein (GFP), yellow fluorescent protein (YFP), red fluorescent protein (RFP), cyan fluorescent protein (CFP), mCherry, and tdTomato.

Nuclease-Dead D2S Effector Proteins

In some embodiments, the D2S effector protein can comprise an enzymatically inactive and/or "dead" (abbreviated by "d") effector protein in combination (e.g., fusion) with a polypeptide comprising recombinase activity. Although a D2S effector protein normally has nuclease activity, in some embodiments, a D2S effector protein does not have nuclease activity. Alternatively, in some embodiments, the D2S effector protein does not have catalytic activity. In some embodiments, a catalytically inactive effector protein is a nuclease-dead D2S effector protein (e.g., dCas). In some embodiments, an effector protein comprising at least 60%, at least 65%, at least 70%, at least 75%, at least 80%, at least 85%, at least 90%, at least 92%, at least 95%, at least 97%, at least 98%, at least 99%, or 100% sequence identity with any one of the sequences recited in TABLE 1 is a nuclease-dead effector protein. In some embodiments, the effector protein comprising at least 60%, at least 65%, at least 70%, at least 75%, at least 80%, at least 85%, at least 90%, at least 92%, at least 95%, at least 97%, at least 98%, at least 99%, or 100% sequence identity with any one of the sequences recited in TABLE 1 is modified or engineered to be a nuclease-dead effector protein. D2S effector protein can comprise a modified form of a wildtype counterpart. The modified form of the wildtype counterpart can comprise an amino acid change (e.g., deletion, insertion, or substitution) that reduces the nucleic acid-cleaving activity of the effector protein. For example, a nuclease domain (e.g., HEPN domain) of a D2S effector polypeptide can be deleted or mutated so that it is no longer functional or comprises reduced nuclease activity. The modified form of the effector protein can have less than 90%, less than 80%, less than 70%, less than 60%, less than 50%, less than 40%, less than 30%, less than 20%, less than 10%, less than 5%, or less than 1% of the nucleic acid-cleaving activity of the wild-type counterpart. The modified form of an effector protein can have no substantial nucleic acid-cleaving activity. When an effector protein is a modified form that has no substantial nucleic acid-cleaving activity, it can be referred to as enzymatically inactive and/or dead. A dead D2S effector polypeptide can bind to a target nucleic acid sequence but may not cleave the target nucleic acid sequence. A dead D2S effector polypeptide can associate with a guide nucleic acid to activate or repress transcription of a target nucleic acid sequence. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, wherein the dead D2S effector polypeptide also comprises alteration at D237, D418, E335, or combinations thereof. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, wherein the dead D2S effector polypeptide also comprises alteration at D237, D418, E335, or combinations thereof. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, wherein the dead D2S effector polypeptide also comprises one or more substitutions selected from D237A, D418A, D418N, E335A, and E335Q. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, wherein the dead D2S effector polypeptide also comprises one or more substitutions selected from D237A, D418A, D418N, E335A, and E335Q. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, wherein the dead D2S effector polypeptide also comprises D237A substitution. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, wherein the dead D2S effector polypeptide also comprises D237A substitution. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, wherein the dead D2S effector polypeptide also comprises E335Q substitution. In some embodiments, a dead D2S effector polypeptide comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1, wherein the dead D2S effector polypeptide also comprises E335Q substitution.

Multimeric Complex Formation Modification Activity

In another example, a fusion partner may inhibit the formation of a multimeric complex of the effector protein (e.g., a D2S effector protein). Alternatively, the fusion partner promotes the formation of a multimeric complex of the effector protein. By way of a non-limiting example, the fusion protein may comprise a D2S effector protein and a fusion partner comprising a Calcineurin A tag, wherein the fusion protein dimerizes in the presence of Tacrolimus (FK506). Also, by way of non-limiting example, the fusion protein may comprise a D2S effector protein and a SpyTag configured to dimerize or associate with another effector protein in a multimeric complex.

Nucleic Acid Modification Activity

In some embodiments, fusion partners have enzymatic activity that modifies the target nucleic acid. The target nucleic acid may comprise or consist of a ssRNA, dsRNA, ssDNA, or a dsDNA. Examples of enzymatic activity that modifies the target nucleic acid include, but are not limited to: nuclease activity such as that provided by a restriction enzyme (e.g., FokI nuclease); methyltransferase activity such as that provided by a methyltransferase (e.g., HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants)); demethylase activity such as that provided by a demethylase (e.g., Ten-Eleven Translocation (TET) dioxygenase 1 (TET1CD), TET1, DME, DML1, DML2, ROS1); DNA repair activity; DNA damage (e.g., oxygenation) activity; deamination activity such as that provided by a deaminase (e.g., a cytosine deaminase enzyme such as rat APOBEC1); dismutase activity; alkylation activity; depurination activity; oxidation activity; pyrimidine dimer forming activity; integrase activity such as that provided by an integrase and/or resolvase (e.g., Gin invertase such as the hyperactive mutant of the Gin invertase, GinH106Y; human immunodeficiency virus type 1 integrase (IN); Tn3 resolvase); transposase activity, recombinase activity such as that provided by a recombinase (e.g., catalytic domain of Gin recombinase); as well as polymerase activity, ligase activity, helicase activity, photolyase activity, and glycosylase activity.

Non-limiting examples of fusion partners for targeting ssRNA include, but are not limited to, splicing factors (e.g., RS domains); protein translation components (e.g., translation initiation, elongation, and/or release factors; e.g., eIF4G); RNA methylases; RNA editing enzymes (e.g., RNA deaminases, e.g., adenosine deaminase acting on RNA (ADAR), including A to I and/or C to U editing enzymes); helicases; and RNA-binding proteins. It is understood that a fusion protein may include the entire protein or in some embodiments may include a fragment of the protein (e.g., a functional domain). In some embodiments, the functional domain interacts with or binds ssRNA, including intramolecular and/or intermolecular secondary structures thereof, e.g., hairpins, stem-loops, etc.). The functional domain may interact transiently or irreversibly, directly or indirectly. Fusion proteins may comprise a protein or domain thereof selected from: endonucleases (e.g., RNase III, the CRR22 DYW domain, Dicer, and PIN (PilT N-terminus); SMG5 and SMG6; domains responsible for stimulating RNA cleavage (e.g., CPSF, CstF, CFIm and CFIIm); exonucleases such as XRN-1 or Exonuclease T; deadenylases such as HNT3; protein domains responsible for nonsense mediated RNA decay (e.g., UPF1, UPF2, UPF3, UPF3b, RNP Sl, Y14, DEK, REF2, and SRm160); protein domains responsible for stabilizing RNA (e.g., PABP); proteins and protein domains responsible for polyadenylation of RNA (e.g., PAP1, GLD-2, and Star-PAP); proteins and protein domains responsible for polyuridinylation of RNA (e.g., CI D1 and terminal uridylate transferase); proteins and protein domains responsible for RNA localization (e.g., from IMP1, ZBP1, She2p, She3p, and Bicaudal-D); proteins and protein domains responsible for nuclear retention of RNA (e.g., Rrp6); and proteins and protein domains responsible for nuclear export of RNA (e.g., TAP, NXF1, THO, TREX, REF, and Aly). Alternatively, the effector domain may be a domain of a protein selected from the group comprising endonucleases; proteins and protein domains capable of stimulating RNA cleavage; exonucleases; deadenylases; proteins and protein domains having nonsense mediated RNA decay activity; proteins and protein domains capable of stabilizing RNA; proteins and protein domains capable of repressing translation; proteins and protein domains capable of stimulating translation; proteins and protein domains capable of modulating translation (e.g., translation factors such as initiation factors, elongation factors, release factors, etc., e.g., eIF4G); proteins and protein domains capable of polyadenylation of RNA; proteins and protein domains capable of polyuridinylation of RNA; proteins and protein domains having RNA localization activity; proteins and protein domains capable of nuclear retention of RNA; proteins and protein domains having RNA nuclear export activity; proteins and protein domains capable of repression of RNA splicing; proteins and protein domains capable of stimulation of RNA splicing; proteins and protein domains capable of reducing the efficiency of transcription; and proteins and protein domains capable of stimulating transcription. Another suitable fusion partner is a PUF RNA-binding domain, which is described in more detail in WO2012068627, which is hereby incorporated by reference in its entirety.

In some embodiments, a fusion partner is an exonuclease fusion partner. In some embodiments, an exonuclease fusion partner comprises an amino acid sequence that is at least 70%, at least 75%, at least 80%, at least 85%, at least 90%, at least 95%, or 100% identical any one of the amino acid sequences recited in TABLE 2.1.

Disclosed herein are fusion proteins that show an improved activity (e.g., enhanced nuclease activity, enhanced potency of nuclease activity, enhanced precision of nuclease activity) relative to the wildtype effector protein counterpart. In some embodiments, a fusion partner of the fusion protein improves the activity of the wildtype effector protein counterpart to which it is has been fused to. In some embodiments, the fusion partner can be at least one of the fusion partners having nucleic acid modification activity as described herein, including, for example, an exonuclease fusion partner. In some embodiments, the fusion partner can be any two, three, four, five, six, seven, eight, nine, or ten of the fusion partners having nucleic acid modification activity as described herein. In some embodiments, the fusion partner enhances precision of nuclease activity of the effector protein. In some embodiments, the fusion partner enhancing precision of nuclease activity of the effector protein comprises one or more exonucleases as described herein. In some embodiments, the fusion partner protein improves precision of the effector protein by at least 10%, at least 20%, at least 40%, at least 60%, at least 80%, at least 100%, at least 120%, at least 140%, at least 160%, at least 180% or at least 200% relative to the effector protein alone. Precision may be evaluated by the size of an indel activity window, also referred to in some embodiments as the cut site. The indel activity window represents where indels start and end. In some embodiments, the fusion partner protein reduces an indel activity window (cut site) of the effector protein by at least 30%, at least 40%, at least 50%, at least 60%, at least 70%, at least 80% or at least 90% relative to the indel activity window (cut site) of the effector protein alone. In some embodiments, the fusion partner protein reduces an indel activity window (cut site) of the effector protein by at least about 50% relative to the indel activity window (cut site) of the effector protein alone. See, e.g., Example 32. In some embodiments, the fusion partner enhances nuclease activity potency of the effector protein. In some embodiments, the fusion partner enhancing nuclease activity potency of the effector protein comprises one or more exonucleases as described herein. In some embodiments, fusion partner protein improves potency of the effector protein by at least 10%, at least 20%, at least 40%, at least 60%, at least 80%, at least 100%, at least 120%, at least 140%, at least 160%, at least 180% or at least 200%.

Base Editing

In some embodiments, fusion partners modify a nucleobase of a target nucleic acid. Fusion proteins comprising such a fusion partner and an effector protein (e.g., a D2S effector protein) may be referred to as base editors. Such a fusion partner may be referred to as a base editing enzyme. In some embodiments, a base editor comprises a base editing enzyme variant that differs from a naturally occurring base editing enzyme, but it is understood that any reference to a base editing enzyme herein also refers to a base editing enzyme variant. In some embodiments, a base editor can be a fusion protein comprising a base editing enzyme fused or linked to an effector protein. In some embodiments, the amino terminus of the fusion partner protein is linked to the carboxy terminus of the effector protein via the linker. In some embodiments, the carboxy terminus of the fusion partner protein is linked to the amino terminus of the effector protein via the linker. The base editor may be functional when the effector protein is coupled to a guide nucleic acid. The base editor may be functional when the effector protein is coupled to a guide nucleic acid. The guide nucleic acid imparts sequence specific activity to the base editor. By way of non-limiting example, the effector protein may comprise a catalytically inactive effector protein (e, a catalytically inactive variant of an effector protein described herein). Also, by way of non-limiting example, the base editing enzyme may comprise deaminase activity. Additional base editors are described herein.

In some embodiments, base editors are capable of catalyzing the chemical modification of a nucleobase of a nucleic acid molecule, such as DNA or RNA (single stranded or double stranded). Non-limiting examples of the type of modification that a base editing enzyme, and therefore a base editor, is capable of catalyzing includes converting an existing nucleobase to a different nucleobase, such as: an adenine (A) to guanine (G); cytosine (C) to thymine (T); cytosine (C) to guanine (G); uracil (U) to cytosine (C); guanine (G) to adenine (A); hydrolytic deamination of an adenine or adenosine, or methylation of cytosine (e.g., CpG, CpA, CpT or CpC). Some base editors modify a nucleobase on a ssDNA. In some embodiments, base editors modify a nucleobase on both strands of dsDNA. Some base editors modify a nucleobase of an RNA.

A base editing enzyme itself may or may not bind to the nucleic acid molecule containing the nucleobase. In some embodiments, upon binding to its target locus in the target nucleic acid (e.g., a DNA molecule), base pairing between the guide nucleic acid and target strand leads to displacement of a small segment of ssDNA in an "R-loop". In some embodiments, DNA bases within the R-loop are modified by the base editor having the deaminase enzyme activity. In some embodiments, base editors for improved efficiency in eukaryotic cells comprise a catalytically inactive effector protein that may generate a nick in the non-edited strand, inducing repair of the non-edited strand using the edited strand as a template.

In some embodiments, the base editing enzyme comprises a deaminase enzyme. Exemplary deaminases are described in US20210198330, WO2021041945, WO2021050571A1, and WO2020123887, all of which are incorporated herein by reference in their entirety. Exemplary deaminase domains are described WO 2018027078 and WO2017070632, and each are hereby incorporated in its entirety by reference. Also, additional exemplary deaminase domains are described in Komor et al., Nature, 533, 420-424 (2016); Gaudelli et al., Nature, 551, 464-471 (2017); Komor et al., Science Advances, 3:eaao4774 (2017), and Rees et al., Nat Rev Genet. 2018 December; 19(12):770-788. doi: 10.1038/s41576-018-0059-1, which are hereby incorporated by reference in their entirety. In some embodiments, the deaminase functions as a monomer. In some embodiments, the deaminase functions as heterodimer with an additional protein. In some embodiments, base editors comprise a DNA glycosylase inhibitor (e.g., an uracil glycosylase inhibitor (UGI) or uracil N-glycosylase (UNG)). In some embodiments, the fusion partner is a deaminase, e.g., ADAR1/2, ADAR-2, or AID.

In some embodiments, the base editor is a cytosine base editor (CBE). A CBE may convert a cytosine to a thymine. In some embodiments, the cytosine base editing enzyme may accept ssDNA as a substrate but may not be capable of cleaving dsDNA, as fused to a catalytically inactive effector protein. In some embodiments, when bound to its cognate DNA, the catalytically inactive effector protein of the CBE may perform local denaturation of the DNA duplex to generate an R-loop in which the DNA strand not paired with the guide nucleic acid exists as a disordered single-stranded bubble. In some embodiments, the catalytically inactive effector protein generated ssDNA R-loop may enable the CBE to perform efficient and localized cytosine deamination in vitro. In some embodiments, deamination activity is exhibited in a window of about 4 to about 10 base pairs. In some embodiments, fusion to the catalytically inactive effector protein presents the target site to the cytosine base editing enzyme in high effective molarity, which may enable the CBE to deaminate cytosines located in a variety of different sequence motifs, with differing efficacies. In some embodiments, the CBE is capable of mediating RNA-programmed deamination of target cytosines in vitro or in vivo. In some embodiments, the cytosine base editing enzyme is a cytidine deaminase. In some embodiments, the cytosine base editing enzyme is a cytosine base editing enzyme described by Koblan et al. (2018) Nature Biotechnology 36:848-846; Komor et al. (2016) Nature 533:420-424; Koblan et al. (2021) "Efficient C•G-to-G•C base editors developed using CRISPRi screens, target-library analysis, and machine learning," Nature Biotechnology; Kurt et al. (2021) Nature Biotechnology 39:41-46; Zhao et al. (2021) Nature Biotechnology 39:35-40; and Chen et al. (2021) Nature Communications 12:1384, all incorporated herein by reference.

In some embodiments, CBEs comprise an uracil glycosylase inhibitor (UGI) or uracil N-glycosylase (UNG). In some embodiments, base excision repair (BER) of U•G in DNA is initiated by a UNG, which recognizes the U•G mismatch and cleaves the glyosidic bond between uracil and the deoxyribose backbone of DNA. In some embodiments, BER results in the reversion of the U•G intermediate created by the first CBE back to a C•G base pair. In some embodiments, UNG may be inhibited by fusion of uracil DNA glycosylase inhibitor (UGI). In some embodiments, a UGI is a small protein from bacteriophage PBS, to the C-terminus of the CBE. In some embodiments, a UGI is a DNA mimic that potently inhibits both human and bacterial UNG. In some embodiments, a UGI inhibitor is any protein or polypeptide that inhibits UNG. In some embodiments, the CBE may mediate efficient base editing in bacterial cells and moderately efficient editing in mammalian cells, enabling conversion of a CG base pair to a T•A base pair through a U•G intermediate. In some embodiments, the CBE is modified to increase base editing efficiency while editing more than one strand of DNA.

In some embodiments, the CBE nicks the non-edited DNA strand. In some embodiments, the non-edited DNA strand nicked by the CBE biases cellular repair of the UG mismatch to favor a UA outcome, elevating base editing efficiency. In some embodiments, the APOBEC1-nickase-UGI fusion efficiently edits in mammalian cells, while minimizing frequency of non-target indels. In some embodiments, base editors do not comprise a functional fragment of the base editing enzyme. For example, in some embodiments base editors do not comprise a function fragment of an UGI, where such a fragment may be capable of excising an uracil residue from DNA by cleaving an N-glycosidic bond.

In some embodiments, the fusion protein further comprises a non-protein uracil-DNA glycosylase inhibitor (npUGI). In some embodiments, the npUGI is selected from a group of small molecule inhibitors of uracil-DNA glycosylase (UDG), or a nucleic acid inhibitor of UDG. In some embodiments, the non-protein uracil-DNA glcosylase inhibitor (npUGI) is a small molecule derived from uracil. Examples of small molecule non-protein uracil-DNA glycosylase inhibitors, fusion proteins, and Cas-CRISPR systems comprising base editing activity are described in WO2021087246, which is incorporated by reference in its entirety.

In some embodiments, the cytosine base editing enzyme is a cytidine deaminase. In some embodiments, the base editor is a cytidine deaminase base editor generated by ancestral sequence reconstruction as described in WO2019226953, which is hereby incorporated by reference in its entirety. Exemplary cytidine deaminases suitable for use with effector proteins described herein include: APOBEC1, APOBEC2, APOBEC3C, APOBEC3D, APOBEC3F, APOBEC3G, APOBEC3H, APOBEC4, APOBEC3A, BE1 (APOBEC1-XTEN-dCas9), BE2 (APOBEC1-XTEN-dCas9-UGI), BE3 (APOBEC1-XTEN-dCas9(A840H)-UGI), BE3-Gam, saBE3, saBE4-Gam, BE4, BE4-Gam, saBE4, and saBE4-Gam as described in WO2021163587, WO2021087246, WO2021062227, and WO2020123887, which are incorporated herein by reference in their entirety.

In some embodiments, the base editor is a cytosine to guanine base editor (CGBE). A CGBE may convert a cytosine to a guanine.

In some embodiments, the base editor is an adenine base editor (ABE). An ABE may convert an adenine to a guanine. In some embodiments, an ABE converts an A•T base pair to a G•C base pair. In some embodiments, the ABE converts a target A•T base pair to G•C in vivo or in vitro. In some embodiments, ABEs provided herein reverse spontaneous cytosine deamination, which has been linked to pathogenic point mutations. In some embodiments, ABEs provided herein enable correction of pathogenic SNPs (~47% of disease-associated point mutations). In some embodiments, the adenine comprises exocyclic amine that has been deaminated (e.g., resulting in altering its base pairing preferences). In some embodiments, deamination of adenosine yields inosine. In some embodiments, inosine exhibits the base-pairing preference of guanine in the context of a polymerase active site, although inosine in the third position of a tRNA anticodon is capable of pairing with A, U, or C in mRNA during translation. Exemplary adenine base editing enzymes suitable for use with effector proteins described herein include: ABE8e, ABE8.20m, APOBEC3A, Anc APOBEC (a.k.a. AncBE4Max), and BtAPOBEC2. Exemplary ABEs suitable for use herein include: ABE7, ABE8.1m, ABE8.2m, ABE8.3m, ABE8.4m, ABE8.5m, ABE8.6m, ABE8.7m, ABE8.8m, ABE8.9m, ABE8.10m, ABE8.11m, ABE8.12m, ABE8.13m, ABE8.14m, ABE8.15m, ABE8.16m, ABE8.17m, ABE8.18m, ABE8.19m, ABE8.20m, ABE8.21m, ABE8.22m, ABE8.23m, ABE8.24m, ABE8.1d, ABE8.2d, ABE8.3d, ABE8.4d, ABE8.5d, ABE8.6d, ABE8.7d, ABE8.8d, ABE8.9d, ABE8.10d, ABE8.11d, ABE8.12d, ABE8.13d, ABE8.14d, ABE8.15d, ABE8.16d, ABE8.17d, ABE8.18d, ABE8.19d, ABE8.20d, ABE8.21d, ABE8.22d, ABE8.23d, and ABE8.24d. In some embodiments, the adenine base editing enzyme is an adenine base editing enzyme described in Chu et al., (2021) The CRISPR Journal 4:2:169-177, incorporated herein by reference. In some embodiments, the adenine deaminase is an adenine deaminase described by Koblan et al. (2018) Nature Biotechnology 36:848-846, incorporated herein by reference. In some embodiments, the adenine base editing enzyme is an adenine base editing enzyme described by Tran et al. (2020) Nature Communications 11:4871.

In some embodiments, the adenine base editing enzyme of the ABE is an adenosine deaminase. Exemplary adenosine base editors suitable for use herein include ABE9. In some embodiments, an ABE comprises an engineered adenosine deaminase enzyme capable of acting on ssDNA. An adenosine deaminase enzyme may be an adenosine deaminase variant that differs from a naturally occurring deaminase. Relative to the naturally occurring deaminase, the adenosine deaminase variant may comprise one or more amino acid alteration, including a V82S alteration, a T166R alteration, a Y147T alteration, a Y147R alteration, a Q154S alteration, a Y123H alteration, a Q154R alteration, or a combination thereof.

In some embodiments, a base editor comprises a deaminase dimer. In some embodiments, a base editor is a deaminase dimer further comprising a base editing enzyme and an adenine deaminase (e.g., TadA). In some embodiments, the adenosine deaminase is a TadA monomer (e.g., Tad*7.10, TadA*8 or TadA*9). In some embodiments, the adenosine deaminase is a TadA*8 variant (e.g., any one of TadA*8.1, TadA*8.2, TadA*8.3, TadA*8.4, TadA*8.5, TadA*8.6, TadA*8.7, TadA*8.8, TadA*8.9, TadA*8.10, TadA*8.11, TadA*8.12, TadA*8.13, TadA*8.14, TadA*8.15, TadA*8.16, TadA*8.17, TadA*8.18, TadA*8.19, TadA*8.20, TadA*8.21, TadA*8.22, TadA*8.23, or TadA*8.24 as described in WO2021163587 and WO2021050571, which are each hereby incorporated by reference in its entirety). In some embodiments, a base editor is a deaminase dimer comprising a base editing enzyme fused to TadA via a linker (e.g., wherein the base editing enzyme is fused to TadA at the N-terminus or the C-terminus via a linker).

In some embodiments, the base editing enzyme is a deaminase dimer comprising an ABE. In some embodiments, the deaminase dimer comprises an adenosine deaminase. In some embodiments, the deaminase dimer comprises TadA fused to a suitable adenine base editing enzyme including an: ABE8e, ABE8.20m, APOBEC3A, Anc APOBEC (a.k.a. AncBE4Max), BtAPOBEC2, and variants thereof. In some embodiments, the adenine base editing enzyme is fused to amino-terminus or the carboxy-terminus of TadA.

In some embodiments, RNA base editors comprise an adenosine deaminase. In some embodiments, ADAR proteins bind to RNAs and alter their sequence by changing an adenosine into an inosine. In some embodiments, RNA base editors comprise an effector protein that is activated by or binds RNA.

In some embodiments, base editors are used to treat a subject having or a subject suspected of having a disease related to a gene of interest. In some embodiments, base editors are useful for treating a disease or a disorder caused by a point mutation in a gene of interest. In some embodiments, compositions, systems, and methods described herein comprise a base editor and a guide nucleic acid, wherein the guide nucleic acid directs the base editor to a sequence in a target gene.

Prime Editing

In some embodiments, a fusion protein and/or a fusion partner can comprise a prime editing enzyme. When used herein, a prime editing enzyme can describe a protein, polypeptide, or fragment thereof that is capable of catalyzing the modification (insertion, deletion, or base-to-base conversion) of a target nucleotide or nucleotide sequence in a nucleic acid. A prime editing enzyme capable of catalyzing such a reaction includes a reverse transcriptase. A non-limiting example of a reverse transcriptase is an M-MLV RT enzyme and variants thereof having polymerase activity. In some embodiments, the M-MLV RT enzyme comprises at least one mutation selected from D200N, L603W, T330P, T306K, and W313F relative to wildtype M-MLV RT enzyme.

A prime editing enzyme may require a prime editing guide RNA (pegRNA) to catalyze the modification. Such a pegRNA can be capable of identifying the nucleotide or nucleotide sequence in the target nucleic acid to be edited and encoding the new genetic information that replaces the targeted nucleotide or nucleotide sequence in the nucleic acid. A prime editing enzyme may require a pegRNA and a single guide RNA to catalyze the modification. In some embodiments, the target nucleic acid is a dsDNA molecule. In some embodiments, the pegRNA comprises a guide RNA comprising a first region that is bound by the effector protein, and a second region comprising a spacer sequence that is complementary to a target sequence of the target dsDNA molecule; a template RNA comprising a primer binding sequence that hybridizes to a primer sequence of the target dsDNA molecule that is formed when target nucleic acid is cleaved, and a template sequence that is complementary to at least a portion of the target sequence of the target dsDNA molecule with the exception of at least one nucleotide. In some embodiments, the spacer sequence is complementary to the target sequence on the target strand of the dsDNA molecule. In some embodiments, the spacer sequence is complementary to the target sequence on the non-target strand of the dsDNA molecule. In some instances, the primer binding sequence hybridizes to a primer sequence on the non-target strand of the target dsDNA molecule. In some instances, the primer binding sequence hybridizes to a primer sequence on the target strand of the target dsDNA molecule. In some instances, the target strand is cleaved. In some instances, the non-target strand is cleaved.

CRISPRa Fusions and CRISPRi Fusions

In some embodiments, fusion partners include, but are not limited to, a protein that directly and/or indirectly provides for increased or decreased transcription and/or translation of a target nucleic acid (e.g., a transcription activator or a fragment thereof, a protein or fragment thereof that recruits a transcription activator, a small molecule/drug-responsive transcription and/or translation regulator, a translation-regulating protein, etc.). In some embodiments, fusion partners that increase or decrease transcription include a transcription activator domain or a transcription repressor domain, respectively.

Non-limiting examples of fusion partners that promote or increase transcription include, but are not limited to: transcriptional activators such as VP16, VP64, VP48, VP160, p65 subdomain (e.g., from NFkB), and activation domain of EDLL and/or TAL activation domain (e.g., for activity in plants); histone lysine methyltransferases such as SET1A, SET1B, MLL1 to 5, ASH1, SYMD2, NSD1; histone lysine demethylases such as JHDM2a/b, UTX, JMJD3; histone acetyltransferases such as GCN5, PCAF, CBP, p300, TAF1, TIP60/PLIP, MOZ/MYST3, MORF/MYST4, SRC1, ACTR, P160, CLOCK; and DNA demethylases such as Ten-Eleven Translocation (TET) dioxygenase 1 (TET1CD), TET1, DME, DML1, DML2, and ROS1; and functional domains thereof.

Non-limiting examples of fusion partners that decrease or inhibit transcription include, but are not limited to: transcriptional repressors such as the Kruppel associated box (KRAB or SKD); KOX1 repression domain; the Mad mSIN3 interaction domain (SID); the ERF repressor domain (ERD), the SRDX repression domain (e.g., for repression in plants); histone lysine methyltransferases such as Pr-SET7/8, SUV4-20H1, RIZ1, and the like; histone lysine demethylases such as JMJD2A/JHDM3A, JMJD2B, JMJD2C/GASC1, JMJD2D, JARID1A/RBP2, JARID1B/PLU-1, JARID1C/SMCX, JARID1D/SMCY; histone lysine deacetylases such as HDAC1, HDAC2, HDAC3, HDAC8, HDAC4, HDAC5, HDAC7, HDAC9, SIRT1, SIRT2, HDAC11; DNA methylases such as HhaI DNA m5c-methyltransferase (M.HhaI), DNA methyltransferase 1 (DNMT1), DNA methyltransferase 3a (DNMT3a), DNA methyltransferase 3b (DNMT3b), METI, DRM3 (plants), ZMET2, CMT1, CMT2 (plants); and periphery recruitment elements such as Lamin A, and Lamin B; and functional domains thereof.

Other non-limiting examples of suitable fusion partners include: proteins and protein domains responsible for (e.g., capable of) modulating translation (e.g., translation factors such as initiation factors, elongation factors, release factors, etc., e.g., eIF4G); proteins and protein domains responsible for stimulating translation (e.g., Staufen); proteins and protein domains responsible for stimulation of RNA splicing (e.g., Serine/Arginine-rich (SR) domains); proteins and protein domains responsible for stimulating transcription (e.g., CDK7 and HIV Tat); proteins and protein domains responsible for repressing translation (e.g., Ago2 and Ago4); proteins and protein domains responsible for repression of RNA splicing (e.g., PTB, Sam68, and hnRNP A1); and proteins and protein domains responsible for reducing the efficiency of transcription (e.g., FUS (TLS)).

In some embodiments, fusion proteins are targeted by a guide nucleic acid (guide RNA) to a specific location in the target nucleic acid and exert locus-specific regulation such as blocking RNA polymerase binding to a promoter (which selectively inhibits transcription activator function), and/or modifying the local chromatin status (e.g., when a fusion sequence is used that modifies the target nucleic acid or modifies a protein associated with the target nucleic acid). In some embodiments, the modifications are transient (e.g., transcription repression or activation). In some embodiments, the modifications are inheritable. For instance, epigenetic modifications made to a target nucleic acid, or to proteins associated with the target nucleic acid, e.g., nucleosomal histones, in a cell, are observed in cells produced by proliferation of the cell.

In some embodiments, the fusion partner comprises an RNA splicing factor. The RNA splicing factor may be used (in whole or as fragments thereof) for modular organization, with separate sequence-specific RNA binding modules and splicing effector domains. Non-limiting examples of RNA splicing factors include members of the Serine/Arginine-rich (SR) protein family contain N-terminal RNA recognition motifs (RRMs) that bind to exonic splicing enhancers (ESEs) in pre-mRNAs and C-terminal RS domains that promote exon inclusion. As another example, the hnRNP protein hnRNP Al binds to exonic splicing silencers (ESSs) through its RRM domains and inhibits exon inclusion through a C-terminal Glycine-rich domain. Some splicing factors may regulate alternative use of splice site (ss) by binding to regulatory sequences between the two alternative sites. For example, ASF/SF2 may recognize ESEs and promote the use of intron proximal sites, whereas hnRNP Al may bind to ESSs and shift splicing towards the use of intron distal sites. One application for such factors is to generate ESFs that modulate alternative splicing of endogenous genes, particularly disease associated genes. For example, Bcl-x pre-mRNA produces two splicing isoforms with two alternative 5' splice sites to encode proteins of opposite functions. The long splicing isoform Bcl-xL is a potent apoptosis inhibitor expressed in long-lived postmitotic cells and is up-regulated in many cancer cells, protecting cells against apoptotic signals. The short isoform Bcl-xS is a pro-apoptotic isoform and expressed at high levels in cells with a high turnover rate (e.g., developing lymphocytes). The ratio of the two Bcl-x splicing isoforms is regulated by multiple c6ω-elements that are located in either the core exon region or the exon extension region (i.e., between the two alternative 5' splice sites). For more examples, see WO2010075303, which is hereby incorporated by reference in its entirety.

Recombinases

In some embodiments, the fusion partners comprise a recombinase domain. In some embodiments, an enzymatically inactive effector protein (e.g., a D2S effector protein) is fused with a recombinase. In some embodiments, the recombinase is a site-specific recombinase. In some embodiments, fusion partners comprise a recombinase domain wherein the recombinase is a site-specific recombinase. In some embodiments, described herein is a programmed nuclease comprising reduced nuclease activity or no nuclease activity and fused with a recombinase, wherein the recombinase can be a site-specific recombinase. Such polypeptides can be used for site-directed transgene insertion. Examples of site-specific recombinases include a tyrosine recombinase (e.g., Cre, Flp or lambda integrase), a serine recombinase (e.g., gamma-delta resolvase, Tn3 resolvase, Sin resolvase, Gin invertase, Hin invertase, Tn5044 resolvase, IS607 transposase and integrase), or mutants or variants thereof. In some embodiments, the recombinase is a serine recombinase. Non-limiting examples of serine recombinases include, but are not limited to, gamma-delta resolvase, Tn3 resolvase, Sin resolvase, Gin invertase, Hin invertase, Tn5044 resolvase, IS607 transposase, and IS607 integrase. In some embodiments, the site-specific recombinase is an integrase. Non-limiting examples of integrases include, but are not limited to:Bxb1, wBeta, BL3, phiR4, A118, TG1, MR11, phi370, SPBc, TP901-1, phiRV, FC1, K38, phiBT1, and phiC31. Further discussion and examples of suitable recombinase fusion partners are described in U.S. Pat. No. 10,975,392, which is incorporated herein by reference in its entirety. In some embodiments, the fusion protein comprises a linker that links the recombinase domain to the Cas-CRISPR domain of the effector protein. In some embodiments, the linker is Thr-Ser.

Linkers

In some embodiments, the effector protein (e.g., a D2S effector protein) and the fusion partner are directly linked via a covalent bond. In some embodiments, effector proteins and fusion partners of a fusion effector protein are connected via a linker. The linker may comprise or consist of a covalent bond. The linker may comprise or consist of a chemical group. In some embodiments, the linker comprises an amino acid. In some embodiments, a linker comprises a bond or molecule that links a first polypeptide to a second polypeptide. In some embodiments, a peptide linker comprises at least two amino acids linked by an amide bond. In general, the linker connects a terminus of the effector protein to a terminus of the fusion partner. In some embodiments, the carboxy terminus of the effector protein is linked to the amino terminus of the fusion partner. In some embodiments, the carboxy terminus of the fusion partner is linked to the amino terminus of the effector protein.

In some embodiments, a terminus of the D2S effector protein is linked to a terminus of the fusion partner through an amide bond. In some embodiments, a D2S effector protein is coupled to a fusion partner via a linker protein. The linker protein may have any of a variety of amino acid sequences. A linker protein may comprise a region of rigidity (e.g., beta sheet, alpha helix), a region of flexibility, or any combination thereof. In some embodiments, the linker comprises small amino acids, such as glycine and alanine, that impart high degrees of flexibility. The ordinarily skilled artisan will recognize that design of a peptide conjugated to any desired element may include linkers that are all or partially flexible, such that the linker may include a flexible linker as well as one or more portions that confer less flexible structure. Suitable linkers include proteins of 4 linked amino acids to 40 linked amino acids in length, or between 4 linked amino acids and 25 linked amino acids in length.

These linkers may be produced by using synthetic, linker-encoding oligonucleotides to couple the proteins, or may be encoded by a nucleic acid sequence encoding a fusion protein (e.g., an effector protein coupled to a fusion partner). Examples of linker proteins include glycine polymers (G)n, glycine-serine polymers (including, for example, (GS)n, GSGGSn, GGSGGSn, and GGGSn, where n is an integer of at least one), glycine-alanine polymers, and alanine-serine polymers. Exemplary linkers may comprise amino acid sequences including, but not limited to, GS (SEQ ID NO: 7), GSGGS (SEQ ID NO: 8), GGSGGS (SEQ ID NO: 9), GGGS (SEQ ID NO: 10), GGSG (SEQ ID NO: 11), GGSGG (SEQ ID NO: 12), GSGSG (SEQ ID NO: 13), GSGGG (SEQ ID NO: 14), GGGSG (SEQ ID NO: 15), and GSSSG (SEQ ID NO: 16).

A linker may be a peptide linker or a non-peptide linker. In some embodiments, the linker is an XTEN linker. In some embodiments, the XTEN linker is an XTEN20 linker. In some embodiments, the XTEN20 linker has an amino acid sequence of GSGGSPAGSPTSTEEGTSESATPGSG (SEQ ID NO: 940). In some embodiments, the XTEN linker is an XTEN80 linker. In some embodiments, the linker comprises one or more repeats as a GGS tri-peptide. In some embodiments, the linker is from 1 to 100 amino acids in length. In some embodiments, the linker is more 100 amino acids in length. In some embodiments, the linker is from 10 to 27 amino acids in length. A non-peptide linker may be a polyethylene glycol (PEG), polypropylene glycol (PPG), co-poly(ethylene/propylene) glycol, polyoxyethylene (POE), polyurethane, polyphosphazene, polysaccharides, dextran, polyvinyl alcohol, polyvinylpyrrolidones, polyvinyl ethyl ether, polyacrylamide, polyacrylate, polycyanoacrylates, lipid polymers, chitins, hyaluronic acid, heparin, or an alkyl linker.

In some embodiments, linkers do not comprise an amino acid. In some instances, linkers do not comprise a peptide. In some embodiments, linkers comprise a nucleotide, a polynucleotide, a polymer, or a lipid.

Protein Modification Activity

In some embodiments, a fusion partner provides enzymatic activity that modifies a protein (e.g., a histone) associated with a target nucleic acid. Such enzymatic activities include, but are not limited to, methyltransferase activity, demethylase activity, acetyltransferase activity, deacetylase activity, kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

In some embodiments, the fusion partner has enzymatic activity that modifies a protein associated with a target nucleic acid. The protein may be a histone, an RNA binding protein, or a DNA binding protein. Examples of such protein modification activities include methyltransferase activity such as that provided by a histone methyltransferase (HMT) (e.g., suppressor of variegation 3-9 homolog 1 (SUV39H1, also known as KMT1A), euchromatic histone lysine methyltransferase 2 (G9A, also known as KMT1C and EHMT2), SUV39H2, ESET/SETDB1, SET1A, SET1B, MLL1 to 5, ASH1, SYMD2, NSD1, DOT1L, Pr-SET7/8, SUV4-20H1, EZH2, RIZ1); demethylase activity such as that provided by a histone demethylase (e.g., Lysine Demethylase 1A (KDM1A also known as LSD1), JHDM2a/b, JMJD2A/JHDM3A, JMJD2B, JMJD2C/GASC1, JMJD2D, JARID1A/RBP2, JARID1B/PLU-1, JARID1C/SMCX, JARID1D/SMCY, UTX, JMJD3); acetyltransferase activity such as that provided by a histone acetylase transferase (e.g., catalytic core/fragment of the human acetyltransferase p300, GCN5, PCAF, CBP, TAF1, TIP60/PLIP, MOZ/MYST3, MORF/MYST4, HBO1/MYST2, HMOF/MYST1, SRC1, ACTR, P160, CLOCK); deacetylase activity such as that provided by a histone deacetylase (e.g., HDAC1, HDAC2, HDAC3, HDAC8, HDAC4, HDAC5, HDAC7, HDAC9, SIRT1, SIRT2, HDAC11); kinase activity, phosphatase activity, ubiquitin ligase activity, deubiquitinating activity, adenylation activity, deadenylation activity, SUMOylating activity, deSUMOylating activity, ribosylation activity, deribosylation activity, myristoylation activity, and demyristoylation activity.

VI. Effector Protein Activity

The effector proteins (e.g., a D2S effector proteins) of the present disclosure may show an enhanced activity (e.g., nucleic acid binding activity, nuclease activity), when measured in a cleavage assay or a reporter assay, under certain conditions relative to a control condition. For example, the effector proteins of the present disclosure may have variable levels of activity based on a buffer formulation, a pH level, temperature, or salt. Buffers consistent with the present disclosure include phosphate buffers, Tris buffers, and HEPES buffers. Effector proteins of the present disclosure can show optimal activity in phosphate buffers, Tris buffers, and HEPES buffers.

By way of non-limiting example, some engineered proteins exhibit optimal activity at lower salinity and viscosity than the protoplasm of their bacterial cell of origin. Also, by way of non-limiting example, bacteria often comprise protoplasmic salt concentrations greater than 250 mM and room temperature intracellular viscosities above 2 centipoise, whereas engineered proteins exhibit optimal activity (e.g., cis cleavage activity) at salt concentrations below 150 mM and viscosities below 1.5 centipoise. The present disclosure leverages these dependencies by providing engineered proteins in solutions optimized for their activity and stability.

Compositions and systems described herein may comprise an engineered effector protein (e.g., a D2S effector protein) in a solution comprising a room temperature viscosity of less than about 15 centipoise, less than about 12 centipoise, less than about 10 centipoise, less than about 8 centipoise, less than about 6 centipoise, less than about 5 centipoise, less than about 4 centipoise, less than about 3 centipoise, less than about 2 centipoise, or less than about 1.5 centipoise.

Compositions and systems may comprise an engineered effector protein in a solution comprising an ionic strength of less than about 500 mM, less than about 400 mM, less than about 300 mM, less than about 250 mM, less than about 200 mM, less than about 150 mM, less than about 100 mM, less than about 80 mM, less than about 60 mM, or less than about 50 mM. Compositions and systems may comprise an engineered effector protein and an assay excipient, which may stabilize a reagent or product, prevent aggregation or precipitation, or enhance or stabilize a detectable signal (e.g., a fluorescent signal). Examples of assay excipients include, but are not limited to, saccharides and saccharide derivatives (e.g., sodium carboxymethyl cellulose and cellulose acetate), detergents, glycols, polyols, esters, buffering agents, alginic acid, and organic solvents (e.g., DMSO).

VII. Multimeric Complexes

Compositions, systems, and methods of the present disclosure may comprise a multimeric complex or uses thereof, wherein the multimeric complex comprises multiple effector proteins (e.g., a D2S effector proteins) that non-covalently interact with one another. A multimeric complex may comprise enhanced activity relative to the activity of any one of its effector proteins alone. For example, a multimeric complex comprising two D2S effector proteins may comprise greater nucleic acid binding affinity, cis cleavage activity, and/or transcollateral cleavage activity than that of either of the D2S effector proteins provided in monomeric form. A multimeric complex may have an affinity for a target region of a target nucleic acid and is capable of catalytic activity (e.g., cleaving, nicking or modifying the nucleic acid) at or near the target region. Multimeric complexes may be activated when complexed with a guide nucleic acid. Multimeric complexes may be activated when complexed with a guide nucleic acid and a target nucleic acid. In some embodiments, the multimeric complex cleaves the target nucleic acid. In some embodiments, the multimeric complex nicks the target nucleic acid.

Various aspects of the present disclosure include compositions and methods comprising multiple effector proteins, and uses thereof, respectively. In some embodiments, the multiple effector proteins form a multimeric complex. In some embodiments, a multimeric complex comprises an effector protein (e.g., a D2S effector protein), wherein the multimeric complex comprises an amino acid sequence that is at least 70% sequence identical to SEQ ID NO: 1 or SEQ ID NO: 2.

In some embodiments, multimeric complexes comprise at least one effector protein (e.g., a D2S effector protein), or a fusion protein thereof, wherein the at least one effector protein comprises an amino acid sequence that is at least 65%, at least 70%, at least 75%, at least 80%, at least 85%, at least 90%, at least 95% or 100% identical to any one of the sequences recited in TABLE 1. In some embodiments, multimeric complexes comprise at least one effector protein (e.g., a D2S effector protein) or a fusion protein thereof, wherein the amino acid sequence of the at least one effector protein is at least 65%, at least 70%, at least 75%, at least 80%, at least 85%, at least 90%, at least 95% or 100% identical to any one of the sequences recited in TABLE 1.

In some embodiments, the multimeric complex is a dimer comprising two effector proteins of identical amino acid sequences. In some embodiments, the multimeric complex comprises a first effector protein and a second effector protein, wherein the amino acid sequence of the first effector protein is at least 90%, at least 92%, at least 94%, at least 96%, at least 98% identical, or at least 99% identical to the amino acid sequence of the second effector protein.

In some embodiments, the multimeric complex is a heterodimeric complex comprising at least two effector proteins of different amino acid sequences. In some embodiments, the multimeric complex is a heterodimeric complex comprising a first effector protein and a second effector protein, wherein the amino acid sequence of the first effector protein is less than 90%, less than 85%, less than 80%, less than 75%, less than 70%, less than 65%, less than 60%, less than 55%, less than 50%, less than 45%, less than 40%, less than 35%, less than 30%, less than 25%, less than 20%, less than 15%, or less than 10% identical to the amino acid sequence of the second effector protein.

In some embodiments, a multimeric complex comprises at least two effector proteins. In some embodiments, a multimeric complex comprises more than two effector proteins. In some embodiments, a multimeric complex comprises two, three or four effector proteins. In some embodiments, at least one effector protein of the multimeric complex comprises an amino acid sequence with at least 65%, at least 70%, at least 75%, at least 80%, at least 85%, at least 90%, at least 95% or 100% identity to any one of the sequences recited in TABLE 1. In some embodiments, each effector protein of the multimeric complex comprises an amino acid sequence with at least 65%, at least 70%, at least 75%, at least 80%, at least 85%, at least 90%, at least 95% or 100% identity to any one of the sequences recited in TABLE 1. In some embodiments, each effector protein of the multimeric complex comprises an amino acid sequence with at least 65%, at least 70%, at least 75%, at least 80%, at least 85%, at least 90%, at least 95% or 100% identity to any one of the sequences recited in TABLE 1.

In some embodiments, an effector protein described herein, or a fusion protein thereof functions as a multimeric complex. In some embodiments, effector proteins form a homodimer. In some embodiments, fusion proteins described herein form a homodimer. In some embodiments, fusion proteins described herein form a heterodimer. In some embodiments, the effector proteins of the multimeric complex dimerize, thereby bringing multiple fusion partners into proximity of one another.

VIII. Engineered Guide RNAs

The compositions, systems, and methods of the present disclosure may comprise a guide nucleic acid or a use thereof. Unless otherwise indicated, compositions, systems and methods comprising guide nucleic acids or uses thereof, as described herein and throughout, include DNA molecules, RNA molecules, or combinations thereof, such as expression vectors that encode a guide nucleic acid. Also, provided herein are compositions comprising a D2S effector protein and an engineered guide RNA. In general, a guide nucleic acid is a nucleic acid molecule that binds to an effector protein (e.g., a Cas effector protein), thereby forming a ribonucleoprotein complex (RNP). In some embodiments, the engineered guide RNA imparts activity or sequence selectivity to the effector protein. When complexed with an effector protein, guide nucleic acids can bring the effector protein into proximity of a target nucleic acid. The guide nucleic acid may also hybridize to a target nucleic acid or a portion thereof. In some embodiments, when a guide nucleic acid and an effector protein form an RNP, at least a portion of the RNP binds, recognizes, and/or hybridizes to a target nucleic acid. Those skilled in the art in reading the below specific examples of guide nucleic acids as used in RNPs described herein, will understand that in some embodiments, a RNP can hybridize to one or more target sequences in a target nucleic acid, thereby allowing the RNP to modify and/or recognize a target nucleic acid or sequence contained therein or to modify and/or recognize non-target sequences depending on the guide nucleic acid, and in some embodiments, the effector protein, used.

In some embodiments, an RNP complex comprising a modified effector protein has a binding affinity for a guide nucleic acid or for a guide nucleic acid-target nucleic acid heteroduplex that is at 1%, 5%, 10%, 20%, 30%, 40%, 50%, 60%, 70%, 80%, 90%, 100%, 120%, 140%, 160%, 180%, 200%, or more relative to the wild-type counterpart. In some embodiments, the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the modified effector protein comprises one or more amino acid alterations at K58, I80, T84, K105, N193, C202, S209, G210, A218, D220, E225, D237, C246, N286, M295, M298, A306, Y315, E335, Q360 and D418. In some embodiments, the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, and wherein the modified effector protein comprises one or more amino acid alterations at K58, I80, T84, K105, N193, C202, S209, G210, A218, D220, E225, D237, C246, N286, M295, M298, A306, Y315, E335, Q360 and D418. In some embodiments, the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the modified effector protein comprises one or more amino acid substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N. In some embodiments, the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, and wherein the modified effector protein comprises one or more amino acid substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N.

In some embodiments, an RNP complex comprising a modified effector protein has a binding affinity for a guide nucleic acid or for a guide nucleic acid-target nucleic acid heteroduplex that is at 1%, 5%, 10%, 20%, 30%, 40%, 50%, 60%, 70%, 80%, 90%, 100%, 120%, 140%, 160%, 180%, 200%, or more relative to the wild-type counterpart, wherein the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1 and also comprises D237A substitution. In some embodiments, an RNP complex comprising a modified effector protein has a binding affinity for a target nucleic acid that is at 1%, 5%, 10%, 20%, 30%, 40%, 50%, 60%, 70%, 80%, 90%, 100%, 120%, 140%, 160%, 180%, 200%, or more relative to the wild-type counterpart, wherein the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1 and also comprises D237A substitution.

In some embodiments, an RNP complex comprising a modified effector protein has a binding affinity for a target nucleic acid that is at 1%, 5%, 10%, 20%, 30%, 40%, 50%, 60%, 70%, 80%, 90%, 100%, 120%, 140%, 160%, 180%, 200%, or more relative to the wild-type counterpart, wherein the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1 and also comprises E335Q substitution. In some embodiments, an RNP complex comprising a modified effector protein has a binding affinity for a target nucleic acid that is at 1%, 5%, 10%, 20%, 30%, 40%, 50%, 60%, 70%, 80%, 90%, 100%, 120%, 140%, 160%, 180%, 200%, or more relative to the wild-type counterpart, wherein the modified effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% similar to SEQ ID NO: 1 and also comprises E335Q substitution.

A guide nucleic acid, as well as any components thereof (e.g., spacer region, repeat region, linker, handle, etc.) may comprise one or more deoxyribonucleotides, ribonucleotides, biochemically or chemically modified nucleotides (e.g., one or more sequence modifications as described herein), and any combinations thereof. A guide nucleic acid may comprise a naturally occurring guide nucleic acid. A guide nucleic acid may comprise a non-naturally occurring guide nucleic acid, including a guide nucleic acid that is designed to contain a chemical or biochemical modification. The guide nucleic acid (e.g., guide RNA) may be chemically synthesized or recombinantly produced. The sequence of the guide nucleic acid, or a portion thereof, may be different from the sequence of a naturally occurring nucleic acid.

Guide nucleic acids and portions thereof may be found in or identified from a CRISPR array present in the genome of a host organism. In some embodiments, a D2S effector protein or a multimeric complex thereof cleaves a precursor RNA ("pre-crRNA") to produce a guide RNA, also referred to as a "mature guide RNA." A D2S effector protein that cleaves pre-crRNA to produce a mature guide RNA is said to have pre-crRNA processing activity. In some embodiments, a repeat region of a guide RNA comprises mutations or truncations relative to respective regions in a corresponding pre-crRNA. In some embodiments, the compositions, systems, and methods of the present disclosure comprise two or more guide nucleic acids (e.g., 2, 3, 4, 5, 6, 7, 9, 10 or more guide nucleic acids), and/or uses thereof. Multiple guide nucleic acids may target an effector protein to different locations in the target nucleic acid by binding to different target sequences within the target nucleic acid. A first guide nucleic acid may bind or cleave a first target sequence and a second guide nucleic acid may bind or cleave a second target sequence. The first target sequence and the second target sequence may be located at least 1, at least 10, at least 20, at least 30, at least 40, at least 50, at least 60, at least 70, at least 80, at least 90 or at least 100 nucleotides apart. The first target sequence and the second target sequence may be located between 100 and 200, 200 and 300, 300 and 400, 400 and 500, 500 and 600, 600 and 700, 700 and 800, 800 and 900 or 900 and 1000 nucleotides of each other. In some embodiments, one or more of the first target sequence and the second target sequence are located in an intron of a gene. In some embodiments, one or more of the first target sequence and the second target sequence are located in an exon of a gene. In some embodiments, one or more of the first target sequence and the second target sequence span an exon-intron junction of a gene. In some embodiments, one or more of the first target sequence and the second target sequence are located on either side of an exon and cutting at both sites results in deletion of the exon. In some embodiments, composition, systems and methods comprise a donor nucleic acid that may be inserted in replacement of a deleted or cleaved sequence of the target nucleic acid. In some embodiments, compositions, systems and methods comprising multiple guide nucleic acids or uses thereof comprise multiple different effector proteins.

In some embodiments, a guide nucleic acid comprises 10, 11, 12, 13, 14, 15, 16, 17, 18, 19, 20, 21, 22, 23, 24, 25, 26, 27, 28, 29, or 30 linked nucleotides. In general, a guide nucleic acid comprises at least 10 linked nucleotides. In some embodiments, a guide nucleic acid comprises at least 25 linked nucleotides. A guide nucleic acid may comprise 10 to 50 linked nucleotides. In some embodiments, the guide nucleic acid comprises or consists essentially of about 12 to about 80 linked nucleotides, about 12 to about 50, about 12 to about 45, about 12 to about 40, about 12 to about 35, about 12 to about 30, about 12 to about 25, from about 12 to about 20, about 12 to about 19, about 19 to about 20, about 19 to about 25, about 19 to about 30, about 19 to about 35, about 19 to about 40, about 19 to about 45, about 19 to about 50, about 19 to about 60, about 20 to about 25, about 20 to about 30, about 20 to about 35, about 20 to about 40, about 20 to about 45, about 20 to about 50, or about 20 to about 60 linked nucleotides. In some embodiments, the guide nucleic acid has about 10 to about 60, about 20 to about 50, or about 30 to about 40 linked nucleotides.

Guide nucleic acids are often referred to as "guide RNA." However, a guide nucleic acid may comprise deoxyribonucleotides. The guide RNA may bind to a target nucleic acid (e.g., a single strand of a target nucleic acid) or a portion thereof (e.g., a target sequence). The guide nucleic acid may comprise a first region complementary to at least a portion of a target nucleic acid (FR1) and a second region that is not complementary to the target nucleic acid (FR2). In some embodiments, FR1 is located 5' to FR2 (FR1-FR2). In some embodiments, FR2 is located 5' to FR1 (FR2-FR1). In some embodiments, the first region comprises a repeat region that interacts with the effector protein. In some embodiments, the second region comprises a spacer region, wherein the spacer region can interact in a sequence-specific manner with (e.g., has complementarity with, or can hybridize to a target sequence in) a target nucleic acid. In some embodiments, a guide nucleic acid comprises at least 10, 11, 12, 13, 14, 15, 16, 17, 18, 19, 20, 21, 22, 23, 24, 25, 26, 27, 28, 29, or 30 contiguous nucleotides that are complementary to a target sequence of a target nucleic acid.

In some embodiments, the guide comprises 10, 11, 12, 13, 14, 15, 16, 17, 18, 19, 20, 21, 22, 23, 24, 25, 26, 27, 28, 29, or 30 linked nucleosides. In general, a guide nucleic acid comprises at least linked nucleosides. In some embodiments, a guide nucleic acid comprises at least 25 linked nucleosides. A guide nucleic acid may comprise 10 to 50 linked nucleosides. In some embodiments, the guide nucleic acid comprises or consists essentially of about 12 to about 80 linked nucleosides, about 12 to about 50, about 12 to about 45, about 12 to about 40, about 12 to about 35, about 12 to about 30, about 12 to about 25, from about 12 to about 20, about 12 to about 19, about 19 to about 20, about 19 to about 25, about 19 to about 30, about 19 to about 35, about 19 to about 40, about 19 to about 45, about 19 to about 50, about 19 to about 60, about 20 to about 25, about 20 to about 30, about 20 to about 35, about 20 to about 40, about 20 to about 45, about 20 to about 50, or about 20 to about 60 linked nucleosides. In some embodiments, the guide nucleic acid has about 10 to about 60, about 20 to about 50, or about 30 to about 40 linked nucleosides.

In some embodiments, the guide nucleic acid comprises a nucleotide sequence as described herein (e.g., TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46). Such nucleotide sequences described herein (e.g., TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46) may be described as a nucleotide sequence of either DNA or RNA, however, no matter the form the sequence is described, it is readily understood that such nucleotide sequences can be revised to be RNA or DNA, as needed, for describing a sequence within a guide nucleic acid itself or the sequence that encodes a guide nucleic acid, such as a nucleotide sequence described herein for a vector. Similarly, disclosure of the nucleotide sequences described herein (e.g., TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46) also discloses the complementary nucleotide sequence, the reverse nucleotide sequence, and the reverse complement nucleotide sequence, any one of which can be a nucleotide sequence for use in a guide nucleic acid as described herein. In some embodiments, the guide nucleic acid comprises a sequence that is at least 65%, at least 70%, at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, a nucleotide sequence encoding the guide nucleic acid comprises a sequence that is at least 65%, at least 70%, at least 75%, at least 80%, at least 85%, at least 90%, at least 95%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46, wherein the nucleotide sequence is a DNA sequence and the guide nucleic acid is an RNA sequence.

In some embodiments, the target nucleic acid is a eukaryotic gene sequence. Such a eukaryotic gene sequence is a sequence of nucleotides that is present in a host eukaryotic cell. Such a sequence of nucleotides is distinguished from nucleotide sequences present in other host cells, such as prokaryotic cells, or viruses. Said sequences present in a eukaryotic cell can be located in a gene, an exon, an intron, a non-coding (e.g., promoter or enhancer) region, a selectable marker, tag, signal, and the like. In some embodiments, the guide nucleic acid may bind to a target nucleic acid, such as DNA or RNA, from a cancer gene or gene associated with a genetic disorder, or an amplicon thereof, as described herein. In some embodiments, the guide nucleic acid comprises a region that is complementary to an equal length portion of a target nucleic acid. In some embodiments, a target nucleic acid is a gene selected from TABLE 8.

In some embodiments, the guide nucleic acid may bind to a target nucleic acid such as a nucleic acid from a bacterium, a virus, a parasite, a protozoa, a fungus or other agents responsible for a disease, or an amplicon thereof. The target nucleic acid may comprise a mutation, such as a single nucleotide polymorphism (SNP). A mutation may confer for example, resistance to a treatment, such as antibiotic treatment. The guide nucleic acid may bind to a target nucleic acid, such as DNA or RNA, from a cancer gene or gene associated with a genetic disorder, or an amplicon thereof, as described herein.

In some embodiments, guide nucleic acids comprise additional elements that contribute additional functionality (e.g., stability, heat resistance, etc.) to the guide nucleic acid. Such elements may be one or more nucleotide alterations, nucleotide sequences, intermolecular secondary structures, or intramolecular secondary structures (e.g., one or more hair pin regions, one or more bulges, etc.).

Guide nucleic acids described herein may bind to a D2S effector protein or multimeric complex thereof, wherein the amino acid sequence of the D2S effector protein is at least 70%, at least 75%, at least 80%, at least 85%, at least 90%, at least 92%, at least 95%, at least 97%, at least 98%, at least 99%, or 100% identical to any one of the sequences recited in TABLE 1, such as SEQ ID NOs: 1-2, or 37. In some embodiments, the effector protein recognizes a PAM sequence comprises any one of sequences recited in TABLE 10, TABLE 36, TABLE 37, TABLE 38, TABLE 42 and TABLE 43, wherein each N is selected from any nucleotide; wherein each V is selected from adenine, cytosine or guanine; and wherein each R is selected from adenine and guanine.

A guide RNA can generally comprise a crRNA or a sgRNA, at least a portion of which is complementary to a target sequence of a target nucleic acid. In some embodiments, the guide RNA is a crRNA. In some embodiments, the guide RNA is a sgRNA.

In some embodiments, the guide RNA comprises a handle sequence that interacts with the effector protein. In some embodiments, the guide RNA comprises a portion of, or all of a repeat sequence that interacts with the effector protein.

In some embodiments, a guide nucleic acid may comprise a spacer sequence, a repeat sequence, a handle sequence, or a combination thereof. In some embodiments, the guide nucleic acid comprises a crRNA comprising a spacer region and a repeat region, or a sgRNA comprising a spacer region and a handle region, wherein at least a portion of the repeat or handle region binds to the D2S effector protein and the spacer region hybridizes to a target sequence of the target nucleic acid.

TABLE 5, TABLE 6, TABLE 7, TABLE 33, TABLE 34 and TABLE 35 provide exemplary compositions comprising D2S effector proteins, crRNAs, tracrRNA sequence, handle sequence, and sgRNAs. Each row in TABLE 5, TABLE 6, TABLE 7, TABLE 33, TABLE 34 and TABLE 35 represents an exemplary composition. In some embodiments, the guide nucleic acid is at least 80% identical to the sequence of any one of SEQ ID NO: 17-21 and 27-30. In some embodiments, the guide nucleic acid is at least 80% identical to the sequence of an equal length portion of any of SEQ ID NO: 22-26. In some embodiments, the guide nucleic acid comprises a nucleotide sequence is at least 65%, at least 70%, at least 75%, at least 80%, at least 85%, at least 90%, at least 95%, or 100% identical to the italic portion of any one of the sequences recited in TABLE 6 and TABLE 7.

In some embodiments, a guide nucleic acid targeting PCSK9 gene comprises any one of the sequences that is at least 65%, at least 70%, at least 75%, at least 80%, at least 85%, at least 90%, at least 95%, or 100% identical to any one of the sequences recited in TABLE 7, wherein the effector protein comprises at least 65%, at least 70%, at least 75%, at least 80%, at least 85%, at least 90%, at least 95%, or 100% sequence identity to the SEQ ID NO: 2. In some embodiments, a guide nucleic acid targeting B2M gene comprises any one of the sequences that is at least 65%, at least 70%, at least 75%, at least 80%, at least 85%, at least 90%, at least 95%, or 100% identical to any one of the sequences recited in TABLE 33, wherein the effector protein comprises at least 65%, at least 70%, at least 75%, at least 80%, at least 85%, at least 90%, at least 95%, or 100% sequence identity to the SEQ ID NO: 1. In some embodiments, a guide nucleic acid targeting TRAC gene comprises any one of the sequences that is at least 65%, at least 70%, at least 75%, at least 80%, at least 85%, at least 90%, at least 95%, or 100% identical to any one of the sequences recited in TABLE 34, wherein the effector protein comprises at least 65%, at least 70%, at least 75%, at least 80%, at least 85%, at least 90%, at least 95%, or 100% sequence identity to the SEQ ID NO: 1. In some embodiments, a guide nucleic acid targeting CIITA gene comprises any one of the sequences that is at least 65%, at least 70%, at least 75%, at least 80%, at least 85%, at least 90%, at least 95%, or 100% identical to any one of the sequences recited in TABLE 35, wherein the effector protein comprises at least 65%, at least 70%, at least 75%, at least 80%, at least 85%, at least 90%, at least 95%, or 100% sequence identity to the SEQ ID NO: 1.

In some embodiments, guide nucleic acids described herein comprise an MS2 aptamer sequence. In some embodiments, the MS2 aptamer sequence comprises a nucleotide sequence that is at least 65%, at least 70%, at least 75%, at least 80%, at least 85%, at least 90%, at least 95%, or 100% identical to ACAUGAGGAUCACCCAUGU (SEQ ID NO: 959). In some embodiments, proteins described herein are fused to an MS2 coat protein (MCP) or an MCP domain that is capable of binding the MS2 aptamer sequence, thereby bringing the protein to the guide nucleic acid. In some embodiments, the protein could be used as a fusion partner described herein. In some embodiments, the protein is an exonuclease. In some embodiments, the MS2 aptamer sequence comprises a nucleotide sequence that is at least 65%, at least 70%, at least 75%, at least 80%, at least 85%, at least 90%, at least 95%, or 100% similar to ACAUGAGGAUCACCCAUGU (SEQ ID NO: 959). In some embodiments, the fusion partner comprises one or more of the MCP domain and sbcB exonuclease. The exemplary sequences for MCP domain and sbcB exonuclease are recited in TABLE 9. In some embodiments, the fusion partner comprises a nucleotide sequence that is at least 65%, at least 70%, at least 75%, at least 80%, at least 85%, at least 90%, at least 95%, at least 99%, or 100% identical to SEQ ID NO: 1098 or SEQ ID NO: 1099. In some embodiments, the fusion partner comprises a nucleotide sequence that is at least 65%, at least 70%, at least 75%, at least 80%, at least 85%, at least 90%, at least 95%, at least 99%, or 100% similar to SEQ ID NO: 1098 or SEQ ID NO: 1099.

Repeat Region

In some embodiments, guide nucleic acids comprise a repeat region that interacts with the effector protein (e.g., a D2S effector protein). The repeat region may also be referred to as a "protein-binding segment." Accordingly, in some embodiments, the repeat sequence of the guide nucleic acid may interact with a D2S effector protein, allowing for the guide nucleic acid and the D2S effector protein to form an RNP complex. Typically, the repeat region is adjacent to the spacer region. In some embodiments, the repeat region is followed by the spacer region in the 5' to 3' direction. In some embodiments, the repeat region is between 10 and 50, 12 and 48, 14 and 46, 16 and 44, and 18 and 42 nucleotides in length. In some embodiments, the repeat region is between 19 and 37 nucleotides in length. In some embodiments, the repeat region comprises a repeat sequence that binds to an effector protein as described herein.

In some embodiments, the repeat region comprises two sequences that are complementary to each other and hybridize to form a double stranded RNA duplex (dsRNA duplex). In some instances, the two sequences are not directly linked and hybridize to form a stem loop structure. In some embodiments, the dsRNA duplex comprises 5, 10, 15, 20 or 25 base pairs (bp). In some embodiments, not all nucleotides of the dsRNA duplex are paired, and therefore the duplex forming region can include a bulge. In some embodiments, the repeat region comprises a hairpin or stem-loop structure, optionally at the 5' portion of the repeat region. In some embodiments, a strand of the stem portion comprises a sequence and the other strand of the stem portion comprises a sequence that is, at least partially, complementary. In some embodiments, a guide nucleic acid comprises nucleotide sequence that when involved in hybridization events may hybridize over one or more segments such that intervening or adjacent segments are not involved in the hybridization event (e.g., a bulge, a loop structure or hairpin structure, etc.).

In some embodiments, the engineered guide RNA comprises a second sequence, at least a portion of which interacts with the effector protein. In some embodiments, the second sequence may be referred to herein as a repeat sequence. TABLE 3 provides illustrative repeat sequences for use with the compositions, systems and methods of the disclosure. In some embodiments, the repeat sequence comprises a sequence that is at least 65%, at least 70%, at least 80%, at least 90%, at least 92%, at least 95%, at least 97%, or at least 99%, or 100% identical to any one of the sequences recited in TABLE 3.

In some embodiments, the repeat sequence comprises one or more nucleotide alterations at one or more positions in any one of the sequences of TABLE 3. Alternative nucleotides can be any one or more of A, C, G, T or U, or a deletion, or an insertion.

In some embodiments, compositions, systems and methods of the disclosure comprises a guide nucleic acid comprising a repeat sequence that is at least 70%, at least 75%, at least 80%, at least 85%, at least 90%, at least 95%, at least 98%, at least 99%, or 100% identical to any one of the sequences recited in TABLE 3, wherein the guide nucleic acid interacts with an effector protein comprising an amino acid sequence that is at least 70%, at least 75%, at least 80%, at least 85%, at least 90%, at least 95%, at least 98%, at least 99%, or 100% identical to any one of the sequences recited in TABLE 1. In some embodiments, the effector protein recognizes a PAM sequence comprises any one of sequences recited in TABLE 10, TABLE 36, TABLE 37, TABLE 38, TABLE 42, and TABLE 43, wherein each N is selected from any nucleotide; wherein each V is selected from adenine, cytosine or guanine; and wherein each R is selected from adenine and guanine.

Handle Sequence

In some embodiments, the engineered guide RNA comprises a second sequence, at least a portion of which interacts with the effector protein (e.g., a D2S effector protein). In some embodiments, the second sequence may be referred to herein as a handle sequence. In some embodiments, the handle sequence may comprise a portion of, or all of a repeat sequence. TABLE 4 provides illustrative handle sequences for use with the compositions, systems and methods of the disclosure. In some embodiments, the repeat sequence comprises a sequence that is at least 65%, at least 70%, at least 80%, at least 90%, at least 92%, at least 95%, at least 97%, or at least 99%, or 100% identical to any one of the sequences recited in TABLE 4.

In some embodiments, the repeat sequence comprises one or more nucleotide alterations at one or more positions in any one of the sequences of TABLE 4. Alternative nucleotides can be any one or more of A, C, G, T or U, or a deletion, or an insertion.

In some embodiments, compositions, systems and methods of the disclosure comprises a guide nucleic acid comprising a handle sequence that is at least 70%, at least 75%, at least 80%, at least 85%, at least 90%, at least 95%, at least 98%, at least 99%, or 100% identical to any one of the sequences recited in TABLE 4, wherein the guide nucleic acid interacts with an effector protein comprising an amino acid sequence that is at least 70%, at least 75%, at least 80%, at least 85%, at least 90%, at least 95%, at least 98%, at least 99%, or 100% identical to any one of the sequences recited in TABLE 1. In some embodiments, the effector protein recognizes a PAM sequence comprises any one of sequences recited in TABLE 10, TABLE 36, TABLE 37, TABLE 38, TABLE 42, and TABLE 43, wherein each N is selected from any nucleotide; wherein each V is selected from adenine, cytosine or guanine; and wherein each R is selected from adenine and guanine.

In some embodiments, compositions, systems and methods of the disclosure comprises a guide nucleic acid comprising a handle sequence comprises an MS2 aptamer sequence. In some embodiments, the MS2 aptamer sequence comprises a nucleotide sequence that is at least 65%, at least 70%, at least 75%, at least 80%, at least 85%, at least 90%, at least 95%, or 100% identical to ACAUGAGGAUCACCCAUGU (SEQ ID NO: 959). In some embodiments, the handle sequence comprising the MS2 aptamer sequence comprises a nucleotide sequence that is at least 65%, at least 70%, at least 75%, at least 80%, at least 85%, at least 90%, at least 95%, or 100% identical to any one of SEQ ID NO: 1065 through SEQ ID NO: 1097. In some embodiments, the handle sequence comprises the intermediary RNA, the repeat sequence, and the MS2 aptamer sequence. In some embodiments, the handle sequence comprises, from 5' to 3' direction, the MS2 aptamer sequence, the intermediary RNA, and the repeat sequence. In some embodiments, the handle sequence comprises, from 5' to 3' direction, the intermediary RNA, the MS2 aptamer sequence, and the repeat sequence.

In some embodiments, the length of a handle sequence is not greater than 50, 56, 66, 67, 68, 69, 70, 71, 72, 73, 95, or 105 linked nucleotides. In some embodiments, the length of a handle sequence is about 30 to about 120 linked nucleotides. In some embodiments, the length of a handle sequence is about 50 to about 105, about 50 to about 95, about 50 to about 73, about 50 to about 71, about 50 to about 70, or about 50 to about 69 linked nucleotides. In some embodiments, the length of a handle sequence is 56 to 105 linked nucleotides, from 56 to 105 linked nucleotides, 66 to 105 linked nucleotides, 67 to 105 linked nucleotides, 68 to 105 linked nucleotides, 69 to 105 linked nucleotides, 70 to 105 linked nucleotides, 71 to 105 linked nucleotides, 72 to 105 linked nucleotides, 73 to 105 linked nucleotides, or 95 to 105 linked nucleotides. In some embodiments, the length of a handle sequence is 40 to 70 nucleotides. In some embodiments, the length of a handle sequence is 50, 56, 66, 67, 68, 69, 70, 71, 72, 73, 95, or 105 linked nucleotides. In some embodiments, the length of a handle sequence is 69 nucleotides.

In some embodiments, a handle sequence comprises a portion of or all of tracrRNA sequences, wherein the portion of or all of the tracrRNA sequences do not comprise repeat hybridization region. In some embodiments, the portion of or all of tracrRNA sequences comprise a stem-loop structure comprising a stem region and a loop region. In some embodiments, the stem region is 4 to 8 linked nucleotides in length. In some embodiments, the stem region is 5 to 6 linked nucleotides in length. In some embodiments, the stem region is 4 to 5 linked nucleotides in length. In some embodiments, the portion of or all of tracrRNA sequence comprises a pseudoknot (e.g., a secondary structure comprising a stem at least partially hybridized to a second stem or half-stem secondary structure). An effector protein may recognize a portion of or all of tracrRNA sequence comprising multiple stem regions. In some embodiments, the nucleotide sequences of the multiple stem regions are identical to one another. In some embodiments, the nucleotide sequences of at least one of the multiple stem regions is not identical to those of the others. In some embodiments, the portion of or all of tracrRNA sequence comprises at least 2, at least 3, at least 4, or at least 5 stem regions.

In some embodiments, the length of a portion of or all of tracrRNA sequence is not greater than 50, 56, 68, 71, 73, 95, or 105 linked nucleotides. In some embodiments, the length of a portion of or all of tracrRNA sequence is about 30 to about 120 linked nucleotides. In some embodiments, the length of a portion of or all of tracrRNA sequence is about 50 to about 105, about 50 to about 95, about 50 to about 73, about 50 to about 71, about 50 to about 68, or about 50 to about 56 linked nucleotides. In some embodiments, the length of a portion of or all of tracrRNA sequence is 56 to 105 linked nucleotides, from 56 to 105 linked nucleotides, 68 to 105 linked nucleotides, 71 to 105 linked nucleotides, 73 to 105 linked nucleotides, or 95 to 105 linked nucleotides.

In some embodiments, the length of a portion of or all of tracrRNA sequence is 40 to 60 nucleotides. In some embodiments, the length of a portion of or all of tracrRNA sequence is 50, 56, 68, 71, 73, 95, or 105 linked nucleotides. In some embodiments, the length of a portion of or all of tracrRNA sequence is 50 nucleotides.

An exemplary portion of or all of tracrRNA sequence may comprise, from 5' to 3', a 5' region, a hairpin region, and a 3' region. In some embodiments, the 5' region may hybridize to the 3' region. In some embodiments, the 5' region does not hybridize to the 3' region. In some embodiments, the 3' region is covalently linked to the crRNA (e.g., through a phosphodiester bond). In some embodiments, a portion of or all of tracrRNA sequence may comprise an un-hybridized region at the 3' end of the portion of or all of tracrRNA sequence. The un-hybridized region may have a length of about 1, about 2, about 3, about 4, about 5, about 6, about 7, about 8, about 9, about 10, about 12, about 14, about 16, about 18, or about 20 linked nucleotides. In some embodiments, the length of the un-hybridized region is 0 to 20 linked nucleotides.

Spacer Region

Typically, the repeat region is adjacent to the spacer region. For example, a guide RNA that interacts with the D2S effector protein comprises a repeat region that is 5' of the spacer region. The spacer region of the guide RNA may comprise complementarity with (e.g., hybridize to) a target sequence of a target nucleic acid. In some embodiments, the spacer region is at least partially complementary to a target nucleic acid. In some embodiments, the spacer region is 15-28 linked nucleosides in length. In some embodiments, the spacer region is 15-26, 15-24, 15-22, 15-20, 15-18, 16-28, 16-26, 16-24, 16-22, 16-20, 16-18, 17-19, 17-26, 17-24, 17-22, 17-20, 17-18, 18-26, 18-24, 18-22, or 18-20 linked nucleosides in length. In some embodiments, the spacer region is 18-24 linked nucleosides in length. In some embodiments, the spacer region is at least 15 linked nucleosides in length. In some embodiments, the spacer region is at least 16, 18, 20, or 22 linked nucleosides in length. In some embodiments, the spacer region comprises at least 10, 11, 12, 13, 14, 15, 16, 17, 18, 19, 20, 21, 22, 23, 24, 25, 26, 27, 28, 29, or 30 nucleotides. In some embodiments, the spacer region is at least 17 linked nucleosides in length. In some embodiments, the spacer region is at least 18 linked nucleosides in length. In some embodiments, the spacer region is at least 20 linked nucleosides in length. In some embodiments, the spacer region is at least 80%, at least 85%, at least 90%, at least 95% or 100% complementary to a target sequence of the target nucleic acid. In some embodiments, the spacer region is 100% complementary to the target sequence of the target nucleic acid. In some embodiments, the spacer region comprises at least 15 contiguous nucleobases that are complementary to the target nucleic acid.

In some embodiments, a spacer sequence or a particular region therein comprises a certain GC content for modulating the activity of an effector protein described herein. For example, in some embodiments, the GC content of a spacer sequence a GC content from about 30% to about 70%, or about 30% to about 40%, or about 40% to about 50%, or about 50% to about 60% or about 60% to about 70%. As another example, in some embodiments, the GC content of a first, a second, and a third nucleotide, or a combination thereof, from the 5' end of a spacer sequence has reduced GC content as described herein. Such GC content can increase nuclease activity of any one of the effector proteins described herein. In some embodiments, the first nucleotide from the 5' end of the spacer sequence is a nucleotide selected from A, T or G. In some embodiments, the first nucleotide from the 5' end of the spacer sequence is a nucleotide selected from A or T. In some embodiments, the first nucleotide from the 5' end of the spacer sequence is a G. In some embodiments, at least two nucleotides of the first three nucleotides from the 5' end of the spacer sequence are nucleotides selected from A and T.

In some embodiments, a length of a spacer sequence modulates nuclease activity of any one of the effector proteins described herein. In some embodiments, the length of the spacer sequence is 15, 16, 17, 18, 19, or 20 nucleotides. In some embodiments, the spacer sequence having a length of 18 or 17 nucleotides relative to the spacer sequence having 20 nucleotides increases nuclease activity of the effector protein. In some embodiments, the spacer sequence having a length of 15 or 16 nucleotides relative to the spacer sequence having 20 nucleotides decreases nuclease activity of the effector protein.

In some embodiments, the guide nucleic acid (gRNA) comprises a spacer sequence, wherein the spacer sequence comprises a nucleotide sequence having at least 80%, at least 85%, at least 90%, at least 95% or 100% sequence identity to a complementary or a reverse complementary sequence of a target sequence. In some embodiments, the target sequence is within a target nucleic acid. In some embodiments, the target nucleic acid comprises any one of the genes recited in TABLE 8.

In some embodiments, the repeat sequence comprises a sequence that is at least 65%, at least 70%, at least 80%, at least 90%, at least 92%, at least 95%, at least 97%, or at least 99%, or 100% identical to any one of the sequences recited in TABLE 28, TABLE 29, TABLE 30, TABLE 31, and TABLE 32. In some embodiments, the guide nucleic acid comprises a spacer sequence targeting PCSK9 gene. In some embodiments, the spacer sequence targeting PCSK9 gene comprises any one of the sequences recited in TABLE 29. In some embodiments, the guide nucleic acid comprises a spacer sequence targeting B2M gene. In some embodiments, the spacer sequence targeting B2M gene comprises any one of the sequences recited in TABLE 30. In some embodiments, the guide nucleic acid comprises a spacer sequence targeting TRAC gene. In some embodiments, the spacer sequence targeting TRAC gene comprises any one of the sequences recited in TABLE 31. In some embodiments, the guide nucleic acid comprises a spacer sequence targeting CIITA gene. In some embodiments, the spacer sequence targeting CIITA gene comprises any one of the sequences recited in TABLE 32.

Intermediary Nucleic Acids

A guide nucleic acid may comprise or be coupled to an intermediary nucleic acid. The intermediary nucleic acid may also be referred to as an intermediary RNA, although it may comprise deoxyribonucleosides in addition to ribonucleosides.

In some embodiments, the intermediary RNA forms a RNP complex along with any one of the effector proteins (e.g., D2S effector protein) described herein. In some embodiments, the RNP complex mediated cleavage of a target nucleic acid is a trans cleavage. In some embodiments, the RNP complex mediated cleavage of a target nucleic acid is a cis cleavage. Sometimes, a guide nucleic acid comprises a portion of crRNA and an intermediary RNA (e.g., the portions of crRNA and intermediary RNA are provided as a single nucleic acid molecule).

In some embodiments, the length of an intermediary RNAs is not greater than 50, 56, 68, 71, 73, 95, or 105 linked nucleosides. In some embodiments, the length of an intermediary RNA is about 30 to about 120 linked nucleosides. In some embodiments, the length of an intermediary RNA is about 50 to about 105, about 50 to about 95, about 50 to about 73, about 50 to about 71, about 50 to about 68, or about 50 to about 56 linked nucleosides. In some embodiments, the length of an intermediary RNA is 56 to 105 linked nucleosides, from 56 to 105 linked nucleosides, 68 to 105 linked nucleosides, 71 to 105 linked nucleosides, 73 to 105 linked nucleosides, or 95 to 105 linked nucleosides. In some embodiments, the length of an intermediary RNA is 40 to 60 nucleotides. In some embodiments, the length of the intermediary RNA is 50, 56, 68, 71, 73, 95, or 105 linked nucleosides. In some embodiments, the length of the intermediary RNA is 50 nucleotides.

In some embodiments, an exemplary intermediary RNA may comprise a stem-loop structure comprising a stem region and a loop region. In some embodiments, the stem region is 4 to 8 linked nucleosides in length. In some embodiments, the stem region is 5 to 6 linked nucleosides in length. In some embodiments, the stem region is 4 to 5 linked nucleosides in length. In some embodiments, the intermediary RNA comprises a pseudoknot (e.g., a secondary structure comprising a stem at least partially hybridized to a second stem or half-stem secondary structure). An effector protein may recognize an intermediary RNA sequence comprising multiple stem regions. In some embodiments, the amino acid sequences of the multiple stem regions are identical to one another. In some embodiments, the amino acid sequences of at least one of the multiple stem regions is not identical to those of the others. In some embodiments, the intermediary RNA sequence comprises at least 2, at least 3, at least 4, or at least 5 stem regions.

In some embodiments, an intermediary RNA may comprise at least a portion of or all of any one of sequences recited in TABLE 4. In some embodiments, the intermediary RNA may comprise at least 8, at least 9, at least 10, at least 11, at least 12, at least 13, at least 14, at least 15, at least 16, at least 17, at least 18, at least 19, at least 20 at least 25, at least 30, at least 40, at least 50, at least 60, at least 70, at least 80, at least 90, at least 100, at least 110, at least 120, at least 130, at least 140, at least 150, at least 160, at least 170, at least 180, at least 190, at least 200, at least 220, at least 240, at least 260, at least 280, at least 300, at least 320, at least 340, or at least 360 contiguous nucleotides of any one of sequences recited in TABLE 4. In some embodiments, the nucleotide sequence of the intermediary RNA comprises at least 70%, at least 75%, at least 80%, at least 85%, at least 90%, at least 95%, at least 98% or 100% sequence identity to any one of sequences recited in TABLE 4. In some embodiments, the nucleotide sequence of the intermediary RNA is at least 70%, at least 75%, at least 80%, at least 85%, at least 90%, at least 95%, at least 98% or 100% identical to an equal length portion of any one of sequences recited in TABLE 4. In some embodiments, the intermediary RNA comprises an MS2 aptamer sequence. In some embodiments, the MS2 aptamer sequence is located within the intermediary RNA. In some embodiments, the MS2 aptamer sequence is located between 5' end and 3' end of the intermediary RNA.

Intermediary RNA in Single Nucleic Acid System

In some embodiments, an intermediary RNA does not comprise a trans activation property when used in a single nucleic acid system. The single nucleic acid system refers to a system wherein the intermediary RNA and a guide nucleic acid function as a single, linked molecule. The trans activation property refers to a property of the intermediary RNA, wherein the intermediary RNA hybridizes with the guide nucleic acid and, thereby, enables an RNP complex to interact with a target nucleic acid, wherein the RNP complex comprises the intermediary RNA, the guide nucleic acid, and any one of the effector proteins described herein. Accordingly, the intermediary RNA lacks trans activation property. In some embodiments, the intermediary RNA comprises a tracrRNA sequence. In some embodiments, the tracrRNA sequence comprises a repeat hybridization region. In some embodiments, the tracrRNA sequence does not comprise a repeat hybridization region. In some embodiments, a repeat sequence of the guide nucleic acid, the intermediary nucleotide sequence, or a combination thereof interacts with the effector protein to form the RNP complex. In some embodiments, the effector protein of the RNP complex recognizes a PAM sequence within the target nucleic acid. In some embodiments, a spacer sequence of the guide nucleic acid is hybridized to a target sequence of the target nucleic acid. In other words, in some embodiments, an RNP complex interacts with a target nucleic acid in a single nucleic acid system, wherein the RNP complex comprises an intermediary RNA, a guide nucleic acid, and any one of the effector proteins described herein, wherein the intermediary RNA and the guide nucleic acid is a single, linked molecule, wherein a repeat sequence of the guide nucleic acid, the intermediary nucleotide sequence, or a combination thereof interacts with the effector protein to form the RNP complex, wherein the effector protein of the RNP complex recognizes a PAM sequence of a target nucleic acid, and wherein a spacer sequence of the guide nucleic acid hybridizes to a target sequence of the target nucleic acid.

In some embodiments, the RNP complex cleaves a target strand of the target nucleic acid. In some embodiments, the RNP complex cleaves a non-target strand of the target nucleic acid. In some embodiments, the effector protein of the RNP complex comprises nuclease activity for cleaving the target nucleic acid. In some embodiments, the effector protein of the RNP complex does not comprise nuclease activity for cleaving the target nucleic acid, wherein a fusion partner protein of the effector protein comprises nuclease activity for cleaving the target nucleic acid. In other words, in some embodiments, an RNP complex interacts with a target nucleic acid in a single nucleic acid system, wherein the RNP complex comprises an intermediary RNA, a guide nucleic acid, and any one of the effector proteins described herein, wherein the intermediary RNA and the guide nucleic acid is a single, linked molecule, wherein a repeat sequence of the guide nucleic acid, the intermediary nucleotide sequence, or a combination thereof interacts with the effector protein to form the RNP complex, wherein the effector protein of the RNP complex recognizes a PAM sequence within the target nucleic acid, wherein a spacer sequence of the guide nucleic acid hybridizes to a target sequence of the target nucleic acid, wherein the effector protein or a fusion partner protein of the effector protein of the RNP complex has nuclease activity, and wherein the RNP complex cleaves a target strand or a non-target strand of the target nucleic acid.

In some embodiments, an intermediary RNA may be linked to a portion of a crRNA to form a composite gRNA. In some embodiments, an intermediary RNA does not comprise a repeat hybridization region. In some embodiments, an intermediary RNA comprises a repeat hybridization region. In some embodiments, an intermediary RNA may comprise a hairpin region. A D2S effector protein may bind a portion of crRNA and/or an intermediary RNA. In some embodiments, a portion of the crRNA and the intermediary RNA are provided as a single nucleic acid (e.g., covalently linked), wherein the intermediary RNA does not comprise a repeat hybridization region. A composition may comprise a crRNA, an intermediary RNA linked to the crRNA, a D2S effector protein, and a detector nucleic acid.

In some embodiments, an exemplary intermediary RNA may comprise, from 5' to 3', a 5' region, a hairpin region, and a 3' region. In some embodiments, the 5' region may hybridize to the 3' region. In some embodiments, the 5' region does not hybridize to the 3' region. In some embodiments, the 3' region is covalently linked to the crRNA (e.g., through a phosphodiester bond). In some embodiments, the intermediary RNA comprises an optional repeat hybridization region. In some embodiments, an intermediary RNA may comprise an un-hybridized region at the 3' end of the intermediary RNA. The un-hybridized region may have a length of about 1, about 2, about 3, about 4, about 5, about 6, about 7, about 8, about 9, about 10, about 12, about 14, about 16, about 18, or about 20 linked nucleosides. In some embodiments, the length of the un-hybridized region is 0 to 20 linked nucleosides.

In some embodiments, compositions, methods and system described herein comprise an effector protein or a nucleic acid (e.g., DNA, RNA or combination thereof) encoding the effector protein and a guide nucleic acid or a nucleotide sequence encoding the guide nucleic acid, wherein the guide nucleic acid comprises an intermediary RNA, and wherein the intermediary RNA interacts with the effector protein. In some embodiments, the nucleotide sequence of the intermediary RNA comprises at least 80%, at least 85%, at least 90%, at least 95%, at least 98% or 100% sequence identity to any one of sequences recited in TABLE 4, wherein the nucleotide sequence is bound by the corresponding effector protein having a sequence that is at least 80%, at least 85%, at least 90%, at least 95%, at least 98% or 100% identical to any one of sequences recited in TABLE 1 as identified in TABLE 4.

In some embodiments, compositions, methods and system described herein comprise intermediary RNA linked to a crRNA or a portion thereof to form a sgRNA (e.g., covalently linked). In some embodiments, a 3' region of the intermediary RNA is covalently linked to the crRNA (e.g., through a phosphodiester bond). In some embodiments, the intermediary RNA comprises at least 80%, at least 85%, at least 90%, at least 95%, at least 98% or 100% identical to any one of sequences recited in TABLE 4, wherein the sgRNA is bound by the corresponding effector protein having a sequence that is at least 80%, at least 85%, at least 90%, at least 95%, at least 98% or 100% identical to any one of sequences recited in TABLE 1 as identified in TABLE 4. In some embodiments, the sgRNA comprises at least 80%, at least 85%, at least 90%, at least 95%, at least 98% or 100% identical to any one of sequences recited in TABLE 4 and TABLE 6, wherein the sgRNA is bound by the corresponding effector protein having a sequence that is at least 80%, at least 85%, at least 90%, at least 95%, at least 98% or 100% identical to any one of sequences recited in TABLE 1 as identified in TABLE 4 and TABLE 6 respectively.

Intermediary RNAs in a Dual Nucleic Acid System

In some embodiments, an intermediary RNA comprises trans activation property when used in a dual nucleic acid system. The dual nucleic acid system refers to a system wherein the intermediary RNA and a guide nucleic acid function as separate, unlinked molecules. In some embodiments, the intermediary RNA comprises a tracrRNA sequence comprising a repeat hybridization region. Accordingly, in the dual nucleic acid system, the repeat hybridization region of the tracrRNA sequence hybridizes with a portion of a repeat sequence of the guide nucleic acid for enabling an RNP complex to interact with a target nucleic acid, wherein the RNP complex comprises the intermediary RNA, the guide nucleic acid, and any one of the effector proteins described herein. In some embodiments, the effector protein of the RNP complex recognizes a PAM sequence within the target nucleic acid. In some embodiments, a spacer sequence of the guide nucleic acid is hybridized to a target sequence of the target nucleic acid. In some embodiments, the intermediary RNA may comprise a tracrRNA sequence comprising the repeat hybridization region. In other words, in some embodiments, an RNP complex interacts with a target nucleic acid in a dual nucleic acid system, wherein the RNP complex comprises an intermediary RNA, a guide nucleic acid, and an effector protein, wherein each of the intermediary RNA, the target nucleic acid, and the guide nucleic acid are separate, unlinked molecules, wherein the intermediary RNA comprises a tracrRNA sequence, wherein a repeat hybridization region of the tracrRNA sequence is hybridized to the guide nucleic acid, wherein the guide nucleic acid, the intermediary nucleotide sequence, or a combination thereof interacts with the effector protein to form the RNP complex, wherein the effector protein of the RNP complex recognizes a PAM sequence within the target nucleic acid, and wherein a spacer sequence of the guide nucleic acid hybridizes to a target sequence of the target nucleic acid.

In some embodiments, the RNP complex cleaves a target strand of the target nucleic acid. In some embodiments, the RNP complex cleaves a non-target strand of the target nucleic acid. In some embodiments, the effector protein of the RNP complex comprises nuclease activity for cleaving the target nucleic acid. In other words, in some embodiments, an RNP complex interacts with a target nucleic acid, wherein the RNP complex comprises an intermediary RNA, a guide nucleic acid, and an effector protein, wherein each of the intermediary RNA, the target nucleic acid, and the guide nucleic acid are separate, unlinked molecules, wherein the intermediary RNA comprises a tracrRNA sequence, wherein a repeat hybridization region of the tracrRNA sequence is hybridized to the guide nucleic acid, wherein the guide nucleic acid, the intermediary nucleotide sequence, or a combination thereof interacts with the effector protein to form the RNP complex, wherein the effector protein of the RNP complex recognizes a PAM sequence within the target nucleic acid, wherein a spacer sequence of the guide nucleic acid hybridizes to a target sequence of the target nucleic acid, wherein the effector protein of the RNP complex has nuclease activity, and wherein the RNP complex cleaves a target strand or a non-target strand of the target nucleic acid.

In some embodiments, the D2S effector protein (RNP) complex may comprise a D2S effector protein complexed with a guide nucleic acid (e.g., a crRNA) and an intermediary RNA. In some embodiments, an intermediary RNA may comprise a repeat hybridization region and a hairpin region. The repeat hybridization region may be positioned 3' of the hairpin region. The hairpin region may comprise a first sequence, a second sequence that is reverse complementary to the first sequence, and a stem-loop linking the first sequence and the second sequence. In some embodiments, the intermediary RNA may be separate from, but forms a complex with a crRNA to form a discrete gRNA system, wherein the intermediary RNA comprises a repeat hybridization region. In some embodiments, the crRNA and the intermediary RNA are separate polynucleotides (e.g., a discrete gRNA system). The repeat hybridization region may hybridize to all or part of the sequence of the repeat of a crRNA. An exemplary intermediary RNA may comprise, from 5' to 3', a 5' region, a hairpin region, a repeat hybridization region, and a 3' region.

crRNA

In general, the engineered guide RNA comprises a CRISPR RNA (crRNA) that is at least partially complementary to a target nucleic acid. In some embodiments, the crRNA of the guide nucleic acid comprises a repeat region and a spacer region, wherein the repeat region binds to the effector protein (e.g., a D2S effector protein) and the spacer region hybridizes to a target sequence of the target nucleic acid. The repeat sequence of the crRNA may interact with an effector protein, allowing for the guide nucleic acid and the effector protein to form an RNP complex. In some embodiments, the repeat region may also be referred to as a "protein-binding segment." Typically, the repeat region is adjacent to the spacer region. For example, a guide RNA that interacts with an effector protein comprises a repeat region that is 5' of the spacer region.

A crRNA may be the product of processing of a longer precursor CRISPR RNA (pre-crRNA) transcribed from the CRISPR array by cleavage of the pre-crRNA within each direct repeat sequence to afford shorter, mature crRNAs. A crRNA may be generated by a variety of mechanisms, including the use of dedicated endonucleases (e.g., Cas6 or Cas5d in Type I and III systems), coupling of a host endonuclease (e.g., RNase III) with tracrRNA (Type II systems), or a ribonuclease activity endogenous to the effector protein itself (e.g., Cpf1, from Type V systems). A crRNA may also be specifically generated outside of processing of a pre-crRNA and individually contacted to an effector protein in vivo or in vitro.

In some embodiments, the compositions comprising a guide RNA and an effector protein (e.g., in a dual nucleic acid system) comprises a trans activating crRNA (tracrRNA) sequence. A tracrRNA sequence may include deoxyribonucleosides, ribonucleosides, chemically modified nucleosides, or any combination thereof. A tracrRNA sequence may be separate from, but form a complex with, a guide nucleic acid and an effector protein. A tracrRNA sequence may include a nucleotide sequence that hybridizes with a portion of a guide nucleic acid (e.g., a repeat hybridization region). A tracrRNA sequence may also form a secondary structure (e.g., one or more hairpin loops) that facilitates the binding of an effector protein to a guide nucleic acid and/or modification activity of an effector protein on a target nucleic acid (e.g., a hairpin region). A tracrRNA sequence may include a repeat hybridization region and a hairpin region. The repeat hybridization region may hybridize to all or part of the repeat sequence of a guide nucleic acid. The repeat hybridization region may be positioned 3' of the hairpin region. The hairpin region may include a first sequence, a second sequence that is reverse complementary to the first sequence, and a stem-loop linking the first sequence and the second sequence. An exemplary tracrRNA sequence may comprise, from 5' to 3', a 5' region, a hairpin region, a repeat hybridization region, and a 3' region.

In some embodiments, the engineered guide RNA comprises a tracrRNA sequence, at least a portion of which interacts with the effector protein. The tracrRNA sequence may hybridize to a portion of the guide RNA that does not hybridize to the target nucleic acid. In some embodiments, a crRNA and tracrRNA sequence function as two separate, unlinked molecules. Accordingly, in some embodiments, a composition comprising effector proteins and guide nucleic acids further comprise a trans activating crRNA (tracrRNA) sequence, at least a portion of which interacts with the effector protein. In some embodiments, a tracrRNA sequence or intermediary RNA is provided separately from the guide nucleic acid. The tracrRNA sequence may hybridize to a portion of the guide nucleic acid that does not hybridize to the target nucleic acid.

In some embodiments, the composition comprising an effector protein and a guide RNA does not comprise a tracrRNA sequence. In some embodiments, an effector protein does not require a tracrRNA sequence to locate and/or cleave a target nucleic acid.

The terms "nucleotide" and "nucleoside" when used in the context of a nucleic acid molecule having multiple residues are used interchangeably and mean the sugar and base of the residue contained in the nucleic acid molecule. The term "nucleobase" when used in the context of a nucleic acid molecule can refer to the base of the residue contained in the nucleic acid molecule, for example, the base of a nucleotide or a nucleoside. The term "guide RNA," as well as crRNA and tracrRNA sequence, includes guide nucleic acids comprising DNA bases and RNA bases.

In some embodiments, the crRNA comprises a nucleobase sequence of any one of SEQ ID NOs: 17-21 as shown in TABLE 5. In some embodiments, the nucleobase sequence of the crRNA is at least 65%, at least 70%, at least 75%, at least 80%, at least 85%, at least 90%, at least 95%, or 100% identical to any one of SEQ ID NO: 17-21. In some embodiments, the tracrRNA sequence comprises a nucleobase sequence of any one of SEQ ID NOs: 22-26 as shown in TABLE 5. In some embodiments, the nucleobase sequence of the tracrRNA sequence is at least 65%, at least 70%, at least 75%, at least 80%, at least 85%, at least 90%, at least 95%, or 100% identical to any one of SEQ ID NO: 22-26.

In some embodiments, compositions disclosed herein comprises an effector protein comprising an amino acid sequence that is at least 70%, at least 75%, at least 80%, at least 85%, at least 90%, at least 95%, at least 99%, or 100% identical to any one of the sequences recited in TABLE 1; a crRNA comprising a nucleobase sequence that is at least 70%, at least 75%, at least 80%, at least 85%, at least 90%, at least 95%, or 100% identical to SEQ ID NO: 17; and a tracrRNA sequence comprising a nucleobase sequence that is at least 70%, at least 75%, at least 80%, at least 85%, at least 90%, at least 95%, or 100% identical to SEQ ID NO: 22. In some embodiments, effector protein comprises an amino acid sequence that is at least 70%, at least 75%, at least 80%, at least 85%, at least 90%, at least 95%, at least 99%, or 100% identical to SEQ ID NO: 1. In some embodiments, the amino acid sequence of the effector protein is at least 70%, at least 75%, at least 80%, at least 85%, at least 90%, at least 95%, at least 99%, or 100% identical to SEQ ID NO: 1. In some embodiments, effector protein comprises an amino acid sequence that is at least 70%, at least 75%, at least 80%, at least 85%, at least 90%, at least 95%, at least 99%, or 100% identical to SEQ ID NO: 37. In some embodiments, the amino acid sequence of the effector protein is at least 70%, at least 75%, at least 80%, at least 85%, at least 90%, at least 95%, at least 99%, or 100% identical to SEQ ID NO: 37.

In some embodiments, compositions, systems and methods of the disclosure comprises a crRNA that is at least 70%, at least 75%, at least 80%, at least 85%, at least 90%, at least 95%, at least 98%, at least 99%, or 100% identical to any one of the sequences recited in TABLE 5, wherein the crRNA interacts with an effector protein comprising an amino acid sequence that is at least 70%, at least 75%, at least 80%, at least 85%, at least 90%, at least 95%, at least 98%, at least 99%, or 100% identical to any one of the sequences recited in TABLE 1. In some embodiments, the effector protein recognizes a PAM sequence comprises any one of sequences recited in TABLE 10, TABLE 36, TABLE 37, TABLE 38, TABLE 42, and TABLE 43, wherein each N is selected from any nucleotide; wherein each V is selected from adenine, cytosine or guanine; and wherein each R is selected from adenine and guanine.

sgRNA

The combination of a spacer sequence (e.g., a nucleotide sequence that hybridizes to a target sequence in a target nucleic acid) with a handle sequence may be referred to herein as a single guide RNA (sgRNA), wherein the spacer sequence and the handle sequence are covalently linked. In some embodiments, the spacer sequence and handle sequence are linked by a phosphodiester bond. In some embodiments, the spacer sequence and handle sequence are linked by one or more linked nucleotides. In some embodiments, the handle sequence may comprise a portion of, or all of, a repeat sequence.

A sgRNA may include deoxyribonucleosides, ribonucleosides, chemically modified nucleosides, or any combination thereof. A sgRNA may also include a nucleotide sequence that forms a secondary structure (e.g., one or more hairpin loops) that facilitates the binding of an effector protein (e.g., a D2S effector protein) to the sgRNA and/or modification activity of an effector protein on a target nucleic acid (e.g., a hairpin region). Such a sequence can be contained within a handle sequence as described herein. A sgRNA may include a handle sequence having a hairpin region, as well as a linker and a repeat sequence. The sgRNA having a handle sequence can have a hairpin region positioned 3' of the linker and/or repeat sequence. The sgRNA having a handle sequence can have a hairpin region positioned 5' of the linker and/or repeat sequence. The hairpin region may include a first sequence, a second sequence that is reverse complementary to the first sequence, and a stem-loop linking the first sequence and the second sequence.

In some embodiments, the handle sequence of a sgRNA comprises a stem-loop structure comprising a stem region and a loop region. In some embodiments, the stem region is 4 to 8 linked nucleotides in length. In some embodiments, the stem region is 5 to 6 linked nucleotides in length. In some embodiments, the stem region is 4 to 5 linked nucleotides in length. In some embodiments, the sgRNA comprises a pseudoknot (e.g., a secondary structure comprising a stem at least partially hybridized to a second stem or half-stem secondary structure). An effector protein may recognize a sgRNA comprising multiple stem regions. In some embodiments, the nucleotide sequences of the multiple stem regions are identical to one another. In some embodiments, the nucleotide sequences of at least one of the multiple stem regions is not identical to those of the others. In some embodiments, the sgRNA comprises at least 2, at least 3, at least 4, or at least 5 stem regions.

In some embodiments, the length of a handle sequence in a sgRNA is not greater than 50, 56, 66, 67, 68, 69, 70, 71, 72, 73, 95, or 105 linked nucleotides. In some embodiments, the length of a handle sequence in a sgRNA is about 30 to about 120 linked nucleotides. In some embodiments, the length of a handle sequence in a sgRNA is about 50 to about 105, about 50 to about 95, about 50 to about 73, about 50 to about 71, about 50 to about 70, or about 50 to about 69 linked nucleotides. In some embodiments, the length of a handle sequence in a sgRNA is 56 to 105 linked nucleotides, from 56 to 105 linked nucleotides, 66 to 105 linked nucleotides, 67 to 105 linked nucleotides, 68 to 105 linked nucleotides, 69 to 105 linked nucleotides, 70 to 105 linked nucleotides, 71 to 105 linked nucleotides, 72 to 105 linked nucleotides, 73 to 105 linked nucleotides, or 95 to 105 linked nucleotides. In some embodiments, the length of a handle sequence in a sgRNA is 40 to 70 nucleotides. In some embodiments, the length of a handle sequence in a sgRNA is 50, 56, 66, 67, 68, 69, 70, 71, 72, 73, 95, or 105 linked nucleotides. In some embodiments, the length of a handle sequence in a sgRNA is 69 nucleotides.

An exemplary handle sequence in a sgRNA may comprise, from 5' to 3', a 5' region, a hairpin region, and a 3' region. In some embodiments, the 5' region may hybridize to the 3' region. In some embodiments, the 5' region does not hybridize to the 3' region. In some embodiments, the 3' region is covalently linked to a spacer sequence (e.g., through a phosphodiester bond). In some embodiments, the 5' region is covalently linked to a spacer sequence (e.g., through a phosphodiester bond).

In some embodiments, sgRNAs comprise a portion of or all of tracrRNA sequences, wherein the portion of or all of the tracrRNA sequences do not comprise repeat hybridization region. In some embodiments, at least a portion of the crRNA, and at least a portion of or all of tracrRNA are provided as a single guide RNA (sgRNA). In some embodiments, the compositions comprising a guide RNA and an effector protein without a tracrRNA sequence (e.g., a single nucleic acid system), wherein the guide RNA is a sgRNA.

In some embodiments, the sgRNA comprises a handle sequence comprising a nucleobase sequence of any one of the sequences recited in TABLE 4. In some embodiments, the sgRNA comprises a repeat sequence comprising a nucleobase sequence of any one of SEQ ID NO: 72, 76, and 77 as shown in TABLE 4. In some embodiments, the sgRNA comprises a nucleobase sequence of any one of the sequences recited in TABLE 6 and TABLE 7. In some embodiments, the nucleobase sequence of the sgRNA is at least 65%, at least 70%, at least 75%, at least 80%, at least 85%, at least 90%, at least 95%, or 100% identical to the sequences recited in TABLE 6 and TABLE 7.

In some embodiments, the sequence of the sgRNA comprises distinct regions as described TABLE 4. For example, in some embodiments, the sgRNA comprises a handle sequence, a handle sequence without a linker or repeat sequence, a linker, a repeat sequence, or a combination thereof. In some embodiments, the handle sequence comprises a sequence having at least 65%, at least 70%, at least 80%, at least 90%, at least 92%, at least 95%, at least 97%, or at least 99%, or 100% sequence identity to any one of the SEQ ID NO: 22, 25, 26, or 73. In some embodiments, the sgRNA comprises a linker comprising the nucleotide sequence of GAAA (SEQ ID NO: 71). In some embodiments, the sgRNA comprises a repeat sequence comprising 70%, at least 80%, at least 90%, at least 92%, at least 95%, at least 97%, or at least 99%, or 100% sequence identity to any one of the SEQ ID NO: 72, 76 or 77. In some embodiments, the sgRNA comprises a portion of the handle sequence of TABLE 4 that is a contiguous sequence of nucleotides of one or more of such distinct regions. For example, in some embodiments, the sgRNA comprises at least 9, at least 10, at least 11, at least 12 contiguous nucleotides of any one of SEQ ID NO: 32, 35, 36, and 70. In some embodiments, the sgRNA comprises at least 30, at least 35, at least 40, at least 45, at least 50 contiguous nucleotides of any one of the SEQ ID NO: 32, 35, 36, and 70.

In some embodiments, compositions disclosed herein comprises a guide nucleic acid comprising a repeat sequence that is at least 65%, at least 70%, at least 75%, at least 80%, at least 85%, at least 90%, at least 95%, or 100% identical to any one of the repeat sequences as set forth in TABLE 3 and comprising a handle sequence without a linker or repeat sequence that is at least 65%, at least 70%, at least 75%, at least 80%, at least 85%, at least 90%, at least 95%, or 100% identical to the handle sequence without a linker or repeat sequence of TABLE 4. In some embodiments, a handle sequence is modified to comprise an MS2 aptamer sequence.

In some embodiments, compositions disclosed herein comprise an effector protein comprising an amino acid sequence that is at least 65%, at least 70%, at least 75%, at least 80%, at least 85%, at least 90%, at least 95%, at least 99%, or 100% identical to the sequence as set forth in TABLE 1; a guide nucleic acid comprising a repeat sequence that is at least 65%, at least 70%, at least 75%, at least 80%, at least 85%, at least 90%, at least 95%, or 100% identical to any one of the sequences as set forth in TABLE 3 and comprising a handle sequence without a linker or repeat sequence that is at least 65%, at least 70%, at least 75%, at least 80%, at least 85%, at least 90%, at least 95%, or 100% identical to the handle sequence without a linker or repeat sequence of TABLE 4.

In some embodiments, the nucleobase sequence of the sgRNA is at least 65%, at least 70%, at least 75%, at least 80%, at least 85%, at least 90%, at least 95%, or 100% identical to any one of the sequences recited in TABLE 3, TABLE 4, TABLE 6, TABLE 7, TABLE 25, TABLE 26, TABLE 30, TABLE 31, TABLE 32, TABLE 33, TABLE 34, TABLE 35, TABLE 45 and TABLE 46.

In some embodiments, compositions, systems and methods of the disclosure comprises an sgRNA comprising a spacer sequence further comprises an MS2 aptamer sequence. In some embodiments, the MS2 aptamer sequence comprises a nucleotide sequence that is at least 65%, at least 70%, at least 75%, at least 80%, at least 85%, at least 90%, at least 95%, or 100% identical to ACAUGAGGAUCACC-CAUGU (SEQ ID NO: 959). In some embodiments, the MS2 aptamer sequence is 5' to the spacer sequence. In some embodiments, the MS2 aptamer sequence is 3' to the spacer sequence. In some embodiments, the sgRNA comprises a nucleotide sequence that is at least 65%, at least 70%, at least 75%, at least 80%, at least 85%, at least 90%, at least 95%, or 100% identical to any one of the sequences recited in TABLE 45, wherein the aptamer sequence comprises a nucleotide sequence that is at least 65%, at least 70%, at least 75%, at least 80%, at least 85%, at least 90%, at least 95%, or 100% identical to ACAUGAGGAUCACCCAUGU (SEQ ID NO: 959).

In some embodiments, the nucleobase sequence of the guide RNA is at least 65%, at least 70%, at least 75%, at least 80%, at least 85%, at least 90%, at least 95%, or 100% identical to any one of SEQ ID NO: 22, 25, 26, 31-36, 70, or 73.

In some embodiments, the nucleobase sequence of the guide RNA is at least 65%, at least 70%, at least 75%, at least 80%, at least 85%, at least 90%, at least 95%, or 100% identical to a guide nucleic acid free of a spacer sequence. In some embodiments, the nucleobase sequence of the guide RNA is any one of: SEQ ID NO: 22, 25, 26, 31-36, 70, or 73.

In some embodiments, at least a portion of the crRNA and at least a portion of the tracrRNA sequence are linked as a sgRNA. In some embodiments, compositions disclosed herein comprises an effector protein comprising an amino acid sequence that is at least 70%, at least 75%, at least 80%, at least 85%, at least 90%, at least 95%, at least 99%, or 100% identical to any one of the sequences recited in TABLE 1; a portion of the crRNA comprising a nucleobase sequence that is at least 70%, at least 75%, at least 80%, at least 85%, at least 90%, at least 95%, or 100% identical to an equal length portion of SEQ ID NO: 17; and a portion of or all of the tracrRNA sequence comprising a nucleobase sequence that is at least 70%, at least 75%, at least 80%, at least 85%, at least 90%, at least 95%, or 100% identical to an equal length portion of SEQ ID NO: 23. In some embodiments, effector protein comprises an amino acid sequence that is at least 70%, at least 75%, at least 80%, at least 85%, at least 90%, at least 95%, at least 99%, or 100% identical to SEQ ID NO: 1 or SEQ ID NO: 37. In some embodiments, the amino acid sequence of the effector protein is at least 70%, at least 75%, at least 80%, at least 85%, at least 90%, at least 95%, at least 99%, or 100% identical to SEQ ID NO: 1 or SEQ ID NO: 37.

In some embodiments, compositions disclosed herein comprises an effector protein comprising an amino acid sequence that is at least 70%, at least 75%, at least 80%, at least 85%, at least 90%, at least 95%, at least 99%, or 100% identical to any one of the sequences recited in TABLE 1; a portion of the crRNA comprising a nucleobase sequence that is at least 70%, at least 75%, at least 80%, at least 85%, at least 90%, at least 95%, or 100% identical to an equal length portion of SEQ ID NO: 19, SEQ ID NO: 20, or SEQ ID NO: 21; and a portion of or all of the tracrRNA sequence comprising a nucleobase sequence that is at least 70%, at least 75%, at least 80%, at least 85%, at least 90%, at least 95%, or 100% identical to an equal length portion of SEQ ID NO: 24, SEQ ID NO: 25, or SEQ ID NO: 26 respectively. In some embodiments, effector protein comprises an amino acid sequence that is at least 70%, at least 75%, at least 80%, at least 85%, at least 90%, at least 95%, at least 99%, or 100% identical to SEQ ID NO: 2 or SEQ ID NO: 37. In some embodiments, the amino acid sequence of the effector protein is at least 70%, at least 75%, at least 80%, at least 85%, at least 90%, at least 95%, at least 99%, or 100% identical to SEQ ID NO: 2 or SEQ ID NO: 37.

In some embodiments, compositions disclosed herein comprises an effector protein comprising an amino acid sequence that is at least 70%, at least 75%, at least 80%, at least 85%, at least 90%, at least 95%, at least 99%, or 100% identical to any one of the sequences recited in TABLE 1; and a guide RNA comprising a nucleobase sequence that is at least 70%, at least 75%, at least 80%, at least 85%, at least 90%, at least 95%, at least 97%, at least 99%, or 100% identical to SEQ ID NO: 27. In some embodiments, the effector protein comprises an amino acid sequence that is at least 70%, at least 75%, at least 80%, at least 85%, at least 90%, at least 95%, at least 99%, or 100% identical to SEQ ID NO: 1 or SEQ ID NO: 37. In some embodiments, the amino acid sequence of the effector protein is at least 70%, at least 75%, at least 80%, at least 85%, at least 90%, at least 95%, at least 99%, or 100% identical to SEQ ID NO: 1 or SEQ ID NO: 37.

In some embodiments, compositions disclosed herein comprises an effector protein comprising an amino acid sequence that is at least 70%, at least 75%, at least 80%, at least 85%, at least 90%, at least 95%, at least 99%, or 100% identical to any one of the sequences recited in TABLE 1; and a guide RNA comprising a nucleobase sequence that is at least 70%, at least 75%, at least 80%, at least 85%, at least 90%, at least 95%, at least 97%, at least 99%, or 100% identical to SEQ ID NO: 22, 25-26, 28-30, 32, 35-36, 70, 73, 129, 146, or 195. In some embodiments, the effector protein comprises an amino acid sequence that is at least 70%, at least 75%, at least 80%, at least 85%, at least 90%, at least 95%, at least 99%, or 100% identical to SEQ ID NO: 2 or SEQ ID NO: 37. In some embodiments, the amino acid sequence of the effector protein is at least 70%, at least 75%, at least 80%, at least 85%, at least 90%, at least 95%, at least 99%, or 100% identical to SEQ ID NO: 2 or SEQ ID NO: 37.

In some embodiments, compositions disclosed herein comprise an effector proteins, wherein an amino acid sequence of the effector protein is at least 70%, at least 75%, at least 80%, at least 85%, at least 90%, at least 95%, at least 99%, or 100% identical to any one of sequences recited in TABLE 1; and a guide RNA comprising a nucleotide sequence that is at least 70%, at least 75%, at least 80%, at least 85%, at least 90%, at least 95%, at least 97%, at least 99%, or 100% identical to any one of sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, any one of the compositions and systems provided herein comprises any one of guide RNA in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, compositions and systems disclosed herein comprises a guide RNA comprising a nucleotide sequence that is at least 70%, at least 75%, at least 80%, at least 85%, at least 90%, at least 95%, at least 97%, at least 99%, or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the effector protein recognizes a PAM sequence comprises any one of sequences recited in TABLE 10, TABLE 36, TABLE 37, TABLE 38, TABLE 42, and TABLE 43, wherein each N is selected from any nucleotide; wherein each V is selected from adenine, cytosine or guanine; and wherein each R is selected from adenine and guanine.

IX. Multiplexed Expression Vectors

Compositions, systems, and methods described herein comprise a vector or a use thereof. A vector can encode one component of a composition or system described herein, or can encode multiple components (e.g., effector proteins, guide nucleic acids, donor nucleic acids, target nucleic acids, etc., as described herein). The vector may be part of a vector system, wherein a vector system comprises a library of vectors each encoding one or more component of a composition or system described herein. In some embodiments, compositions, systems, and methods provided herein comprise a multi-vector system encoding an effector protein (e.g., a D2S effector protein) and a guide nucleic acid described herein, wherein the guide nucleic acid and the effector protein are encoded by the same or different vectors. In some embodiments, the engineered guide and the engineered effector protein are encoded by different vectors of the system.

In some embodiments, a vector may encode one or more engineered effector proteins as described herein. In some embodiments, a vector may encode 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 engineered effector proteins. In some embodiments, an encoded effector protein is operably linked to a promoter that is operable in a target cell, such as a eukaryotic cell. In some embodiments, a vector can encode one or more engineered effector proteins comprising an amino acid sequence of any one of the sequences recited in TABLE 1. In some embodiments, a vector can encode one or more engineered effector proteins comprising an amino acid sequence that is identical to any one of the sequences recited in TABLE 1. In some embodiments, a vector can encode one or more engineered effector proteins comprising an amino acid sequence with at least 75%, 80%, 85%, 90%, 95% or 98% sequence identity to any one of the sequences recited in TABLE 1. In some embodiments, a vector can encode an effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, wherein the effector protein comprises one or more alterations as described herein, such as an alteration at K58, I80, T84, K105, N193, C202, S209, G210, A218, D220, E225, D237, C246, N286, M295, M298, A306, Y315, E335, Q360 and D418. In some embodiments, a vector can encode one or more engineered effector proteins comprising an amino acid sequence that is similar to any one of the sequences recited in TABLE 1. In some embodiments, a vector can encode one or more engineered effector proteins comprising an amino acid sequence with at least 75%, 80%, 85%, 90%, 95% or 98% sequence similarity to any one of the sequences recited in TABLE 1. In some embodiments, a vector can encode an effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the one or more alterations comprises one or more substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N.

In some embodiments, a vector may encode one or more guide nucleic acids. In some embodiments, a vector may encode 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, or 45 different guide nucleic acids. In some embodiments, an encoded guide nucleic acid is operably linked to a promoter that is operable in a target cell, such as a eukaryotic cell. In some embodiments, a vector can encode one or more guide nucleic acids comprising a crRNA sequence of any one of SEQ ID NOs: 17-21. In some embodiments, a vector can encode one or more guide nucleic acids comprising a crRNA sequence with at least 75%, 80%, 85%, 90%, 95% or 98% sequence identity to any one of SEQ ID NOs: 17-21. In some embodiments, a vector can encode one or more guide nucleic acids comprising a crRNA sequence of any one of SEQ ID NOs: 17-21. In some embodiments, a vector can encode one or more guide nucleic acids comprising a portion of or all of tracrRNA sequence with at least 75%, 80%, 85%, 90%, 95% or 98% sequence identity to an equal length portion of any one of SEQ ID NOs: 22-26. In some embodiments, a vector can encode one or more guide nucleic acids comprising a crRNA comprising a portion of sequence of any one of SEQ ID NOs: 22-26. In some embodiments, a portion of or all of the tracrRNA sequence, and a portion of the crRNA may be linked into a single guide RNA. In some embodiments, a vector can encode one or more guide nucleic acids comprising any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, a vector can encode one or more guide nucleic acids comprising a guide sequence with at least 75%, 80%, 85%, 90%, 95% or 98% sequence identity to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, a vector can encode one or more engineered effector proteins comprising an amino acid sequence that is at least 65%, at least 70%, at least 75%, at least 80%, at least 85%, at least 90%, at least 95% or 100% identical to any one of the sequences recited in TABLE 1, and one or more guide nucleic acids comprising a nucleotide sequence that is at least 65%, at least 70%, at least 75%, at least 80%, at least 85%, at least 90%, at least 95% or 100% identical to any one of the sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the vector encoding one or more engineered effector proteins, one or more guide nucleic acids, or combinations thereof are delivered to eukaryotic cells. In some embodiments, the eukaryotic cells comprise cancer cells, HEK293T cells, naïve T cells (cells that have not encountered their cognate antigens), T-helper cells (CD4$^+$ cells), cytotoxic T-cells (CD8$^+$ cells), natural killer T-cells, primary T-cells, T-regulatory cells (T-reg), and gamma-delta T cells.

In some embodiments, an encoded donor nucleic acid is operably linked to a promoter that is operable in a target cell, such as a eukaryotic cell. In some embodiments, a vector may encode 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more donor nucleic acids.

In some embodiments, an encoded target nucleic acid is operably linked to a promoter that is operable in a target cell, such as a eukaryotic cell. In some embodiments, a vector may encode 1, 2, 3, 4, 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 41, 42, 43, 44, 45, 46, 47, 48, 49, 50 or more target nucleic acids.

In some embodiments, a vector can comprise or encode one or more regulatory elements. Regulatory elements can refer to transcriptional and translational control sequences, such as promoters, enhancers, polyadenylation signals, terminators, protein degradation signals, and the like, that provide for and/or regulate transcription of a non-coding sequence or a coding sequence and/or regulate translation of an encoded polypeptide. In some embodiments, a vector can comprise or encode for one or more additional elements, such as, for example, replication origins, antibiotic resistance (or a nucleic acid encoding the same), a tag (or a nucleic acid encoding the same), selectable markers, and the like.

Vectors described herein can encode a promoter—a regulatory region on a nucleic acid, such as a DNA sequence, capable of initiating transcription of a downstream (3' direction) coding or non-coding sequence. As used herein, a promoter can be bound at its 3' terminus to a nucleic acid the expression or transcription of which is desired, and extends upstream (5' direction) to include bases or elements necessary to initiate transcription or induce expression, which could be measured at a detectable level. A promoter can comprise a nucleotide sequence, referred to herein as a "promoter sequence". A promoter sequence can include a transcription initiation site, and one or more protein binding domains responsible for the binding of transcription machinery, such as RNA polymerase. When eukaryotic promoters are used, such promoters can contain "TATA" boxes and "CAT" boxes. Various promoters, including inducible promoters, may be used to drive expression, i.e., transcriptional activation, of the nucleic acid of interest. Accordingly, in some embodiments, the nucleic acid of interest can be operably linked to a promoter.

Promotors can be any suitable type of promoter envisioned for the compositions, systems, and methods described herein. Examples include constitutively active promoters (e.g., CMV promoter), inducible promoters (e.g., heat shock promoter, tetracycline-regulated promoter, steroid-regulated promoter, metal-regulated promoter, estrogen receptor-regulated promoter, etc.), spatially restricted and/or temporally restricted promoters (e.g., a tissue specific promoter, a cell type specific promoter, etc.), etc. Suitable promoters include, but are not limited to: SV40 early promoter, mouse mammary tumor virus long terminal repeat (LTR) promoter; adenovirus major late promoter (Ad MLP); a herpes simplex virus (HSV) promoter, a cytomegalovirus (CMV) promoter such as the CMV immediate early promoter region (CMVIE), a rous sarcoma virus (RSV) promoter, a human U6 small nuclear promoter (U6), an enhanced U6 promoter, and a human H1 promoter (H1). By transcriptional activation, it is intended that transcription will be increased above basal levels in the target cell by 10 fold, by 100 fold, or by 1000 fold, or more. In addition, vectors used for providing a nucleic acid that, when transcribed, produces an engineered guide nucleic acid and/or a nucleic acid that encodes an effector protein to a cell may include nucleic acid sequences that encode for selectable markers in the target cells, so as to identify cells that have taken up the engineered guide nucleic acid and/or an effector protein.

In general, vectors provided herein comprise at least one promotor or a combination of promoters driving expression or transcription of one or more genome editing tools described herein. In some embodiments, the viral vector comprises a nucleotide sequence of a promoter. In some embodiments, the viral vector comprises two promoters. In some embodiments, the viral vector comprises three promoters. In some embodiments, the length of the promoter is less than about 500, less than about 400, or less than about 300 linked nucleotides. In some embodiments, the length of the promoter is at least 100 linked nucleotides. Non-limiting examples of promoters include CMV, 7SK, EF1a, RPBSA, hPGK, EFS, SV40, PGK1, Ube, human beta actin promoter, CAG, TRE, UAS, Ac5, Polyhedrin, CaMKIIa, GAL1, H1, TEF1, GDS, ADH1, CaMV35S, Ubi, U6, MNDU3, MSCV, Ck8e, SPC5-12, Desmin, MND and CAG.

In some embodiments, the promoter is an inducible promoter that only drives expression of its corresponding gene when a signal is present, e.g., a hormone, a small molecule, a peptide. Non-limiting examples of inducible promoters are the T7 RNA polymerase promoter, the T3 RNA polymerase promoter, the Isopropyl-beta-D-thiogalactopyranoside (IPTG)-regulated promoter, a lactose induced promoter, a heat shock promoter, a tetracycline-regulated promoter (tetracycline-inducible or tetracycline-repressible), a steroid regulated promoter, a metal-regulated promoter, and an estrogen receptor-regulated promoter. In some embodiments, the promoter is an activation-inducible promoter, such as a CD69 promoter, as described further in Kulemzin et al., (2019), BMC Med Genomics, 12:44. In some embodiments, the promoter for expressing effector protein is a muscle-specific promoter. In some embodiments, the muscle-specific promoter comprises Ck8e, SPC5-12, or Desmin promoter sequence. In some embodiments, the promoter for expressing effector protein is a ubiquitous promoter. In some embodiments, the ubiquitous promoter comprises MND or CAG promoter sequence.

In some embodiments, an effector protein (or a nucleic acid (e.g., DNA, RNA or combination thereof) encoding same) and/or an engineered guide nucleic acid (or a nucleic acid that, when transcribed, produces same) are coadministered with a donor nucleic acid. Coadministration can be contact with a target nucleic acid, administered to a cell, such as a host cell, or administered as method of nucleic acid detection, editing, and/or treatment as described herein, in a single vehicle, such as a single expression vector. In some embodiments, an effector protein (or a nucleic acid (e.g., DNA, RNA or combination thereof) encoding same) and/or an engineered guide nucleic acid (or a nucleic acid that, when transcribed, produces same) are not co-administered with donor nucleic acid in a single vehicle. In some embodiments, an effector protein (or a nucleic acid (e.g., DNA, RNA or combination thereof) encoding same), an engineered guide nucleic acid (or a nucleic acid that, when transcribed, produces same), and/or donor nucleic acid are administered in one or more or two or more vehicles, such as one or more, or two or more expression vectors. In some embodiments, the expression vector comprises a nucleotide sequence encoding the effector proteins described herein. In some embodiments, the expression vector comprises a nucleotide sequence encoding the guide nucleic acids described herein. In some embodiments, the expression vector comprises the donor nucleic acids described herein.

Lipid Particles

In some embodiments, compositions and systems provided herein comprise a lipid particle. In some embodiments, a lipid particle is a lipid nanoparticle (LNP). In some embodiments, a lipid or a lipid nanoparticle can encapsulate an expression vector. In some embodiments, a lipid or a lipid nanoparticle can encapsulate the effector protein (e.g., a D2S effector protein), the sgRNA or crRNA, the nucleic acid (e.g., DNA) encoding the effector protein and/or the DNA molecule encoding the sgRNA or crRNA. LNPs are effective for delivery of nucleic acids. Beneficial properties of LNP include ease of manufacture, low cytotoxicity and immunogenicity, high efficiency of nucleic acid encapsulation and cell transfection, multi-dosing capabilities and flexibility of design (Kulkarni et al., (2018) Nucleic Acid Therapeutics, 28(3):146-157). In some embodiments, a method can comprise contacting a cell with an expression vector. In some embodiments, contacting can comprise electroporation, lipofection, or lipid nanoparticle (LNP) delivery of an expression vector.

Viral Vectors

An expression vector can be a viral vector. In some embodiments, a viral vector comprises a nucleic acid to be delivered into a host cell via a recombinantly produced virus or viral particle. The nucleic acid may be single-stranded or double stranded, linear or circular, segmented or non-segmented. The nucleic acid may comprise DNA, RNA, or a combination thereof. In some embodiments, the expression vector is an adeno-associated viral vector. There are a variety of viral vectors that are associated with various types of viruses, including but not limited to retroviruses (e.g., lentiviruses and γ-retroviruses), adenoviruses, arenaviruses, alphaviruses, adeno-associated viruses (AAVs), baculoviruses, vaccinia viruses, herpes simplex viruses and poxviruses. A viral vector provided herein can be derived from or based on any such virus. Often the viral vectors provided herein are an adeno-associated viral vector (AAV vector). Generally, an AAV vector has two inverted terminal repeats (ITRs). According, in some embodiments, the viral vector provided herein comprises two inverted terminal repeats of AAV. The DNA sequence in between the ITRs of an AAV vector provided herein may be referred to herein as the sequence encoding the genome editing tools. These genome editing tools can include, but are not limited to, an effector protein (e.g., a D2S effector protein), effector protein modifications (e.g., nuclear localization signal (NLS), polyA tail), guide nucleic acid(s), respective promoter(s), and a donor nucleic acid, or combinations thereof. In some embodiments, a nuclear localization signal comprises an entity (e.g., peptide) that facilitates localization of a nucleic acid, protein, or small molecule to the nucleus, when present in a cell that contains a nuclear compartment.

In general, viral vectors provided herein comprise at least one promotor or a combination of promoters driving expression or transcription of one or more genome editing tools described herein. In some embodiments, the length of the promoter is less than about 500, less than about 400, or less than about 300 linked nucleotides. In some embodiments, the length of the promoter is at least 100 linked nucleotides. Non-limiting examples of promoters include CMV, EF1a, RPBSA, hPGK, EFS, SV40, PGK1, Ube, human beta actin promoter, CAG, TRE, UAS, Ac5, Polyhedrin, CaMKIIa, GAL1, H1, TEF1, GDS, ADH1, CaMV35S, Ubi, U6, MNDU3, and MSCV. In some embodiments, the promoter is an inducible promoter that only drives expression of its corresponding gene when a signal is present, e.g., a hormone, a small molecule, a peptide. Non-limiting examples of inducible promoters are the T7 RNA polymerase promoter, the T3 RNA polymerase promoter, the Isopropyl-beta-D-thiogalactopyranoside (IPTG)-regulated promoter, a lactose induced promoter, a heat shock promoter, a tetracycline-regulated promoter (tetracycline-inducible or tetracycline-repressible), a steroid regulated promoter, a metal-regulated promoter, and an estrogen receptor-regulated promoter. In some embodiments, the promoter is an activation-inducible promoter, such as a CD69 promoter, as described further in Kulemzin et al., (2019), BMC Med Genomics, 12:44.

In some embodiments, the coding region of the AAV vector forms an intramolecular double-stranded DNA template thereby generating an AAV vector that is a self-complementary AAV (scAAV) vector. In general, the sequence encoding the genome editing tools of an scAAV vector has a length of about 2 kb to about 3 kb. The scAAV vector can comprise nucleotide sequences encoding an effector protein, providing guide nucleic acids described herein, and a donor nucleic acid described herein. In some embodiments, the AAV vector provided herein is a self-inactivating AAV vector.

In some embodiments, an AAV vector provided herein comprises a modification, such as an insertion, deletion, chemical alteration, or synthetic modification, relative to a wild-type AAV vector.

In some embodiments, the viral particle that delivers the viral vector described herein is an AAV. AAVs are characterized by their serotype. Non-limiting examples of AAV serotypes are AAV1, AAV2, AAV3, AAV4, AAV5, AAV6, AAV7, AAV8, AAV9, AAV10, AAV 11, AAV12, scAAV, AAV-rh10, chimeric or hybrid AAV, or any combination, derivative, or variant thereof Producing AAV Particles The AAV particles described herein can be referred to as recombinant AAV (rAAV). Often, rAAV particles are generated by transfecting AAV producing cells with an AAV-containing plasmid carrying the sequence encoding the genome editing tools, a plasmid that carries viral encoding regions, i.e., Rep and Cap gene regions; and a plasmid that provides the helper genes such as E1A, E1B, E2A, E4ORF6 and VA. In some embodiments, the AAV producing cells are mammalian cells. In some embodiments, host cells for rAAV viral particle production are mammalian cells. In some embodiments, a mammalian cell for rAAV viral particle production is a COS cell, a HEK293T cell, a HeLa cell, a KB cell, a derivative thereof, or a combination thereof. In some embodiments, rAAV virus particles can be produced in the mammalian cell culture system by providing the rAAV plasmid to the mammalian cell. In some embodiments, producing rAAV virus particles in a mammalian cell can comprise transfecting vectors that express the rep protein, the capsid protein, and the gene-of-interest expression construct flanked by the ITR sequence on the 5' and 3' ends. Methods of such processes are provided in, for example, Naso et al., BioDrugs, 2017 August; 31(4):317-334 and Benskey et al., (2019), Methods Mol Biol., 1937:3-26, each of which is incorporated by reference in their entireties.

In some embodiments, rAAV is produced in a non-mammalian cell. In some embodiments, rAAV is produced in an insect cell. In some embodiments, an insect cell for producing rAAV viral particles comprises a Sf9 cell. In some embodiments, production of rAAV virus particles in insect cells can comprise baculovirus. In some embodiments, production of rAAV virus particles in insect cells can comprise infecting the insect cells with three recombinant baculoviruses, one carrying the cap gene, one carrying the rep gene, and one carrying the gene-of-interest expression construct enclosed by an ITR on both the 5' and 3' end. In some embodiments, rAAV virus particles are produced by the One Bac system. In some embodiments, rAAV virus particles can be produced by the Two Bac system. In some embodiments, in the Two Bac system, the rep gene and the cap gene of the AAV is integrated into one baculovirus virus genome, and the ITR sequence and the gene-of-interest expression construct is integrated into another baculovirus virus genome. In some embodiments, in the One Bac system, an insect cell line that expresses both the rep protein and the capsid protein is established and infected with a baculovirus virus integrated with the ITR sequence and the gene-of-interest expression construct. Details of such processes are provided in, for example, Smith et. al., (1983), Mol. Cell. Biol., 3(12):2156-65; Urabe et al., (2002), Hum. Gene. Ther., 1; 13(16):1935-43; and Benskey et al., (2019), Methods Mol Biol., 1937:3-26, each of which is incorporated Pooling Guide Nucleic Acids In some embodiments, compositions, systems or methods provided herein comprise a pool of guide nucleic acids. In some embodiments, the pool of guide nucleic acids were tiled against a target nucleic acid, e.g., the genomic locus of interest or uses thereof. In some embodiments, a guide nucleic acid is selected from a group of guide nucleic acids that have been tiled against a nucleic acid sequence of a genomic locus of interest. The genomic locus of interest may belong to a viral genome, a bacterial genome, or a mammalian genome. Non-limiting examples of viral genomes are an HPV genome, an HIV genome, an influenza genome, or a coronavirus genome. Often, these guide nucleic acids are pooled for detecting a target nucleic acid in a single assay. Pooling of guide nucleic acids may ensure broad spectrum identification, or broad coverage, of a target species within a single reaction. This may be particularly helpful in diseases or indications, like sepsis, that may be caused by multiple organisms. The pool of guide nucleic acids may enhance the detection of a target nucleic using systems of methods described herein relative to detection with a single guide nucleic acid. The pool of guide nucleic acids may ensure broad coverage of the target nucleic acid within a single reaction using the methods described herein. In some embodiments, the pool of guide nucleic acids are collectively complementary to at least 50%, at least 55%, at least 60%, at least 65%, at least 70%, at least 75%, at least 80%, at least 85%, at least 90%, at least 95% or 100% of the target nucleic acid. In some embodiments, at least a portion of the guide nucleic acids of the pool overlap in sequence. In some embodiments, at least a portion of the guide nucleic acids of the pool do not overlap in sequence. In some embodiments, the pool of guide nucleic acids comprises at least 2, at least 3, at least 4, at least 5, or at least 6 guide nucleic acids targeting different sequences of a target nucleic acid.

X. Sequence Modifications

Polypeptides (e.g., effector proteins such as D2S effector proteins) and nucleic acids (e.g., engineered guide nucleic acids) described herein can be further modified as described throughout and as further described herein. Examples are modifications of interest that do not alter primary sequence, including chemical derivatization of polypeptides, e.g., acylation, acetylation, carboxylation, amidation, etc. Also included are modifications of glycosylation, e.g. those made by modifying the glycosylation patterns of a polypeptide during its synthesis and processing or in further processing steps; e.g. by exposing the polypeptide to enzymes which affect glycosylation, such as mammalian glycosylating or deglycosylating enzymes. Also embraced are sequences that have phosphorylated amino acid residues, e.g. phosphotyrosine, phosphoserine, or phosphothreonine.

Modifications disclosed herein can also include modification of described polypeptides and/or engineered guide nucleic acids through any suitable method, such as molecular biological techniques and/or synthetic chemistry, to improve their resistance to proteolytic degradation, to change the target sequence specificity, to optimize solubility properties, to alter protein activity (e.g., transcription modulatory activity, enzymatic activity, etc.) or to render them more suitable. Analogs of such polypeptides include those containing residues other than naturally occurring L-amino acids, e.g. D-amino acids or non-naturally occurring synthetic amino acids. D-amino acids may be substituted for some or all of the amino acid residues. Modifications can also include modifications with non-naturally occurring unnatural amino acids. The particular sequence and the manner of preparation will be determined by convenience, economics, purity required, and the like.

Modifications can further include the introduction of various groups to polypeptides and/or engineered guide nucleic acids described herein. For example, groups can be introduced during synthesis or during expression of a polypeptide (e.g., an effector protein), which allow for linking to other molecules or to a surface. Thus, e.g., cysteines can be used to make thioethers, histidines for linking to a metal ion complex, carboxyl groups for forming amides or esters, amino groups for forming amides, and the like.

Modifications can further include modification of nucleic acids described herein (e.g., engineered guide nucleic acids) to provide the nucleic acid with a new or enhanced feature, such as improved stability. Such modifications of a nucleic acid include a base modification, a backbone modification, a sugar modification, or combinations thereof, of one or more nucleotides, nucleosides, or nucleobases in a nucleic acid.

In some embodiments, nucleic acids described herein comprise one or more modifications comprising: 2'O-methyl modified nucleotides, 2' Fluoro modified nucleotides; locked nucleic acid (LNA) modified nucleotides; peptide nucleic acid (PNA) modified nucleotides; nucleotides with phosphorothioate linkages; a 5' cap (e.g., a 7-methylguanylate cap (m7G)), phosphorothioates, chiral phosphorothioates, phosphorodithioates, phosphotriesters, aminoalkylphosphotriesters, methyl and other alkyl phosphonates including 3'-alkylene phosphonates, 5'-alkylene phosphonates and chiral phosphonates, phosphinates, phosphoramidates including 3'-amino phosphoramidate and aminoalkyl phosphoramidates, phosphorodiamidates, thionophosphor amidates, thionoalkylphosphonates, thionoalkylphosphotriesters, selenophosphates and boranophosphates having normal 3'-5' linkages, 2'-5' linked analogs of these, and those having inverted polarity wherein one or more internucleotide linkages is a 3' to 3', 5' to 5' or 2' to 2' linkage; phosphorothioate and/or heteroatom internucleoside linkages, such as —CH2-NH—O—CH2-, —CH2-N(CH3)-O—CH2- (known as a methylene (methylimino) or MMI backbone), —CH2-O—N(CH3)-CH2-, —CH2-N(CH3)-N(CH3)-CH2- and —O—N(CH3)-CH2-CH2- (wherein the native phosphodiester internucleotide linkage is represented as —O—P(=O)(OH)—O—CH2-); morpholino linkages (formed in part from the sugar portion of a nucleoside); morpholino backbones; phosphorodiamidate or other non-phosphodiester internucleoside linkages; siloxane backbones; sulfide, sulfoxide and sulfone backbones; formacetyl and thioformacetyl backbones; methylene formacetyl and thioformacetyl backbones; riboacetyl backbones; alkene containing backbones; sulfamate backbones; methyleneimino and methylenehydrazino backbones; sulfonate and sulfonamide backbones; amide backbones; other backbone modifications having mixed N, O, S and CH2 component parts; and combinations thereof.

XI. Systems

Disclosed herein, in some aspects, are systems for modifying a nucleic acid, comprising any one of the D2S effector proteins described herein, or a multimeric complex thereof. Systems may be used to detect, modify, or edit a target nucleic acid. Systems may be used to modify the activity or expression of a target nucleic acid. In some embodiments, systems comprise a D2S effector protein described herein, a reagent, support medium, or a combination thereof. In some embodiments, the D2S effector protein comprises a D2S effector protein, or a fusion protein thereof, described herein. In some embodiments, the D2S effector protein comprises an amino acid sequence that is at least 70%, at least 75%, at least 80%, at least 85%, at least 90%, at least 95%, or 100% identical to any one of the sequences recited in TABLE 1. In some embodiments, the D2S effector protein comprises an amino acid sequence that is at least 70%, at least 75%, at least 80%, at least 85%, at least 90%, at least 95%, or 100% similar to any one of the sequences recited in TABLE 1. In some embodiments, the amino acid sequence of the D2S effector protein is at least 70%, at least 75%, at least 80%, at least 85%, at least 90%, at least 95%, or 100% identical to any one of the sequences recited in TABLE 1. In some embodiments, the amino acid sequence of the D2S effector protein is at least 70%, at least 75%, at least 80%, at least 85%, at least 90%, at least 95%, or 100% similar to any one of the sequences recited in TABLE 1. In some embodiments, systems described herein comprises an effector protein or a nucleic acid encoding the effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% identical to SEQ ID NO: 1. In some embodiments, systems described herein comprises an effector protein or a nucleic acid encoding the effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1. In some embodiments, systems described herein comprises an effector protein or a nucleic acid encoding the effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or less than 100% identical to SEQ ID NO: 1, and wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, systems described herein comprises an effector protein or a nucleic acid encoding the effector protein, wherein the effector protein comprises an amino acid sequence that is at least 60%, at least 65%, at least 70%, at least 75%, at least 80%, at least 85%, at least 90%, at least 92%, at least 95%, at least 97%, at least 98%, at least 99%, or 100% similar to SEQ ID NO: 1, and wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the one or more alterations comprises one or more substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N. In some embodiments, the system comprises an engineered guide nucleic acid described herein or a nucleic acid encoding the engineered guide nucleic acid. In some embodiments, the engineered guide nucleic acid Such systems may be used for detecting the presence of a target nucleic acid associated with or causative of a disease, such as cancer, a genetic disorder, or an infection. In some embodiments, such methods and systems are useful for phenotyping, genotyping, or determining ancestry. Unless specified otherwise, systems include kits and may be referred to as kits. Unless specified otherwise, systems include devices and may also be referred to as devices. Systems described herein may be provided in the form of a companion diagnostic assay or device, a point-of-care assay or device, or an over-the-counter diagnostic assay/device.

Disclosed herein, in some aspects, are systems comprising at least two components each individually comprising one of the following: (1) any one of the effector proteins described herein or a nucleic acid encoding the effector protein; and (2) any one of the engineered guide RNA described herein or a nucleic acid encoding the engineered guide RNA. In some embodiments, the two components are provided separately. For example, in some embodiments, the effector protein or nucleic acid encoding the effector protein, and the engineered guide nucleic acid or a nucleic acid encoding the engineered guide nucleic acid are in separate compositions. In some embodiments, the two components are provided together. In some embodiments, the effector protein or nucleic acid encoding the effector protein, and the engineered guide nucleic acid or a nucleic acid encoding the engineered guide nucleic acid are in a single composition. In some embodiments, the systems are used for modifying a nucleic acid (e.g., target nucleic acid). In some embodiments, the systems are used for generating a genetically modified cell. In some embodiments, the systems described herein may be used to treat, prevent, or inhibit a disease or syndrome in a subject. Accordingly, in some embodiments, the systems are used in therapy. In some embodiments, the systems are used for agricultural engineering.

Reagents and effector proteins of various systems may be provided in a reagent chamber or on the support medium. Alternatively, the reagent and/or effector protein may be contacted with the reagent chamber or the support medium by the individual using the system. An exemplary reagent chamber is a test well or container. The opening of the reagent chamber may be large enough to accommodate the support medium. Optionally, the system comprises a buffer and a dropper. The buffer may be provided in a dropper bottle for ease of dispensing. The dropper may be disposable and transfer a fixed volume. The dropper may be used to place a sample into the reagent chamber or on the support medium.

System Solutions

In general, systems comprise a solution in which the activity of an effector protein (e.g., a D2S effector protein) occurs. Often, the solution comprises or consists essentially of a buffer. The solution or buffer may comprise a buffering agent, a salt, a crowding agent, a detergent, a reducing agent, a competitor, or a combination thereof. Often the buffer is the primary component or the basis for the solution in which the activity occurs. Thus, concentrations for components of buffers described herein (e.g., buffering agents, salts, crowding agents, detergents, reducing agents, and competitors) are the same or essentially the same as the concentration of these components in the solution in which the activity occurs. In some embodiments, a buffer is required for cell lysis activity or viral lysis activity.

In some embodiments, systems comprise a buffer, wherein the buffer comprise at least one buffering agent. Exemplary buffering agents include HEPES, TRIS, MES, ADA, PIPES, ACES, MOPSO, BIS-TRIS propane, BES, MOPS, TES, DISO, Trizma, TRICINE, GLY-GLY, HEPPS, BICINE, TAPS, A MPD, A MPSO, CHES, CAPSO, AMP, CAPS, phosphate, citrate, acetate, imidazole, or any combination thereof. In some embodiments, the concentration of the buffering agent in the buffer is 1 mM to 200 mM. A buffer compatible with an effector protein may comprise a buffering agent at a concentration of 10 mM to 30 mM. A buffer compatible with an effector protein may comprise a buffering agent at a concentration of about 20 mM. A buffering agent may provide a pH for the buffer or the solution in which the activity of the effector protein occurs. The pH may be 3 to 4, 3.5 to 4.5, 4 to 5, 4.5 to 5.5, 5 to 6, 5.5 to 6.5, 6 to 7, 6.5 to 7.5, 7 to 8, 7.5 to 8.5, 8 to 9, 8.5 to 9.5, 9 to 10, or 9.5 to 10.5.

In some embodiments, systems comprise a solution, wherein the solution comprises at least one salt. In some embodiments, the at least one salt is selected from potassium acetate, magnesium acetate, sodium chloride, potassium chloride, magnesium chloride, calcium chloride, and any combination thereof. In some embodiments, the concentration of the at least one salt in the solution is 5 mM to 100 mM, 5 mM to 10 mM, 1 mM to 60 mM, or 1 mM to 10 mM. In some embodiments, the concentration of the at least one salt is about 105 mM. In some embodiments, the concentration of the at least one salt is about 55 mM. In some embodiments, the concentration of the at least one salt is about 7 mM. In some embodiments, the solution comprises potassium acetate and magnesium acetate. In some embodiments, the solution comprises sodium chloride and magnesium chloride. In some embodiments, the solution comprises potassium chloride and magnesium chloride. In some embodiments, the salt is a magnesium salt and the concentration of magnesium in the solution is at least 5 mM, 7 mM, at least 9 mM, at least 11 mM, at least 13 mM, or at least 15 mM. In some embodiments, the concentration of magnesium is less than 20 mM, less than 18 mM or less than 16 mM.

In some embodiments, systems comprise a solution, wherein the solution comprises at least one crowding agent. A crowding agent may reduce the volume of solvent available for other molecules in the solution, thereby increasing the effective concentrations of said molecules. Exemplary crowding agents include glycerol and bovine serum albumin. In some embodiments, the crowding agent is glycerol. In some embodiments, the concentration of the crowding agent in the solution is 0.01% (v/v) to 10% (v/v). In some embodiments, the concentration of the crowding agent in the solution is 0.5% (v/v) to 10% (v/v).

In some embodiments, systems comprise a solution, wherein the solution comprises at least one detergent. Exemplary detergents include Tween, Triton-X, and IGEPAL. A solution may comprise Tween, Triton-X, or any combination thereof. A solution may comprise Triton-X. A solution may comprise IGEPAL CA-630. In some embodiments, the concentration of the detergent in the solution is 2% (v/v) or less. In some embodiments, the concentration of the detergent in the solution is 1% (v/v) or less. In some embodiments, the concentration of the detergent in the solution is 0.00001% (v/v) to 0.01% (v/v). In some embodiments, the concentration of the detergent in the solution is about 0.010% (v/v).

In some embodiments, systems comprise a solution, wherein the solution comprises at least one reducing agent. Exemplary reducing agents comprise dithiothreitol (DTT), ß-mercaptoethanol (BME), or tris(2-carboxyethyl) phosphine (TCEP). In some embodiments, the reducing agent is DTT. In some embodiments, the concentration of the reducing agent in the solution is 0.01 mM to 100 mM. In some embodiments, the concentration of the reducing agent in the solution is 0.1 mM to 10 mM. In some embodiments, the concentration of the reducing agent in the solution is 0.5 mM to 2 mM. In some embodiments, the concentration of the reducing agent in the solution is 0.01 mM to 100 mM. In some embodiments, the concentration of the reducing agent in the solution is 0.1 mM to 10 mM. In some embodiments, the concentration of the reducing agent in the solution is about 1 mM.

In some embodiments, systems comprise a solution, wherein the solution comprise a competitor. In general, competitors compete with the target nucleic acid or the reporter nucleic acid for cleavage by the effector protein or a dimer thereof. Exemplary competitors include heparin, and imidazole, and salmon sperm DNA. In some embodiments, the concentration of the competitor in the solution is 1 µg/mL to 100 µg/mL. In some embodiments, the concentration of the competitor in the solution is 40 µg/mL to 60 µg/mL.

In some embodiments, systems comprise a solution, wherein the solution comprise a co-factor. In some embodiments, the co-factor allows an effector protein or a multimeric complex thereof to perform a function, including pre-crRNA processing and/or target nucleic acid cleavage. The suitability of a co-factor for an effector protein or a multimeric complex thereof may be assessed, such as by methods based on those described by Sundaresan et al. (*Cell Rep.* 2017 Dec. 26; 21(13): 3728-3739). In some embodiments, an effector or a multimeric complex thereof forms a complex with a co-factor. In some embodiments, the co-factor is a divalent metal ion. In some embodiments, the divalent metal ion is selected from $Mg^{2+}$, $Mn^{2+}$, $Zn^{2+}$, $Ca^{2+}$, $Cu^{2+}$. In some embodiments, the divalent metal ion is $Mg^{2+}$. In some embodiments, the effector protein is a D2S effector protein and the co-factor is $Mg^{2+}$.

Reporters

In some embodiments, systems disclosed herein comprise a reporter. By way of non-limiting and illustrative example, a reporter may comprise a single stranded nucleic acid and a detection moiety (e.g., a labeled single stranded RNA reporter), wherein the nucleic acid is capable of being cleaved by an effector protein (e.g., a D2S CRISPR/Cas protein as disclosed herein) or a multimeric complex thereof, releasing the detection moiety, and, generating a detectable signal. As used herein, "reporter" is used interchangeably with "reporter nucleic acid" or "reporter molecule". The effector proteins disclosed herein, activated upon hybridization of a guide RNA to a target nucleic acid, may cleave the reporter. Cleaving the "reporter" may be referred to herein as cleaving the "reporter nucleic acid," the "reporter molecule," or the "nucleic acid of the reporter." Reporters may comprise RNA. Reporters may comprise DNA. Reporters may be double-stranded. Reporters may be single-stranded.

In some embodiments, reporters comprise a protein capable of generating a signal. A signal may be a calorimetric, potentiometric, amperometric, optical (e.g., fluorescent, colorimetric, etc.), or piezo-electric signal. In some embodiments, the reporter comprises a detection moiety. Suitable detectable labels and/or moieties that may provide a signal include, but are not limited to, an enzyme, a radioisotope, a member of a specific binding pair; a fluorophore; a fluorescent protein; a quantum dot; and the like.

In some embodiments, the reporter comprises a detection moiety and a quenching moiety. In some embodiments, the reporter comprises a cleavage site, wherein the detection moiety is located at a first site on the reporter and the quenching moiety is located at a second site on the reporter, wherein the first site and the second site are separated by the cleavage site. Sometimes the quenching moiety is a fluorescence quenching moiety. In some embodiments, the quenching moiety is 5' to the cleavage site and the detection moiety is 3' to the cleavage site. In some embodiments, the detection moiety is 5' to the cleavage site and the quenching moiety is 3' to the cleavage site. Sometimes the quenching moiety is at the 5' terminus of the nucleic acid of a reporter. Sometimes the detection moiety is at the 3' terminus of the nucleic acid of a reporter. In some embodiments, the detection moiety is at the 5' terminus of the nucleic acid of a reporter. In some embodiments, the quenching moiety is at the 3' terminus of the nucleic acid of a reporter.

Suitable fluorescent proteins include, but are not limited to, green fluorescent protein (GFP) or variants thereof, blue fluorescent variant of GFP (BFP), cyan fluorescent variant of GFP (CFP), yellow fluorescent variant of GFP (YFP), enhanced GFP (EGFP), enhanced CFP (ECFP), enhanced YFP (EYFP), GFPS65T, Emerald, Topaz (TYFP), Venus, Citrine, mCitrine, GFPuv, destabilised EGFP (dEGFP), destabilised ECFP (dECFP), destabilised EYFP (dEYFP), mCFPm, Cerulean, T-Sapphire, CyPet, YPet, mKO, HcRed, t-HcRed, DsRed, DsRed2, DsRed-monomer, J-Red, dimer2, t-dimer2(12), mRFP1, pocilloporin, Renilla GFP, Monster GFP, paGFP, Kaede protein and kindling protein, Phycobiliproteins and Phycobiliprotein conjugates including B-Phycoerythrin, R-Phycoerythrin and Allophycocyanin. Suitable enzymes include, but are not limited to, horse radish peroxidase (HRP), alkaline phosphatase (AP), beta-galactosidase (GAL), glucose-6-phosphate dehydrogenase, beta-N-acetylglucosaminidase, β-glucuronidase, invertase, Xanthine Oxidase, firefly luciferase, and glucose oxidase (GO).

In some embodiments, the detection moiety comprises an invertase. The substrate of the invertase may be sucrose. A DNS reagent may be included in the system to produce a colorimetric change when the invertase converts sucrose to glucose. In some embodiments, the reporter nucleic acid and invertase are conjugated using a heterobifunctional linker via sulfo-SMCC chemistry.

Suitable fluorophores may provide a detectable fluorescence signal in the same range as 6-Fluorescein (Integrated DNA Technologies), IRDye 700 (Integrated DNA Technologies), TYE 665 (Integrated DNA Technologies), Alex Fluor 594 (Integrated DNA Technologies), or ATTO™ 633 (NHS Ester) (Integrated DNA Technologies). Non-limiting examples of fluorophores are fluorescein amidite, 6-Fluorescein, IRDye 700, TYE 665, Alex Fluor 594, or ATTO™ 633 (NHS Ester). The fluorophore may be an infrared fluorophore. The fluorophore may emit fluorescence in the range of 500 nm and 720 nm. In some embodiments, the fluorophore emits fluorescence at a wavelength of 700 nm or higher. In other embodiments, the fluorophore emits fluorescence at about 665 nm. In some embodiments, the fluorophore emits fluorescence in the range of 500 nm to 520 nm, 500 nm to 540 nm, 500 nm to 590 nm, 590 nm to 600 nm, 600 nm to 610 nm, 610 nm to 620 nm, 620 nm to 630 nm, 630 nm to 640 nm, 640 nm to 650 nm, 650 nm to 660 nm, 660 nm to 670 nm, 670 nm to 680 nm, 690 nm to 690 nm, 690 nm to 700 nm, 700 nm to 710 nm, 710 nm to 720 nm, or 720 nm to 730 nm. In some embodiments, the fluorophore emits fluorescence in the range 450 nm to 750 nm, 500 nm to 650 nm, or 550 to 650 nm.

Systems may comprise a quenching moiety. A quenching moiety may be chosen based on its ability to quench the detection moiety. A quenching moiety may be a non-fluorescent fluorescence quencher. A quenching moiety may quench a detection moiety that emits fluorescence in the range of 500 nm and 720 nm. A quenching moiety may quench a detection moiety that emits fluorescence in the range of 500 nm and 720 nm. In some embodiments, the quenching moiety quenches a detection moiety that emits fluorescence at a wavelength of 700 nm or higher. In other embodiments, the quenching moiety quenches a detection moiety that emits fluorescence at about 660 nm or about 670 nm. In some embodiments, the quenching moiety quenches a detection moiety that emits fluorescence in the range of 500 to 520, 500 to 540, 500 to 590, 590 to 600, 600 to 610, 610 to 620, 620 to 630, 630 to 640, 640 to 650, 650 to 660, 660 to 670, 670 to 680, 690 to 690, 690 to 700, 700 to 710, 710 to 720, or 720 to 730 nm. In some embodiments, the quenching moiety quenches a detection moiety that emits fluorescence in the range 450 nm to 750 nm, 500 nm to 650 nm, or 550 to 650 nm. A quenching moiety may quench fluorescein amidite, 6-Fluorescein, IRDye 700, TYE 665, Alex Fluor 594, or ATTO™ 633 (NHS Ester). A quenching moiety may be Iowa Black RQ, Iowa Black FQ or IRDye QC-1 Quencher. A quenching moiety may quench fluorescein amidite, 6-Fluorescein (Integrated DNA Technologies), IRDye 700 (Integrated DNA Technologies), TYE 665 (Integrated DNA Technologies), Alex Fluor 594 (Integrated DNA Technologies), or ATTO™ 633 (NHS Ester) (Integrated DNA Technologies). A quenching moiety may be Iowa Black RQ (Integrated DNA Technologies), Iowa Black FQ (Integrated DNA Technologies) or IRDye QC-1 Quencher (LiCor). Any of the quenching moieties described herein may be from any commercially available source, may be an alternative with a similar function, a generic, or a non-tradename of the quenching moieties listed.

The generation of the detectable signal from the release of the detection moiety indicates that cleavage by the effector protein has occurred and that the sample contains the target nucleic acid. In some embodiments, the detection moiety comprises a fluorescent dye. Sometimes the detection moiety comprises a fluorescence resonance energy transfer (FRET) pair. In some embodiments, the detection moiety comprises an infrared (IR) dye. In some embodiments, the detection moiety comprises an ultraviolet (UV) dye. Alternatively, or in combination, the detection moiety comprises a protein. Sometimes the detection moiety comprises a biotin. Sometimes the detection moiety comprises at least one of avidin or streptavidin. In some embodiments, the detection moiety comprises a polysaccharide, a polymer, or a nanoparticle. In some embodiments, the detection moiety comprises a gold nanoparticle or a latex nanoparticle.

A detection moiety may be any moiety capable of generating a calorimetric, potentiometric, amperometric, optical (e.g., fluorescent, colorimetric, etc.), or piezo-electric signal. A nucleic acid of a reporter, sometimes, is protein-nucleic acid that is capable of generating a calorimetric, potentiometric, amperometric, optical (e.g., fluorescent, colorimetric, etc.), or piezo-electric signal upon cleavage of the nucleic acid. Often a calorimetric signal is heat produced after cleavage of the nucleic acids of a reporter. Sometimes, a calorimetric signal is heat absorbed after cleavage of the nucleic acids of a reporter. A potentiometric signal, for example, is electrical potential produced after cleavage of the nucleic acids of a reporter. An amperometric signal may be movement of electrons produced after the cleavage of nucleic acid of a reporter. Often, the signal is an optical signal, such as a colorimetric signal or a fluorescence signal. An optical signal is, for example, a light output produced after the cleavage of the nucleic acids of a reporter. Sometimes, an optical signal is a change in light absorbance between before and after the cleavage of nucleic acids of a reporter. Often, a piezo-electric signal is a change in mass between before and after the cleavage of the nucleic acid of a reporter.

The detectable signal may be a colorimetric signal or a signal visible by eye. In some embodiments, the detectable signal may be fluorescent, electrical, chemical, electrochemical, or magnetic. In some embodiments, the first detection signal may be generated by binding of the detection moiety to the capture molecule in the detection region, where the first detection signal indicates that the sample contained the target nucleic acid. Sometimes systems are capable of detecting more than one type of target nucleic acid, wherein the system comprises more than one type of guide nucleic acid and more than one type of reporter nucleic acid. In some embodiments, the detectable signal may be generated directly by the cleavage event. Alternatively, or in combination, the detectable signal may be generated indirectly by the signal event. Sometimes the detectable signal is not a fluorescent signal. In some embodiments, the detectable signal may be a colorimetric or color-based signal. In some embodiments, the detected target nucleic acid may be identified based on its spatial location on the detection region of the support medium. In some embodiments, the second detectable signal may be generated in a spatially distinct location than the first generated signal.

In some embodiments, the reporter nucleic acid is a single-stranded nucleic acid sequence comprising ribonucleotides. The nucleic acid of a reporter may be a single-stranded nucleic acid sequence comprising at least one ribonucleotide. In some embodiments, the nucleic acid of a reporter is a single-stranded nucleic acid comprising at least one ribonucleotide residue at an internal position that functions as a cleavage site. In some embodiments, the nucleic acid of a reporter comprises at least 2, at least 3, at least 4, at least 5, at least 6, at least 7, at least 8, at least 9, or at least 10 ribonucleotide residues at an internal position. In some embodiments, the nucleic acid of a reporter comprises from 2 to 10, from 3 to 9, from 4 to 8, or from 5 to 7 ribonucleotide residues at an internal position. Sometimes the ribonucleotide residues are continuous. Alternatively, the ribonucleotide residues are interspersed in between non-ribonucleotide residues. In some embodiments, the nucleic acid of a reporter has only ribonucleotide residues. In some embodiments, the nucleic acid of a reporter has only deoxyribonucleotide residues. In some embodiments, the nucleic acid comprises nucleotides resistant to cleavage by the effector protein described herein. In some embodiments, the nucleic acid of a reporter comprises synthetic nucleotides. In some embodiments, the nucleic acid of a reporter comprises at least one ribonucleotide residue and at least one non-ribonucleotide residue.

In some embodiments, the nucleic acid of a reporter comprises at least one uracil ribonucleotide. In some embodiments, the nucleic acid of a reporter comprises at least two uracil ribonucleotides. Sometimes the nucleic acid of a reporter has only uracil ribonucleotides. In some embodiments, the nucleic acid of a reporter comprises at least one adenine ribonucleotide. In some embodiments, the nucleic acid of a reporter comprises at least two adenine ribonucleotide. In some embodiments, the nucleic acid of a reporter has only adenine ribonucleotides. In some embodiments, the nucleic acid of a reporter comprises at least one cytosine ribonucleotide. In some embodiments, the nucleic acid of a reporter comprises at least two cytosine ribonucleotide. In some embodiments, the nucleic acid of a reporter comprises at least one guanine ribonucleotide. In some embodiments, the nucleic acid of a reporter comprises at least two guanine ribonucleotide. In some embodiments, a nucleic acid of a reporter comprises a single unmodified ribonucleotide. In some embodiments, a nucleic acid of a reporter comprises only unmodified deoxyribonucleotides.

In some embodiments, the nucleic acid of a reporter is 5 to 20, 5 to 15, 5 to 10, 7 to 20, 7 to 15, or 7 to 10 nucleotides in length. In some embodiments, the nucleic acid of a reporter is 3 to 20, 4 to 10, 5 to 10, or 5 to 8 nucleotides in length. In some embodiments, the nucleic acid of a reporter is 5 to 12 nucleotides in length. In some embodiments, the reporter nucleic acid is at least 2, at least 3, at least 4, at least 5, at least 6, at least 7, at least 8, at least 9, at least 10, at least 11, at least 12, at least 13, at least 14, at least 15, at least 16, at least 17, at least 18, at least 19, at least 20, at least 21, at least 22, at least 23, at least 24, at least 25, at least 26, at least 27, at least 28, at least 29, or at least 30 nucleotides in length. In some embodiments, the reporter nucleic acid is 2, 3, 4, 5, 6, 7, 8, 9, 10, 11, 12, 13, 14, 15, 16, 17, 18, 19, 20, 21, 22, 23, 24, 25, 26, 27, 28, 29, or 30 nucleotides in length.

In some embodiments, systems comprise a plurality of reporters. The plurality of reporters may comprise a plurality of signals. In some embodiments, systems comprise at least 2, at least 3, at least 4, at least 5, at least 6, at least 7, at least 8, at least 9, at least 10, at least 11, at least 12, at least 13, at least 14, at least 15, at least 20, at least 30, at least 40, or at least 50 reporters. In some embodiments, there are 2 to 50, 3 to 40, 4 to 30, 5 to 20, or 6 to 10 different reporters.

In some embodiments, systems comprise a D2S effector protein, and a reporter nucleic acid configured to undergo transcollateral cleavage by the D2S effector protein. Transcollateral cleavage of the reporter may generate a signal from reporter or alter a signal from the reporter. In some embodiments, the signal is an optical signal, such as a fluorescence signal or absorbance band. Transcollateral cleavage of the reporter may alter the wavelength, intensity, or polarization of the optical signal. For example, the reporter may comprise a fluorophore and a quencher, such that transcollateral cleavage of the reporter separates the fluorophore and the quencher thereby increasing a fluorescence signal from the fluorophore. Herein, detection of reporter cleavage to determine the presence of a target nucleic acid sequence may be referred to as 'DETECTR'. In some embodiments described herein is a method of assaying for a target nucleic acid in a sample comprising contacting the target nucleic acid with an effector protein, a non-naturally occurring guide nucleic acid that hybridizes to a segment of the target nucleic acid, and a reporter nucleic acid, and assaying for a change in a signal, wherein the change in the signal is produced by cleavage of the reporter nucleic acid.

In the presence of a large amount of non-target nucleic acids, an activity of an effector protein (e.g., a D2S effector protein as disclosed herein) may be inhibited. This is because the activated effector proteins collaterally cleave any nucleic acids. If total nucleic acids are present in large amounts, they may outcompete reporters for the effector proteins. In some embodiments, systems comprise an excess of reporter(s), such that when the system is operated and a solution of the system comprising the reporter is combined with a sample comprising a target nucleic acid, the concentration of the reporter in the combined solution-sample is greater than the concentration of the target nucleic acid. In some embodiments, the sample comprises amplified target nucleic acid. In some embodiments, the sample comprises an unamplified target nucleic acid. In some embodiments, the concentration of the reporter is greater than the concentration of target nucleic acids and non-target nucleic acids. The non-target nucleic acids may be from the original sample, either lysed or unlysed. The non-target nucleic acids may comprise byproducts of amplification. In some embodiments, systems comprise a reporter wherein the concentration of the reporter in a solution 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, at least 20 fold, at least 30 fold, at least 40 fold, at least 50 fold, at least 60 fold, at least 70 fold, at least 80 fold, at least 90 fold, at least 100 fold excess of total nucleic acids. 1.5 fold to 100 fold, 2 fold to 10 fold, 10 fold to 20 fold, 20 fold to 30 fold, 30 fold to 40 fold, 40 fold to 50 fold, 50 fold to 60 fold, 60 fold to 70 fold, 70 fold to 80 fold, 80 fold to 90 fold, 90 fold to 100 fold, 1.5 fold to 10 fold, 1.5 fold to 20 fold, 10 fold to 40 fold, 20 fold to 60 fold, or 10 fold to 80 fold excess of total nucleic acids.

Amplification Reagents Components

In some embodiments, systems described herein comprise a reagent or component for amplifying a nucleic acid. Non-limiting examples of reagents for amplifying a nucleic acid include polymerases, primers, and nucleotides. In some embodiments, systems comprise reagents for nucleic acid amplification of a target nucleic acid in a sample. Nucleic acid amplification of the target nucleic acid may improve at least one of sensitivity, specificity, or accuracy of the assay in detecting the target nucleic acid. In some embodiments, nucleic acid amplification is isothermal nucleic acid amplification, providing for the use of the system or system in remote regions or low resource settings without specialized equipment for amplification. In some embodiments, amplification of the target nucleic acid increases the concentration of the target nucleic acid in the sample relative to the concentration of nucleic acids that do not correspond to the target nucleic acid.

The reagents for nucleic acid amplification may comprise a recombinase, an oligonucleotide primer, a single-stranded DNA binding (SSB) protein, a polymerase, or a combination thereof that is suitable for an amplification reaction. Non-limiting examples of amplification reactions are transcription mediated amplification (TMA), helicase dependent amplification (HDA), or circular helicase dependent amplification (cHDA), strand displacement amplification (SDA), recombinase polymerase amplification (RPA), loop mediated amplification (LAMP), exponential amplification reaction (EXPAR), rolling circle amplification (RCA), ligase chain reaction (LCR), simple method amplifying RNA targets (SMART), single primer isothermal amplification (SPIA), multiple displacement amplification (MDA), nucleic acid sequence based amplification (NASBA), hinge-initiated primer-dependent amplification of nucleic acids (HIP), nicking enzyme amplification reaction (NEAR), and improved multiple displacement amplification (IMDA).

In some embodiments, amplification of the target nucleic acid results in PCR amplicons. In some embodiments, systems comprise a PCR tube, a PCR well or a PCR plate. The wells of the PCR plate may be pre-aliquoted with the reagent for amplifying a nucleic acid, as well as a guide nucleic acid, an effector protein (e.g., a D2S effector protein), a multimeric complex, or any combination thereof. The wells of the PCR plate may be pre-aliquoted with a guide nucleic acid targeting a target sequence, an effector protein capable of being activated when complexed with the guide nucleic acid and the target sequence, and at least one population of a single stranded reporter nucleic acid comprising a detection moiety. A user may thus add the biological sample of interest to a well of the pre-aliquoted PCR plate and measure for the detectable signal with a fluorescent light reader or a visible light reader.

In some embodiments, systems comprise a PCR plate; a guide nucleic acid targeting a target sequence; an effector protein capable of being activated when complexed with the guide nucleic acid and the target sequence; and a single stranded reporter nucleic acid comprising a detection moiety, wherein the reporter nucleic acid is capable of being cleaved by the activated nuclease, thereby generating a detectable signal.

In some embodiments, systems comprise a support medium; a guide nucleic acid targeting a target sequence; and an effector protein capable of being activated when complexed with the guide nucleic acid and the target sequence. In some embodiments, nucleic acid amplification is performed in a nucleic acid amplification region on the support medium. Alternatively, or in combination, the nucleic acid amplification is performed in a reagent chamber, and the resulting sample is applied to the support medium.

In some embodiments, a system for modifying a target nucleic acid comprises a PCR plate; a guide nucleic acid targeting a target sequence; and an effector protein capable of being activated when complexed with the guide nucleic acid and the target sequence. The wells of the PCR plate may be pre-aliquoted with the guide nucleic acid targeting a target sequence, and an effector protein capable of being activated when complexed with the guide nucleic acid and the target sequence. A user may thus add the biological sample of interest to a well of the pre-aliquoted PCR plate.

Often, the nucleic acid amplification is performed for no greater than 1, 2, 3, 4, 5, 6, 7, 8, 9, 10, 11, 12, 13, 14, 15, 16, 17, 18, 19, 20, 25, 30, 40, 50, or 60 minutes, or any value 1 to 60 minutes. Sometimes, the nucleic acid amplification is performed for 1 to 60, 5 to 55, 10 to 50, 15 to 45, 20 to 40, or 25 to 35 minutes. Sometimes, the nucleic acid amplification reaction is performed at a temperature of around 20-45° C. In some embodiments, the nucleic acid amplification reaction is performed at a temperature no greater than 20° C., 25° C., 30° C., 35° C., 37° C., 40° C., 45° C., or any value 20° C. to 45° C. In some embodiments, the nucleic acid amplification reaction is performed at a temperature of at least 20° C., 25° C., 30° C., 35° C., 37° C., 40° C., or 45° C., or any value 20° C. to 45° C. In some embodiments, the nucleic acid amplification reaction is performed at a temperature of 20° C. to 45° C., 25° C. to 40° C., 30° C. to 40° C., or 35° C. to 40° C.

Often, systems comprise primers for amplifying a target nucleic acid to produce an amplification product comprising the target nucleic acid and a PAM. For instance, at least one of the primers may comprise the PAM that is incorporated into the amplification product during amplification. The compositions for amplification of target nucleic acids and methods of use thereof, as described herein, are compatible with any of the methods disclosed herein including methods of assaying for at least one base difference (e.g., assaying for a SNP or a base mutation) in a target nucleic acid sequence, methods of assaying for a target nucleic acid that lacks a PAM by amplifying the target nucleic acid sequence to introduce a PAM, and compositions used in introducing a PAM via amplification into the target nucleic acid sequence.

Additional System Components

In some embodiments, systems include a package, carrier, or container that is compartmentalized to receive one or more containers such as vials, tubes, and the like, each of the container(s) comprising one of the separate elements to be used in a method described herein. Suitable containers include, for example, test wells, bottles, vials, and test tubes. In one embodiment, the containers are formed from a variety of materials such as glass, plastic, or polymers. The system or systems described herein contain packaging materials. Examples of packaging materials include, but are not limited to, pouches, blister packs, bottles, tubes, bags, containers, bottles, and any packaging material suitable for intended mode of use.

A system may include labels listing contents and/or instructions for use, or package inserts with instructions for use. A set of instructions will also typically be included. In one embodiment, a label is on or associated with the container. In some embodiments, a label is on a container when letters, numbers or other characters forming the label are attached, molded or etched into the container itself, a label is associated with a container when it is present within a receptacle or carrier that also holds the container, e.g., as a package insert. In one embodiment, a label is used to indicate that the contents are to be used for a specific therapeutic application. The label also indicates directions for use of the contents, such as in the methods described herein. After packaging the formed product and wrapping or boxing to maintain a sterile barrier, the product may be terminally sterilized by heat sterilization, gas sterilization, gamma irradiation, or by electron beam sterilization. Alternatively, the product may be prepared and packaged by aseptic processing.

In some embodiments, systems comprise a solid support. An RNP or effector protein may be attached to a solid support. The solid support may be an electrode or a bead. The bead may be a magnetic bead. Upon cleavage, the RNP is liberated from the solid support and interacts with other mixtures. For example, upon cleavage of the nucleic acid of the RNP, the effector protein of the RNP flows through a chamber into a mixture comprising a substrate. When the effector protein meets the substrate, a reaction occurs, such as a colorimetric reaction, which is then detected. As another example, the protein is an enzyme substrate, and upon cleavage of the nucleic acid of the enzyme substrate-nucleic acid, the enzyme flows through a chamber into a mixture comprising the enzyme. When the enzyme substrate meets the enzyme, a reaction occurs, such as a calorimetric reaction, which is then detected.

Certain System Conditions

In some embodiments, systems and methods are employed under certain conditions that enhance an activity of the effector protein (e.g., a D2S effector protein) relative to alternative conditions, as measured by a detectable signal released from cleavage of a reporter in the presence of the target nucleic acid. The detectable signal may be generated at about the rate of transcollateral cleavage of a reporter nucleic acid. In some embodiments, the reporter nucleic acid is a homopolymeric reporter nucleic acid comprising 5 to 20 consecutive adenines, 5 to 20 consecutive thymines, 5 to 20 consecutive cytosines, or 5 to 20 consecutive guanines. In some embodiments, the reporter is an RNA-FQ reporter.

In some embodiments, effector proteins disclosed herein recognize, bind, or are activated by, different target nucleic acids having different sequences, but are active toward the same reporter nucleic acid, allowing for facile multiplexing in a single assay having a single ssRNA-FQ reporter.

In some embodiments, systems are employed under certain conditions that enhance transcollateral cleavage activity of an effector protein. In some embodiments, under certain conditions, transcolateral cleavage occurs at a rate of at least 0.005 mmol/min, at least 0.01 mmol/min, at least 0.05 mmol/min, at least 0.1 mmol/min, at least 0.2 mmol/min, at least 0.5 mmol/min, or at least 1 mmol/min. In some embodiments, systems and methods are employed under certain conditions that enhance cis cleavage activity of the effector protein.

Certain conditions that may enhance the activity of an effector protein include a certain salt presence or salt concentration of the solution in which the activity occurs. For example, cis cleavage activity of an effector protein may be inhibited or halted by a high salt concentration. The salt may be a sodium salt, a potassium salt, or a magnesium salt. In some embodiments, the salt is NaCl. In some embodiments, the salt is $KNO_3$. In some embodiments, the salt concentration is less than 150 mM, less than 125 mM, less than 100 mM, less than 75 mM, less than 50 mM, or less than 25 mM.

Certain conditions that may enhance the activity of an effector protein includes the pH of a solution in which the activity. For example, increasing pH may enhance transcollateral activity. For example, the rate of transcollateral activity may increase with increase in pH up to pH 9. In some embodiments, the pH is about 7, about 7.1, about 7.2, about 7.3, about 7.4, about 7.5, about 7.6, about 7.7, about 7.8, about 7.9, about 8, about 8.1, about 8.2, about 8.3, about 8.4, about 8.5, about 8.6, about 8.7, about 8.8, about 8.9, or about 9. In some embodiments, the pH is 7 to 7.5, 7.5 to 8, 8 to 8.5, 8.5 to 9, or 7 to 8.5. In some embodiments, the pH is less than 7. In some embodiments, the pH is greater than 7.

Certain conditions that may enhance the activity of an effector protein includes the temperature at which the activity is performed. In some embodiments, the temperature is about 25° C. to about 50° C. In some embodiments, the temperature is about 20° C. to about 40° C., about 30° C. to about 50° C., or about 40° C. to about 60° C. In some embodiments, the temperature is about 25° C., about 30° C., about 35° C., about 40° C., about 45° C., or about 50° C.

In some embodiments, a final concentration an effector protein in a buffer of a system is 1 pM to 1 nM, 1 pM to 10 pM, 10 pM to 100 pM, 100 pM to 1 nM, 1 nM to 10 nM, 10 nM to 20 nM, 20 nM to 30 nM, 30 nM to 40 nM, 40 nM to 50 nM, 50 nM to 60 nM, 60 nM to 70 nM, 70 nM to 80 nM, 80 nM to 90 nM, 90 nM to 100 nM, 100 nM to 200 nM, 200 nM to 300 nM, 300 nM to 400 nM, 400 nM to 500 nM, 500 nM to 600 nM, 600 nM to 700 nM, 700 nM to 800 nM, 800 nM to 900 nM, 900 nM to 1000 nM. The final concentration of the sgRNA complementary to the target nucleic acid may be 1 pM to 1 nM, 1 pM to 10 pM, 10 pM to 100 pM, 100 pM to 1 nM, 1 nM to 10 nM, 10 nM to 20 nM, 20 nM to 30 nM, 30 nM to 40 nM, 40 nM to 50 nM, 50 nM to 60 nM, 60 nM to 70 nM, 70 nM to 80 nM, 80 nM to 90 nM, 90 nM to 100 nM, 100 nM to 200 nM, 200 nM to 300 nM, 300 nM to 400 nM, 400 nM to 500 nM, 500 nM to 600 nM, 600 nM to 700 nM, 700 nM to 800 nM, 800 nM to 900 nM, 900 nM to 1000 nM. The concentration of the ssDNA-FQ reporter may be 1 pM to 1 nM, 1 pM to 10 pM, 10 pM to 100 pM, 100 pM to 1 nM, 1 nM to 10 nM, 10 nM to 20 nM, 20 nM to 30 nM, 30 nM to 40 nM, 40 nM to 50 nM, 50 nM to 60 nM, 60 nM to 70 nM, 70 nM to 80 nM, 80 nM to 90 nM, 90 nM to 100 nM, 100 nM to 200 nM, 200 nM to 300 nM, 300 nM to 400 nM, 400 nM to 500 nM, 500 nM to 600 nM, 600 nM to 700 nM, 700 nM to 800 nM, 800 nM to 900 nM, 900 nM to 1000 nM.

In some embodiments, systems comprise an excess volume of solution comprising the guide nucleic acid, the effector protein and the reporter, which contacts a smaller volume comprising a sample with a target nucleic acid. The smaller volume comprising the sample may be unlysed sample, lysed sample, or lysed sample which has undergone any combination of reverse transcription, amplification, and in vitro transcription. The presence of various reagents, (such as buffer, magnesium sulfate, salts, the pH, a reducing agent, primers, dNTPs, NTPs, cellular lysates, non-target nucleic acids, primers, or other components), in a crude, non-lysed sample, a lysed sample, or a lysed and amplified sample, may inhibit the ability of the effector protein to become activated or to find and cleave the nucleic acid of the reporter. This may be due to nucleic acids that are not the reporter outcompeting the nucleic acid of the reporter, for the effector protein. Alternatively, various reagents in the sample may simply inhibit the activity of the effector protein. Thus, the compositions and methods provided herein for contacting an excess volume comprising the engineered guide nucleic acid, the effector protein, and the reporter to a smaller volume comprising the sample with the target nucleic acid of interest provides for superior detection of the target nucleic acid by ensuring that the effector protein is able to find and cleaves the nucleic acid of the reporter. In some embodiments, the volume comprising the guide nucleic acid, the effector protein, and the reporter (may be referred to as "a second volume") is 4-fold greater than a volume comprising the sample (may be referred to as "a first volume"). In some embodiments, the volume comprising the guide nucleic acid, the effector protein, and the reporter (may be referred to as "a second volume") is at least 1.5 fold, at least 2 fold, at least 3 fold, at least 4 fold, at least 5 fold, at least 6 fold, at least 7 fold, at least 8 fold, at least 9 fold, at least 10 fold, at least 11 fold, at least 12 fold, at least 13 fold, at least 14 fold, at least 15 fold, at least 16 fold, at least 17 fold, at least 18 fold, at least 19 fold, at least 20 fold, at least 30 fold, at least 40 fold, at least 50 fold, at least 60 fold, at least 70 fold, at least 80 fold, at least 90 fold, at least 100 fold, 1.5 fold to 100 fold, 2 fold to 10 fold, 10 fold to 20 fold, 20 fold to 30 fold, 30 fold to 40 fold, 40 fold to 50 fold, 50 fold to 60 fold, 60 fold to 70 fold, 70 fold to 80 fold, 80 fold to 90 fold, 90 fold to 100 fold, 1.5 fold to 10 fold, 1.5 fold to 20 fold, 10 fold to 40 fold, 20 fold to 60 fold, or 10 fold to 80 fold greater than a volume comprising the sample (may be referred to as "a first volume"). In some embodiments, the volume comprising the sample is at least 0.5 µL, at least 1 µL, at least at least 1 µL, at least 2 µL, at least 3 µL, at least 4 µL, at least 5 µL, at least 6 µL, at least 7 µL, at least 8 µL, at least 9 µL, at least 10 µL, at least 11 µL, at least 12 µL, at least 13 µL, at least 14 µL, at least 15 µL, at least 16 µL, at least 17 µL, at least 18 µL, at least 19 µL, at least 20 µL, at least 25 µL, at least 30 µL, at least 35 µL, at least 40 µL, at least 45 µL, at least 50 µL, at least 55 µL, at least 60 µL, at least 65 µL, at least 70 µL, at least 75 µL, at least 80 µL, at least 85 µL, at least 90 µL, at least 95 µL, at least 100 µL, 0.5 µL to 5 µL µL, 5 µL to 10 µL, 10 µL to 15 µL, 15 µL to 20 µL, 20 µL to 25 µL, 25 µL to 30 µL, 30 µL to 35 µL, 35 µL to 40 µL, 40 µL to 45 µL, 45 µL to 50 µL, 10 µL to 20 µL, 5 µL to 20 µL, 1 µL to 40 µL, 2 µL to 10 µL, or 1 µL to 10 µL. In some embodiments, the volume comprising the effector protein, the guide nucleic acid, and the reporter is at least 10 µL, at least 11 µL, at least 12 µL, at least 13 µL, at least 14 µL, at least 15 µL, at least 16 µL, at least 17 µL, at least 18 µL, at least 19 µL, at least 20 µL, at least 21 µL, at least 22 µL, at least 23 µL, at least 24 µL, at least 25 µL, at least 26 µL, at least 27 µL, at least 28 µL, at least 29 µL, at least 30 µL, at least 40 µL, at least 50 µL, at least 60 µL, at least 70 µL, at least 80 µL, at least 90 µL, at least 100 µL, at least 150 µL, at least 200 µL, at least 250 µL, at least 300 µL, at least 350 µL, at least 400 µL, at least 450 µL, at least 500 µL, 10 µL to 15 µL µL, 15 µL to 20 µL, 20 µL to 25 µL, 25 µL to 30 µL, 30 µL to 35 µL, 35 µL to 40 µL, 40 µL to 45 µL, 45 µL to 50 µL, 50 µL to 55 µL, 55 µL to 60 µL, 60 µL to 65 µL, 65 µL to 70 µL, 70 µL to 75 µL, 75 µL to 80 µL, 80 µL to 85 µL, 85 µL to 90 µL, 90 µL to 95 µL, 95 µL to 100 µL, 100 µL to 150 µL, 150 µL to 200 µL, 200 µL to 250 µL, 250 µL to 300 µL, 300 µL to 350 µL, 350 µL to 400 µL, 400 µL to 450 µL, 450 µL to 500 µL, 10 µL to 20 µL, 10 µL to 30 µL, 25 µL to 35 µL, 10 µL to 40 µL, 20 µL to 50 µL, 18 µL to 28 µL, or 17 µL to 22 µL.

In some embodiments, systems comprise an effector protein that nicks a target nucleic acid, thereby producing a nicked product. In some embodiments, systems cleave a target nucleic acid, thereby producing a linearized product. In some embodiments, systems produce at least 50%, at least 55%, at least 60%, at least 65%, at least 70%, at least 75%, at least 80%, at least 85%, at least 90 or at least 95% of a maximum amount of nicked product within 1 minute, where the maximum amount of nicked product is the maximum amount detected within a 60 minute period from when the target nucleic acid is mixed with the effector protein or the multimeric complex thereof. In some embodiments, systems produce at least 50%, at least 55%, at least 60%, at least 65%, at least 70%, at least 75%, at least 80%, at least 85%, at least 90 or at least 95% of a maximum amount of linearized product within 1 minute, where the maximum amount of linearized product is the maximum amount detected within a 60 minute period from when the target nucleic acid is mixed with the effector protein. In some embodiments, at least 80% of the maximum amount of linearized product is produced within 1 minute. In some embodiments, at least 90% of the maximum amount of linearized product is produced within 1 minute.

Formulations for Introducing Systems and Compositions into a Target Cell

A guide RNA (or a nucleic acid comprising a nucleotide sequence encoding same) and/or an effector protein (e.g., a D2S effector protein) described herein can be introduced into a host cell by any of a variety of well-known methods. As a non-limiting example, a guide RNA and/or effector protein can be combined with a lipid. As another non-limiting example, a guide RNA and/or effector protein can be combined with a particle, or formulated into a particle.

Methods of introducing a nucleic acid and/or protein into a host cell are known in the art, and any convenient method can be used to introduce a subject nucleic acid (e.g., an expression construct/vector) into a target cell (e.g., a human cell, and the like). Suitable methods include, e.g., viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery (see, e.g., Panyam et al. Adv Drug Deliv Rev. 2012 Sep. 13. pii: S0169-409X(12)00283-9. doi: 10.1016/j.addr.2012.09.023), and the like. In some embodiments, the methods and compositions disclosed herein comprise any of the suitable methods of introducing a nucleic acid (e.g., a purified/non-purified expression construct/vector) into a target cell (e.g., any eukaryotic cell) known in the art. In some embodiments, any of the suitable methods of introducing a nucleic acid into a target cell result in the permanent/non-permanent modification of the target cell. In some embodiments, any of the suitable methods of introducing a nucleic acid (e.g., DNA, RNA, small non-coding RNAs, siRNA, shRNA, miRNA) into a eukaryotic cell (e.g., immune cell, T cell, HEK293 cell, and the like) comprise transfection (e.g., stable and/or transient transfection) via viral/non-viral approaches. In some embodiments, transfection comprises co-transfection. In some embodiments, transfection comprises stable transduction, transient transduction, chemical transfection, lipid-based transfection (lipofection), non-lipid-based transfection, physical/mechanical transfection (e.g., electroporation, laser beam, gene injection, sonoporation, magnetofection). In some embodiments, transfection comprises electroporation as known in the art. In some embodiments, transfection comprises electroporation followed by a period of cell incubation. In some embodiments, electroporation comprises using an electroporation system to electroporate a cell suspension comprising the viral vector and the target cell. In some embodiments, the viral vector can be a single-stranded or double stranded, linear or circular, segmented or non-segmented nucleic acid. In some embodiments, the nucleic acid may comprise DNA, RNA, or a combination thereof. In some embodiments, the viral vector comprises an AAV viral vector or a self-complementary AAV (scAAV) vector. A person skilled in the art would appreciate that the coding region of the scAAV vector forms an intramolecular double-stranded DNA (dsDNA) that does not require cell mediated synthesis and is ready for expression. In some embodiments, the viral vector comprises a nucleic acid (e.g., DNA) encoding the effector proteins described herein. In some embodiments, the viral vector comprises the guide nucleic acid described herein or a nucleic acid (e.g., DNA) encoding the guide nucleic acid. In some embodiments, the viral vector co-expressing an effector protein mRNA comprising at least 90% identity from any effector protein listed in TABLE 1 and a gRNA comprising at least 90% identity from any gRNA listed in TABLE 5, TABLE 6, TABLE 7, TABLE 33, TABLE 34, TABLE 35, TABLE 45 and TABLE 46. In some embodiments, the viral vector co-expressing an effector protein mRNA comprising at least 90% identity from any effector protein listed in TABLE 1 and a gRNA comprising at least 90% identity from any gRNA listed in TABLE 5, TABLE 6, TABLE 7, TABLE 33, TABLE 34, TABLE 35, TABLE 45 and TABLE 46. In some embodiments, the target cells comprise eukaryotic cells. In some embodiments, the eukaryotic cells comprise but not limited to cancer cells, HEK293T cells, naïve T cells (cells that have not encountered their cognate antigens), T-helper cells ($CD4^+$ cells), cytotoxic T-cells ($CD8^+$ cells), natural killer T-cells, primary T-cells, T-regulatory cells (T-reg), and gamma-delta T cells. In some embodiments, the gRNA is designed to target exon 1 in the eukaryotic cells. In some embodiments, the viral vector is delivered by viral infection, transfection, conjugation, protoplast fusion, lipofection, electroporation, calcium phosphate precipitation, polyethyleneimine (PEI)-mediated transfection, DEAE-dextran mediated transfection, liposome-mediated transfection, particle gun technology, calcium phosphate precipitation, direct micro injection, nanoparticle-mediated nucleic acid delivery, and the like.

In some embodiments, the nuclei acid and/or protein are introduced into a disease cell comprised in a pharmaceutical composition comprising the guide RNA and/or D2S effector protein and a pharmaceutically acceptable excipient. In some aspects of the present disclosure the effector protein is provided in a pharmaceutical composition comprising the effector protein and any pharmaceutically acceptable excipient.

XII. Methods of Detecting a Target Nucleic Acid

Provided herein are methods of detecting target nucleic acids. Methods may comprise detecting target nucleic acids with compositions or systems described herein. Methods may comprise detecting a target nucleic acid with systems described herein that comprise a DETECTR assay. Methods may comprise detecting a target nucleic acid in a sample, e.g., a cell lysate, a biological fluid, or environmental sample. Methods may comprise detecting a target nucleic acid in a cell. In some embodiments, methods of detecting a target nucleic acid in a sample or cell comprises contacting the sample or cell with a D2S effector protein or a multimeric complex thereof, a guide nucleic acid, wherein at least a portion of the guide nucleic acid is complementary to at least a portion of the target nucleic acid, and a reporter nucleic acid that is cleaved in the presence of the D2S effector protein, the guide nucleic acid, and the target nucleic acid, and detecting a signal produced by cleavage of the reporter nucleic acid, thereby detecting the target nucleic acid in the sample. In some embodiments, methods of detecting the target nucleic acid described herein comprises contacting the sample or cell with the D2S effector proteins described herein, the guide nucleic acids described herein, and the reporter nucleic acids described herein sequentially. In some embodiments, methods of detecting the target nucleic acid described herein comprises contacting the sample or cell with the D2S effector proteins described herein, the guide nucleic acids described herein, and the reporter nucleic acids described herein simultaneously. In some embodiments, methods result in transcollateral cleavage of the reporter nucleic acid. In some embodiments, methods result in cis cleavage of the reporter nucleic acid.

In some embodiments, the effector protein comprises an amino acid sequence that is at least 70%, at least 75%, at least 80%, at least 85%, at least 90%, at least 92%, at least 95%, at least 97%, at least 98%, at least 99%, or 100% identical to any one of the sequences recited in TABLE 1. In some embodiments, the effector protein comprises an amino acid sequence that is at least 70%, at least 75%, at least 80%, at least 85%, at least 90%, at least 92%, at least 95%, at least 97%, at least 98%, at least 99%, or 100% similar to any one of the sequences recited in TABLE 1. In some embodiments, the effector protein comprises an amino acid sequence that is at least is at least 70%, at least 75%, at least 80%, at least 85%, at least 90%, at least 92%, at least 95%, at least 97%, at least 98%, at least 99%, or 100% identical to SEQ ID NO: 1. In some embodiments, the effector protein comprises an amino acid sequence that is at least is at least 70%, at least 75%, at least 80%, at least 85%, at least 90%, at least 92%, at least 95%, at least 97%, at least 98%, at least 99%, or 100% similar to SEQ ID NO: 1. In some embodiments, the effector protein comprises an amino acid sequence that is at least is at least 70%, at least 75%, at least 80%, at least 85%, at least 90%, at least 92%, at least 95%, at least 97%, at least 98%, at least 99%, or less than 100% identical to SEQ ID NO: 1, wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the effector protein comprises an amino acid sequence that is at least is at least 70%, at least 75%, at least 80%, at least 85%, at least 90%, at least 92%, at least 95%, at least 97%, at least 98%, at least 99%, or 100% similar to SEQ ID NO: 1, wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the one or more alterations comprises one or more substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N. In some embodiments, the amino acid sequence of the effector protein is at least 70%, at least 75%, at least 80%, at least 85%, at least 90%, at least 92%, at least 95%, at least 97%, at least 98%, at least 99%, or 100% identical to any one of the sequences recited in TABLE 1. In some embodiments, the amino acid sequence of the effector protein is at least 70%, at least 75%, at least 80%, at least 85%, at least 90%, at least 92%, at least 95%, at least 97%, at least 98%, at least 99%, or 100% similar to any one of the sequences recited in TABLE 1. In some embodiments, the nucleobase sequence of the guide is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide comprises a crRNA nucleobase sequence that is at least 70%, at least 75%, at least 80%, at least 85%, at least 90%, at least 92%, at least 95%, or 100% identical to any one of SEQ ID NOs: 17-21. In some embodiments, the guide comprises a portion of or all of a tracrRNA nucleobase sequence that is at least 70%, at least 75%, at least 80%, at least 85%, at least 90%, at least 92%, at least 95%, or 100% identical to an equal length portion of any one of SEQ ID NOs: 22-26.

Methods may comprise contacting the sample to a complex comprising a guide nucleic acid comprising a segment that is reverse complementary to a segment of the target nucleic acid and a D2S effector protein that exhibits sequence independent cleavage upon forming a complex comprising the segment of the guide nucleic acid binding to the segment of the target nucleic acid; and assaying for a signal indicating cleavage of at least some protein-nucleic acids of a population of protein-nucleic acids, wherein the signal indicates a presence of the target nucleic acid in the sample and wherein absence of the signal indicates an absence of the target nucleic acid in the sample.

Methods may comprise contacting the sample comprising the target nucleic acid with a guide nucleic acid targeting a target nucleic acid segment, a D2S effector protein capable of being activated when complexed with the guide nucleic acid and the target nucleic acid segment, a single stranded nucleic acid of a reporter comprising a detection moiety, wherein the nucleic acid of a reporter is capable of being cleaved by the activated D2S effector protein, thereby generating a first detectable signal, cleaving the single stranded nucleic acid of a reporter using the D2S effector protein that cleaves as measured by a change in color, and measuring the first detectable signal on the support medium.

Methods may comprise contacting the sample or cell with a D2S effector protein or a multimeric complex thereof and a guide nucleic acid at a temperature of at least about 25° C., at least about 30° C., at least about 35° C., at least about 40° C., at least about 50° C., or at least about 65° C. In some embodiments, the temperature is not greater than 80° C. In some embodiments, the temperature is about 25° C., about 30° C., about 35° C., about 40° C., about 45° C., about 50° C., about 55° C., about 60° C., about 65° C., or about 70° C. In some embodiments, the temperature is about 25° C. to about 45° C., about 35° C. to about 55° C., or about 55° C. to about 65° C.

Methods may comprise cleaving a strand of a single-stranded target nucleic acid with a D2S or a multimeric complex thereof, as assessed with an in vitro cis cleavage assay. An example of such an assay may follow a procedure comprising: (i) providing equimolar (e.g., 500 nM) amounts of a D2S effector protein comprising at least 70% sequence identity to any one of the sequences recited in TABLE 1, and a guide nucleic acid at 40 to 45° C. for 5 minutes in pH 7.5

Tris-HCl buffer, 40 mM NaCl, 2 mM Ca(N03)2, 1 mM BME, thereby forming a ribonucleoprotein complex comprising a dimer of the D2S effector protein and the guide nucleic acid; (ii) adding linear dsDNA comprising a nucleic acid sequence targeted by the guide nucleic acid and adjacent to a PAM comprising the sequence 5'-NNTNTR-3'; (iii) incubating the mixture at 45° C. for 20 minutes, thereby enabling cleavage of the plasmid; (iv) quenching the reaction with EDTA and a protease; and (v) analyzing the reaction products (e.g., viewing the cleaved and uncleaved linear dsDNA with gel electrophoresis).

Methods may comprise cleaving a strand of a single-stranded target nucleic acid with a D2S or a multimeric complex thereof, as assessed with an in vitro cis cleavage assay. An example of such an assay may follow a procedure comprising: (i) providing equimolar (e.g., 500 nM) amounts of a D2S effector protein comprising at least 70% sequence identity to any one of the sequences recited in TABLE 1, and a guide nucleic acid at 40 to 45° C. for 5 minutes in pH 7.5 Tris-HCl buffer, 40 mM NaCl, 2 mM Ca(NO$_3$)2, 1 mM BME, thereby forming a ribonucleoprotein complex comprising a dimer of the D2S effector protein and the guide nucleic acid; (ii) adding linear dsDNA comprising a nucleic acid sequence targeted by the guide nucleic acid and adjacent to a PAM comprising the sequence 5'-TNTR-3'; (iii) incubating the mixture at 45° C. for 20 minutes, thereby enabling cleavage of the plasmid; (iv) quenching the reaction with EDTA and a protease; and (v) analyzing the reaction products (e.g., viewing the cleaved and uncleaved linear dsDNA with gel electrophoresis).

In some embodiments, there is a threshold of detection for methods of detecting target nucleic acids. In some embodiments, methods are not capable of detecting target nucleic acids that are present in a sample or solution at a concentration less than or equal to 10 nM. The term "threshold of detection" is used herein to describe the minimal amount of target nucleic acid that must be present in a sample in order for detection to occur. For example, when a threshold of detection is 10 nM, then a signal can be detected when a target nucleic acid is present in the sample at a concentration of 10 nM or more. In some embodiments, the threshold of detection is less than or equal to 5 nM, 1 nM, 0.5 nM, 0.1 nM, 0.05 nM, 0.01 nM, 0.005 nM, 0.001 nM, 0.0005 nM, 0.0001 nM, 0.00005 nM, 0.00001 nM, 10 pM, 1 pM, 500 fM, 250 fM, 100 fM, 50 fM, 10 fM, 5 fM, 1 fM, 500 attomole (aM), 100 aM, 50 aM, 10 aM, or 1 aM. In some embodiments, the threshold of detection is in a range of from 1 aM to 1 nM, 1 aM to 500 pM, 1 aM to 200 pM, 1 aM to 100 pM, 1 aM to 10 pM, 1 aM to 1 pM, 1 aM to 500 fM, 1 aM to 100 fM, 1 aM to 1 fM, 1 aM to 500 aM, 1 aM to 100 aM, 1 aM to 50 aM, 1 aM to 10 aM, 10 aM to 1 nM, 10 aM to 500 pM, 10 aM to 200 pM, 10 aM to 100 pM, 10 aM to 10 pM, 10 aM to 1 pM, 10 aM to 500 fM, 10 aM to 100 fM, 10 aM to 1 fM, 10 aM to 500 aM, 10 aM to 100 aM, 10 aM to 50 aM, 100 aM to 1 nM, 100 aM to 500 pM, 100 pM to 200 pM, 100 aM to 100 pM, 100 aM to 10 pM, 100 aM to 1 pM, 100 aM to 500 fM, 100 aM to 100 fM, 100 aM to 1 fM, 100 aM to 500 aM, 500 aM to 1 nM, 500 aM to 500 pM, 500 aM to 200 pM, 500 aM to 100 pM, 500 aM to 10 pM, 500 aM to 1 pM, 500 aM to 500 fM, 500 aM to 100 fM, 500 aM to 1 fM, 1 fM to 1 nM, 1 fM to 500 pM, 1 fM to 200 pM, 1 fM to 100 pM, 1 fM to 10 pM, 1 fM to 1 pM, 10 fM to 1 nM, 10 fM to 500 pM, 10 fM to 200 pM, 10 fM to 100 pM, 10 fM to 10 pM, 10 fM to 1 pM, 500 fM to 1 nM, 500 fM to 500 pM, 500 fM to 200 pM, 500 fM to 100 pM, 500 fM to 10 pM, 500 fM to 1 pM, 800 fM to 1 nM, 800 fM to 500 pM, 800 fM to 200 pM, 800 fM to 100 pM, 800 fM to 10 pM, 800 fM to 1 pM, 1 pM to 1 nM, 1 pM to 500 pM, 1 pM to 200 pM, 1 pM to 100 pM, or 1 pM to 10 pM. In some embodiments, the threshold of detection in a range of from 800 fM to 100 pM, 1 pM to 10 pM, 10 fM to 500 fM, 10 fM to 50 fM, 50 fM to 100 fM, 100 fM to 250 fM, or 250 fM to 500 fM. In some embodiments, the threshold of detection is in a range of from 2 aM to 100 pM, from 20 aM to 50 pM, from 50 aM to 20 pM, from 200 aM to 5 pM, or from 500 aM to 2 pM. In some embodiments, the minimum concentration at which a target nucleic acid is detected in a sample is in a range of from 1 aM to 1 nM, 10 aM to 1 nM, 100 aM to 1 nM, 500 aM to 1 nM, 1 fM to 1 nM, 1 fM to 500 pM, 1 fM to 200 pM, 1 fM to 100 pM, 1 fM to 10 pM, 1 fM to 1 pM, 10 fM to 1 nM, 10 fM to 500 pM, 10 fM to 200 pM, 10 fM to 100 pM, 10 fM to 10 pM, 10 fM to 1 pM, 500 fM to 1 nM, 500 fM to 500 pM, 500 fM to 200 pM, 500 fM to 100 pM, 500 fM to 10 pM, 500 fM to 1 pM, 800 fM to 1 nM, 800 fM to 500 pM, 800 fM to 200 pM, 800 fM to 100 pM, 800 fM to 10 pM, 800 fM to 1 pM, 1 pM to 1 nM, 1 pM to 500 pM, from 1 pM to 200 pM, 1 pM to 100 pM, or 1 pM to 10 pM. In some embodiments, the minimum concentration at which a target nucleic acid is detected in a sample is in a range of from 2 aM to 100 pM, from 20 aM to 50 pM, from 50 aM to 20 pM, from 200 aM to 5 pM, or from 500 aM to 2 pM. In some embodiments, the minimum concentration at which a single stranded target nucleic acid can be detected in a sample is in a range of from 1 aM to 100 pM. In some embodiments, the minimum concentration at which a target nucleic acid can be detected in a sample is in a range of from 1 fM to 100 pM. In some embodiments, the minimum concentration at which a single stranded target nucleic acid can be detected in a sample is in a range of from 10 fM to 100 pM. In some embodiments, the minimum concentration at which a single stranded target nucleic acid can be detected in a sample is in a range of from 800 fM to 100 pM. In some embodiments, the minimum concentration at which a single stranded target nucleic acid can be detected in a sample is in a range of from 1 pM to 10 pM. In some embodiments, the devices, systems, fluidic devices, kits, and methods described herein detect a target single-stranded nucleic acid in a sample comprising a plurality of nucleic acids such as a plurality of non-target nucleic acids, where the target single-stranded nucleic acid is present at a concentration as low as 1 aM, 10 aM, 100 aM, 500 aM, 1 fM, 10 fM, 500 fM, 800 fM, 1 pM, 10 pM, 100 pM, or 1 pM.

In some embodiments, the target nucleic acid is present in a cleavage reaction at a concentration of about 10 nM, about 20 nM, about 30 nM, about 40 nM, about 50 nM, about 60 nM, about 70 nM, about 80 nM, about 90 nM, about 100 nM, about 200 nM, about 300 nM, about 400 nM, about 500 nM, about 600 nM, about 700 nM, about 800 nM, about 900 nM, about 1 µM, about 10 µM, or about 100 µM. In some embodiments, the target nucleic acid is present in the cleavage reaction at a concentration of from 10 nM to 20 nM, from 20 nM to 30 nM, from 30 nM to 40 nM, from 40 nM to 50 nM, from 50 nM to 60 nM, from 60 nM to 70 nM, from 70 nM to 80 nM, from 80 nM to 90 nM, from 90 nM to 100 nM, from 100 nM to 200 nM, from 200 nM to 300 nM, from 300 nM to 400 nM, from 400 nM to 500 nM, from 500 nM to 600 nM, from 600 nM to 700 nM, from 700 nM to 800 nM, from 800 nM to 900 nM, from 900 nM to 1 µM, from 1 µM to 10 µM, from 10 µM to 100 µM, from 10 nM to 100 nM, from 10 nM to 1 µM, from 10 nM to 10 µM, from 10 nM to 100 µM, from 100 nM to 1 µM, from 100 nM to 10 µM, from 100 nM to 100 µM, or from 1 µM to 100 µM. In some embodiments, the target nucleic acid is present in the cleavage reaction at a concentration of from 20 nM to 50 µM, from 50 nM to 20 µM, or from 200 nM to 5 µM.

In some embodiments, methods detect a target nucleic acid in less than 60 minutes. In some embodiments, methods detect a target nucleic acid in less than about 120 minutes, less than about 110 minutes, less than about 100 minutes, less than about 90 minutes, less than about 80 minutes, less than about 70 minutes, less than about 60 minutes, less than about 55 minutes, less than about 50 minutes, less than about 45 minutes, less than about 40 minutes, less than about 35 minutes, less than about 30 minutes, less than about 25 minutes, less than about 20 minutes, less than about 15 minutes, less than about 10 minutes, less than about 5 minutes, less than about 4 minutes, less than about 3 minutes, less than about 2 minutes, or less than about 1 minute.

In some embodiments, methods require at least about 120 minutes, at least about 110 minutes, at least about 100 minutes, at least about 90 minutes, at least about 80 minutes, at least about 70 minutes, at least about 60 minutes, at least about 55 minutes, at least about 50 minutes, at least about 45 minutes, at least about 40 minutes, at least about 35 minutes, at least about 30 minutes, at least about 25 minutes, at least about 20 minutes, at least about 15 minutes, at least about 10 minutes, or at least about 5 minutes to detect a target nucleic acid. In some embodiments, the sample is contacted with the reagents for from 5 minutes to 120 minutes, from 5 minutes to 100 minutes, from 10 minutes to 90 minutes, from 15 minutes to 45 minutes, or from 20 minutes to 35 minutes.

In some embodiments, methods of detecting are performed in less than 10 hours, less than 9 hours, less than 8 hours, less than 7 hours, less than 6 hours, less than 5 hours, less than 4 hours, less than 3 hours, less than 2 hours, less than 1 hour, less than 50 minutes, less than 45 minutes, less than 40 minutes, less than 35 minutes, less than 30 minutes, less than 25 minutes, less than 20 minutes, less than 15 minutes, less than 10 minutes, less than 9 minutes, less than 8 minutes, less than 7 minutes, less than 6 minutes, or less than 5 minutes. In some embodiments, methods of detecting are performed in about 5 minutes to about 10 hours, about 10 minutes to about 8 hours, about 15 minutes to about 6 hours, about 20 minutes to about 5 hours, about 30 minutes to about 2 hours, or about 45 minutes to about 1 hour.

Methods may comprise detecting a detectable signal within 5 minutes of contacting the sample and/or the target nucleic acid with the guide nucleic acid and/or the D2S effector protein. In some embodiments, detecting occurs within 1, 2, 3, 4, 5, 6, 7, 8, 9, 10, 11, 12, 13, 14, 15, 20, 25, 30, 35, 40, 45, 50, 55, 60, 70, 80, 90, 100, 110, or 120 minutes of contacting the target nucleic acid. In some embodiments, detecting occurs within 1 to 120, 5 to 100, 10 to 90, 15 to 80, 20 to 60, or 30 to 45 minutes of contacting the target nucleic acid.

In some embodiments, the methods for detecting a target nucleic acid molecule in a sample or cell comprise assaying for at least one base difference (e.g., assaying for a SNP, insertion, deletion, or a base mutation) in a nucleic acid sequence. In some embodiments, the methods for detecting a target nucleic acid molecule in a sample or cell comprise assaying for at least one base difference in a nucleic acid sequence in at least one exon. In some embodiments, the methods for detecting a target nucleic acid molecule in a sample or cell comprise assaying for at least one base difference in an exonic and/or intronic region of a nucleic acid sequence. In some embodiments, the methods for detecting a target nucleic acid molecule in a sample or cell comprise assaying for at least one difference in a nucleic acid sequence which may result in a gene knockout. In some embodiments, the methods for detecting a target nucleic acid molecule in a sample or cell comprise a detection assay such as, for example, a sequencing assay (e.g., next generation sequencing (NGS)). In some embodiments, detecting a target nucleic acid with methods for detection described herein further comprises amplification of the target nucleic acid. In some embodiments, detecting at least one base difference in a target nucleic acid sequence in a sample or cell comprises measuring % Indels.

In some embodiments, the methods for detecting a target nucleic acid molecule in a sample comprise assaying a population of cells, wherein the guide nucleic acid and effector protein were previously delivered into individual cells in the population of cells by any of the methods disclosed herein. In some embodiments, the methods for detecting a target nucleic acid molecule in a sample comprise assaying a homogeneous population of cells. In some embodiments, the methods for detecting a target nucleic acid molecule in a sample comprise assaying a heterogeneous population of cells. In some embodiments, the methods for detecting at least one base difference (e.g., insertion or deletion) in a target nucleic acid sequence in a population of cells comprise a detection assay such as, for example, flow cytometry (FACS). Flow cytometry provides rapid multi-parametric analysis of single cells or particles in solution (i.e. buffer solution or salt-based solution as described herein) as they flow past at least one laser used to detect fluorescent light signals from the sample. In some embodiments, detecting at least one base difference in a target nucleic acid sequence in a population of cells comprises preparing the sample(s) for fluorescence measurement. In some embodiments, preparing samples for fluorescence measurement comprises transfection and expression of suitable fluorescent proteins as described herein (e.g., Green Fluorescent Protein, GFP), or using flow cytometry reagents known in the art. In some embodiments, preparing samples for fluorescence measurement comprises using flow cytometry reagents such as fluorescently conjugated antibodies (e.g., B2M, TRAC, CIITA, CD3, FITC) and/or fluorescent dyes (e.g., LIVE/DEAD™ Fixable Near-IR stain, Propidium Iodide, DNA). In some embodiments, detecting at least one base difference in a target nucleic acid sequence in a population of cells comprises measuring % Cells.

Amplification of a Target Nucleic Acid

Methods may comprise amplifying a target nucleic acid for detection using any of the compositions or systems described herein. Amplifying may comprise changing the temperature of the amplification reaction, also known as thermal amplification (e.g., PCR). Amplifying may be performed at essentially one temperature, also known as isothermal amplification. Amplifying may improve at least one of sensitivity, specificity, or accuracy of the detection of the target nucleic acid.

Amplifying may comprise subjecting a target nucleic acid to an amplification reaction selected from transcription mediated amplification (TMA), helicase dependent amplification (HDA), or circular helicase dependent amplification (cHDA), strand displacement amplification (SDA), recombinase polymerase amplification (RPA), loop mediated amplification (LAMP), exponential amplification reaction (EXPAR), rolling circle amplification (RCA), ligase chain reaction (LCR), simple method amplifying RNA targets (SMART), single primer isothermal amplification (SPIA), multiple displacement amplification (MDA), nucleic acid sequence based amplification (NASBA), hinge-initiated primer-dependent amplification of nucleic acids (HIP), nicking enzyme amplification reaction (NEAR), and improved multiple displacement amplification (IMDA).

In some embodiments, amplification of the target nucleic acid comprises modifying the sequence of the target nucleic acid. For example, amplification may be used to insert a PAM sequence into a target nucleic acid that lacks a PAM sequence. In some embodiments, amplification may be used to increase the homogeneity of a target nucleic acid in a sample. For example, amplification may be used to remove a nucleic acid variation that is not of interest in the target nucleic acid sequence.

Amplifying may take 1, 2, 3, 4, 5, 6, 7, 8, 9, 10, 11, 12, 13, 14, 15, 16, 17, 18, 19, 20, 25, 30, 40, 50, or 60 minutes. Amplifying may be performed at a temperature of around 20-45° C. Amplifying may be performed at a temperature of less than about 20° C., less than about 25° C., less than about 30° C., 35° C., less than about 37° C., less than about 40° C., or less than about 45° C. The nucleic acid amplification reaction may be performed at a temperature of at least about 20° C., at least about 25° C., at least about 30° C., at least about 35° C., at least about 37° C., at least about 40° C., or at least about 45° C.

Certain Methods of Detection

An illustrative method for detecting a target nucleic acid molecule in a sample comprises contacting the sample comprising the target nucleic acid molecule with (i) a D2S effector protein comprising at least 75% sequence identity to a sequence selected from the group consisting of SEQ ID NOs: 1-2, or 37; (ii) an engineered guide nucleic acid comprising a region that binds to the effector protein and an additional region that binds to the target nucleic acid; and (iii) a labeled, single stranded RNA reporter; cleaving the labeled single stranded RNA reporter by the effector protein to release a detectable label; and detecting the target nucleic acid by measuring a signal from the detectable label. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 92%, at least 95%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, or 100% identical to an equal length portion of any one of SEQ ID NOs: 22-26.

A further illustrative method for detecting a target nucleic acid molecule in a sample comprises contacting the sample comprising the target nucleic acid molecule with (i) a dimeric protein complex comprising a D2S effector protein comprising at least 75% sequence identity to a sequence selected from the group consisting of SEQ ID NOs: 1-2, or 37; (ii) an engineered guide nucleic acid comprising a first region that binds to the target nucleic acid; (iii) a nucleic acid comprising a first region that binds to the effector protein and an additional region that hybridizes to second region of the engineered guide nucleic acid; and (iv) a labeled, single stranded RNA reporter; cleaving the labeled single stranded RNA reporter by the effector protein to release a detectable label; and detecting the target nucleic acid by measuring a signal from the detectable label. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 92%, at least 95%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, or 100% identical to an equal length portion of any one of SEQ ID NOs: 22-26.

XIII. Methods of Nucleic Acid Editing

Provided herein are compositions, methods, and systems of editing target nucleic acids. In general, editing refers to modifying the nucleobase sequence of a target nucleic acid. However, methods, compositions and systems disclosed herein may also be capable of making epigenetic modifications of target nucleic acids. The target nucleic acid may be a gene or a portion thereof. Methods, systems and compositions may modify a coding portion of a gene, a non-coding portion of a gene, or a combination thereof. Modifying at least one gene using the compositions, systems and methods described herein may reduce or increase expression of one or more genes. In some embodiments, compositions, systems and methods reduce expression of one or more genes by at least 10%, at least 20%, at least 30%, at least 40%, at least 50%, at least 60%, at least 70%, at least 80%, at least 90%, or at least 95%. In some embodiments, compositions, systems and methods remove all expression of a gene, also referred to as genetic knock out. In some embodiments, compositions, systems and methods increase expression of one or more genes by at least 10%, at least 20%, at least 30%, at least 40%, at least 50%, at least 60%, at least 70%, at least 80%, at least 90%, or at least 100%.

In some embodiments, compositions, systems and methods use Cas proteins that are fused to a heterologous protein. Heterologous proteins include, but are not limited to, transcriptional activators, transcriptional repressors, deaminases, methyltransferases, acetyltransferases, and other nucleic acid modifying proteins. In some embodiments, Cas proteins need not be fused to a partner protein to accomplish the required protein (expression) modification.

In some embodiments, compositions, systems and methods comprise a nucleic acid expression vector, or use thereof, to introduce a Cas protein, guide nucleic acid, donor template or any combination thereof to a cell. In some embodiments, the nucleic acid expression vector comprises one or more genes of interest and one or more regulatory elements. In some embodiments, the nucleic acid expression vector comprises at least one multiple cloning site (MCS). In some embodiments, the nucleic acid expression vector comprises circular double-stranded DNA. In some embodiments, the nucleic acid expression vector is linear. In some embodiments, the nucleic acid expression vector is a minicircle plasmid. In some embodiments, the nucleic acid expression vector comprises a bacterial backbone containing an origin of replication. In some embodiments, the nucleic acid expression vector comprises a bacterial backbone containing an antibiotic resistance gene or other selectable marker for plasmid amplification in bacteria. In some embodiments, the nucleic acid expression vector comprises one or more genes that provide a selective marker to induce a target cell to retain the plasmid. In some embodiments, the nucleic acid expression vector is a non-viral vector. In some embodiments, the nucleic acid expression vector is a viral vector. In some embodiments, compositions, systems and methods comprise a viral vector encoding a fusion effector protein, an effector protein, a fusion partner, a guide nucleic acid, or a combination thereof. Viral vectors include, but are not limited to, retroviruses, adenoviruses, adeno-associated viruses, and herpes simplex viruses. In some embodiments, the viral vector is a replication-defective viral vector, comprising an insertion of a therapeutic gene inserted in genes essential to the lytic cycle, preventing the virus from replicating and exerting cytotoxic effects. In some embodiments, the viral vector is an adeno associated viral (AAV) vector. The AAV may be any AAV known in the art. In some embodiments, the viral vector corresponds to a virus of a specific serotype. In some examples, the serotype is selected from an AAV1 serotype, an AAV2 serotype, AAV3 serotype, an AAV4 serotype, AAV5 serotype, an AAV6 serotype, AAV7 serotype, an AAV8 serotype, an AAV9 serotype, an AAV10 serotype, an AAV 11 serotype, and an AAV12 serotype. In some embodiments the AAV vector is a recombinant vector, a hybrid AAV vector, a chimeric AAV vector, a self-complementary AAV (scAAV) vector, a single-stranded AAV (ssAAV) or any combination thereof. In some embodiments, the scAAV vector encodes a guide nucleic acid and an effector protein mRNA.

In some embodiments, compositions, systems and methods comprise a viral vector (e.g., AAV vector) comprising at least one promoter. In some embodiments, the AAV vector comprises at least one constitutive promoter. In some embodiments, the AAV vector comprises at least one inducible promoter. In some embodiments, the AAV vector comprises at least one eukaryotic and/or prokaryotic promoter. In some embodiments, the AAV vector comprises promoters such as CMV, EFS, EF1a, SV40, PGK1, Ube, human beta actin, CAG, TRE, UAS, Ac5, polyhedron, CaMKIIa, GAL1-10, TEF1, GDS, ADH1, CaMV35S, Ubi, H1, U6, CaMV35S, SV40, CMV, 7SK, HSV TK promoter, and the like. In some embodiments, the promoter is U6. In some embodiments, the promoter is H1. In some embodiments, the promoter drives the expression of a guide nucleic acid (gRNA) encoding sequence. In some embodiments, the guide nucleic acid comprises a sequence that has at least 65%, at least 70%, at least 75%, at least 80%, at least 85%, at least 90%, at least 95%, or 100% identity to any one of sequences recited in TABLE 3, TABLE 4, TABLE 5, TABLE 6, TABLE 7, TABLE 25, TABLE 26, TABLE 30, TABLE 31, TABLE 32, TABLE 33, TABLE 34, TABLE 35, TABLE 45 and TABLE 46. In some embodiments, the AAV vector comprises a second promoter. In some embodiments, the second promoter is a constitutive promoter, inducible promoter, ubiquitous promoter, site-specific promoter, tissue-specific promoter, or any combination thereof. In some embodiments, the AAV vector second promoter is selected from promoters such as CMV, EFS, EF1a, SV40, PGK1, Ube, human beta actin, CAG, TRE, UAS, Ac5, polyhedron, CaMKIIa, GAL1-10, TEF1, GDS, ADH1, CaMV35S, Ubi, H1, U6, CaMV35S, SV40, CMV, 7SK, HSV TK promoter, and the like. In some embodiments, the second promoter is CMV. In some embodiments, the second promoter is EFS. In some embodiments, the EFS promoter comprises EFS1, EFS2, or EFS3. In some embodiments, the second promoter drives the expression of the effector protein encoding sequence. In some embodiments, the promoter may affect the expression and/or nuclease activity of the effector protein. In some embodiments, the effector protein is ubiquitously expressed. In some embodiments, the effector protein has an amino acid sequence that has at least 65%, at least 70%, at least 75%, at least 80%, at least 85%, at least 90%, at least 95%, or 100% sequence identity to any one of sequences listed in TABLE 1. In some embodiments, the effector protein is ubiquitously expressed. In some embodiments, the effector protein has an amino acid sequence that has at least 65%, at least 70%, at least 75%, at least 80%, at least 85%, at least 90%, at least 95%, or 100% sequence similarity to any one of sequences listed in TABLE 1. In some embodiments, the effector protein has an amino acid sequence that is at least 65%, at least 70%, at least 75%, at least 80%, at least 85%, at least 90%, at least 95%, or 100% identical to SEQ ID NO: 1. In some embodiments, the effector protein has an amino acid sequence that is at least 65%, at least 70%, at least 75%, at least 80%, at least 85%, at least 90%, at least 95%, or less than 100% identical to SEQ ID NO: 1, wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the effector protein has an amino acid sequence that is at least 65%, at least 70%, at least 75%, at least 80%, at least 85%, at least 90%, at least 95%, or 100% similar to any one of sequences listed in TABLE 1. In some embodiments, the effector protein has an amino acid sequence that is at least 65%, at least 70%, at least 75%, at least 80%, at least 85%, at least 90%, at least 95%, or 100% similar to SEQ ID NO: 1. In some embodiments, the effector protein has an amino acid sequence that is at least 65%, at least 70%, at least 75%, at least 80%, at least 85%, at least 90%, at least 95%, or 100% similar to SEQ ID NO: 1, wherein the effector protein comprises one or more alterations at K58, I80, T84, K105, N193, C202, S209, G210, A218, D220, E225, D237, C246, N286, M295, M298, A306, Y315, E335, Q360 and D418. In some embodiments, the one or more alterations comprises one or more substitutions selected from I80R, T84R, K105R, C202R, G210R, A218R, D220R, E225R, D237A, C246R, Q360R, I80K, T84K, G210K, N193K, C202K, A218K, D220K, E225K, C246K, N286K, A306K, Q360K, I80H, T84H, K105H, G210H, C202H, A218H, D220H, E225H, C246H, E335A, E335Q, Q360H, K58W, S209F, M295W, M298L, Y315M, D418A and D418N. In some embodiments, the AAV vector comprises one or more inverted terminal repeat (ITR) regions. In some embodiments, the inverted terminal repeat regions flank the one or more sequences of interest and one or more regulatory elements. In some embodiments, the AAV vector comprises one or more polyadenylation (poly A) signal sequences. In some embodiments, the polyadenylation signal sequence comprises hGH poly A signal sequence. In some embodiments, the polyadenylation signal sequence comprises sv40 poly A signal sequence. In some embodiments, the AAV vector comprises one or more untranslated (UTR) regions. In some embodiments, the untranslated regions flank the effector protein coding sequence. In some embodiments, the untranslated regions comprise at least one intron, sequence elements, enhancer, or any combination thereof. In some embodiments, the AAV vector comprises a selectable marker for plasmid amplification in bacteria. In some embodiments, the AAV vector comprises an antibiotic resistance gene. In some embodiments, the antibiotic resistance gene conveys resistance to antibiotics such as gentamicin, penicillin, kanamycin, spectinomycin, streptomycin, ampicillin, carbenicillin, bleomycin, erythromycin, erythromycin, polymyxin B, tetracycline, chloramphenicol, and the like. In some embodiments, the antibiotic resistance gene conveys resistance to ampicillin. In some embodiments, the AAV vector is a scAAV vector. In some embodiments, the scAAV vector contains both DNA strands which can anneal together to form double-stranded DNA (dsDNA).

In some embodiments, the dsDNA of the scAAV coding region do not require cell mediated synthesis and are ready for expression. In some embodiments, the scAAV vector is the pscAAV-MCS Vector (Cell Biolabs Catalog No. VPK-430). In some embodiments, the length of the scAAV vector carrying genome editing components allows for delivery to any eukaryotic cell (e.g., immune cell, T cell, HEK cell). In some embodiments, the scAAV vector carrying genome editing components has a total length of at least about 1 kb. In some embodiments, the scAAV vector carrying genome editing components has a total length of at most about 4.5 kb. In some embodiments, the scAAV vector carrying genome editing components has a total length of about 1.5 kb to about 4 kb. In some embodiments, the scAAV vector carrying genome editing components has a total length of about 2 kb to about 3 kb.

In some embodiments, compositions, systems and methods comprise a lipid, polymer, nanoparticle, or a combination thereof, or use thereof, to introduce a Cas protein, guide nucleic acid, donor template or any combination thereof to a cell. Non-limiting examples of lipids and polymers are cationic polymers, cationic lipids, or bio-responsive polymers. In some embodiments, the bio-responsive polymer exploits chemical-physical properties of the endosomal environment (e.g., pH) to preferentially release the genetic material in the intracellular space.

D2S effector proteins, multimeric complexes thereof and systems described herein may be used for editing or modifying a target nucleic acid. Editing a target nucleic acid may comprise one or more of cleaving the target nucleic acid, deleting one or more nucleotides of the target nucleic acid, inserting one or more nucleotides into the target nucleic acid, mutating one or more nucleotides of the target nucleic acid, or modifying (e.g., methylating, demethylating, deaminating, or oxidizing) of one or more nucleotides of the target nucleic acid.

Disclosed herein are methods for modifying a target nucleic acid by contracting a cell with compositions or systems described herein. In some embodiments, the methods comprise transducing cells with compositions or systems described herein.

Methods of editing may comprise contacting a target nucleic acid with a D2S effector protein and a guide nucleic acid, wherein the effector protein comprises an amino acid sequence that is at least 70%, at least 75%, at least 80%, at least 85%, at least 90%, at least 95%, at least 97%, or at least 98%, at least 99%, or 100% identical to any one of the sequences recited in TABLE 1. In some embodiments, the contacting of the target nucleic acid with the D2S effector protein and the guide nucleic acid is sequential. In some embodiments, the contacting of the target nucleic acid with the D2S effector protein and the guide nucleic acid is simultaneous. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 92%, at least 95%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, or 100% identical to an equal length portion of any one of SEQ ID NOs: 22-26.

Methods of editing a target nucleic acid comprising contacting the target nucleic acid with any of the systems described herein, wherein the system comprises the effector protein described herein or a nucleic acid encoding the effector protein, and the engineered guide nucleic acid described herein or a nucleic acid encoding the engineered guide nucleic acid. In some embodiments, contacting the target nucleic acid with the effector protein or nucleic acid encoding the effector protein, and the engineered guide nucleic acid or a nucleic acid encoding the engineered guide nucleic acid sequentially. In some embodiments, contacting the target nucleic acid with the effector protein or nucleic acid encoding the effector protein, and the engineered guide nucleic acid or a nucleic acid encoding the engineered guide nucleic acid simultaneously.

Editing may introduce a mutation (e.g., point mutations, deletions) in a target nucleic acid relative to a corresponding wildtype nucleobase sequence. Editing may remove or correct a disease-causing mutation in a nucleic acid sequence to produce a corresponding wildtype nucleobase sequence. Editing may remove/correct point mutations, deletions, null mutations, or tissue-specific mutations in a target nucleic acid. Editing may be used to generate gene knock-out, gene knock-in, gene editing, gene tagging, exon removal (e.g., by use of a dual guide nucleic acid system as described in Example 7), or a combination thereof. In some embodiments, editing may be used to generate a target nucleic acid molecule comprising at least one base difference (e.g., SNP, insertion, deletion, or base mutation) relative to a corresponding wildtype nucleobase sequence. In some embodiments, editing may be used to generate a target nucleic acid molecule comprising at least one base difference in at least one exon. In some embodiments, editing may be used to generate a target nucleic acid molecule comprising at least one base difference in an exonic and/or intronic region. In some embodiments, editing may be used to generate a target nucleic acid molecule comprising at least one base difference in multiple exons. In some embodiments, editing may be used to generate a target nucleic acid molecule comprising at least one base difference in exons 1, 2, 4, or any combination thereof. In some embodiments, editing may be used to generate a target nucleic acid molecule comprising indels. In some embodiments, editing may be used to generate a target nucleic acid molecule comprising indels in genes of interest. Methods of the disclosure may be targeted to any locus in a genome of a cell.

Editing may comprise single stranded cleavage, double stranded cleavage, donor nucleic acid insertion, epigenetic modification (e.g., methylation, demethylation, acetylation, or deacetylation), or a combination thereof. In some embodiments, cleavage (single-stranded or double-stranded) is site-specific, meaning cleavage occurs at a specific site in the target nucleic acid, often within the region of the target nucleic acid that hybridizes with the guide nucleic acid spacer region. In some embodiments, the D2S effector proteins introduce a single-stranded break in a target nucleic acid to produce a cleaved nucleic acid. In some embodiments, the effector protein is capable of introducing a break in a single stranded RNA (ssRNA). The D2S effector protein may be coupled to a guide nucleic acid that targets a particular region of interest in the ssRNA. In some embodiments, the target nucleic acid, and the resulting cleaved nucleic acid is contacted with a nucleic acid for homologous recombination (e.g., homology directed repair (HDR)) or non-homologous end joining (NHEJ). In some embodiments, a double-stranded break in the target nucleic acid may be repaired (e.g., by NHEJ or HDR) without insertion of a donor template, such that the repair results in an indel in the target nucleic acid at or near the site of the double-stranded break.

In some embodiments, the D2S effector protein is fused to a chromatin-modifying enzyme. In some embodiments, the fusion protein chemically modifies the target nucleic acid, for example by methylating, demethylating, or acetylating the target nucleic acid in a sequence specific or non-specific manner.

Methods may comprise use of two or more D2S effector proteins. An illustrative method for introducing a break in a target nucleic acid comprises contacting the target nucleic acid with: (a) a first engineered guide nucleic acid comprising a region that binds to a first D2S effector protein, wherein the effector protein comprises at least 75% sequence identity to a sequence selected from the group consisting of SEQ ID NOs: 1-2, or 37; and (b) a second engineered guide nucleic acid comprising a region that binds to a second D2S effector protein, wherein the effector protein comprises at least 75% sequence identity to a sequence selected from the group consisting of SEQ ID NOs: 1-2, or 37, wherein the first engineered guide nucleic acid comprises an additional region that binds to the target nucleic acid and wherein the second engineered guide nucleic acid comprises an additional region that binds to the target nucleic acid. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 92%, at least 95%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, or 100% identical to an equal length portion of any one of SEQ ID NOs: 22-26.

In some embodiments, editing a target nucleic acid comprises genome editing. Genome editing may comprise modifying a genome, chromosome, plasmid, or other genetic material of a cell or organism. In some embodiments, the genome, chromosome, plasmid, or other genetic material of the cell or organism is modified in vivo. In some embodiments, the genome, chromosome, plasmid, or other genetic material of the cell or organism is modified in a cell. In some embodiments, the genome, chromosome, plasmid, or other genetic material of the cell or organism is modified in vitro. For example, a plasmid may be modified in vitro using a composition or systems described herein and introduced into a cell or organism. In some embodiments, modifying a target nucleic acid may comprise deleting a sequence from a target nucleic acid. For example, a mutated sequence or a sequence associated with a disease may be removed from a target nucleic acid. In some embodiments, modifying a target nucleic acid may comprise replacing a sequence in a target nucleic acid with a second sequence. For example, a mutated sequence or a sequence associated with a disease may be replaced with a second sequence lacking the mutation or that is not associated with the disease. In some embodiments, modifying a target nucleic acid may comprise introducing a sequence into a target nucleic acid. For example, a beneficial sequence or a sequence that may reduce or eliminate a disease may be inserted into the target nucleic acid.

In some embodiments, methods comprise inserting a donor nucleic acid into a cleaved target nucleic acid. The donor nucleic acid may be inserted at a specified (e.g., effector protein targeted) point within the target nucleic acid. In some embodiments, methods comprise contacting a target nucleic acid with a D2S effector protein comprising an amino acid sequence that is at least 70%, at least 75%, at least 80%, at least 85%, at least 90%, at least 95%, at least 97%, at least 98%, at least 99%, or 100% identical to any one of the sequences recited in TABLE 1, thereby introducing a single-stranded break in the target nucleic acid; contacting the target nucleic acid with a second effector protein, optionally comprising an amino acid sequence that is at least 70%, at least 75%, at least 80%, at least 85%, at least 90%, at least 95%, at least 97%, at least 98%, or at least 99% identical to any one of the sequences recited in TABLE 1, to generate a second cleavage site in the target nucleic acid, ligating the regions flanking the first and second cleavage site, optionally through NHEJ or single-strand annealing, thereby resulting in the excision of a portion of the target nucleic acid between the first and second cleavage sites from the target nucleic acid; and contacting the target nucleic acid with a donor nucleic acid for homologous recombination, optionally via HDR or NHEJ, thereby introducing a new sequence into the target nucleic acid (e.g., at a cleavage site or in between two cleavage sites).

In some embodiments, methods comprise editing a target nucleic acid with two or more effector proteins. Editing a target nucleic acid may comprise introducing a two or more single-stranded breaks in a target nucleic acid. In some embodiments, a break may be introduced by contacting a target nucleic acid with an effector protein and a guide nucleic acid. The guide nucleic acid may bind to the effector protein, e.g., a D2S effector protein, and hybridize to a region of the target nucleic acid, thereby recruiting the effector protein to the region of the target nucleic acid. Binding of the effector protein to the guide nucleic acid and the region of the target nucleic acid may activate the effector protein, and the effector protein may introduce a break (e.g., a single stranded break) in the region of the target nucleic acid. In some embodiments, modifying a target nucleic acid may comprise introducing a first break in a first region of the target nucleic acid and a second break in a second region of the target nucleic acid. For example, modifying a target nucleic acid may comprise contacting a target nucleic acid with a first guide nucleic acid that binds to a first effector protein and hybridizes to a first region of the target nucleic acid and a second guide nucleic acid that binds to a second programmable nickase and hybridizes to a second region of the target nucleic acid. The first effector protein, e.g., a D2S effector protein, may introduce a first break in a first strand at the first region of the target nucleic acid, and the second effector protein may introduce a second break in a second strand at the second region of the target nucleic acid. In some embodiments, a segment of the target nucleic acid between the first break and the second break may be removed, thereby modifying the target nucleic acid. In some embodiments, a segment of the target nucleic acid between the first break and the second break may be replaced (e.g., with donor nucleic acid), thereby modifying the target nucleic acid. In some embodiments, the D2S effector protein comprises an amino acid sequence that is at least 70%, at least 75%, at least 80%, at least 85%, at least 90%, at least 95%, at least 97%, at least 98%, at least 99%, or 100% identical to any one of the sequences recited in TABLE 1. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 95%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, or 100% identical to an equal length portion of any one of SEQ ID NOs: 22-26.

In some embodiments, editing is achieved by fusing an effector protein, e.g., a D2S effector protein, to a heterologous sequence. The heterologous sequence may be a suitable fusion partner, e.g., a protein that provides recombinase activity by acting on the target nucleic acid sequence. In some embodiments, the fusion protein comprises a D2S effector protein fused to a heterologous sequence by a linker. The heterologous sequence or fusion partner may be a base editing domain. The base editing domain may be an ADAR1/2 or any functional variant thereof. The heterologous sequence or fusion partner may be fused to the C-terminus, N-terminus, or an internal portion (e.g., a portion other than the N- or C-terminus) of the D2S effector protein. The heterologous sequence or fusion partner may be fused to the D2S effector protein by a linker as described herein.

Specific Targets and Indications

Described herein are compositions, systems and methods for editing or detecting a target nucleic acid, wherein the target nucleic acid is a gene, a portion thereof, a transcript thereof. In some embodiments, the target nucleic acid is a reverse transcript (e.g., a cDNA) of an mRNA transcribed from the gene, or an amplicon thereof. In some embodiments, the target nucleic acid is an amplicon of at least a portion of a gene. Non-limiting examples of genes are recited in TABLE 8.

Further description of editing or detecting a target nucleic acid in the foregoing genes can be found in more detail in Kim et al., "Enhancement of target specificity of CRISPR-Cas12a by using a chimeric DNA-RNA guide", Nucleic Acids Res. 2020 Sep. 4; 48(15):8601-8616; Wang et al., "Specificity profiling of CRISPR system reveals greatly enhanced off-target gene editing", Scientific Reports volume 10, Article number: 2269 (2020); Tuladhar et al., "CRISPR-Cas9-based mutagenesis frequently provokes on-target mRNA misregulation", Nature Communications volume 10, Article number: 4056 (2019); Dong et al., "Genome-Wide Off-Target Analysis in CRISPR-Cas9 Modified Mice and Their Offspring", G3, Volume 9, Issue 11, 1 Nov. 2019, Pages 3645-3651; Winter et al., "Genome-wide CRISPR screen reveals novel host factors required for *Staphylococcus aureus* α-hemolysin-mediated toxicity", Scientific Reports volume 6, Article number: 24242 (2016); and Ma et al., "A CRISPR-Based Screen Identifies Genes Essential for West-Nile-Virus-Induced Cell Death", *Cell Rep.* 2015 Jul. 28; 12(4):673-83, which are hereby incorporated by reference in their entirety.

Donor Nucleic Acids

Donor nucleic acids of any suitable size may be integrated into a target nucleic acid or genome. In some embodiments, the donor polynucleotide integrated into a genome is less than 3, about 3, 3.5, 4, 4.5, 5, 5.5, 6, 6.5, 7, 7.5, 8, 8.5, 9, 9.5, 10, 10.5, 11, 11.5, 12, 12.5, 13, 13.5, 14, 14.5, 15, 16, 17, 18, 19, 20, 25, 30, 35, 40, 45, 50, 100, 150, 200, 250, 300, 350, 400, 450, 500 kilobases in length. In some embodiments, donor nucleic acids are more than 500 kilobases (kb) in length.

The donor nucleic acid may comprise a sequence that is derived from a plant, bacteria, virus or an animal. The animal may be human. The animal may be a non-human animal, such as, by way of non-limiting example, a mouse, rat, hamster, rabbit, pig, bovine, deer, sheep, goat, chicken, cat, dog, ferret, a bird, non-human primate (e.g., marmoset, rhesus monkey). The non-human animal may be a domesticated mammal or an agricultural mammal.

In reference to a viral vector, the term donor nucleic acid refers to a sequence of nucleotides that will be or has been introduced into a cell following transfection of the viral vector. The donor nucleic acid may be introduced into the cell by any mechanism of the transfecting viral vector, including, but not limited to, integration into the genome of the cell or introduction of an episomal plasmid or viral genome. As another example, when used in reference to the activity of an effector protein (e.g., a D2S effector protein), the term donor nucleic acid refers to a sequence of nucleotides that will be or has been inserted at the site of cleavage by the effector protein (cleaving (hydrolysis of a phosphodiester bond) of a nucleic acid resulting in a nick or double strand break-nuclease activity). In some embodiments, the donor nucleic acid comprises a nucleotide sequence encoding any one of the gene recited in TABLE 8. As yet another example, when used in reference to homologous recombination, the term donor nucleic acid refers to a sequence of DNA that serves as a template in the process of homologous recombination, which may carry the modification that is to be or has been introduced into the target nucleic acid. By using this donor nucleic acid as a template, the genetic information, including the modification, is copied into the target nucleic acid by way of homologous recombination.

Genetically Modified Cells and Organisms

Methods of editing described herein may be employed to generate a genetically modified cell. The cell may be a eukaryotic cell (e.g., a mammalian cell) or a prokaryotic cell (e.g., an archaeal cell). The cell may be derived from a multicellular organism and cultured as a unicellular entity. The cell may comprise a heritable genetic modification, such that progeny cells derived therefrom comprise the heritable genetic mutation. The cell may be progeny of a genetically modified cell comprising a genetic modification of the genetically modified parent cell. A genetically modified cell may comprise a deletion, insertion, mutation, or non-native sequence relative to a wild-type version of the cell or the organism from which the cell was derived.

Methods may comprise contacting a cell with a nucleic acid (e.g., a plasmid or mRNA) comprising a nucleobase sequence encoding an effector protein, e.g., a D2S effector protein, wherein the effector protein comprises an amino acid sequence that is at least 70%, at least 75%, at least 80%, at least 85%, at least 90%, at least 95%, at least 97%, at least 98%, or at least 99% identical to any one of the sequences recited in TABLE 1.

Methods may comprise contacting cells with a nucleic acid (e.g., a plasmid or mRNA) comprising a nucleobase sequence encoding a guide nucleic acid, an sgRNA, a tracrRNA sequence, a crRNA, or any combination thereof. In some embodiments, the nucleobase sequence of the guide nucleic acid is at least 70%, at least 75%, at least 80%, at least 85%, at least 90%, at least 92%, at least 95%, at least 97%, at least 98%, at least 99%, or 100% identical to any one of SEQ ID NOs: 17-21 and 27-30. In some embodiments, the guide nucleic acid comprises a crRNA sequence that is at least 70%, at least 75%, at least 80%, at least 85%, at least 90%, at least 92%, at least 95%, at least 97%, at least 98%, at least 99%, or 100% identical to any one of SEQ ID NOs: 17-21. In some embodiments, the guide nucleic acid comprises a portion of or all of a tracrRNA sequence that is at least 70%, at least 75%, at least 80%, at least 85%, at least 90%, at least 92%, at least 95%, at least 97%, at least 98%, at least 99%, or 100% identical to an equal length portion of any one of SEQ ID NOs: 22-26. Contacting may comprise electroporation, acoustic poration, optoporation, viral vector-based delivery, iTOP, nanoparticle delivery (e.g., lipid or gold nanoparticle delivery), cell-penetrating peptide (CPP) delivery, DNA nanostructure delivery, or any combination thereof.

Methods may comprise contacting a cell with an effector protein, e.g., a D2S effector protein or a multimeric complex thereof, wherein the effector protein comprises an amino acid sequence that is at least 70%, at least 75%, at least 80%, at least 85%, at least 90%, at least 95%, at least 97%, at least 98%, or at least 99% identical to any one of the sequences recited in TABLE 1. Methods may comprise contacting a cell with an D2S effector protein, wherein the amino acid sequence of the D2S effector protein is at least 70%, at least 75%, at least 80%, at least 85%, at least 90%, at least 95%, at least 97%, at least 98%, or at least 99% identical to any one of the sequences recited in TABLE 1.

Disclosed herein are methods of generating a genetically modified cell. In some embodiments, the methods comprise contacting a cell comprising a target nucleic acid with the systems, compositions, or pharmaceutical compositions described herein. In some embodiments, the system or composition independently comprises the effector protein described herein or a nucleic acid encoding the effector protein, the engineered guide nucleic acid described herein or a nucleic acid encoding the engineered guide nucleic acid, or a combination thereof. In some embodiments, contacting the cell with the effector protein or nucleic acid encoding the effector protein, and the engineered guide nucleic acid or a nucleic acid encoding the engineered guide nucleic acid is sequential. In some embodiments, contacting the cell with the effector protein or nucleic acid encoding the effector protein, and the engineered guide nucleic acid or a nucleic acid encoding the engineered guide nucleic acid is simultaneous.

Methods may comprise cell line engineering (e.g., engineering a cell from a cell line for bioproduction). Cell lines may be used to produce a desired protein. In some embodiments, target nucleic acids comprise a genomic sequence. In some embodiments, the cell line is a Chinese hamster ovary cell line (CHO), human embryonic kidney cell line (HEK), cell lines derived from cancer cells, cell lines derived from lymphocytes, and the like. Non-limiting examples of cell lines includes: C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, CIR, Rat6, CV1, RPTE, A10, T24, J82, A375, ARH-77, Calu1, SW480, SW620, SKOV3, SK-UT, CaCo2, P388D1, SEMK2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, and YAR.

Non-limiting examples of cells that may be engineered or modified with compositions, systems and methods described herein include eukaryotic cells, immune cells, such as CART, T-cells, B-cells, NK cells, granulocytes, basophils, eosinophils, neutrophils, mast cells, monocytes, macrophages, dendritic cells, antigen-presenting cells (APC), or adaptive cells. Non-limiting examples of cells that may be engineered or modified with compositions, systems and methods described herein include plant cells, such as parenchyma, sclerenchyma, collenchyma, xylem, phloem, germline (e.g., pollen). Cells from lycophytes, ferns, gymnosperms, angiosperms, bryophytes, charophytes, chloropytes, rhodophytes, or glaucophytes. Non-limiting examples of cells that may be engineered or modified with compositions, systems and methods described herein include stem cells, such as human stem cells, animal stem cells, stem cells that are not derived from human embryonic stem cells, embryonic stem cells, mesenchymal stem cells, pluripotent stem cells, induced pluripotent stem cells (iPS), somatic stem cells, adult stem cells, hematopoietic stem cells, tissue-specific stem cells.

Methods of the disclosure may be performed in a subject. Compositions or systems of the disclosure may be administered to a subject. A subject may be a human. A subject may be a mammal (e.g., rat, mouse, cow, dog, pig, sheep, horse). A subject may be a vertebrate or an invertebrate. A subject may be a laboratory animal. A subject may be a patient. A subject may be suffering from a disease. A subject may display symptoms of a disease. A subject may not display symptoms of a disease, but still have a disease. A subject may be under medical care of a caregiver (e.g., the subject is hospitalized and is treated by a physician). Methods of the disclosure may be performed in a plant, bacteria, or a fungus.

Methods of the disclosure may be performed in a cell. A cell may be in vitro. A cell may be in vivo. A cell may be ex vivo. A cell may be an isolated cell. A cell may be a cell inside of an organism. A cell may be an organism. A cell may be a cell in a cell culture. A cell may be one of a collection of cells. A cell may be a mammalian cell or derived from a mammalian cell. A cell may be a rodent cell or derived from a rodent cell. A cell may be a human cell or derived from a human cell. A cell may be a prokaryotic cell or derived from a prokaryotic cell. A cell may be a bacterial cell or may be derived from a bacterial cell. A cell may be an archaeal cell or derived from an archaeal cell. A cell may be a eukaryotic cell or derived from a eukaryotic cell. A cell may be a pluripotent stem cell. A cell may be a plant cell or derived from a plant cell. A cell may be an animal cell or derived from an animal cell. A cell may be an invertebrate cell or derived from an invertebrate cell. A cell may be a vertebrate cell or derived from a vertebrate cell. A cell may be a microbe cell or derived from a microbe cell. A cell may be a fungi cell or derived from a fungi cell. A cell may be from a specific organ or tissue.

Methods of the disclosure may be performed in a eukaryotic cell or cell line. In some embodiments, the eukaryotic cell is a Chinese hamster ovary (CHO) cell. In some embodiments, the eukaryotic cell is a Human embryonic kidney 293 cells (also referred to as HEK or HEK 293) cell. Non-limiting examples of cell lines that may be used with compositions, systems and methods of the present disclosure include C8161, CCRF-CEM, MOLT, mIMCD-3, NHDF, HeLa-S3, Huh1, Huh4, Huh7, HUVEC, HASMC, HEKn, HEKa, MiaPaCell, Panel, PC-3, TF1, CTLL-2, CIR, Rat6, CV1, RPTE, A10, T24, J82, A375, ARH-77, Calu1, SW480, SW620, SKOV3, SK-UT, CaCo2, P388D1, SEM-K2, WEHI-231, HB56, TIB55, Jurkat, J45.01, LRMB, Bcl-1, BC-3, IC21, DLD2, Raw264.7, NRK, NRK-52E, MRC5, MEF, Hep G2, HeLa B, HeLa T4, COS, COS-1, COS-6, COS-M6A, BS-C-1 monkey kidney epithelial, BALB/3T3 mouse embryo fibroblast, 3T3 Swiss, 3T3-L1, 132-d5 human fetal fibroblasts; 10.1 mouse fibroblasts, 293-T, 3T3, 721, 9L, A2780, A2780ADR, A2780cis, A172, A20, A253, A431, A-549, ALC, B16, B35, BCP-1 cells, BEAS-2B, bEnd.3, BHK-21, BR 293, BxPC3, C3H-10T1/2, C6/36, Cal-27, CHO, CHO-7, CHO-IR, CHO-K1, CHO-K2, CHO-T, CHO Dhfr-/-, COR-L23, COR-L23/CPR, COR-L23/5010, COR-L23/R23, COS-7, COV-434, CML T1, CMT, CT26, D17, DH82, DU145, DuCaP, EL4, EM2, EM3, EMT6/AR1, EMT6/AR10.0, FM3, H1299, H69, HB54, HB55, HCA2, HEK-293, HeLa, Hepa1c1c7, HL-60, HMEC, HT-29, Jurkat, JY cells, K562 cells, Ku812, KCL22, KG1, KYO1, LNCap, Ma-Mel 1-48, MC-38, MCF-7, MCF-10A, MDA-MB-231, MDA-MB-468, MDA-MB-435, MDCK II, MDCK II, MOR/0.2R, MONO-MAC 6, MTD-1A, MyEnd, NCI-H69/CPR, NCI-H69/LX10, NCI-H69/LX20, NCI-H69/LX4, NIH-3T3, NALM-1, NW-145, OPCN/OPCT cell lines, Peer, PNT-1A/PNT 2, RenCa, RIN-5F, RMA/RMAS, Saos-2 cells, Sf-9, SkBr3, T2, T-47D, T84, THP1 cell line, U373, U87, U937, VCaP, Vero cells, WM39, WT-49, X63, YAC-1, and YAR. Non-limiting examples of other cells that may be used with the disclosure include eukaryotic cells, immune cells, such as CART, T-cells, B-cells, NK cells, granulocytes, basophils, eosinophils, neutrophils, mast cells, monocytes, macrophages, dendritic cells, antigen-presenting cells (APC), or adaptive cells. Non-limiting examples of cells that may be used with this disclosure also include plant cells, such as Parenchyma, sclerenchyma, collenchyma, xylem, phloem, germline (e.g., pollen). Cells from lycophytes, ferns, gymnosperms, angiosperms, bryophytes, charophytes, chloropytes, rhodophytes, or glaucophytes. Non-limiting examples of cells that may be used with this disclosure also include stem cells, such as human stem cells, animal stem cells, stem cells that are not derived from human embryonic stem cells, embryonic stem cells, mesenchymal stem cells, pluripotent stem cells, induced pluripotent stem cells (iPS), somatic stem cells, adult stem cells, hematopoietic stem cells, tissue-specific stem cells.

Agricultural Engineering

Compositions, systems and methods of the disclosure may be used for agricultural engineering. For example, compositions, systems and methods of the disclosure may be used to confer desired traits on a plant. A plant may be engineered for the desired physiological and agronomic characteristic using the present disclosure. In some embodiments, the target nucleic acid sequence comprises a nucleic acid sequence of a plant. In some embodiments, the target nucleic acid sequence comprises a genomic nucleic acid sequence of a plant cell. In some embodiments, the target nucleic acid sequence comprises a nucleic acid sequence of an organelle of a plant cell. In some embodiments, the target nucleic acid sequence comprises a nucleic acid sequence of a chloroplast of a plant cell.

The plant may be a dicotyledonous plant. Non-limiting examples of orders of dicotyledonous plants include Magniolales, Illiciales, Laurales, Piperales, Aristochiales, Nymphaeales, Ranunculales, Papeverales, Sarraceniaceae, Trochodendrales, Hamamelidales, Eucomiales, Leitneriales, Myricales, Fagales, Casuarinales, Caryophyllales, Batales, Polygonales, Plumbaginales, Dilleniales, Theales, Malvales, Urticales, Lecythidales, Violales, Salicales, Capparales, Ericales, Diapensales, Ebenales, Primulales, Rosales, Fabales, Podostemales, Haloragales, Myrtales, Cornales, Proteales, San tales, Rafflesiales, Celastrales, Euphorbiales, Rhamnales, Sapindales, Juglandales, Geraniales, Polygalales, Umbellales, Gentianales, Polemoniales, Lamiales, Plantaginales, Scrophulariales, Campanulales, Rubiales, Dipsacales, and Asterales.

The plant may be a monocotyledonous plant. Non-limiting examples of orders of monocotyledonous plants include Alismatales, Hydrocharitales, Najadales, Triuridales, Commelinales, Eriocaulales, Restionales, Poales, Juncales, Cyperales, Typhales, Bromeliales, Zingiberales, Arecales, Cyclanthales, Pandanales, Arales, Lilliales, and Orchid ales. A plant may belong to the order, for example, Gymnospermae, Pinales, Ginkgoales, Cycadales, Araucariales, Cupressales and Gnetales.

Non-limiting examples of plants include plant crops, fruits, vegetables, grains, soy bean, corn, maize, wheat, seeds, tomatoes, rice, cassava, sugarcane, pumpkin, hay, potatoes, cotton, *cannabis*, tobacco, flowering plants, conifers, gymnosperms, ferns, clubmosses, hornworts, liverworts, mosses, wheat, maize, rice, millet, barley, tomato, apple, pear, strawberry, orange, acacia, carrot, potato, sugar beets, yam, lettuce, spinach, sunflower, rape seed, *Arabidopsis*, alfalfa, amaranth, apple, apricot, artichoke, ash tree, asparagus, avocado, banana, barley, beans, beet, birch, beech, blackberry, blueberry, broccoli, Brussel's sprouts, cabbage, canola, cantaloupe, carrot, cassava, cauliflower, cedar, a cereal, celery, chestnut, cherry, Chinese cabbage, citrus, clementine, clover, coffee, corn, cotton, cowpea, cucumber, cypress, eggplant, elm, endive, *eucalyptus*, fennel, figs, fir, geranium, grape, grapefruit, groundnuts, ground cherry, gum hemlock, hickory, kale, kiwifruit, kohlrabi, larch, lettuce, leek, lemon, lime, locust, pine, maidenhair, maize, mango, maple, melon, millet, mushroom, mustard, nuts, oak, oats, oil palm, okra, onion, orange, an ornamental plant or flower or tree, *papaya*, palm, parsley, parsnip, pea, peach, peanut, pear, peat, pepper, persimmon, pigeon pea, pine, pineapple, plantain, plum, pomegranate, potato, pumpkin, radicchio, radish, rapeseed, raspberry, rice, rye, sorghum, safflower, sallow, soybean, spinach, spruce, squash, strawberry, sugar beet, sugarcane, sunflower, sweet potato, sweet corn, tangerine, tea, tobacco, tomato, trees, triticale, turf grasses, turnips, vine, walnut, watercress, watermelon, wheat, yams, yew, and zucchini. A plant may include algae.

XIV. Methods of Treatment

Described herein are methods for treating a disease in a subject by modifying a target nucleic acid associated with a gene or expression of a gene related to the disease. In some embodiments, methods comprise administering a composition, a system or cell described herein to a subject. By way of non-limiting example, the disease may be a cancer, an ophthalmological disorder, neurological disorder, a blood disorder, a metabolic disorder, a genetic disorder, an infection, or any combination thereof. The disease may be an inherited disorder, also referred to as a genetic disorder. The disease may be the result of an infection or associated with an infection.

In some embodiments, the compositions described herein are for use in therapy. In some embodiments, the compositions described herein are for use in treating a disease or condition described herein. Also provided is the use of the compositions described herein in the manufacture of a medicament. Also provided is the use of the compositions described herein in the manufacture of a medicament for therapeutic and/or prophylactic treatment of a disease or condition described herein.

In some embodiments, the effector proteins described herein are for use in therapy. In some embodiments, the effector proteins described herein are for use in treating a disease or condition described herein. Also provided is the use of the effector proteins described herein in the manufacture of a medicament. Also provided is the use of the effector proteins described herein in the manufacture of a medicament for therapeutic and/or prophylactic treatment of a disease or condition described herein.

In some embodiments, the guide nucleic acids described herein are for use in therapy. In some embodiments, the guide nucleic acids described herein are for use in treating a disease or condition described herein. Also provided is the use of the guide nucleic acids described herein in the manufacture of a medicament. Also provided is the use of the guide nucleic acids described herein in the manufacture of a medicament for therapeutic and/or prophylactic treatment of a disease or condition described herein.

The compositions, systems and methods described herein may be used to treat, prevent, or inhibit a disease or syndrome in a subject. In some embodiments, the disease is a liver disease, a lung disease, an eye disease, or a muscle disease. Exemplary diseases and syndromes include, but are not limited to: 11-hydroxylase deficiency; 17,20-desmolase deficiency; 17-hydroxylase deficiency; 3-hydroxyisobutyrate aciduria; 3-hydroxysteroid dehydrogenase deficiency; 46,XY gonadal dysgenesis; AAA syndrome; ABCA3 deficiency; ABCC8-associated hyperinsulinism; aceruloplasminemia; acromegaly; achondrogenesis type 2; acral peeling skin syndrome; acrodermatitis enteropathica; adrenocortical micronodular hyperplasia; congenital adrenal hyperplasia; adrenoleukodystrophies; adrenomyeloneuropathies; Aicardi-Goutieres syndrome; Alagille disease (also called Alagille Syndrome); Alexander Disease, Alpers syndrome; alpha-1 antitrypsin deficiency (AATD); alpha-mannosidosis; Alstrom syndrome; Alzheimer's disease; amebic dysentery; amelogenesis imperfecta; amish type microcephaly; amyotrophic lateral sclerosis (ALS); anauxetic dysplasia; androgen insensitivity syndrome; antiphospholipid syndrome; Antley-Bixler syndrome; APECED, Apert syndrome, aplasia of lacrimal and salivary glands, argininemia, arrhythmogenic right ventricular dysplasia, Arts syndrome, ARVD2, arylsulfatase deficiency type metachromatic leokodystrophy, ataxia telangiectasia, autoimmune lymphoproliferative syndrome; autoimmune polyglandular syndrome type 1; autosomal dominant anhidrotic ectodermal dysplasia; autosomal dominant polycystic kidney disease; autosomal recessive microtia; autosomal recessive renal glucosuria; autosomal visceral heterotaxy; babesiosis; balantidial dysentery; Bardet-Biedl syndrome; Bartter syndrome; basal cell nevus syndrome; Batten disease; benign recurrent intrahepatic cholestasis; beta-mannosidosis; Bethlem myopathy; Blackfan-Diamond anemia; bleeding disorder (coagulation); blepharophimosis; Byler disease; C syndrome; cachexia; CADASIL; Calcific Aortic Stenosis, carbamyl phosphate synthetase deficiency; cardiofaciocutaneous syndrome; Carney triad; carnitine palmitoyltransferase deficiencies; cartilage-hair hypoplasia; cblC type of combined methylmalonic aciduria; CD18 deficiency; CD3Z-associated primary T-cell immunodeficiency; CD40L deficiency; CDAGS syndrome; CDG1A; CDG1B; CDG1M; CDG2C; CEDNIK syndrome; central core disease; centronuclear myopathy; cerebral capillary malformation; cerebrooculofacioskeletal syndrome type 4; cerebrooculogacioskeletal syndrome; cerebrotendinous xanthomatosis; Chaga's Disease; Charcot Marie Tooth Disesase; cherubism; CHILD syndrome; chronic granulomatous disease; chronic recurrent multifocal osteomyelitis; citrin deficiency; classic hemochromatosis; CMT Type 2A; CNPPB syndrome; cobalamin C disease; Cockayne syndrome; coenzyme Q10 deficiency; Coffin-Lowry syndrome; Cohen syndrome; combined deficiency of coagulation factors V; common variable immune deficiency; complete androgen insentivity; cone rod dystrophies; conformational diseases; congenital bile adid synthesis defect type 1; congenital bile adid synthesis defect type 2; congenital defect in bile acid synthesis type; congenital erythropoietic porphyria; congenital generalized osteosclerosis; Cornelia de Lange syndrome; coronary heart disease; Cousin syndrome; Cowden disease; COX deficiency; Cri du chat syndrome; Crigler-Najjar disease; Crigler-Najjar syndrome type 1; Crisponi syndrome; Crouzon syndrome; Currarino syndrome; Curth-Macklin type ichthyosis hystrix; cutis laxa; cystic fibrosis; cystinosis; d-2-hydroxyglutaric aciduria; DDP syndrome; Dejerine-Sottas disease; Denys-Drash syndrome; Dercum disease; desmin cardiomyopathy; desmin myopathy; DGUOK-associated mitochondrial DNA depletion; diabetes Type I; diabetes Type II; disorders of glutamate metabolism; distal spinal muscular atrophy type 5; DNA repair diseases; dominant optic atrophy; Doyne honeycomb retinal dystrophy; Dravet Syndrome; Duchenne muscular dystrophy; dyskeratosis congenita; Ehlers-Danlos syndrome type 4; Ehlers-Danlos syndromes; Elejalde disease; Ellis-van Creveld disease; Emery-Dreifuss muscular dystrophies; encephalomyopathic mtDNA depletion syndrome; encephalitis; enzymatic diseases; EPCAM-associated congenital tufting enteropathy; epidermolysis bullosa with pyloric atresia; epilepsy; facioscapulohumeral muscular dystrophy (FSHD); Factor V Leiden Thrombophilia; Faisalabad histiocytosis; familial atypical mycobacteriosis; familial capillary malformation-arteriovenous; Familial Creutzfeld-Jakob Disease; familial esophageal achalasia; familial glomuvenous malformation; familial hemophagocytic lymphohistiocytosis; familial mediterranean fever; familial megacalyces; familial schwannomatosisl; familial spina bifida; familial splenic asplenia/hypoplasia; familial thrombotic thrombocytopenic purpura; Fanconi disease (Fanconi anemia); Feingold syndrome; FENIB; fibrodysplasia ossificans progressiva; FKTN; Fragile X syndrome; Francois-Neetens fleck corneal dystrophy; Frasier syndrome; Friedreich's ataxia; FTDP-17; Fuchs Corneal Dystrophy; fucosidosis; G6PD deficiency; galactosialidosis; Galloway syndrome; Gardner syndrome; Gaucher disease; Gitelman syndrome; GLUT1 deficiency; GM2-Gangliosidoses (e.g., Tay Sachs Disease, Sandhoff Disease) glycogen storage disease type 1b; glycogen storage disease type 2; glycogen storage disease type 3; glycogen storage disease type 4; glycogen storage disease type 9a; glycogen storage diseases; GM1-gangliosidosis; Greenberg syndrome; Greig cephalopolysyndactyly syndrome; hair genetic diseases; HANAC syndrome; harlequin type ichtyosis congenita; HDR syndrome; hearing loss; hemochromatosis type 3; hemochromatosis type 4; hemophilia A; hemophilia B; hereditary angioedema type 3; hereditary angioedemas; hereditary hemorrhagic telangiectasia; hereditary hypofibrinogenemia; hereditary intraosseous vascular malformation; hereditary leiomyomatosis and renal cell cancer; hereditary neuralgic amyotrophy; hereditary sensory and autonomic neuropathy type; Hermansky-Pudlak disease; HHH syndrome; HHT2; hidrotic ectodermal dysplasia type 1; hidrotic ectodermal dysplasias; HNF4A-associated hyperinsulinism; HNPCC; homozygous familial hypercholesterolemia; hypercholesterolemia; human immunodeficiency with microcephaly; Huntington's disease; hyper-IgD syndrome; hyperinsulinism-hyperammonemia syndrome; hypercholesterolemia; hypertrophy of the retinal pigment epithelium; hypochondrogenesis; hypohidrotic ectodermal dysplasia; ICF syndrome; idiopathic congenital intestinal pseudo-obstruction; immunodeficiency with hyper-IgM type 1; immunodeficiency with hyper-IgM type 3; immunodeficiency with hyper-IgM type 4; immunodeficiency with hyper-IgM type 5; inbor errors of thyroid metabolism; infantile visceral myopathy; infantile X-linked spinal muscular atrophy; intrahepatic cholestasis of pregnancy; IPEX syndrome; IRAK4 deficiency; isolated congenital asplenia; Jeune syndrome; Johanson-Blizzard syndrome; Joubert syndrome; JP-HHT syndrome; juvenile hemochromatosis; juvenile hyalin fibromatosis; juvenile nephronophthisis; Kabuki mask syndrome; Kallmann syndromes; Kartagener syndrome; KCNJ11-associated hyperinsulinism; Kearns-Sayre syndrome; Kostmann disease; Kozlowski type of spondylometaphyseal dysplasia; Krabbe disease; LADD syndrome; late infantile-onset neuronal ceroid lipofuscinosis; LCK deficiency; LDHCP syndrome; Leber Congenital Amaurosis Teyp 10; Legius syndrome; Leigh syndrome; lethal congenital contracture syndrome 2; lethal congenital contracture syndromes; lethal contractural syndrome type 3; lethal neonatal CPT deficiency type 2; lethal osteosclerotic bone dysplasia; Li Fraumeni syndrome; LIG4 syndrome; lipodystrophy; lissencephaly type 1 Imag; lissencephaly type 3; Loeys-Dietz syndrome; low phospholipid-associated cholelithiasis; Lynch Syndrome; lysinuric protein intolerance; a lysosomal storage disease (e.g., Hunter syndrome, Hurler syndrome); macular dystrophy; Maffucci syndrome; Majeed syndrome; mannose-binding protein deficiency; Marfan disease; Marshall syndrome; MASA syndrome; MCAD deficiency; McCune-Albright syndrome; MCKD2; Meckel syndrome; MECP2 Duplication Syndrome; Meesmann corneal dystrophy; megacystis-microcolon-intestinal hypoperistalsis; megaloblastic anemia type 1; MEHMO; MELAS; Melnick-Needles syndrome; MEN2s; meningitis; Menkes disease; metachromatic leukodystrophies; methylmalonic acidurias; methylvalonic aciduria; microcoria-congenital nephrosis syndrome; microvillous atrophy; migraine; mitochondrial neurogastrointestinal encephalomyopathy; monilethrix; monosomy X; mosaic trisomy 9 syndrome; Mowat-Wilson syndrome; mucolipidosis type 2; mucolipidosis type Ma; mucolipidosis type IV; mucopolysaccharidoses; mucopolysaccharidosis type 3A; mucopolysaccharidosis type 3C; mucopolysaccharidosis type 4B; multiminicore disease; multiple acyl-CoA dehydrogenation deficiency; multiple cutaneous and mucosal venous malformations; multiple endocrine neoplasia type 1; multiple sulfatase deficiency; myotonic dystrophy; NAIC; nail-patella syndrome; nemaline myopathies; neonatal diabetes mellitus; neonatal surfactant deficiency; nephronophtisis; Netherton disease; neurofibromatoses; neurofibromatosis type 1; neurofibromatosis type 2; Niemann-Pick disease type A; Niemann-Pick disease type B; Niemann-Pick disease type C; NKX2E; non-alcoholic fatty liver disease (NAFLD); non-alcoholic steatohepatitis (NASH); Noonan syndrome; North American Indian childhood cirrhosis; NROB1 duplication-associated DSD; ocular genetic diseases; oculo-auricular syndrome; OLEDAID; oligomeganephronia; oligomeganephronic renal hypolasia; Ollier disease; Opitz-Kaveggia syndrome; orofaciodigital syndrome type 1; orofaciodigital syndrome type 2; osseous Paget disease; osteogenesis imperfecta; OTC deficiency; otopalatodigital syndrome type 2; OXPHOS diseases; palmoplantar hyperkeratosis; panlobar nephroblastomatosis; Parkes-Weber syndrome; Parkinson's disease; partial deletion of 21q22.2-q22.3; Pearson syndrome; Pelizaeus-Merzbacher disease; Pendred syndrome; pentalogy of Cantrell; peroxisomal acyl-CoA-oxidase deficiency; Peutz-Jeghers syndrome; Pfeiffer syndrome; Pierson syndrome; pigmented nodular adrenocortical disease; pipecolic acidemia; Pitt-Hopkins syndrome; PRKAG2 cardiac syndrome; plasmalogens deficiency; pleuropulmonary blastoma and cystic nephroma; polycystic kidney disease; polycystic ovarian disease; polycystic lipomembranous osteodysplasia; Pompe disease; infantile onset Pompe Disease (IOPD); late onset Pompe disease (LOPD); porphyrias; premature ovarian failure; primary erythermalgia; primary hemochromatoses; primary hyperoxaluria; progressive familial intrahepatic cholestasis; propionic acidemia; pyruvate decarboxylase deficiency; RAPADILINO syndrome; renal cystinosis; retinitis pigmentosa; Rett Syndrome; rhabdoid tumor predisposition syndrome; Rieger syndrome; ring chromosome 4; Roberts syndrome; Robinow-Sorauf syndrome; Rothmund-Thomson syndrome; severe combined immunodeficiency disorder (SCID); Saethre-Chotzen syndrome; Sandhoff disease; SC phocomelia syndrome; SCAS; severe combined immune deficiency; Schinzel phocomelia syndrome; short rib-polydactyly syndrome type 1; short rib-polydactyly syndrome type 4; short-rib polydactyly syndrome type 2; short-rib polydactyly syndrome type 3; Shwachman disease; Shwachman-Diamond disease; sickle cell anemia; Silver-Russell syndrome; Simpson-Golabi-Behmel syndrome; Smith-Lemli-Opitz syndrome; SPG7-associated hereditary spastic paraplegia; spherocytosis; spinocerebellar ataxia; split-hand/foot malformation with long bone deficiencies; spondylocostal dysostosis; sporadic visceral myopathy with inclusion bodies; storage diseases; Stargardt macular dystrophy; STRA6-associated syndrome; stroke; Tay-Sachs disease; thanatophoric dysplasia; thyroid metabolism diseases; Tourette syndrome; transthyretin-associated amyloidosis; trisomy 13; trisomy 22; trisomy 2p syndrome; tuberous sclerosis; tufting enteropathy; urea cycle diseases; Usher Syndrome; Van Den Ende-Gupta syndrome; Van der Woude syndrome; variegated mosaic aneuploidy syndrome; VLCAD deficiency; von Hippel-Lindau disease; von Willebrand disease; Waardenburg syndrome; WAGR syndrome; Walker-Warburg syndrome; Werner syndrome; Wilson disease; Wiskott-Aldrich Syndrome, Wolcott-Rallison syndrome; Wolfram syndrome; X-linked agammaglobulinemia; X-linked chronic idiopathic intestinal pseudo-obstruction; X-linked cleft palate with ankyloglossia; X-linked dominant chondrodysplasia punctata; X-linked ectodermal dysplasia; X-linked Emery-Dreifuss muscular dystrophy; X-linked lissencephaly; X-linked lymphoproliferative disease; X-linked visceral heterotaxy; xanthinuria type 1; xanthinuria type 2; xeroderma pigmentosum; XPV; and Zellweger disease.

In some embodiments, compositions, systems and methods modify at least one gene associated with the disease or the expression thereof. In some embodiments, the disease is Alzheimer's disease and the gene is selected from APP, BACE-1, PSD95, MAPT, PSEN1, PSEN2, APOE and APOEε4. In some embodiments, the disease is Parkinson's disease and the gene is selected from SNCA, GDNF, and LRRK2. In some embodiments, the disease comprises Centronuclear myopathy and the gene is DNM2. In some embodiments, the disease is Huntington's disease and the gene is HTT. In some embodiments, the disease is Alpha-1 antitrypsin deficiency (AATD) and the gene is SERPINA1. In some embodiments, the disease is amyotrophic lateral sclerosis (ALS) and the gene is selected from SOD1, FUS, C9ORF72, ATXN2, TARDBP, and CHCHD10. In some embodiments, the disease comprises Alexander Disease and the gene is GFAP. In some embodiments, the disease comprises Angelman Syndrome and the gene is UBE3A. In some embodiments, the disease comprises MECP2 Duplication syndrome and Rett syndrome and the gene is MECP2. In some embodiments, the disease comprises fragile X syndrome and the gene is FMR1. In some embodiments, the disease comprises CNS trauma and the gene is VEGF. In some embodiments, the disease comprises GM2-Gangliosidoses (e.g., Tay Sachs Disease, Sandhoff disease) and the gene is selected from HEXA and HEXB. In some embodiments, the disease comprises Hearing loss disorders and the gene is DFNA36. In some embodiments, the disease is Pompe disease and the gene is GAA. In some embodiments, the disease is infantile onset Pompe Disease (IOPD) and the gene is GAA. In some embodiments, the disease is late onset Pompe disease (LOPD) and the gene is GAA. In some embodiments, the disease is Retinitis pigmentosa and the gene is selected from PDE6B, RHO, RP1, RP2, RPGR, PRPH2, IMPDH1, PRPF31, CRB1, PRPF8, TULP1, CA4, HPRPF3, ABCA4, EYS, CERKL, FSCN2, TOPORS, SNRNP200, PRCD, NR2E3, MERTK, USH2A, PROM1, KLHL7, CNGB1, TTC8, ARL6, DHDDS, BEST1, LRAT, SPARA7, CRX CLRN1, RPE65, and WDR19. In some embodiments, the disease comprises Leber Congenital Amaurosis Type 10 and the gene is CEP290. In some embodiments, the disease comprises Calcific Aortic Stenosis and the gene is Apo(a). In some embodiments, the disease is cardiovascular disease and/or lipodystrophies and the gene is selected from APOA1, ANGPTL3, APOCIII, CFB, AGT, FXI, FXII, PKK, PCSK9, APOL1, and TTR. In some embodiments, the disease comprises acromegaly and the gene is GHR. In some embodiments, the disease is coronary heart disease and the gene is a Fibrinogen gene. In some embodiments, the disease is coronary heart disease and the gene is FGB-FGA-FGG. In some embodiments, the disease is diabetes and the gene is GCGR. In some embodiments, the disease is NAFLD/NASH and the gene is selected from DGAT2 and PNPLA3. In some embodiments, the disease is cancer and the gene is selected from STAT3, YAP1, FOXP3, AR (Prostate cancer), and IRF4 (multiple myeloma). In some embodiments, the disease is cystic fibrosis and the gene is CFTR. In some embodiments, the disease is Duchenne Muscular Dystrophy and the gene is DMD. In some embodiments, the disease comprises angioedema and the gene is PKK. In some embodiments, the disease comprises thalassemia and the gene is TMPRSS6. In some embodiments, the disease comprises achondroplasia and the gene is FGFR3. In some embodiments, the disease comprises a bleeding disorder with coagulation and the gene is FAY. In some embodiments, the disease comprises cachexia and the gene is SMAD7. In some embodiments, the disease comprises Cri du chat syndrome and the gene is selected from CTNND2. In some embodiments, the disease comprises cystic fibrosis and the gene is CFTR. In some embodiments, the disease comprises sickle cell anemia and the gene is Beta globin gene. In some embodiments, the disease comprises Alagille Syndrome and the gene is selected from JAG1 and NOTCH2. In some embodiments, the disease comprises Charcot Marie Tooth Disease and the gene is selected from PMP22 and MFN2. In some embodiments, the disease comprises Crouzon syndrome and the gene is selected from FGFR2, FGFR3, and FGFR3. In some embodiments, the disease comprises CMT Type 2A and the gene is Mitofusin 2. In some embodiments, the disease comprises Dravet Syndrome and the gene is selected from SCN1A and SCN2A. In some embodiments, the disease comprises Emery-Dreifuss syndrome and the gene is selected from EMD, LMNA, SYNE1, SYNE2, FHL1, and TMEM43. In some embodiments, the disease comprises Factor V Leiden Thrombophilia and the gene is F5. In some embodiments, the disease comprises Fanconi anemia and the gene is selected from FANCA, FANCB, FANCC, FANCD1, FANCD2, FANCE, FANCF, FANCG, FANCI, FANCJ, FANCL, FANCM, FANCN, FANCP, FANCS, RAD51C, and XPF. In some embodiments, the disease comprises Familial Creutzfeld-Jakob Disease and the gene is PRNP. In some embodiments, the disease comprises Familial Mediterranean Fever and the gene is MEFV. In some embodiments, the disease comprises Friedreich's ataxia and the gene is FXN. In some embodiments, the disease comprises Fuchs Corneal Dystrophy and the gene is selected from ZEB1 and TCF4. In some embodiments, the disease comprises Gaucher disease and the gene is GBA. In some embodiments, the disease comprises Hemochromatosis and the gene is C282Y. In some embodiments, the disease comprises Hemophilia A and the gene is selected from Coagulation Factor 8 and FVIII. In some embodiments, the disease comprises Hemophilia B and the gene is FIX. In some embodiments, the disease comprises human papillomavirus (HPV) and the gene is selected from HPV16 and HPV18 E7. In some embodiments, the disease is Huntington's Disease and the gene is Huntingtin. In some embodiments, the disease is congenital adrenal hyperplasia and the gene is CYP21A2. In some embodiments, the disease comprises hypercholesterolemia and the gene is selected from PCSK9 and ANGPTL3. In some embodiments, the disease comprises Joubert syndrome and the gene is selected from INPP5E, TMEM216, AHI1, NPHP1, CEP290, TMEM67, RPGRIP1L, ARL13B, CC2D2A, OFD1, TMEM138, TCTN3, ZNF423, and AMRC9. In some embodiments, the disease comprises Li-Fraumeni syndrome and the gene is TP53. In some embodiments, the disease comprises Lynch syndrome and the gene is selected from MSH2, MLH1, MSH6, PMS2, PMS1, TGFBR2, and MLH3. In some embodiments, the disease comprises Marfan syndrome and the gene is FBN1. In some embodiments, the disease comprises methylmalonic acidemia and the gene is selected from MMAA, MIAB, and MUT. In some embodiments, the disease is myotonic dystrophy and the gene is selected from CNBP and DMPK. In some embodiments, the disease comprises neurofibromatosis and the gene is selected from NF1, and NF2. In some embodiments, the disease comprises neurofibromatosis type 2 and the gene is NF2. In some embodiments, the disease comprises osteogenesis imperfecta and the gene is selected from COL1A1, COL1A2, and IFITM5. In some embodiments, the disease is non-small cell lung cancer and the gene is selected from KRAS, EGFR, ALK, METex14, BRAF V600E, ROS1, RET, and NTRK. In some embodiments, the disease comprises OTC deficiency and the gene is OTC. In some embodiments, the disease comprises Peutz-Jeghers syndrome and the gene is STKI1. In some embodiments, the disease comprises polycystic kidney disease and the gene is selected from PKD1 and PKD2. In some embodiments, the disease comprises PRKAG2 cardiac syndrome and the gene is PRKAG2. In some embodiments, the disease comprises severe combined immune deficiency and the gene is selected from IL7R, RAG1, and JAK3. In some embodiments, the disease comprises Spinocerebellar ataxia and the gene is selected from ATXN1, ATXN2, ATXN3, PLEKHG4, SPTBN2, CACNA1A, ATXN7, ATXN8OS, ATXN10, TTBK2, PPP2R2B, KCNC3, PRKCG, ITPR1, TBP, KCND3, and FGF14. In some embodiments, the disease comprises Usher Syndrome and the gene is selected from MYO7A, USH1C, CDH23, PCDH15, USH1G, USH2A, GPR98, DFNB31, and CLRN1. In some embodiments, the disease comprises von Willebrand disease and the gene is VWF. In some embodiments, the disease comprises Waardenburg syndrome and the gene is selected from PAX3, MITF, WS2B, WS2C, SNAI2, EDNRB, EDN3, and SOX10. In some embodiments, the disease comprises von Hippel-Lindau disease and the gene is VHL. In some embodiments, the disease comprises Zellweger syndrome and the gene is selected from PEX1, PEX2, PEX3, PEX5, PEX6, PEX10, PEX12, PEX13, PEX14, PEX16, PEX19, and PEX26.

In some embodiments, the present disclosure discloses treating, preventing, or inhibiting genetic disease or disorder in a subject a by generating indels, exon skipping, forced exon skipping, whole exon deletion, partial exon deletion, and/or refraining to correct the frame of the at least one gene associated with the disease. In some embodiments, treating, preventing, or inhibiting genetic disease or disorder in a subject comprises contacting target nucleic acids with systems for editing target nucleic acids comprising effector proteins (e.g., a D2S effector protein) or endonucleases such as those set forth in TABLE 1. In some embodiments, treating, preventing, or inhibiting genetic disease or disorder in a subject comprises contacting target nucleic acids with effector proteins and guide nucleic acids comprising spacer sequences such as those targeting any one of the gene recited in TABLE 8. In some embodiments, the genetic disease or disorder is Duchenne Muscular Dystrophy.

Cancer

In some embodiments, the disease is cancer. In some embodiments, the cancer is a solid cancer (i.e., a tumor). In some embodiments, the cancer is selected from a blood cell cancer, a leukemia, and a lymphoma. The cancer can be a leukemia, such as, by way of non-limiting example, acute myeloid (or myelogenous) leukemia (AML), chronic myeloid (or myelogenous) leukemia (CML), acute lymphocytic (or lymphoblastic) leukemia (ALL), and chronic lymphocytic leukemia (CLL). In some embodiments, the cancer is any one of colon cancer, rectal cancer, renal-cell carcinoma, liver cancer, bladder cancer, cancer of the kidney or ureter, lung cancer, non small cell lung cancer, cancer of the small intestine, esophageal cancer, melanoma, bone cancer, pancreatic cancer, skin cancer, brain cancer (e.g., glioblastoma), cancer of the head or neck, melanoma, uterine cancer, ovarian cancer, breast cancer, testicular cancer, cervical cancer, stomach cancer, Hodgkin's Disease, non-Hodgkin's lymphoma, and thyroid cancer.

In some embodiments, mutations are associated with cancer or are causative of cancer. The target nucleic acid, in some embodiments, comprises a portion of a gene comprising a mutation associated with cancer, a gene whose overexpression is associated with cancer, a tumor suppressor gene, an oncogene, a checkpoint inhibitor gene, a gene associated with cellular growth, a gene associated with cellular metabolism, a gene associated with cell cycle, or a combination thereof. Non-limiting examples of genes comprising a mutation associated with cancer are ABL, AF4/HRX AKT-2, ALK, ALK/NPM, AML1, AML1/MTG8, APC, ATM, AXIN2, AXL, BAP1, BARD1, BCL-2, BCL-3, BCL-6, BCR/ABL, BLM, BMPR1A, BRCA1, BRCA2, BRIP1, c-MYC, CASR, CCR5, CDC73, CDH1, CDK4, CDKN1B, CDKN1C, CDKN2A, CEBPA, CHEK2, CREBBP, CTNNA1, CXCR3, DBL, DEK/CAN, DICER1, DIS3L2, E2A/PBX1, EGFR, ENL/HRX, EPCAM, ERG/TLS, ERBB, ERBB-2, ETS-1, EWS/FLI-1, FH, FLCN, FMS, FOS, FPS, GATA2, GLI, GPGSP, GREM1, HER2/neu, HOX11, HOXB13, HST, IL-3, INT-2, JAK1, JUN, KIT, KS3, K-SAM, LBC, LCK, LMO1, LMO2, L-MYC, LYL-1, LYT-10, LYT-10/Cα1, MAS, MAX MDM-2, MEN1, MET, MITF, MLH1, MLL, MOS, MSH1, MSH2, MSH3, MSH6, MTG8/AML1, MUTYH, MYB, MYH11/CBFB, NBN, NEU, NF1, NF2, N-MYC, NTHL1, OST, PALB2, PAX-5, PBX1/E2A, PDCD1, PDGFRA, PHOX2B, PIM-1, PMS2, POLD1, POLE, POT1, PRAD-1, PRKAR1A, PTCH1, PTEN, RAD50, RAD51C, RAD51D, RAF, RAR/PML, RAS-H, RAS-K, RAS-N, RB1, RECQL4, REL/NRG, RET, RHOM1, RHOM2, ROS, RUNX1, SDHA, SDHAF, SDHB, SDHC, SDHD, SET/CAN, SIS, SKI, SMAD4, SMARCA4, SMARCB1, SMARCE1, SRC, STKI1, SUFU, TAL1, TAL2, TAN-4, TIAM1, TERC, TERT, TMEM127, TP53, TRAC, TSC1, TSC2, TRK, VHL, WRN, and WT1. Non-limiting examples of oncogenes are KRAS, NRAS, BRAF, MYC, CTNNB1, and EGFR. In some embodiments, the oncogene is a gene that encodes a cyclin dependent kinase (CDK). Non-limiting examples of CDKs are Cdk1, Cdk4, Cdk5, Cdk7, Cdk8, Cdk9, Cdk11 and Cdk20. Non-limiting examples of tumor suppressor genes are TP53, RB1, and PTEN.

Infections

Described herein are compositions, systems and methods for treating an infection in a subject. Infections may be caused by a pathogen, e.g., bacteria, viruses, fungi, and parasites. Compositions, systems and methods may modify a target nucleic acid associated with the pathogen or parasite causing the infection. In some embodiments, the target nucleic acid may be in the pathogen or parasite itself or in a cell, tissue or organ of the subject that the pathogen or parasite infects. In some embodiments, the methods described herein include treating an infection caused by one or more bacterial pathogens. Non-limiting examples of bacterial pathogens include *Acholeplasma laidlawii, Brucella abortus, Chlamydia psittaci, Chlamydia trachomatis, Cryptococcus neoformans, Escherichia coli, Legionella pneumophila*, Lyme disease spirochetes, methicillin-resistant *Staphylococcus aureus, Mycobacterium leprae, Mycobacterium tuberculosis, Mycoplasma arginini, Mycoplasma arthritidis, Mycoplasma genitalium, Mycoplasma hyorhinis, Mycoplasma orale, Mycoplasma pneumoniae, Mycoplasma salivarium, Neisseria gonorrhoeae, Neisseria meningitidis, Pneumococcus, Pseudomonas aeruginosa*, sexually transmitted infection, *Streptococcus agalactiae, Streptococcus pyogenes*, and *Treponema pallidum*.

In some embodiments, methods described herein include treating an infection caused by one or more viral pathogens. Non-limiting examples of viral pathogens include adenovirus, blue tongue virus, chikungunya, coronavirus (e.g., SARS-CoV-2), cytomegalovirus, Dengue virus, Ebola, Epstein-Barr virus, feline leukemia virus, Hemophilus influenzae B, Hepatitis Virus A, Hepatitis Virus B, Hepatitis Virus C, herpes simplex virus I, herpes simplex virus II, human papillomavirus (HPV), human serum parvo-like virus, human T-cell leukemia viruses, immunodeficiency virus (e.g., HIV), influenza virus, lymphocytic choriomeningitis virus, measles virus, mouse mammary tumor virus, mumps virus, murine leukemia virus, polio virus, rabies virus, Reovirus, respiratory syncytial virus (RSV), rubella virus, Sendai virus, simian virus 40, Sindbis virus, varicella-zoster virus, vesicular stomatitis virus, wart virus, West Nile virus, yellow fever virus, or any combination thereof.

In some embodiments, methods described herein include treating an infection caused by one or more parasites. Non-limiting examples of parasites include helminths, annelids, platyhelminthes, nematodes, and thorny-headed worms. In some embodiments, parasitic pathogens comprise, without limitation, *Babesia bovis, Echinococcus granulosus, Eimeria tenella, Leishmania tropica, Mesocestoides corti, Onchocerca volvulus, Plasmodium falciparum, Plasmodium vivax, Schistosoma japonicum, Schistosoma mansoni, Schistosoma* spp., *Taenia hydatigena, Taenia ovis, Taenia saginata, Theileria parva, Toxoplasma gondii, Toxoplasma* spp., *Trichinella spiralis, Trichomonas vaginalis, Trypanosoma brucei, Trypanosoma cruzi, Trypanosoma rangeli, Trypanosoma rhodesiense, Balantidium coli, Entamoeba histolytica, Giardia* spp., *Isospora* spp., *Trichomonas* spp., or any combination thereof.

In some embodiments, the method for treating a disease comprises modifying at least one gene associated with the disease or modifying expression of the at least one gene such that the disease is treated. In some embodiments, the disease is Alzheimer's disease and the gene is selected from APP, BACE-1, PSD95, MAPT, PSEN1, PSEN2, and APOEε4. In some embodiments, the disease is Parkinson's disease and the gene is selected from SNCA, GDNF, and LRRK2. In some embodiments, the disease is Huntington's disease and the gene is HTT. In some embodiments, the disease is amyotrophic lateral sclerosis (ALS) and the gene is selected from SOD1, FUS, C9ORF72, ATXN2, TARDBP, and CHCHD10. In some embodiments, the disease is Retinitis pigmentosa and the gene is selected from PDE6B, RHO, RP1, RP2, RPGR, PRPH2, IMPDH1, PRPF31, CRB1, PRPF8, TULP1, CA4, HPRPF3, ABCA4, EYS, CERKL, FSCN2, TOPORS, SNRNP200, PRCD, NR2E3, MERTK, USH2A, PROM1, KLHL7, CNGB1, TTC8, ARL6, DHDDS, BEST1, LRAT, SPARA7, CRX, CLRN1, RPE65, and WDR19. In some embodiments, the disease is cardiovascular disease and/or lipodystrophies and the gene is selected from APOA1, ANGPTL3, APOCIII, CFB, AGT, FXI, FXII, PKK, PCSK9, APOL1, and TTR. In some embodiments, the disease is diabetes and the gene is GCGR. In some embodiments, the disease is NAFLD/NASH and the gene is selected from DGAT2 and PNPLA3. In some embodiments, the disease is cancer and the gene is selected from STAT3, YAP1, FOXP3, AR (Prostate cancer), and IRF4 (multiple myeloma). In some embodiments, the disease is cystic fibrosis and the gene is CFTR. In some embodiments, the disease is myotonic dystrophy and the gene is selected from CNBP and DMPK. In some embodiments, the disease is non-small cell lung cancer and the gene is selected from KRAS, EGFR, ALK, METex14, BRAF V600E, ROS1, RET, and NTRK.

Described herein are methods for treating an infection in a subject, wherein the infection is caused by one or more pathogens, parasites, or any combination thereof. Such methods can include modifying a target nucleic acid associated with the pathogen or parasite causing the infection. In some embodiments, the target nucleic acid can be in the pathogen or parasite itself or in a cell, tissue or organ of the subject that the pathogen or parasite infects. In some embodiments, the pathogen is a bacteria, a virus, a fungus, or any combination thereof. In some embodiments, the methods described herein include treating an infection cause by one or more bacterial pathogens. Such bacterial pathogens, in some embodiments, comprise, without limitation, *Acholeplasma laidlawii, Brucella abortus, Chlamydia psittaci, Chlamydia trachomatis, Cryptococcus neoformans, Escherichia coli, Legionella pneumophila,* Lyme disease spirochetes, methicillin-resistant *Staphylococcus aureus, Mycobacterium leprae, Mycobacterium tuberculosis, Mycoplasma arginini, Mycoplasma arthritidis, Mycoplasma genitalium, Mycoplasma hyorhinis, Mycoplasma orale, Mycoplasma pneumoniae, Mycoplasma salivarium, Neisseria gonorrhoeae, Neisseria meningitidis,* Pneumococcus, *Pseudomonas aeruginosa,* sexually transmitted infection, *Streptococcus agalactiae, Streptococcus pyogenes, Treponema pallidum,* or any combination thereof.

In some embodiments, the methods described herein include treating an infection cause by one or more viral pathogens. Such viral pathogens, in some embodiments, comprise, without limitation, adenovirus, blue tongue virus, chikungunya, coronavirus (e.g. SARS-CoV-2), cytomegalovirus, Dengue virus, Ebola, Epstein-Barr virus, feline leukemia virus, Hemophilus *influenzae* B, Hepatitis Virus A, Hepatitis Virus B, Hepatitis Virus C, herpes simplex virus I, herpes simplex virus II, human papillomavirus (HPV), human serum parvo-like virus, human T-cell leukemia viruses, immunodeficiency virus (e.g. HIV), influenza virus, lymphocytic choriomeningitis virus, measles virus, mouse mammary tumor virus, mumps virus, murine leukemia virus, polio virus, rabies virus, Reovirus, respiratory syncytial virus (RSV), rubella virus, Sendai virus, simian virus 40, Sindbis virus, varicella-zoster virus, vesicular stomatitis virus, wart virus, West Nile virus, yellow fever virus, or any combination thereof.

In some embodiments, the methods described herein include treating an infection cause by one or more parasites. Such parasites, in some embodiments comprise, without limitation, helminths, annelids, platyhelminthes, nematodes, and thorny-headed worms. In some embodiments, parasitic pathogens comprise, without limitation, *Babesia bovis, Echinococcus granulosus, Eimeria tenella, Leishmania tropica, Mesocestoides corti, Onchocerca volvulus, Plasmodium falciparum, Plasmodium vivax, Schistosoma japonicum, Schistosoma mansoni, Taenia hydatigena, Taenia ovis, Taenia saginata, Theileria parva, Toxoplasma gondii, Trichinella spiralis, Trichomonas vaginalis, Trypanosoma brucei, Trypanosoma cruzi, Trypanosoma rangeli, Trypanosoma rhodesiense, Balantidium coli, Entamoeba histolytica, Giardia* spp., *Isospora* spp., *Trichomonas* spp., or any combination thereof.

Modifying at least one gene using the compositions, systems and methods described herein can, in some embodiments, induce a reduction or increase in expression of the one or more genes. In some embodiments, the at least one modified gene results in a reduction in expression, also referred to as gene silencing. In some embodiments, the gene silencing reduces expression of one or more genes by at least 10%, at least 20%, at least 30%, at least 40%, at least 50%, at least 60%, at least 70%, at least 80%, at least 90%, or at least 95%. In some embodiments, gene silencing is accomplished by transcriptional silencing, post-transcriptional silencing, or meiotic silencing. In some embodiments, transcriptional silencing is by genomic imprinting, paramutation, transposon silencing, position effect, or RNA-directed DNA methylation. In some embodiments, post-transcriptional silencing is by RNA interference, RNA silencing, or nonsense mediated decay. In some embodiments, meiotic silencing is by transvection or meiotic silencing of unpaired DNA. In some embodiments, the at least one modified gene results in removing all expression, also referred to as the gene being knocked out (KO).

In some embodiments, a gene is modified by repairing or editing a mutation as described herein. In some embodiments, a Cas protein is used to effect the modification. Cas proteins may be fused to transcription activators or transcriptional repressors or deaminases or other nucleic acid modifying proteins. In some embodiments, Cas proteins need not be fused to a partner protein to accomplish the required protein (expression) modification.

In some embodiments, treatment of a disease comprises administration of a gene therapy. "Gene therapy", as used herein, comprises use of a recombinant nucleic acid (DNA or RNA), administered for the purpose to adjust, repair, replace, add, or remove a gene sequence. In some embodiments, a gene therapy comprises use of a vector to introduce a functional gene or transgene. In some embodiments, vectors comprise nonviral vectors, including cationic polymers, cationic lipids, or bio-responsive polymers. In some embodiments, the bio-responsive polymer exploits chemical-physical properties of the endosomal environment (e.g., pH) to preferentially release the genetic material in the intracellular space. In some embodiments, vectors comprise viral vectors, including retroviruses, adenoviruses, adeno-associated viruses, and herpes simplex viruses. In some embodiments, the vector comprises a replication-defective viral vector, comprising an insertion of a therapeutic gene inserted in genes essential to the lytic cycle, preventing the virus from replicating and exerting cytotoxic effects. Methods of gene therapy are described in more detail in Ingusci et al., "*Gene Therapy Tools for Brain Diseases*", Front. Pharmacol. 10:724 (2019) which is hereby incorporated by reference in its entirety.

It is known that CRISPR-Cas9 gene editing techniques may select for p53-mutated cells. Similarly, the presence of KRAS mutations provides a selective advantage during CRISPR-Cas9 gene editing, as further described in Sinha et al., "A systematic genome-wide mapping of oncogenic mutation selection during CRISPR-Cas9 genome editing", Nature Comm. 12:6512 (2021), which is hereby incorporated by reference in its entirety. In some embodiments, a genome targeted for treatment comprises a wild-type p53 gene, a wild-type KRAS gene, a mutated p53 gene, a mutated KRAS gene, or any combination thereof. In some embodiments, the genome comprises a p53 mutation and the target gene comprises WDR48, H2AFX, FANCG, BRIP1, HUS1, XRCC3, PALB2, FANCL, FANCA, FANCC, BRCA1, BRCA2, or any combination thereof. In some embodiments, the genome comprises a wild-type p53 and the target gene comprises CCNB1, MCM6, ANAPC11, ANAPC10, CDKN1A, or any combination thereof. In some embodiments, the genome comprises a KRAS mutation and the target gene comprises CRYAA, RTCA, LOR, SLC35B4, EN1, CELA3B, NOG, or any combination thereof.

XV. Target Nucleic Acids and Samples

Disclosed herein are compositions, systems and methods for detecting and/or modifying a target nucleic acid. In some embodiments, the target nucleic acid is a single stranded nucleic acid. Alternatively, or in combination, the target nucleic acid is a double stranded nucleic acid and is prepared into single stranded nucleic acids before or upon contacting the reagents. In some embodiments, the target nucleic acid is a double stranded nucleic acid. In some embodiments, the double stranded nucleic acid is DNA. The target nucleic acid may be a RNA. The target nucleic acids include but are not limited to mRNA, rRNA, tRNA, non-coding RNA, long non-coding RNA, and microRNA (miRNA). In some embodiments, the target nucleic acid is complementary DNA (cDNA) synthesized from a single-stranded RNA template in a reaction catalyzed by a reverse transcriptase. In some embodiments, the target nucleic acid is single-stranded RNA (ssRNA) or mRNA. In some embodiments, the target nucleic acid is from a virus, a parasite, or a bacterium described herein.

In some embodiments, an effector protein (e.g., a D2S effector protein) or a multimeric complex thereof recognizes a PAM on a target nucleic acid. In some embodiments, multiple effector proteins of the multimeric complex recognize a PAM on a target nucleic acid. In some embodiments, only one effector protein of the multimeric complex recognizes a PAM on a target nucleic acid. In some embodiments, the PAM is 3' to the spacer region of the crRNA. In some embodiments, the PAM is directly 3' to the spacer region of the crRNA. In some embodiments, the PAM sequence comprises a sequence listed in TABLE 10, TABLE 36, TABLE 37, TABLE 38, TABLE 42 and TABLE 43 wherein each N is selected from any nucleotide; wherein each V is selected from adenine, cytosine or guanine; and wherein each R is selected from adenine and guanine.

A D2S effector protein of the present disclosure, a dimer thereof, or a multimeric complex thereof may cleave or nick a target nucleic acid within or near a protospacer adjacent motif (PAM) sequence of the target nucleic acid. In some embodiments, cleavage occurs within 1, 2, 3, 4, 5, 6, 7, 8, 9 or 10 nucleosides of a 5' or 3' terminus of a PAM sequence. A target nucleic acid may comprise a PAM sequence adjacent to a sequence that is complementary to a guide nucleic acid spacer region. In some embodiments, the PAM sequence is 5'-NNTNTR-3' (SEQ ID NO: 3), wherein each N is selected from any nucleotide; and wherein each R is selected from adenine and guanine. In some embodiments, the PAM sequence is 5'-TNTR-3' (SEQ ID NO: 4), wherein each N is selected from any nucleotide; and wherein each R is selected from adenine and guanine. In some embodiments, the PAM sequence is 5'-NNTN-3' (SEQ ID NO: 764), wherein each N is selected from any nucleotide. In some embodiments, the PAM sequence is any one of the sequences recited in TABLE 10, TABLE 36, TABLE 37, TABLE 38, TABLE 42 and TABLE 43 wherein each N is selected from any nucleotide; wherein each V is selected from adenine, cytosine or guanine; and wherein each R is selected from adenine and guanine.

In some embodiments, the effector protein comprises an amino acid sequence that is at least 70%, at least 75%, at least 80%, at least 85%, at least 90%, at least 95%, at least 98%, at least 99%, or 100% identical to any one of the sequences recited in TABLE 1, and the target nucleic acid comprises a PAM sequence comprises any one of sequences recited in TABLE 10, TABLE 36, TABLE 37, TABLE 38, TABLE 42 and TABLE 43 wherein each N is selected from any nucleotide; wherein each V is selected from adenine, cytosine or guanine; and wherein each R is selected from adenine and guanine.

In some embodiments, the effector protein comprises an amino acid sequence that is at least 70%, at least 75%, at least 80%, at least 85%, at least 90%, at least 95%, at least 98%, at least 99%, or 100% identical to any one of the sequences recited in TABLE 1, and the target nucleic acid comprises a PAM sequence of 5'-NNTNTR-3' (SEQ ID NO: 3), wherein each N is selected from any nucleotide; and wherein each R is selected from adenine and guanine. In some embodiments, the effector protein comprises an amino acid sequence that is at least 70%, at least 75%, at least 80%, at least 85%, at least 90%, at least 95%, at least 98%, at least 99%, or 100% identical to any one of the sequences recited in TABLE 1, and the target nucleic acid comprises a PAM sequence of 5'-TNTR-3' (SEQ ID NO: 4), wherein each N is selected from any nucleotide; and wherein each R is selected from adenine and guanine. In some embodiments, the effector protein comprises an amino acid sequence that is at least 70%, at least 75%, at least 80%, at least 85%, at least 90%, at least 95%, at least 98%, at least 99%, or 100% identical to any one of the sequences recited in TABLE 1, and the target nucleic acid comprises a PAM sequence of 5'-NNTN-3' (SEQ ID NO: 764), wherein each N is selected from any nucleotide.

In some embodiments, the target nucleic acid comprises 5 to 100, 5 to 90, 5 to 80, 5 to 70, 5 to 60, 5 to 50, 5 to 40, 5 to 30, 5 to 25, 5 to 20, 5 to 15, or 5 to 10 linked nucleosides. In some embodiments, the target nucleic acid comprises 10 to 90, 20 to 80, 30 to 70, or 40 to 60 linked nucleosides. In some embodiments, the target nucleic acid comprises 5, 6, 7, 8, 9, 10, 11, 12, 13, 14, 15, 16, 17, 18, 19, 20, 21, 22, 23, 24, 25, 26, 27, 28, 29, 30, 31, 32, 33, 34, 35, 36, 37, 38, 39, 40, 45, 50, 60, 70, 80, 90, or 100 linked nucleosides. In some embodiments, the target nucleic acid comprises at least 10, at least 20, at least 30, at least 40, at least 50, at least 60, at least 70, at least 80, at least 90, or at least 100 linked nucleosides.

In some embodiments, the target nucleic acid is any one of the gene recited in TABLE 8. In some embodiments, the one or more target sequence is within any one of the genes set forth in TABLE 8. In some embodiments, the target sequence is within an exon of any one of the genes set forth in TABLE 8. In some embodiments, then target sequence covers the junction of two exons. In some embodiments, the target sequence is located within about 1 to about 300 nucleotides, about 10 to about 250, about 20 to about 200, about 30 to about 150, about 40 to about 100, or about 50 nucleotides of the 5' untranslated region (UTR). In some embodiments, the target sequence is located within about 1 to about 300 nucleotides, about 10 to about 250, about 20 to about 200, about 30 to about 150, about 40 to about 100, or about 50 nucleotides of the 3' UTR.

In some embodiments, the target sequence is at least partially within a targeted exon within any one of the genes set forth in TABLE 8. A targeted exon can mean any portion within, contiguous with, or adjacent to a specified exon of interest can be targeted by the compositions, systems, and methods described herein. In some embodiments, one or more of the exons are targeted. In some embodiments, one or more of exons of any one the genes set forth in TABLE 8 are targeted.

In some embodiments, the start of an exon is referred to interchangeably herein as the 5' end of an exon. In some embodiments, the 5' region of an exon comprises a sequence about 1 to about 300 nucleotides adjacent to the 5' end of an exon when moving upstream in the 5' direction, or a sequence about 1 to about 300 nucleotides adjacent to the 5' end of an exon when moving downstream in the 3' direction, or both.

In some embodiments, the end of an exon is referred to interchangeably herein as the 3' end of an exon. In some embodiments, the 3' region of an exon comprises a sequence about 1 to about 300 nucleotides adjacent to the 3' end of an exon when moving upstream in the 5' direction, or a sequence about 1 to about 300 nucleotides adjacent to the 3' end of an exon when moving downstream in the 3' direction, or both.

Nucleic acids, such as DNA and pre-mRNA, can contain at least one intron and at least one exon, wherein as read in the 5' to the 3' direction of a nucleic acid strand, the 3' end of an intron can be adjacent to the 5' end of an exon, and wherein said intron and exon correspond for transcription purposes. If a nucleic acid strand contains more than one intron and exon, the 5' end of the second intron is adjacent to the 3' end of the first exon, and 5' end of the second exon is adjacent to the 3' end of the second intron. The junction between an intron and an exon can be referred to herein as a splice junction, wherein a 5' splice site (SS) can refer to the +1/+2 position at the 5' end of intron and a 3'SS can refer to the last two positions at the 3' end of an intron. Alternatively, a 5' SS can refer to the 5' end of an exon and a 3'SS can refer to the 3' end of an exon. In some embodiments, nucleic acids can contain one or more elements that act as a signal during transcription, splicing, and/or translation. In some embodiments, signaling elements include a 5'SS, a 3'SS, a premature stop codon, U1 and/or U2 binding sequences, and cis acting elements such as branch site (BS), polypyridine tract (PYT), exonic and intronic splicing enhancers (ESEs and ISEs) or silencers (ESSs and ISSs).

In some embodiments, a target sequence that a guide nucleic acid binds is at least partially within a targeted exon within any one of the genes set forth in TABLE 8, and wherein at least a portion of the target nucleic acid is within a sequence about 1 to about 300 nucleotides adjacent to: the start of a targeted exon, the end of a targeted exon, or both. In some embodiments, at least a portion of the target sequence that a guide nucleic acid binds can comprise a sequence about 1 to about 300 nucleotides, about 10 to about 250, about 20 to about 200, about 30 to about 150, about 40 to about 100, or about 50 nucleotides adjacent to: the start of a targeted exon, the end of a targeted exon, or both.

In some embodiments, at least a portion of the target nucleic acid that a guide nucleic acid binds is within a sequence about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, about 100 or more, about 105 or more, about 110 or more, about 115 or more, about 120 or more, about 125 or more, about 130 or more, about 135 or more, about 140 or more, about 145 or more, or about 150 or more nucleotides adjacent to: the start of a targeted exon, the end of a targeted exon, or both.

In some embodiments, a target sequence that a guide nucleic acid binds is at least partially within a targeted exon within any one of the genes set forth in TABLE 8, and wherein at least a portion of the target nucleic acid is within a sequence about 1 to about 300 nucleotides adjacent to: the start of a targeted exon, the end of a targeted exon, or both. In some embodiments, at least a portion of the target sequence that a guide nucleic acid binds can comprise a sequence about 1 to about 300 nucleotides, about 10 to about 250, about 20 to about 200, about 30 to about 150, about 40 to about 100, or about 50 nucleotides adjacent to: one or more signaling element comprising a 5'SS, a 3'SS, a premature stop codon, U1 binding sequence, U2 binding sequence, a BS, a PYT, ESE, an ISE, an ESS, an ISS, more than one of the foregoing, or any combination thereof.

In some embodiments, at least a portion of the target nucleic acid that a guide nucleic acid binds is within a sequence about 5 or more, about 10 or more, about 15 or more, about 20 or more, about 25 or more, about 30 or more, about 35 or more, about 40 or more, about 45 or more, about 50 or more, about 55 or more, about 60 or more, about 65 or more, about 70 or more, about 75 or more, about 80 or more, about 85 or more, about 90 or more, about 95 or more, about 100 or more, about 105 or more, about 110 or more, about 115 or more, about 120 or more, about 125 or more, about 130 or more, about 135 or more, about 140 or more, about 145 or more, or about 150 or more nucleotides adjacent to: one or more signaling element comprising a 5'SS, a 3'SS, a premature stop codon, U1 binding sequence, U2 binding sequence, a BS, a PYT, ESE, an ISE, an ESS, an ISS, more than one of the foregoing, or any combination thereof.

In some embodiments, the target nucleic acid is in a cell. In general, the cell is a human cell. In some embodiments, the human cell is a: muscle cell, cardiac cell, visceral cell, cardiac muscle cell, smooth muscle cell, cardiomyocyte, nodal cardiac muscle cell, smooth muscle cell, visceral muscle cell, skeletal muscle cell, myocyte, red (or slow) skeletal muscle cell, white (fast) skeletal muscle cell, intermediate skeletal muscle, muscle satellite cell, muscle stem cell, myoblast, muscle progenitor cell, induced pluripotent stem cell (iPS), or a cell derived from an iPS cell, modified to have its gene edited and differentiated into myoblasts, muscle progenitor cells, muscle satellite cells, muscle stem cells, skeletal muscle cells, cardiac muscle cells or smooth muscle cells. In some embodiments, the target nucleic acid is selected from the target nucleic acids is any one of the gene selected from AAVS1, ALKBH5, ARFRP1, AXIN1, BAP1, BCL2L2, CCR5, CDK11, CLTA, CTNNB1, DERL2, DNMT1, EMC2, EMC3, EMX1, FANCF, GRIN2B, H2AX, HPRT1, HRD1, LRP6, MMD, OCT4, PAQR8, POU5F1, PPM1A, PTEN, RICTOR, RPL32P3, SEL1L, SIRT1, SUFU, SYS1, TBK1, TLE3, TOP1, TSPAN14, UBE2G2, UBE2J1, and VPS35.

In some embodiments, the target nucleic acid comprises a target locus. In some embodiments, the target nucleic acid comprises more than one target loci. In some embodiments, the target nucleic acid is B2M. In some embodiments, the B2M target nucleic acid comprises one or more target loci. In some embodiments, the target nucleic acid is TRAC. In some embodiments, the TRAC target nucleic acid comprises one or more target loci. In some embodiments, the target nucleic acid is CIITA. In some embodiments, the CIITA target nucleic acid comprises one or more target loci.

A D2S effector protein-guide nucleic acid complex may comprise high selectivity for a target sequence. In some embodiments, a ribonucleoprotein may comprise a selectivity of at least 200:1, 100:1, 50:1, 20:1, 10:1, or 5:1 for a target nucleic acid over a single nucleotide variant of the target nucleic acid. In some embodiments, a ribonucleoprotein may comprise a selectivity of at least 5:1 for a target nucleic acid over a single nucleotide variant of the target nucleic acid. Leveraging D2S effector protein selectivity, some methods described herein may detect a target nucleic acid present in the sample in various concentrations or amounts as a target nucleic acid population. In some embodiments, the sample has at least 2 target nucleic acids. In some embodiments, the sample has at least 3, 5, 10, 20, 30, 40, 50, 100, 200, 300, 400, 500, 600, 700, 800, 900, 1000, 2000, 3000, 4000, 5000, 6000, 7000, 8000, 9000, or 10000 target nucleic acids. In some embodiments, the sample comprises 1 to 10,000, 100 to 8000, 400 to 6000, 500 to 5000, 1000 to 4000, or 2000 to 3000 target nucleic acids. In some embodiments, the method detects target nucleic acid present at least at one copy per 10 non-target nucleic acids, $10^2$ non-target nucleic acids, $10^3$ non-target nucleic acids, $10^4$ non-target nucleic acids, $10^5$ non-target nucleic acids, $10^6$ non-target nucleic acids, $10^7$ non-target nucleic acids, $10^8$ non-target nucleic acids, $10^9$ non-target nucleic acids, or $10^{10}$ non-target nucleic acids.

Often, the target nucleic acid may be from 0.05% to 20% of total nucleic acids in the sample. Sometimes, the target nucleic acid is 0.1% to 10% of the total nucleic acids in the sample. The target nucleic acid, in some embodiments, is 0.1% to 5% of the total nucleic acids in the sample. The target nucleic acid may also be 0.1% to 1% of the total nucleic acids in the sample. The target nucleic acid may be DNA or RNA. The target nucleic acid may be any amount less than 100% of the total nucleic acids in the sample. The target nucleic acid may be 100% of the total nucleic acids in the sample.

The target nucleic acid may be 0.05% to 20% of total nucleic acids in the sample. Sometimes, the target nucleic acid is 0.1% to 10% of the total nucleic acids in the sample. The target nucleic acid, in some embodiments, is 0.1% to 5% of the total nucleic acids in the sample. Often, a sample comprises the segment of the target nucleic acid and at least one nucleic acid comprising less than 100% sequence identity to the segment of the target nucleic acid but no less than 50% sequence identity to the segment of the target nucleic acid. For example, the segment of the target nucleic acid comprises a mutation as compared to at least one nucleic acid comprising less than 100% sequence identity to the segment of the target nucleic acid but no less than 50% sequence identity to the segment of the target nucleic acid. Often, the segment of the target nucleic acid comprises a single nucleotide mutation as compared to at least one nucleic acid comprising less than 100% sequence identity to the segment of the target nucleic acid but no less than 50% sequence identity to the segment of the target nucleic acid.

A target nucleic acid may be an amplified nucleic acid of interest. The nucleic acid of interest may be any nucleic acid disclosed herein or from any sample as disclosed herein. The nucleic acid of interest may be an RNA that is reverse transcribed before amplification. The nucleic acid of interest may be amplified then the amplicons may be transcribed into RNA.

In some embodiments, compositions described herein exhibit indiscriminate trans cleavage of ssRNA, enabling their use for detection of RNA in samples. In some embodiments, target ssRNA are generated from many nucleic acid templates (RNA) in order to achieve cleavage of the FQ reporter in the DETECTR platform. Certain D2S effector proteins may be activated by ssRNA, upon which they may exhibit trans cleavage of ssRNA and may, thereby, be used to cleave ssRNA FQ reporter molecules in the DETECTR system. These D2S effector proteins may target ssRNA present in the sample or ssRNA generated and/or amplified from any number of nucleic acid templates (RNA). Described herein are reagents comprising a single stranded reporter nucleic acid comprising a detection moiety, wherein the reporter nucleic acid (e.g., the ssDNA-FQ reporter described above) is capable of being cleaved by the D2S effector protein, upon generation and amplification of ssRNA from a nucleic acid template using the methods disclosed herein, thereby generating a first detectable signal.

In some embodiments, target nucleic acids comprise at least one nucleic acid comprising at least 50% sequence identity to the target nucleic acid or a portion thereof.

Sometimes, the at least one nucleic acid comprises an amino acid sequence that is at least 60%, 70%, 75%, 80%, 85%, 90%, 91%, 92%, 93%, 94%, 95%, 96%, 97%, 98%, or 99% identical to an equal length portion of the target nucleic acid. Sometimes, the at least one nucleic acid comprises an amino acid sequence that is 100% identical to an equal length portion of the target nucleic acid. Sometimes, the amino acid sequence of the at least one nucleic acid is at least 60%, 70%, 75%, 80%, 85%, 90%, 91%, 92%, 93%, 94%, 95%, 96%, 97%, 98%, or 99% identical to the target nucleic acid. Sometimes, the target nucleic acid comprises an amino acid sequence that is less than 60%, 70%, 75%, 80%, 85%, 90%, 91%, 92%, 93%, 94%, 95%, 96%, 97%, 98%, or 99% identical to an equal length portion of the at least one nucleic acid.

In some embodiments, samples comprise a target nucleic acid at a concentration of less than 1 nM, less than 2 nM, less than 3 nM, less than 4 nM, less than 5 nM, less than 6 nM, less than 7 nM, less than 8 nM, less than 9 nM, less than 10 nM, less than 20 nM, less than 30 nM, less than 40 nM, less than 50 nM, less than 60 nM, less than 70 nM, less than 80 nM, less than 90 nM, less than 100 nM, less than 200 nM, less than 300 nM, less than 400 nM, less than 500 nM, less than 600 nM, less than 700 nM, less than 800 nM, less than 900 nM, less than 1 µM, less than 2 µM, less than 3 µM, less than 4 µM, less than 5 µM, less than 6 µM, less than 7 µM, less than 8 µM, less than 9 µM, less than 10 µM, less than 100 µM, or less than 1 mM. In some embodiments, the sample comprises a target nucleic acid sequence at a concentration of 1 nM to 2 nM, 2 nM to 3 nM, 3 nM to 4 nM, 4 nM to 5 nM, 5 nM to 6 nM, 6 nM to 7 nM, 7 nM to 8 nM, 8 nM to 9 nM, 9 nM to 10 nM, 10 nM to 20 nM, 20 nM to 30 nM, 30 nM to 40 nM, 40 nM to 50 nM, 50 nM to 60 nM, 60 nM to 70 nM, 70 nM to 80 nM, 80 nM to 90 nM, 90 nM to 100 nM, 100 nM to 200 nM, 200 nM to 300 nM, 300 nM to 400 nM, 400 nM to 500 nM, 500 nM to 600 nM, 600 nM to 700 nM, 700 nM to 800 nM, 800 nM to 900 nM, 900 nM to 1 µM, 1 µM to 2 µM, 2 µM to 3 µM, 3 µM to 4 µM, 4 µM to 5 µM, 5 µM to 6 µM, 6 µM to 7 µM, 7 µM to 8 µM, 8 µM to 9 µM, 9 µM to 10 µM, 10 µM to 100 µM, 100 µM to 1 mM, 1 nM to 10 nM, 1 nM to 100 nM, 1 nM to 1 µM, 1 nM to 10 µM, 1 nM to 100 µM, 1 nM to 1 mM, 10 nM to 100 nM, 10 nM to 1 µM, 10 nM to 10 µM, 10 nM to 100 µM, 10 nM to 1 mM, 100 nM to 1 µM, 100 nM to 10 µM, 100 nM to 100 µM, 100 nM to 1 mM, 1 µM to 10 µM, 1 µM to 100 µM, 1 µM to 1 mM, 10 µM to 100 µM, 10 µM to 1 mM, or 100 µM to 1 mM. In some embodiments, the sample comprises a target nucleic acid at a concentration of 20 nM to 200 µM, 50 nM to 100 µM, 200 nM to 50 µM, 500 nM to 20 µM, or 2 µM to 10 µM. In some embodiments, the target nucleic acid is not present in the sample.

In some embodiments, samples comprise fewer than 10 copies, fewer than 100 copies, fewer than 1000 copies, fewer than 10,000 copies, fewer than 100,000 copies, or fewer than 1,000,000 copies of a target nucleic acid sequence. In some embodiments, the sample comprises 10 copies to 100 copies, 100 copies to 1000 copies, 1000 copies to 10,000 copies, 10,000 copies to 100,000 copies, 100,000 copies to 1,000,000 copies, 10 copies to 1000 copies, 10 copies to 10,000 copies, 10 copies to 100,000 copies, 10 copies to 1,000,000 copies, 100 copies to 10,000 copies, 100 copies to 100,000 copies, 100 copies to 1,000,000 copies, 1,000 copies to 100,000 copies, or 1,000 copies to 1,000,000 copies of a target nucleic acid sequence. In some embodiments, the sample comprises 10 copies to 500,000 copies, 200 copies to 200,000 copies, 500 copies to 100,000 copies, 1000 copies to 50,000 copies, 2000 copies to 20,000 copies, 3000 copies to 10,000 copies, or 4000 copies to 8000 copies. In some embodiments, the target nucleic acid is not present in the sample.

A number of target nucleic acid populations are consistent with the methods, systems and compositions disclosed herein. Some methods described herein may detect two or more target nucleic acid populations present in the sample in various concentrations or amounts. In some embodiments, the sample has at least 2 target nucleic acid populations. In some embodiments, the sample has at least 3, 4, 5, 6, 7, 8, 9, 10, 20, 30, 40, or 50 target nucleic acid populations. In some embodiments, the sample has 3 to 50, 5 to 40, or 10 to 25 target nucleic acid populations. In some embodiments, the method detects target nucleic acid populations that are present at least at one copy per $10^1$ non-target nucleic acids, $10^2$ non-target nucleic acids, $10^3$ non-target nucleic acids, $10^4$ non-target nucleic acids, $10^5$ non-target nucleic acids, $10^6$ non-target nucleic acids, $10^7$ non-target nucleic acids, $10^8$ non-target nucleic acids, $10^9$ non-target nucleic acids, or $10^{10}$ non-target nucleic acids. The target nucleic acid populations may be present at different concentrations or amounts in the sample.

In some embodiments, target nucleic acids may activate a D2S effector protein to initiate sequence-independent cleavage of a nucleic acid-based reporter (e.g., a reporter comprising an RNA sequence, or a reporter comprising DNA and RNA). For example, a D2S effector protein of the present disclosure is activated by a target nucleic acid to cleave reporters having an RNA (also referred to herein as an "RNA reporter"). Alternatively, a D2S effector protein of the present disclosure is activated by a target nucleic acid to cleave reporters having an RNA. Alternatively, a D2S effector protein of the present disclosure is activated by a target RNA to cleave reporters having an RNA (also referred to herein as a "RNA reporter"). The RNA reporter may comprise a single-stranded RNA labelled with a detection moiety or may be any RNA reporter as disclosed herein.

In some embodiments, the target nucleic acid as described in the methods herein does not initially comprise a PAM sequence. However, any target nucleic acid of interest may be generated using the methods described herein to comprise a PAM sequence, and thus be a PAM target nucleic acid. A PAM target nucleic acid, as used herein, refers to a target nucleic acid that has been amplified to insert a PAM sequence that is recognized by a D2S effector system.

In some embodiments, the target nucleic acid is in a cell. In some embodiments, the cell is a single-cell eukaryotic organism; a plant cell an algal cell; a fungal cell; an animal cell; a cell an invertebrate animal; a cell a vertebrate animal such as fish, amphibian, reptile, bird, and mammal; or a cell a mammal such as a human, a non-human primate, an ungulate, a feline, a bovine, an ovine, and a cell.

In some embodiments, the target nucleic acid comprises a nucleic acid sequence from a pathogen responsible for a disease. Non-limiting examples of pathogens are bacteria, a virus and a fungus. The target nucleic acid, in some embodiments, is a portion of a nucleic acid from a sexually transmitted infection or a contagious disease. In some embodiments, the target nucleic acid is a portion of a nucleic acid from a genomic locus, or any DNA amplicon, such as a reverse transcribed mRNA or a cDNA from a gene locus, a transcribed mRNA, or a reverse transcribed cDNA from a gene locus in at least one of: human immunodeficiency virus (HIV), human papillomavirus (HPV), *chlamydia*, gonorrhea, syphilis, trichomoniasis, sexually transmitted infection, malaria, Dengue fever, Ebola, chikungunya, and leishmaniasis. Pathogens include viruses, fungi, helminths, protozoa, malarial parasites, *Plasmodium* parasites, *Toxoplasma* parasites, and *Schistosoma* parasites. Helminths include roundworms, heartworms, and phytophagous nematodes, flukes, Acanthocephala, and tapeworms. Protozoan infections include infections from *Giardia* spp., *Trichomonas* spp., African trypanosomiasis, amoebic dysentery, babesiosis, balantidial dysentery, Chaga's disease, coccidiosis, malaria and toxoplasmosis. Examples of pathogens such as parasitic/protozoan pathogens include, but are not limited to: *Plasmodium falciparum, P. vivax, Trypanosoma cruzi* and *Toxoplasma gondii*. Fungal pathogens include, but are not limited to *Cryptococcus neoformans, Histoplasma capsulatum, Coccidioides immitis, Blastomyces dermatitidis, Chlamydia trachomatis*, and *Candida albicans*. Pathogenic viruses include but are not limited to coronavirus (e.g., SARS-CoV-2); immunodeficiency virus (e.g., HIV); influenza virus; dengue; West Nile virus; herpes virus; yellow fever virus; Hepatitis Virus C; Hepatitis Virus A; Hepatitis Virus B; papillomavirus; and the like. Pathogens include, e.g., HIV virus, *Mycobacterium tuberculosis, Streptococcus agalactiae*, methicillin-resistant *Staphylococcus aureus, Legionella pneumophila, Streptococcus pyogenes, Escherichia coli, Neisseria gonorrhoeae, Neisseria meningitidis, Pneumococcus, Cryptococcus neoformans, Histoplasma capsulatum, Hemophilus influenzae* B, *Treponema pallidum*, Lyme disease spirochetes, *Pseudomonas aeruginosa, Mycobacterium leprae, Brucella abortus*, rabies virus, influenza virus, cytomegalovirus, herpes simplex virus I, herpes simplex virus II, human serum parvo-like virus, respiratory syncytial virus (RSV), *M. genitalium, T. vaginalis*, varicella-zoster virus, hepatitis B virus, hepatitis C virus, measles virus, adenovirus, human T-cell leukemia viruses, Epstein-Barr virus, murine leukemia virus, mumps virus, vesicular stomatitis virus, Sindbis virus, lymphocytic choriomeningitis virus, wart virus, blue tongue virus, Sendai virus, feline leukemia virus, Reovirus, polio virus, simian virus 40, mouse mammary tumor virus, dengue virus, rubella virus, West Nile virus, *Plasmodium falciparum, Plasmodium vivax, Toxoplasma gondii, Trypanosoma rangeli, Trypanosoma cruzi, Trypanosoma rhodesiense, Trypanosoma brucei, Schistosoma mansoni, Schistosoma japonicum, Babesia bovis, Eimeria tenella, Onchocerca volvulus, Leishmania tropica, Mycobacterium tuberculosis, Trichinella spiralis, Theileria parva, Taenia hydatigena, Taenia ovis, Taenia saginata, Echinococcus granulosus, Mesocestoides corti, Mycoplasma arthritidis, M hyorhinis, M. orale, M. arginini, Acholeplasma laidlawii, M. salivarium* and *M. pneumoniae*. In some embodiments, the target sequence is a portion of a nucleic acid from a genomic locus, a transcribed mRNA, or a reverse transcribed cDNA from a gene locus of bacterium or other agents responsible for a disease in the sample comprising a mutation that confers resistance to a treatment, such as a single nucleotide mutation that confers resistance to antibiotic treatment.

In some embodiments, the target nucleic acid sequence comprises a nucleic acid sequence of a virus, a bacterium, or other pathogen responsible for a disease in a plant (e.g., crop). Methods, systems and compositions of the disclosure may be used to treat or detect a disease in a plant. For example, the methods of the disclosure may be used to target a viral nucleic acid sequence in a plant. A D2S effector protein of the disclosure (e.g., Cas14) may cleave the viral nucleic acid. In some embodiments, the target nucleic acid sequence comprises a nucleic acid sequence of a virus or a bacterium or other agents (e.g., any pathogen) responsible for a disease in the plant (e.g., a crop). In some embodiments, the target nucleic acid comprises RNA. The target nucleic acid, in some embodiments, is a portion of a nucleic acid from a virus or a bacterium or other agents responsible for a disease in the plant (e.g., a crop). In some embodiments, the target nucleic acid is a portion of a nucleic acid from a genomic locus, or any NA amplicon, such as a reverse transcribed mRNA or a cDNA from a gene locus, a transcribed mRNA, or a reverse transcribed cDNA from a gene locus in at a virus or a bacterium or other agents (e.g., any pathogen) responsible for a disease in the plant (e.g., a crop). A virus infecting the plant may be an RNA virus. A virus infecting the plant may be a DNA virus. Non-limiting examples of viruses that may be targeted with the disclosure include Tobacco mosaic virus (TMV), Tomato spotted wilt virus (TSWV), Cucumber mosaic virus (CMV), Potato virus Y (PVY), Cauliflower mosaic virus (CaMV) (RT virus), Plum pox virus (PPV), Brome mosaic virus (BMV) and Potato virus X (PVX).

Mutations

In some embodiments, target nucleic acids comprise a mutation. In some embodiments, a sequence comprising a mutation may be modified to a wildtype sequence with a composition, system or method described herein. In some embodiments, a sequence comprising a mutation may be detected with a composition, system or method described herein. In some embodiments, a composition, system or method described herein can be used to detect a target nucleic acid comprising a mutation. The mutation may be a mutation of 1, 2, 3, 4, 5, 6, 7, 8, 9, 10, 11, 12, 13, 14, 15, 16, 17, 18, 19, 20 or more nucleotides. The mutation may comprise a deletion of about 5, about 10, about 15, about 20, about 25, about 30, about 35, about 40, about 45, about 50, about 55, about 60, about 65, about 70, about 75, about 80, about 85, about 90, about 95, about 100, about 200, about 300, about 400, about 500, about 600, about 700, about 800, about 900, or about 1000 nucleotides. The mutation may comprise a deletion of 1 to 5, 5 to 10, 10 to 15, 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 200, 200 to 300, 300 to 400, 400 to 500, 500 to 600, 600 to 700, 700 to 800, 800 to 900, 900 to 1000, 1 to 50, 1 to 100, 25 to 50, 25 to 100, 50 to 100, 100 to 500, 100 to 1000, or 500 to 1000 nucleotides. Non-limiting examples of mutations are insertion-deletion (indel), single nucleotide polymorphism (SNP), and frameshift mutations. In some embodiments, guide nucleic acids described herein hybridize to a region of the target nucleic acid comprising the mutation. The mutation may be located in a non-coding region or a coding region of a gene.

A mutation may be in an open reading frame of a target nucleic acid. A mutation may result in the insertion of at least one amino acid in a protein encoded by the target nucleic acid. A mutation may result in the deletion of at least one amino acid in a protein encoded by the target nucleic acid. A mutation may result in the substitution of at least one amino acid in a protein encoded by the target nucleic acid. A mutation that results in the deletion, insertion, or substitution of one or more amino acids of a protein encoded by the target nucleic acid may result in misfolding of a protein encoded by the target nucleic acid. A mutation may result in a premature stop codon, thereby resulting in a truncation of the encoded protein.

In some embodiments, a mutation comprises a point mutation or single nucleotide polymorphism (SNP), a chromosomal mutation, a copy number mutation, or any combination thereof. A point mutation optionally comprises a substitution, insertion, or deletion. In some embodiments, a mutation comprises a chromosomal mutation. A chromosomal mutations can comprise an inversion, a deletion, a duplication, or a translocation. In some embodiments, a mutation comprises a copy number variation. A copy number variation can comprise a gene amplification or an expanding trinucleotide repeat. In some embodiments, guide nucleic acids described herein hybridize to a target sequence of a target nucleic acid comprising the mutation. In some embodiments, mutations are located in a non-coding region of a gene.

In some embodiments, target nucleic acids described herein comprise a mutation, wherein the mutation is a single nucleotide polymorphism (SNP). The SNP may be associated with a phenotype of the sample or a phenotype of the organism from which the sample was taken. A SNP, in some embodiments, is associated with an altered phenotype as compared to a wild-type phenotype. In some embodiments, a single nucleotide mutation, SNP, or deletion described herein is associated with a disease, such as a genetic disease. A SNP may be a synonymous substitution or a nonsynonymous substitution. A nonsynonymous substitution can be a missense substitution, or a nonsense point mutation. A synonymous substitution may be a silent substitution. The mutation, such as a single nucleotide mutation, a SNP, or a deletion, may be encoded in the sequence of a target nucleic acid from the germline of an organism or may be encoded in a target nucleic acid from a diseased cell, such as a cancer cell.

In some examples, a mutation associated with a disease refers to a mutation whose presence in a subject indicates that the subject is susceptible to, or suffers from, a disease, disorder, or pathological state. In some examples, a mutation associated with a disease refers to a mutation which causes the disease, contributes to the development of the disease, or indicates the existence of the disease. A mutation associated with a disease may also refer to any mutation which generates transcription or translation products at an abnormal level, or in an abnormal form, in cells affected by a disease relative to a control without the disease. In some examples, a mutation associated with a disease refers to a mutation whose presence in a subject indicates that the subject is susceptible to, or suffers from, a disease, disorder, or pathological state. In some embodiments, a mutation associated with a disease, comprises the co-occurrence of a mutation and the phenotype of a disease. The mutation may occur in a gene, wherein transcription or translation products from the gene occur at a significantly abnormal level or in an abnormal form in a cell or subject harboring the mutation as compared to a non-disease control subject not having the mutation.

In some embodiments, target nucleic acids comprise a mutation, wherein the mutation is a deletion of 1, 2, 3, 4, 5, 6, 7, 8, 9, 10, 11, 12, 13, 14, 15, 16, 17, 18, 19, 20 or more nucleotides. The mutation may be a deletion of about 5, about 10, about 15, about 20, about 25, about 30, about 35, about 40, about 45, about 50, about 55, about 60, about 65, about 70, about 75, about 80, about 85, about 90, about 95, about 100, about 200, about 300, about 400, about 500, about 600, about 700, about 800, about 900, or about 1000 nucleotides. The mutation may be a deletion of 1 to 5, 5 to 10, 10 to 15, 15 to 20, 20 to 25, 25 to 30, 30 to 35, 35 to 40, 40 to 45, 45 to 50, 50 to 55, 55 to 60, 60 to 65, 65 to 70, 70 to 75, 75 to 80, 80 to 85, 85 to 90, 90 to 95, 95 to 100, 100 to 200, 200 to 300, 300 to 400, 400 to 500, 500 to 600, 600 to 700, 700 to 800, 800 to 900, 900 to 1000, 1 to 50, 1 to 100, 25 to 50, 25 to 100, 50 to 100, 100 to 500, 100 to 1000, or 500 to 1000 nucleotides.

Certain Samples

Various sample types comprising a target nucleic acid of interest are consistent with the present disclosure. These samples may comprise a target nucleic acid sequence for detection. In some embodiments, the detection of the target nucleic acid indicates an ailment, such as a disease, cancer, or genetic disorder, or genetic information, such as for phenotyping, genotyping, or determining ancestry and are compatible with the reagents and support mediums as described herein. Generally, a sample from an individual or an animal or an environmental sample may be obtained to test for presence of a disease, cancer, genetic disorder, or any mutation of interest.

In some embodiments, the sample is a biological sample, an environmental sample, or a combination thereof. Non-limiting examples of biological samples are blood, serum, plasma, saliva, urine, mucosal sample, peritoneal sample, cerebrospinal fluid, gastric secretions, nasal secretions, sputum, pharyngeal exudates, urethral or vaginal secretions, an exudate, an effusion, and a tissue sample (e.g., a biopsy sample). A tissue sample from a subject may be dissociated or liquified prior to application to detection system of the present disclosure. Non-limiting examples of environmental samples are soil, air, or water. In some embodiments, an environmental sample is taken as a swab from a surface of interest or taken directly from the surface of interest.

In some embodiments, the sample is a raw (unprocessed, unmodified) sample. Raw samples may be applied to a system for detecting or modifying a target nucleic acid, such as those described herein. In some embodiments, the sample is diluted with a buffer or a fluid or concentrated prior to its application to the system or be applied neat to the detection system. Sometimes, the sample contains no more 20 µl of buffer or fluid. The sample, in some embodiments, is contained in no more than 1, 5, 10, 15, 20, 25, 30, 35 40, 45, 50, 55, 60, 65, 70, 75, 80, 90, 100, 200, 300, 400, 500 µl, or any of value 1 µl to 500 µl, preferably 10 µL to 200 µL, or more preferably 50 µL to 100 µL of buffer or fluid. Sometimes, the sample is contained in more than 500 µl.

In some embodiments, the sample is taken from a single-cell eukaryotic organism; a plant or a plant cell; an algal cell; a fungal cell; an animal cell, tissue, or organ; a cell, tissue, or organ from an invertebrate animal; a cell, tissue, fluid, or organ from a vertebrate animal such as fish, amphibian, reptile, bird, and mammal; a cell, tissue, fluid, or organ from a mammal such as a human, a non-human primate, an ungulate, a feline, a bovine, an ovine, and a caprine. In some embodiments, the sample is taken from nematodes, protozoans, helminths, or malarial parasites. In some embodiments, the sample comprises nucleic acids from a cell lysate from a eukaryotic cell, a mammalian cell, a human cell, a prokaryotic cell, or a plant cell. In some embodiments, the sample comprises nucleic acids expressed from a cell.

In some embodiments, samples are used for diagnosing a disease. In some embodiments the disease is cancer. The sample used for cancer testing may comprise at least one target nucleic acid that may bind to a guide nucleic acid of the reagents described herein. The target nucleic acid, in some embodiments, comprises a portion of a gene comprising a mutation associated with cancer, a gene whose overexpression is associated with cancer, a tumor suppressor gene, an oncogene, a checkpoint inhibitor gene, a gene associated with cellular growth, a gene associated with cellular metabolism, or a gene associated with cell cycle. Sometimes, the target nucleic acid encodes a cancer biomarker, such as a prostate cancer biomarker or non-small cell lung cancer. In some embodiments, the assay may be used to detect "hotspots" in target nucleic acids that may be predictive of lung cancer. In some embodiments, the target nucleic acid comprises a portion of a nucleic acid that is associated with a blood fever. In some embodiments, the target nucleic acid is a portion of a nucleic acid from a genomic locus, any DNA amplicon of, a reverse transcribed mRNA, or a cDNA from a locus of at least one of: ALK, APC, ATM, AXIN2, BAP1, BARD1, BLM, BMPR1A, BRCA1, BRCA2, BRIP1, CASR, CDC73, CDH1, CDK4, CDKN1B, CDKN1C, CDKN2A, CEBPA, CHEK2, CTNNA1, DICER1, DIS3L2, EGFR, EPCAM, FH, FLCN, GATA2, GPC3, GREM1, HOXB13, HRAS, system, MAX, MEN1, MET, MITF, MLH1, MSH2, MSH3, MSH6, MUTYH, NBN, NF1, NF2, NTHL1, PALB2, PDGFRA, PHOX2B, PMS2, POLD1, POLE, POT1, PRKAR1A, PTCH1, PTEN, RAD50, RAD51C, RAD51D, RB1, RECQL4, RET, RUNX1, SDHA, SDHAF2, SDHB, SDHC, SDHD, SMAD4, SMARCA4, SMARCB1, SMARCE1, STK11, SUFU, TERC, TERT, TMEM127, TP53, TSC1, TSC2, VHL, WRN, and WT1. Any region of the aforementioned gene loci may be probed for a mutation or deletion using the compositions, systems and methods disclosed herein. For example, in the EGFR gene locus, the compositions, systems and methods for detection disclosed herein may be used to detect a single nucleotide polymorphism or a deletion.

In some embodiments, samples are used to diagnose a genetic disorder, also referred to as genetic disorder testing. The sample used for genetic disorder testing may comprise at least one target nucleic acid that may bind to a guide nucleic acid of the reagents described herein. In some embodiments, the genetic disorder is hemophilia, sickle cell anemia, 0-thalassemia, Duchene muscular dystrophy, severe combined immunodeficiency, Huntington's disease, or cystic fibrosis. The target nucleic acid, in some embodiments, is from a gene with a mutation associated with a genetic disorder, from a gene whose overexpression is associated with a genetic disorder, from a gene associated with abnormal cellular growth resulting in a genetic disorder, or from a gene associated with abnormal cellular metabolism resulting in a genetic disorder. In some embodiments, the target nucleic acid is a nucleic acid from a genomic locus, a transcribed mRNA, or a reverse transcribed mRNA, a DNA amplicon of or a cDNA from a locus of at least one of: CFTR, FMR1, SMN1, ABCB11, ABCC8, ABCD1, ACAD9, ACADM, ACADVL, ACAT1, ACOX1, ACSF3, ADA, ADAMTS2, ADGRG1, AGA, AGL, AGPS, AGXT, AIRE, ALDH3A2, ALDOB, ALG6, ALMS1, ALPL, AMT, AQP2, ARG1, ARSA, ARSB, ASL, ASNS, ASPA, ASS1, ATM, ATP6V1B1, ATP7A, ATP7B, ATRX, BBS1, BBS10, BBS12, BBS2, BCKDHA, BCKDHB, BCS1L, BLM, BSND, CAPN3, CBS, CDH23, CEP290, CERKL, CHM, CHRNE, CIITA, CLN3, CLN5, CLN6, CLN8, CLRN1, CNGB3, COL27A1, COL4A3, COL4A4, COL4A5, COL7A1, CPS1, CPT1A, CPT2, CRB1, CTNS, CTSK, CYBA, CYBB, CYP11B1, CYP11B2, CYP17A1, CYP19A1, CYP27A1, DBT, DCLRE1C, DHCR7, DHDDS, DLD, DMD, DNAH5, DNAI1, DNAI2, DYSF, EDA, EIF2B5, EMD, ERCC6, ERCC8, ESCO2, ETFA, ETFDH, ETHE1, EVC, EVC2, EYS, F9, FAH, FAM161A, FANCA, FANCC, FANCG, FH, FKRP, FKTN, G6PC, GAA, GALC, GALK1, GALT, GAMT, GBA, GBE1, GCDH, GFM1, GJB1, GJB2, GLA, GLB1, GLDC, GLE1, GNE, GNPTAB, GNPTG, GNS, GRHPR, HADHA, HAX1, HBA1, HBA2, HBB, HEXA, HEXB, HGSNAT, HLCS, HMGCL, HOGA1, HPS1, HPS3, HSD17B4, HSD3B2, HYAL1, HYLS1, IDS, IDUA, IKBKAP, IL2RG, IVD, KCNJ11, LAMA2, LAMA3, LAMB3, LAMC2, LCA5, LDLR, LDLRAP1, LHX3, LIFR, LIPA, LOXHD1, LPL, LRPPRC, MAN2B1, MCOLN1, MED17, MESP2, MFSD8, MKS1, MLC1, MMAA, MMAB, MMACHC, MMADHC, MPI, MPL, MPV17, MTHFR, MTM1, MTRR, MTTP, MUT, MYO7A, NAGLU, NAGS, NBN, NDRG1, NDUFAF5, NDUFS6, NEB, NPC1, NPC2, NPHS1, NPHS2, NR2E3, NTRK1, OAT, OPA3, OTC, PAH, PC, PCCA, PCCB, PCDH15, PDHA1, PDHB, PEX1, PEX10, PEX12, PEX2, PEX6, PEX7, PFKM, PHGDH, PKHD1, PMM2, POMGNT1, PPT1, PROP1, PRPS1, PSAP, PTS, PUS1, PYGM, RAB23, RAG2, RAPSN, RARS2, RDH12, RMRP, RPE65, RPGRIP1L, RS1, RTEL1, SACS, SAMHD1, SEPSECS, SGCA, SGCB, SGCG, SGSH, SLC12A3, SLC12A6, SLC17A5, SLC22A5, SLC25A13, SLC25A15, SLC26A2, SLC26A4, SLC35A3, SLC37A4, SLC39A4, SLC4A11, SLC6A8, SLC7A7, SMARCAL1, SMPD1, STAR, SUMF1, TAT, TCIRG1, TECPR2, TFR2, TGM1, TH, TMEM216, TPP1, TRMU, TSFM, TTPA, TYMP, USH1C, USH2A, VPS13A, VPS13B, VPS45, VRK1, VSX2, WNT10A, XPA, XPC, and ZFYVE26.

The sample used for phenotyping testing may comprise at least one target nucleic acid that may bind to a guide nucleic acid of the reagents described herein. The target nucleic acid, in some embodiments, is a nucleic acid (e.g., DNA) encoding a sequence (e.g., RNA or amino acid) associated with a phenotypic trait.

The sample used for genotyping testing may comprise at least one target nucleic acid that may bind to a guide nucleic acid of the reagents described herein. The target nucleic acid, in some embodiments, is a nucleic acid (e.g., DNA) encoding a sequence (e.g., RNA or amino acid) associated with a genotype of interest.

The sample used for ancestral testing may comprise at least one target nucleic acid that may bind to a guide nucleic acid of the reagents described herein. The target nucleic acid, in some embodiments, is a nucleic acid (e.g., DNA) encoding a sequence (e.g., RNA or amino acid) associated with a geographic region of origin or ethnic group.

The sample may be used for identifying a disease status. For example, a sample is any sample described herein, and is obtained from a subject for use in identifying a disease status of a subject. The disease may be a cancer or genetic disorder. Sometimes, a method comprises obtaining a serum sample from a subject; and identifying a disease status of the subject. Often, the disease status is prostate disease status, but the status of any disease may be assessed.

Any of the above disclosed samples are consistent with the methods, compositions, systems, reagents, enzymes, and systems disclosed herein.

XVI. Pharmaceutical Compositions

In some embodiments, provided herein are pharmaceutical compositions comprising a composition or system described herein. In some embodiments, the pharmaceutical composition comprises a pharmaceutically acceptable salt, one or more of a vehicle, adjuvant, excipient, or carrier, such as a filler, disintegrant, a surfactant, a binder, a lubricant, or combinations thereof. Remington: The Science and Practice of Pharmacy, 21st edition, 2005, ed. D. B. Troy, Lippincott Williams & Wilkins, Philadelphia, *Encyclopedia of Pharmaceutical Technology*, eds. J. Swarbrick and J. C. Boylan, 1988-1999, Marcel Dekker, New York; and *Encyclopedia of Pharmaceutical Technology*, eds. J. Swarbrick, 2015, CRC Press, Boca Raton disclose various carriers used in formulating pharmaceutically acceptably compositions and known techniques for the preparation thereof. In some embodiments, a composition described herein can be mixed with excipients which are pharmaceutically acceptable and compatible with the active ingredient and in amounts suitable for use in the therapeutic methods described herein. Suitable excipients include, for example, water, saline, dextrose, glycerol, ethanol or the like and combinations thereof. In addition, if desired, the composition can contain minor amounts of auxiliary substances such as wetting or emulsifying agents, pH buffering agents and the like which enhance the effectiveness of the active ingredient. The compositions described herein can include pharmaceutically acceptable salts of the components therein. Some examples of materials which can serve as pharmaceutically acceptable carriers include, but are not limited to, ion exchanger, alumina, aluminum stearate, lecithin, serum proteins such as human serum albumin, buffer substances such as phosphates, glycine, sorbic acid, or potassium sorbate, partial glyceride mixtures of saturated vegetable fatty acids, water, salts or electrolytes such as protamine sulfate, disodium hydrogen phosphate, potassium hydrogen phosphate, sodium chloride, zinc salts, colloidal silica, magnesium trisilicate, polyvinyl pyrrolidone, polyacrylates, waxes, polyethylene-polyoxypropylene-block polymers, wool fat, sugars such as lactose, glucose and sucrose; starches such as corn starch and potato starch; cellulose and its derivatives such as sodium carboxymethyl cellulose, ethyl cellulose and cellulose acetate, powdered tragacanth, malt, gelatin, talc, excipients such as cocoa butter and suppository waxes, oils such as peanut oil, cottonseed oil, safflower oil, sesame oil, olive oil, corn oil and soybean oil, glycols such as propylene glycol or polyethylene glycol, esters such as ethyloleate and ethyl laurate, agar, buffering agents such as magnesium hydroxide and aluminum hydroxide, alginic acid, pyrogen-free water, isotonic saline, Ringer's solution, ethyl alcohol, and phosphate buffer solutions, as well as other non-toxic compatible lubricants such as sodium lauryl sulfate and magnesium stearate, as well as coloring agents, releasing agents, coating agents, sweetening, flavoring and perfuming agents, preservatives, and antioxidants can also be present in the composition, according to the judgment of the formulator.

Disclosed herein, in some aspects, are pharmaceutical compositions for modifying a target nucleic acid in a cell or a subject, comprising any one of the effector proteins, engineered effector proteins, fusion effector proteins, or guide nucleic acids as described herein and any combination thereof. Also disclosed herein, in some aspects, are pharmaceutical compositions comprising a nucleic acid encoding any one of the effector proteins, engineered effector proteins, fusion effector proteins, or guide nucleic acids as described herein and any combination thereof. In some embodiments, pharmaceutical compositions comprise a plurality of guide nucleic acids. Pharmaceutical compositions may be used to modify a target nucleic acid or the expression thereof in a cell in vitro, in vivo or ex vivo.

In some embodiments, pharmaceutical compositions comprise one or more nucleic acids encoding an effector protein, fusion effector protein, fusion partner, a guide nucleic acid, or a combination thereof, and a pharmaceutically acceptable carrier or diluent. The effector protein, fusion effector protein, fusion partner protein, or combination thereof may be any one of those described herein. The one or more nucleic acids may comprise a plasmid. The one or more nucleic acids may comprise a nucleic acid expression vector. The one or more nucleic acids may comprise a viral vector. In some embodiments, the viral vector is a lentiviral vector. In some embodiments, the vector is an adeno-associated viral (AAV) vector. In some instances, the AAV vector is a self-complementary AAV (scAAV) vector. In some embodiments, compositions, including pharmaceutical compositions, comprise a viral vector encoding a fusion effector protein and a guide nucleic acid, wherein at least a portion of the guide nucleic acid binds to the effector protein of the fusion effector protein.

In some embodiments, pharmaceutical compositions comprise a virus comprising a viral vector encoding a fusion effector protein, an effector protein, a fusion partner, a guide nucleic acid, or a combination thereof, and a pharmaceutically acceptable carrier or diluent. The virus may be a lentivirus. The virus may be an adenovirus. The virus may be a non-replicating virus. The virus may be an adeno-associated virus (AAV). The viral vector may be a retroviral vector. Retroviral vectors may include gamma-retroviral vectors such as vectors derived from the Moloney Murine Leukemia Virus (MoMLV, MMLV, MuLV, or MLV) or the Murine Stem cell Virus (MSCV) genome. Retroviral vectors may include lentiviral vectors such as those derived from the human immunodeficiency virus (HIV) genome. In some embodiments, the viral vector is a chimeric viral vector, comprising viral portions from two or more viruses. In some embodiments, the viral vector is a recombinant viral vector.

In some embodiments, the viral vector is an AAV. The AAV may be any AAV known in the art. In some embodiments, the viral vector corresponds to a virus of a specific serotype. In some examples, the serotype is selected from an AAV1 serotype, an AAV2 serotype, AAV3 serotype, an AAV4 serotype, AAV5 serotype, an AAV6 serotype, AAV7 serotype, an AAV8 serotype, an AAV9 serotype, an AAV10 serotype, an AAV 11 serotype, and an AAV12 serotype. In some embodiments the AAV vector is a recombinant vector, a hybrid AAV vector, a chimeric AAV vector, a self-complementary AAV (scAAV) vector, a single-stranded AAV or any combination thereof scAAV genomes are generally known in the art and contain both DNA strands which can anneal together to form double-stranded DNA.

In some embodiments, the AAV vector is a self-complementary AAV (scAAV) vector. In some embodiments, the coding region of the scAAV vector forms an intramolecular double-stranded DNA template in contrast to a standard AAV vector having a single-stranded DNA template. In some embodiments, the two complementary sequences of the scAAV coding region associate to form dsDNA. In some embodiments, the dsDNA is ready for expression and does not require cell mediated synthesis. In some embodiments, the scAAV vector provides greater and longer expression of the genome editing components (also referred to collectively as the transgene) that it carries relative to the standard AAV vector. In some embodiments, the standard AAV vector carrying genome editing components has a total length of about 4 kb to about 5 kb. In some embodiments, the scAAV vector carrying genome editing components has a total length of about 2 kb to about 3 kb. In some embodiments, the length of the scAAV vector carrying genome editing components allows for delivery to any eukaryotic cells. In some embodiments, the length of the Cas effector protein encoded by the scAAV vector transgene is less than 500 amino acids.

Figure 6:
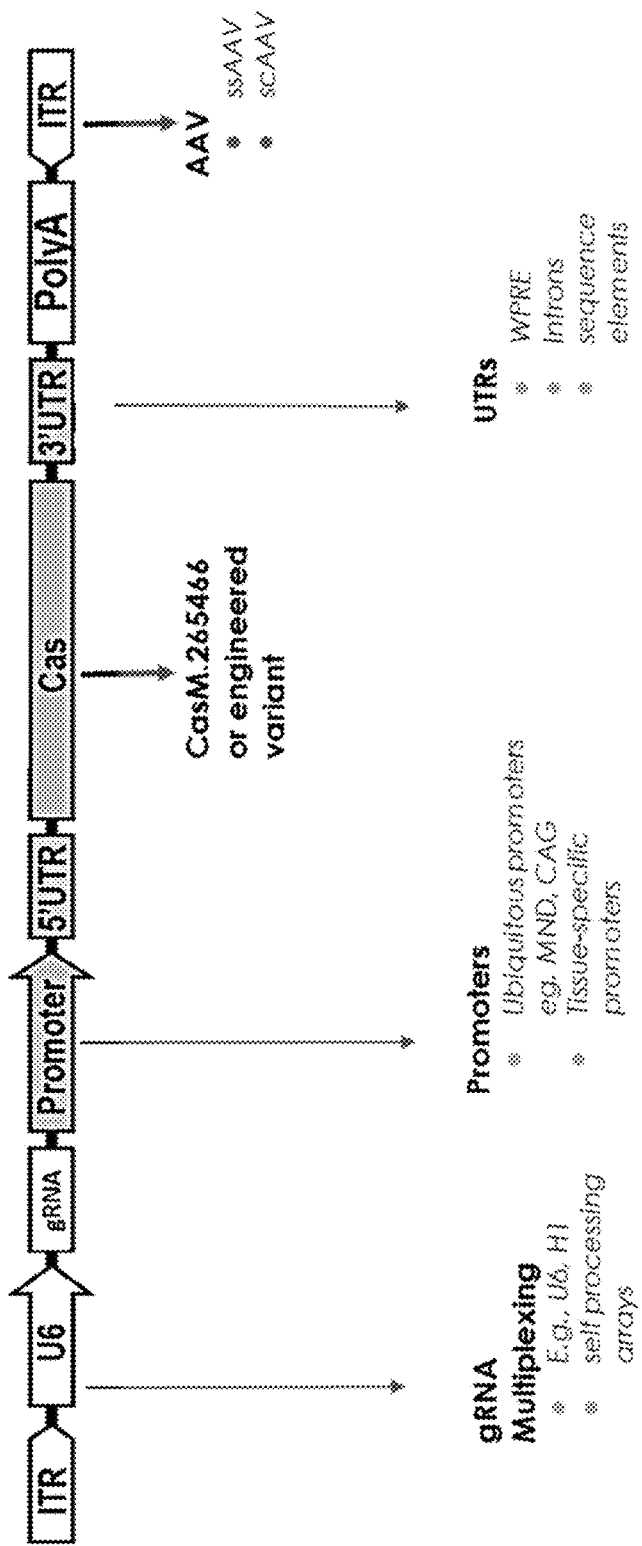
FIG. 6 illustrates an exemplary schematic of AAV construct for gene editing according to one or more embodiments of the present disclosure. Included in FIG. 6 are the following abbreviations representing elements of the AAV construct: ITR=Inverted terminal repeat; gRNA=guide RNA; UTR=untranslated region; ssAAV=single-stranded AAV; scAAV=self-complementary AAV; and WPRE=Woodchuck Hepatitis Virus (WHV) posttranscriptional regulatory element.

In some embodiments, methods of producing delivery vectors herein comprise packaging a nucleic acid encoding an effector protein and a guide nucleic acid, or a combination thereof, into an AAV vector. In some embodiments, methods of producing the delivery vector comprises, (a) contacting a cell with at least one nucleic acid encoding: (i)

a guide nucleic acid; (ii) a Replication (Rep) gene; and (iii) a Capsid (Cap) gene that encodes an AAV capsid protein; (b) expressing the AAV capsid protein in the cell; (c) assembling an AAV particle; and (d) packaging a Cas effector encoding nucleic acid into the AAV particle, thereby generating an AAV delivery vector. In some embodiments, promoters, stuffer sequences, and any combination thereof may be packaged in the AAV vector. In some embodiments, the AAV vector comprises a sequence encoding a guide nucleic acid. In some embodiments, the guide nucleic acid comprises a crRNA. In some embodiments, the guide nucleic acid is a crRNA. In some embodiments, the guide nucleic acid comprises a sgRNA. In some embodiments, the guide nucleic acid is a sgRNA. In some examples, the AAV vector can package 1, 2, 3, 4, or 5 nucleotide sequences encoding guide nucleic acids or copies thereof. In some examples, the AAV vector packages 1 or 2 nucleotide sequences encoding guide nucleic acids or copies thereof. In some embodiments, the AAV vector packages a nucleotide sequence encoding a first guide nucleic acid and a nucleotide sequence encoding a second guide nucleic acid, wherein the first guide nucleic acid and the second guide nucleic acid are the same. In some embodiments, the AAV vector packages a nucleotide sequence encoding a first guide nucleic acid and a nucleotide sequence encoding a second guide nucleic acid, wherein the first guide nucleic acid and the second guide nucleic acid are different. In some embodiments, the AAV vector comprises inverted terminal repeats, e.g., a 5' inverted terminal repeat and a 3' inverted terminal repeat. In some embodiments, the inverted terminal repeat comprises inverted terminal repeats from AAV. In some embodiments, the inverted terminal repeat comprises inverted terminal repeats of ssAAV vector or scAAV vector. In some embodiments, the AAV vector comprises a mutated inverted terminal repeat that lacks a terminal resolution site. FIG. 6 illustrates an exemplary schematic of AAV construct.

In some embodiments, a hybrid AAV vector is produced by transcapsidation, e.g., packaging an inverted terminal repeat (ITR) from a first serotype into a capsid of a second serotype, wherein the first and second serotypes may be not the same. In some examples, the Rep gene and ITR from a first AAV serotype (e.g., AAV2) may be used in a capsid from a second AAV serotype (e.g., AAV9), wherein the first and second AAV serotypes may be not the same. As a non-limiting example, a hybrid AAV serotype comprising the AAV2 ITRs and AAV9 capsid protein may be indicated AAV2/9. In some examples, the hybrid AAV delivery vector comprises an AAV2/1, AAV2/2, AAV 2/4, AAV2/5, AAV2/8, or AAV2/9 vector.

In some embodiments, the AAV vector may be a chimeric AAV vector. In some embodiments, the chimeric AAV vector comprises an exogenous amino acid or an amino acid substitution, or capsid proteins from two or more serotypes. In some examples, a chimeric AAV vector may be genetically engineered to increase transduction efficiency, selectivity, or a combination thereof.

In some examples, the delivery vector may be a eukaryotic vector, a prokaryotic vector (e.g., a bacterial vector) a viral vector, or any combination thereof. In some embodiments, the delivery vehicle may be a non-viral vector. In some embodiments, the delivery vehicle may be a plasmid. In some embodiments, the plasmid comprises DNA. In some embodiments, the plasmid comprises RNA. In some examples, the plasmid comprises circular double-stranded DNA. In some examples, the plasmid may be linear. In some examples, the plasmid comprises one or more genes of interest and one or more regulatory elements. In some examples, the plasmid comprises a bacterial backbone containing an origin of replication and an antibiotic resistance gene or other selectable marker for plasmid amplification in bacteria. In some examples, the plasmid may be a minicircle plasmid. In some examples, the plasmid contains one or more genes that provide a selective marker to induce a target cell to retain the plasmid. In some examples, the plasmid may be formulated for delivery through injection by a needle carrying syringe. In some examples, the plasmid may be formulated for delivery via electroporation. In some examples, the plasmids may be engineered through synthetic or other suitable means known in the art. For example, in some embodiments, the genetic elements may be assembled by restriction digest of the desired genetic sequence from a donor plasmid or organism to produce ends of the DNA which may then be readily ligated to another genetic sequence.

In some embodiments, the vector is a non-viral vector, and a physical method or a chemical method is employed for delivery into the somatic cell. Exemplary physical methods include electroporation, gene gun, sonoporation, magnetofection, or hydrodynamic delivery. Exemplary chemical methods include delivery of the recombinant polynucleotide via liposomes such as, cationic lipids or neutral lipids; dendrimers; nanoparticles; or cell-penetrating peptides.

In some embodiments, a fusion effector protein as described herein is inserted into a vector. In some embodiments, the vector comprises one or more promoters, enhancers, ribosome binding sites, RNA splice sites, polyadenylation sites, a replication origin, and/or transcriptional terminator sequences.

In some embodiments, the AAV vector comprises a self-processing array system for guide nucleic acid. In general, plasmids and vectors described herein comprise at least one promoter. In some embodiments, the promoters are constitutive promoters. In other embodiments, the promoters are inducible promoters. In additional embodiments, the promoters are prokaryotic promoters (e.g., drive expression of a gene in a prokaryotic cell). In some embodiments, the promoters are eukaryotic promoters, (e.g., drive expression of a gene in a eukaryotic cell). Exemplary promoters include, but are not limited to, CMV, EF1a, SV40, PGK1, Ube, human beta actin, CAG, TRE, UAS, Ac5, polyhedron, CaMKIIa, GAL1-10, TEF1, GDS, ADH1, CaMV35S, Ubi, H1, U6, CaMV35S, SV40, CMV, 7SK, and HSV TK promoter. In some embodiments, the promoter is CMV. In some embodiments, the promoter is EF1a. In some embodiments, the promoter is U6. In some embodiments, the promote is H1. In some embodiments, the promoter is 7SK. In some embodiments, the promoter is ubiquitin. In some embodiments, vectors are bicistronic or polycistronic vector (e.g., having or involving two or more loci responsible for generating a protein) having an internal ribosome entry site (IRES) is for translation initiation in a cap-independent manner.

In some embodiments, the AAV vector comprises a promoter for expressing effector proteins. In some embodiments, the promoter for expressing effector protein is a site-specific promoter. In some embodiments, the promoter for expressing effector protein is a muscle-specific promoter. In some embodiments, the muscle-specific promoter comprises Ck8e, SPC5-12, or Desmin promoter sequence. In some embodiments, the promoter for expressing effector protein is a ubiquitous promoter. In some embodiments, the ubiquitous promoter comprises MND or CAG promoter sequence.

In some embodiments, the stuffer sequence comprises 5' untranslated region, 3' untranslated region or combination thereof. In some embodiments, the 3'-untranslated region comprises an intron. In some embodiments, the 3'-untranslated region comprises one or more sequence elements. In some embodiments, the 3'-untranslated region comprises an enhancer. In some embodiments, vectors comprise an enhancer. Enhancers are nucleotide sequences that have the effect of enhancing promoter activity. In some embodiments, enhancers augment transcription regardless of the orientation of their sequence. In some embodiments, enhancers activate transcription from a distance of several kilo basepairs. Furthermore, enhancers are located optionally upstream or downstream of a gene region to be transcribed, and/or located within the gene, to activate the transcription. Exemplary enhancers include, but are not limited to, WPRE; CMV enhancers; the R-U5' segment in LTR of HTLV-I (Mol. Cell. Biol., Vol. 8(1), p. 466-472, 1988); SV40 enhancer; the intron sequence between exons 2 and 3 of rabbit p3-globin (Proc. Natl. Acad. Sci. USA, Vol. 78(3), p. 1527-31, 1981); and the genome region of human growth hormone (J Immunol., Vol. 155(3), p. 1286-95, 1995). In some embodiments, the enhancer is WPRE.

In some embodiments, the AAV vector comprises one or more polyadenylation (poly A) signal sequences. In some embodiments, the polyadenlyation signal sequence comprises hGH poly A signal sequence. In some embodiments, the polyadenlyation signal sequence comprises sv40 poly A signal sequence.

Figure 7A:
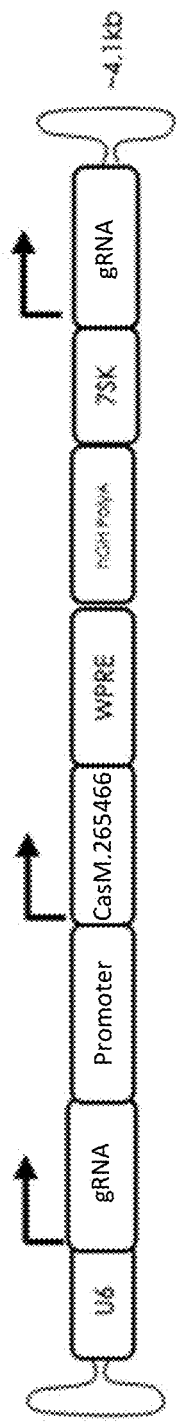
FIGS. 7A-7C illustrates exemplary schematics of ssAAV and scAAV constructs for gene editing according to one or more embodiments of the present disclosure.
Figure 7B:
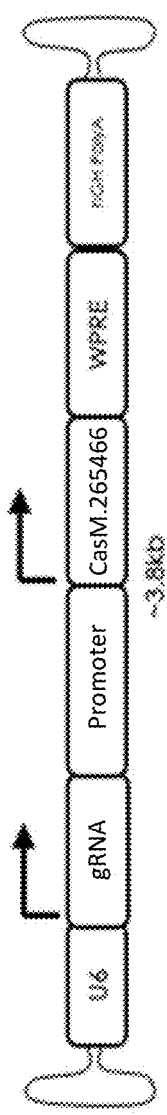
Figure 7C:
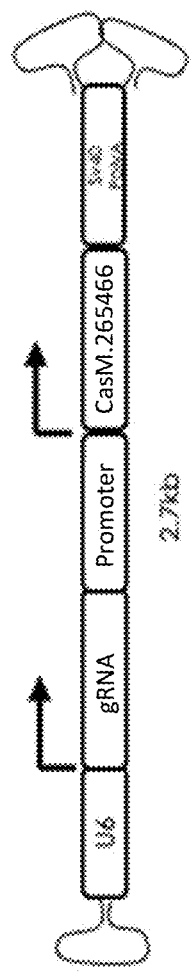

FIGS. 7A-7C illustrates exemplary ssAAV and scAAV constructs having a nucleic acid (e.g., DNA) encoding one or two guide nucleic acids. In some embodiments, the guide nucleic acid comprises a guide RNA (e.g., crRNA or sgRNA). Single cutting can be assessed by delivery of a nucleic acid (e.g., DNA) encoding the one or two guide nucleic acids. Accordingly, in some embodiments, any one of AAV construct illustrated in FIGS. 7B-7C can be used for introducing a single cut within or near about a target nucleic acid.

FIG. 7A illustrates an exemplary ssAAV construct having two nucleic acids encoding two guide nucleic acids. In some embodiments, a first nucleic acid (e.g., DNA) encoding a first guide nucleic acid comprises a first guide RNA and a second nucleic acid (e.g., DNA) encoding a second guide nucleic acid comprises a second guide RNA. In some embodiments, the first nucleic acid and the second nucleic acid are same. Accordingly, in some embodiments, exemplary AAV constructs of FIG. 7A can be used to insert a single cut at a higher rate that the construct having a single copy of a nucleic acid (e.g., DNA) encoding one guide nucleic acid. Alternatively, in some embodiments, the first nucleic acid and the second nucleic acid are different. Dual cutting can be assessed by delivery of two different nucleic acids each encoding guide nucleic acid. Accordingly, in some embodiments, AAV constructs illustrated in FIG. 7A can be used for dual cutting within or near about a target nucleic acid.

Sequences and Tables

TABLE 1 provides illustrative amino acid sequences of effector proteins.

TABLE 1

Exemplary Amino Acid Sequences of Effector Proteins

| SEQ ID NO | Effector Protein Amino Acid sequence | Effector Protein Name |
|---|---|---|
| 1 | MSVLTRKVQLIPVGDKEERDRVYKYLRDGIEAQNRAMNLYMSGL YFAAINEASKEDRKELNQLYSRIATSSKGSAYTTDIEFPTGLASTSTL SMAVRQDFTKSLKDGLMYGRVSLPTYRKDNPLFVDVRFVALRGT KQKYNGLYHEYKSHTEFLDNLYSSDLKVYIKFANDITFQVIFGNPR KSSALRSEFQNIFEEYYKVCQSSIQFSGTKIILNMAMDIPDKEIELDE DVCVGVDLGIAIPAVCALNKNRYSRVSIGSKEDFLRVRTKIRNQRK RLQTNLKSSNGGHGRKKKMKPMDRFRDYEANWVQNYNHYVSRQ VVDFAVKNKAKYINLENLEGIRDDVKNEWLLSNWSYYQLQQYIT YKAKTYGIEVRKINPYHTSQRCSCCGYEDAGNRPKKEKGQAYFKC LKCGEEMNADFNAARNIAMSTEFQSGKKTKKQKKEQHENK | CasM. 265466 |
| 2 | MVITRKIALTVVGNKEEKDRVYTYIRDGIKNONLAMNQYMSALY VANMQDISKDDRKELNHLYTRISTSKKGSAYSTDIQFPKGLPCTSSL GQEVRAKFKKACKDGLMYGRVSLPTYRANNPLLIHVDYVRLRST NPHNDTGLYHNYESHTEFLEHLYKNDCEVFIKFANNITFQLFFGQP HKSHELRSVIQKVFEEYYSVCGSSIEISKKGKIMLNMCIEIPVEKKEL DENIVVGVDLGISTPAMCGLNCNDYVREGIGSKDTLLSKRTQLRQ YRELQGRMKMTNGGHGRGKKLKKMDDYRNHERHFVQTYNHQV SKKIVDFALKYKAKYINVEDLSGFGNRDTNQWVLRNWSYYELQQ YITYKAQKYGIEVRKVKPYLTSQTCSHCGHYEPGQRLDQAHFECK NCGLKINADFNASRNIAMSTEFV | CasM. 292007 |
| 37 | MXVJTRKXXLXXVGBKEEXDRVYXYJRDGIXXQNXAMNXYMSX LYXAXXXXXSKXDRKELNXLYXRIXTSXKGSAYXTDIZFPXGLXX TSXLXXXVRXXFXKXXXKDGLMYGRVSLPTYRXBNPLXXXVXXV XLRXTXXXXXXGLYHXYXSHTEFLXXLYXXDXXVXIKFANBITFQ XXFGXPXKSXXLRSXXQXXFEEYYXVCXSSIZXSXXXKIXLNMXX XIPXXXXELDEBXXVGVDLGIXXPAXCXLNXNXYXRXXIGSKXXX LXXRTXJXXQXXXLQXXXKXXNGGHGRXKKXKXMDXXRBXEX XXVQXYNHXVSXXXV TABLE 1-continued Exemplary Amino Acid Sequences of Effector Proteins

| SEQ ID NO | Effector Protein Amino Acid sequence | Effector Protein Name |
|---|---|---|
| 871 | MILTRKIQLIPVGDKEEVNRVYSYLRDGIFNQNRAMNQYISALYTA TMQGVSKEDRQELNRLYSRMPTSKLGSAYTEDIVFPKGLGTPSSLT LKVKQDFSKQCKDGLLYGKVSLITYKKDNPLLVESEYVKLRKYSK RQNGIYHNYSSHQEFLDKLYSNDLDIFIKFANGITFKMVFGNPHKS AGLRSEIQQIFEEHYKVCGSSIQIDGKKIILNLSMEIPKKEIELNSDTV VGVDLGIAIPAVCALNNNDYIRQSIGSKEDFLRVRTQLQSQRRRLQ KALKSTSGGHGRTKKLKALDKLKTRERNFVKTYNHYVSKQVIDFA VKNKAKYINLEDLTGFDSSKFILRNWSYYELQQFITYKAAQYGIEV RKVNPYHTSQICSKCGHWEEGQRIDQAHFVCRNCGAELNADFNAA RNIAMSADFIDKKTTKSNKAA | 2728047 |
| 872 | MILTRKIQIIPLGEKEEIDRVYKYLRDGIFYQNKAMNQYMSALYIAA IKDISKEDRKELNRLYSRVSNSKKGSAYDKSIEFAKNMNLGYVVK QVKQDFANSCKNGLLCGKVSLPTYRKNNPLLVHVNFVRLRSTNYH QDNGMYHNYESHTDFLDHLYSKDLEVFIKFANNITFKMIFGNPHKS ASLRSEIQQIFEENYKVCGSSIQIDGKKIILNLSMDIPKQELELDENIV VGVDLGLAIPAVCGLNTNDYIRQSIGSKDDFLRIRTQLQSQRRRLQ KSLASTSGGHGRQKKLKPL | 2727755 |
| 873 | MILTRKIQLLIVGNNDEVNRVFNYIREGMISQNKAMNEYMSALYL AELNKASKEDRKELNQLYGRISNSKKGSAYSQDIVFPKGLPVASSL SMKVKQDFKQSCKNGLMYGKVSLPTYRSDNPLLIHVDYVRLRSN NPHRDSGLYHNYKNHAEFLEHLDNKDLEVFIKFANNITFKLILGNV KKSASLRHEIQMIFEEYYKVCSSSIEIDGRKIILNLSMDIPKEKRELD ENVVVGVDVGIAIPAVCGLNINDYSRKYIGSVNDFMRVKTKIQHQ KSRLQTNLKMTKGGHGRKRKLKTMDKFTDYERNWVQSYNHYISK QVIDFALKNKAKYINIEDLSGITKGKNVNKFLKGWSYYQLQSFITY KANKYGIEVRKIDPHYTSQTCSCCGYVDEKNRPKNEKGQSYFRCL KCGHEENADFNAAKNIAKSVNFVK | 2452922 |
| 874 | MIQNRRQNRLILTRKIQIIPLGEKEEIDRVYKYLRDGIFYQNKAMNQ YMSALYIAAIKDISKEDRKELNRLYSRVSNSKKGSAYDKSIEFAKN MNLGYVVKQVKQDFANSCKNGLLCGKVSLPTYRKNNPLLVHVNF VRLRSTNYHQDNGMYHNYESHTDFLDHLYSKDLEVFIKFANNITF KMIFGNPHKSAYLRSEIQQIFEENYKVCGSSIQIDGKKIILNLSMDIP KQELELDENIVVGVDLGLAIPAMCGLNTNDYIRQSIGSKDDFLRIRT QLQSQRRRLQKSLASTSGGHGRQKKLKPLEKLKDRERNFVKTYNH YVSKNVVDFAVKNKAKYINVEDLSGFDSNQFILRNWSFYELQQFIT YKAAKYGIEVRKINPYHTSQICSCCGHWEEGQRIDQAHFKCKSCG AELNADFNASRNIAMSTDFV | 2699855 |
| 875 | MILTRKIQLIPVGDKEEIDRVYSYLRDGIFNQNKAMNQYLSALYTA TIQEASKEDRQELDRLYTRIATSKKGSAYQTDIEFPKGLPIGAFGIKV RQDFAKQCKDGLLYGKVSLATYKKDNPLLVHVDYVRLRKTNPHL DNGMYHNYESHQEFLDHLYSNDLEVFIKFANKITFKLIFGNPRRSA VLRSEIKEIFEEYYKVCGSSIQIDGKKIILNMSMEIPKEEAELDEDTV VGVDLGIAVPAMCALNNNMYVRAAIGNKDDFLRIRTKIQAQRRRL QHSLKYTSGGHGRNKKLKALEKLKKSEAHFVETYNHMVSRRIVDF AVKNHAKYINVENLTGYNTSKFILRNWSFYQLQQYITYKAARYGI EVRKINPCYTSQVCSVCGHWEEGQRKSQSVFECANPDCESYTKYE YGFNADFNAARNIAMSTLFMEKGEVTEKSKQEAREYYGIIS | 2729320 |
| 876 | MILTRKIQLYPIGDKEEVKRVYKYLSDGIFNQNKAMNQYISALYMS TIQEASKEDKQELNRLYTRISTSKKGSAYDKDIEFAKGLPIGSLGQK VKQDFQKSIKDGLLYGKVSLPTYRKDNPLLIHVDYVRLRKTNPHR DNGIYHNYFNHQDFLDNLYSKDLEILIKFANNITFKMILGQPHKSAT LREEIKQIFEENYKVCGSSIQIDGTKIILNLSMDVPKKEVELDENTVV GVDLGIAIPAVCGLNNNEYIKQSIGNKEDFLRIRTQMQSERRRVQS NLKLSKGGHGRKKKLKHLDNLSDRERNFVKTYNHYVSKQVVDFA LKNKAKYINVEDLSGFDSSQFILRNWSYYELQQFITYKANKYGIEV KKINPYHTSQICSCCGYWEEGQRDSQSHFKCKSCGYETNADFNAS RNIAKSVDFR | 2451449 |
| 877 | MILTRKIQLLVVGNNDEVNRVFDYIREGMISQNKAMNQYMSALYL AELDKISKEDRKELNQLYGRISNSKKGSAYSQDIVFPKGLPTASSLS MKVKQDFKQSCKNGLMYGRVSLPTYRSDNPLLIHVDWVRLRSSN PHNDFGLYYNYKNHAEFLEHLDDKDLEVFIKFANNITFKLILGNVK KSASLRHEIQMIFEKYYKVCNSSIEIDGRKIILNLSMDIPEQKIELDEN VIVGVDIGIAIPAVCGLNTNDYSRKYIGSVNDFMRIKIKIQHQKNRL QTNLKMAKGGHGRKRKLKAMDKFTDYERNWVQSYNHYVSKQII NFALKNKAKYINIEDLSGITKGKNVNKFLKGWSYYQLQSFITYKAN KYGIEVRKIDPHYTSQTCSCCGYVDEKNRSKNEKGQSYFKCLKCG HEENADFNAAKNIAKSVNFVK | 273482 |

TABLE 1-continued

Exemplary Amino Acid Sequences of Effector Proteins

| SEQ ID NO | Effector Protein Amino Acid sequence | Effector Protein Name |
|---|---|---|
| 878 | MSMLTRKIQLIPIGDKEEINRVYSYLRDGIFNQNKAMNQYISALYT AAMQDASKDDRQELNRLYSRMPSSKLGSAYTDTIEFPKGLGTPSSL TMKVKQDFSKQCKDGLLYGKVSLITYRMDNPLLVEAEYIKLRKHS KKQCGIYHNYSSHQEFLDHLYSNDLDIFIKFANKITFKMVLGNPRK SASLRSELQQIFEEYYQVCGSSIQIDGKKIILNLSMEIPKKEIKLKEDT VIGVDLGIAIPAMCALNNNEYIRKSIGSKDEFLRIRTHLQSQRRRLQ KSLASTSGGHGRKKKLKALDKLKARERNFVKTYNHYISKQVVDFA VKNEAKYINIEDLSGFNGSDFILRNWSYYELQQFITYKAAQYGIEV RKINPYYTSQVCSKCGHWEEGQRIDQAHFICKECGNEMNADLNAA RNIALSTNFAETKKTKKDKKVA | 2735110 |
| 879 | MSNTYIITRKIQVVPVGDKEEINRVYTYLREGIKAQNMAMNQYMS ALYSTMMMDISKEDRKELNKLYARVSSSKLGSAYDKSIEFAKGLP MGGSIQQKVKQDFDNAMKKGLQYGKLSLPSYREDNPLLIHVDYV RLRSTNPHIDNGLYHNYESHQDFLDHLFKSDLELFIKFANKITFKVI VGQPHKSAEIRSVFKNIFEDYYHIKGSSIEFSGTKIILNMSIEIPKQQK ELDENVVVGVDLGIAIPAVCALNTNDYVRKSIGSKDDFLRVRTQIQ NQRRRLQSNLKMSNGGHGRKKKMKPMDKFTKYEKHWVQTYNH QISKQIIDFALKNNAKYINLEDLSSFNQKRLRDNFLLANWSYYQLQ QYIKYKAEKYGIVVRFINPYHTSQNCSCCGHYEDGQRVKQSEFICK NPECKNFGIKINADFNAARNIAMSTDFIKNK | 2453838 |
| 880 | MILTRKIQLYPVGDKEEVNRVYQYIRDGIFNQNKAMNQYMTALYV STIQDISKEDRQELNRLYTRIATSKKGSAYDLDVEFAKGLPTTSSLG QKVRQDFSKACKDGLLYGKVSLPTYRKDNPLLVHVDYVRLRETN PHKDNGIYHNYESYDEFISKLYDKDLEIFIRFANGITFKMILGQPHKS TYLREEIKKIFDGEYNVCGSSIQFNDKKIILNMSMDIPKISRELDENT VVGVDLGIAVPAVCGLNNSVKKQFIGSKEDFLRIRTQLQAQRKRL QKNVKITNGGHGRNKKLKALDKLSNKERNFVKTYNHYVSKQVID FALKNNAKYINMEDLSGFNTNKFILRNWSFYELQQFITYKAQRYGI EVRKINPYHTSQICSKCGHWEEGQRDTQDHFKCKACGYEDNADFN ASKNIAKSIDFRK | 290956 |
| 881 | MNNILSRKIQLFPIGDKEEINRVYKYLRDGMKAQNLAMNQYMSAL YISMQNEATKEDRKELRNLYGRISTSKKGSAYNLSIEFAKGLPSASS VTQKVEKDFKNAMKKGLAYGKISLPTYRDTNPLIIHPDYVRLRTKS KCDNGFYHNYENHFEFLSHLYNKDLELFLKFANGITFKVILGNPHK SVEIRNVFGNIFEENYSINQSTIEIDGTKIILNLSLSMPQCEIKLDENIC VGVDVGLAIPAVCALNTDVYKKFIGSKDDFLRVRTKIQNQYKRL QKSIAQSNGGHGRKKKLQAMDRFKEYESNWTKTYNHWVSKQVV DFAVKNKAKYINIEDLSGIGNGNKNQFVLRNWSYYQLQQFITYKA NKYGIIVRNVNPYHTSQVCSCCGHWEKGQRISQSEFICKNPECDNF GKKINADFNAARNIAMSTDFVDDKKKAV | 270998 |
| 882 | MNETCVITRKVKLFPVGNKEEVNRVYKYLRDGIESQNKAMNQYM TALYVAMIQEASSEERKELKNLYQRISTSKKGSAYDKTIEFAKGLP MGGSITTKVKSDFDNAMKKGLKYGRISLPSYRDKNPLLIHRDYVR LLETNPHLNNGIYHNYKNSDEFKEHLYKDDFEMFIKFANDITFKVIF GNPHKSKELRSVFGNIVDGIYNVGGSSIGIDGNKIILNLSIEIPKKKV ELSEDIVCGVDLGIAVPAMCALNTDDYKRMSIGSANDFIRVRTKIQ AQYKRLQMSLKNTSGGHGRKKKLSPLNKFKEYEKNWVNNYNHM VSRRVVDFAIKNGAKYINIENLEGFGKSKHTYILRNWSYYQLQQDII YKANMVGIEVRKVNPYHTSQNCSCCGHWEEGQRLDQAHFVCGSC GATLNADFNAARNIAMSTDFIE | 270966 |
| 883 | MNETCVITRKVKLFPVGNKEEVNRVYKYLRDGIESQNKAMNQYM TALYVAMIQEASSEERKELKNLYQRISTSKKGSAYDKTIEFAKGLP MGGSITTKVKSDFDNAMKKGLKYGRISLPSYRDKNPLLIHRDYVR LLETNPHLNNGIYHNYKNSDEFKEHLYKDDFEMFIKFANDITFKVIF GNPHKSKELRSVFGNIVDGIYNVGGSSIGIDGNKIILNLSIEIPKKKV ELSEDIVCGVDLGIAVPAMCALNADDYKRMSIGSANDFIRVRTKIQ AQYKRLQMSLKNTSGGHGRKKKLSPLNKFKEYEKNWVNNYNHM VSRRVVDFAIKNGAKYINIENLEGFGKSKHTYILRNWSYYQLQQDII YKANMVGIEVRKVNPYHTSQNCSCCGHWEEGQRLDQAHFVCGSC GATLNADFNAARNIAMSTDFIE | 279660 |
| 884 | MNETCTIVRKIKLFPVGDNEEINRVYTYLREGIESQNRAMNQYMSA LYMAMMQDVSKEDRKELNALYQRISTSKKGSAYDDTIEFAKGLL MGGSITQKVKADFDNAMKKGLKYGRISLPTYRDKNPLLVHRDYV RLLETNPHLKNGIYHNYETMDEFKEHLYKDDFEMFIKFANDITFKII FGNPHKSRELRSVFENIVDGTYDVQGSTIGIEGKSIILNLSIKIPKKKI ELLEDVVVGVDLGVAIPAVCALNTNDYVRLSIGSADDFIRVRTKIQ AQRKRLQKDLAKSNGGHGRKKKMAAIERFEQYESNWVRSYNHM | 2728226 |

TABLE 1-continued

Exemplary Amino Acid Sequences of Effector Proteins

| SEQ ID NO | Effector Protein Amino Acid sequence | Effector Protein Name |
|---|---|---|
| | VSRRIVDFAIKNQAKYINIECLDGFAEAGHTYILRNWSYYQLQQDI VYKANMVGIEVRKVNPYHTSQICSCCGHWEEGQRKDQAHFVCGS CGAKLNADFNAARNIAMSTAFVK | |
| 885 | MILTRKIQLYPVGDKEEVNRVYQYIRDGIFNQNKAMNQYMTALYV STIQDISKEDRQELNRLYTRIATSKKGSAYDLDVEFAKGLPTASSLG QKVKQDFSKACKDGLLYGKVSLPTYRKDNPLLVHVDYVRLRETN PHKDNGIYHNYESYDEFISKLYDKDLEIFIRFANGITFKMILGQPHKS TYLREEIKKIFDGEYNVCGSSIQFNDKKIILNMSMDIPKISRELDENT VVGVDLGIAVPAVCGLNNSNVKKQFIGSKEDFLRIRTQLQAQRKRL QKNVKITNGGHGRNKKLKALDKLSNKERNFVKTYNHYVSKQVID FALKNNAKYINMEDLSGFNTNKFILRNWSFYELQQFITYKAQRYGI EVRKINPYHTSQICSKCGHWEEGQRDTQDHFKCKACGYEDNADFN ASKNIAKSIDFRK | 2453822 |
| 886 | MTETQIITRKIQLIPVGDKEEINRVYTYLQDGIKSQNMAMNQYMSA LYSSMVVEISKDDRKELNKLFGRISTSNLGSAYDKTIEFAKGLPMG GAIQQKVKRDFDNAMKKGLKYGKLSLPTYRENNPLLVHVDYVRL RTTNPHSDNGLYHNYESHEDFLNSLYSKDLELFIKFANKITFQIVLG NPHKSAEIRSVFKNIFEDYYHIKGSSIQIDGKKIILNMSIEIPKQKVEL DENVVVGVDLGLAIPAMCALNTNDYVRLRIGSRDDFLRVRTQIKS QRRRLYSNLKFAHGGHGRSKKMQATDRFTNYEKNWVQTYNHMV SKRVVDFALKHKAKYINLECLDGFSKKQLRDNYLLANWSYYQLQ QYIKYKAEKYGIVVRFVNPYHTSQNCSCCGHWEEGQRVKQAEFIC KNPECKNYGKKINADFNAARNIAMSTDFVEKEEKKKKKTKKAA | 284082 |
| 887 | MKFVNGIWFEVKFGQPHKSKELRSVFQNIFNGTYKTMGSSIEISRN NKIIMNLTLQMPKQEVELDPNVVVGVDLGVAIPAYCALNTNDYVK KACGNADDFLRVSTQIKAERRRLQKPLKYNSGGHGRKKKLAPMD RFTDYESNWAKTYNHKISNDIVDFAVKNHAKYINIENLQGFGSVES ADEVRAEREPKSKNFLLGNWRYYQLQQFITYKAEKYNIEVRKVNP YYTSRRCSCCGNEDANNRKSQAEFVCTKCGAKMNADFNVARNIA MSTDFSDGKTSKETKKRQHKEYIAKNQKAIA | 2735104 |
| 888 | MAKDTFTITRKIQLVPVGDKTEVNRVYNYIREGMKAQNLAMNQYI SALYLGMQNDVSKDDRKELNNLFSRISTSKKGSAYDESIQFAKGLP IGSMTRKVKSDFDTAMKKGLKYGKLSLPTYKDSNPLLVHVDYVRL RSTNPHQDSGLYHNYTNHTEFLEHLYKSDFELFIKFANYITFKIILG NPHKSAEIRDVFKNIFEECYAIQGSSIGIYNNKIICNLSISIPKKQLCL DENIVVGVDLGLAVPAVCALNTVPYIHKSLGNYDDFVRERTKMQS QRKRLQKSLNYANGGHGRKKKLQSLERLKKRERNWVQTYNHKIS KQIVDFAIKNKAQYINIEDLSGFDSSQFVLRNWSYFELQQFIEYKAN KYGIIVRKINPYHTSQTCSFCGHWEEGQRISQSEFICKNPECVNHNK SINADYNAARNIAMSTDFVKNN | 2734884 |
| 889 | MPTITRKYQLKVVGDKEETDRVYTYLRNGIEAQNKALNEAISALY AAKILEMSTDDNKELTKLFQRVTHGKNETGFTDDITFPVGLPTAGG VGRKAKQDLDNAFKKGLRYGRVSLPSYKADNPLMIHVDYVRLRS TNPHKDNGIYHEYETPIDLIEALEKENNPKVFLKFVNGIVFRFVFGN PWKGREQRKVFEKIFSEEYKVCGSSIEVDGKKIILNLCMDVPKAEH KLDKNVTVGVDLGLAIPAVCALNNNEYERLFIGNIDDFLRVRTQLQ SQRRRLQKNMRNGSGGHGRSKKLKAMDRLRDRERNFVQTYNHM VSRRVVDFAVKNNAAYINIEDLSGFGKDRNGDIHKDKEIVLRNWS YYELQNYITYKAQMHGIEVRKVKPEYTSQICSYCGKRGIRREQAKF VCINPECRSHKIYDKGFVNADFNAARNIAMSANFVEDTETKQTRK GA | 275447 |
| 890 | MPNLTRKYKLIPVGDKEEVNRVYTYLREGMEMQNKAMNQYMTA LYVAQMREASKEDRKELSKLFSRVSTSKKGSAYTDDIVFPKGLGTP SMIKRKVNEDFGNAMKKGLMYGRISLPTYRQDNPLLIHPDYVRLR SLSTRDNGIYHKYDSPMDLINGLEKDTNPEVYIKFANGITFKIVFGN PHKGREQRKVFENIFSETYKVCGSSIGIDKNRKIILNLCLEVPKQEH NLDGNVIVGVDVGIAINAMCALNNNYHIREAIGDESNLLRVKEQM NAERKRLQEGLKFSKGGHGRKKKLKALDRLKDRERNFTQTYNHK VSNKVVEFALRHNASQINIEDLSGFGKDRKGNVKDDKKDILRSWC YYELQNYITYKAQLHGIIVRKVNKDYTSQTCSCCGQRGIRLSQSEF MCQNPDCKCHTLYGKYINADFNAARNIAMSTDYK | 292203 |
| 891 | VDAQTITRKIQLPVGDNEEVDRVYKFIRDGMYAQYQASNLLMG QLASEYFKSNRDFKSESFKTAQKEILKAVNPLLQEISFPKGNDTISIV IQKVKQDFSTSLKNGLARGERAITNYKRTNPLLIRSRNLEFYNEYKS YNDFLDKLFTDELEVFIKWVNHIKFKVVFGNPHKSHELRCVVQNIF EEIYKVKGSSIQFDNTEKKIILNLSLSIPKKIMELDENTVVGVDLGIA VPAVCALNNDEYTREFIGSKDDFIRVRTKIQAQKRRLQKSLKYTNG | 2733240 |

TABLE 1-continued

Exemplary Amino Acid Sequences of Effector Proteins

| SEQ ID NO | Effector Protein Amino Acid sequence | Effector Protein Name |
|---|---|---|
|  | GHGRNKKLKPLNKFEEYEKNFVQTYSHMVSKNVVEFAIKNKAKYI NIEDLEGYNSNGFILRNWSYSKLEEYIIYKARLHGIEVRKVNPYHTS QVCSCCGHWEEEQRIDQSHFKCKLCGAELNADFNAARNIAKSNNF R |  |
| 892 | MPKITRKYQLKVIGDKEEIDRVYKYIREGTEAQNKALNEAMSALY AANLLDMSKDDKKELSKLFSRVTNGKNESGFTDDICFATGLGTTSS IKQKVKQDFNNACKKGLMYGRVSLPSYKTDNPLLVSKSYVQLLSE SDKNFGIYNAYETPMDLVDALEKETNPEVYLKFANNILFKFVFGNP WRGREQRKVFERIFSGEYKICGSSIGIDGKKIILNLCMDIPKQKHNL DENIIVGVDLGLAIPAMCALNNDDYKRLSIGSIDDLLRVRIQLQNER KRIQGNLKNSKGGHGRQRKLKALENLKDRERNFVQTYNHMVSKR VVDFAVKNNARYINMEDLSGFGKTRYGKSKSEDEKVLRNWSYYE LQNYITYKAQLHGITVRKVRAEYTSQTCSYCGSKGIRKEQKKFVCV NPDCKCHKIYDGYINADFNAARNIAMSNDFVE | 2340775 |
| 893 | MANKSSKKPLIITRKYALIPIESPSPIWTKSVISFLNKDYISKIEYKKQ LIEIENKKGKKKDNNKIEKWEKEIANIESKIELVDNGDFTSGIVNDY TYNLIRKCCEEQSIIKNHTMFAMGAAYKDCIIKGIDEKERTEIVTDV FNSWSRVPNSSKGSMLDKMNIDLSIGSYELAYVNALKNKFWECVK DGFAYARQTLPYYKSDCPMDIASKEMSFTHDYESFEELCEHINEKP NLYFNYGGNGKPHIFRFKINTGHGKNNDELMATLMKVYAKEYKV CGSSIQIQKSGNDKKDKIILNLSLEIPKVKRELDKNICVGVDLGIAIP AMCALNTNDYVRQSIGSKDDFLRVRTKISNQRSRLQASLKMSNGG HGRKKKMKPMDRFEDYEANWVQNYNHFVSKQVVDFAIKNKAKY INIENLEGFDANNYLLAKWSYYQLQQYISYKAKINGIEVRKINPYH TSQRCSCCGYEDKGNRPKGKKKQAYFKCLKCGKEMNADFNAAR NIAMSTEWSDGKTTKEQKKKQHEEYIKKE | 270534 |
| 894 | LILTRKIQLIPCTEGMTTDEAKVEVNRIYQLLRDGIYAQNKAYNIFIS RMYTAILLGASKEELKEIRLKGERTPKESDSDYSLYDFDKIKFIKGL PQASALGEQALKALKQQKDGLYKGKVSLACRKLDAPMWIKTKF SFFHKYNDYQEFLDHLYCDDLKIYMKFVQGIVFEVVLGNPHKSETI RTEFQQIFEGHYKLCSSSLQIKDKKIMLNLAIDIPEKGIELNDETVVG VDIGIAIPAVCALNNREYVHKSIGSAEELLRIRTQLQSQKRRLQKNL KNTTGGHGRSHKLAPLDKLAKRERNFVQTYNHMISKTVVEFAVK NKAKYINLEDLSNYKDNGSEFILRNWSYFELQSQIEYKAKMHGIIV RKINPYHTSQICSKCGHWEEGQRISQSKFKCKSCGYESNADFNAAR NIALSTDFIE | 2735249 |
| 895 | MPTLTRKVELYVVGDKEEVSRVYDYIRLAMNATYKCFNECMTAL YIAQVKEDTKEDRKELNHLYSRQTYTKKETAFTNDIVFPEGLALAA YVNRMAQQKFVTSLKNGLMYGCVSLPTFKKDCAVPLHVKFVSLA GEKGTNTGFYHEYADVNDLVNALEYDNSPKVFLRFPNNITFGVVF GNPYRGREQRSVFSKIFLGEYKIQGSSIQINSRGKIILNLSMEVPKKK MEHIEGRVVGVDVGLAIPAMCAINDDDYTRSAIGNIDDFLKVRTQI QSQRRRLQKSLKNTSSGHGRTKKLKPLERIAEKERNFANTYNHMV SKRVVDFAVKNGASQINIEDLSGFAKDKNGKSVEDDNMKRVLSN WSYFELQQQIRYKAEQYDIKVRTVNPAYTSQTCSYCGQIGKRETQS KFVCTNPDCKCHKMYKKDWFNADFNAARNIALSTDYTDDEDGKK TKKKKSAKKKPEKKTEEA | 286672 |
| 896 | MPKLTRKYRLQVVGDDQERSRVYKYIRNAMDATYKCYNEYMSA RYIAELKSETGEEKKELTKLVNKLYSRQTGTKLESAFTSNIEFPKGL ALAATIENSASKKFEDIKYDVINGRVSLPTYKKDGAVPLHVRYVSL KGEKGSGHGFHHGYDTLEQLYYGLEKDLEPKVFLRFPDKIEFRVCF GNPYKSSEQRKVFMRIFSGEYKSQGSSIQINSKGKIILNLVMEVPKK EMKHIDGVVVGVDLGMAIPAMCALNNDLYDKCDIGNINDFLRVR TAIAARRRLQKSLTTTNGGHGRTKKLQALDRFAETERNFVQTYN HMVSRNVVDYAVKHGAVQINVEDLSGFGRDKNGKSLDDERKKK VLRNWSYFELQQQITYKAAQYGIEVRKVNPAYTSQTCSYCGTMGE RPKQAVFICSNPDCKCHEIYQKNKDHCFNADFNAARNIAMSTDYT DVNSDGEKKKTVKKKKKADKKED | 283594 |
| 897 | MSKDYNVTTRKFNLKVVGDQKEKDRVNKYLSDGMYAQNAAYNI LISKVYSKLHEKGSTFADVDEILKKGSRKPKENDPDHSLSEYEGLH FPTGLSVPGCLGREVNADIKKNGLMKMDSSLPTRKIGCPLYVTYQ NGKIFSFYHNYDSYDDLVDNLYNNKNVKIFMKFANNITFEVVFGNI NKSRELRSVFEHIFDGTYGIGDSKIAIENPKSIYAENINNETNDTKKP KRQAKDKEITFYLSVKMPKKYIDLDENVVAGVDLGIKVPAMCALN TNSYIKESIGDIEDFLRVRTKINAERSRLQHSLKYSNGGHGRYKKM KAMDAFKNYEKNFATTYNHKVSKDVVDFAIKNKAKYINIENLEGF | 2735101 |

TABLE 1-continued

Exemplary Amino Acid Sequences of Effector Proteins

| SEQ ID NO | Effector Protein Amino Acid sequence | Effector Protein Name |
|---|---|---|
| | GNSDSGVEEKEYRKKSFFLRYWSYYQLQQFITYKAEQNGIIVRKVN PYYTSRRCSCCGNEDKNNRKSQENFVCTKCGKKMNADFNAARNI AMSTDFSDGKKTKKENKKTA | |
| 898 | MTICRKIKLFPVGDKDEINRVYDFIRNGQYAQYQACNLLMGQLMS EYYKYNRDIKNEEFKARQKEIMTNSNIILKDIDFATGVDTPSAVTQ KVKQDFSTALKNGLAKGERTVTNYKRTNPLITRGRNLTFYHEYET YHDFLDKINDFDLAVYVKWVNKIVFKVVFGNPHRSLELRSVVQNI LEENYKVQGSSIEIDGKSIILNLSISIPKQLRELDENTVVGVDLGIAVP AMCALNNNLYERLAIGNADDFLRIRTKMQAQRRRLQKSLRNTSGG HGRAKKLKALERLQKTEAHFVETYCHMISKRVVDFALKHNAKYIN IENLTGYDTSDFILRNWNYYKLQDYITYKAAKYGIEVRKINPCYTS QVCSVCGNWEFGQRKSQSVFECANENCDSHKKYEKTGFNADFNA ARNIAMSTLWMEGGQVTEKSKQEAREYYDISEKYEQNKNDSENN KVA | 2734535 |
| 899 | VNTFISTKKIIISPIEEDKYKKNDIYSYLRKAITAQNRAFNLLLTKTAS AILDNKSSKTIEDIYYSYSHQKPDVSLETEKLLYEVLALAPITEEVIE SKIAELKEFLKSKGKSEKSIKTSCDKKEKSYRKFLGKSKEDIQRDIV RLQNYCAYPEDIYNDFANGLSTPSYVMQQVKKYWKTNKNNVIKG EGVRTMSLTNPLILPPNIFYNNNGNLQGITHGYSSDEEFYNNLYGD KKLKVYFSMPYRKGEDKILFQLILGNPYKSHELRYVLENIFIGTYKI RGSSIGFIKNRETGKMTDLCLYLVVEHQQKEHVLDENVTCGVDLG QAVPAVCAVSNNKYDRLYIGSAADFLRQRTKIQDQYKRLKKSLKN TSGGHGRKKKLKALDRFEDYEKNFVSSYNHMVSKRVVDFALKHN AKYINLEYLKGYDTSKFILRNWSYYQLQTYIEQKAAKYGIVVRYIN PCYTSQVCSECGHWEENQRKSQADFVCGDGCFSNDKYKKINADV NAARNISNSTLFLDRTEDYEKEDLIKQARAYYGIE | 291805 |
| 900 | MPILTRTIELIPIGDKEERDRCYKWIRDFMEEQSKMMNQYMSALYI AAVEEVSKDDRKELNNLYNRIATSKKGSAFSKEECNLPKGLGANY GQRVRSDFDTACENGLLHGRVSLPTYKKNFPIILAPIYVNLQKNNIE EKGKSAGFYHNYASYNELYDALKEENKPEIIWNFVQKMQYQIKFG NPYKSAFLRDEILHFLEGEYKAVGSQLSINSRGKIILNLSLDVPQKK VKLDENIVVGIDIGLAVPVMCAINNDYYKRLAVGDFEAFTRMREK LYSQKCKLQRQLKYTSGGHGRKKKLASLNAIRDREHRFVHTMNH KYSSEVINFALKNNAKYINMEDLTGFGKDNKGNAIDDYQFVLRNW SYFELQKMIQDKAQKYGIVVRKVESAYTSQLCSCCGEMGERVSQS VFRCLNPNCISHNKYEKQRKSGVGNYHFNADFNAARNISMSTNYT KKKRKTKAEKVEERKKNAIEKTAG | 275549 |
| 901 | MNNDRITICRKIKLTPLGDKEERNRVFQYIRNGQYAQYQACNLLM GQLISEYYKYDRDIKNEDFKARQKEIMKNSNPLFHEIEFAIGNDTPS AVTQKVKADFNTALKNGLAKGERSVTNYKRTNPLITRGRSIQFYH NYGTYQEFLDNINSTDLEIYLKWVNKIKFKVILGNPYRSAELRSVIK NIIEENYGIQGSSIYIDEKDIILNLSLSIPKKIQKLDENTVVGVNLGLIV PAMCALNNNEYKRLAIGNTDDFVRMRIKLQEQRKRIQKGLRSAAG GHGRSKKLKGLSKLKKREQKFVETYCHMISRRIVDFALINNAKYIN LEYLQGYDTNEFVLRNWSYYKIQQYCKYKASIYGIEVRFVNPCYN AQVCSFCGHWSETQRISREVFKCENPNCISHKLYKDGYLNADFNN ARNVALSSLFVNDGNITDDKFKEAREYYDIDISR | 19874 |
| 902 | MDTMMITRKFVLLPVASCKKEWVKKITTYIISDTDKKLDYFNEKL KKTEKEMKKANGSEQLSKEYNKLKSKKAEYESLLKDAKEGIFSPK AINNYTYHLVREAMESEARRKNYILSWAFSEMIANGVPYMETYKE KCKFINEMIKPAYRTKGSKKGSLFDESEIQNILGGYGISFSQELTQKL KDCVKDGLLEGKVVLPNYKLNSPFTVAKTHISLSHDFETYEELCEH IGKKDGKIYLNYGGYGEPTIARFAIDTGSNKNKEELNTTLLRLISGE YEVCASSIGLCKDEKKIVLNLSMKIPKKELELDENTVVGVDLGLVV PACCALNNNMYVKKAIGSVAEFLRVRTQLQSQYRRMQKQVATNN GGHGRKKKMQPLDKFREKERNFVKTYNHYVSKEVVDFAVKNNA KYINMEDLSGFGKDNRILRNWSYYELQQFIEYKAAKYGIVVRYINP YHTSQVCSCCGHWEEGQRMDQAHFVCKKCGTELNADYNAARNIS MSTEFKKQKLSV | 2735207 |
| 903 | MDNTITITRKYTLIPTFSDTKEWTKKVMEYTKTSYIEKIKYYEEKIK KTKKKDKEEREKYENRLSQLKEQQLDFEENGTLLQTNVNDYTYDL VREAMASESDRKNMIISYVCGELINRDAKDMDFKERNKLISELCNY GYRVKGSKKGSLFDHLDINNPLGGYGVSFCQDLTKKIKELINNKR WLDGKASTLHYKDDSPFSIAKATMGFAYDCDTFEELCEHIREKNC NLYFNGNNGKATIARFKINLGANRKNKDELISTILRVYSGEYQYC GSSIGIEGTKIILNLSMKIPKQEKELDENTVVGVDLGIAVPAVCALN NNVYARKFVGNKDDFFKARKQLNAQYKRVQSALKRASGGHGRK KKLKALERLRKKEAHFVETYCHMVSKAVVDFALKYNAKYINLEN | 2733195 |

TABLE 1-continued

Exemplary Amino Acid Sequences of Effector Proteins

| SEQ ID NO | Effector Protein Amino Acid sequence | Effector Protein Name |
|---|---|---|
| | LTGYDTDDIVLRNWSYYKLQQYITYKASKYGIEVRKINPCYTSQIC SECGNYHPENRPKGDKGQAYFNCHNEECITHGKKSPYQYGINADF NAARNIAKSTLWMEKGKITEESKKKAREYYGIEEEYEELNKEVA | |
| 904 | MINKDKNENTVTITRKYALIPVSSDKTQWYKKVYDFTIEDLTRKIE YYKEKLKKEKDKEKKEQIKTKIKNFEEGLESIYNGGDFTQKMINDY TYNLVRTAMEEEARRKNYILSWIFSEMRLNRVDQMESLKDKFKFIS DTLNYAYRKKGSNKGSLFDDTEINSILNAYGIAWNQELTKEIKDLV KNGALEGKVSLTNYKLDSPFTIAKAHFSFDHDYDSFEELCEHIDDS DCKMYMNYGGDNKKDGTNPASLARFRINLGQGKNRNELKSTLLK VYSGEYQYCGSSIQISKNKIILNLSMKIPKIETELDENTVCGVDLGIA VPAMCALNNDMYKRLAIGSADDFLRVRTKHQEQRRRLQKSLKNS NGGHGRKKKLKPLERMNKAEAHFVETYCHMVSKRVVEFAVKNR AKYINIENLNGYDSSEFILRNWSFYKLQQYITYKAARYGIVVRRINP CYTSQICSVCGNWEPDQRKTQAKFECANEECASYDKYKYGFNADF NAARNIAMSTLFMETGEVTEKKKEEARKYYGIEEKYQASLKEKDD KVA | 2733157 |
| 905 | MATEYTCITRKIEVHLHRHGEDEDAVQRYKNEFQIWNEINNNLYK VANFISSHLFFNDAFVDRLRVQSNEYRDLLDLISKTTDAKEIKALEN RKKALDAEFKRQQKIFLKGGSEDEKGSEKTAIRRIAVETFPNIPYSII NSLNDQISKTYNSSRFDVSIGKRTVPNYKKGIPVPFLMANGSGKIAL REREDGSPYVLFPRGLEWDLHFGKDSSNNREIVKRVFNGEYKACD SSLQQAKNKKIFLSLVVKIPKKNHNLNPDRIVGVDLGINIPLYAALN DNDYGGMGIGSREQFLKVRMRMSAQKRELQRNLRQSTNGGHGRA QKLQALERLEGKERNWVHLQNHIFSKSIIEYALKNNAGAIQMERLT GFGRDKNDEVDSNFKFILRYWSFYELQTMIEYKANAAGIEVRYVD PYHTSQTCSFCGHYEKGQRLNQSTFVCKNPDCEKGKGKKLSDGTY QGINADWNAARNIALSDKIVDRKKK | 2390798 |
| 906 | MANEFTCITRKIEVHLHKHGDSDEAIQRYKEEYRMWDDINNNLYK AANRIVSHCFFNDTYEYRLKLHSPRFQEIEKLLSNPKRNKLSDDDIK ELKAERKLLFSDFKSQRQTFLRGGIETGTNPEQNSTYKVISNEFIDCI PSEVLTNLNQNISSTYREYTLDVERGIRTIPNFKKGIPVPFSIKQHGEI ALKKRDDGTIYVRFPKGLEWDLNFGRDRSNNREIVERVLSGQYGV GNSSIQESKNKKQFLLLVVKIPKENRVLDKERIVGVDLGVNTPLYA ALNDNEYGGMGIGSREQFLKVRERMNAQKRELQRNLRHSTNGGH GRSQKLQALDRLEGKERNWVHLQNHIFSKSIIEYALKNDAGVIQM ERLTGFGRDNNEEVQNEYKYILRYWSFYELQTMIEYKAKAAGIEV RYINPYHTSQTCSFCGHYEKGQRINQPTFICKNPDCTKGKGKQKSN GAYEGINADWNAARNIARSNEFVEKKKK | 2391641 |
| 907 | MGENITEVVTKKTKKDVKKIMSNRKITIFIDEEDKELKKEYYKKLN DWFYHARHYANDVVNILQCVVVMENINKSIEGDLHLKLTDYLDC KSQSINYKLLTQKYKELLPSYVRGAVGNNVYKNYCENIKSILKGEK TVSTYNVGFPLYFMSIGFKFDKSDKNNFTFKLFGIPFKTKLGRDRSN NEEIIYRIISGEYTISDSSLKKDGSDLYLLLSFRLPKKENKLDKDKVV GVDLGITTPAYVSVCGKSNVRKSIGDREGFLKQRLSIQVQRRSLQG SLKYTTGGRGRNNKLSKLESIKDRERNFVKNMNHKYSKEIIDFALV NGCGSINIEDLSGIGSMERNEFILRNWSYFELQSMIKYKAEREGIIVN VINPRYSSQRCSVCGHIHTDNRITQSKFECLSCGNKDNADYNASKN ISIAHTESYIEEITQHKKRMDKEKNKNI | 2390229 |
| 908 | MENINIKDDNNNRMTITRKYAIIPTSSPYKEWKKKVYNFTVEDLEF RIKYNEEKLKSIKNKEEKQKIGLYIDELKKSLQNVKDGNDFTQKMI NDYTYHLVRESMESESARKNYILSWMRDQLRLNHVAQFPSLAEKK KFVSDTINCAYRVKGSKKGSLFDDTDIKNALGSYGIAFCQNLTEIIK GQIEDGLLEGKCNPVEFKCDSPFTVAKTAMGFSHNYKDICDLQAHI DDKDCKLYFDFGGNGNPTIARFRINLGSWKNRDELKATLLKVYTG EYQYCGSSIQISKNKIILNLSLSIPKKEMELDENTVVGVDLGIKIPAV CALNNNPYARSYIGSVDDFIRVKTQLQAKRRLSIALKNTSGGHGR KKKLKPLDRFNKRELHFTESYCHKVSREVVDFAVKHRAKYINVEN LTGYDTSDFVLRNWNYYRLQNYITYKAAKYGIIVRKINPCYTSQVC SVCGNWHEENRPKGDKGQAYFNCHNEDCLTHDKKKF | 2733161 |
| 909 | MPTITRKIELTLCTDGLSDEERKAQWGLLYHINDNLYKAANNISSK LYLDEHVSSMVRLKHAEYLSLQKELAKAERQKMPDVDVIEELRER LSAAEQEMSDQELAICKYATEMSTNTLAYRFATEIETNIFGQILARL ENNAQAVFLTDAPDVKRGERAIRNYKKGMPIPFPWNNSIKIECEGG EFYLRWYSGLRFHFNFGKDRSGNRLIVQRCLKLDKEYDGEYKLCN SSIQMVKRDGSTKFFLLMVVNIPQEYVELNKHIVVGVDLGINVPAY VATNITPERKAIGDREHFLNTRMAFQRRYKSLQRLKTTAGGKGRT KKLEPLERLRQAEHNWVHTQNHLFSREVVNFALQTHAATIHLEDL | 2390405 |

TABLE 1-continued

Exemplary Amino Acid Sequences of Effector Proteins

| SEQ ID NO | Effector Protein Amino Acid sequence | Effector Protein Name |
|---|---|---|
| | SGFGKDSDGNADERKEFVLRNWSYYELQNMITYKAAKYGIRVEKI<br>RPAFTSRTCSCCGHEGFREGVTFICENPECQQFGEKVHADYNAARN<br>IANSKDIIKKNE | |
| 910 | MATEFTCITRKIEVHLHRHGDSEEAKQRFNEEYRIWNEINDNLYKA<br>ANRIVSHCFFNDAYEYRLKIQSPRYNEIQKLLRYSKRNKLTDDDIKS<br>LKAERKNLFDEFKKQRMTFLRGGESEGANPEQNSTYKVVSNEFLDI<br>IPSTILTCLNQNVSSTYKCYSKEVEFGNRTIPNFKKGMPVPFSIKTHK<br>TLMLKRREDGSIFVYFPKGLEWDLSFGRDRSNNREIVERILSGQYD<br>VGNSSLQESKNGKIFLLLVVKIPKRSTALDPNRVVGIDLGINIPLYA<br>ALNDNEYGGMSIGSREQFLKMRMRMTAQKRELQSNLRYSTNGGH<br>GRSHKLQALERLEGKERNWVHLQNHIFSKSIIEFAVKNNAGVIQME<br>RLTGFGHDKNDEVDEGFKFILRYWSFFELQQLIEYKAEAAGIEVRY<br>IDPYHTSQTCSFCGHYEKGQRINQSTFVCKNPECEKGKGKKHADG<br>TYAGINADWNAARNIALSDKFVDKKKSDLKY | 2390160 |
| 911 | MDNTITITRKYALIPEFSDRKEWKKRVYDFTINDLEQKIDYRNKKK<br>QDASELESQLEYIKNGGDFTRNMVNNYTYSLVRTAMEEEARRKN<br>YILSWIFSEMRANRVDQMESLKDKFKFVSDTINYAYRKAGSNKGS<br>LFDETEIHCILKSYGIAFSQELTKEIKELVKNGVLEGKVVIPTYKLDS<br>PFTIAKSHFSFEHDYDSFEELCEHISDSDCKMYMNYGGDNRKDGIN<br>PASIAKFKISIGHGKNKDELKSTLLKVYSGEYQYCGSSIQIAKNKIIL<br>NLTMKIPKIETKLDENTVVGVDLGIAIPAMCALNNNMYERLAIGSA<br>DDFLRTRTKLQSQRRRLQKSLKNSNGGHGRNKKLKVLERLGKSET<br>HFVETYCHMVSKRVVEFAVKNRAKYININENLNGYDTSQFILRNWS<br>YYKLQQYITYKAERYGILVRKINPCYTSQVCSVCGNWEEGQRKTQ<br>SSFECANPECKSHEKYKYGFNADFNAARNIAMSTLFMETGNVTEK<br>SKEEARKYYGIEKD | 2733944 |
| 912 | MKTTIVTRKIEFYVNESDKDLKKQFYQTLRDFSYYTFKHANELVDT<br>NRMVDVIKRGFGNSKNEITSEEMTEQLSGMFGCKPVSVPYKFSNQ<br>EFRDKLPSNIRVALSATINALYAKDRSDVARGNRTIRSYKNGMPVP<br>FTKTSIRQFKFDVERKNFTFIFNGIPLITRLGRDRSNNKSILESIIEGKY<br>QLCDSSFQIKDGKFFLLLVHKVPVEKYKLNEKRVLGIDLGINVPLY<br>GAINDKKDRIALGDRDSFLNQRLKFQKRKRQLQRDLKLTKGGKGR<br>GKKLKALESLSTKERNFAKNYNHNLSREVINFALKHKCGIINLEDL<br>SGFKKNTNDFILRNWSFYELQTMIEQKAKKVGITVNKVKAKYTSQ<br>RCNNCGYIDKESRKSQSEFECTSCGHEESADYNAAKNISMAHTKEF<br>QKEIEKHASSLKLCEA | 2391055 |
| 913 | MATEYTCITRKIEVHLHKHGDSEEALQRLNEECRIWDEINNNLYKA<br>ANRIISHCFFNDTYEYRLKLQSPRLQEIEKLLSNPKRNKLSDEDIKQL<br>KAERKQLFANFKKQRQVFLRGGVEEGANPEQNSTYRVVSNEFIDVI<br>PSEVLTNLNQNISSTYREYSLDVERGSRTIPNYKKGIPVPFSIKRSGE<br>LMLKKREDGSIYVRFPKCLEWDLFFGRDRSNNREIVERVLNGQYD<br>VGISTIQEKTKNKKRFLLLVVKIPKESKKLNPNRVVGVDLGINIPLYA<br>ALNDNEYGGLGIGSREQFLKVRMRMVAQKRALQRNLRHTTNGGH<br>GRAQKLQALDQLEGKERNWVHLQNHIFSKSIIEYALKNGAGVIQM<br>ERLAGFGRDKNEEVENEFKFILRYWSFFELQTMIEYKANVAGIEVR<br>YIDPYHTSQTCSFCGHYEKGQRINQSTFVCKNPDCVKGKGKQHAD<br>GSYDGINADWNAARNIALSTTVVDKKKK | 2391980 |
| 914 | MYITRKIELWVKEDDKNLRNEIWRTIRDYEHMVFKSANLIVTNQLF<br>NQTFTDRIVLTDEELSVKREKIERDIDKLNEKLKDEKDDTKKDKLK<br>ENRNKLYRQINQLTIEARKMAEEFYTTSEKNTTYQLIRKEFPTLPSH<br>ISASLNDMVTKNYSNEIFDVRLGKRSLRTYRKGMPIPFMKLSLKLK<br>KVDDEICLKWVNNIEFTLHFGRDKSNNQIIVERILKGDYKVGDSSIQ<br>LKKGKIFLLLVVDVPEEENKLNDDVYVGVDLGLSIPAVCSLNVGD<br>ERLFIGSYNDFIRVRTQLQSRKRRLQRSLTLTKGGKGRGKKLKAFD<br>RLKTKERNFVKTYNHTLTNRIVKFAKDNLASTIKLEFLEGYGEDET<br>NSFVLRNWSYYELQTQLQYKAEREGMEVVFIDPYHTSQMCSFCNH<br>YEEGQRLKQSEFLCKNVDCSNKDKKGENKIINADWNASRNIAKSE<br>KFVTKKSDCEYFKRKKDEKN | 2390134 |
| 915 | MYITRKIELWVKEDDKNLRNEIWRTIRDYEHMVFKSANLIVTNQLF<br>NQTFTDRIVLTDEELSVKREKIERDIDKLNEKLKDEKDDTKKDKLK<br>ENRNKLYRQINQLSTEARKMAEEFYTTSEKNTTYQLIRKEFPTLPSH<br>ISASLNDMVTKNYSNEIFDVRLGKRSLRTYRKGMPIPFMKLSLKLK<br>KVDDEICLKWVNNIEFTLHFGRDKSNNQIIVERILKGDYKVGDSSIQ<br>LKKGKIFLLLVVDIPKEENQLNDEVSVGVDLGLSIPAVCSLNVGDE<br>RLFIGSYNDFIRVRTQLQSRKRRLQRSLTLTKGGKGRGKKLKAFDR | 2390183 |

TABLE 1-continued

Exemplary Amino Acid Sequences of Effector Proteins

| SEQ ID NO | Effector Protein Amino Acid sequence | Effector Protein Name |
|---|---|---|
| | LKTKERNFVKTYNHTLTNRIVKFAKDNLASTIKLEFLEGYGEDETN SFVLRNWSYYELQTQLQYKAEREGMEVVFIDPYHTSQMCSFCNHY EEGQRLKQSEFLCKNVDCSNKDKKGENKIINADWNASMNIAKSEK FVTKKSDCEYFKRKKDEKN | |
| 916 | MITVRKLKIVCKDKEFYDFFKWEQREQNKALNIAIGLIHSSTVLRSI DSGAEVQLKKSIEKLTQNNEKLEKELEKEKITDKKKEKLLKAIKTN KELIASKEKELKAGQKFRCGIDKKFDELYMNKTTLYHVLDSICDFK YKRTIELVRQKVKQDYSNSFIDIVTGKVSIQNYKSTFPLMIDGSCISI LKEVDEVGIVNGYKIKIMLGYELNIVLGKRKNENTMELQKTLEKCI SGEYKICASSIQRDKNNNIIFNLTLDIPIDKGYKPVKGRVCGVDLGIK YPAYMCLSDDTYKKEAVGSINNFLRIRKQMQERRKKLQKELLLTN GGKGRTKKIQALEKLRENEKNFVKTYNHAISKRIVGFAKKNKCEYI NLEKLTKEGFGDSILRNWSYFELQKMIEYKAKRESIEVRYIDPHFTS QKCSKCGYIDKENRDIQNTNEDIIAFESQSNKNDEKIFGTFDFDIKAI KNIGSKNFFPKE | 295007 |
| 917 | NYTYGLVRISMQEEAERKNYIVEYVRMILTAEHAYTLSPVERNKRI KEILKYAYRKKGSKSGSLFDEVEIGNILGSYGLAFNQMLTKKIQDC CNKGALVGRAGYPFFKMDSPFTIAKADMGFTHEYDTFEELCEHVN DCKLYFSYGGNGNPHIARFRIDLGHGKNRRELMSTILKVYSGEYPY CGSSIQLEKNKIVLNLTMQVPKQTKELDENTVVGVNLGMVVPAM CALNNDKYKRLAIGDENDFIRMRTKLQQQRSRLQAGLRNTAGGH GREKKLKALERLKKQEAHYNETYSHMVSRRIVEFALNNNAKYINL ENFTGMDKDNVVLKNFIYYKIEQYTTYKAEHYGIIVRKINPCYNGQ VCSIDGNWAPGQRISRNVFKCANPDCESHIIYKKSGFDADFNNARN NAMSTLFMTKGQVSGKSMEEAREYYGFEEEYKKFL | 2735273 |
| 918 | MSVITRKIEVFVSESNTELKKEFYKTLRDWSNTSRNYANDIMNLLQ STYFLDSINKDIDPSNKKSLNEYLETSKRNLGYKVFAQKYRETLPSS YRSCINSYVFSNFGNSIKDVLKGESSIISYKKDFPLLFMSKSIRGLQM DDSGASFEFFSIPFRMKFGRDRSNNREIVDKVISGQYKMCDSSFKFY DNKLFMLMVVDIPQTKVNLIEDNVLGVDLGITHPAYVSVNTNKKF RQAIGCSESFLQVRLAIQKQRKNISKNLKYTNGGKGRTKKMQKLD SLGIKERNFAKTMNHTISKEIINAAIKNNCAIINIENLKGIGKDEKNS FILRNWSYHELQTMIKYKAKKYGITVNLINPRYSSQRCSNCGHIHE DNRISQSKFKCQNCDFEDNADFNASKNISIAHTKDYIKQIEKYSKNK EKKETELLKV | 2391272 |
| 919 | MYITRKIELHISEPDLEKRKEHWKFLRMIDAELYRAANLIVTNQLF NDYYENRVINKDGTLTHIDSKIRSLYRNKEKNAEEINLLKEKKKEL WEQAKKFYDTSKQNVTYQITSRDFPAIPSSIVTALNATIIKTLKQEW NEVKRGSRSLRTYKKGMPIPFNFGTSKQWFEKSGEEIYLNWFGNIQ FHLFFGRDKSNNRIIVNRCLTGEYKYADSSIQLKDRKIFLLLLVLDIPV SDNTVDENISVGVDLGVTVPAYCALSDGLKRLSIGSKDDLLRVRLQ FQNRKRSLQKRLKMVSGGKGREKKLKTFNDLTDKEKRYVTTYNH MISHSVVKFAKDNKAATIKMEMLEGFGEDEKNKFILRNWSYYQLQ TMTEYKAKKENIKVVFVDPYHTSQTCSLCGNYEEGQREKQDEFIC KNKECKNFNEKVNADYNAAVNIAKSDKIVTSKEECEYFKKEEI | 2390217 |
| 920 | MILTRKIELLIAEDDQDKRLDIWKYLRSVEMDTFKAANLIISHQYFN DTFKERILLTKNELKERHQKIENKIEKLTEKLKAEKDKEKKKKLTA DRKGLYTQRDKLKPEAREEMVSVYTTSEKNSTYQLISKHFPHMSS YISASLNDMVTKNFSNELFDVKRGDRSLRSYRKGMPIPFMKSGMSF ESTDEGIHMNWVNNIKFYLRFGRDASNNRAVMERVLAGEYKMSD SQIQIKKNKIFLLLVVDIPNKTVKLDKKLSVGVDLGINNPAYCALSK GPARFAIGSREDFFRVRVQMQSRRRRLQKNLKLTKGGKGRQKKLK ALERLRDKERNFVRTYNHTVTHQIVKFARDNHAGVINMELLEGFM EEEKSNFILRNWSYYELQQMLSYKSKREGMEVRFVDPYHTSQDCG ECGHYEEGQRLDQAKFLCGNPDCTRKDKKGNNEEVNADYNAALN IAKSKKFVTRKEECEYFKKSQSESG | 2391607 |
| 921 | MSVVTRKIEIFVFETDTDKRKEYYKQLRDWSYISRNYANDVMNVL QSARVLDNLMKDTAEENAKGLSDYIETSKRNLGYKMLANKYKET LPSTYRTCINSYVFSNFNNTIKEVLRGDRAINSYKKDFPLLFMSKSIR NLSLDDLGGSFEFYSIPFRINFGRDKSNNRSIVEKVLTGQYKMCDSS IKFDGTKLFLFLVVNIPDKKMELDENKVMGVDLGIQYPAYVSINSD KNFRQSIGNAETFLNVRLSLQKQRRSLQANLKYAKGGRGRNNKLA KLNDIRDKERNFAKTMNHTFSKEIIDLAIKNNCGTINIEDLKGFGKN DKNGFVLRNWSFFELQSFIQYKADKFGIKLNVVNPKYSSQRCSKCG HIHEDNRQTQSKFECTSCGFTENADYNASKNISVAHTKEYKKEIET HIKNKEKK | 2390639 |

TABLE 1-continued

Exemplary Amino Acid Sequences of Effector Proteins

| SEQ ID NO | Effector Protein Amino Acid sequence | Effector Protein Name |
|---|---|---|
| 922 | MNIATRKIQIVVNESDPVKRKEYYEQLREISYNSYRYANEIVNINYF NHVLKKGMGNAKNTLTPKEISEKVSDMYGCSELNSTYKFASEEFK AKLPSYVTATLSNTVSKNFKSDLKDVMRGDKTVRNYRRNMPVPF HNKALRKLSKDGVDFTFNLFSIPLKTHLGRDRSNNRHILDSIISGEY GLSDSSFKFVKNKLFVYLVFKSPDKKVNLSKENVIGVDLGINIPLYA SINNQKSVVLRMGDRESFLNARLSLQKRKRNLQSALKFTKGGRGR TKKLKALDSLRTKERNFVKNYNHKLSKGLIDFALKNDCGVINIENL SKINKDGYDFILRNWSYFELQNFIKTKAEKYGIVVNVIDATYSSQR CSSCGHISKENRLDQQKFKCVSCGEEMNADKNASKNISIANTKEYI KQIEEHKKAKNDQVLQEEVL | 2390685 |
| 923 | MRILRLSLSVDSSNLYDDKQKIWDRLYQIINDSWKSANHIATGQY MNDNFIRHVYARKQIDPKNIEQVTEIENLIFSKDGFFETKRQATTER DIKEVFPNIPPSVTNPLNQIVYASYIKEKKDMLGNRSLRSYKQNM PIPIRLNSMNFNKNFQFIWNLQRNETITFNIYFGKDRANYKSTIAKIL NNEISTTASSIQLKDKKLYLLLGVKDPINKIKLDPNKAIGVDCGITIP AFCATNFNDDKLPIGNIESFANVRVQMQCRYKRIQKSVIMAKSQH GRKRKTKALETLREKERNFAQSYNHMISKKVVDFAIKNSASKIIME KLSFDKNFASTLRNWSYFELQSMIKYKAKKFGIEFQQIPSAYTSTTC SKCGHNDKNNRIEQSMFQCVKCGYKENADYNAAKNIACFAK | 284084 |
| 924 | MSQNTLTTRKIEIYVSESDKDLRKEYYKTLRNWSYISRNYANDTIN ALQSSFFLDNITKDSNEENKKALTEYLGIKKMGMGYKILANKYE HLPSYFRSAINSFVYKNFSESIRDVLRGDSSVTSFKKDFPLLFDSRSI RNLSIDDKGGSFEFSAIPFRFVFGRDKSNNKSIVEKITTGEYKMSNSS FKFIDNKLFFFLTVSIPKEKFELDENKTLGVDLGIANPAYVSINNDK HFKQAIGSTDAFLHTRLAIQKSRKLSLQKNLTHTKGGRGRNHKLDK LNDIGSKERNFAKTMNHSWSKQIIEAAVKNKCGTINIEDLKGIGRD EKNSFVLRNWSYFELQTMIQYKADRAGIKVNMVNPKYSSQRCSSC GFIHEDNRISQSKFICLECKTEMNADYNASKNISIAHTKEYVKEIEN HSKAIEKLKKLNKEEKNVEEML | 2391169 |
| 925 | MLITRKIEIYFNPETTKEEYDEYWIKLRDLERDTFKAANFIVNNQFF NEIIDERLLFMDDKTSQKKLDIGEKISDIFKKKSLSEEESKKQRDKL YKELNELTKESRIFAKDFYLKSKQNSTYELITKEFPNLGSYVASSLN QSIVSVFNNDMKEIRTGKRTVRNYKKGMPIPFMKTGIIFQKIEDKY HIKWIGKFNPIIKFGRDRSNNKAIIDKVLSAEYSFSDSSVQIKDNKIF LLLIVNIPDSVVVLDKNICVGVDLGLNIPVYLALNNGFERQALGDR ESFLKFRVRMQQVRRRLQQSLKLAAGGKGRDKKMKALDNSKANE KKFATTYNHQITAEIIKFALKHNAGIIKMENLKGIAQDEKNSFILRN WSYFQLQQFVEYKAKRNNIEIKYINPKYTSQMCSYCENREDGQRL SQSEFLCKNPDCTNKDDKNENLKINADFNAARNIAKSEKYS | 2391563 |
| 926 | MAKKTKSETISLTRTLRAEIVCSPDMAWAELGPRLRAWRSLVSHM VNEAVFRCREAERDQVAARAADVDKDDMPPGPATAAYQACADA QADFQAWARRAKGLSDAERGRLSTVAFGGASQSCIGQEAFGYFKK WKKERNSIPSAGRGQPIPCRAAETKFYEDDSGKLILDARIGPNEVPR SRFVLAVSRGWHWEQLRKIVSGECRHGQVDIVLDERAVRKNGGK GKWYALISYSFAKPERPEKCDPDGMLVMHRGMHNALQFLGSDGE GSGKTTIRGNKLQAYKRRCKAIRRSMGSVSAPERGDGAKGRGIAR RYEHAQKLLDAEARHVRTFCQQSAARAIELAIQWRKGVIVIEDYG GIEPSDDRGERRFFDRFPYYQLKQAIVCAAEGAGLEVREVPAAYIS QTCPRCGNQDASQRLHRTGMFHCAVCEFDRTADMVAAIHMLRLA GPKNNGWDGKLRKEHEAAKRLRKPDAGQSEEETEKVRELPKAKK RKPPEDAE | 278419 |
| 927 | MKKEKESKEAARVTITRKIELVLHCEDEQLRKDQFKQLLEWKYQV FRAANMVINHQHFTYLLRRKIKDTVSENEKQGWKEAKQMVETLY DTSLLNDTYRMVSEEFPDLPSSIRTCINMQVAQKYNNDLKEVLRGE RTIANYKYGMPIPFAISAKDNLERIPTEHGEDIILKFFKGIKFRLNFG RDKSNNQVMIDRAIAGEYKLCNSSIILEKKQNKYSIYLLAVIQHDRL KTSLDYDKVAATNLGMNCPIFLTTSEGHEMPIGSKDEFLRVRLQFQ ARRRKLQKDLDMAKAGHGRERKLKALEHLKKVEANYANTYNHK LSKKIVMFCYNNGIGTIKTENLLGGAETLEKTFVLRNWSYFQLQAD LEYKAAMYNIKVIKVAPQYITRKCNCCGNIAEEAVNLQDRTYICVN DACKLFGVKVDIDKNASLNVLDTEESKVEKTELIEVV | 2391875 |
| 928 | MLKAYKYRIYPNKEQKLYLSKTFGCTRFIYNQMLANRIDIYETHKD NLTSKEMSKLYPTPAQYKKEFEWLKEVDSLALANAQLNLDKAYK NFFRDKSIGFPKFKSKKSNYHSYTTNNQKGTIYIENSRIKIPKLKTMI KIKQHRQFNGLIKSCTISQIPSGKYYISILVDTENIQLPKTDKKVGID VGLKEFAITSDGEFFGNPKWLRKSEKRLKKLQKNLSRKKKGSNNR | 2733280 |

TABLE 1-continued

Exemplary Amino Acid Sequences of Effector Proteins

| SEQ ID NO | Effector Protein Amino Acid sequence | Effector Protein Name |
|---|---|---|
|  | RKARLKVAKLCEKIVNQRKDFLHKLSMQIISENQAIVIEDLKVSNM<br>LKNHRLAKAISEISWYEFRRMLEYKADWYGRKIIVAPPNYASSQLC<br>SSCGNKSNQTKDLSCRTYICPVCGMIMGRDLNASKNLLKLAI |  |
| 929 | MKKCLFSTYIKTDDMDIIKEEIELFNAMKRIAFSNVRILGGDKTVKE<br>NLSIHMFLKSQFHVSDYFINSARQEAKAVYRSAMEVLTLQKENLES<br>RIKQMEKKIKEINTRLAHLEKEKQSLIKRSKTGKGKFVSYRGGRES<br>EPSPGVFQVRYKKKTVRYENQYLFEVLYLTPEIKKLKARLRMISQR<br>ITSNRCRLQKVEGKIENHLPAVCFGSKKLFQQQNTIYQNQHEDWK<br>RAMYKGRNPGMTISGRKDALQGNFLFKYDVKTKNLTYRTTTGEII<br>VLKNVTFPYGQELVEQAVNATANERNAIAWRLEVHGSCVLVKCM<br>VKVFNRQKNYDFSEGCVAFDTNVDHLAYTELDGHGNLLSHNIIPFT<br>LRGLSTGQREQVLSKVLEEIFQYARNAAKPIIMERLEDIKQKPMYQ<br>HKRLNEVLSSFAYTKVTMLAESKSNKYSIGLVKVNPAFTSQIGKPK<br>YMRHYGISVHEAAAFVIGRRGLGYQDKVPKPMRHLIPKGKKNRH<br>HWSHWSYLMTQLKNYASGVFYQPIDYAAISTMKELKQQLN | 2735223 |

TABLE 2 provides exemplary NLS sequences.

TABLE 2

Sequences of Exemplary NLS sequences

| SEQ ID NO: | Description | Sequence* |
|---|---|---|
| 863 | NLS | KR(K/R)R |
| 864 | NLS | (P/R)XXKR(^D/E)(K/R)* |
| 865 | NLS | KRX(W/F/Y)XXAF* |
| 866 | NLS | (R/P)XXKR(K/R)(^D/E)* |
| 867 | NLS | LGKR(K/R)(W/F/Y)* |
| 868 | NLS | KRX$_{10-12}$K(K/R)(K/R) |
| 83 | NLS | MAPKKKRKV |
| 85 | NLS | KRPAATKKAGQAKKKK |
| 1105 | NLS | KRX$_{10-12}$K(KR)X(K/R)* |
| 1106 | NLS | K(K/R)RK* |
| 1107 | NLS | KRPAATKKAGQAKKKKEF |
| 1108 | NLS | PKKKRKV |
| 1109 | NLS | PAAKRVKLD |
| 1110 | NLS | PKKKRKVGIHGVPAA |

*wherein X is any naturally occurring amino-acid; and ^D/E is any amino-acid except Asp or Glu TABLE 2. Sequences of Exemplary NLS sequences

TABLE 2.1

Exemplary Exonuclease Fusion Partner Sequences

| SEQ ID NO: | Description | Sequence* |
|---|---|---|
| 930 | dem1 having 5'=>3' exonuclease activity for ssDNA | MLGRALINKYGFLIHPRRFVHLNDKSLDGTFILPSKKNHMYDVPTN<br>DPSGILNASDIDRINNLPFFDNTSPTKETNTKEGALLSEKLASVKELF<br>GEDPENPSFINYRFPRGLENPYFDIQVNQLKKKRLSVTQLCTTQNW<br>CELRNFYDFYSQNLSNQLLNLKFQVQKGKKIHKSLEDETHPELNQY<br>KSFTHNFLALTKLSMDIDNDMDALLDNWFNSINRLVSLFTKGDGH<br>AREIVCHGFINLEDGKLVEHLLNSDSKTKENVIISGVIDHLTLRNRH<br>NHQVQKGAAHLDTEYQSWGNILTNLLSNLKELKSNNEIVISDIKTRS<br>VPKIPSIESVIESSKLQTMYYKFFFSHLSQDMTQTYHSFLINAQRRGL<br>DVDAPINPTKILTFILTNPLFANDVKNLLYGLPINHSAFDNDAKGSN<br>TFDMTAFNDLLDRGPTSFNVPIEQDEDSSESTKCVSLRDYGHFYTK<br>WKTPLTLKYFAARLSQIYFIVGNLVSNDLMIEYYYHNDNFHNIIFPY<br>DPLKLGTHAHDSAMVWFGGRDMHPIEPTQKNFNTYCKFCDYRHV<br>CSWKNKNELKLIDLGKELKKIILESSMK |
| 931 | exo1 having 5'=>3' exonuclease activity for dsDNA | MGIQGLLPQLKPIQNPVSLRRYEGEVLAIDGYAWLHRAACSCAYEL<br>AMGKPTDKYLQFFIKRFSLLKTFKVEPYLVFDGDAIPVKKSTESKRR<br>DKRKENKAIAERLWACGEKKNAMDYFQKCVDITPEMAKCIICYCK<br>LNGIRYIVAPFEADSQMVYLEQKNIVQGIISEDSDLLVFGCRRLITKL<br>NDYGECLEICRDNFIKLPKKFPLGSLTNEEIITMVCLSGCDYTNGIPK<br>VGLITAMKLVRRFNTIERIILSIQREGKLMIPDTYINEYEAAVLAFQF<br>QRVFCPIRKKIVSLNEIPYLYKDTESKRKRLYACIGFVIHRETQKKQI<br>VHFDDDIDHHLHLKIAQGDLNPYDFHQPLANREHKLQLASKSNIEF |

TABLE 2.1-continued

Exemplary Exonuclease Fusion Partner Sequences

| SEQ ID NO: | Description | Sequence* |
|---|---|---|
| | | GKTNTTNSEAKVKPIESFFQKMTKLDHNPKVANNIHSLRQAEDKLT MAIKRRKLSNANVVQETLKDTRSKFFNKPSMTVVENFKEKGDSIQD FKEDTNSQSLEEPVSESQLSTQIPSSFITTNLEDDDNLSEEVSEVVSDI EEDRKNSEGKTIGNEIYNTDDDGDGDTSEDYSETAESRVPTSSTTSF PGSSQRSISGCTKVLQKFRYSSSFSGVNANRQPLFPRHVNQKSRGM VYVNQNRDDDCDDNDGKNQITQRPSLRKSLIGARSQRIVIDMKSVD ERKSFNSSPILHEESKKRDIETTKSSQARPAVRSISLLSQFVYKGK |
| 932 | exo5 having 5'=>3' exonuclease activity for ssDNA and dsDNA | MSKSWGKFIEEEEAEMASRRNLMIVDGTNLGFRFKHNNSKKPFASS YVSTIQSLAKSYSARTTIVLGDKGKSVFRLEHLPEYKGNRDEKYAQ RTEEEKALDEQFFEYLKDAFELCKTTFPTFTIRGVEADDMAAYIVKL IGHLYDHVWLISTDGDWDTLLTDKVSRFSFTTRREYHLRDMYEHH NVDDVEQFISLKAIMGDLGDNIRGVEGIGAKRGYNIIREFGNVLDIID QLPLPGKQKYIQNLNASEELLFRNLILVDLPTYCVDAIAAVGQDVL DKFTKDILEIAEQ |
| 933 | FenA having 5'=>3' exonuclease activity for ssDNA and dsDNA | MTAPILLLDGASMWFRSYFGVPSSIKAPDGRPVNAVRGFIDAISTLV TREKPRRLVVCRDDDWRPQWRVDLIPSYKAHRVAEPEPDGVPDIEE VPDDLTPQVNMILELLLDAFGIPTAGAAGFEADDVLGTLSAREERDP VVVVSGDRDLLQLVRDEPAPQVRVLYLGRGLAKATKWGPAEVAE QYGVPLDRAGTAYAELALLRGDPSDGLPGVAGIGEKTAASLLAKH GSLQNILDAAHDPKSGLSKAHRTKLLGAVDYIAAAETVVRVATDA PVTFSTPTDTLPLAAGDPARVAELAAAYGVSSSISRLQTALDQLPD |
| 934 | nurA having 5'=>3' exonuclease activity for ssDNA and dsDNA | MIDKAYEELIKMKEKIMRDSYTIHKELSESVESILNELWINYSPESVE HSKKLLAIDGGMWVKETRQGVIFIVNAKAIVFEGINEINSEGKVLVH IFSPGNYAKERIELLMQLLELQLALKLVENVDYVLLDGSFSKKLGR HKSELKVDLLDDIVSIDKILSLEEKDEDNMLRFLIAENQLVLSELVSR YKDKLLFISKNSKSSDLFKQAYSDITILELFTQNCGYSKILEKKIDEN YILSRKASKLLSGLNYYFTNLRLEPSERLFRLDFFNADKIFEYLKVLK PVSLKGYPYPLIKVHKDVRVGKEDRERIYSILEMKRKDISWWPSQF Y |
| 935 | recJ having 5'=>3' exonuclease activity for ssDNA | MKKLIKRREIPIGNSVSNHPLLDRLYRARHIQNTKELDRTLKSMLNP NQLYGIEQAVNLLVEAYQPQQKIVIVGDFDADGATSTALSVLALRQ LGFSDVDYLVPNRFEQGYGLSIPVAEMAIEKGVQLLMTVDNGVSSF DGVAFLKEKGIRVLVTDHHLPPETLPPADAIVNPNLSQCGFPSKSLA GVGVAFYLMLAVRAKFRELGIFTAETQPNFTDLLLDLVALGTIADVV PLDQNNRILAYQGLMRIRARHCRLGIIALAEVANRNVEQFTSSDLGF CIGPRLNAAGRLDNMSIGVELLLANEMSKARELALDLDQLNQTRKE IEAGMKLEAIKICQNLTALFKELPYGITLYQPDWHQGVLGIVSSRIK DQYHRPVIAFAQDSEGILKGSARSIEGLHMRDVLERIHSQHPNMILK FGGHAMAAGLSIREEHFADFQHIFNQTVADWLDEEHLQGVIWTDG ELNSNEFNLETAELIKSVGTWGQGFPEPCFDGEFKILDQRAIGQNKN HLKMLLEPKQGGVLLDAIAFNINTRLYPDLSIKQARLAYKLEINEFR GNRSLQLLVDYIEPIDE |
| 936 | sbcB having 5'=>3' exonuclease activity for ssDNA | MMNDGKQQSTFLFHDYETFGTHPALDRPAQFAAIRTDSEFNVIGEP EVFYCKPADDYLPQPGAVLITGITPQEARAKGENEAAFAARIHSLFT VPKTCILGYNNVRFDDEVTRNIFYRNFYDPYAWSWQHDNSRWDLL DVMRACYALRPEGINWPENDDGLPSFRLEHLTKANGIEHSNAHDA MADVYATIAMAKLVKTRQPRLFDYLFTHRNKHKLMALIDVPQMK PLVHVSGMFGAWRGNTSWVAPLAWHPENRNA VIMVDLAGDISPL LELDSDTLRERLYTAKTDLGDNAAVPVKLVHINKCPVLAQANTLRP EDADRLGINRQHCLDNLKILRENPQVREKVVAIFAEAEPFTPSDNVD AQLYNGFFSDADRAAMKIVLETEPRNLPALDITFVDKRIEKLLFNYR ARNFPGTLDYAEQQRWLEHRRQVFTPEFLQGYADELQMLVQQYA DDKEKVALLKALWQYAEEIV |
| 937 | snm1 having 5'=>3' exonuclease activity for ssDNA and dsDNA | MSRKSIVQIRRSEVKRKRSSTASSTSEGKTLHKNTHTSSKRQRTLTE FNIPTSSNLPVRSSSYSFSRFSCSTSNKNTEPVIINDDDHNSICLEDTA KVEITIDTDEEELVSLHDNEVSAIENRTEDRIVTELEEQVNVKVSTEV IQCPICLENLSHLELYERETHCDTCIGSDPSNMGTPKKNIRSFISNPSS PAKTKRDIATSKKPTRVKLVLPSFKIIKFNNGHEIVVDGFNYKASETI SQYFLSHFHSDHYIGLKKSWNNPDENPIKKTLYCSKITAILVNLKFKI PMDEIQILPMNKRFWITDTISVVTLDANHCPGAIIMLFQEFLANSYD KPIRQILHTGDFRSNAKMIETIQKWLAETANETIDQVYLDTTYMTM GYNFPSQHSVCETVADFTLRLIKHGKNKTFGDSQRNLFHFQRKKTL TTHRYRVLFLVGTYTIGKEKLAIKICEFLKTKLFVMPNSVKFSMMLT VLQNNENQNDMWDESLLTSNLHESSVHLVPIRVLKSQETIEAYLKS LKELETDYVKDIEDVVGFIPTGWSHNFGLKYQKKNDDDENEMSGN TEYCLELMKNDRDNDDENGFEISSILRQYKKYNKFQVFNVPYSEHS SFNDLVKFGCKLKCSEVIPTVNLNNLWKVRYMTNWFQCWENVRK TRAAK |

TABLE 2.1-continued

Exemplary Exonuclease Fusion Partner Sequences

| SEQ ID NO: | Description | Sequence* |
|---|---|---|
| 938 | TatD having 5'=>3' exonuclease activity for ssDNA and RNA | MFDIGVNLTSSQFVKDRDDVVTRALAAGVSGMLLTGTNLHESQQA QKLAQRYACCWSTAGVHPHDSSQWQSETEDAIVALARQPDVVAIG ECGLDFNRNFSTPQEQERAFQAQLRIAAELQMPVFMHCRDAHARFL ALLEPWLDKLPGAVLHCFTGTREEMQECIDRGLYIGITGWVCDERR GLELRELLPFIPAEKLLIETDAPYLLPRDLTPKPASRRNEPAHLAHIL ARVAHWRGEDPQWLAATTDANVKTLFGIAF |
| 939 | TREX1 having 5'=>3' exonuclease activity for ssDNA and dsDNA | MGSQALPPGPMQTLIFFDMEATGLPFSQPKVTELCLLAVHRCALESP PTSQGPPPTVPPPPRVVDKLSLCVAPGKACSPAASEITGLSTAVLAA HGRQCFDDNLANLLLAFLRRQPQPWCLVAHNGDRYDFPLLQAELA MLGLTSALDGAFCVDSITALKALERASSPSEHGPRKSYSLGSIYTRL YGQSPPDSHTAEGDVLALLSICQWRPQALLRWVDAHARPFGTIRPM YGVTASARTKPRPSAVTTTAHLATTRNTSPSLGESRGTKDLPPVKDP GALSREGLLAPLGLLAILTLAVATLYGLSLATPGE |

TABLE 3 provides exemplary repeat sequences.

TABLE 3

Exemplary Repeat Sequence

| Effector Protein | Repeat Sequences (5'-to-3'), shown as RNA | Sequence Description |
|---|---|---|
| CasM.265466 | AAGGAUGCCAAAC (SEQ ID NO: 72) | Repeat sequence |
| CasM.265466 | UGGUACAUCCAAC (SEQ ID NO: 1027) | Repeat sequence |
| CasM.265466 | GUGGAUAUCCAAC (SEQ ID NO: 1029) | Repeat sequence |
| CasM.265466 | AGCAGAAUACAAC (SEQ ID NO: 1030) | Repeat sequence |
| CasM.265466 | GUGAAUAUCCAAC (SEQ ID NO: 1031) | Repeat sequence |
| CasM.265466 | AGGUAUAUCCAAC (SEQ ID NO: 1032) | Repeat sequence |
| CasM.265466 | AGCAAUAUACAAC (SEQ ID NO: 1033) | Repeat sequence |
| CasM.292007 | AUAGGUACAAAAC (SEQ ID NO: 76) | Repeat sequence |
| CasM.292007 | AUGGUAGUCAAAC (SEQ ID NO: 77) | Repeat sequence |

TABLE 4 provides exemplary handle sequences.

TABLE 4

Exemplary Handle Sequence and Portions Thereof

| Effector Protein | Handle Sequences (5'-to-3'), shown as RNA | Sequence Description |
|---|---|---|
| CasM.265466 | ACAGCUUAUUUGGAAGCUGAAAUGUGAGGUUUA UAACACUCACAAGAAUCCUGAAAAAGGAUGCCA AAC (SEQ ID NO: 70) | Handle sequence |
| CasM.265466 | ACAGCUUAUUUGGAAGCUGAAAUGUGAGGUUUA UAACACUCACAAGAAUCCU (SEQ ID NO: 22) | Handle sequence without Linker or Repeat sequence |
| CasM.265466 | AAGGAUGCCAAAC (SEQ ID NO: 72) | Repeat sequence |
| CasM.292007 | UGGCUGAUUUUGCAGCCAUAAGGUGAGGAAAAU UCACUCACCAAAGCCUAUGUGAAAAUAGGUACA AAAC (SEQ ID NO: 32) | Handle sequence |
| CasM.292007 | UGGCUGAUUUUGCAGCCAUAAGGUGAGGAAAAU UCACUCACCAAAGCCUAUGU (SEQ ID NO: 73) | Handle sequence without Linker or Repeat sequence |
| CasM.292007 | AUAGGUACAAAAC (SEQ ID NO: 76) | Repeat sequence |
| CasM.292007 | AGGGUAGAUUUGACUGCCCAAAGGUGAGGAUGA AAUCACUCACCAAAUACUGAAAAUGGUAGUCAA AC (SEQ ID NO: 35) | Handle sequence |

TABLE 4-continued

Exemplary Handle Sequence and Portions Thereof

| Effector Protein | Handle Sequences (5'-to-3'), shown as RNA | Sequence Description |
|---|---|---|
| CasM.292007 | AGGGUAGAUUUGACUGCCCAAAGGUGAGGAUGA AAUCACUCACCAAAUACU (SEQ ID NO: 25) | Handle sequence without Linker or Repeat sequence |
| CasM.292007 | ACGGUGGAUUUUGCCGCCGAAAGGUGAGGGAAA AUUUCCACUCACCAAAGCCGAAAAUAGGUACAA AAC (SEQ ID NO: 36) | Handle sequence |
| CasM.292007 | ACGGUGGAUUUUGCCGCCGAAAGGUGAGGGAAA AUUUCCACUCACCAAAGCC (SEQ ID NO: 26) | Handle sequence without Linker or Repeat sequence |
| CasM.265466 | UGGGGCAGUUGGUUGCCCUUAGCCUGAGGCAU UUAUUGCACUCGGGAAGUACCAUUUCUCAGAAA UGGUACAUCCAAC (SEQ ID NO: 1034) | Handle sequence |
| CasM.265466 | UGGGGCAGUUGGUUGCCCUUAGCCUGAGGCAU UUAUUGCACUCGGGAAGUACCAUUUCUCAGAAA (SEQ ID NO: 1035) | Handle sequence without Repeat sequence |
| CasM.265466 | UGGGGCAGUUGGUUGCCCUUAGCCUGAGGCAU UUAUUGCACUCGGGAAGUACCAUUUCUCA (SEQ ID NO: 1036) | Handle sequence without Linker or Repeat sequence |
| CasM.265466 | UGGUACAUCCAAC (SEQ ID NO: 1027) | Repeat sequence |
| CasM.265466 | ACAGCUUAUUUGGAAGCUGAAAUGUGAGGUUUA UAACACUCACAAGAAUCCUGAAAAAGGAUGCCA AAC (SEQ ID NO: 1037) | Handle sequence |
| CasM.265466 | ACAGCUUAUUUGGAAGCUGAAAUGUGAGGUUUA UAACACUCACAAGAAUCCUGAAA (SEQ ID NO: 1038) | Handle sequence without Repeat sequence |
| CasM.265466 | ACAGCUUAUUUGGAAGCUGAAAUGUGAGGUUUA UAACACUCACAAGAAUCCU (SEQ ID NO: 1039) | Handle sequence without Linker or Repeat sequence |
| CasM.265466 | AAGGAUGCCAAAC (SEQ ID NO: 1028) | Repeat sequence |
| CasM.265466 | UGGGGCAGUUGGUUGCCCUUAGCCUGAGGCAU UUAUUGCACUCGGGAAGUACCAGAAAUGGUAC AUCCAAC (SEQ ID NO: 1040) | Handle sequence |
| CasM.265466 | UGGGGCAGUUGGUUGCCCUUAGCCUGAGGCAU UUAUUGCACUCGGGAAGUACCAGAAA (SEQ ID NO: 1041) | Handle sequence without Repeat sequence |
| CasM.265466 | UGGGGCAGUUGGUUGCCCUUAGCCUGAGGCAU UUAUUGCACUCGGGAAGUACCA (SEQ ID NO: 1042) | Handle sequence without Linker or Repeat sequence |
| CasM.265466 | AGGGCGUGUUGGAGCGCCUUAGUUUGAGGUAU CAAGCACUCAAAAAAUCUACGAAAGUGGAUAUC CAAC (SEQ ID NO: 1043) | Handle sequence |
| CasM.265466 | AGGGCGUGUUGGAGCGCCUUAGUUUGAGGUAU CAAGCACUCAAAAAAUCUACGAAA (SEQ ID NO: 1044) | Handle sequence without Repeat sequence |
| CasM.265466 | AGGGCGUGUUGGAGCGCCUUAGUUUGAGGUAU CAAGCACUCAAAAAAUCUAC (SEQ ID NO: 1045) | Handle sequence without Linker or Repeat sequence |
| CasM.265466 | GUGGAUAUCCAAC (SEQ ID NO: 1029) | Repeat sequence |
| CasM.265466 | ACGGGUGGUUGUACACCCGAAGAGUGAGGUCUU AACGGGCACUCGCUAAUCUGAUGAAAAGCAGAA UACAAC (SEQ ID NO: 1046) | Handle sequence |
| CasM.265466 | ACGGGUGGUUGUACACCCGAAGAGUGAGGUCUU AACGGGCACUCGCUAAUCUGAUGAAA (SEQ ID NO: 1047) | Handle sequence without Repeat sequence |

TABLE 4-continued

Exemplary Handle Sequence and Portions Thereof

| Effector Protein | Handle Sequences (5'-to-3'), shown as RNA | Sequence Description |
|---|---|---|
| CasM.265466 | *ACGGGUGGUUGUACACCCGAAGAGUGAGGUCUU AACGGGCACUCGCUAAUCUGAU* (SEQ ID NO: 1048) | Handle sequence without Linker or Repeat sequence |
| CasM.265466 | <u>AGCAGAAUACAAC</u> (SEQ ID NO: 1030) | Repeat sequence |
| CasM.265466 | *UGGGCGCGUUGGAGCGCCUUGGUUCGAGGUUC CCUGCACUCGAAAAAUUCAC*GAAA<u>*GUGAAUAUC CAAC*</u> (SEQ ID NO: 1049) | Handle sequence |
| CasM.265466 | *UGGGCGCGUUGGAGCGCCUUGGUUCGAGGUUC CCUGCACUCGAAAAAUUCAC*GAAA (SEQ ID NO: 1050) | Handle sequence without Repeat sequence |
| CasM.265466 | *UGGGCGCGUUGGAGCGCCUUGGUUCGAGGUUC CCUGCACUCGAAAAAUUCAC* (SEQ ID NO: 1051) | Handle sequence without Linker or Repeat sequence |
| CasM.265466 | <u>GUGAAUAUCCAAC</u> (SEQ ID NO: 1031) | Repeat sequence |
| CasM.265466 | *UGGGCGUGUUGGAACGCCUUAGUUUGAGGUUU CAAGCACUCAAAAAAUUCAC*GAAA<u>*GUGGAUAUC CAAC*</u> (SEQ ID NO: 1052) | Handle sequence |
| CasM.265466 | *UGGGCGUGUUGGAACGCCUUAGUUUGAGGUUU CAAGCACUCAAAAAAUUCAC*GAAA (SEQ ID NO: 1053) | Handle sequence without Repeat sequence |
| CasM.265466 | *UGGGCGUGUUGGAACGCCUUAGUUUGAGGUUU CAAGCACUCAAAAAAUUCAC* (SEQ ID NO: 1054) | Handle sequence without Linker or Repeat sequence |
| CasM.265466 | *CGGGGUGGUUGGACACCCUUAAAUUGAGGUUCA UCGCACUCGAUAAAUACCA*GAAA<u>*AGGUAUAUCC AAC*</u> (SEQ ID NO: 1055) | Handle sequence |
| CasM.265466 | *CGGGGUGGUUGGACACCCUUAAAUUGAGGUUCA UCGCACUCGAUAAAUACCA*GAAA (SEQ ID NO: 1056) | Handle sequence without Repeat sequence |
| CasM.265466 | *CGGGGUGGUUGGACACCCUUAAAUUGAGGUUCA UCGCACUCGAUAAAUACCA* (SEQ ID NO: 1057) | Handle sequence without Linker or Repeat sequence |
| CasM.265466 | <u>AGGUAUAUCCAAC</u> (SEQ ID NO: 1032) | Repeat sequence |
| CasM.265466 | *GGGGCUGGUUGUACAGCCUGAAGUUGAGGGAU GAUUCCACUCGACAAAUUGCU*GAAA<u>*AGCAAUAU ACAAC*</u> (SEQ ID NO: 1058) | Handle sequence |
| CasM.265466 | *GGGGCUGGUUGUACAGCCUGAAGUUGAGGGAU GAUUCCACUCGACAAAUUGCU*GAAA (SEQ ID NO: 1059) | Handle sequence without Repeat sequence |
| CasM.265466 | *GGGGCUGGUUGUACAGCCUGAAGUUGAGGGAU GAUUCCACUCGACAAAUUGCU* (SEQ ID NO: 1060) | Handle sequence without Linker or Repeat sequence |
| CasM.265466 | <u>AGCAAUAUACAAC</u> (SEQ ID NO: 1033) | Repeat sequence |
| CasM.265466 | *CGGGCUGGUUGGACAGCCUUAAACUGAGGUUUA ACGCACUCGGUAAAUACCC*GAAA<u>*AGGUAUAUCC AAC*</u> (SEQ ID NO: 1061) | Handle sequence |
| CasM.265466 | *CGGGCUGGUUGGACAGCCUUAAACUGAGGUUUA ACGCACUCGGUAAAUACCC*GAAA (SEQ ID NO: 1062) | Handle sequence without Repeat sequence |
| CasM.265466 | *CGGGCUGGUUGGACAGCCUUAAACUGAGGUUUA ACGCACUCGGUAAAUACCC* (SEQ ID NO: 1063) | Handle sequence without Linker or Repeat sequence |

TABLE 4-continued

Exemplary Handle Sequence and Portions Thereof

| Effector Protein | Handle Sequences (5'-to-3'), shown as RNA | Sequence Description |
|---|---|---|
| CasM.292007 or CasM.265466 | GAAA (SEQ ID NO: 71) | Linker |
| CasM.292007 or CasM.265466 | GS (SEQ ID NO: 7) | Linker |
| CasM.292007 or CasM.265466 | GSGGS (SEQ ID NO: 8) | Linker |
| CasM.292007 or CasM.265466 | GGSGGS (SEQ ID NO: 9) | Linker |
| CasM.292007 or CasM.265466 | GGGS (SEQ ID NO: 10) | Linker |
| CasM.292007 or CasM.265466 | GGSG (SEQ ID NO: 11) | Linker |
| CasM.292007 or CasM.265466 | GGSGG (SEQ ID NO: 12) | Linker |
| CasM.292007 or CasM.265466 | GSGSG (SEQ ID NO: 13) | Linker |
| CasM.292007 or CasM.265466 | GSGGG (SEQ ID NO: 14) | Linker |
| CasM.292007 or CasM.265466 | GGGSG (SEQ ID NO: 15) | Linker |
| CasM.292007 or CasM.265466 | GSSSG (SEQ ID NO: 16) | Linker |
| CasM.292007 | <u>AUGGUAGUCAAAC</u> (SEQ ID NO: 77) | Repeat sequence |
| CasM.265466 | *ACAGCUUAUUUGGAAGCUGAAAUGUGAGGUUUA UAACACUCACAAGAAUCCU*GAAA (SEQ ID NO: 828) | Handle sequence without Repeat sequence |
| CasM.292007 | *UGGCUGAUUUUGCAGCCAUAAGGUGAGGAAAAU UCACUCACCAAAGCCUAUGU*GAAA (SEQ ID NO: 829) | Handle sequence without Repeat sequence |
| CasM.292007 | *AGGGUAGAUUUGACUGCCCAAAGGUGAGGAUGA AAUCACUCACCAAAUACU*GAAA (SEQ ID NO: 830) | Handle sequence without Repeat sequence |
| CasM.292007 | *ACGGUGGAUUUGCCGCCGAAAGGUGAGGGAAA AUUUCCACUCACCAAAGCC*GAAA (SEQ ID NO: 831) | Handle sequence without Repeat sequence |
| CasM.265466 | *mA\*mC\*mA\*GCUUAUUUGGAAGCUGAAAUGUGAG GUUUAUAACACUCACAAGAAUCCU*GAAA<u>AAGGA UGCCAAAC</u> (SEQ ID NO: 833) | Handle sequence |
| CasM.265466 | *GACAGCUUAUUUGGAAGCUGAAAUGUGAGGUUU AUAACACUCACAAGAAUCCU*GAAA<u>AAGGAUGCC AAAC</u> (SEQ ID NO: 941) | Handle sequence |
| CasM.265466 | *GACAGCUUAUUUGGAAGCUGAAAUGUGAGGUUU AUAACACUCACAAGAAUCCU*GAAA (SEQ ID NO: 942) | Handle sequence without Repeat sequence |

TABLE 4-continued

Exemplary Handle Sequence and Portions Thereof

| Effector Protein | Handle Sequences (5'-to-3'), shown as RNA | Sequence Description |
|---|---|---|
| CasM.265466 | *GACAGCUUAUUUGGAAGCUGAAAUGUGAGGUUU AUAACACUCACAAGAAUCCU* (SEQ ID NO: 943) | Handle sequence without Linker or Repeat sequence |
| CasM.265466 | ACAUGAGGAUCACCCAUGUACAGCUUAUUUGG AAGCUGAAAUGUGAGGUUUAUAACACUCACAA GAAUCCUGAAAAAGGAUGCCAAAC (SEQ ID NO: 1065) | Handle sequence with aptamer sequence |
| CasM.265466 | GCACAUGAGGAUCACCCAUGUGCACAGCUUAU UUGGAAGCUGAAAUGUGAGGUUUAUAACACU CACAAGAAUCCUGAAAAAGGAUGCCAAAC (SEQ ID NO: 1066) | Handle sequence with aptamer sequence |
| CasM.265466 | GCAGCACAUGAGGAUCACCCAUGUGCUGCACA GCUUAUUUGGAAGCUGAAAUGUGAGGUUUAU AACACUCACAAGAAUCCUGAAAAGGAUGCCA AAC (SEQ ID NO: 1067) | Handle sequence with aptamer sequence |
| CasM.265466 | CGCUAUACGCACAUGAGGAUCACCCAUGUGCG UAUAGCGACAGCUUAUUUGGAAGCUGAAAUG UGAGGUUUAUAACACUCACAAGAAUCCUGAAA AAGGAUGCCAAAC (SEQ ID NO: 1068) | Handle sequence with aptamer sequence |
| CasM.265466 | GCACAUGAGGAUCACCCAUGUGCAAACAGCUU AUUUGGAAGCUGAAAUGUGAGGUUUAUAACA CUCACAAGAAUCCUGAAAAAGGAUGCCAAAC (SEQ ID NO: 1069) | Handle sequence with aptamer sequence |
| CasM.265466 | GCACAUGAGGAUCACCCAUGUGCAAAAAACAG CUUAUUUGGAAGCUGAAAUGUGAGGUUUAUA ACACUCACAAGAAUCCUGAAAAAGGAUGCCAA AC (SEQ ID NO: 1070) | Handle sequence with aptamer sequence |
| CasM.265466 | GCACAUGAGGAUCACCCAUGUGCAAAAAAAAA AACAGCUUAUUUGGAAGCUGAAAUGUGAGGU UUAUAACACUCACAAGAAUCCUGAAAAAGGAU GCCAAAC (SEQ ID NO: 1071) | Handle sequence with aptamer sequence |
| CasM.265466 | ACAUGAGGAUCACCCAUGUAAACAGCUUAUUU GGAAGCUGAAAUGUGAGGUUUAUAACACUCAC AAGAAUCCUGAAAAAGGAUGCCAAAC (SEQ ID NO: 1072) | Handle sequence with aptamer sequence |
| CasM.265466 | ACAUGAGGAUCACCCAUGUAAAAAACAGCUUA UUUGGAAGCUGAAAUGUGAGGUUUAUAACAC UCACAAGAAUCCUGAAAAAGGAUGCCAAAC (SEQ ID NO: 1073) | Handle sequence with aptamer sequence |
| CasM.265466 | ACAUGAGGAUCACCCAUGUAAAAAAAAAAACA GCUUAUUUGGAAGCUGAAAUGUGAGGUUUAU AACACUCACAAGAAUCCUGAAAAAGGAUGCCA AAC (SEQ ID NO: 1074) | Handle sequence with aptamer sequence |
| CasM.265466 | ACAGCUUAUUUGGAAGCUGAAAUGUGAGGUU ACAUGAGGAUCACCCAUGUAACACUCACAAGA AUCCUGAAAAAGGAUGCCAAAC (SEQ ID NO: 1075) | Handle sequence with aptamer sequence |
| CasM.265466 | ACAGCUUAUUUGGAAGCUGAAAUGUGAGGUU UAACAUGAGGAUCACCCAUGUAUAACACUCAC AAGAAUCCUGAAAAAGGAUGCCAAAC (SEQ ID NO: 1076) | Handle sequence with aptamer sequence |
| CasM.265466 | ACAGCUUAUUUGGAAGCUGAAAUGUGAGGUU GCACAUGAGGAUCACCCAUGUGCAACACUCAC AAGAAUCCUGAAAAAGGAUGCCAAAC (SEQ ID NO: 1077) | Handle sequence with aptamer sequence |
| CasM.265466 | ACAGCUUAUUUGGAAGCUGAAAUGUGAGGUU GCAGCACAUGAGGAUCACCCAUGUGCUGCAAC ACUCACAAGAAUCCUGAAAAAGGAUGCCAAAC (SEQ ID NO: 1078) | Handle sequence with aptamer sequence |

TABLE 4-continued

Exemplary Handle Sequence and Portions Thereof

| Effector Protein | Handle Sequences (5'-to-3'), shown as RNA | Sequence Description |
|---|---|---|
| CasM.265466 | ACAGCUUAUUUGGAAGCUGAAAUGUGAGGUUCGCUAUACGCACAUGAGGAUCACCCAUGUGCGUAUAGCGAACACUCACAAGAAUCCUGAAAAAGGAUGCCAAAC (SEQ ID NO: 1079) | Handle sequence with aptamer sequence |
| CasM.265466 | ACAGCUUAUUUGGAAGCUGAAAUGUGAGGUUUAGCACAUGAGGAUCACCCAUGUGCAUAACACUCACAAGAAUCCUGAAAAAGGAUGCCAAAC (SEQ ID NO: 1080) | Handle sequence with aptamer sequence |
| CasM.265466 | ACAGCUUAUUUGGAAGCUGAAAUGUGAGGUUUAGCAGCACAUGAGGAUCACCCAUGUGCUGCAUAACACUCACAAGAAUCCUGAAAAAGGAUGCCAAAC (SEQ ID NO: 1081) | Handle sequence with aptamer sequence |
| CasM.265466 | ACAGCUUAUUUGGAAGCUGAAAUGUGAGGUUUACGCUAUACGCACAUGAGGAUCACCCAUGUGCGUAUAGCGAUAACACUCACAAGAAUCCUGAAAAAGGAUGCCAAAC (SEQ ID NO: 1082) | Handle sequence with aptamer sequence |
| CasM.265466 | ACAGCUUAUUUGGAAGCUGAAAUGUGAGGUGUAGCACAUGAGGAUCACCCAUGUGCAUCACACUCACAAGAAUCCUGAAAAAGGAUGCCAAAC (SEQ ID NO: 1083) | Handle sequence with aptamer sequence |
| CasM.265466 | ACAGCUUAUUUGGAAGCUGAAAUGUGAGGUGAAGCACAUGAGGAUCACCCAUGUGCAACACACUCACAAGAAUCCUGAAAAAGGAUGCCAAAC (SEQ ID NO: 1084) | Handle sequence with aptamer sequence |
| CasM.265466 | ACAGCUUAUUUGGAAGCUGAAAUGUGAGGUUUAUAACACUCACAAGAAUCCUUACAUGAGGAUCACCCAUGUAAGGAUGCCAAAC (SEQ ID NO: 1085) | Handle sequence with aptamer sequence |
| CasM.265466 | ACAGCUUAUUUGGAAGCUGAAAUGUGAGGUUUAUAACACUCACAAGAAUCCUAAACAUGAGGAUCACCCAUGUAAAGGAUGCCAAAC (SEQ ID NO: 1086) | Handle sequence with aptamer sequence |
| CasM.265466 | ACAGCUUAUUUGGAAGCUGAAAUGUGAGGUUUAUAACACUCACAAGAAUCCUUGCACAUGAGGAUCACCCAUGUGCAAGGAUGCCAAAC (SEQ ID NO: 1087) | Handle sequence with aptamer sequence |
| CasM.265466 | ACAGCUUAUUUGGAAGCUGAAAUGUGAGGUUUAUAACACUCACAAGAAUCCUUGCAGCACAUGAGGAUCACCCAUGUGCUGCAAGGAUGCCAAAC (SEQ ID NO: 1088) | Handle sequence with aptamer sequence |
| CasM.265466 | ACAGCUUAUUUGGAAGCUGAAAUGUGAGGUUUAUAACACUCACAAGAAUCCUUCGCUAUACGCACAUGAGGAUCACCCAUGUGCGUAUAGCGAAGGAUGCCAAAC (SEQ ID NO: 1089) | Handle sequence with aptamer sequence |
| CasM.265466 | ACAGCUUAUUUGGAAGCUGAAAUGUGAGGUUUAUAACACUCACAAGAAUCCUGCACAUGAGGAUCACCCAUGUGCAAGGAUGCCAAAC (SEQ ID NO: 1090) | Handle sequence with aptamer sequence |
| CasM.265466 | ACAGCUUAUUUGGAAGCUGAAAUGUGAGGUUUAUAACACUCACAAGAAUCCUGCAGCACAUGAGGAUCACCCAUGUGCUGCAAGGAUGCCAAAC (SEQ ID NO: 1091) | Handle sequence with aptamer sequence |
| CasM.265466 | ACAGCUUAUUUGGAAGCUGAAAUGUGAGGUUUAUAACACUCACAAGAAUCCUAAGCAGCACAUGAGGAUCACCCAUGUGCUGCAAAGGAUGCCAAAC (SEQ ID NO: 1092) | Handle sequence with aptamer sequence |
| CasM.265466 | ACAGCUUAUUUGGAAGCUGAAAUGUGAGGUUUAUAACACUCACAAGAAUCCUAACGCUAUACGCACAUGAGGAUCACCCAUGUGCGUAUAGCGAAAGGAUGCCAAAC (SEQ ID NO: 1093) | Handle sequence with aptamer sequence |

TABLE 4-continued

Exemplary Handle Sequence and Portions Thereof

| Effector Protein | Handle Sequences (5'-to-3'), shown as RNA | Sequence Description |
|---|---|---|
| CasM.265466 | ACAGCUUAUUUGGAAGCUGAAAUGUGAGGUUUAUAACACUCACAAGAAUCCUUGUAAACAUGAGGAUCACCCAUGUUUACAAGGAUGCCAAAC (SEQ ID NO: 1094) | Handle sequence with aptamer sequence |
| CasM.265466 | ACAGCUUAUUUGGAAGCUGAAAUGUGAGGUUUAUAACACUCACAAGAAUCCUUGUAAAACAUGAGGAUCACCCAUGUAAUUACAAGGAUGCCAAAC (SEQ ID NO: 1095) | Handle sequence with aptamer sequence |
| CasM.265466 | ACAGCUUAUUUGGAAGCUGAAAUGUGAGGUUUAUAACACUCACAAGAAUCCUUGUACAUGAGGAUCACCCAUGUACAAGGAUGCCAAAC (SEQ ID NO: 1096) | Handle sequence with aptamer sequence |
| CasM.265466 | ACAGCUUAUUUGGAAGCUGAAAUGUGAGGUUUAUAACACUCACAAGAAUCCUUGUAAACAUGAGGAUCACCCAUGUAAACAAGGAUGCCAAAC (SEQ ID NO: 1097) | Handle sequence with aptamer sequence |

Note:
In italics is a handle sequence without a linker or repeat sequence, in bold is a linker, underlined is a repeat sequence, and no formatting is a spacer sequence.
RNA Modification: "*" represents a phosphorothioate bond between the nucleotides, "m" denotes a 2'-OMe modification.

TABLE 5 provides exemplary compositions of D2S effector Proteins, crRNAs and tracrRNAs sequences.

TABLE 5

Exemplary Compositions of D2S Effector Protein, crRNA and tracrRNA sequence

| Comp. No. | Protein | crRNA | tracrRNA sequence |
|---|---|---|---|
| 1 | CasM.265466 (SEQ ID NO: 1) | GUUUGAGAACCUUAUGAAAUUACAAGGAUGCCAAACUAUUAAAUACUCGUAUUGCU (SEQ ID NO: 17) | ACAGCUUAUUUGGAAGCUGAAAUGUGAGGUUUAUAACACUCACAAGAAUCCU (SEQ ID NO: 22) |
| 2 | CasM.265466 (SEQ ID NO: 1) | GUUUGAGAACCUUAUGAAAUUACAAGGAUGCCAAACUAUUAAAUACUCGUAUUGCU (SEQ ID NO: 17) | UAUAUUUGAUAAAAAUAUACAGCUUAUUUGGAAGCUGAAAUGUGAGGUUUAACACUCACAAGAAUCC (SEQ ID NO: 23) |
| 3 | CasM.292007 (SEQ ID NO: 2) | CUUUUGGAAGUAUAUAAAUUUACAUAGGUACAAAACUAUUAAAUACUCGUAUUGCU (SEQ ID NO: 19) | UGGCUGAUUUUGCAGCCAUAAGGUGAGGAAAAUUCACUCACCAAAGCCUAUGU (SEQ ID NO: 24) |
| 4 | CasM.292007 (SEQ ID NO: 2) | GUUUGAGAACCAUAUAAAUUUACAUGGUAGUCAAACUAUUAAAUACUCGUAUUGCU (SEQ ID NO: 20) | AGGGUAGAUUUGACUGCCCAAAGGUGAGGAUGAAAUCACUCACCAAAUACU (SEQ ID NO: 25) |
| 5 | CasM.292007 (SEQ ID NO: 2) | GUUUUGGAAUCCUAUAAAUUUACAUAGGUACAAAACUAUUAAAUACUCGUAUUGCU (SEQ ID NO: 21) | ACGGUGGAUUUUGCCGCCGAAAGGUGAGGGAAAAUUUCCACUCACCAAAGC (SEQ ID NO: 26) |

TABLE 6 provides exemplary sgRNA sequences for CasM.292007 effector protein.

TABLE 6

Exemplary sgRNA for CasM.292007

| Comp. No. | Effector Protein SEQ ID NO: | sgRNA SEQ ID NO | sgRNA |
|---|---|---|---|
| 7 | 2 | 28 | *UGGCUGAUUUUGCAGCCAUA AGGUGAGGAAAAUUCACUCA CCAAAGCCUAUGU*GAAAAUA GGUACAAAACUAUUAAAUAC UCGUAUUGCU |
| 8 | 2 | 29 | *AGGGUAGAUUUGACUGCCCA AAGGUGAGGAUGAAAUCACU CACCAAAUACU*GAAAAUGGU |
| 9 | 2 | 30 | AGUCAAACUAUUAAAUACUC GUAUUGCU<br>*ACGGUGGAUUUUGCCGCCGA AAGGUGAGGGAAAAUUUCCA CUCACCAAAGCC*GAAAAUAG GUACAAAACUAUUAAAUACU CGUAUUGCU |

Note:
In italics is a handle sequence without a linker or repeat sequence, in bold is a linker, underlined is a repeat sequence, and no formatting is a spacer sequence.

TABLE 7 provides exemplary sgRNA sequences for CasM.265466 effector protein.

TABLE 7

Exemplary sgRNA for CasM.265466

| Comp. No. | Effector Protein SEQ ID NO | sgRNA SEQ ID NO | sgRNA |
|---|---|---|---|
| 6 | 1 | 27 | *ACAGCUUAUUUGGAAGCUGAAAUGUGAGGUUUAUAACA CUCACAAGAAUCCU*GAAAAAGGAUGCCAAACUAUUAA AUACUCGUAUUGCU |
| 10 | 1 | 42 | *ACAGCUUAUUUGGAAGCUGAAAUGUGAGGUUUAUAACA CUCACAAGAAUCCU*GAAAAAGGAUGCCAAACUCACAG CCCAAGAUAGUUAA |
| 11 | 1 | 43 | *ACAGCUUAUUUGGAAGCUGAAAUGUGAGGUUUAUAACA CUCACAAGAAUCCU*GAAAAAGGAUGCCAAACCUCACG UCAUCCAGCAGAGA |
| 12 | 1 | 44 | *ACAGCUUAUUUGGAAGCUGAAAUGUGAGGUUUAUAACA CUCACAAGAAUCCU*GAAAAAGGAUGCCAAACUUGUGC UGUAGGAAGCUCAU |
| 13 | 1 | 45 | *ACAGCUUAUUUGGAAGCUGAAAUGUGAGGUUUAUAACA CUCACAAGAAUCCU*GAAAAAGGAUGCCAAACCGCCUU UGUCUUCGUGGCCC |
| 14 | 1 | 46 | *ACAGCUUAUUUGGAAGCUGAAAUGUGAGGUUUAUAACA CUCACAAGAAUCCU*GAAAAAGGAUGCCAAACCUGCAG CCAUGUCCAGGUAA |
| 15 | 1 | 47 | *ACAGCUUAUUUGGAAGCUGAAAUGUGAGGUUUAUAACA CUCACAAGAAUCCU*GAAAAAGGAUGCCAAACCCCGGA GAAAGAUGAACCUA |
| 16 | 1 | 48 | *ACAGCUUAUUUGGAAGCUGAAAUGUGAGGUUUAUAACA CUCACAAGAAUCCU*GAAAAAGGAUGCCAAACGCCAAA GGCAUGUGAGGUAC |
| 17 | 1 | 49 | *ACAGCUUAUUUGGAAGCUGAAAUGUGAGGUUUAUAACA CUCACAAGAAUCCU*GAAAAAGGAUGCCAAACCCUUUC UUGGGUACGGCUUC |
| 18 | 1 | 5 | *ACAGCUUAUUUGGAAGCUGAAAUGUGAGGUUUAUAACA CUCACAAGAAUCCU*GAAAAAGGAUGCCAAACCUCAGA GGCUGCAGAAAUGC |
| 19 | 1 | 51 | *ACAGCUUAUUUGGAAGCUGAAAUGUGAGGUUUAUAACA CUCACAAGAAUCCU*GAAAAAGGAUGCCAAACUUGUAU CCCCCUCCAAGCUC |
| 20 | 1 D220R, E225R | 52 | *ACAGCUUAUUUGGAAGCUGAAAUGUGAGGUUUAUAACA CUCACAAGAAUCCU*GAAAAAGGAUGCCAAACAGUCUC CAGGAAGAAAUUAA |

TABLE 7-continued

Exemplary sgRNA for CasM.265466

| Comp. No. | Effector Protein SEQ ID NO | sgRNA SEQ ID NO | sgRNA |
|---|---|---|---|
| 21 | 1 | 53 | ACAGCUUAUUUGGAAGCUGAAAUGUGAGGUUUAUAACACUCACAAGAAUCCUGAAAAAGGAUGCCAAACGGGCAGCUGGUGGAAUUUUU |
| 22 | 1 | 54 | ACAGCUUAUUUGGAAGCUGAAAUGUGAGGUUUAUAACACUCACAAGAAUCCUGAAAAAGGAUGCCAAACAAGAAAAUGGAAUCUCGAGG |
| 23 | 1 | 55 | ACAGCUUAUUUGGAAGCUGAAAUGUGAGGUUUAUAACACUCACAAGAAUCCUGAAAAAGGAUGCCAAACCAGGUUGAGAACUUGUUGCU |
| 24 | 1 | 56 | ACAGCUUAUUUGGAAGCUGAAAUGUGAGGUUUAUAACACUCACAAGAAUCCUGAAAAAGGAUGCCAAACUCCCGACCCUCCCGUCGCCG |
| 25 | 1 | 57 | ACAGCUUAUUUGGAAGCUGAAAUGUGAGGUUUAUAACACUCACAAGAAUCCUGAAAAAGGAUGCCAAACGGACGAGCCUACCCGUCCCC |
| 26 | 1 | 58 | ACAGCUUAUUUGGAAGCUGAAAUGUGAGGUUUAUAACACUCACAAGAAUCCUGAAAAAGGAUGCCAAACUCGGGGGGCGGGGGGAGAA |
| 27 | 1 | 59 | ACAGCUUAUUUGGAAGCUGAAAUGUGAGGUUUAUAACACUCACAAGAAUCCUGAAAAAGGAUGCCAAACCAGACUGGCCCCAGAGAUGC |
| 28 | 1 | 125 | ACAGCUUAUUUGGAAGCUGAAAUGUGAGGUUUAUAACACUCACAAGAAUCCUGAAAAAGGAUGCCAAACAGCGUCAUUUGACGCUGUCU |
| 29 | 1 | 126 | ACAGCUUAUUUGGAAGCUGAAAUGUGAGGUUUAUAACACUCACAAGAAUCCUGAAAAAGGAUGCCAAACAAGAGCUGAUGCUCGCCCUC |
| 30 | 1 | 127 | ACAGCUUAUUUGGAAGCUGAAAUGUGAGGUUUAUAACACUCACAAGAAUCCUGAAAAAGGAUGCCAAACAGGCUAGAGGACUGAGCCAG |
| 31 | 1 | 128 | ACAGCUUAUUUGGAAGCUGAAAUGUGAGGUUUAUAACACUCACAAGAAUCCUGAAAAAGGAUGCCAAACCCCCACCGGCGCUGGUGCCC |
| 32 | 1 | 129 | ACAGCUUAUUUGGAAGCUGAAAUGUGAGGUUUAUAACACUCACAAGAAUCCUGAAAAAGGAUGCCAAACGGGUUUGUCCUCACUCUGA |
| 33 | 1 | 130 | ACAGCUUAUUUGGAAGCUGAAAUGUGAGGUUUAUAACACUCACAAGAAUCCUGAAAAAGGAUGCCAAACACGCUGUCUGGGGAGGGCGA |
| 34 | 1 | 131 | ACAGCUUAUUUGGAAGCUGAAAUGUGAGGUUUAUAACACUCACAAGAAUCCUGAAAAAGGAUGCCAAACGCCACCGCCACCUUCCGCCG |
| 35 | 1 | 132 | ACAGCUUAUUUGGAAGCUGAAAUGUGAGGUUUAUAACACUCACAAGAAUCCUGAAAAAGGAUGCCAAACCGUGGCUGCGGUGGCCGCUG |
| 36 | 1 | 133 | ACAGCUUAUUUGGAAGCUGAAAUGUGAGGUUUAUAACACUCACAAGAAUCCUGAAAAAGGAUGCCAAACCAGCCCAAUUAGGAUUUGGG |
| 37 | 1 | 134 | ACAGCUUAUUUGGAAGCUGAAAUGUGAGGUUUAUAACACUCACAAGAAUCCUGAAAAAGGAUGCCAAACGGGAGGGCGAGGCCGAAACC |
| 38 | 1 | 135 | ACAGCUUAUUUGGAAGCUGAAAUGUGAGGUUUAUAACACUCACAAGAAUCCUGAAAAAGGAUGCCAAACUCCUCACUCUGAGCGUCAUU |

TABLE 7-continued

Exemplary sgRNA for CasM.265466

| Comp. No. | Effector Protein SEQ ID NO | sgRNA SEQ ID NO | sgRNA |
|---|---|---|---|
| 39 | 1 | 136 | ACAGCUUAUUUGGAAGCUGAAAUGUGAGGUUUAUAACA CUCACAAGAAUCCUGAAAAAGGAUGCCAAACGGGAGC CAAGGACUGGCUCA |
| 40 | 1 | 137 | ACAGCUUAUUUGGAAGCUGAAAUGUGAGGUUUAUAACA CUCACAAGAAUCCUGAAAAAGGAUGCCAAACGGGUGU GGGUACUGGACGCC |
| 41 | 1 | 138 | ACAGCUUAUUUGGAAGCUGAAAUGUGAGGUUUAUAACA CUCACAAGAAUCCUGAAAAAGGAUGCCAAACGGUACU GGACGCCUGGGGGC |
| 42 | 1 | 139 | ACAGCUUAUUUGGAAGCUGAAAUGUGAGGUUUAUAACA CUCACAAGAAUCCUGAAAAAGGAUGCCAAACAUUAAA CAUUAACGGGCCCC |
| 43 | 1 | 140 | ACAGCUUAUUUGGAAGCUGAAAUGUGAGGUUUAUAACA CUCACAAGAAUCCUGAAAAAGGAUGCCAAACCGGCCU CAUCAGCCAGGCCA |
| 44 | 1 | 141 | ACAGCUUAUUUGGAAGCUGAAAUGUGAGGUUUAUAACA CUCACAAGAAUCCUGAAAAAGGAUGCCAAACUCAUCA AGGUUCUACAUAUC |
| 45 | 1 | 142 | ACAGCUUAUUUGGAAGCUGAAAUGUGAGGUUUAUAACA CUCACAAGAAUCCUGAAAAAGGAUGCCAAACACCUCU UCCCUGGCUUCUUG |
| 46 | 1 | 143 | ACAGCUUAUUUGGAAGCUGAAAUGUGAGGUUUAUAACA CUCACAAGAAUCCUGAAAAAGGAUGCCAAACGUGCUG AUGGAGGAGACCCA |
| 47 | 1 | 144 | ACAGCUUAUUUGGAAGCUGAAAUGUGAGGUUUAUAACA CUCACAAGAAUCCUGAAAAAGGAUGCCAAACGGUCUC CUCCAUCAGCACCA |
| 48 | 1 | 145 | ACAGCUUAUUUGGAAGCUGAAAUGUGAGGUUUAUAACA CUCACAAGAAUCCUGAAAAAGGAUGCCAAACCAGGCG GUGGGCAGUUUGUU |
| 49 | 1 | 146 | ACAGCUUAUUUGGAAGCUGAAAUGUGAGGUUUAUAACA CUCACAAGAAUCCUGAAAAAGGAUGCCAAACUAGAAC CUUGAUGACAUAGC |
| 50 | 1 | 147 | ACAGCUUAUUUGGAAGCUGAAAUGUGAGGUUUAUAACA CUCACAAGAAUCCUGAAAAAGGAUGCCAAACUAGCCU CUGGGUCUCCUCCA |
| 5 | 1 | 148 | ACAGCUUAUUUGGAAGCUGAAAUGUGAGGUUUAUAACA CUCACAAGAAUCCUGAAAAAGGAUGCCAAACUUCAAU CUGUAGCCUCUGGG |
| 52 | 1 | 149 | ACAGCUUAUUUGGAAGCUGAAAUGUGAGGUUUAUAACA CUCACAAGAAUCCUGAAAAAGGAUGCCAAACUCUUCG CCCAGAGCAUCCCA |
| 53 | 1 | 150 | ACAGCUUAUUUGGAAGCUGAAAUGUGAGGUUUAUAACA CUCACAAGAAUCCUGAAAAAGGAUGCCAAACGAGUAC AUUGAGGAAGACUC |
| 54 | 1 | 151 | ACAGCUUAUUUGGAAGCUGAAAUGUGAGGUUUAUAACA CUCACAAGAAUCCUGAAAAAGGAUGCCAAACUCUGGU GCCAUGCUGGGAUA |
| 55 | 1 | 152 | ACAGCUUAUUUGGAAGCUGAAAUGUGAGGUUUAUAACA CUCACAAGAAUCCUGAAAAAGGAUGCCAAACGUGCCA UGCUGGGAUAAUUC |
| 56 | 1 | 153 | ACAGCUUAUUUGGAAGCUGAAAUGUGAGGUUUAUAACA CUCACAAGAAUCCUGAAAAAGGAUGCCAAACGGCGAA GACAAAGGAGUCUU |

TABLE 7-continued

Exemplary sgRNA for CasM.265466

| Comp. No. | Effector Protein SEQ ID NO | sgRNA SEQ ID NO | sgRNA |
|---|---|---|---|
| 57 | 1 | 154 | ACAGCUUAUUUGGAAGCUGAAAUGUGAGGUUUAUAACACUCACAAGAAUCCUGAAAAAGGAUGCCAAACGAAGCGUGUCCCAUCCUCCU |
| 58 | 1 | 155 | ACAGCUUAUUUGGAAGCUGAAAUGUGAGGUUUAUAACACUCACAAGAAUCCUGAAAAAGGAUGCCAAACUGGAAGCGUGUCCCAUCCUC |
| 59 | 1 | 156 | ACAGCUUAUUUGGAAGCUGAAAUGUGAGGUUUAUAACACUCACAAGAAUCCUGAAAAAGGAUGCCAAACACAGCCACGGCACCCACCUG |
| 60 | 1 | 157 | ACAGCUUAUUUGGAAGCUGAAAUGUGAGGUUUAUAACACUCACAAGAAUCCUGAAAAAGGAUGCCAAACCUCAACUGUCAAGGGAAGGG |
| 61 | 1 | 158 | ACAGCUUAUUUGGAAGCUGAAAUGUGAGGUUUAUAACACUCACAAGAAUCCUGAAAAAGGAUGCCAAACGCCAAGGGCACCAGCCUGCA |
| 62 | 1 | 159 | ACAGCUUAUUUGGAAGCUGAAAUGUGAGGUUUAUAACACUCACAAGAAUCCUGAAAAAGGAUGCCAAACGUCAGCGGCCGGGAUGCUGG |
| 63 | 1 | 160 | ACAGCUUAUUUGGAAGCUGAAAUGUGAGGUUUAUAACACUCACAAGAAUCCUGAAAAAGGAUGCCAAACCAGGCUGGUGCCCUUGGCCA |
| 64 | 1 | 161 | ACAGCUUAUUUGGAAGCUGAAAUGUGAGGUUUAUAACACUCACAAGAAUCCUGAAAAAGGAUGCCAAACAGGGUGCCGCUGACUGUGCC |
| 65 | 1 | 162 | ACAGCUUAUUUGGAAGCUGAAAUGUGAGGUUUAUAACACUCACAAGAAUCCUGAAAAAGGAUGCCAAACCCCUUCCCUUGACAGUUGAG |
| 66 | 1 | 163 | ACAGCUUAUUUGGAAGCUGAAAUGUGAGGUUUAUAACACUCACAAGAAUCCUGAAAAAGGAUGCCAAACCUGCCCUGGCCGGUGGGUA |
|  | 1 | 164 | ACAGCUUAUUUGGAAGCUGAAAUGUGAGGUUUAUAACACUCACAAGAAUCCUGAAAAAGGAUGCCAAACGAGCAGAAGCUGGGGAGUAG |
| 68 | 1 | 165 | ACAGCUUAUUUGGAAGCUGAAAUGUGAGGUUUAUAACACUCACAAGAAUCCUGAAAAAGGAUGCCAAACGAUCUCUUUGCCCCGGGAA |
| 69 | 1 | 166 | ACAGCUUAUUUGGAAGCUGAAAUGUGAGGUUUAUAACACUCACAAGAAUCCUGAAAAAGGAUGCCAAACGGGACUAAUUUUGGACGCUG |
| 70 | 1 | 167 | ACAGCUUAUUUGGAAGCUGAAAUGUGAGGUUUAUAACACUCACAAGAAUCCUGAAAAAGGAUGCCAAACUGGAUCUCUUUGCCCCGGG |
| 71 | 1 | 168 | ACAGCUUAUUUGGAAGCUGAAAUGUGAGGUUUAUAACACUCACAAGAAUCCUGAAAAAGGAUGCCAAACCCCCCGGGAAGGACAUCAUC |
| 72 | 1 | 169 | ACAGCUUAUUUGGAAGCUGAAAUGUGAGGUUUAUAACACUCACAAGAAUCCUGAAAAAGGAUGCCAAACGACGCUGUGUGGAUCUCUUU |
| 73 | 1 | 170 | ACAGCUUAUUUGGAAGCUGAAAUGUGAGGUUUAUAACACUCACAAGAAUCCUGAAAAAGGAUGCCAAACACAUGAAGCAUGUGCUGCAG |
| 74 | 1 | 171 | ACAGCUUAUUUGGAAGCUGAAAUGUGAGGUUUAUAACACUCACAAGAAUCCUGAAAAAGGAUGCCAAACCUGCAGUCACUGGACGCUCC |

TABLE 7-continued

Exemplary sgRNA for CasM.265466

| Comp. No. | Effector Protein SEQ ID NO | sgRNA SEQ ID NO | sgRNA |
|---|---|---|---|
| 75 | 1 | 172 | *ACAGCUUAUUUGGAAGCUGAAAUGUGAGGUUUAUAACA CUCACAAGAAUCCU*GAAAAAGGAUGCCAAACAGGUCC CACUCUGUGACAUG |
| 76 | 1 | 173 | *ACAGCUUAUUUGGAAGCUGAAAUGUGAGGUUUAUAACA CUCACAAGAAUCCU*GAAAAAGGAUGCCAAACUGACAU GAAGCAUGUGCUGC |
| 77 | 1 | 174 | *ACAGCUUAUUUGGAAGCUGAAAUGUGAGGUUUAUAACA CUCACAAGAAUCCU*GAAAAAGGAUGCCAAACGCUCGG AUGCUGAGCCGGGA |
|    | 1 | 175 | *ACAGCUUAUUUGGAAGCUGAAAUGUGAGGUUUAUAACA CUCACAAGAAUCCU*GAAAAAGGAUGCCAAACGUAGAG AAGUGGAUCAGCCU |
| 79 | 1 | 176 | *ACAGCUUAUUUGGAAGCUGAAAUGUGAGGUUUAUAACA CUCACAAGAAUCCU*GAAAAAGGAUGCCAAACGCCACC AGGUUGGGGGUCAG |
| 80 | 1 | 177 | *ACAGCUUAUUUGGAAGCUGAAAUGUGAGGUUUAUAACA CUCACAAGAAUCCU*GAAAAAGGAUGCCAAACGGCUCC CGGCUCAGCAUCCG |
| 81 | 1 | 178 | *ACAGCUUAUUUGGAAGCUGAAAUGUGAGGUUUAUAACA CUCACAAGAAUCCU*GAAAAAGGAUGCCAAACCCGCAG CUCGGCCAGGGUAA |
| 82 | 1 | 179 | *ACAGCUUAUUUGGAAGCUGAAAUGUGAGGUUUAUAACA CUCACAAGAAUCCU*GAAAAAGGAUGCCAAACCCCCAG AAGAGGAGCUGCUG |
| 83 | 1 | 180 | *ACAGCUUAUUUGGAAGCUGAAAUGUGAGGUUUAUAACA CUCACAAGAAUCCU*GAAAAAGGAUGCCAAACUAGGAC GGUGUGGUCGGCAC |
| 84 | 1 | 181 | *ACAGCUUAUUUGGAAGCUGAAAUGUGAGGUUUAUAACA CUCACAAGAAUCCU*GAAAAAGGAUGCCAAACGUCGGC ACACUCGGGGCCCA |
| 85 | 1 | 182 | *ACAGCUUAUUUGGAAGCUGAAAUGUGAGGUUUAUAACA CUCACAAGAAUCCU*GAAAAAGGAUGCCAAACCCGACC ACACCGUCCUACAG |
| 86 | 1 | 183 | *ACAGCUUAUUUGGAAGCUGAAAUGUGAGGUUUAUAACA CUCACAAGAAUCCU*GAAAAAGGAUGCCAAACGGGCAC AGCGGGCUGUAGCU |
| 87 | 1 | 184 | *ACAGCUUAUUUGGAAGCUGAAAUGUGAGGUUUAUAACA CUCACAAGAAUCCU*GAAAAAGGAUGCCAAACCAAGGC CCUCAAUGCAUUUG |
| 88 | 1 | 185 | *ACAGCUUAUUUGGAAGCUGAAAUGUGAGGUUUAUAACA CUCACAAGAAUCCU*GAAAAAGGAUGCCAAACCCGUCG CGAGAUGCUGCCUG |
| 89 | 1 | 186 | *ACAGCUUAUUUGGAAGCUGAAAUGUGAGGUUUAUAACA CUCACAAGAAUCCU*GAAAAAGGAUGCCAAACGGGGUG AGGGUGUCUAUGCC |
| 90 | 1 | 187 | *ACAGCUUAUUUGGAAGCUGAAAUGUGAGGUUUAUAACA CUCACAAGAAUCCU*GAAAAAGGAUGCCAAACGCUGCA GGGGUGUUGUGGAU |
| 91 | 1 | 188 | *ACAGCUUAUUUGGAAGCUGAAAUGUGAGGUUUAUAACA CUCACAAGAAUCCU*GAAAAAGGAUGCCAAACAGAACA UGGUCCUUCUGGUG |
| 92 | 1 | 189 | *ACAGCUUAUUUGGAAGCUGAAAUGUGAGGUUUAUAACA CUCACAAGAAUCCU*GAAAAAGGAUGCCAAACGUGGCA GUGGACAUGGGUCU |

TABLE 7-continued

Exemplary sgRNA for CasM.265466

| Comp. No. | Effector Protein SEQ ID NO | sgRNA SEQ ID NO | sgRNA |
|---|---|---|---|
| 93 | 1 | 190 | ACAGCUUAUUUGGAAGCUGAAAUGUGAGGUUUAUAACA<br>CUCACAAGAAUCCUGAAAAAGGAUGCCAAACGAUGCU<br>GCAGUUGGCACGGG |
| 94 | 1 | 191 | ACAGCUUAUUUGGAAGCUGAAAUGUGAGGUUUAUAACA<br>CUCACAAGAAUCCUGAAAAAGGAUGCCAAACCUUCCU<br>GCUGCCAUGCCCCA |
| 95 | 1 | 192 | ACAGCUUAUUUGGAAGCUGAAAUGUGAGGUUUAUAACA<br>CUCACAAGAAUCCUGAAAAAGGAUGCCAAACCAUUCC<br>AGCCCUGGGGCAUG |
| 96 | 1 | 193 | ACAGCUUAUUUGGAAGCUGAAAUGUGAGGUUUAUAACA<br>CUCACAAGAAUCCUGAAAAAGGAUGCCAAACAAGGAC<br>CUGAGAUCCCAUGC |
| 97 | 1 | 194 | ACAGCUUAUUUGGAAGCUGAAAUGUGAGGUUUAUAACA<br>CUCACAAGAAUCCUGAAAAAGGAUGCCAAACGACCUC<br>AGCGCAGGCUGCCU |
| 98 | 1 | 195 | ACAGCUUAUUUGGAAGCUGAAAUGUGAGGUUUAUAACA<br>CUCACAAGAAUCCUGAAAAAGGAUGCCAAACAAAGCC<br>ACAAGGACAGUCAA |
| 99 | 1 | 196 | ACAGCUUAUUUGGAAGCUGAAAUGUGAGGUUUAUAACA<br>CUCACAAGAAUCCUGAAAAAGGAUGCCAAACGAAGCA<br>CCUCCUUCACGGUC |
| 100 | 1 | 197 | ACAGCUUAUUUGGAAGCUGAAAUGUGAGGUUUAUAACA<br>CUCACAAGAAUCCUGAAAAAGGAUGCCAAACGCCAGC<br>UGCUCCAGUGUACC |
| 101 | 1 | 198 | ACAGCUUAUUUGGAAGCUGAAAUGUGAGGUUUAUAACA<br>CUCACAAGAAUCCUGAAAAAGGAUGCCAAACAGCUCU<br>UCUGUCUUUUUAUA |
| 102 | 1 | 199 | ACAGCUUAUUUGGAAGCUGAAAUGUGAGGUUUAUAACA<br>CUCACAAGAAUCCUGAAAAAGGAUGCCAAACGCCUGC<br>GAAGCAGGAUGGAC |
| 103 | 1 | 200 | ACAGCUUAUUUGGAAGCUGAAAUGUGAGGUUUAUAACA<br>CUCACAAGAAUCCUGAAAAAGGAUGCCAAACUAGUGA<br>CUUUUCAGAAUAAA |
| 104 | 1 | 201 | ACAGCUUAUUUGGAAGCUGAAAUGUGAGGUUUAUAACA<br>CUCACAAGAAUCCUGAAAAAGGAUGCCAAACUGGCAA<br>GAGUCCAUGACACU |
| 105 | 1 | 202 | ACAGCUUAUUUGGAAGCUGAAAUGUGAGGUUUAUAACA<br>CUCACAAGAAUCCUGAAAAAGGAUGCCAAACUGUGGC<br>AAGAGUCCAUGACA |
| 106 | 1 | 203 | ACAGCUUAUUUGGAAGCUGAAAUGUGAGGUUUAUAACA<br>CUCACAAGAAUCCUGAAAAAGGAUGCCAAACCUGCCG<br>GAGCCGGCCUUCAG |
| 107 | 1 | 204 | ACAGCUUAUUUGGAAGCUGAAAUGUGAGGUUUAUAACA<br>CUCACAAGAAUCCUGAAAAAGGAUGCCAAACGCUUGC<br>UCCUGGACCUAUAC |
| 108 | 1 | 205 | ACAGCUUAUUUGGAAGCUGAAAUGUGAGGUUUAUAACA<br>CUCACAAGAAUCCUGAAAAAGGAUGCCAAACCUUGGC<br>UUUCUGCCAUCAGA |
| 109 | 1 | 206 | ACAGCUUAUUUGGAAGCUGAAAUGUGAGGUUUAUAACA<br>CUCACAAGAAUCCUGAAAAAGGAUGCCAAACGGAGCC<br>UACAGCGUGGACAA |
| 110 | 1 | 207 | ACAGCUUAUUUGGAAGCUGAAAUGUGAGGUUUAUAACA<br>CUCACAAGAAUCCUGAAAAAGGAUGCCAAACCCAUCA<br>GACAUUAAGCUGUA |

TABLE 7-continued

Exemplary sgRNA for CasM.265466

| Comp. No. | Effector Protein SEQ ID NO | sgRNA SEQ ID NO | sgRNA |
|---|---|---|---|
| 111 | 1 | 208 | ACAGCUUAUUUGGAAGCUGAAAUGUGAGGUUUAUAACA CUCACAAGAAUCCUGAAAAAGGAUGCCAAACCACACC UCCAGGGGUGGAUC |
| 112 | 1 | 209 | ACAGCUUAUUUGGAAGCUGAAAUGUGAGGUUUAUAACA CUCACAAGAAUCCUGAAAAAGGAUGCCAAACCCUGCA UGGCUCUCUUGUAG |
| 113 | 1 | 210 | ACAGCUUAUUUGGAAGCUGAAAUGUGAGGUUUAUAACA CUCACAAGAAUCCUGAAAAAGGAUGCCAAACCAGGGU UUUGUAGUUUUUAU |
| 114 | 1 | 211 | ACAGCUUAUUUGGAAGCUGAAAUGUGAGGUUUAUAACA CUCACAAGAAUCCUGAAAAAGGAUGCCAAACUACUGG AGAACCAUACAGGA |
| 115 | 1 | 212 | ACAGCUUAUUUGGAAGCUGAAAUGUGAGGUUUAUAACA CUCACAAGAAUCCUGAAAAAGGAUGCCAAACUUGCUU UUGUAACUUGAUAU |
| 116 | 1 | 213 | ACAGCUUAUUUGGAAGCUGAAAUGUGAGGUUUAUAACA CUCACAAGAAUCCUGAAAAAGGAUGCCAAACAGCCCU CAUCUGACUCUCAG |
| 117 | 1 | 214 | ACAGCUUAUUUGGAAGCUGAAAUGUGAGGUUUAUAACA CUCACAAGAAUCCUGAAAAAGGAUGCCAAACCUCCCU GGGGCAUCCCUCAC |
| 118 | 1 | 215 | ACAGCUUAUUUGGAAGCUGAAAUGUGAGGUUUAUAACA CUCACAAGAAUCCUGAAAAAGGAUGCCAAACUCUUUC AGGAAGAUCAUAAU |
| 119 | 1 | 216 | ACAGCUUAUUUGGAAGCUGAAAUGUGAGGUUUAUAACA CUCACAAGAAUCCUGAAAAAGGAUGCCAAACUCUUUU UAUAGUAAGCUUCC |
| 120 | 1 | 217 | ACAGCUUAUUUGGAAGCUGAAAUGUGAGGUUUAUAACA CUCACAAGAAUCCUGAAAAAGGAUGCCAAACCUGCAG GGCUUUGGCCCUGC |
| 121 | 1 | 218 | ACAGCUUAUUUGGAAGCUGAAAUGUGAGGUUUAUAACA CUCACAAGAAUCCUGAAAAAGGAUGCCAAACCUAUGA GCCCUCAUCUGACU |
| 122 | 1 | 219 | ACAGCUUAUUUGGAAGCUGAAAUGUGAGGUUUAUAACA CUCACAAGAAUCCUGAAAAAGGAUGCCAAACACUCUC AGUUUGUACUGGAG |
| 123 | 1 | 220 | ACAGCUUAUUUGGAAGCUGAAAUGUGAGGUUUAUAACA CUCACAAGAAUCCUGAAAAAGGAUGCCAAACGUGGG AGAACUUGGUGUCU |
| 124 | 1 | 221 | ACAGCUUAUUUGGAAGCUGAAAUGUGAGGUUUAUAACA CUCACAAGAAUCCUGAAAAAGGAUGCCAAACGCAAGA GUCCAUGACACUGC |
| 125 | 1 | 222 | ACAGCUUAUUUGGAAGCUGAAAUGUGAGGUUUAUAACA CUCACAAGAAUCCUGAAAAAGGAUGCCAAACCACUGA CUGGCCUCAUUUUA |
| 126 | 1 | 223 | ACAGCUUAUUUGGAAGCUGAAAUGUGAGGUUUAUAACA CUCACAAGAAUCCUGAAAAAGGAUGCCAAACAAGGAA GAGACAGGACCAGA |
| 127 | 1 | 224 | ACAGCUUAUUUGGAAGCUGAAAUGUGAGGUUUAUAACA CUCACAAGAAUCCUGAAAAAGGAUGCCAAACUAACUU GAUAUUUAUGCAGG |
| 128 | 1 | 225 | ACAGCUUAUUUGGAAGCUGAAAUGUGAGGUUUAUAACA CUCACAAGAAUCCUGAAAAAGGAUGCCAAACGGCUCC CUGAUUAAAUGCAG |

TABLE 7-continued

Exemplary sgRNA for CasM.265466

| Comp. No. | Effector Protein SEQ ID NO | sgRNA SEQ ID NO | sgRNA |
|---|---|---|---|
| 129 | 1 | 226 | ACAGCUUAUUUGGAAGCUGAAAUGUGAGGUUUAUAACA CUCACAAGAAUCCUGAAAAAGGAUGCCAAACGCCCUG CUCAGGAUAAUGUG |
| 130 | 1 | 227 | ACAGCUUAUUUGGAAGCUGAAAUGUGAGGUUUAUAACA CUCACAAGAAUCCUGAAAAAGGAUGCCAAACAACCUC CAAGGAUCUCUGUC |
| 131 | 1 | 228 | ACAGCUUAUUUGGAAGCUGAAAUGUGAGGUUUAUAACA CUCACAAGAAUCCUGAAAAAGGAUGCCAAACCUGAAG GCCGGCUCCGGCAG |
| 132 | 1 | 229 | ACAGCUUAUUUGGAAGCUGAAAUGUGAGGUUUAUAACA CUCACAAGAAUCCUGAAAAAGGAUGCCAAACAAUUUA UGUCCUGACAUCAC |
| 133 | 1 | 230 | ACAGCUUAUUUGGAAGCUGAAAUGUGAGGUUUAUAACA CUCACAAGAAUCCUGAAAAAGGAUGCCAAACAGUUGA CUGUCCUUGUGGCU |
| 134 | 1 | 231 | ACAGCUUAUUUGGAAGCUGAAAUGUGAGGUUUAUAACA CUCACAAGAAUCCUGAAAAAGGAUGCCAAACUGGGAC UGGGGCUAAGGGAG |
| 135 | 1 | 232 | ACAGCUUAUUUGGAAGCUGAAAUGUGAGGUUUAUAACA CUCACAAGAAUCCUGAAAAAGGAUGCCAAACGAAGAU AUAGGUAUGGCCUU |
| 136 | 1 | 233 | ACAGCUUAUUUGGAAGCUGAAAUGUGAGGUUUAUAACA CUCACAAGAAUCCUGAAAAAGGAUGCCAAACACAUCG CCUCUCUGGUCCUG |
| 137 | 1 | 234 | ACAGCUUAUUUGGAAGCUGAAAUGUGAGGUUUAUAACA CUCACAAGAAUCCUGAAAAAGGAUGCCAAACGUUCUC CAGUACAAACUGAG |
| 138 | 1 | 235 | ACAGCUUAUUUGGAAGCUGAAAUGUGAGGUUUAUAACA CUCACAAGAAUCCUGAAAAAGGAUGCCAAACGUCCUG UCUCUUCCUUCAUA |
| 139 | 1 | 236 | ACAGCUUAUUUGGAAGCUGAAAUGUGAGGUUUAUAACA CUCACAAGAAUCCUGAAAAAGGAUGCCAAACGCCUUG GUACAGUCGCCCUC |
| 140 | 1 | 237 | ACAGCUUAUUUGGAAGCUGAAAUGUGAGGUUUAUAACA CUCACAAGAAUCCUGAAAAAGGAUGCCAAACGCUACA AGAGAGCCAUGCAG |
| 141 | 1 | 238 | ACAGCUUAUUUGGAAGCUGAAAUGUGAGGUUUAUAACA CUCACAAGAAUCCUGAAAAAGGAUGCCAAACCUCUGG CAGUGUCAUGGACU |
| 142 | 1 | 239 | ACAGCUUAUUUGGAAGCUGAAAUGUGAGGUUUAUAACA CUCACAAGAAUCCUGAAAAAGGAUGCCAAACGCUUCU CCACUGGUCCUGUC |
| 143 | 1 | 240 | ACAGCUUAUUUGGAAGCUGAAAUGUGAGGUUUAUAACA CUCACAAGAAUCCUGAAAAAGGAUGCCAAACCAUUUA AUCAGGGAGCCCAA |
| 144 | 1 | 241 | ACAGCUUAUUUGGAAGCUGAAAUGUGAGGUUUAUAACA CUCACAAGAAUCCUGAAAAAGGAUGCCAAACUCCAUU AUGAUCUUCCUGAA |
| 145 | 1 | 242 | ACAGCUUAUUUGGAAGCUGAAAUGUGAGGUUUAUAACA CUCACAAGAAUCCUGAAAAAGGAUGCCAAACAGCUGG CUGUGAGUUGACUG |
| 146 | 1 | 243 | ACAGCUUAUUUGGAAGCUGAAAUGUGAGGUUUAUAACA CUCACAAGAAUCCUGAAAAAGGAUGCCAAACCAGAAC UGAUCUGCAUUUAA |

TABLE 7-continued

Exemplary sgRNA for CasM.265466

| Comp. No. | Effector Protein SEQ ID NO | sgRNA SEQ ID NO | sgRNA |
|---|---|---|---|
| 147 | 1 | 244 | ACAGCUUAUUUGGAAGCUGAAAUGUGAGGUUUAUAACACUCACAAGAAUCCUGAAAAAGGAUGCCAAACGCCUUACAGCUGGAUCCACC |
| 148 | 1 | 245 | ACAGCUUAUUUGGAAGCUGAAAUGUGAGGUUUAUAACACUCACAAGAAUCCUGAAAAAGGAUGCCAAACGCAGUGUCAUGGACUCUUGC |
| 149 | 1 | 246 | ACAGCUUAUUUGGAAGCUGAAAUGUGAGGUUUAUAACACUCACAAGAAUCCUGAAAAAGGAUGCCAAACCAAUGUGAGCUGGCUGUGAG |
| 150 | 1 | 247 | ACAGCUUAUUUGGAAGCUGAAAUGUGAGGUUUAUAACACUCACAAGAAUCCUGAAAAAGGAUGCCAAACGGACUGGGGCUAAGGGAGUA |
| 151 | 1 | 248 | ACAGCUUAUUUGGAAGCUGAAAUGUGAGGUUUAUAACACUCACAAGAAUCCUGAAAAAGGAUGCCAAACGUACUUGGUCUUUGAACCUC |
| 152 | 1 | 249 | ACAGCUUAUUUGGAAGCUGAAAUGUGAGGUUUAUAACACUCACAAGAAUCCUGAAAAAGGAUGCCAAACUCCUGACAUCACUGGCUGUG |
| 153 | 1 | 250 | ACAGCUUAUUUGGAAGCUGAAAUGUGAGGUUUAUAACACUCACAAGAAUCCUGAAAAAGGAUGCCAAACUCACUCCAGUCUCCACCUGA |
| 154 | 1 | 251 | ACAGCUUAUUUGGAAGCUGAAAUGUGAGGUUUAUAACACUCACAAGAAUCCUGAAAAAGGAUGCCAAACGCUUUCAGACUCAAUUUUCC |
| 155 | 1 | 252 | ACAGCUUAUUUGGAAGCUGAAAUGUGAGGUUUAUAACACUCACAAGAAUCCUGAAAAAGGAUGCCAAACAUGGCAGAAAGCCAAGCACA |
| 156 | 1 | 253 | ACAGCUUAUUUGGAAGCUGAAAUGUGAGGUUUAUAACACUCACAAGAAUCCUGAAAAAGGAUGCCAAACUGACAUCGCCUCUCUGGUCC |
| 157 | 1 | 254 | ACAGCUUAUUUGGAAGCUGAAAUGUGAGGUUUAUAACACUCACAAGAAUCCUGAAAAAGGAUGCCAAACCUGGUCAGCUGGUGUGGCCU |
| 158 | 1 | 255 | ACAGCUUAUUUGGAAGCUGAAAUGUGAGGUUUAUAACACUCACAAGAAUCCUGAAAAAGGAUGCCAAACAUCUUCCUGAAAGACAAAUA |
| 159 | 1 | 256 | ACAGCUUAUUUGGAAGCUGAAAUGUGAGGUUUAUAACACUCACAAGAAUCCUGAAAAAGGAUGCCAAACCACCCAGCCUCAAGCACCAU |
| 160 | 1 | 257 | ACAGCUUAUUUGGAAGCUGAAAUGUGAGGUUUAUAACACUCACAAGAAUCCUGAAAAAGGAUGCCAAACGUACACUGGAGCAGCUGGCC |
| 161 | 1 | 260 | ACAGCUUAUUUGGAAGCUGAAAUGUGAGGUUUAUAACACUCACAAGAAUCCUGAAAAAGGAUGCCAAACUUCACUAGCAACCUCAAACA |
| 162 | 1 | 261 | ACAGCUUAUUUGGAAGCUGAAAUGUGAGGUUUAUAACACUCACAAGAAUCCUGAAAAAGGAUGCCAAACACUCCUGAGGAGAAGUCUGC |
| 163 | 1 | 262 | ACAGCUUAUUUGGAAGCUGAAAUGUGAGGUUUAUAACACUCACAAGAAUCCUGAAAAAGGAUGCCAAACAAGCUAGUCUAGUGCAAGCU |
| 164 | 1 | 263 | ACAGCUUAUUUGGAAGCUGAAAUGUGAGGUUUAUAACACUCACAAGAAUCCUGAAAAAGGAUGCCAAACGUGCAAGCUAACAGUUGCUU |

TABLE 7-continued

Exemplary sgRNA for CasM.265466

| Comp. No. | Effector Protein SEQ ID NO | sgRNA SEQ ID NO | sgRNA |
|---|---|---|---|
| 165 | 1 | 264 | ACAGCUUAUUUGGAAGCUGAAAUGUGAGGUUUAUAACACUCACAAGAAUCCUGAAAAAGGAUGCCAAACCCUUGUCAAGGCUAUUGGUC |
| 166 | 1 | 265 | ACAGCUUAUUUGGAAGCUGAAAUGUGAGGUUUAUAACACUCACAAGAAUCCUGAAAAAGGAUGCCAAACCAUUGAGAUAGUGUGGGGAA |
| 167 | 1 | 266 | ACAGCUUAUUUGGAAGCUGAAAUGUGAGGUUUAUAACACUCACAAGAAUCCUGAAAAAGGAUGCCAAACCUCGCGCUACUCUCUCUUUC |
| 168 | 1 | 267 | ACAGCUUAUUUGGAAGCUGAAAUGUGAGGUUUAUAACACUCACAAGAAUCCUGAAAAAGGAUGCCAAACGGUUUCAUCCAUCCGACAUU |
| 169 | 1 | 268 | ACAGCUUAUUUGGAAGCUGAAAUGUGAGGUUUAUAACACUCACAAGAAUCCUGAAAAAGGAUGCCAAACUCUCUUGUACUACACUGAAU |
| 170 | 1 | 43 | ACAGCUUAUUUGGAAGCUGAAAUGUGAGGUUUAUAACACUCACAAGAAUCCUGAAAAAGGAUGCCAAACCUCACGUCAUCCAGCAGAGA |
| 171 | - | 270 | ACAGCUUAUUUGGAAGCUGAAAUGUGAGGUUUAUAACACUCACAAGAAUCCUGAAAAAGGAUGCCAAACCCUGCCGUGUGAACCAUGUG |
| 172 | 1 | 42 | ACAGCUUAUUUGGAAGCUGAAAUGUGAGGUUUAUAACACUCACAAGAAUCCUGAAAAAGGAUGCCAAACUCACAGCCCAAGAUAGUUAA |
| 173 | 1 | 272 | ACAGCUUAUUUGGAAGCUGAAAUGUGAGGUUUAUAACACUCACAAGAAUCCUGAAAAAGGAUGCCAAACACUUUGUCACAGCCCAAGAU |
| 174 | 1 | 273 | ACAGCUUAUUUGGAAGCUGAAAUGUGAGGUUUAUAACACUCACAAGAAUCCUGAAAAAGGAUGCCAAACUCUGGGUUUCAUCCAUCCGA |
| 175 | 1 | 274 | ACAGCUUAUUUGGAAGCUGAAAUGUGAGGUUUAUAACACUCACAAGAAUCCUGAAAAAGGAUGCCAAACAACCAUGUGACUUUGUCACA |
| 176 | 1 | 275 | ACAGCUUAUUUGGAAGCUGAAAUGUGAGGUUUAUAACACUCACAAGAAUCCUGAAAAAGGAUGCCAAACAAUGCUCCACUUUUUCAAUU |
| 177 | 1 | 276 | ACAGCUUAUUUGGAAGCUGAAAUGUGAGGUUUAUAACACUCACAAGAAUCCUGAAAAAGGAUGCCAAACACUUUCCAUUCUCUGCUGGA |
| 178 | 1 | 277 | ACAGCUUAUUUGGAAGCUGAAAUGUGAGGUUUAUAACACUCACAAGAAUCCUGAAAAAGGAUGCCAAACACAAAGUCACAUGGUUCACA |
| 179 | 1 | 278 | ACAGCUUAUUUGGAAGCUGAAAUGUGAGGUUUAUAACACUCACAAGAAUCCUGAAAAAGGAUGCCAAACGUACAAGAGAUAGAAAGACC |
| 180 | 1 | 279 | ACAGCUUAUUUGGAAGCUGAAAUGUGAGGUUUAUAACACUCACAAGAAUCCUGAAAAAGGAUGCCAAACCUGGAUGACGUGAGUAAACC |
| 247 | 1 | 869 | ACAGCUUAUUUGGAAGCUGAAAUGUGAGGUUUAUAACACUCACAAGAAUCCUGAAAAAGGAUGCCAAACACCAAAAAAUAUACGCUAUA |
| 248 | 1 | 944 | GACAGCUUAUUUGGAAGCUGAAAUGUGAGGUUUAUAACACUCACAAGAAUCCUGAAAAAGGAUGCCAAACAUCUUGGAACUACUGUAUCG |

TABLE 7-continued

Exemplary sgRNA for CasM.265466

| Comp. No. | Effector Protein SEQ ID NO | sgRNA SEQ ID NO | sgRNA |
|---|---|---|---|
| 249 | 1 | 956 | *ACAGCUUAUUUGGAAGCUGAAAUGUGAGGUUUAUAA CACUCACAAGAAUCCU*GAAA<u>AAGGAUGCCAAAC</u>- [SPACER] |
| 250 | 1 | 957 | UGGGGCAGUUGGUUGCCCUUAGCCUGAGGCAUUUAUU GCACUCGGGAAGUACCAUUUCUCAGAAAUGGUACAUCC AACUAUUAAAUACUCGUAUUGCU |
| 251 | 1 | 958 | *ACAGCUUAUUUGGAAGCUGAAAUGUGAGGUUUAUAACA CUCACAAGAAUCCU*GAAA<u>AAGGAUGCCAAAC</u>AGUCUC CAGGAAGAAAUUAA |
| 252 | 1 | 1019 | *UGGGGCAGUUGGUUGCCCUUAGCCUGAGGCAUUUAUU GCACUCGGGAAGUACCA*GAAA<u>UGGUACAUCCAACUAU</u> UAAAUACUCGUAUUGCU |
| 253 | 1 | 1020 | *AGGGCGUGUUGGAGCGCCUUAGUUUGAGGUAUCAAGC ACUCAAAAAAUCUAC*GAAA<u>GUGGAUAUCCAACUAUUA</u> AAUACUCGUAUUGCU |
| 254 | 1 | 1021 | *ACGGGUGGUUGUACACCCGAAGAGUGAGGUCUUAACG GGCACUCGCUAAUCUGAU*GAAA<u>AGCAGAAUACAACU</u> AUUAAAUACUCGUAUUGCU |
| 255 | 1 | 1022 | *UGGGCGCGUUGGAGCGCCUUGGUUCGAGGUUCCCUG CACUCGAAAAAUUCAC*GAAA<u>GUGAAUAUCCAACUAUU</u> AAAUACUCGUAUUGCU |
|  | 1 | 1023 | *UGGGCGUGUUGGAACGCCUUAGUUUGAGGUUUCAAGC ACUCAAAAAAUUCAC*GAAA<u>GUGGAUAUCCAACUAUUA</u> AAUACUCGUAUUGCU |
| 257 | 1 | 1024 | *CGGGGUGGUUGGACACCCUUAAAUUGAGGUUCAUCGC ACUCGAUAAAUACCA*GAAA<u>AGGUAUAUCCAACUAUUA</u> AAUACUCGUAUUGCU |
| 258 | 1 | 1025 | GGGGCUGGUUGUACAGCCUGAAGUUGAGGGAUGAUUC CACUCGACAAAUUGCUGAAA<u>AGCAAUAUACAACUAUU</u> AAAUACUCGUAUUGCU |
| 259 | 1 | 1026 | *CGGGCUGGUUGGACAGCCUUAAACUGAGGUUUAACGC ACUCGGUAAAUACCC*GAAA<u>AGGUAUAUCCAACUAUUA</u> AAUACUCGUAUUGCU |
|  |  | 1100 | ACAGCUUAUUUGGAAGCUGAAAUGUGAGGUUUAUAA CACUCACAAGAAUCCUGAAAAAGGAUGCCAAAC-- [SPACER]-ACAUGAGGAUCACCCAUGU |
|  |  | 1101 | ACAGCUUAUUUGGAAGCUGAAAUGUGAGGUUUAUAA CACUCACAAGAAUCCUGAAAAAGGAUGCCAAAC-- [SPACER]-AAAGCACAUGAGGAUCACCCAUGUGC |
|  |  | 1102 | ACAGCUUAUUUGGAAGCUGAAAUGUGAGGUUUAUAA CACUCACAAGAAUCCUGAAAAAGGAUGCCAAAC-- [SPACER]-AAAAAAGCACAUGAGGAUCACCCAUGUGC |
|  |  | 1103 | ACAGCUUAUUUGGAAGCUGAAAUGUGAGGUUUAUAA CACUCACAAGAAUCCUGAAAAAGGAUGCCAAAC-- [SPACER]- AAAAAAAAAAGCACAUGAGGAUCACCCAUGUGC |
|  |  | 1104 | ACAGCUUAUUUGGAAGCUGAAAUGUGAGGUUUAUAA CACUCACAAGAAUCCUGAAAAAGGAUGCCAAAC-- [SPACER]- AAAAGCAGCACAUGAGGAUCACCCAUGUGCUGC |

Note:
In italics is a handle sequence without a linker or repeat sequence, in bold is a linker, underlined is a repeat sequence, and no formatting is a spacer sequence.
The term "[SPACER]" indicates a sequence of 15 to 28 nucleotides.

TABLE 8 provides non-Limiting examples of target nucleic acids.

TABLE 8

Non-Limiting examples of target nucleic acid
Non-limiting examples of target nucleic acid AAVS1, ABCA4, ABCB11, ABCC8, ABCD1, ABCG5, ABCG8, ACAD9, ACADM, ACADVL, ACAT1, ACOX1, ACSF3, ADA, ADAMTS2, ADGRG1, AGA, AGL, AGPS, AGXT, AHI1, AIRE, ALDH3A2, ALDOB, ALG6, ALK, ALKBH5, ALMS1, ALPL, AMRC9, AMT, ANAPC10, ANAPC11, ANGPTL3, APC, Apo(a), APOCIII, APOε4, APOL1, APP, AQP2, AR, ARFRP1, ARG1, ARH, ARL13B, ARL6, ARSA, ARSB, ASL, ASNS, ASPA, ASS1, ATM, ATP6V1B1, ATP7A, ATP7B, ATRX, ATXN1, ATXN10, ATXN2, ATXN3, ATXN7, ATXN8OS, AXIN1, AXIN2, B2M, BACE-1, BAK1, BAP1, BARD1, BAX2, BBS1, BBS10, BBS12, BBS2, BCKDHA, BCKDHB, BCL2L2, BCS1L, BEST1, Betaglobin gene, BLM, BMPR1A, BRAF, BRAFV600E, BRCA1, BRCA2, BRIP1, BSND, C9orf72, C282Y, CA4, CACNA1A, CAH1, CAPN3, CASR, CBS, CCNB1 CC2D2A, CCR5, CD1, CD2, CD3, CD3D, CD3Z, CD4, CD5, CD6, CD7, CD8A, CD8B, CD9, CD14, CD18, CD19, CD21, CD22, CD23, CD27, CD28, CD30, CD33, CD34, CD36, CD38, CD40, CD40L, CD44, CD46, CD47, CD48, CD52, CD55, CD57, CD58, CD59, CD68, CD69, CD72, CD73, CD74, CD79A, CD80, CD81, CD83, CD84, CD86, CD90, CD93, CD96, CD99, CD100, CD123, CD160, CD163, CD164, CD164L2, CD166, CD200, CD204, CD207, CD209, CD226, CD244, CD247, CD274, CD276, CD300, CD320, CDC73, CDH1, CDH23, CDK11, CDK4, CDKN1A, CDKN1B, CDKN1C, CDKN2A, CDKN2B, CEBPA, CELA3B, CEP290, CERKL, CFB, CFTR, CHCHD10, CHEK2, CHM, CHRNE, CIITA, CLN3, CLN5, CLN6, CLN8, CLRN1, CLTA, CMT1A, CNBP, CNGB1, CNGB3, COL1A1, COL1A2, COL27A1, COL4A3, COL4A4, COL4A5, COL7A1, CPS1, CPT1A, CPT2, CRB1, CREBBP, CRX, CRYAA, CTNNA1, CTNNB1, CTNND2, CTNS, CTSK, CXCL12, CYBA, CYBB, CYP11B1, CYP11B2, CYP17A1, CYP19A1, CYP27A1, DBT, DCC, DCLRE1C, DERL2, DFNA36, DFNB31, DGAT2, DHCR7, DHDDS, DICER1, DIS3L2, DLD, DMD, DMPK, DNAH5, DNAI1, DNAI2, DNM2, DNMT1, DPC4, DUX4, DYSF, EDA, EDN3, EDNRB, EGFR, EIF2B5, EMC2, EMC3, EMD, EMX1, EN1, EPCAM, ERCC6, ERCC8, ESCO2, ETFA, ETFDH, ETHE1, EVC, EVC2, EYS, F5, F9, FXI, FAH, FAM161A, FANCA, FANCB, FANCC, FANCD1, FANCD2, FANCE, FANCF, FANCG, FANCI, FANCJ, FANCL, FANCM, FANCN, FANCP, FANCS, FBN1, FGF14, FGFR2, FGFR3, FGA, FGB, FGG, FH, FHL1, FIX, FKRP, FKTN, FLCN, FMR1, FOXP3, FSCN2, FSHD1, FUS, FUT8, FVIII, FXI, FXII, FXN, G6PC, GAA, GALC, GALK1, GALT, GAMT, GATA2, GATA-4, GBA, GBE1, GCDH, GCGR, GDNF, GFAP, GFM1, GHR, GJB1, GJB2, GLA, GLB1, GLDC, GLE1, GNE, GNPTAB, GNPTG, GNS, GPC3, GPR98, GREM1, GRHPR, GRIN2B, H2AFX, H2AX, HADHA, HAX1, HBA1, HBA2, HBB, HER2, HEXA, HEXB, HFE, HGSNAT, HLCS, HMGCL, HOGA1, HOXB13, HPRPF3, HPRT1, HPS1, HPS3, HRAS, HRD1, HSD17B4, HSD3B2, HTT, HUS1, HYALI, HYLS1, IDS, IDUA, IFITM5, IKBKAP, IL2RG, IL7R, IMPDH1, INPP5E, IRF4, ITGB2, ITPR1, IVD, JAG1, JAK1, JAK3, KCNC3, KCND3, KCNJ11, KLHL7, KRAS, LAMA2, LAMA3, LAMB3, LAMC2, LCA5, LDLR, LDLRAP1, LHX3, LIFR, LIPA, LMNA, LOR, LOXHD1, LPL, LRAT, LRP6, LRPPRC, LRRK2, MADR2, MAN2B1, MAPT, MAX, MCM6, MCOLN1, MECP2, MED17, MEFV, MEN1, MERTK, MESP2, MET, METex14, MFN2, MFSD8, MIA3, MITF, MKL2, MKS1, MLC1, MLH1, MLH3, MMAA, MMAB, MMACHC, MMADHC, MMD, MPI, MPL, MPV17, MSH2, MSH3, MSH6, MTHFD1L, MTHFR, MTM1, MTRR, MTTP, MUT, MUTYH, MYC, MYH7, MYO7A, NAGLU, NAGS, NBN, NDRG1, NDUFAF5, NDUFS6, NEB, NF1, NF2, NKX2-5, NOG, NOTCH1, NOTCH2, NPC1, NPC2, NPHP1, NPHS1, NPHS2, NRAS, NR2E3, NTHL1, NTRK, NTRK1, OAT, OCT4, OFD1, OPA3, OTC, PAH, PALB2, PAQR8, PAX3, PC, PCCA, PCCB, PCDH15, PCSK9, PD1, PDCD1, PDE6B, PDGFRA, PDHA1, PDHB, PEX1, PEX10, PEX12, PEX13, PEX14, PEX16, PEX19, PEX2, PEX26, PEX3, PEX5, PEX6, PEX7, PFKM, PHGDH, PHOX2B, PKD1, PKD2, PKHD1, PKK, PLEKHG4, PMM2, PMP22, PMS1, PMS2, PNPLA3, POLD1, POLE, POMGNT1, POT1, POU5F1, PPM1A, PPP2R2B, PPT1, PRCD, PRKAG2, PRKAR1A, PRKCG, PRNP, PROM1, PROP1, PRPF31, PRPF8, PRPH2, PRPS1, PSAP, PSD95, PSEN1, PSEN2, PSRC1, PTCH1, PTEN, PTS, PUS1, PYGM, RAB23, RAD50, RAD51C, RAD51D, RAG1, RAG2, RAPSN, RARS2, RB1, RDH12, RECQL4, RET, RHO, RICTOR, RMRP, ROS1, RP1, RP2, RPE65, RPGR, RPGRIP1L, RPL32P3, RS1, RTCA, RTEL1, RUNX1, SACS, SAMHD1, SCN1A, SCN2A, SDHA, SDHAF2, SDHB, SDHC, SDHD, SEL1L, SEPSECS, SERPINA1, SERPINC1, SERPING1, SGCA, SGCB, SGCG, SGSH, SIRT1, SLC12A3, SLC12A6, SLC17A5, SLC22A5, SLC25A13, SLC25A15, SLC26A2, SLC26A4, SLC35A3, SLC35B4, SLC37A4, SLC39A4, SLC4A11, SLC6A8, SLC7A7, SMAD3, SMAD4, SMARCA4, SMARCAL1, SMARCB1, SMARCE1, SMN1, SMPD1, SNAI2, SNCA, SNRNP200, SOD1, SOX10, SPARA7, SPTBN2, STAR, STAT3, STK11, SUFU, SUMF1, SYNE1, SYNE2, SYS1, TARDBP, TAT, TBK1, TBP, TCIRG1, TCTN3, TECPR2, TERC, TERT, TFR2, TGFBR2, TGM1, TH, TLE3, TMEM127, TMEM138, TMEM216, TMEM43, TMEM67, TMPRSS6, TOP1, TOPORS, TP53, TPP1, TRAC, TRMU, TSC1, TSC2, TSFM, TSPAN14, TTBK2, TTC8, TTPA, TTR, TULP1, TYMP, UBE2G2, UBE2J1, UBE3A, USH1C, USH1G, USH2A, VEGF, VHL, VPS13A, VPS13B, VPS35, VPS45, VRK1, VSX2, VWF, WAS, WDR19, WDR48, WFS1, WNT10A, WRN, WS2B, WS2C, WT1, XPA, XPC, XPF, XRCC3, YAP1, ZAC1, ZEB1, ZFYVE26, and ZNF423.

TABLE 9 provides sequences of fusion partners that can be fused with the effector proteins described herein.

TABLE 9

Exemplary fusion partner sequences

| Description | Sequences |
|---|---|
| MCP domain | MASNFTQFVLVDNGGTGDVTVAPSNFANGV AEWISSNSRSQAYKVTCSVRQSSAQKRKYT IKVEVPKVATQTVGGVELPVAAWRSYLNME LTIPIFATNSDCELIVKAMQGLLKDGNPIP SAIAANSGIY (SEQ ID NO: 1098) |
| sbcB exonuclease | MMNDGKQQSTFLFHDYETFGTHPALDRPAQ FAAIRTDSEFNVIGEPEVFYCKPADDYLPQ PGAVLITGITPQEARAKGENEAAFAARIHS LFTVPKTCILGYNNVRFDDEVTRNIFYRNF YDPYAWSWQHDNSRWDLLDVMRACYALRPE GINWPENDDGLPSFRLEHLTKANGIEHSNA HDAMADVYATIAMAKLVKTRQPRLFDYLFT HRNKHKLMALIDVPQMKPLVHVSGMFGAWR GNTSWVAPLAWHPENRNAVIMVDLAGDISP LLELDSDTLRERLYTAKTDLGDNAAVPVKL VHINKCPVLAQANTLRPEDADRLGINRQHC LDNLKILRENPQVREKVVAIFAEAEPFTPS DNVDAQLYNGFFSDADRAAMKIVLETEPRN LPALDITFVDKRIEKLLFNYRARNFPGTLD YAEQQRWLEHRRQVFTPEFLQGYADELQML VQQYADDKEKVALLKALWQYAEEIV (SEQ ID NO: 1099) |

EXAMPLES

The following examples are included for illustrative purposes only and are not intended to limit the scope of the inventions disclosed herein.

Example 1: PAM Screening for D2S Effector Protein CasM.265466

D2S effector protein CasM.265466 and guide RNA combinations represented in TABLE 5 and TABLE 7 were screened by in vitro enrichment (IVE) for PAM recognition. Specifically, compositions included in the PAM screening assay included Comp. Nos.: 1, 2, and 6 as shown in TABLE 5 and TABLE 7. TABLE 5 and TABLE 7 show the components of each effector protein-guide RNA complex assayed for PAM recognition. The amino acid sequence of CasM.265466 is shown in TABLE 1 herein. The nucleotide sequences of the guide components are shown in TABLE 5 and TABLE 7 herein. For example, as shown in TABLE 5, an effector protein comprising an amino acid sequence of SEQ ID NO: 1 complexed with a guide comprising a crRNA of SEQ ID NO: 17 and a tracrRNA sequence of SEQ ID NO: 22 was screened for PAM recognition.

Briefly, effector proteins were complexed with corresponding guide RNAs for 15 minutes at 37° C. The complexes were added to an IVE reaction mix. PAM screening reactions used 10 µl of RNP in 100 µl reactions with 1,000 ng of a 5' PAM library in 1× Cutsmart buffer and were carried out for 15 minutes at 25° C., 45 minutes at 37° C. and 15 minutes at 45° C. Reactions were terminated with 1 µl of proteinase K and 5 µl of 500 mM EDTA for 30 minutes at 37° C. Next generation sequencing was performed on cut sequences to identify enriched PAM sequence for CasM.265466 as shown in TABLE 10. Cis cleavage by each complex was confirmed by gel electrophoresis. The most enriched PAM was represented by the sequence 5'-TNTR-3' (SEQ ID NO: 4), wherein N is any nucleotide and R is adenine or guanine.

The assay conducted in Example 1 can also be repeated using CasM.292007 (SEQ ID NO: 2). Based on significant homology between SEQ ID NO: 1 and SEQ ID NO: 2, and based on the results of Example 1, the PAM for CasM.292007 is predicted to be 5'-NNTNTR-3' (SEQ ID NO: 3), or more simply written as 5'-TNTR-3' (SEQ ID NO: 4).

TABLE 10

Exemplary PAM Sequences

| PAM Sequence |
|---|
| NNTNTR (SEQ ID NO: 3) |
| TNTR (SEQ ID NO: 4) |

*wherein each N is independently any one of A, G, C, or T.
*wherein each R is independently any one of A, or G.

Example 2: In Vitro Enrichment in Mammalian Cells

In this experiment CasM.265466 was expressed in HEK293T cells, and cell lysate was tested for nucleic acid cleaving activity. Purified CasM.265466 from HEK293T cells was also tested for nucleic acid cleaving activity. In both cases, cis cleavage activity was detected by the presence of bands. The PAM requirements were determined to be TNTR (SEQ ID NO: 4) by NGS after in vitro enrichment of DNA fragments.

In vitro enrichment involved the amplification of DNA fragments excised by potential CRISPR-Cas candidates. The method began with a cis cleavage assay, which was then followed by dA end repair, ligation, and multiple rounds of PCR. Magnetic bead purification was also performed after interference, ligation, and both rounds of PCR. The final purified PCR product was then sequenced on a MiSeq instrument. Details of these steps are provided as follows.

HEK293 Lipofection and Lysis

Opti-MEM media was warmed to 37° C. and transfection reagent was equilibrated at room temperature. Final transfection ratio was prepared at pDNA:Lipid—300 ng pDNA: 0.6 ul tx reagent per transfection. A first solution was prepared by diluting pDNA with Opti-MEM—360 ng pDNA diluted with media to final volume of 12 µL. A second solution was prepared by diluting the transfection reagent with Opti-MEM—0.72 ul tx reagent diluted with media to final volume of 12 µL. 12 µL of the first solution and 12 µL of the second solution were mixed and incubated at room temperature for 15 minutes, and then a 20 µL aliquot of the mixture was dispensed over the cells followed by incubation at 37° C. for approximately 72 hours before harvesting.

Interference Assay

Purified CRISPR effector protein CasM.265466 (50 µM) was added to a reaction containing 10 µl 10× Cutsmart buffer, and a plasmid (1000 ng per reaction). Additionally, prepared in parallel was a solution containing 3 µL of EcoRI and 7 µL dH$_2$O as a positive control. Dilutions and volumes of the prepared reactions for 3' PAM and 5' PAM are shown in TABLE 11. The reaction was incubated at 37° C. for 30 minutes, 5 µL EDTA+1 µL Proteinase K solution were then added, and the reaction was further incubated at 37° C. for 30 minutes. NGS was subsequently performed, and the required PAM determined was 5'-TNTR-3' (SEQ ID NO: 4).

TABLE 11

| Interference Assay Reaction | | | | |
|---|---|---|---|---|
| | 3'PAM | | 5'PAM | |
| | 1x Volume (μL) | 50 | 1X Volume (uL) | 20 |
| 10x CutSmart Buffer | 10 | 500 | 10 | 200 |
| Plasmid (1000 ng/rxn) | 0.9496676163 | 47.4833808167 | 3.0303030303 | 60.6060606061 |
| dH2O | | 3852.5166191833 | | 1499.3939393939 |
| Protein (50 μM) | 12 | 600 | 12 | 240 |
| Total | 100 | 5000 | 100 | 2000 |

Magnetic Bead Purification I

SPRIselect beads for resuspension in solution were prepared. 60 μL of each bead solution was added to each interference assay reaction and incubated for 5 minutes at 25° C. The reactions were then placed on a magnetic stand. After 1 minute, clear liquid was aspirated from each reaction without disturbing the magnetic beads. To each reaction still containing the magnetic beads, 190 μL of 80% ethanol was added. The ethanol was then removed from each well without disturbing the magnetic beads. The addition and removal of ethanol was repeated with 200 μL of 80% ethanol to each reaction. The magnetic beads in each reaction vessel were then resuspended in 55 μL nuclease free 1× TE buffer or dH$_2$O. The resuspension solutions were incubated for 1 minute at 25° C. and returned to the magnetic stand. 50 μL of each resuspension solution were then transferred into new reaction plates.

End Repair—dA-Tailing

Reactions containing purified DNA were expose to 7 μL of Ultra II EP buffer and diluted to 180 μL. An additional 3 μL of Ultra II End Prep Enzyme Mix was added to each reaction. The reactions were then mixed thoroughly and then placed in a thermocycler according to the timeline in TABLE 12.

TABLE 12

| Thermocycler Programming | | |
|---|---|---|
| Steps | Time (minutes) | Temperature (° C.) |
| 1 | 30 | 20 |
| 2 | 30 | 65 |
| 3 | ∞ | 4 |

Adapter Ligation

To the end prepared reactions described above, the following components described in TABLE 13 were added at 0° C. An adapter sequence of ILM8-UDI-UMI was used and the reactions were mixed thoroughly and incubated at 20° C. for 15 minutes in a thermocycler with the heated lid removed from the apparatus.

TABLE 13

| Adapter Ligation Reaction Components | |
|---|---|
| | Volume (μL) |
| EndRepair Reaction | 60 |
| NEBNext Ultra II Ligation Master Mix | 30 |
| NEBNext Ligation Enhancer | 1 |

TABLE 13-continued

| Adapter Ligation Reaction Components | |
|---|---|
| | Volume (μL) |
| ILM8-UDI-UMI adaptor (1.5 μM) | 2.5 |
| dH2O | 6.5 |
| Total | 100 |

Magnetic Bead Purification II

SPRIselect Beads were mixed to resuspend the beads in solution. To each ligation reaction described above, 60 μL of the SPRIselect Bead suspension were added and then 25 μL of nuclease-free water was added.

PCR for Target Enrichment

PCR for target enrichment was conducted by preparing reactions with various IVE primers possessing different overhang sequences as shown in TABLE 14 and TABLE 15.

TABLE 14

| PCR for Target Enrichment Reaction Components | | |
|---|---|---|
| Reagent | 1x Volume (μL) | 96 |
| 2X Q5 NEBNext | 12.5 | 1200 |
| IVE F pool (100 μM) | 0.125 | 12 |
| P7 Reverse Primer (100 μM) | 0.125 | 12 |
| Water | 2.25 | 216 |
| Post Clean up Ligation Reaction | 10 | |
| Total Volume | 25 | 2400 |

TABLE 15

| IVE Primer Sequences | |
|---|---|
| Name | Sequence |
| IVE longF-A AJD001 | ACACTCTTTCCCTACACGACGCTC TTCCGATCtNcctttcgtctcgcg cgtttcgg (SEQ ID NO: 38) |
| IVE longF-B AJD001 | ACACTCTTTCCCTACACGACGCTC TTCCGATCtNNNcctttcgtctcg cgcgtttcgg (SEQ ID NO: 39) |
| IVE longF-C AJD001 | ACACTCTTTCCCTACACGACGCTC TTCCGATCtNNNNNcctttcgtct cgcgcgtttcgg (SEQ ID NO: 40) |

TABLE 15-continued

IVE Primer Sequences

| Name | Sequence |
|---|---|
| IVE longF-D AJD001 | ACACTCTTTCCCTACACGACGCTC TTCCGATCtNNNNNNNcctttcgt ctcgcgcgtttcgg (SEQ ID NO: 41) |

Example 3: Indel Generation by CasM.265466

CasM.265466 was tested for its ability to produce indels in HEK293T cells. Briefly, a plasmid encoding CasM.265466 and a guide RNA was delivered by lipofection to HEK293T cells. This was performed for a variety of guide RNAs as shown in TABLE 16 targeting up to twenty-four loci adjacent to biochemically determined PAM sequences. For lipofections, 300 ng of the nuclease and guide RNA encoding plasmid was delivered to ~30,000 HEK293T cells in 200 μl using TransIT-293 lipofection reagent. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence as shown in TABLE 17. Sequencing libraries with less than 20% of reads aligning to the reference sequence were excluded from the analysis for quality control purposes. "No plasmid" and SpyCas9 were included as negative and positive controls, respectively.

TABLE 16

Guide RNA Sequences used for Indel Formation Assay

| Composition No. | Effector Protein SEQ ID NO | gRNA Sequence SEQ ID NO |
|---|---|---|
| 10 | 1 | 42 |
| 11 | 1 | 43 |
| 12 | 1 | 44 |
| 13 | 1 | 45 |
| 14 | 1 | 46 |
| 15 | 1 | 47 |
| 16 | 1 | 48 |
| 17 | 1 | 49 |
| 18 | 1 | 50 |
| 19 | 1 | 51 |
| 20 | 1 | 52 |
| 21 | 1 | 53 |
| 22 | 1 | 54 |
| 23 | 1 | 55 |
| 24 | 1 | 56 |
| 25 | 1 | 57 |
| 26 | 1 | 58 |
| 27 | 1 | 59 |

TABLE 17

Indel Assay Efficacy

| Composition No | Indel percentage | Indel aligned read count | Indel aligned read percentage |
|---|---|---|---|
| 10 | 57.01490319 | 26907 | 91.41469049 |
| 11 | 30.37826264 | 19616 | 89.7593118 |
| 12 | 15.1432399 | 19408 | 93.28526796 |
| 13 | 1.80936813 | 17741 | 86.51192276 |
| 14 | 48.41149773 | 661 | 8.671126853 |
| 15 | 44.71172043 | 23779 | 85.36401493 |
| 16 | 22.38493724 | 478 | 6.637045265 |
| 17 | 1.476510067 | 1490 | 29.07884465 |
| 18 | 25.86459095 | 19142 | 79.61237731 |
| 19 | 31.2847498 | 10072 | 86.85004743 |
| 20 | 50.18450185 | 21680 | 88.42122436 |
| 21 | 38.60099471 | 6233 | 85.97241379 |
| 22 | 29.17357943 | 19288 | 85.98814141 |
| 23 | 0.304894357 | 37390 | 94.79261738 |
| 24 | 67.40576497 | 1804 | 26.84923352 |
| 25 | 25.07956354 | 17596 | 87.98879888 |
| 26 | 3.668128876 | 13222 | 65.87942202 |
| 27 | 19.85986953 | 4139 | 90.19394204 |

Example 4: Indel Formation Evaluation by CasM.265466 with gRNA

CasM.265466 was tested for its ability to produce indels in HEK293T cells. Briefly, a plasmid encoding CasM.265466 and a plasmid encoding a guide RNA (sgRNA sequence shown in TABLE 18) targeting the MLH1 gene was delivered by lipofection to HEK293T cells. For the lipofection, both plasmids were delivered at equal mass with a total delivered plasmid mass of 400 ng. Indel activity was then assessed at different concentrations. 300 ng of the nuclease and guide RNA encoding plasmid was delivered to ~30,000 HEK293T cells in 200 μl using TransIT-X2® lipofection reagent. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence as shown in TABLE 19. All samples tested resulted in over 89% of the sequencing reads aligned to the reference genome (hg38) and were tested in duplicate or triplicate.

TABLE 18

Guide RNA Sequence used for Indel Formation Assay, Example 4

| Composition No. | Effector Protein SEQ ID NO | sgRNA Sequence SEQ ID NO |
|---|---|---|
| 20 | 1 | 52 |

TABLE 19

Indel Assay Efficacy for Composition 28

| Nuclease dose (ng) | gRNA dose (ng) | # of reads | % aligned | indel % |
|---|---|---|---|---|
| 0 | 0 | 1788 | 91.7226 | 0 |
| 0 | 0 | 14601 | 91.02116 | 0 |
| 0 | 0 | 16049 | 90.1863 | 0.034545 |
| 6.25 | 6.25 | 16032 | 88.31712 | 0.056501 |
| 6.25 | 6.25 | 4928 | 90.15828 | 0.112537 |
| 6.25 | 6.25 | 16600 | 89.05422 | 1.447609 |
| 12.5 | 12.5 | 18128 | 92.11717 | 1.748608 |
| 12.5 | 12.5 | 19162 | 92.88175 | 1.848522 |
| 12.5 | 12.5 | 3233 | 92.88586 | 2.863803 |
| 25 | 25 | 15014 | 92.39377 | 4.152249 |
| 25 | 25 | 20966 | 92.44968 | 8.182428 |
| 25 | 25 | 4813 | 92.2086 | 8.675079 |
| 50 | 50 | 2684 | 88.04024 | 19.5091 |
| 50 | 50 | 19422 | 92.24076 | 22.38348 |
| 100 | 100 | 3244 | 92.72503 | 33.31117 |

TABLE 19-continued

Indel Assay Efficacy for Composition 28

| Nuclease dose (ng) | gRNA dose (ng) | # of reads | % aligned | indel % |
|---|---|---|---|---|
| 200 | 200 | 2577 | 90.49282 | 34.94854 |
| 100 | 100 | 19512 | 92.3893 | 35.95718 |
| 200 | 200 | 16222 | 90.77796 | 37.43719 |

Example 5: Potency Evaluation of CasM.265466

The ability of CasM.265466 to form indels in two targets was tested with increasing concentration of plasmid delivered using plasmid transfection followed by amplicon sequencing of the target loci. A single plasmid encoding CasM.265466 and a guide RNA was delivered by lipofection to HEK293T cells. Two different plasmids were tested and their corresponding guide RNA sequences are shown in TABLE 20. For the lipofection, the plasmid was delivered in each case with a plasmid mass of 300 ng with an empty pUC19 vector. 300 ng of the nuclease and guide RNA expressing plasmid was delivered to ~30,000 HEK293T cells in 200 µl using TransIT-X2® lipofection reagent. Lipofected cells were grown for ~72 hours at 37° C. to allow for indel formation. Indels were detected by next generation sequencing of PCR amplicons at the targeted loci and indel percentage was calculated as the fraction of sequencing reads containing insertions or deletions relative to an unedited reference sequence at varying concentrations. All samples tested resulted in over ~90% or more of the sequencing reads aligned to the reference genome (hg38) and were tested in duplicate or triplicate. Results confirmed CasM.265466 as active and provided a preliminary indication that it was also potent as shown in FIG. 1. CasM.265466 provided as much as about 60% indel at a 150 ng dose under the experimental conditions described above.

TABLE 20

Guide RNA Sequences used for Indel Formation Assay, Example 5

| Composition No | Effector Protein SEQ ID NO | gRNA SEQ ID NO |
|---|---|---|
| 10 | 1 | 42 |
| 20 | 1 | 52 |

Example 6: Potency Evaluation of CasM.265466 Compared to SpyCas9 and SaCas9

The ability of CasM.265466 to form indels in comparison to SpyCas9 and SaCas9 in two targets is tested with increasing concentration of plasmid delivered using plasmid transfection followed by amplicon sequencing of the target loci. A single plasmid encoding CasM.265466 and a guide RNA are delivered by lipofection to HEK293T cells. For the lipofection, the plasmid is delivered in each case. The nuclease and guide RNA expressing plasmid are delivered to HEK293T cells using TransIT-X2® lipofection reagent. Lipofected cells are grown for ~72 hours at 37° C. to allow for indel formation. Indels are detected by next generation sequencing of PCR amplicons at the targeted loci and indel percentage are calculated as the fraction of sequencing reads containing insertions or deletions relative to an unedited reference sequence at varying concentrations.

Example 7. CasM.265466 DMD Locus Dual Cut Pair Screening in HEK293T Cells

Guide pairs targeting DMD were screened in HEK293T cells for the identification and selection of guides for exon skipping, exon deletion/forced exon skipping and refraining therapeutic strategies. Plasmids co-expressing CasM.265466 and gRNA (1 plasmid/target) were tested in pairs for dual cut deletions of DMD locus targeting intronic and exonic regions of multiple exons (45, 50, 51 and 53). Plasmid pairs were co-transfected in HEK293T cells via lipofection with a total of 150 ng of each plasmid (300 ng total). Cells were incubated for 48 hours before being harvested for DNA, PCR amplified and sequenced via NGS. The sequencing data were then analyzed using CRISPRESSO to detect/quantify % indel.

Guide sequences used an sgRNA handle represented by the sequence: ACAGCUUAUUUGGAAGCUGAAAU-GUGAGGUUUAUAACACUCACAAGAAUCCUGAA-AAAGGAU GCCAAAC (SEQ ID NO: 78), wherein ACA-GCUUAUUUGGAAGCUGAAAUGUGAGGUUUAU-AACACUCACAAGAAUCCU (SEQ ID NO: 22) is a portion of a CasM.265466 tracrRNA sequence, GAAA is the linker, and AAGGAUGCCAAAC (SEQ ID NO: 72) is the repeat. Spacer sequences were located 3' of the sgRNA handle.

The full sequence of the polypeptide used in this experiment is:

(SEQ ID NO: 81)
MDYKDHDGDYKDHDIDYKDDDDKMAPKKKRKVGIHGVPAAMSVLTRKVQL

IPVGDKEERDRVYKYLRDGIEAQNRAMNLYMSGLYFAAINEASKEDRKEL

NQLYSRIATSSKGSAYTTDIEFPTGLASTSTLSMAVRQDFTKSLKDGLMY

GRVSLPTYRKDNPLFVDVRFVALRGTKQKYNGLYHEYKSHTEFLDNLYSS

DLKVYIKFANDITFQVIFGNPRKSSALRSEFQNIFEEYYKVCQSSIQFSG

TKIILNMAMDIPDKEIELDEDVCVGVDLGIAIPAVCALNKNRYSRVSIGS

KEDFLRVRTKIRNQRKRLQTNLKSSNGGHGRKKKMKPMDRFRDYEANWVQ

NYNHYVSRQVVDFAVKNKAKYINLENLEGIRDDVKNEWLLSNWSYYQLQQ

YITYKAKTYGIEVRKINPYHTSQRCSCCGYEDAGNRPKKEKGQAYFKCLK

CGEEMNADFNAARNIAMSTEFQSGKKTKKQKKEQHENKKRPAATKKAGQA

KKKKEFGSGEGRGSLLTCGDVEENPGPMAKPLSQEESTLIERATATINSI

PISEDYSVASAALSSDGRIFTGVNVYHFTGGPCAELVVLGTAAAAAAGNL

TCIVAIGNENRGILSPCGRCRQVLLDLHPGIKAIVKDSDGQPTAVGIREL

LPSGYVWEG* wherein MDYKDHDGDYKDHDIDYKDDDDK (SEQ ID NO: 82) is a FLAG tag; MAPKKKRKV (SEQ ID NO: 83) is a nuclear localization signal (NLS) (SV40); GIHGVPAA (SEQ ID NO: 84) is a linker; KRPAATKK-AGQAKKKK (SEQ ID NO: 85) is nucleoplasmin NLS; EFGSGEGRGSLLTCGDVEENPGP (SEQ ID NO: 86) is a linker+T2A sequence (self cleaving peptide); MAK-PLSQEESTLIERATATINSIPISEDYSVASAALSSDGRI-FTGVNVYHFTGGPCAELVVLGTAAA AAAGNLTCIV-AIGNENRGILSPCGRCRQVLLDLHPGIKAIVKDSDG-QPTAVGIRELLPSGYVWEG (SEQ ID NO: 87) confers blasticidin resistance; and the remainder of the sequence represents the 265466 protein.

Total indel and break down of different mutation patterns are provided in TABLE 21 (obtained from NGS data). Results demonstrated that combinations of nuclease and gRNA pairs (dual cut) can enhance overall target activity when compared to single cut. Additionally, pairing allows for deletion of relatively small, but also large fragments, although optimal distance between each guide must be further investigated. Dual pair cutting may have resulted in deletion of an exon/intron junction, thereby resulting in skipping of that exon.

TABLE 21

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| AAAGAAAUUCUACCC ACUAA (SEQ ID NO: 88), ACAGAAAAGCAUACA CAUUA (SEQ ID NO: 89) | 50 | 81.32 | 7.90 | 0.00 | 0.00 | 0.00 | 70.26 | 11.06 |
| GGGUGGUUGGCUAAA AUAAU (SEQ ID NO: 90), ACAGAAAAGCAUACA CAUUA (SEQ ID NO: 89) | 50 | 83.97 | 4.85 | 0.00 | 0.00 | 0.00 | 62.40 | 21.57 |
| AAAGAAAUUCUACCC ACUAA (SEQ ID NO: 88), ACAGAAAAGCAUACA CAUUA (SEQ ID NO: 89) | 50 | 68.50 | 6.64 | 0.00 | 0.00 | 0.00 | 55.78 | 12.72 |
| UUAAAGAGGAAGUUA GAAGA (SEQ ID NO: 91), AACAAAUAGCUAGAG CCAAA (SEQ ID NO: 92) | 50 | 65.36 | 58.37 | 1.94 | 1.71 | 2.24 | 53.65 | 11.70 |
| GGGUGGUUGGCUAAA AUAAU (SEQ ID NO: 90), ACAGAAAAGCAUACA CAUUA (SEQ ID NO: 89) | 50 | 68.52 | 3.30 | 0.00 | 0.00 | 0.00 | 44.29 | 24.23 |
| UUAAAGAGGAAGUUA GAAGA (SEQ ID NO: 91), AACAAAUAGCUAGAG CCAAA (SEQ ID NO: 92) | 50 | 53.48 | 45.57 | 1.83 | 2.12 | 2.11 | 41.07 | 12.41 |
| UUAAAGAGGAAGUUA GAAGA (SEQ ID NO: 91), CCGCCUUCCACUCAGA GCUC (SEQ ID NO: 93) | 50 | 42.54 | 13.45 | 10.81 | 8.63 | 9.65 | 39.98 | 2.56 |
| UUAAAGAGGAAGUUA GAAGA (SEQ ID NO: 91), CUUACAGGCUCCAAU AGUGG (SEQ ID NO: 94) | 50 | 57.87 | 29.77 | 9.31 | 9.41 | 9.38 | 37.20 | 20.67 |
| UUAAAGAGGAAGUUA GAAGA (SEQ ID NO: 91), CUUACAGGCUCCAAU AGUGG (SEQ ID NO: 94) | 50 | 55.42 | 27.03 | 9.31 | 9.79 | 9.29 | 34.71 | 20.71 |
| CCCACUAAAGUUAAU UUAGA (SEQ ID NO: 95), CCGCCUUCCACUCAGA GCUC (SEQ ID NO: 93) | 45 | 46.03 | 35.43 | 3.02 | 2.65 | 2.87 | 32.17 | 13.86 |
| GGGUGGUUGGCUAAA AUAAU (SEQ ID NO: 90), ACUUCCUCUUUAACA GAAAA (SEQ ID NO: 96) | 50 | 43.34 | 7.71 | 0.00 | 0.00 | 0.00 | 29.52 | 13.82 |
| GCUCUAGCUAUUUGU UCAAA (SEQ ID NO: 97), CUUACAGGCUCCAAU AGUGG (SEQ ID NO: 94) | 50 | 37.25 | 29.07 | 1.32 | 2.05 | 1.64 | 27.37 | 9.88 |
| CCCACUAAAGUUAAU UUAGA (SEQ ID NO: 95), CCGCCUUCCACUCAGA GCUC (SEQ ID NO: 93) | 45 | 41.25 | 28.98 | 3.96 | 2.96 | 3.04 | 25.75 | 15.50 |
| GCUCUAGCUAUUUGU UCAAA (SEQ ID NO: 97), CUUACAGGCUCCAAU AGUGG (SEQ ID NO: 94) | 50 | 36.35 | 25.97 | 1.71 | 2.65 | 2.01 | 24.23 | 12.11 |
| CCCACUAAAGUUAAU UUAGA (SEQ ID NO: 95), ACAGAAAAGCAUACA CAUUA (SEQ ID NO: 89) | 45 | 52.89 | 7.12 | 0.00 | 0.00 | 0.00 | 22.69 | 30.20 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| CCCACUAAAGUUAAU UUAGA (SEQ ID NO: 95), ACAGAAAAGCAUACA CAUUA (SEQ ID NO: 89) | 45 | 51.97 | 6.16 | 0.00 | 0.00 | 0.00 | 21.80 | 30.17 |
| GGGUGGUUGGCUAAA AUAAU (SEQ ID NO: 90), ACUUCCUCUUUAACA GAAAA (SEQ ID NO: 96) | 50 | 32.03 | 3.55 | 0.00 | 0.00 | 0.00 | 19.04 | 12.99 |
| UUAAAGAGGAAGUUA GAAGA (SEQ ID NO: 91), ACAGAAAAGCAUACA CAUUA (SEQ ID NO: 89) | 50 | 62.27 | 24.61 | 9.71 | 8.24 | 8.63 | 18.36 | 43.91 |
| CUUCAAGAGCUGAGG GCAAA (SEQ ID NO: 98), CUUACAGGCUCCAAU AGUGG (SEQ ID NO: 94) | 50 | 32.38 | 4.72 | 8.32 | 9.26 | 10.07 | 17.46 | 14.92 |
| CUUCAAGAGCUGAGG GCAAA (SEQ ID NO: 98), CUUACAGGCUCCAAU AGUGG (SEQ ID NO: 94) | 50 | 31.74 | 4.51 | 8.08 | 8.83 | 10.32 | 16.38 | 15.36 |
| UUAAAGAGGAAGUUA GAAGA (SEQ ID NO: 91), ACAGAAAAGCAUACA CAUUA (SEQ ID NO: 89) | 50 | 54.40 | 20.67 | 8.29 | 7.39 | 7.38 | 15.27 | 39.13 |
| CCCACUAAAGUUAAU UUAGA (SEQ ID NO: 95), ACUUCCUCUUUAACA GAAAA (SEQ ID NO: 96) | 45 | 24.11 | 14.94 | 0.00 | 0.00 | 0.00 | 14.93 | 9.18 |
| UCACCAGAGUAACAG UCUGA (SEQ ID NO: 99), GUUACUAAGGAAACU GCCAU (SEQ ID NO: 100) | 51 | 38.14 | 29.53 | 3.21 | 3.21 | 2.18 | 13.45 | 24.68 |
| UCACCAGAGUAACAG UCUGA (SEQ ID NO: 99), GCAGAUUUCAACCGG GCUUG (SEQ ID NO: 101) | 51 | 41.62 | 33.40 | 3.27 | 3.04 | 1.90 | 12.95 | 28.67 |
| UCACCAGAGUAACAG UCUGA (SEQ ID NO: 99), GUUACUAAGGAAACU GCCAU (SEQ ID NO: 100) | 51 | 38.12 | 29.85 | 2.95 | 3.33 | 2.00 | 12.82 | 25.30 |
| CCCACUAAAGUUAAU UUAGA (SEQ ID NO: 95), ACUUCCUCUUUAACA GAAAA (SEQ ID NO: 96) | 45 | 20.31 | 11.42 | 0.00 | 0.00 | 0.00 | 12.24 | 8.07 |
| GUUGAAAGAAUUCAG AAUCA (SEQ ID NO: 102), GGGACCCUCCUUCCAU GACU (SEQ ID NO: 103) | 53 | 34.21 | 2.47 | 9.49 | 11.48 | 10.77 | 12.16 | 22.05 |
| UCACCAGAGUAACAG UCUGA (SEQ ID NO: 99), GCAGAUUUCAACCGG GCUUG (SEQ ID NO: 101) | 51 | 40.16 | 31.97 | 3.40 | 3.02 | 1.77 | 11.73 | 28.43 |
| GUUGAAAGAAUUCAG AAUCA (SEQ ID NO: 102), GGGACCCUCCUUCCAU GACU (SEQ ID NO: 103) | 53 | 35.63 | 2.96 | 10.11 | 12.55 | 10.01 | 11.69 | 23.94 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| AAAGAAAUUCUACCC ACUAA (SEQ ID NO: 88), ACUUCCUCUUUAACA GAAAA (SEQ ID NO: 96) | 50 | 35.60 | 4.75 | 0.00 | 0.00 | 0.00 | 9.07 | 26.52 |
| AAAGAAAUUCUACCC ACUAA (SEQ ID NO: 88), CUUCUAAAUUAACUU UAGUG (SEQ ID NO: 104) | 50 | 32.65 | 0.77 | 0.00 | 0.00 | 0.00 | 8.74 | 23.90 |
| UUAAAGAGGAAGUUA GAAGA (SEQ ID NO: 91), ACUUCCUCUUUAACA GAAAA (SEQ ID NO: 96) | 50 | 40.96 | 14.71 | 9.65 | 8.12 | 8.36 | 8.69 | 32.27 |
| UUCACCAAAUGGAUU AAGAU (SEQ ID NO: 105), CUUACAGGCUCCAAU AGUGG (SEQ ID NO: 94) | 50 | 29.21 | 13.65 | 4.66 | 5.48 | 5.08 | 8.08 | 21.12 |
| UCACCAGAGUAACAG UCUGA (SEQ ID NO: 99), GUGACACAACCUGUG GUUAC (SEQ ID NO: 106) | 51 | 34.62 | 27.59 | 2.64 | 2.56 | 1.83 | 7.58 | 27.04 |
| UAGGGUGGUUGGCUA AAAUA (SEQ ID NO: 107), CUUCUAAAUUAACUU UAGUG (SEQ ID NO: 104) | 50 | 12.59 | 0.01 | 0.00 | 0.00 | 0.00 | 7.56 | 5.03 |
| AAAGAAAUUCUACCC ACUAA (SEQ ID NO: 88), ACUUCCUCUUUAACA GAAAA (SEQ ID NO: 96) | 50 | 31.31 | 3.80 | 0.00 | 0.00 | 0.00 | 7.26 | 24.05 |
| UCACCAGAGUAACAG UCUGA (SEQ ID NO: 99), GUGACACAACCUGUG GUUAC (SEQ ID NO: 106) | 51 | 35.24 | 28.20 | 2.65 | 2.59 | 1.81 | 7.22 | 28.03 |
| CCCACUAAAGUUAAU UUAGA (SEQ ID NO: 95), CUUCUAAAUUAACUU UAGUG (SEQ ID NO: 104) | 45 | 31.71 | 24.30 | 0.00 | 0.00 | 0.00 | 6.83 | 24.88 |
| UAGGGUGGUUGGCUA AAAUA (SEQ ID NO: 107), CUUCUAAAUUAACUU UAGUG (SEQ ID NO: 104) | 50 | 11.65 | 0.01 | 0.00 | 0.00 | 0.00 | 6.82 | 4.83 |
| UUAAAGAGGAAGUUA GAAGA (SEQ ID NO: 91), ACUUCCUCUUUAACA GAAAA (SEQ ID NO: 96) | 50 | 38.91 | 11.90 | 8.95 | 8.72 | 9.27 | 6.77 | 32.13 |
| UCACCAGAGUAACAG UCUGA (SEQ ID NO: 99), GCUCCUACUCAGACU GUUAC (SEQ ID NO: 108) | 51 | 35.52 | 15.59 | 8.17 | 6.26 | 5.50 | 5.67 | 29.84 |
| UUCACCAAAUGGAUU AAGAU (SEQ ID NO: 105), CUUACAGGCUCCAAU AGUGG (SEQ ID NO: 94) | 50 | 26.11 | 11.02 | 4.51 | 5.13 | 5.12 | 5.60 | 20.51 |
| UUCUAGUUGAAAGAA UUCAG (SEQ ID NO: 109), CUGUAUAGGGACCCU CCUUC (SEQ ID NO: 110) | 53 | 11.49 | 0.87 | 3.45 | 3.27 | 3.90 | 5.56 | 5.93 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| AAAGAAAUUCUACCC ACUAA (SEQ ID NO: 88), CUUCUAAAUUAACUU UAGUG (SEQ ID NO: 104) | 50 | 23.46 | 0.14 | 0.00 | 0.00 | 0.00 | 5.49 | 17.96 |
| CCCACUAAAGUUAAU UUAGA (SEQ ID NO: 95), CCCUCAGCUCUUGAA GUAAA (SEQ ID NO: 111) | 45 | 57.30 | 47.36 | 0.18 | 0.29 | 0.27 | 5.23 | 52.06 |
| UCACCAGAGUAACAG UCUGA (SEQ ID NO: 99), GCUCCUACUCAGACU GUUAC (SEQ ID NO: 108) | 51 | 32.19 | 14.12 | 7.73 | 5.44 | 4.91 | 5.08 | 27.11 |
| UUCUAGUUGAAAGAA UUCAG (SEQ ID NO: 109), ACAUUUCAUUCAACU GUUGC (SEQ ID NO: 112) | 53 | 13.85 | 1.26 | 4.20 | 4.67 | 3.72 | 4.60 | 9.25 |
| AGCUCUGAGUGGAAG GCGGU (SEQ ID NO: 113), CCCUCAGCUCUUGAA GUAAA (SEQ ID NO: 111) | 50 | 4.55 | 3.66 | 0.22 | 0.34 | 0.32 | 4.55 | 0.00 |
| UUCUAGUUGAAAGAA UUCAG (SEQ ID NO: 109), ACAUUUCAUUCAACU GUUGC (SEQ ID NO: 112) | 53 | 12.99 | 1.08 | 4.26 | 4.43 | 3.21 | 4.51 | 8.48 |
| CCCACUAAAGUUAAU UUAGA (SEQ ID NO: 95), CCCUCAGCUCUUGAA GUAAA (SEQ ID NO: 111) | 45 | 47.84 | 36.85 | 0.24 | 0.24 | 0.25 | 4.46 | 43.38 |
| UUCUAGUUGAAAGAA UUCAG (SEQ ID NO: 109), CUGUAUAGGGACCCU CCUUC (SEQ ID NO: 110) | 53 | 9.16 | 0.54 | 3.10 | 2.69 | 2.82 | 4.17 | 4.99 |
| AGCUCUGAGUGGAAG GCGGU (SEQ ID NO: 113), CCCUCAGCUCUUGAA GUAAA (SEQ ID NO: 111) | 50 | 4.14 | 3.49 | 0.23 | 0.20 | 0.23 | 4.14 | 0.00 |
| UAGGGUGGUUGGCUA AAAUA (SEQ ID NO: 107), GCCAACCACCCUACAA AUAU (SEQ ID NO: 114) | 50 | 11.59 | 0.00 | 0.00 | 0.00 | 0.00 | 4.09 | 7.50 |
| CCCACUAAAGUUAAU UUAGA (SEQ ID NO: 95), CUUCUAAAUUAACUU UAGUG (SEQ ID NO: 104) | 45 | 25.89 | 19.68 | 0.00 | 0.00 | 0.00 | 3.88 | 22.01 |
| UAUGCUUUCUGUUA AAGAG (SEQ ID NO: 115), AACAAAUAGCUAGAG CCAAA (SEQ ID NO: 92) | 50 | 20.66 | 9.86 | 0.05 | 0.19 | 0.16 | 3.81 | 16.85 |
| UAGGGUGGUUGGCUA AAAUA (SEQ ID NO: 107), GCCAACCACCCUACAA AUAU (SEQ ID NO: 114) | 50 | 11.97 | 0.00 | 0.00 | 0.00 | 0.00 | 3.57 | 8.39 |
| CUUUUCUGUUAAAGA GGAAG (SEQ ID NO: 116), CCCUCAGCUCUUGAA GUAAA (SEQ ID NO: 111) | 50 | 36.35 | 21.78 | 5.27 | 4.48 | 4.81 | 3.51 | 32.84 |
| UUCUAGUUGAAAGAA UUCAG (SEQ ID NO: 109), UUGAAUCCUUUAACA UUUCA (SEQ ID NO: 117) | 53 | 12.16 | 1.04 | 3.21 | 4.07 | 3.83 | 3.42 | 8.74 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| UAUGCUUUCUGUUA AAGAG (SEQ ID NO: 115), AACAAAUAGCUAGAG CCAAA (SEQ ID NO: 92) | 50 | 21.93 | 10.04 | 0.20 | 0.18 | 0.17 | 3.34 | 18.59 |
| GUUGAAAGAAUUCAG AAUCA (SEQ ID NO: 102), CUUCAUCCCACUGAU UCUGA (SEQ ID NO: 118) | 53 | 9.73 | 4.51 | 1.59 | 1.91 | 1.73 | 3.03 | 6.71 |
| AAAGAAAUUCUACCC ACUAA (SEQ ID NO: 88), AAUUAACUUUAGUGG GUAGA (SEQ ID NO: 119) | 50 | 21.21 | 0.49 | 0.00 | 0.00 | 0.00 | 2.92 | 18.29 |
| AAAGAAAUUCUACCC ACUAA (SEQ ID NO: 88), AAUUAACUUUAGUGG GUAGA (SEQ ID NO: 119) | 50 | 22.09 | 0.25 | 0.00 | 0.00 | 0.00 | 2.78 | 19.31 |
| AAAGAAAUUCUACCC ACUAA (SEQ ID NO: 88), CCGCCUUCCACUCAGA GCUC (SEQ ID NO: 93) | 50 | 32.84 | 3.20 | 0.64 | 0.76 | 0.60 | 2.66 | 30.17 |
| CUUUUCUGUUAAAGA GGAAG (SEQ ID NO: 116), CCCUCAGCUCUUGAA GUAAA (SEQ ID NO: 111) | 50 | 37.32 | 22.09 | 6.09 | 4.55 | 4.58 | 2.65 | 34.66 |
| AAAGAAAUUCUACCC ACUAA (SEQ ID NO: 88), CCCUCAGCUCUUGAA GUAAA (SEQ ID NO: 111) | 50 | 66.54 | 56.55 | 0.02 | 0.04 | 0.07 | 2.42 | 64.13 |
| UAGGGUGGUUGGCUA AAAUA (SEQ ID NO: 107), AAUUAACUUUAGUGG GUAGA (SEQ ID NO: 119) | 50 | 3.97 | 0.00 | 0.00 | 0.00 | 0.00 | 2.40 | 1.57 |
| UUCUAGUUGAAAGAA UUCAG (SEQ ID NO: 109), UUGAAUCCUUUAACA UUUCA (SEQ ID NO: 117) | 53 | 9.08 | 0.54 | 2.25 | 3.39 | 2.90 | 2.37 | 6.71 |
| GUAUCUUACAGGAAC UCCAG (SEQ ID NO: 120), AGGAUUGCUGAAUUA UUUCU (SEQ ID NO: 121) | 45 | 30.12 | 20.70 | 2.67 | 3.37 | 3.38 | 2.34 | 27.78 |
| GUUGAAAGAAUUCAG AAUCA (SEQ ID NO: 102), CUUCAUCCCACUGAU UCUGA (SEQ ID NO: 118) | 53 | 7.17 | 3.47 | 0.90 | 1.43 | 1.37 | 2.17 | 5.00 |
| CUUCAAGAGCUGAGG GCAAA (SEQ ID NO: 98), AACAAAUAGCUAGAG CCAAA (SEQ ID NO: 92) | 50 | 23.77 | 8.51 | 0.03 | 0.01 | 0.00 | 2.13 | 21.64 |
| CUUCAAGAGCUGAGG GCAAA (SEQ ID NO: 98), AACAAAUAGCUAGAG CCAAA (SEQ ID NO: 92) | 50 | 22.84 | 8.29 | 0.01 | 0.00 | 0.01 | 2.12 | 20.72 |
| UAGGGUGGUUGGCUA AAAUA (SEQ ID NO: 107), AAUUAACUUUAGUGG GUAGA (SEQ ID NO: 119) | 50 | 4.29 | 0.00 | 0.00 | 0.00 | 0.00 | 2.11 | 2.18 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| UAUGCUUUCUGUUA AAGAG (SEQ ID NO: 115), CUUACAGGCUCCAAU AGUGG (SEQ ID NO: 94) | 50 | 19.58 | 4.49 | 4.66 | 5.54 | 4.88 | 2.10 | 17.47 |
| UAUGCUUUCUGUUA AAGAG (SEQ ID NO: 115), ACAGAAAAGCAUACA CAUUA (SEQ ID NO: 89) | 50 | 60.05 | 3.59 | 0.17 | 0.23 | 0.19 | 2.09 | 57.96 |
| GUAUCUUACAGGAAC UCCAG (SEQ ID NO: 120), AGGAUUGCUGAAUUA UUUCU (SEQ ID NO: 121) | 45 | 28.93 | 21.28 | 2.22 | 2.83 | 2.59 | 1.97 | 26.96 |
| AAAGAAAUUCUACCC ACUAA (SEQ ID NO: 88), CCGCCUUCCACUCAGA GCUC (SEQ ID NO: 93) | 50 | 29.32 | 2.31 | 0.62 | 0.70 | 0.58 | 1.85 | 27.47 |
| UAUGCUUUCUGUUA AAGAG (SEQ ID NO: 115), CUUACAGGCUCCAAU AGUGG (SEQ ID NO: 94) | 50 | 22.38 | 4.96 | 5.09 | 6.59 | 5.73 | 1.83 | 20.55 |
| UAUGCUUUCUGUUA AAGAG (SEQ ID NO: 115), ACAGAAAAGCAUACA CAUUA (SEQ ID NO: 89) | 50 | 45.95 | 2.80 | 0.19 | 0.25 | 0.22 | 1.54 | 44.41 |
| AAAGAAAUUCUACCC ACUAA (SEQ ID NO: 88), CCCUCAGCUCUUGAA GUAAA (SEQ ID NO: 111) | 50 | 53.94 | 44.86 | 0.01 | 0.06 | 0.04 | 1.53 | 52.41 |
| CUUCAAGAGCUGAGG GCAAA (SEQ ID NO: 98), CCCUCAGCUCUUGAA GUAAA (SEQ ID NO: 111) | 50 | 3.24 | 2.61 | 0.23 | 0.23 | 0.16 | 1.45 | 1.78 |
| CUUCAAGAGCUGAGG GCAAA (SEQ ID NO: 98), CCCUCAGCUCUUGAA GUAAA (SEQ ID NO: 111) | 50 | 2.73 | 2.29 | 0.12 | 0.18 | 0.14 | 1.28 | 1.44 |
| CUUUUCUGUUAAAGA GGAAG (SEQ ID NO: 116), CUUCUAAAUUAACUU UAGUG (SEQ ID NO: 104) | 50 | 3.74 | 1.27 | 0.05 | 0.13 | 0.15 | 1.23 | 2.51 |
| GUAUCUUACAGGAAC UCCAG (SEQ ID NO: 120), UUUUUGAGGAUUGCU GAAUU (SEQ ID NO: 122) | 45 | 23.34 | 15.89 | 2.06 | 2.73 | 2.65 | 1.18 | 22.15 |
| UGCUUUCUGUUAAA GAGGA (SEQ ID NO: 123), GUGGGUAGAAUUUCU UUUAA (SEQ ID NO: 124) | 50 | 19.12 | 1.29 | 0.17 | 0.34 | 0.44 | 1.13 | 17.99 |
| GCUCUAGCUAUUUGU UCAAA (SEQ ID NO: 97), AACAAAUAGCUAGAG CCAAA (SEQ ID NO: 92) | 50 | 15.73 | 1.88 | 0.00 | 0.00 | 0.00 | 1.12 | 14.62 |
| CUUUUCUGUUAAAGA GGAAG (SEQ ID NO: 116), CUUCUAAAUUAACUU UAGUG (SEQ ID NO: 104) | 50 | 4.15 | 1.21 | 0.14 | 0.20 | 0.15 | 1.11 | 3.05 |

TABLE 21-continued

Indel and mutation patterns from NGS data, Example 7

| GUIDE RNA PAIR SPACER SEQUENCES (separated by comma) | A | B | C | D | E | F | G | H |
|---|---|---|---|---|---|---|---|---|
| UGCUUUUCUGUUAAA GAGGA (SEQ ID NO: 123), GUGGGUAGAAUUUCU UUUAA (SEQ ID NO: 124) | 50 | 23.24 | 1.69 | 0.36 | 0.73 | 0.40 | 1.10 | 22.14 |
| GUAUCUUACAGGAAC UCCAG (SEQ ID NO: 120), UUUUUGAGGAUUGCU GAAUU (SEQ ID NO: 122) | 45 | 22.34 | 14.40 | 2.34 | 3.06 | 2.54 | 1.02 | 21.32 |

A = exon targeted
B = % of target nucleic acids modified (% indel)(modified/unmodified x 100%)
C = % of modifications predicted to result in a splice disruption
D = % of modifications predicted to result in an in frame deletion
E = % of modifications predicted to result in a +1 nucleotide frameshift
F = % of modifications predicted to result in a +2 nucleotide frameshift
G = % of target nucleic acids having a full region deletion
H = % of target nucleic acids modified (% indel) minus % full region deletion Example 8: Pcsk9 Editing of Hepatocytes with CasM.265466

Pcsk9 editing was demonstrated by indel formation using CasM.265466. 133 guide RNA sequences directed to various target sequences were tested and their ability to introduce indels was measured at various plasmid loading amounts. In a high-throughput well plate format, wells were seeded with 20,000 Hepa1-6 cells. Lipofection was subsequently performed using Lipofectamine 3000 with titrations of 100 ng, 20 ng, and 4 ng of plasmid in a 96-well plate in singlet. The plasmids used were eukaryotic expression vectors encoding both the nuclease and the guide nucleic acid as described in TABLE 6, Composition Nos.: 28-160 The most effective guide RNA sequences for this assay are shown in TABLE 22. DNA was extracted after 48 hours with a Promega 96 wizard Kit, and adapter PCR was performed. Indels were detected by next generation sequencing of PCR amplicons at the targeted loci. Indel percentage was calculated as the percentage of sequencing reads that show at least one nucleotide has been deleted and the percentage indel value reflects the percentage of target nucleic acids that are modified by a given nuclease. A read contributing to the percent indel value can be a read where one nucleotide is deleted, a read contributing to the percent indel value can be a read where 10 nucleotides are deleted. The extent of deletion does not change the weight of the indel percent value calculation. A 60% alignment cut off wherein all 00 alignments were 60% or greater were used to calculate indel percent.

The full NGS results of this experiment are shown in TABLE 24. TABLE 24 includes indel 0 values for the 100 ng plasmid titration, only. NGS results of the plasmid titrations at all three plasmid loading conditions for the three most effective gRNA sequences as a function of indel percentage are shown in TABLE 23.

TABLE 22

Guide RNA Sequences used for Indel Formation Assay, Example 8

| Comp No. | Effector Protein SEQ ID NO | gRNA SEQ ID NO |
|---|---|---|
| 32 | 1 | 129 |
| 49 | 1 | 146 |
| 98 | 1 | 195 |

TABLE 23

Indel occurrence from NGS data, Example 8

| | Indel % | | |
|---|---|---|---|
| Comp. No. | 4 ng plasmid | 20 ng plasmid | 100 ng plasmid |
| 32 | 11.4327551 | 12.4679387 | 2.82097367 |
| 49 | 4.42354138 | 10.9800754 | 7.48193283 |
| 98 | 8.0565468 | 12.4251314 | 8.67850099 |

TABLE 24

Composition, PAM, and indel occurrence data, Example 8

| Comp. No. | PAM | % indels |
|---|---|---|
| 28 | TCTG | 0.057562 |
| 29 | TATG | 5.145253 |
| 30 | TCTG | 2.221377 |
| 31 | TGTG | 3.246964 |
| 32 | TTTG | 2.820974 |
| 33 | TTTG | 3.618553 |
| 34 | TGTG | 0.011361 |
| 35 | TCTG | 0 |
| 36 | TTTG | 6.377719 |
| 37 | TCTG | 2.503582 |
| 38 | TTTG | 0 |
| 39 | TCTG | 4.035652 |
| 40 | TCTG | 3.26087 |
| 41 | TGTG | 4.927536 |
| 42 | TCTG | 3.492092 |
| 43 | TGTG | nd |
| 44 | TATG | 6.867332 |
| 45 | TATG | 4.746943 |
| 46 | TGTG | 6.960771 |
| 47 | TCTG | 4.361971 |

TABLE 24-continued

Composition, PAM, and indel occurrence data, Example 8

| Comp. No. | PAM | % indels |
|---|---|---|
| 48 | TCTG | 1.483715 |
| 49 | TATG | 7.481933 |
| 50 | TCTG | 3.825604 |
| 51 | TTTG | 1.111263 |
| 52 | TTTG | nd |
| 53 | TGTG | 9.735361 |
| 54 | TCTG | 1.974518 |
| 55 | TCTG | 0 |
| 56 | TCTG | |
| 57 | TGTG | 6.116036 |
| 58 | TCTG | 4.654992 |
| 59 | TGTG | 2.970863 |
| 60 | TGTG | 0.219734 |
| 61 | TGTG | 3.654731 |
| 62 | TGTG | 0.351038 |
| 63 | TGTG | 0.34823 |
| 64 | TATG | 0.022181 |
| 65 | TGTG | 5.152581 |
| 66 | TCTG | 0.376623 |
| 67 | TCTG | 0.460081 |
| 68 | TGTG | 1.823929 |
| 69 | TTTG | 1.137373 |
| 70 | TGTG | 2.323033 |
| 71 | TTTG | nd |
| 72 | TTTG | 3.674623 |
| 73 | TGTG | 4.421425 |
| 74 | TGTG | 2.792905 |
| 75 | TGTG | 7.960467 |
| 76 | TCTG | 6.270507 |
| 77 | TGTG | 3.429643 |
| 78 | TTTG | 5.971415 |
| 79 | TGTG | 0.786445 |
| 80 | TGTG | 2.477527 |
| 81 | TCTG | nd |
| 82 | TGTG | nd |
| 83 | TCTG | nd |
| 84 | TGTG | 2.253267 |
| 85 | TGTG | 3.15236427 |
| 86 | TCTG | 2.887193 |
| 87 | TCTG | 5.044272 |
| 88 | TATG | 5.213984 |
| 89 | TTTG | 2.326524 |
| 90 | TCTG | 1.747573 |
| 91 | TGTG | 1.840299 |
| 92 | TCTG | 2.339584 |
| 93 | TGTG | nd |
| 94 | TATG | nd |
| 95 | TTTG | 0.175879 |
| 96 | TCTG | 2.603627 |
| 97 | TCTG | 0.86346465 |
| 98 | TCTG | 8.678501 |
| 99 | TATG | 4.536766 |
| 100 | TCTG | 2.175209 |
| 101 | TTTG | 0.46729 |
| 102 | TGTG | 1.079914 |
| 103 | TATG | 3.007614 |
| 104 | TGTG | 1.994967 |
| 105 | TGTG | nd |
| 106 | TCTG | nd |
| 107 | TATG | nd |
| 108 | TGTG | 0.817908 |
| 109 | TCTG | 0.478297 |
| 110 | TCTG | 3.160383 |
| 111 | TCTG | 0.006128 |
| 112 | TATG | 4.675772 |
| 113 | TATG | nd |
| 114 | TTTG | 6.142035 |
| 115 | TGTG | 0 |
| 116 | TATG | 4.934677 |
| 117 | TGTG | 3.249485 |
| 118 | TTTG | 3.92824 |
| 119 | TCTG | 0.00698 |
| 120 | TCTG | 0.167736 |
| 121 | TGTG | 0 |
| 122 | TCTG | nd |
| 123 | TCTG | 2.146936 |
| 124 | TGTG | 11.3422 |
| 125 | TGTG | 4.34782609 |
| 126 | TATG | 8.772462 |
| 127 | TTTG | 4 |
| 128 | TTTG | 4.78581 |
| 129 | TTTG | 4.53892 |
| 130 | TTTG | 9.798893 |
| 131 | TTTG | 1.5625 |
| 132 | TCTG | 2.087961 |
| 133 | TGTG | 8.511697 |
| 134 | TCTG | 2.404526 |
| 135 | TCTG | 0 |
| 136 | TGTG | 2.378398 |
| 137 | TATG | 8.719797 |
| 138 | TCTG | 4.301075 |
| 139 | TGTG | 15.51724 |
| 140 | TTTG | 3.741039 |
| 141 | TCTG | 4.979253 |
| 142 | TGTG | 4.335775 |
| 143 | TCTG | 0.803213 |
| 144 | TCTG | 2.383245 |
| 145 | TGTG | 5.426743 |
| 146 | TGTG | 11.1111111 |
| 147 | TATG | 1.244168 |
| 148 | TCTG | 2.4 |
| 149 | TCTG | 1.23159 |
| 150 | TGTG | 1.994302 |
| 151 | TCTG | 5.317974 |
| 152 | TATG | 1.711984 |
| 153 | TCTG | 0 |
| 154 | TGTG | 4.295713 |
| 155 | TCTG | 0 |
| 156 | TGTG | 2.777778 |
| 157 | TGTG | nd |
| 158 | TATG | 1.349325 |
| 159 | TCTG | 1.655539 |
| 160 | TCTG | 7.988885 |

"nd" indicates no data.

Example 9. Editing Hematopoietic Stem Cells (HSC) with CasM.265466

Figure 3:
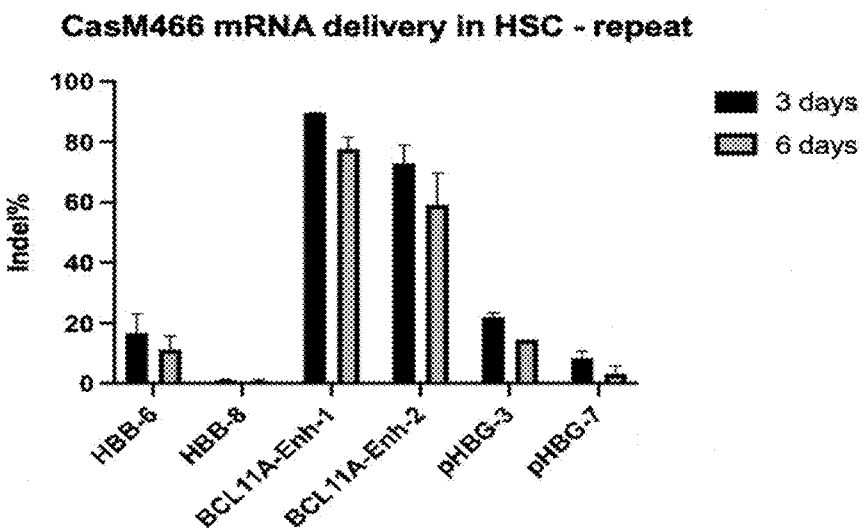
FIG. 3 is a is a graphical representation illustrating percentage indel occurrence after 3-day and 6-day mRNA incubation periods with CasM.265466 (SEQ ID NO: 1) in hematopoietic stem cells for various sgRNA editing sequences described in TABLE 25 and Example 9.

CasM.265466 mRNA and various sgRNA were introduced into HSC using a Neon electroporation system at a setting of 1500 volts/30 ms/2 pulse. Briefly, 2e5 HSC were spun down at 300 g for 10 mins; washed with PBS and spin down at 300×g for 5 to 10 mins; and resuspended with 10 ul Buffer T. 5 micrograms of Cas265466 mRNA was incubated with 500 pmol sgRNA targeting HBB, BCL 11A enhancer (BCL11A-Enh), or the promoter of HBG1 (pHBG) to form an RNP and added to the cell suspension. (Alternatively, one or more plasmids encoding CasM.265466 and the gRNA could be delivered to the cells). Cells were electroporated and immediately transferred to the culture medium and incubated at 37 degrees Celsius.

sgRNAs were designed to target a PAM of TNTR. The handle sequence of the sgRNAs comprised a sequence of ACAGCUUAUUUGGAAGCUGAAAUGUGAGGUUUA-UAACACUCACAAGAAUCCU (SEQ ID NO: 22), and a repeat and linker sequence comprising GAAAAA-GGAUGCCAAAC (SEQ ID NO: 259). Full guide sequences are provided in TABLE 25 below. Results are shown in FIG. 3. About 90% indel was achieved with CasM.265466.

TABLE 25 sgRNA sequences for editing in HSCs

| Comp. No. | Effector Protein SEQ ID NO | Target Gene | sgRNA SEQ ID NO |
|---|---|---|---|
| 161 | 1 | HBB-6 | 260 |
| 162 | 1 | HBB-8 | 261 |
| 163 | 1 | BCL11A-Enh-1 | 262 |
| 164 | 1 | BCL11A-Enh-2 | 263 |
| 165 | 1 | pHBG-3 | 264 |
| 166 | 1 | pHBG-7 | 265 |

Example 10. Editing Induced Pluripotent Stem Cells (iPSC) with CasM.265466

Figure 4:
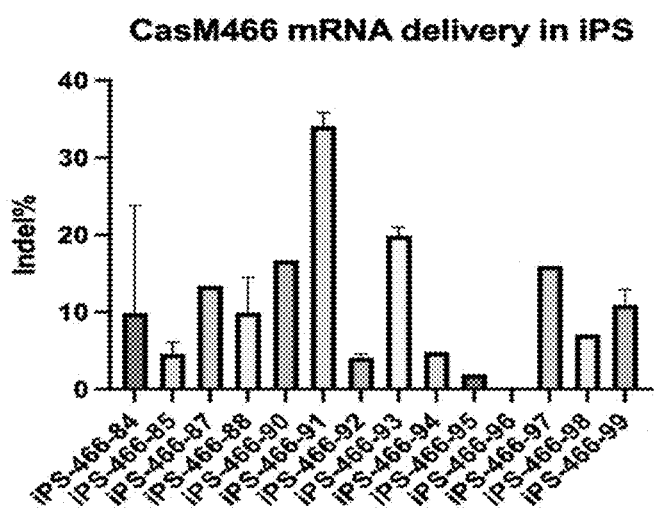
FIG. 4 is a graphical representation illustrating percentage indel occurrence after 3-day and 6-day mRNA incubation periods with CasM.265466 (SEQ ID NO: 1) in pluripotent stem cells (iPSC) for various sgRNA editing sequences described in TABLE 26 and Example 10.

CasM.265466 mRNA and various sgRNA provided in Table 26 were introduced into iPSCs using a Neon electroporation system at a setting of 1050 volts/30 ms/2 pulse. Briefly, 2e5 iPSCs were disassociated and spun down at 300×g for 5 mins; and resuspended with 10 ul Buffer R. 5 micrograms of CasM.265466 mRNA was incubated with 500 pmol sgRNA targeting HBB or BCL11A (listed TABLE 26) to form an RNP and added to the cell suspension. (Alternatively, one or more plasmids encoding CasM.265466 and the gRNA could be delivered to the cells). Cells were electroporated and immediately transferred to the culture medium and incubated at 37 degrees Celsius. Results are shown in FIG. 4. These results demonstrate successful editing of a target nucleic acid in iPSC cells by CasM.265466.

TABLE 26 sgRNAs tested in iPSCs

| Comp No. | Effector Protein SEQ ID NO | sgRNA name | sgRNA SEQ ID NO |
|---|---|---|---|
| 167 | 1 | iPS-466-84 | 266 |
| 168 | 1 | iPS-466-85 | 267 |
| 169 | 1 | iPS-466-87 | 268 |
| 170 | 1 | iPS-466-88 | 43 |
| 171 | 1 | iPS-466-90 | 270 |
| 172 | 1 | iPS-466-91 | 42 |
| 173 | 1 | iPS-466-92 | 272 |
| 174 | 1 | iPS-466-93 | 273 |
| 175 | 1 | iPS-466-94 | 274 |
| 176 | 1 | iPS-466-95 | 275 |
| 177 | 1 | iPS-466-96 | 276 |
| 178 | 1 | iPS-466-97 | 277 |
| 179 | 1 | iPS-466-98 | 278 |
| 180 | 1 | iPS-466-99 | 279 |

Example 11. Blunt Cutting with CasM.265466

Figure 5:
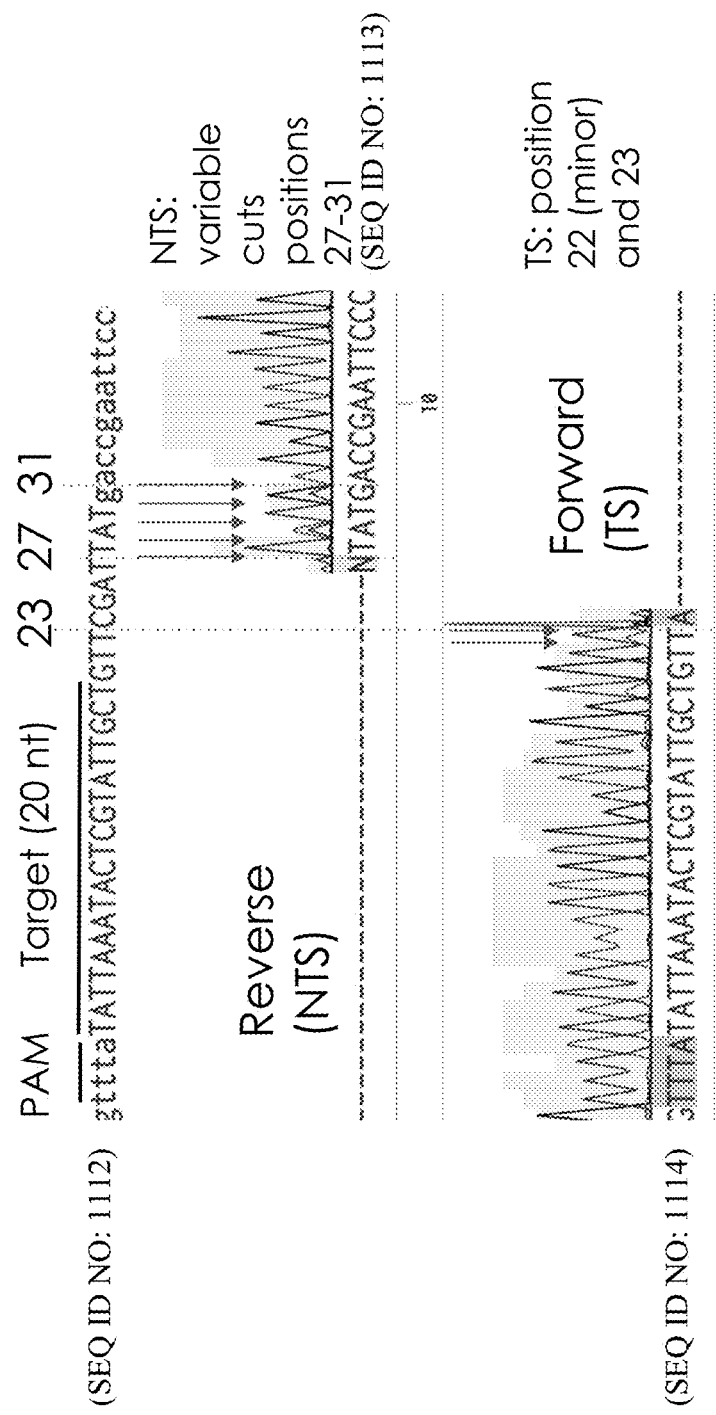
FIG. 5 is schematic representation of a Sanger Sequencing chromatogram showing variable cuts at positions 27-31 from the 3' end of the PAM on the non-target strand (NTS), and most cuts on the target strand (TS) at position 22 from the 3' end of the PAM.

Blunt cutting of target nucleic acids were performed using CasM.265466 was demonstrated and efficacy analyzed by NGS. An RNP complex of CasM.265466 (SEQ ID NO: 1) and a guide nucleic acid (200 nM) was incubated with a target nucleic acid (10 nM) having a PAM of TTTA at 37 degrees Celsius for 1 hour in CutSmart buffer. Purified and amplified fragments were subjected to Sanger sequencing using multiple forward and reverse primers to read both the target and non-target strands. FIG. 5 shows a chromatogram from Sanger sequencing. The chromatogram showed variable cuts at positions 27-31 from the 3' end of the PAM on the non-target strand (NTS), and most cuts on the target strand (TS) at position 22 from the 3' end of the PAM. Thus, both cuts were outside of the heteroduplex created by the guide nucleic acid and the target nucleic acid. The chromatogram shows no overhanging nucleotides which was interpreted as blunt cutting.

Example 12: AAV Vectors for Gene Editing

An AAV vector is constructed to contain a transgene between its ITRs, the transgene providing or encoding, in a 5' to 3' direction, a U6 promoter, a guide nucleic acid, a second promoter, an effector protein, and a poly A signal as illustrated in FIG. 6 are packaged into an AAV vector. Optionally, the AAV vector comprises additional promoters, guide nucleic acids, transcriptional enhancers (e.g., WPRE), or a combination thereof, as illustrated in FIGS. 7A-7C. The effector protein has an amino acid sequence that has at least 80% identity to a sequence recited in TABLE 1. The guide nucleic acid comprises a sequence that has at least 90% identity to any one of sequences recited in TABLE 4, TABLE 5, TABLE 6, and TABLE 7. As illustrated in FIG. 6, the effector protein can be expressed either ubiquitously or tissue-specifically based on the second promotor the AAV vector is engineered to have. Any one of the additional promoters may be a tissue specific promoter. The Poly A signal sequence can be either hGH Poly A signal sequence or sv40 Poly A signal sequence. The AAV vector is expressed with supporting plasmids to produce an adeno-associated virus (AAV).

Example 13: AAV Vectors for Dual Cut Gene Editing

An AAV vector is constructed to contain a transgene between its ITRs, the transgene providing or encoding, in a 5' to 3' direction, U6 promoter, a first guide nucleic acid, a second promoter, an effector protein, an enhancer, a poly A signal, 7SK promotor, and a second guide nucleic acid as illustrated in FIG. 7A are packaged into an AAV vector, wherein the first guide nucleic acid and the second guide nucleic acid comprise different spacer sequences targeting different sequences in a target nucleic acid. In some instances, the different sequences are located on either side of an exon. Thus, contact of both guide nucleic acids to the target nucleic acid results in an exon deletion. The effector protein has an amino acid sequence that has at least 80% identity to a sequence recited in TABLE 1. The first guide nucleic acid and the second guide nucleic acid independently comprises a sequence that has at least 90% identity to any one of sequences recited in TABLE 4, TABLE 5, TABLE 6, and TABLE 7. As illustrated in FIG. 6, the effector protein can be expressed either ubiquitously or tissue-specifically based on the second promotor the AAV vector is engineered to have. The AAV vector is expressed with supporting plasmids to produce an adeno-associated virus (AAV).

Example 14: Determining Potency of CasM.265466 in HEK293T Cells

Figure 8:
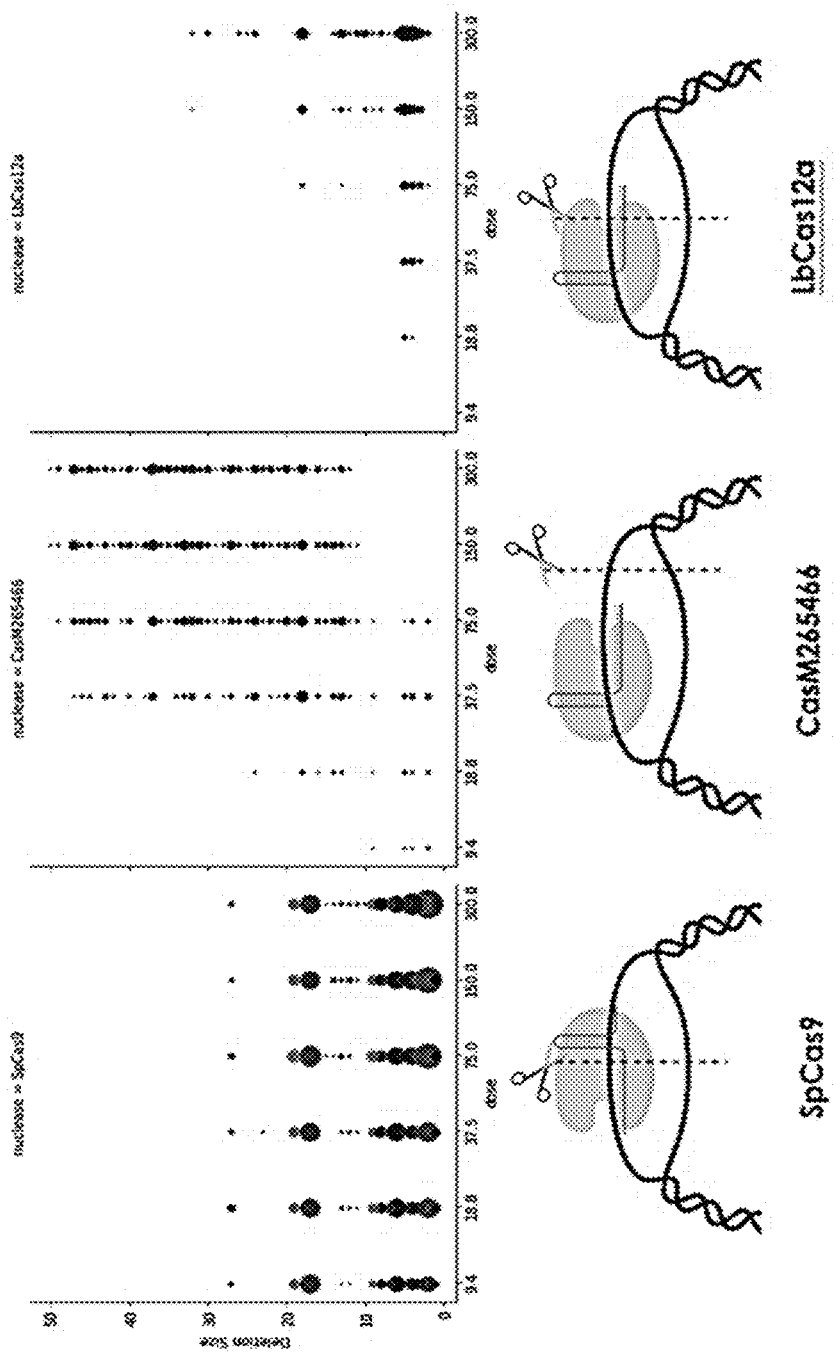
FIG. 8 is a graphical representation illustrating deletion size generated with CasM.265466 (SEQ ID NO: 1), paired with a guide RNA (SEQ ID NO: 42) as described in Example 14.

CasM.265466 (SEQ ID NO: 1) was tested for its potency to form indels within a target nucleic acid at increasing concentrations in HEK293T cells. Briefly, a scAAV plasmid was constructed to contain a transgene between its ITRs, the transgene providing or encoding, in a 5' to 3' direction, a U6 promoter, a guide RNA, an EFS promoter, the CasM.265466 effector protein, and a SV40 poly A tail. The guide nucleic acids comprised a nucleic acid sequence recited in SEQ ID NO: 42. The potency of CasM.265466 to form indels was tested using the plasmid at a concentration ranging from 9.375 ng to 300 ng. The plasmid was delivered to HEK293T cells via lipofection using TransIT®-23 lipofection reagent. Lipofected cells were grown for ~72 hours at 37° C. to allow for indel formation. Indels were detected by next generation sequencing (NGS) of PCR amplicons at the targeted loci, and indel percentage was calculated as the fraction of sequencing reads containing insertions or deletions relative to an unedited reference sequence at varying concentrations. The sequencing data was analyzed using CRISPRESSO to detect/quantify % indel. Results of the experiment are summarized in TABLE 27 and FIG. 8. LbCas12a and Cas9 were used as a positive control.

(gRNA), a second promoter, a D2S effector protein, and a poly A signal, as shown in FIG. 6. The AAV vector includes a ssAAV vector and a scAAV vector. The effector protein has an amino acid sequence that has at least 80% identity to any one of the sequences recited in TABLE 1. The guide nucleic acid comprises a sequence that is at least 90% identical to a target sequence within any one of the gene recited in TABLE 8. The effector protein can be expressed ubiquitously, wherein the second promoter the AAV vector is engineered to have includes but not limited to an EFS promoter, an MND promoter, and a CAG promoter. The Poly A tail sequence can be a sv40 Poly A tail sequence. The AAV vector is expressed with supporting plasmids to produce an adeno-associated virus (AAV).

| No. | Dose (ng) | Spacer SEQ ID NO: | % Aligned Read Rep 1. | % Aligned Read Rep 2. | % DELETION Rep 1. | % DELETION Rep 2. | % INDEL Rep 1. | % INDEL Rep 2 | % INSERTION Rep 1. | % INSERTION Rep 2. | EFFECTOR PROTEIN |
|---|---|---|---|---|---|---|---|---|---|---|---|
| 1 | 300 | 400 | ••• | •• | ♦♦ | ♦♦ | ++ | ++ | ▲▲▲ | ▲▲▲ | Cas9 |
| 2 | 300 | 401 | ••• | ••• | ♦ | ♦♦ | + | ++ | ▲▲ | ▲▲ | LbCas12a |
| 3 | 300 | 401 | •• | ••• | ♦♦ | ♦♦ | ++ | ++ | ▲ | ▲ | CasM.265466 |
| 4 | 150 | 400 | •• | •• | ♦♦ | ♦♦ | ++ | ++ | ▲▲▲ | ▲▲▲ | Cas9 |
| 5 | 150 | 401 | ••• | ••• | ♦ | ♦ | + | + | ▲▲ | ▲▲ | LbCas12a |
| 6 | 150 | 401 | •• | ••• | ♦♦ | ♦♦ | ++ | ++ | ▲ | ▲ | CasM.265466 |
| 7 | 75 | 400 | ••• | •• | ♦♦ | ♦♦ | ++ | ++ | ▲▲▲ | ▲▲▲ | Cas9 |
| 8 | 75 | 401 | ••• | ••• | ♦ | ♦ | + | + | ▲▲ | ▲▲ | LbCas12a |
| 9 | 75 | 401 | •• | ••• | ♦♦ | ♦♦ | ++ | ++ | ▲ | ▲ | CasM.265466 |
| 10 | 37.5 | 400 | ••• | ••• | ♦♦ | ♦♦ | ++ | ++ | ▲▲▲ | ▲▲▲ | Cas9 |
| 11 | 37.5 | 401 | ••• | ••• | ♦ | ♦ | + | + | ▲▲ | ▲▲ | LbCas12a |
| 12 | 37.5 | 401 | ••• | ••• | ♦♦ | ♦ | ++ | + | ▲ | ▲ | CasM.265466 |
| 13 | 18.75 | 400 | ••• | •• | ♦ | ♦♦ | + | ++ | ▲▲▲ | ▲▲▲ | Cas9 |
| 14 | 18.75 | 401 | ••• | ••• | ♦ | ♦ | + | + | ▲▲ | ▲▲ | LbCas12a |
| 15 | 18.75 | 401 | ••• | ••• | ♦ | ♦ | + | + | ▲▲ | ▲ | CasM.265466 |
| 16 | 9.375 | 400 | ••• | •• | ♦ | ♦♦ | + | ++ | ▲▲▲ | ▲▲▲ | Cas9 |
| 17 | 9.375 | 401 | ••• | ••• | ♦ | ♦ | + | + | ▲ | ▲ | LbCas12a |
| 18 | 9.375 | 401 | ••• | ••• | ♦ | ♦ | + | + | ▲ | ▲ | CasM.265466 |

* Magnitude of Aligned Read percentage data:
"•••" represents a value over 66.67,
"••" represents a value under 66.67 but over 33.33,
"•" represents a value under 33.33.
Magnitude of Deletion percentage data:
"♦♦♦" represents a value over 66.67,
"♦♦" represents a value under 66.67 but over 33.33,
"♦" represents a value under 33.33.
Magnitude of Indel percentage data:
"+++" represents a value over 66.67,
"++" represents a value under 66.67 but over 33.33,
"+" represents a value under 33.33.
Magnitude of Insertion percentage data:
"▲▲▲" represents a value over 1,
"▲▲" represents a value under 1 but over 0.1,
"▲" represents a value under 0.1.

An analysis of results further suggests that CasM.265466 appear to cut far outside a target sequence of the target nucleic acid. Therefore, CasM.265466 can hybridize and cleave the target nucleic acid multiple times before ultimately disrupting the target sequence. In contrast, Cas9 and LbCas12a appears to cleave the target sequence of the target nucleic acid disrupting the target sequence, and thereby losing the ability to hybridize and cleave the target nucleic acid again.

Example 15: AAV for D2S Effector Protein Delivery into Primary T Cells

An AAV vector is constructed to contain a transgene between its ITRs, the transgene providing or encoding, in a 5' to 3' direction, a U6 promoter, a guide nucleic acid The AAV is then used to transduce T cells. The T cell includes all types of immune cells expressing CD3, including: naïve T cells (cells that have not encountered their cognate antigens), T-helper cells (CD4+ cells), cytotoxic T-cells (CD8+ cells), natural killer T-cells, primary T-cells, T-regulatory cells (T-reg), and gamma-delta T cells. Briefly, the T cells are contacted with the AAV for 24 hours. After about 96 hours, post AAV contact, DNA or RNA is isolated from the effected T cells. Indels are detected by next generation sequencing (NGS) of PCR amplicons at the targeted loci, and indel percentage is calculated as the fraction of sequencing reads containing insertions or deletions relative to an unedited reference sequence.

Example 16: D2S Effector Protein for Gene Editing Gene in Eukaryotic Cells

Eukaryotic cells are transfected with nucleic acids encoding a D2S effector protein and a guide nucleic acid for modifying the target nucleic acid. The nucleic acid encoding the effector protein can be delivered as a plasmid or an mRNA. The effector protein has an amino acid sequence that has at least 8000 identity to any one of the sequences recited in TABLE 1. The nucleic acid encoding the guide nucleic acid can be delivered as a plasmid or a guide RNA. The guide RNA comprises a handle sequence and a spacer sequence. The handle sequence can be at least 80% identical to any one of the sequences recited in TABLE 4. The spacer sequence can target any one of the genes listed in TABLE 8. Exemplary spacer sequence can have at least 80% identical to any one of the sequences recited in TABLE 30, TABLE 31, and TABLE 32.

TABLE 30

Exemplary spacer sequences targeting B2M gene

| SEQ ID NO | Spacer Sequence |
|---|---|
| 325 | CUCGCGCUACUCUCUCUUUC |
| 326 | GGUUUCAUCCAUCCGACAUU |
| 474 | CUACACUGAAUUCACCCCCA |
| 327 | UCUCUUGUACUACACUGAAU |
| 302 | CUCACGUCAUCCAGCAGAGA |
| 477 | UGUCUGGGUUUCAUCCAUCC |
| 329 | CCUGCCGUGUGAACCAUGUG |
| 301 | UCACAGCCCAAGAUAGUUAA |
| 331 | ACUUUGUCACAGCCCAAGAU |
| 332 | UCUGGGUUUCAUCCAUCCGA |
| 333 | AACCAUGUGACUUUGUCACA |
| 334 | AAUGCUCCACUUUUUCAAUU |
| 335 | ACUUUCCAUUCUCUGCUGGA |
| 336 | ACAAAGUCACAUGGUUCACA |
| 337 | GUACAAGAGAUAGAAAGACC |
| 338 | CUGGAUGACGUGAGUAAACC |
| 488 | GUUUAUUUUUGUUCCACAAG |
| 489 | CACAAAAUGUAGGGUUAUAA |
| 490 | GGGGAAAUUUAGAAAUAUA |
| 491 | CUUGCUUGCUUUUUAAUAUU |
| 492 | CUUUGAGUGCUGUCUCCAUG |
| 493 | AUAAAGUAAGGCAUGGUUGU |
| 494 | GUUAAUCUGGUUUAUUUUUG |
| 495 | AUGUAUCUGAGCAGGUUGCU |
| 496 | CUUAGAAUUUGGGGGAAAAU |
| 497 | GAUUGGAUGAAUUCCAAAUU |
| 498 | UGCACAAAAUGUAGGGUUAU |
| 499 | GAAAUAUAAUUGACAGGAUU |
| 500 | AGUGCUGUCUCCAUGUUUGA |
| 501 | GGAGGGCUGGCAACUUAGAG |
| 502 | AACUCUUCAAUCUCUUGCAC |
| 503 | AUAAUGUUAACAUGGACAUG |
| 504 | CUUAUACACUUACACUUUAU |
| 505 | AUAUUGAUAUGCUUAUACAC |
| 506 | GGGUUAUAAUAAUGUUAACA |
| 507 | CAUUUGAUAAAGUAAGGCAU |
| 508 | UUUUUGUUCCACAAGUUAAA |
| 509 | UUCCACAAGUUAAAUAAAUC |
| 510 | UCUGAGCAGGUUGCUCCACA |
| 511 | AUUCUACUUUGAGUGCUGUC |
| 512 | AGCAGGUUGCUCCACAGGUA |
| 513 | AUUGACAGGAUUAUUGGAAA |
| 514 | AAGAUGCCGCAUUUGGAUUG |
| 515 | AUGAAUGAAACAUUUUGUCA |
| 516 | CAUACUCUGCUUAGAAUUUG |
| 517 | UAAUUCUACUUUGAGUGCUG |
| 518 | CACUUACACUUUAUGCACAA |
| 519 | ACCAAGAUGUUGAUGUUGGA |
| 520 | CAUAAAGUGUAAGUGUAUAA |
| 521 | GAACAAAAUAAACCAGAUU |
| 522 | CUCCCCACCUCUAAGUUGCC |
| 523 | AGUUGCCAGCCCUCCUAGAG |
| 524 | AAUUGGAAGUUAACUUAUGC |
| 525 | AGCAGAGUAUGUAAAUUGGA |
| 526 | ACAAAUUUCCAAUAAUCCUG |
| 527 | CACGCUUAACUAUCUUAACA |
| 528 | UUUAACUUGUGGAACAAAAA |
| 529 | UGAUUUAUUUAACUUGUGGA |
| 530 | GAGCAACCUGCUCAGAUACA |
| 531 | ACUUGUGGAACAAAAAUAAA |
| 532 | AGUGCAAGAGAUUGAAGAGU |
| 533 | AGUGUAUAAGCAUAUCAAUA |
| 534 | AUUUAUUUAACUUGUGGAAC |

TABLE 30-continued

Exemplary spacer sequences targeting B2M gene

| SEQ ID NO | Spacer Sequence |
|---|---|
| 535 | UGACAAAAUGUUUCAUUCAU |
| 536 | UGCAUAAAGUGUAAGUGUAU |
| 537 | AAGAAGAUCAUGUCCAUGUU |
| 538 | AAUUUUCCCCCAAAUUCUAA |
| 539 | GAAUUCAUCCAAUCCAAAUG |
| 540 | UUUCUAAAUUUUCCCCCAAA |
| 541 | ACCCUACAUUUGUGCAUAA |
| 542 | CUCGCGCUACUCUCUCUmU*mU*mC |
| 543 | GGUUUCAUCCAUCCGACmA*mU*mU |
| 544 | CUACACUGAAUUCACCCmC*mC*mA |
| 545 | UCUCUUGUACUACACUGmA*mA*mU |
| 546 | CUCACGUCAUCCAGCAGmA*mG*mA |
| 547 | UGUCUGGGUUUCAUCCAmU*mC*mC |
| 548 | CCUGCCGUGUGAACCAUmG*mU*mG |
| 549 | UCACAGCCCAAGAUAGUmU*mA*mA |
| 550 | ACUUUGUCACAGCCCAAmG*mA*mU |
| 551 | UCUGGGUUUCAUCCAUCmC*mG*mA |
| 552 | AACCAUGUGACUUUGUCmA*mC*mA |
| 553 | AAUGCUCCACUUUUUCAmA*mU*mU |
| 554 | ACUUUCAUUCUCUGCUmG*mG*mA |
| 555 | ACAAAGUCACAUGGUUCmA*mC*mA |
| 556 | GUACAAGAGAUAGAAAGmA*mC*mC |
| 557 | CUGGAUGACGUGAGUAAmA*mC*mC |
| 558 | GUUUAUUUUGUUCCACmA*mA*mG |
| 559 | CACAAAAUGUAGGGUUAmU*mA*mA |
| 560 | GGGGAAAAUUUAGAAAUmA*mU*mA |
| 561 | CUUGCUUGCUUUUUAAUmA*mU*mU |
| 562 | CUUUGAGUGCUGUCUCCmA*mU*mG |
| 563 | AUAAAGUAAGGCAUGGUmU*mG*mU |
| 564 | GUUAAUCGGUUUAUUUmU*mU*mG |
| 565 | AUGUAUCUGAGCAGGUUmG*mC*mU |
| 566 | CUUAGAAUUUGGGGGAmA*mA*mU |
| 567 | GAUUGGAUGAAUUCCAAmA*mU*mU |
| 568 | UGCACAAAUGUAGGGUmA*mU*mU |
| 569 | GAAAUAUAAUUGACAGGmA*mU*mU |
| 570 | AGUGCUGUCUCCAUGUUmU*mG*mA |
| 571 | GGAGGGCUGGCAACUUAmG*mA*mG |
| 572 | AACUCUUCAAUCUCUUGmC*mA*mC |

TABLE 30-continued

Exemplary spacer sequences targeting B2M gene

| SEQ ID NO | Spacer Sequence |
|---|---|
| 573 | AUAAUGUUAACAUGGACmA*mU*mG |
| 574 | CUUAUACACUUACACUUmU*mA*mU |
| 575 | AUAUUGAUAUGCUUAUAmC*mA*mC |
| 576 | GGGUUAUAAUAAUGUUAmA*mC*mA |
| 577 | CAUUUGAUAAAGUAAGGmC*mA*mU |
| 578 | UUUUUGUUCCACAAGUUmA*mA*mA |
| 579 | UUCCACAAGUUAAAUAAmA*mU*mC |
| 580 | UCUGAGCAGGUUGCUCCmA*mC*mA |
| 581 | AUUCUACUUUGAGUGCUmG*mU*mC |
| 582 | AGCAGGUUGCUCCACAGmG*mU*mU |
| 583 | AUUGACAGGAUUAUUGGmA*mA*mA |
| 584 | AAGAUGCCGCAUUUGGAmU*mU*mG |
| 585 | AUGAAUGAAACAUUUUGmU*mC*mA |
| 586 | CAUACUCUGCUUAGAAUmU*mU*mG |
| 587 | UAAUUCUACUUUGAGUGmC*mU*mG |
| 588 | CACUUACACUUUAUGCAmC*mA*mA |
| 589 | ACCAAGAUGUUGAUGUUmG*mG*mA |
| 590 | CAUAAAGUGUAAGUGUAmU*mA*mA |
| 591 | GAACAAAAAUAAACCAGmA*mU*mU |
| 592 | CUCCCCACCUCUAAGUUmG*mC*mC |
| 593 | AGUUGCCAGCCCUCCUAmG*mA*mG |
| 594 | AAUUGGAAGUUAACUUAmU*mG*mC |
| 595 | AGCAGAGUAUGUAAAUUmG*mG*mA |
| 596 | ACAAAUUCCAAUAAUCmC*mU*mG |
| 597 | CACGCUUAACUAUCUUAmA*mC*mA |
| 598 | UUUAACUUGUGGAACAAmA*mA*mA |
| 599 | UGAUUUAUUUAACUUGUmG*mG*mA |
| 600 | GAGCAACCUGCUCAGAUmA*mC*mA |
| 601 | ACUUGUGGAACAAAAAUmA*mA*mA |
| 602 | AGUGCAAGAGAUUGAAGmA*mG*mU |
| 603 | AGUGUAUAAGCAUAUCAmA*mU*mA |
| 604 | AUUUAUUUAACUUGUGGmA*mA*mC |
| 605 | UGACAAAAUGUUUCAUUmC*mA*mU |
| 606 | UGCAUAAAGUGUAAGUGmU*mA*mU |
| 607 | AAGAAGAUCAUGUCCAUmG*mU*mU |
| 608 | AAUUUUCCCCCAAAUUCmU*mA*mA |
| 609 | GAAUUCAUCCAAUCCAAmA*mU*mG |

TABLE 30-continued

Exemplary spacer sequences targeting B2M gene

| SEQ ID NO | Spacer Sequence |
|---|---|
| 610 | UUUCUAAAUUUUCCCCmA*mA*mA |
| 611 | ACCCUACAUUUUGUGCAmU*mA*mA |

NOTE:
RNA Modification: "*" represents a phosphorothioate bond between the nucleotides, "m" denotes a 2'-OMe modification.

TABLE 31

Exemplary spacer sequences targeting TRAC gene

| SEQ ID NO | Spacer Sequence |
|---|---|
| 612 | UCACAAAGUAAGGAUUCUGA |
| 613 | UGGACUUCAAGAGCAACAGU |
| 614 | AUUCUCAAACAAAUGUGUCA |
| 615 | ACUUUGCAUGUGCAAACGCC |
| 616 | CAAACGCCUUCAACAACAGC |
| 617 | UAUAUCACAGACAAAACUGU |
| 618 | AAUCCAGUGACAAGUCUGUC |
| 619 | AUGUGUAUAUCACAGACAAA |
| 620 | CAUGUGCAAACGCCUUCAAC |
| 621 | UCACAGACAAAACUGUGCUA |
| 622 | UAUCACAGACAAAACUGUGC |
| 623 | UCUGCCUAUUCACCGAUUUU |
| 624 | GCCUGGAGCAACAAAUCUGA |
| 625 | CCAGCUGAGAGACUCUAAAU |
| 626 | CCUAUUCACCGAUUUUGAUU |
| 627 | CUAGACAUGAGGUCUAUGGA |
| 628 | GACUUCAAGAGCAACAGUGC |
| 629 | GCACAGUUUUGUCUGUGAUA |
| 630 | AGAAUCAAAAUCGGUGAAUA |
| 631 | CACAUCAGAAUCCUUACUUU |
| 632 | UGAUAUACACAUCAGAAUCC |
| 633 | ACACAUUUGUUUGAGAAUCA |
| 634 | UGACACAUUUGUUUGAGAAU |
| 635 | GAGUCUCUCAGCUGGUACAC |
| 636 | UUGCUCCAGGCCACAGCACU |
| 637 | CACAUGCAAAGUCAGAUUUG |
| 638 | UUUGAGAAUCAAAAUCGGUG |
| 639 | AUAUACACAUCAGAAUCCUU |
| 640 | GAAUAAUGCUGUUGUUGAAG |

TABLE 31-continued

Exemplary spacer sequences targeting TRAC gene

| SEQ ID NO | Spacer Sequence |
|---|---|
| 641 | UCUGUGAUAUACACAUCAGA |
| 642 | AUGUCAAGCUGGUCGAGAAA |
| 643 | CUCAUGACGCUGCGGCUGUG |
| 644 | AUCUGCUCAUGACGCUGCGG |
| 645 | CUCCCUCGCUCCUUCCUCUG |
| 646 | GGCGUGUUGUAUGUCCUGCU |
| 647 | CACAUUCCCUCCUGCUCCCC |
| 648 | CAAGAUUGUAAGACAGCCUG |
| 649 | CAUUGCCCCUCUUCUCCCUC |
| 650 | UAUCUGGGCGUGUUGUAUGU |
| 651 | UGUCCUGCUGCCGAUGCCUU |
| 652 | AGACAGCCUGUGCUCCCUCG |
| 653 | UUCCCUUAUUCUGCUUGUC |
| 654 | AUUAAGAUUGCUGAAGAGCU |
| 655 | CCCCCCCGGCAAUGCCACCA |
| 656 | UCUGGGCGUGUUGUAUGUCC |
| 657 | UGAUUAAGAUUGCUGAAGAG |
| 658 | GGUCCUGCAGAAUGUUGUGA |
| 659 | UGCCCCCCGGCAAUGCCAC |
| 660 | CUGUGUAUCUGGGCGUGUUG |
| 661 | UUUGGAGAGGGAGAAGAGGG |
| 662 | CAGGACCUAGAGCCCAAGAG |
| 663 | CCGUGAAUGUCAGGCAGUGA |
| 664 | GAGAGGGAGAAGAGGGGCAA |
| 665 | GGGAGCAGGAGGGAAUGUGC |
| 666 | CACAGCCAGGGGAGGCUGCA |
| 667 | GGAUGGCGGAGGCAGUCUCU |
| 668 | UGGGAUGGCGGAGGCAGUCU |
| 669 | GCAGCUCUUCAGCAAUCUUA |
| 670 | UCACAAAGUAAGGAUUCmU*mG*mA |
| 671 | UGGACUUCAAGAGCAACmA*mG*mU |
| 672 | AUUCUCAAACAAAUGUGmU*mC*mA |
| 673 | ACUUUGCAUGUGCAAACmG*mC*mC |
| 674 | CAAACGCCUUCAACAACmA*mG*mC |
| 675 | UAUAUCACAGACAAAACmU*mG*mU |
| 676 | AAUCCAGUGACAAGUCUmG*mU*mC |
| 677 | AUGUGUAUAUCACAGACmA*mA*mA |

TABLE 31-continued

Exemplary spacer sequences targeting TRAC gene

| SEQ ID NO | Spacer Sequence |
|---|---|
| 678 | CAUGUGCAAACGCCUUCmA*mA*mC |
| 679 | UCACAGACAAAACUGUGmC*mU*mA |
| 680 | UAUCACAGACAAAACUGmU*mG*mC |
| 681 | UCUGCCUAUUCACCGAUmU*mU*mU |
| 682 | GCCUGGAGCAACAAAUCmU*mG*mA |
| 683 | CCAGCUGAGAGACUCUAmA*mA*mU |
| 684 | CCUAUUCACCGAUUUUGmA*mU*mU |
| 685 | CUAGACAUGAGGUCUAUmG*mG*mA |
| 686 | GACUUCAAGAGCAACAGmU*mG*mC |
| 687 | GCACAGUUUUGUCUGUGmA*mU*mA |
| 688 | AGAAUCAAAAUCGGUGAmA*mU*mA |
| 689 | CACAUCAGAAUCCUUACmU*mU*mU |
| 690 | UGAUAUACACAUCAGAAmU*mC*mC |
| 691 | ACACAUUUGUUUGAGAAmU*mC*mA |
| 692 | UGACACAUUUGUUUGAGmA*mA*mU |
| 693 | GAGUCUCUCAGCUGGUAmC*mA*mC |
| 694 | UUGCUCCAGGCCACAGCmA*mC*mU |
| 695 | CACAUGCAAAGUCAGAUmU*mU*mG |
| 696 | UUUGAGAAUCAAAAUCGmU*mU*mG |
| 697 | AUAUACACAUCAGAAUCmC*mU*mU |
| 698 | GAAUAAUGCUGUUUGUUmG*mA*mG |
| 699 | UCUGUGAUAUACACAUCmA*mG*mA |
| 700 | AUGUCAAGCUGGUCGAGmA*mA*mA |
| 701 | CUCAUGACGCUGCGGCUmG*mU*mG |
| 702 | AUCUGCUCAUGACGCUGmC*mG*mG |
| 703 | CUCCCUCGCUCCUUCCUmC*mU*mG |
| 704 | GGCGUGUUGUAUGUCCUmG*mC*mU |
| 705 | CACAUUCCCUCCUGCUCmC*mC*mC |
| 706 | CAAGAUUGUAAGACAGCmC*mU*mG |
| 707 | CAUUGCCCCUCUUUCUCmC*mC*mC |
| 708 | UAUCUGGGCGUGUUUGUAmU*mG*mU |
| 709 | UGUCCUGCUGCCGAUGCmC*mU*mU |
| 710 | AGACAGCCUGUGCUCCCmU*mC*mG |
| 711 | UUCCCUUAUUGCUGCUUmG*mU*mC |
| 712 | AUUAAGAUUGCUGAAGAmG*mC*mU |
| 713 | CCCCCCCGGCAAUGCCAmC*mC*mA |
| 714 | UCUGGGCGUGUUGUAUGmU*mC*mC |

TABLE 31-continued

Exemplary spacer sequences targeting TRAC gene

| SEQ ID NO | Spacer Sequence |
|---|---|
| 715 | UGAUUAAGAUUGCUGAAmG*mA*mG |
| 716 | GGUCCUGCAGAAUGUUGmU*mG*mA |
| 717 | UGCCCCCCGGCAAUGCmC*mA*mC |
| 718 | CUGUGUAUCUGGGCGUGmU*mU*mG |
| 719 | UUUGGAGAGGGAGAAGAmG*mG*mG |
| 720 | CAGGACCUAGAGCCCAAmG*mA*mG |
| 721 | CCGUGAAUGUCAGGCAGmU*mG*mA |
| 722 | GAGAGGGAGAAGAGGGGmC*mA*mA |
| 723 | GGGAGCAGGAGGGAAUGmU*mG*mC |
| 724 | CACAGCCAGGGGAGGCUmG*mC*mA |
| 725 | GGAUGGCGGAGGCAGUCmU*mC*mU |
| 726 | UGGGAUGGCGGAGGCAGmU*mC*mU |
| 727 | GCAGCUCUUCAGCAAUCmU*mU*mA |

NOTE:
RNA Modification: "*" represents a phosphorothioate bond between the nucleotides, "m" denotes a 2'-OMe modification.

TABLE 32

Exemplary spacer sequences targeting CIITA gene

| SEQ ID NO | Spacer Sequence |
|---|---|
| 728 | UGCUUCUGAGCUGGGCAUCC |
| 729 | AGCUGGGCAUCCGAAGGCAU |
| 730 | CUUCUGAGCUGGGCAUCCGA |
| 731 | GGAAUCCCAGCCAGGCAGCA |
| 732 | UAGGAAUCCCAGCCAGGCAG |
| 733 | GCAGCCCCUCCUCGUGCCCU |
| 734 | ACAGGUAGGACCCAGCAGGG |
| 735 | UGACCAGAUGGACCUGGCUG |
| 736 | CCACUUCUAUGACCAGAUGG |
| 737 | ACCAGAUGGACCUGGCUGGA |
| 738 | CCACCAUGGAGUUGGGGCCC |
| 739 | CCUCUACCACUUCUAUGACC |
| 740 | GGGGCCCCAACUCCAUGGUG |
| 741 | GUCAUAGAAGUGGUAGAGGC |
| 742 | ACAUGGAAGGUGAUGAAGAG |
| 743 | UGACAUGGAAGGUGAUGAAG |
| 744 | UCUUCCAGGACUCCCAGCUG |
| 745 | UGCUUCUGAGCUGGGCAmU*mC*mC |

TABLE 32-continued

Exemplary spacer sequences targeting CIITA gene

| SEQ ID NO | Spacer Sequence |
|---|---|
| 746 | AGCUGGGCAUCCGAAGGmC*mA*mU |
| 747 | CUUCUGAGCUGGGCAUCmC*mG*mA |
| 748 | GGAAUCCCAGCCAGGCAmG*mC*mA |
| 749 | UAGGAAUCCCAGCCAGGmC*mA*mG |
| 750 | GCAGCCCCUCCUCGUGCmC*mC*mU |
| 751 | ACAGGUAGGACCCAGCAmG*mG*mG |
| 752 | UGACCAGAUGGACCUGGmC*mU*mG |
| 753 | CCACUUCUAUGACCAGAmU*mG*mG |
| 754 | ACCAGAUGGACCUGGCUmG*mG*mA |
| 755 | CCACCAUGGAGUUGGGGmC*mC*mC |
| 756 | CCUCUACCACUUCUAUGmA*mC*mC |
| 757 | GGGGCCCCAACUCCAUGmG*mU*mG |
| 758 | GUCAUAGAAGUGGUAGAmG*mG*mC |
| 759 | ACAUGGAAGGUGAUGAAmG*mA*mG |
| 760 | UGACAUGGAAGGUGAUGmA*mA*mG |
| 761 | UCUUCCAGGACUCCCAGmC*mU*mG |

NOTE:
RNA Modification: "*" represents a phosphorothioate bond between the nucleotides, "m" denotes a 2'-OMe modification.

The eukaryotic cells can be transfected by electroporation, lipofection, acoustic poration, optoporation, viral vector-based delivery, iTOP, nanoparticle delivery (e.g., lipid or gold nanoparticle delivery), cell-penetrating peptide (CPP) delivery, DNA nanostructure delivery, or any combination thereof. After about 48 hours to about 96 hours of post-transfection, the eukaryotic cells are screened for deletions in intronic and exonic regions of multiple exons to assess percentage of indel generation and/or gene knockouts. DNA or RNA is isolated from the transfected eukaryotic cells and indels are detected by next generation sequencing (NGS) of PCR amplicons at the targeted loci. Indel percentage is calculated as the fraction of sequencing reads containing insertions or deletions relative to an unedited reference sequence.

Example 17. Indel Generation in Eukaryotic Cells with CasM.265466 and Guides Targeting B2M Guides targeting exon 1 or exon 2 of B2M were tested with Cas 265466 (SEQ ID NO: 1) for the ability to produce indels in primary T Cells. 16 modified guide RNA sequences (i.e., a phosphorothioate bond between the nucleotides, a 2'-OMe modification) directed to various target sequences were tested and their ability to introduce indels was measured. Briefly, about $30\times10^6$ T cells were electroporated with a mixture of mRNA of the Cas 265466 (5 μg) and different guides (500 pmol). The transfected cells were incubated for ~72 hours to allow for indel formation followed by DNA extraction.

After the 72-hour incubation, a portion of the cells were incubated with a Live/Dead cell stain and a B2M antibody for fluorescence-activated cell sorting (FACS) analysis. Indels were detected by next generation sequencing (NGS) of PCR amplicons at the targeted loci 3 days and 7 days post-transfection. Indel percentage was calculated as the fraction of sequencing reads containing insertions or deletions relative to an unedited reference sequence. The effector proteins Cas9 and Cas12a were used as a positive control. The results are summarized in TABLE 33. An analysis of the results indicates that the effector protein CasM.265466 mRNA and the guides targeting B2M gene can be used for editing the gene.

TABLE 33

Exemplary modified guides for B2M editing in T cells

| Comp. No. | Effector Protein SEQ ID NO | 5' PAM Seq | gRNA SEQ ID NO: | sgRNA Sequence with Modification | Target Gene | FACS %-ve Cells (3 days) | Sequence Analysis % Indels (3 days) | Sequence Analysis % Indels (7 days) |
|---|---|---|---|---|---|---|---|---|
| 181 | 1 | TGTG | 762 | mA*mC*mA*G CUUAUUUGG AAGCUGAAA UGUGAGGUU UAUAACACU CACAAGAAU CCUGAAAAA GGAUGCCAA ACCUCGCGC UACUCUCUC UmU*mU*mC | B2M exon: #1 | • | •• | •• |
| 182 | 1 | TCTG | 763 | mA*mC*mA*G CUUAUUUGG AAGCUGAAA UGUGAGGUU UAUAACACU CACAAGAAU CCUGAAAAA GGAUGCCAA | B2M exon: #2 | •• | ••• | •• |

TABLE 33-continued

Exemplary modified guides for B2M editing in T cells

| Comp. No. | Effector Protein SEQ ID NO | 5' PAM Seq | gRNA SEQ ID NO: | sgRNA Sequence with Modification | Target Gene | FACS %-ve Cells (3 days) | Sequence Analysis | |
|---|---|---|---|---|---|---|---|---|
| | | | | | | | % Indels (3 days) | % Indels (7 days) |
| | | | | ACGGUUUCA UCCAUCCGA CmA*mU*mU | | | | |
| 183 | 1 | TGTA | 764 | mA*mC*mA*G CUUAUUUGG AAGCUGAAA UGUGAGGUU UAUAACACU CACAAGAAU CCUGAAAAA GGAUGCCAA ACCUACACU GAAUUCACC CmC*mC*mA | B2M exon: #2 | ••• | ••• | ••• |
| 184 | 1 | TCTA | 765 | mA*mC*mA*G CUUAUUUGG AAGCUGAAA UGUGAGGUU UAUAACACU CACAAGAAU CCUGAAAAA GGAUGCCAA ACUCUCUUG UACUACACU GmA*mA*mU | B2M exon: #2 | • | •• | •• |
| 185 | 1 | TTTA | 766 | mA*mC*mA*G CUUAUUUGG AAGCUGAAA UGUGAGGUU UAUAACACU CACAAGAAU CCUGAAAAA GGAUGCCAA ACCUCACGU CAUCCAGCA GmA*mG*mA | B2M exon: #2 | • | •• | •• |
| 186 | 1 | TATG | 767 | mA*mC*mA*G CUUAUUUGG AAGCUGAAA UGUGAGGUU UAUAACACU CACAAGAAU CCUGAAAAA GGAUGCCAA ACUGUCUGG GUUUCAUCC AmU*mC*mC | B2M exon: #2 | •• | ••• | •• |
| 187 | 1 | TATG | 768 | mA*mC*mA*G CUUAUUUGG AAGCUGAAA UGUGAGGUU UAUAACACU CACAAGAAU CCUGAAAAA GGAUGCCAA ACCCUGCCG UGUGAACCA UmG*mU*mG | B2M exon: #2 | • | • | • |
| 188 | 1 | TTTG | 769 | mA*mC*mA*G CUUAUUUGG AAGCUGAAA UGUGAGGUU UAUAACACU CACAAGAAU CCUGAAAAA | B2M exon: #2 | • | • | • |

TABLE 33-continued

Exemplary modified guides for B2M editing in T cells

| Comp. No. | Effector Protein SEQ ID NO | 5' PAM Seq | gRNA SEQ ID NO: | sgRNA Sequence with Modification | Target Gene | FACS %-ve Cells (3 days) | Sequence Analysis % Indels (3 days) | % Indels (7 days) |
|---|---|---|---|---|---|---|---|---|
| | | | | GGAUGCCAA ACUCACAGC CCAAGAUAG UmU*mA*mA | | | | |
| 189 | 1 | TGTG | 770 | mA*mC*mA*G CUUAUUUGG AAGCUGAAA UGUGAGGUU UAUAACACU CACAAGAAU CCUGAAAAA GGAUGCCAA ACACUUUGU CACAGCCCA AmG*mA*mU | B2M exon: #2 | •• | •• | •• |
| 190 | 1 | TGTG | 771 | mA*mC*mA*G CUUAUUUGG AAGCUGAAA UGUGAGGUU UAUAACACU CACAAGAAU CCUGAAAAA GGAUGCCAA ACUCUGGGU UUCAUCCAU CmC*mG*mA | B2M exon: #2 | • | • | • |
| 191 | 1 | TGTG | 772 | mA*mC*mA*G CUUAUUUGG AAGCUGAAA UGUGAGGUU UAUAACACU CACAAGAAU CCUGAAAAA GGAUGCCAA ACAACCAUG UGACUUUGU CmA*mC*mA | B2M exon: #2 | • | • | • |
| 192 | 1 | TCTG | 773 | mA*mC*mA*G CUUAUUUGG AAGCUGAAA UGUGAGGUU UAUAACACU CACAAGAAU CCUGAAAAA GGAUGCCAA ACAAUGCUC CACUUUUUC AmA*mU*mU | B2M exon: #2 | •• | ••• | ••• |
| 193 | 1 | TTTG | 774 | mA*mC*mA*G CUUAUUUGG AAGCUGAAA UGUGAGGUU UAUAACACU CACAAGAAU CCUGAAAAA GGAUGCCAA ACACUUUCC AUUCUCUGC UmG*mG*mA | B2M exon: #2 | • | •• | •• |
| 194 | 1 | TGTG | 775 | mA*mC*mA*G CUUAUUUGG AAGCUGAAA UGUGAGGUU UAUAACACU CACAAGAAU | B2M exon: #2 | ••• | ••• | ••• |

TABLE 33-continued

Exemplary modified guides for B2M editing in T cells

| Comp. No. | Effector Protein SEQ ID NO | 5' PAM Seq | gRNA SEQ ID NO: | sgRNA Sequence with Modification | Target Gene | FACS %-ve Cells (3 days) | Sequence Analysis % Indels (3 days) | Sequence Analysis % Indels (7 days) |
|---|---|---|---|---|---|---|---|---|
| | | | | CCUGAAAAA GGAUGCCAA ACACAAAGU CACAUGGUU CmA*mC*mA | | | | |
| 195 | 1 | TGTA | 776 | mA*mC*mA*G CUUAUUUGG AAGCUGAAA UGUGAGGUU UAUAACACU CACAAGAAU CCUGAAAAA GGAUGCCAA ACGUACAAG AGAUAGAAA GmA*mC*mC | B2M exon: #2 | • | • | • |
| 196 | 1 | TCTG | 777 | mA*mC*mA*G CUUAUUUGG AAGCUGAAA UGUGAGGUU UAUAACACU CACAAGAAU CCUGAAAAA GGAUGCCAA ACCUGGAUG ACGUGAGUA AmA*mC*mC | B2M exon: #2 | ••• | ••• | ••• |

NOTE:
RNA Modification: "*" represents a phosphorothioate bond between the nucleotides, "m" denotes a 2'-OMe modification. Magnitude of data: "•••" represents a value >40, "••" represents a value between ≤40 and ≥20, "•" represents a value <20.

Example 18. Indel Generation in Eukaryotic Cells with CasM.265466 and Guides Targeting TRAC Guides targeting exon 1, exon 2 and exon 3 of TRAC were tested with Cas 265466 (SEQ ID NO: 1) for the ability to produce indels in primary T Cells. 33 modified guide RNA sequences (i.e., a phosphorothioate bond between the nucleotides, a 2'-OMe modification) directed to various target sequences were tested and their ability to introduce indels was measured. Briefly, about 30×10⁶ T cells were electroporated with a mixture of mRNA of the Cas 265466 (5 µg) and different guides (500 pmol). The transfected cells were incubated for ~72 hours to allow for indel formation followed by DNA extraction.

After the 72-hour incubation, a portion of the cells were incubated with a Live/Dead cell stain and a CD3 antibody for fluorescence-activated cell sorting (FACS) analysis. Indels were detected by next generation sequencing (NGS) of PCR amplicons at the targeted loci 3 days post-transfection. Indel percentage was calculated as the fraction of sequencing reads containing insertions or deletions relative to an unedited reference sequence. The effector proteins Cas9 and Cas12a were used as a positive control. The results are summarized in TABLE 34. An analysis of the results indicates that the effector protein CasM.265466 mRNA and the guides targeting TRAC gene can be used for editing the gene.

TABLE 34

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| 197 | 1 | TGTG | 778 | mA*mC*mA*GCU UAUUUGGAAGCU GAAAUGUGAGG UUUAUAACACUC ACAAGAAUCCUG AAAAGGAUGCC | TRAC exon: #1 | ••• | ••• |

TABLE 34-continued

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| | | | | AAACUCACAAAG UAAGGAUUCmU* mG*mA | | | |
| 198 | 1 | TCTA | 779 | mA*mC*mA*GCU UAUUUGGAAGCU GAAAUGUGAGG UUUAUAACACUC ACAAGAAUCCUG AAAAAGGAUGCC AAACUGGACUUC AAGAGCAACmA* mG*mU | TRAC exon: #1 | •• | ••• |
| 199 | 1 | TTTG | 780 | mA*mC*mA*GCU UAUUUGGAAGCU GAAAUGUGAGG UUUAUAACACUC ACAAGAAUCCUG AAAAAGGAUGCC AAACAUUCUCAA ACAAAUGUGmU* mC*mA | TRAC exon: #1 | • | • |
| 200 | 1 | TCTG | 781 | mA*mC*mA*GCU UAUUUGGAAGCU GAAAUGUGAGG UUUAUAACACUC ACAAGAAUCCUG AAAAAGGAUGCC AAACACUUUGCA UGUGCAAACmG* mC*mC | TRAC exon: #1 | •• | •• |
| 201 | 1 | TGTG | 782 | mA*mC*mA*GCU UAUUUGGAAGCU GAAAUGUGAGG UUUAUAACACUC ACAAGAAUCCUG AAAAAGGAUGCC AAACCAAACGCC UUCAACAACmA* mG*mC | TRAC exon: #1 | • | •• |
| 202 | 1 | TGTG | 783 | mA*mC*mA*GCU UAUUUGGAAGCU GAAAUGUGAGG UUUAUAACACUC ACAAGAAUCCUG AAAAAGGAUGCC AAACUAUAUCAC AGACAAAACmU* mG*mU | TRAC exon: #1 | •• | ••• |
| 203 | 1 | TCTA | 784 | mA*mC*mA*GCU UAUUUGGAAGCU GAAAUGUGAGG UUUAUAACACUC ACAAGAAUCCUG AAAAAGGAUGCC AAACAAUCCAGU GACAAGUCUmG* mU*mC | TRAC exon: #1 | •• | ••• |
| 204 | 1 | TCTG | 785 | mA*mC*mA*GCU UAUUUGGAAGCU GAAAUGUGAGG UUUAUAACACUC ACAAGAAUCCUG AAAAAGGAUGCC | TRAC exon: #1 | •• | ••• |

TABLE 34-continued

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| | | | | AAACAUGUGUAU AUCACAGACmA* mA*mA | | | |
| 205 | 1 | TTTG | 786 | mA*mC*mA*GCU UAUUUGGAAGCU GAAAUGUGAGG UUUAUAACACUC ACAAGAAUCCUG AAAAAGGAUGCC AAACCAUGUGCA AACGCCUUCmA* mA*mC | TRAC exon: #1 | •• | • |
| 206 | 1 | TATA | 787 | mA*mC*mA*GCU UAUUUGGAAGCU GAAAUGUGAGG UUUAUAACACUC ACAAGAAUCCUG AAAAAGGAUGCC AAACUCACAGAC AAAACUGUGmC* mU*mA | TRAC exon: #1 | ••• | ••• |
| 207 | 1 | TGTA | 788 | mA*mC*mA*GCU UAUUUGGAAGCU GAAAUGUGAGG UUUAUAACACUC ACAAGAAUCCUG AAAAAGGAUGCC AAACUAUCACAG ACAAAACUGmU* mG*mC | TRAC exon: #1 | ••• | ••• |
| 208 | 1 | TCTG | 789 | mA*mC*mA*GCU UAUUUGGAAGCU GAAAUGUGAGG UUUAUAACACUC ACAAGAAUCCUG AAAAAGGAUGCC AAACUCUGCCUA UUCACCGAUmU* mU*mU | TRAC exon: #1 | •• | •• |
| 209 | 1 | TGTG | 790 | mA*mC*mA*GCU UAUUUGGAAGCU GAAAUGUGAGG UUUAUAACACUC ACAAGAAUCCUG AAAAAGGAUGCC AAACGCCUGGAG CAACAAAUCmU* mG*mA | TRAC exon: #1 | •• | • |
| 210 | 1 | TGTA | 791 | mA*mC*mA*GCU UAUUUGGAAGCU GAAAUGUGAGG UUUAUAACACUC ACAAGAAUCCUG AAAAAGGAUGCC AAACCCAGCUGA GAGACUCUAmA* mA*mU | TRAC exon: #1 | •• | ••• |
| 211 | 1 | TCTG | 792 | mA*mC*mA*GCU UAUUUGGAAGCU GAAAUGUGAGG UUUAUAACACUC ACAAGAAUCCUG AAAAAGGAUGCC | TRAC exon: #1 | • | • |

TABLE 34-continued

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| | | | | AAACCCUAUUCA CCGAUUUUGmA* mU*mU | | | |
| 212 | 1 | TGTG | 793 | mA*mC*mA*GCU UAUUUGGAAGCU GAAAUGUGAGG UUUAUAACACUC ACAAGAAUCCUG AAAAAGGAUGCC AAACCUAGACAU GAGGUCUAUmG* mG*mA | TRAC exon: #1 | •• | • |
| 213 | 1 | TATG | 794 | mA*mC*mA*GCU UAUUUGGAAGCU GAAAUGUGAGG UUUAUAACACUC ACAAGAAUCCUG AAAAAGGAUGCC AAACGACUUCAA GAGCAACAGmU* mG*mC | TRAC exon: #1 | •• | •• |
| 214 | 1 | TCTA | 795 | mA*mC*mA*GCU UAUUUGGAAGCU GAAAUGUGAGG UUUAUAACACUC ACAAGAAUCCUG AAAAAGGAUGCC AAACGCACAGUU UUGUCUGUGmA* mU*mA | TRAC exon: #1 | • | • |
| 215 | 1 | TTTG | 796 | mA*mC*mA*GCU UAUUUGGAAGCU GAAAUGUGAGG UUUAUAACACUC ACAAGAAUCCUG AAAAAGGAUGCC AAACAGAAUCAA AAUCGGUGAmA* mU*mA | TRAC exon: #1 | • | • |
| 216 | 1 | TATA | 797 | mA*mC*mA*GCU UAUUUGGAAGCU GAAAUGUGAGG UUUAUAACACUC ACAAGAAUCCUG AAAAAGGAUGCC AAACCACAUCAG AAUCCUUACmU* mU*mU | TRAC exon: # 1 | •• | ••• |
| 217 | 1 | TCTG | 798 | mA*mC*mA*GCU UAUUUGGAAGCU GAAAUGUGAGG UUUAUAACACUC ACAAGAAUCCUG AAAAAGGAUGCC AAACUGAUAUAC ACAUCAGAAmU* mC*mC | TRAC exon: #1 | •• | ••• |
| 218 | 1 | TGTG | 799 | mA*mC*mA*GCU UAUUUGGAAGCU GAAAUGUGAGG UUUAUAACACUC ACAAGAAUCCUG AAAAAGGAUGCC | TRAC exon: #1 | • | •• |

TABLE 34-continued

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| | | | | AAACACACAUUU GUUUGAGAAmU* mC*mA | | | |
| 219 | 1 | TTTG | 800 | mA*mC*mA*GCU UAUUUGGAAGCU GAAAUGUGAGG UUUAUAACACUC ACAAGAAUCCUG AAAAAGGAUGCC AAACUGACACAU UUGUUUGAGmA* mA*mU | TRAC exon: #1 | • | • |
| 220 | 1 | TTTA | 801 | mA*mC*mA*GCU UAUUUGGAAGCU GAAAUGUGAGG UUUAUAACACUC ACAAGAAUCCUG AAAAAGGAUGCC AAACGAGUCUCU CAGCUGGUAmC* mA*mC | TRAC exon: #1 | ••• | ••• |
| 221 | 1 | TTTG | 802 | mA*mC*mA*GCU UAUUUGGAAGCU GAAAUGUGAGG UUUAUAACACUC ACAAGAAUCCUG AAAAAGGAUGCC AAACUUGCUCCA GGCCACAGCmA* mC*mU | TRAC exon: #1 | ••• | ••• |
| 222 | 1 | TTTG | 803 | mA*mC*mA*GCU UAUUUGGAAGCU GAAAUGUGAGG UUUAUAACACUC ACAAGAAUCCUG AAAAAGGAUGCC AAACCACAUGCA AAGUCAGAUmU* mU*mG | TRAC exon: #1 | • | • |
| 223 | 1 | TTTG | 804 | mA*mC*mA*GCU UAUUUGGAAGCU GAAAUGUGAGG UUUAUAACACUC ACAAGAAUCCUG AAAAAGGAUGCC AAACUUUGAGAA UCAAAAUCGmG* mU*mG | TRAC exon: #1 | •• | •• |
| 224 | 1 | TGTG | 805 | mA*mC*mA*GCU UAUUUGGAAGCU GAAAUGUGAGG UUUAUAACACUC ACAAGAAUCCUG AAAAAGGAUGCC AAACAUAUACAC AUCAGAAUCmC* mU*mU | TRAC exon: #1 | •• | ••• |
| 225 | 1 | TCTG | 806 | mA*mC*mA*GCU UAUUUGGAAGCU GAAAUGUGAGG UUUAUAACACUC ACAAGAAUCCUG AAAAAGGAUGCC | TRAC exon: #1 | • | • |

TABLE 34-continued

Exemplary modified guides for TRAC editing in T cells

| Comp. No. | Effector Protein SEQ ID NO | 5' PAM Seq | gRNA SEQ ID NO: | sgRNA Sequence with Modification | Target Gene | FACS Analysis %-ve Cells (3 days) | Sequence Analysis % Indels (3 days) |
|---|---|---|---|---|---|---|---|
| | | | | AAACGAAUAAUG CUGUUGUUGmA* mA*mG | | | |
| 226 | 1 | TTTG | 807 | mA*mC*mA*GCU UAUUUGGAAGCU GAAAUGUGAGG UUUAUAACACUC ACAAGAAUCCUG AAAAAGGAUGCC AAACUCUGUGAU AUACACAUCmA* mG*mA | TRAC exon: #1 | •• | ••• |
| 227 | 1 | TGTG | 808 | mA*mC*mA*GCU UAUUUGGAAGCU GAAAUGUGAGG UUUAUAACACUC ACAAGAAUCCUG AAAAAGGAUGCC AAACAUGUCAAG CUGGUCGAGmA* mA*mA | TRAC exon: #2 | • | •• |
| 228 | 1 | TCTG | 809 | mA*mC*mA*GCU UAUUUGGAAGCU GAAAUGUGAGG UUUAUAACACUC ACAAGAAUCCUG AAAAAGGAUGCC AAACCUCAUGAC GCUGCGGCUmG* mU*mG | TRAC exon: #3 | • | •• |
| 229 | 1 | TTTA | 810 | mA*mC*mA*GCU UAUUUGGAAGCU GAAAUGUGAGG UUUAUAACACUC ACAAGAAUCCUG AAAAAGGAUGCC AAACAUCUGCUC AUGACGCUGmC* mG*mG | TRAC exon: #3 | ••• | ••• |

NOTE:
RNA Modification: "*" represents a phosphorothioate bond between the nucleotides, "m" denotes a 2'-OMe modification. Magnitude of data: "•••" represents a value >45, "••" represents a value between ≤45 and ≥20, "•" represents a value <20.

Example 19. Indel Generation in Eukaryotic Cells with CasM.265466 and Guides Targeting CIITA Guides targeting exon 1, exon 2 and exon 3 of CIITA were tested with Cas 265466 (SEQ ID NO: 1) for the ability to produce indels in primary T Cells. 27 modified guide RNA sequences (i.e., a phosphorothioate bond between the nucleotides, a 2'-OMe modification) directed to various target sequences were tested and their ability to introduce indels was measured. Briefly, 30×10$^6$ T cells were electroporated with a mixture of mRNA of the Cas 265466 (5 μg) and different guides (500 pmol The transfected cells were incubated for ~72 hours to allow for indel formation followed by DNA extraction.

After the 72-hour incubation, indels were detected by next generation sequencing (NGS) of PCR amplicons at the targeted loci. Indel percentage was calculated as the fraction of sequencing reads containing insertions or deletions relative to an unedited reference sequence. The effector proteins Cas9 and Cas12a were used as a positive control. The results are summarized in TABLE 35. An analysis of the results indicates that the effector protein CasM.265466 mRNA and the guides targeting CIITA gene can be used for editing the gene.

TABLE 35

Exemplary modified guides for CIITA editing in T cells

| Comp. No. | Effector Protein SEQ ID NO: | 5' PAM Seq | gRNA SEQ ID NO: | RNA Sequence with Modification | Target Gene | % Indels (3 days) |
|---|---|---|---|---|---|---|
| 230 | 1 | TGTG | 811 | mA*mC*mA*GCUUAUUU GGAAGCUGAAAUGUGA GGUUUAUAACACUCACA AGAAUCCUGAAAAAGG AUGCCAAACUGCUUCUG AGCUGGGCAmU*mC*mC | CIITA exon: #1 | •• |
| 231 | 1 | TCTG | 812 | mA*mC*mA*GCUUAUUU GGAAGCUGAAAUGUGA GGUUUAUAACACUCACA AGAAUCCUGAAAAAGG AUGCCAAACAGCUGGGC AUCCGAAGGmC*mA*mU | CIITA exon: #1 | •• |
| 232 | 1 | TGTG | 813 | mA*mC*mA*GCUUAUUU GGAAGCUGAAAUGUGA GGUUUAUAACACUCACA AGAAUCCUGAAAAAGG AUGCCAAACCUUCUGAG CUGGGCAUCmC*mG*mA | CIITA exon: #1 | • |
| 233 | 1 | TGTA | 814 | mA*mC*mA*GCUUAUUU GGAAGCUGAAAUGUGA GGUUUAUAACACUCACA AGAAUCCUGAAAAAGG AUGCCAAACGGAUCCC AGCCAGGCAmG*mC*mA | CIITA exon: #1 | ••• |
| 234 | 1 | TGTG | 815 | mA*mC*mA*GCUUAUUU GGAAGCUGAAAUGUGA GGUUUAUAACACUCACA AGAAUCCUGAAAAAGG AUGCCAAACUAGGAAUC CCAGCCAGGmC*mA*mG | CIITA exon: #1 | ••• |
| 235 | 1 | TCTG | 816 | mA*mC*mA*GCUUAUUU GGAAGCUGAAAUGUGA GGUUUAUAACACUCACA AGAAUCCUGAAAAAGG AUGCCAAACGCAGCCCC UCCUCGUGCmC*mC*mU | CIITA exon: #1 | ••• |
| 236 | 1 | TCTG | 817 | mA*mC*mA*GCUUAUUU GGAAGCUGAAAUGUGA GGUUUAUAACACUCACA AGAAUCCUGAAAAAGG AUGCCAAACACAGGUAG GACCCAGCAmG*mG*mG | CIITA exon: #1 | •• |
| 237 | 1 | TCTA | 818 | mA*mC*mA*GCUUAUUU GGAAGCUGAAAUGUGA GGUUUAUAACACUCACA AGAAUCCUGAAAAAGG AUGCCAAACUGACCAGA UGGACCCUGGmC*mU*mG | CIITA exon: #2 | •• |
| 238 | 1 | TCTA | 819 | mA*mC*mA*GCUUAUUU GGAAGCUGAAAUGUGA GGUUUAUAACACUCACA AGAAUCCUGAAAAAGG AUGCCAAACCCACUUCU AUGACCAGAmU*mG*mG | CIITA exon: #2 | • |
| 239 | 1 | TATG | 820 | mA*mC*mA*GCUUAUUU GGAAGCUGAAAUGUGA GGUUUAUAACACUCACA AGAAUCCUGAAAAAGG AUGCCAAACACCAGAUG GACCUGGCUmG*mG*mA | CIITA exon: #2 | • |

TABLE 35-continued

Exemplary modified guides for CIITA editing in T cells

| Comp. No. | Effector Protein SEQ ID NO: | 5' PAM Seq | gRNA SEQ ID NO: | RNA Sequence with Modification | Target Gene | % Indels (3 days) |
|---|---|---|---|---|---|---|
| 240 | 1 | TGTG | 821 | mA*mC*mA*GCUUAUUU GGAAGCUGAAAUGUGA GGUUUAUAACACUCACA AGAAUCCUGAAAAAGG AUGCCAAACCCACCAUG GAGUUGGGGmC*mC*mC | CIITA exon: #2 | • |
| 241 | 1 | TGTG | 822 | mA*mC*mA*GCUUAUUU GGAAGCUGAAAUGUGA GGUUUAUAACACUCACA AGAAUCCUGAAAAAGG AUGCCAAACCCUCUACC ACUUCUAUGmA*mC*mC | CIITA exon: #2 | • |
| 242 | 1 | TCTA | 823 | mA*mC*mA*GCUUAUUU GGAAGCUGAAAUGUGA GGUUUAUAACACUCACA AGAAUCCUGAAAAAGG AUGCCAAACGGGGCCCC AACUCCAUGmG*mU*mG | CIITA exon: #2 | •• |
| 243 | 1 | TCTG | 824 | mA*mC*mA*GCUUAUUU GGAAGCUGAAAUGUGA GGUUUAUAACACUCACA AGAAUCCUGAAAAAGG AUGCCAAACGUCAUAGA AGUGGUAGAmG*mG*mC | CIITA exon: #2 | • |
| 244 | 1 | TGTG | 825 | mA*mC*mA*GCUUAUUU GGAAGCUGAAAUGUGA GGUUUAUAACACUCACA AGAAUCCUGAAAAAGG AUGCCAAACACAUGGAA GGUGAUGAAmG*mA*mG | CIITA exon: #3 | •• |
| 245 | 1 | TGTG | 826 | mA*mC*mA*GCUUAUUU GGAAGCUGAAAUGUGA GGUUUAUAACACUCACA AGAAUCCUGAAAAAGG AUGCCAAACUGACAUGG AAGGUGAUGmA*mA*mG | CIITA exon: #3 | •• |
| 246 | 1 | TATG | 827 | mA*mC*mA*GCUUAUUU GGAAGCUGAAAUGUGA GGUUUAUAACACUCACA AGAAUCCUGAAAAAGG AUGCCAAACUCUUCCAG GACUCCCAGmC*mU*mG | CIITA exon: #4 | N/A |

NOTE:
RNA Modification: "*" represents a phosphorothioate bond between the nucleotides, "m" denotes a 2'-OMe modification. Magnitude of data: "•••" represents a value >60, "••" represents a value between ≤60 and ≥30, "•" represents a value <30.

Example 20: Gene Editing of B2M, TRAC or CIITA

Guides targeting B32M, TRAC, or CIITA gene are tested with Cas 265466 (SEQ ID NO: 1) for the ability to produce indels in eukaryotic cells. Briefly, eukaryotic cells are delivered with a combination of mRNA or gene encoding Cas 265466 and a gRNA or a nucleic acid encoding the gRNA, wherein the gRNA comprises a handle sequence of SEQ ID NO: 70 or 833 and anyone of spacer sequences recited in TABLE 36, TABLE 37, and TABLE 38. The CAS 265466 protein (SEQ ID NO: 1) and the gRNA targeting B32M, TRAC, or CIITA gene forms an RNP complex that recognizes a specific 5' PAM sequence as identified in TABLE 36, TABLE 37, and TABLE 38.

TABLE 36

CasM.265466 paired with various gRNA comprising spacer sequences targeting B2M gene

| Effector Protein SEQ ID NO | Spacer SEQ ID NO | 5'PAM Sequence | Target Gene |
|---|---|---|---|
| 1 | 325, 331, 332, 333, 336, 494, 520, 521, 530, 542, 550, 551, 552, 555, 564, 590, 591, 600 | TGTG | B2M |
| 1 | 326, 334, 338, 488, 491, 496, 512, 519, 522, 543, 553, 557, 558, 561, 566, 582, 589, 592 | TCTG | B2M |
| 1 | 337, 474, 506, 510, 524, 533, 544, 556, 576, 580, 594, 603 | TGTA | B2M |
| 1 | 327, 492, 501, 523, 525, 538, 545, 562, 571, 593, 595, 608 | TCTA | B2M |

TABLE 36-continued

CasM.265466 paired with various gRNA comprising spacer sequences targeting B2M gene

| Effector Protein SEQ ID NO | Spacer SEQ ID NO | 5'PAM Sequence | Target Gene |
|---|---|---|---|
| 1 | 302, 498, 499, 505, 508, 516, 517, 528, 529, 531, 546, 568, 569, 575, 578, 586, 587, 598, 599, 601 | TTTA | B2M |
| 1 | 329, 477, 489, 504, 527, 534, 547, 548, 559, 574, 597, 604 | TATG | B2M |
| 1 | 301, 335, 490, 493, 495, 497, 500, 502, 509, 514, 532, 536, 539, 549, 554, 560, 563, 565, 567, 570, 572, 579, 584, 602, 606, 609 | TTTG | B2M |
| 1 | 503, 507, 511, 513, 515, 518, 526, 535, 537, 540, 541, 573, 577, 581, 583, 585, 588, 596, 605, 607, 610, 611 | TATA | B2M |

TABLE 37

CasM.265466 paired with various gRNA comprising spacer sequences targeting TRAC gene

| Effector Protein SEQ ID NO | Spacer SEQ ID NO | 5'PAM Sequence | Target Gene |
|---|---|---|---|
| 1 | 612, 616, 617, 624, 627, 633, 639, 642, 645, 647, 650, 655, 666, 667, 670, 674, 675, 682, 685, 691, 697, 700, 703, 705, 708, 713, 724, 725 | TGTG | TRAC |
| 1 | 613, 618, 629, 658, 671, 676, 687, 716 | TCTA | TRAC |
| 1 | 614, 620, 630, 634, 636, 637, 638, 641, 664, 669, 672, 678, 688, 692, 694, 695, 696, 699, 722, 727 | TTTG | TRAC |
| 1 | 615, 619, 623, 626, 632, 640, 643, 646, 648, 649, 653, 659, 661, 662, 663, 665, 668, 673, 677, 681, 684, 690, 698, 701, 704, 706, 707, 711, 717, 719, 720, 721, 723, 726 | TCTG | TRAC |
| 1 | 621, 631, 679, 689 | TATA | TRAC |
| 1 | 622, 625, 651, 652, 656, 680, 683, 709, 710, 714 | TGTA | TRAC |
| 1 | 628, 654, 660, 686, 712, 718 | TATG | TRAC |
| 1 | 635, 644, 657, 693, 702, 715 | TTTA | TRAC |

TABLE 38

CasM.265466 paired with various gRNA comprising spacer sequences targeting CIITA gene

| Effector Protein SEQ ID NO | Spacer SEQ ID NO | 5' PAM Sequence | Target Gene |
|---|---|---|---|
| 1 | 728, 730, 732, 738, 739, 742, 743, 745, 747, 749, 755, 756, 759, 760 | TGTG | CIITA |
| 1 | 729, 733, 734, 741, 746, 750, 751, 758 | TCTG | CIITA |
| 1 | 731, 748 | TGTA | CIITA |
| 1 | 735, 736, 740, 752, 753, 757 | TCTA | CIITA |
| 1 | 737, 744, 754, 761 | TATG | CIITA |

The cells are incubated for about 48 hours to 96 hours to allow indel formation. Indels are detected by next generation sequencing of PCR amplicons at the targeted loci and indel percentage is calculated as the fraction of sequencing reads containing insertions or deletions relative to an unedited reference sequence.

Example 21: Determining Ability of CasM.265466 to Generate Indels in T Cells

Figure 9:
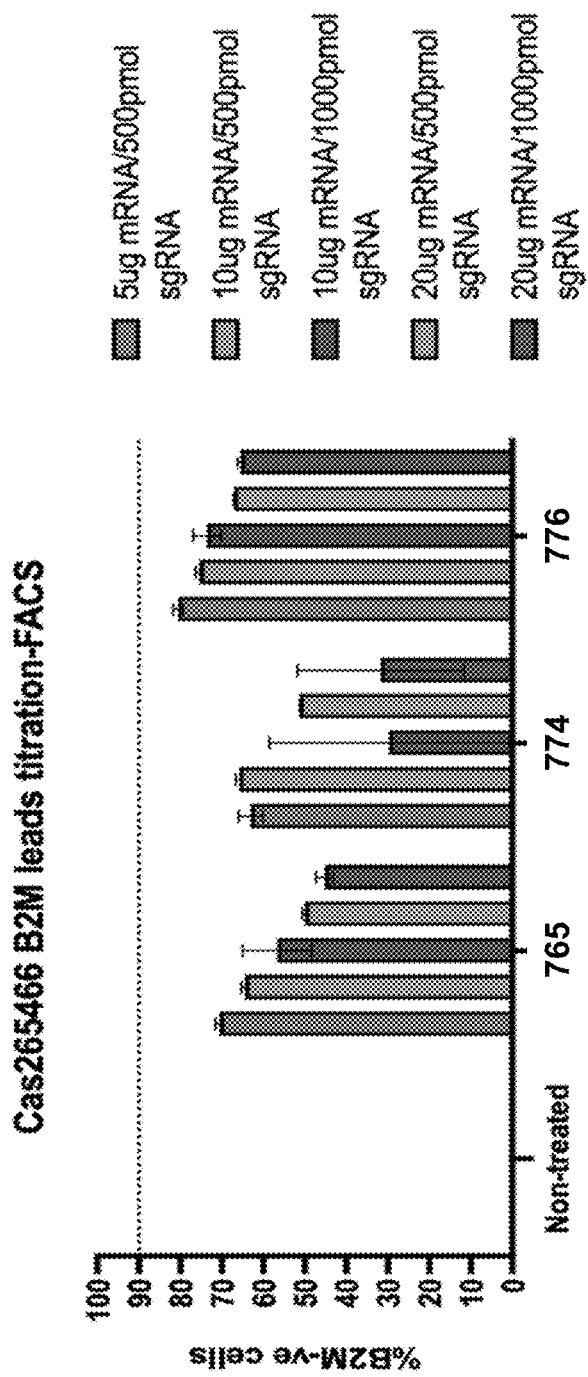
FIG. 9 illustrates an exemplary schematic of AAV construct for gene editing according to one or more embodiments of the present disclosure. Included in FIG. 9 are the following abbreviations representing elements of the AAV construct: ITR=Inverted terminal repeat; gRNA=guide RNA; Poly A=polyadenylation signal; ssAAV=single-stranded AAV; and scAAV=self-complementary AAV.

A dose titration for mRNA encoding CasM.265466 (SEQ ID NO: 1) and nucleic acid encoding sgRNAs was performed to identify combinations with improved indel formation in T cells. Briefly, sgRNAs having a handle sequence of SEQ ID NO: 833 and a spacer sequence of each of SEQ ID NO: 545, 554, or 556 (or sgRNA of SEQ ID NO: 765, 774, and 776, respectively) were dose titrated with mRNA encoding Cas 265466 (SEQ ID NO: 1) to determine gene editing efficiency at different doses following a similar protocol as described in Example 17, but with varying amounts of sgRNA and Cas 265466 effector mRNA. Specifically, sgRNAs having the spacer sequences of SEQ ID NO: 545, 554, or 556 (or sgRNAs of SEQ ID NO: 765, 774, or 776, respectively) were electroporated with Cas 265466 mRNA in the following conditions: 1) 5 µg Cas 265466 mRNA and 500 pmol sgRNA; 2) 10 µg Cas 265466 mRNA and 500 pmol sgRNA; 3) 10 µg Cas 265466 mRNA and 1000 pmol sgRNA; 4) 20 µg Cas 265466 mRNA and 500 pmol sgRNA; and 5) 20 µg Cas 265466 mRNA and 1000 pmol sgRNA. The T cells were electroporated with the combination and incubated for about 72 hours. Indels were detected by flow cytometry (FACS) using B2M antibody and next generation sequencing (NGS) of PCR amplicons at the targeted loci 3 days post electroporation. The results of the FACS analysis are shown in FIG. 9. The Y-axis shows the percent B2M negative cells. The X-axis shows the different sgRNAs. The conditions indicated above are presented left to right on the graphs for each sgRNA. Indel percentage was calculated as the fraction of sequencing reads containing insertions or deletions relative to an unedited reference sequence which are summarized in TABLE 39. An analysis of results demonstrate successful editing of B2M gene in the T cells by CasM.265466 and sgRNA at a range of concentration ratios.

TABLE 39

Indel Formation using CasM.265466 mRNA paired with various sgRNA in T cells

| No. | mRNA Dose (ng) | sgRNA Dose (ng) | gRNA SEQ ID NO: | % INDELS |
|---|---|---|---|---|
| 1 | 5 | 500 | 765 | • • |
|   |   |   | 774 | • • |
|   |   |   | 776 | • • • |
| 2 | 10 | 500 | 765 | • • |
|   |   |   | 774 | • • |
|   |   |   | 776 | • • • |
| 3 | 10 | 1000 | 765 | • • |
|   |   |   | 774 | • • |
|   |   |   | 776 | • • • |
| 4 | 20 | 500 | 765 | • • |
|   |   |   | 774 | • • |
|   |   |   | 776 | • • • |
| 5 | 20 | 1000 | 765 | • • |
|   |   |   | 774 | • • |
|   |   |   | 776 | • • • |

NOTE:
% Indels represents 3 day post editing NGS Indel percentage data. Magnitude of Indel percentage data:
"• • •" represents a value over 80,
"• •" represents a value under 80 but over 50,
"•" represents a value under 50.

Example 22: Dose Titration for TRAC Editing

Figure 10:
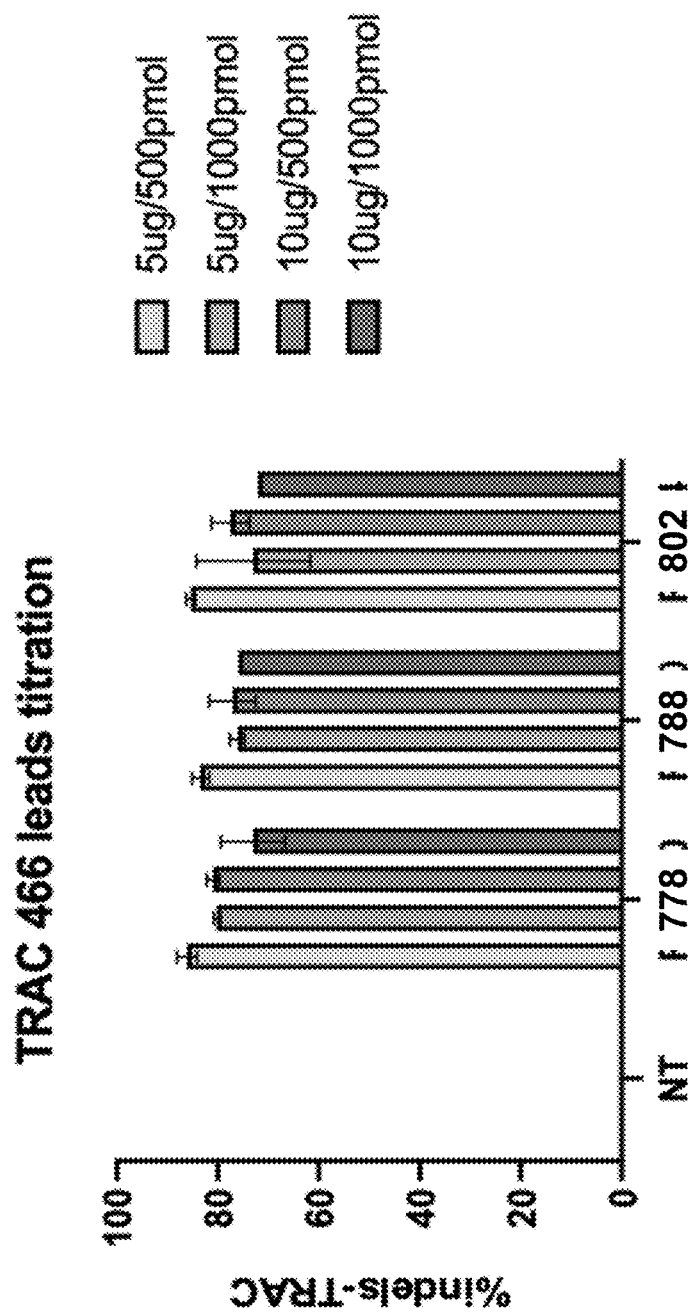
FIG. 10 shows editing of TRAC in primary T cells with different amounts of Cas 265466 and different amounts of guide constructs. The graph shows sequencing results at day 3 post electroporation of the percent indels in TRAC in primary T cells treated with different amounts of Cas 265466 and different amounts of guide constructs.

A dose titration for mRNA encoding CasM.265466 and nucleic acid encoding sgRNAs was performed to identify combinations with improved indel formation in T cells. Briefly, sgRNAs having a handle sequence of SEQ ID NO: 833 and a spacer sequence of each of SEQ ID NO: 670, 680, and 694 (or sgRNA of SEQ ID NO: 778, 788 and 802, respectively) were dose titrated with mRNA encoding Cas 265466 (SEQ ID NO: 1) to determine gene editing efficiency at different doses following a similar protocol as described in Example 18 but with different amounts of sgRNA and Cas 265466 effector mRNA. Specifically, sgRNAs having spacer sequences of each of SEQ ID NO: 670, 680, and 694 (or sgRNA of SEQ ID NO: 778, 788 and 802, respectively) were electroporated with Cas 265466 mRNA in the following conditions: 1) 5 µg Cas 265466 mRNA and 500 pmol sgRNA; 2) 5 µg Cas 265466 mRNA and 1000 pmol sgRNA; 3) 10 µg Cas 265466 mRNA and 500 pmol sgRNA; and 4) 10 µg Cas 265466 mRNA and 1000 pmol sgRNA. The results of the sequence analysis are shown in FIG. 10. The Y-axis shows the percent indels in the TRAC gene. The X-axis shows the different sgRNAs, and NT indicates non-treated. The conditions indicated above are presented left to right on the graphs for each sgRNA. The sequencing graph shown in FIG. 10, shows of the percent indels of TRAC. An analysis of FIG. 10 indicates that the 5 µg Cas 265466 mRNA in combination with 500 pmol sgRNA having spacer sequences of each of SEQ ID NO: 670, 680, and 694 (or sgRNA of SEQ ID NO: 778, 788 and 802, respectively) had about 80% indels. The analysis further suggests that the 5 µg Cas 265466 mRNA and 500 pmol sgRNA condition produced the highest amount of editing.

Example 23: Dose Titration for CIITA Editing

Figure 11:
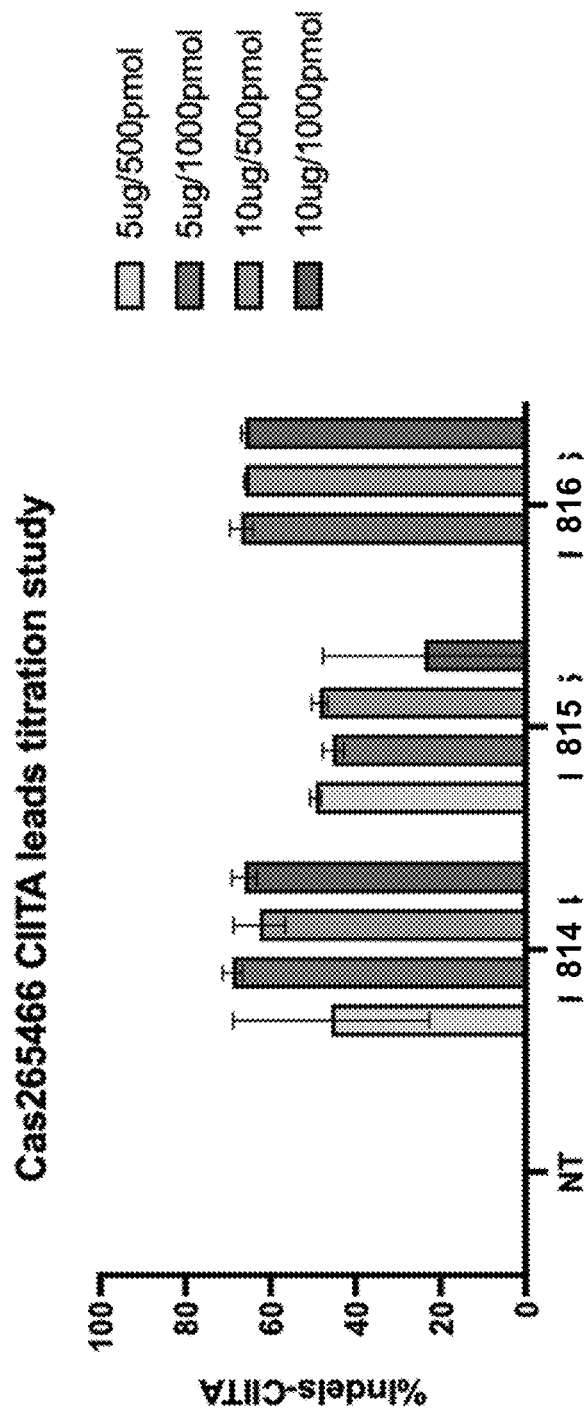
FIG. 11 shows editing of CIITA in primary T cells with different amounts of Cas 265466 and different amounts of guide constructs. The graph shows sequencing results at day 3 post electroporation of the percent indels in CIITA in primary T cells treated with different amounts of Cas 265466 and different amounts of guide constructs.

A dose titration for mRNA encoding CasM.265466 and nucleic acid encoding sgRNAs was performed to identify combinations with improved indel formation in T cells. Briefly, sgRNAs having a handle sequence of SEQ ID NO: 833 and a spacer sequence of each of SEQ ID NO: 748, 749, and 750 (SEQ ID NO: 814, 815 and 816, respectively) were dose titrated with mRNA encoding Cas 265466 (SEQ ID NO: 1) to determine gene editing efficiency at different doses following a similar protocol as described in Example 19 but with different amounts of sgRNA and Cas 265466 effector mRNA. Briefly, sgRNAs having spacer sequences of each of SEQ ID NO: 748, 749, and 750 (SEQ ID NO: 814, 815 and 816, respectively) were electroporated with Cas 265466 mRNA in the following conditions: 1) 5 µg Cas 265466 mRNA and 500 pmol sgRNA; 2) 5 µg Cas 265466 mRNA and 1000 pmol sgRNA; 3) 10 µg Cas 265466 mRNA and 500 pmol sgRNA; and 4) 10 µg Cas 265466 mRNA and 1000 pmol sgRNA. The results of the sequence analysis are shown in FIG. 11. The Y-axis shows the percent indels in the CIITA gene. The X-axis shows the different sgRNAs, and NT indicates non-treated. The conditions indicated above are presented left to right on the graphs for each sgRNA. The sequencing graph shown in FIG. 11, shows of the percent indels of CIITA. An analysis of FIG. 11 indicates that: 5 µg Cas 265466 mRNA and 1000 pmol sgRNA; 10 µg Cas 265466 mRNA and 500 pmol sgRNA; and 10 µg Cas 265466 mRNA and 1000 pmol sgRNA conditions produced the highest amount of editing.

Example 24: B2M Editing in NK Cells

B2M guides targeting exon 2 of B2M were tested with Cas 265466 (SEQ ID NO: 1) for the ability to produce indels in primary NK Cells. Briefly, the NK cells were electroporated with a mixture of mRNA encoding the Cas 265466 (SEQ ID NO: 1) and gRNA having a handle sequence (SEQ ID NO: 833) and a spacer sequence (SEQ ID NO: 545 or 554) (or gRNA having SEQ ID NO: 765 or 774) was mixed and then electroporated. 5 µg of Cas 265466 was added for the assay and 500 pmol of gRNA was added for the assay. Different electroporation conditions were used to determine the highest efficiency for NK cell electroporation and are described below. Individual gRNA were used with the effector proteins. After electroporation, the cells were incubated at 37° C. and 5% $CO_2$ for 72 hours.

Figure 12:
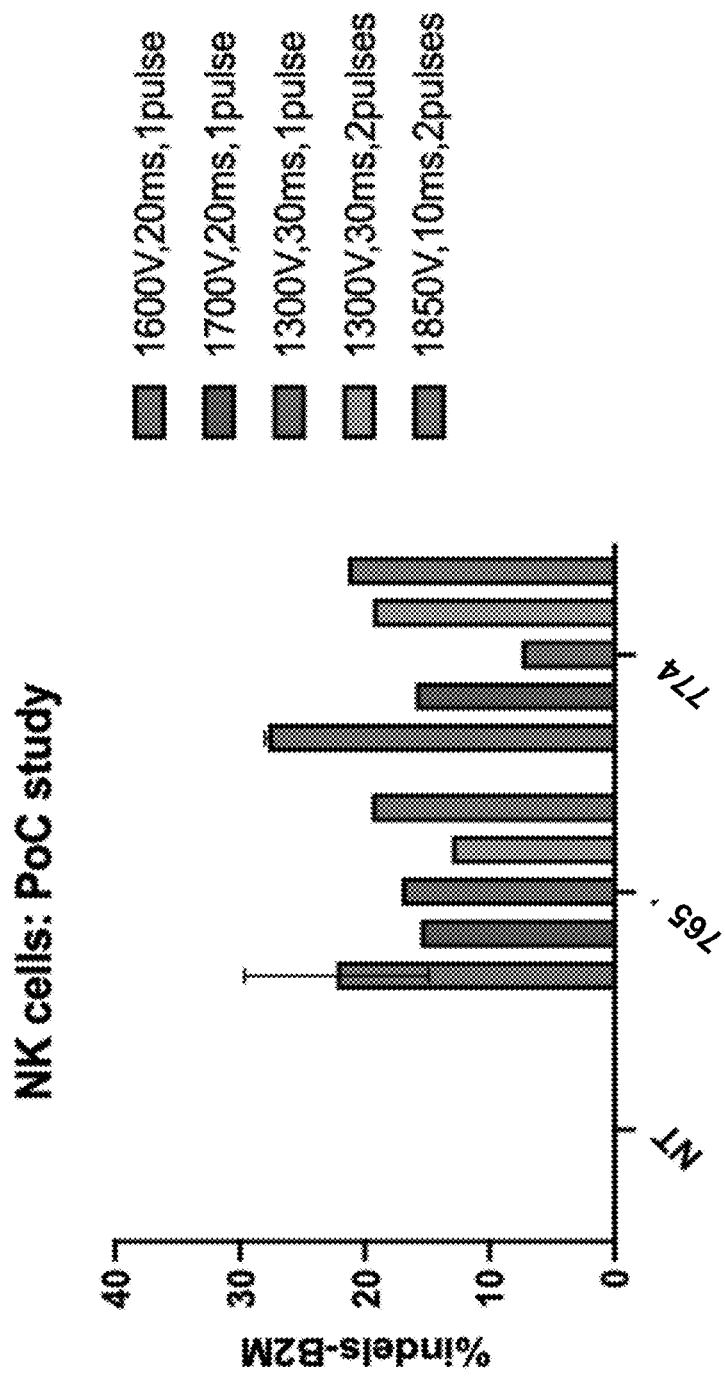
FIG. 12 shows editing of B2M in primary NK cells with Cas 265466 and different guide constructs. The graph shows sequencing results at day 3 post electroporation of the percent indels in B2M in primary NK cells treated with Cas 265466 and different guide constructs. Different electroporation conditions were tested to identify conditions for NK cell electroporation.

After the 72-hour incubation, cells were analyzed for indels in B2M. FIG. 12 shows sequencing data at Day 3 showing the percent indels in B2M for the Cas 265466 and gRNA with different electroporation conditions. The Y-axis shows the percent of indels. The X-axis shows the different gRNAs, and NT indicates non-treated. The gRNAs and Cas 265466 were electroporated with different conditions. Briefly, the sgRNAs were electroporated with Cas 265466 mRNA in the following conditions: 1) 1600 Volts (V) for 20 milliseconds (ms) with 1 pulse; 2) 1700 V for 20 ms with 1 pulse; 3) 1300 V for 30 ms with 1 pulse; 4) 1300 V for 30 ms with 2 pulses; and 5) 1850 V for 10 ms with 2 pulses. The conditions indicated above are presented left to right on the graph for each gRNA. The conditions of 1) 1600 V for 20 ms with 1 pulse and 5) 1850 V for 10 ms with 2 pulses produced the highest percentage of indels in guides having a spacer sequence of SEQ ID NO: 545 or 554 (or guides having SEQ ID NO: 765 or 774). The condition of 1) 1600 V for 20 ms with 1 pulse produced about 20-30% indels in B2M of the primary NK cells with either guides having spacer sequences of SEQ ID NO: 545 or 554 (or guides having SEQ ID NO: 765 or 774), and the condition of 5) 1850 V for 10 ms with 2 pulses produced about 20% indels in B2M of the primary NK cells. The results show Cas 265466 with different guide constructs can edit B2M in NK cells.

Example 25: CasM.265466 Mediated Integration of a Bidirectional AAV Reporter in Eukaryotic Cells A CasM.265466 system is tested for its ability to facilitate homology-independent targeted insertion (HITI) of a donor nucleic acid encoding luciferase protein into the intron 1 of human albumin gene in Hep3B cells and primary human hepatocyte cells. Briefly, 20,000 cells are seeded in a 96-well plate and transfected using lipofectamine MessengerMax. Hep3B cells are transfected with 200 ng total RNA (1:1 mRNA to gRNA ratio), whereas primary human hepatocyte cells are transfected with 500 ng RNA (1:1 mRNA to gRNA ratio). The gRNA comprises a handle sequence of SEQ ID NO: 70, and any one of a spacer sequence of SEQ ID NO: 834-862. One or more spyCas9 gRNA sequences are as positive controls. The transfection is carried in conjunction with AAV transduction, where AAV carrying reporter AAV vector is added to the media. The reporter AAV vector is packaged with the donor nucleic acid encoding a luciferase protein. The donor nucleic acid is co-delivered to the cells with the nuclease mRNA (SEQ ID NO: 1) and gRNA. The cells are harvested, and the media is collected from three days to seven days post-transfection and transduction. The media is subject to a luciferase assay using the Promega Nano-Glo system. The cells are subject to DNA extraction, PCR amplified and sequenced via NGS sequencing analysis.

TABLE 40

Exemplary Compositions of Effector Protein and Guide Nucleic Acids

| Comp No. | Effector Protein SEQ ID No. | gRNA ID No. | PAM | Spacer Seq ID No. | Spacer sequence |
|---|---|---|---|---|---|
| 1 | 1 | R10234 | TCTG | 834 | CAUCUUUAAAGAAUUAUUUU |
| 2 | 1 | R10235 | TATG | 835 | CCAUUUUAGAAAUAAAUGCC |
| 3 | 1 | R10236 | TTTG | 836 | GCAUUUAUUUCUAAAAUGGC |
| 4 | 1 | R10237 | TTTG | 837 | UAUUUGUGAAGUCUUACAAG |
| 5 | 1 | R10238 | TTTG | 838 | AAUUUUAUUAAUAAGAUAAC |
| 6 | 1 | R10239 | TTTG | 839 | UGAAGUCUUACAAGGUUAUC |
| 7 | 1 | R10240 | TGTG | 840 | AAGUCUUACAAGGUUAUCUU |
| 8 | 1 | R10241 | TCTG | 841 | ACCUUUUUUUUUUUUUACCU |
| 9 | 1 | R10242 | TTTG | 842 | CACUUUCCUUAGUGCGCAAA |
| 10 | 1 | R10243 | TTTG | 843 | CGCACUAAGGAAAGUGCAAA |
| 11 | 1 | R10244 | TGTG | 844 | AAGUUUCAGUCACUCUAAGU |
| 12 | 1 | R10245 | TCTG | 845 | UGAAGUUUCAGUCACUCUAA |
| 13 | 1 | R10246 | TATG | 846 | AAUUCAAUCUUCAACCCUAU |
| 14 | 1 | R10247 | TTTG | 847 | GGAUAGUUAUGAAUUCAAUC |
| 15 | 1 | R10248 | TGTG | 848 | GUUUUUAAAUAAAGCAUAGU |
| 16 | 1 | R10249 | TTTG | 849 | UGGUUUUUAAAUAAAGCAUA |
| 17 | 1 | R10250 | TATG | 850 | AGAUCAACAGCACAGGUUUU |
| 18 | 1 | R10251 | TATG | 851 | CUUUAUUUAAAAACCACAAA |
| 19 | 1 | R10252 | TGTG | 852 | CUGUUGAUCUCAUAAAUAGA |
| 20 | 1 | R10253 | TCTG | 853 | UCUUCUUGGUUGCUGUUGAU |
| 21 | 1 | R10254 | TTTG | 854 | AAUAUAAGGCUAUAAAUAUU |
| 22 | 1 | R10255 | TCTG | 855 | CCUUUAAACAGAAGAAUAAU |
| 23 | 1 | R10256 | TCTG | 856 | UUUAAAGGCAGAAGAAAUAA |
| 24 | 1 | R10257 | TCTG | 857 | AUUCCUACAGAAAAACUCAG |
| 25 | 1 | R10258 | TTTG | 858 | UUUCAAAAUAUUGGGCUCUG |
| 26 | 1 | R10259 | TATG | 859 | CAUUUGUUUCAAAAUAUUGG |
| 27 | 1 | R10260 | TCTG | 860 | UAGGAAUCAGAGCCCAAUAU |
| 28 | 1 | R10261 | TTTG | 861 | ACUUAGAUUAUGCAUUUGUU |
| 29 | 1 | R10262 | TTTG | 862 | AAACAAAUGCAUAAUCUAAG |

Example 26: CasM.265466 Mediated Integration of a Bidirectional AAV Reporter in Primary Human Hepatocyte Cells A CasM.265466 system was tested for its ability to facilitate homology-independent targeted insertion (HITI) of a donor nucleic acid encoding a luciferase/green fluorescent fusion protein into the intron 1 of human albumin gene in primary human hepatocyte cells. The CasM.265466 system including the effector protein CasM.265466 (SEQ ID NO: 1) and a gRNA comprising each of the spacer sequences described in TABLE 41.

TABLE 41

Exemplary Compositions of Effector Protein and Guide Nucleic Acids

| Comp No. | Effector Protein SEQ ID No. | gRNA ID No. | PAM | Spacer Seq ID No. |
|---|---|---|---|---|
| 2 | 1 | R10235 | TATG | 835 |
| 4 | 1 | R10237 | TTTG | 837 |
| 5 | 1 | R10238 | TTTG | 838 |

TABLE 41-continued

Exemplary Compositions of
Effector Protein and Guide Nucleic Acids

| Comp No. | Effector Protein SEQ ID No. | gRNA ID No. | PAM | Spacer Seq ID No. |
|---|---|---|---|---|
| 6 | 1 | R10239 | TTTG | 839 |
| 7 | 1 | R10240 | TGTG | 840 |
| 9 | 1 | R10242 | TTTG | 842 |
| 11 | 1 | R10244 | TGTG | 844 |
| 12 | 1 | R10245 | TCTG | 845 |
| 13 | 1 | R10246 | TATG | 846 |
| 15 | 1 | R10248 | TGTG | 848 |
| 16 | 1 | R10249 | TTTG | 849 |
| 17 | 1 | R10250 | TATG | 850 |
| 19 | 1 | R10252 | TGTG | 852 |
| 20 | 1 | R10253 | TCTG | 853 |
| 21 | 1 | R10254 | TTTG | 854 |
| 23 | 1 | R10256 | TCTG | 856 |
| 24 | 1 | R10257 | TCTG | 857 |
| 25 | 1 | R10258 | TTTG | 858 |
| 27 | 1 | R10260 | TCTG | 860 |
| 28 | 1 | R10261 | TTTG | 861 |
| 29 | 1 | R10262 | TTTG | 862 |

Figure 13:
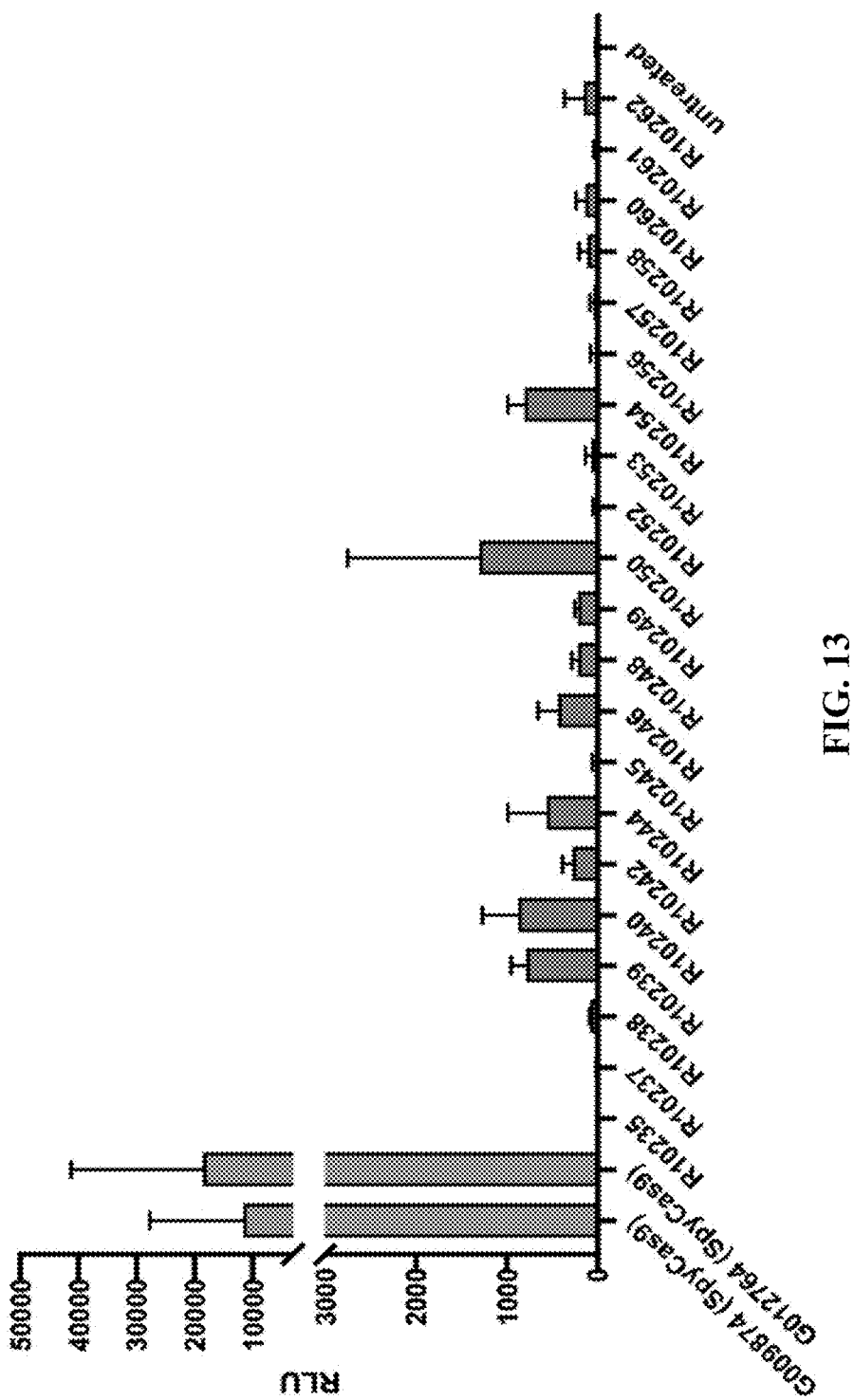
FIG. 13 shows a graphic representation of luciferase activity measured in relative light units (RLU) in bidirectional AAV reporters integrating a CasM.265466 system.

Briefly, 20,000 cells were seeded in a 96-well plate and transfected using lipofectamine MessengerMax. The cells were transfected with 500 ng RNA (1:1 mRNA to gRNA ratio). SpyCas9 system having one of two SpyCas9 gRNA sequences were used as positive controls. The transfection was carried out in conjunction with AAV6 transduction to introduce the donor nucleic acid, where the AAV6 carried a bi-direction reporter donor nucleic acid encoding a luciferase/green fluorescent fusion protein that included a P2A peptide linker between the luciferase and green fluorescent protein portions. Successful insertion of the donor nucleic acid into intron 1 of the human albumin gene would allow expression of the fusion protein by using exon 1 of the human albumin gene. The AAV6 was co-delivered to the cells with the nuclease mRNA and gRNA. After 72 hours post-transfection and transduction, the cells were harvested, and the media was collected. The media was subject to a luciferase assay using the Promega Nano-Glo system. FIG. 13 shows detectible luciferase activity measured in relative light units (RLU) for each gRNA. An analysis of FIG. 13 indicates that the CasM.265466 system can be used to cleave intron 1 of human albumin gene, and a donor nucleic acid can be inserted into the cleaved intron 1.

Figure 14:
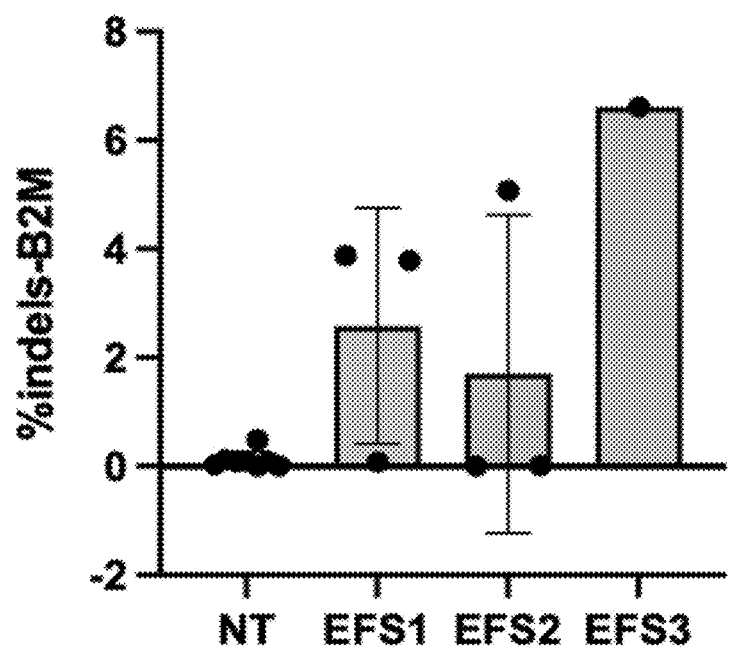
FIG. 14 shows editing of B2M in primary T cells with Cas 265466 and a guide construct in an scAAV vector. The graph shows sequencing results post transduction of the percent indels in B2M in primary T cells treated with Cas 265466 and a guide construct.

Example 27. Gene Editing of Primary T Cells with scAAV Vector Encoding CasM.265466 and Guide RNA scAAV plasmid constructs were tested for their ability to produce indels in B2M of primary T cells. Briefly, a scAAV plasmid was constructed to contain a transgene between its ITRs, the transgene providing or encoding, in a 5' to 3' direction, a U6 promoter, a guide RNA, an EFS promoter, a Cas effector protein, and a SV40 poly A tail. The EFS promoter was EFS1, EFS2, or EFS3, wherein EFS1 promoter construct refers to the scAAV plasmid encoding the guide RNA having SEQ ID NO: 268, EFS2 promoter construct refers to the scAAV plasmid encoding the guide RNA having SEQ ID NO: 278, and EFS3 promoter construct refers to the scAAV plasmid encoding the guide RNA having SEQ ID NO: 276. The Cas effector protein was Cas 265466 (SEQ ID NO: 1). The guide RNA (SEQ ID NO: 268, 278, or 276) had a nucleotide sequence that targets B2M gene. The scAAV vector was expressed with supporting plasmids to produce an adeno-associated virus (AAV). Activated primary T cells were transduced with the AAV (1e^4MOI GC/cell). DNA was isolated from the infected cells post transduction. An indel in B2M caused by the guide nucleic acid was confirmed by sequencing. The scAAV results are summarized in FIG. 14, which shows the percent indels in B2M on the Y-axis and the different scAAV constructs varying in the EFS promoter on the X-axis. NT on the X-axis indicates non-treated. The EFS3 promoter construct produced the highest percent (6%) of indels in B2M. The results indicate that AAV encoding Cas 265466 and an sgRNA can be used to edit genes in primary T cells.

Example 28. Pooled CasM.265466 Guide RNA (gRNA) Screen to Identify Guide-Dependent Rules of Editing A pool of 10,517 engineered gRNA-target nucleic acid pairs were tested in a pooled guide screen to identify guide-specific features associated with CasM.265466 editing activity. A high-throughput screening was performed in HEK 293T cells stably expressing the CasM.265466 nuclease to better understand the rules of editing for the CasM.265466 nuclease.

A library of 12,000 gRNA-target nucleic acid pairs were designed, of which 10,517 passed quality control checks and were used for screening. For each gRNA-target nucleic acid pair, an oligonucleotide was designed, which included a gRNA sequence, an optional linker sequence, and a target nucleic acid for editing by the CasM.265466 nuclease. The gRNA sequence included at least a handle sequence comprising a structural sequence and a repeat sequence, and a spacer sequence at least partially complementary to a target sequence of the target nucleic acid. Each gRNA-target nucleic acid pair also included a unique barcode, allowing the nuclease activity on each target sequence to be mapped back to its corresponding gRNA. Variant oligonucleotides were designed to assess target preference, PAM preference, PAM mismatch tolerance, target mismatch tolerance, repeat length variants, spacer length variants, intermediary RNA variants, and GC content.

The library of gRNA-target nucleic acid pairs was infected into the stable cells using lentivirus at a low multiplicity of infection of approximately 0.3 to ensure a single integration while maintaining greater than 500-fold representation of the library at each time point. Cells were allowed to recover for 5 days after 3-day puromycin selection and next-generation sequencing (NGS) libraries were prepared and sequenced on an Illumina NovaSeq at greater than 1000-fold coverage. Two biological replicates of the screen were performed, each of which included generation of a separate respective batch of gRNA-target oligonucleotide-containing lentiviral vectors, subsequent infection of a separate respective replicate of the stable cells, and separate respective sequencing steps. Evaluation of nuclease activity was performed based on the sequencing data by identifying indels at the integrated target sequences and determining indel frequencies across the more than 500 cells representing each gRNA-target nucleic acid pair. Unless otherwise indicated, data plots were generated in PRISM (GraphPad, San Diego, CA, USA).

Figure 15:
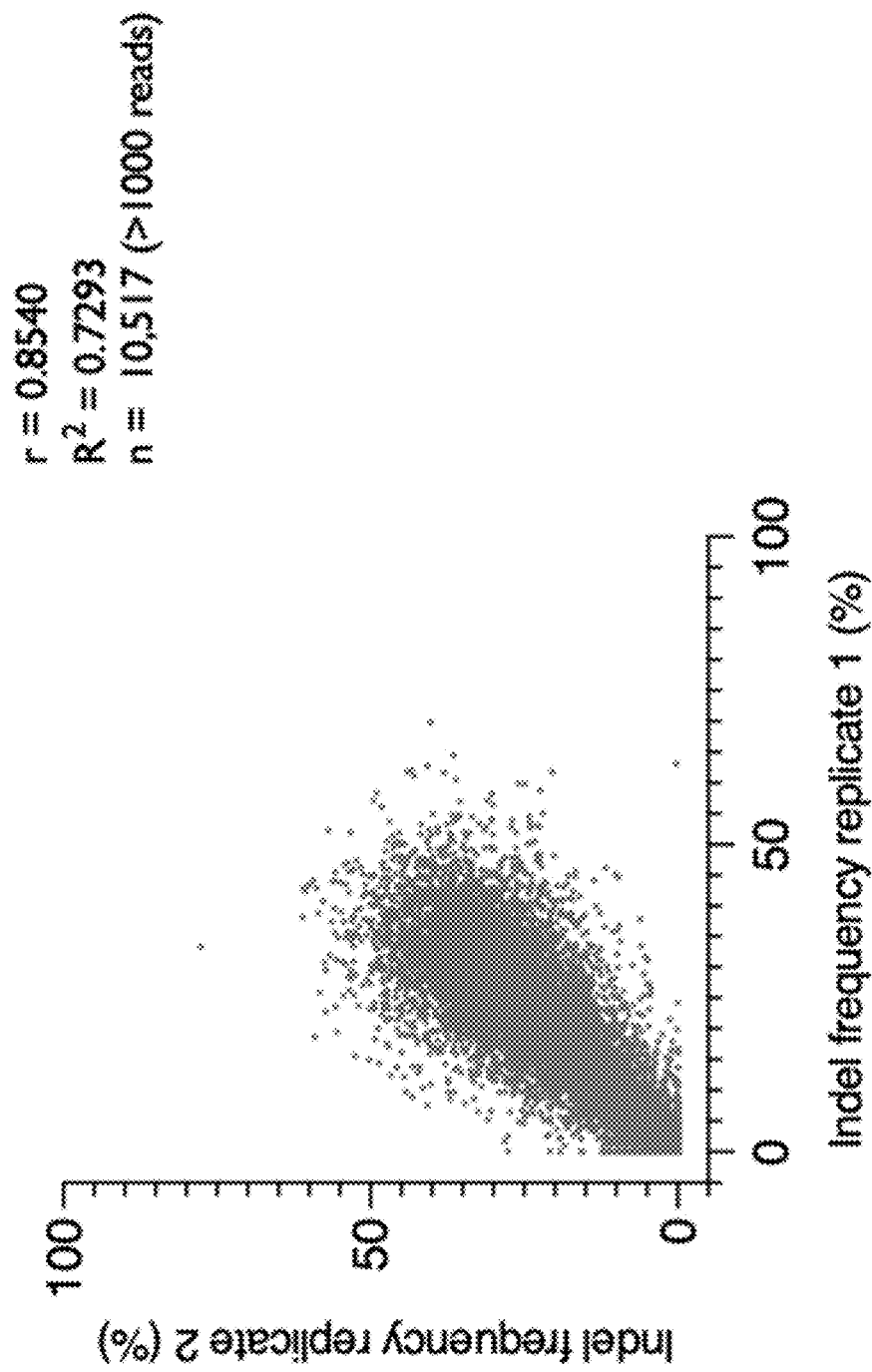
FIG. 15 illustrates the results of a high-throughput, pooled guide RNA (gRNA) screen compared between two biological replicates, in accordance with an embodiment of the present disclosure.

FIG. 15 illustrates the observed indel frequencies of each gRNA-target nucleic acid pair for each of the two biological replicates of the high-throughput screen, where each gRNA-target nucleic acid pair is represented by an individual data point in the plot. Data points showing 50% or greater indel frequencies in one or both of the two replicates indicate high quality gRNA-target nucleic acid pairs inducing high levels of activity from the Cas nuclease. Good correlation was observed between the biological replicates ($R^2$=0.7293), indicating reproducibility and robustness of the assays.

As described above, the library of gRNA-target variants included variants designed to assess mismatch tolerance, where mismatches were engineered to occur between the spacer sequence and the target sequence. The gRNA-target variants included variants in which different mismatches (A, T, G, or C) were introduced at different positions (e.g., positions 1 to 20) in a given spacer sequence. Multiple gRNA-target variants were obtained for a given target sequence, such that the relative effects of different spacer sequence variants corresponding to different mismatches could be compared in the context of the same target sequence.

Figure 16:
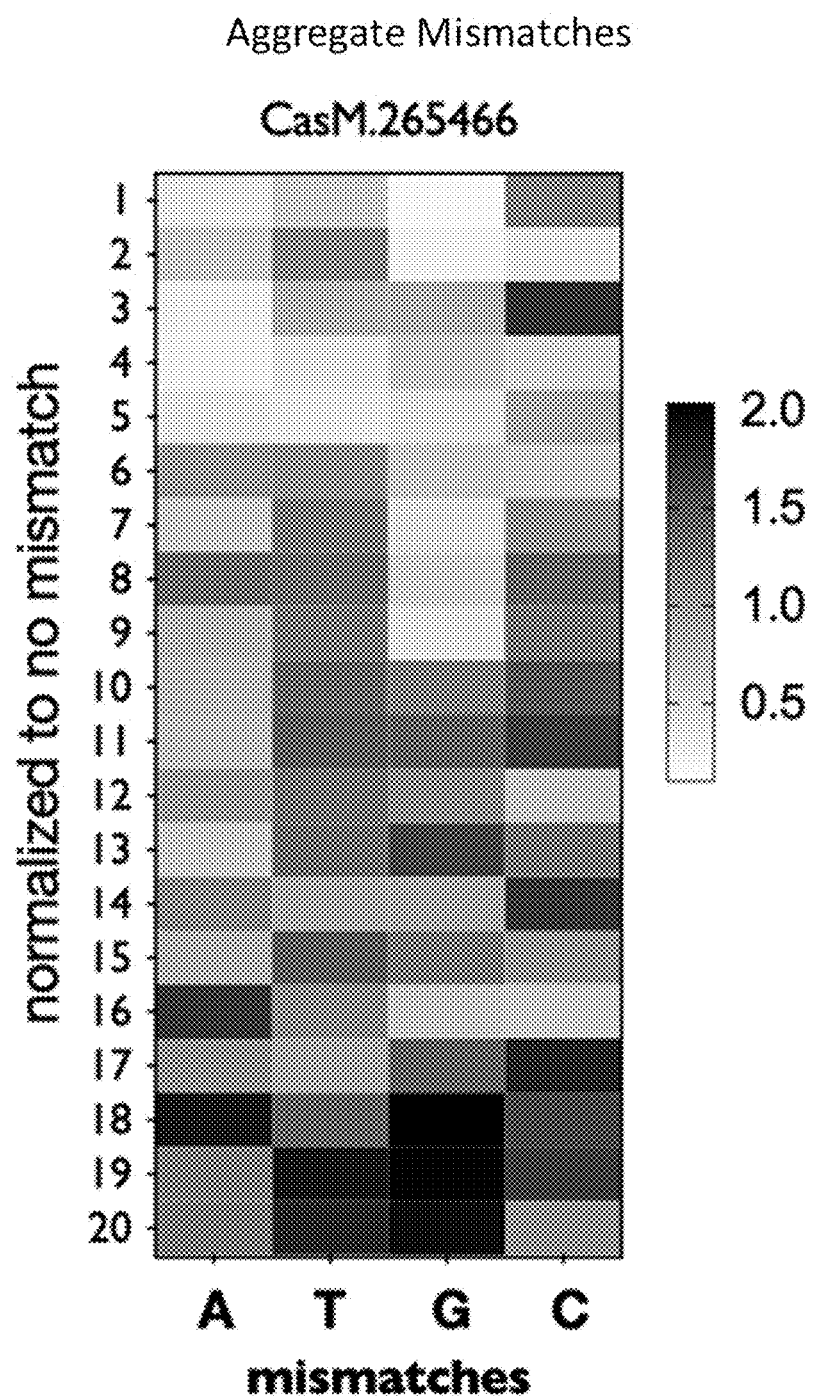
FIG. 16 illustrates the effects of positional gRNA-target sequence mismatches on CasM.265466 nuclease activity, in accordance with an embodiment of the present disclosure.

FIG. 16 illustrates the effects of various positional and identity mismatches on CasM.265466 activity, aggregated across all gRNA-target nucleic acid pairs assessed. Mismatches are presented as the mean fold change in indel frequency induced by mismatched spacer-target nucleic acid pairs, normalized to indel frequency for spacer-target nucleic acid pairs with no mismatches. Mean fold change is represented by intensity of shading, scaled between negative (<1.0) and positive (>1.0) fold changes. The results illustrate that, in some cases, certain regions of the spacer are less sensitive to mismatches and are still capable of driving editing at the target nucleic acid even in the presence of mismatches. Furthermore, the results indicate that, in some cases, CasM.265466 nuclease activity is differentially affected by mismatches of varying identities and at various positions in the spacer. For instance, as illustrated at position 1 of the heatmap in FIG. 16, a gRNA-target mismatch involving a guanine (G) at position 1 in the spacer sequence resulted in a substantial loss of nuclease activity, whereas a mismatch involving a cytosine (C) at the same position did not noticeably affect nuclease activity. Overall, CasM.265466 nuclease activity was generally more sensitive to mismatches closer to the 5' end of the spacer (position 1), whereas mismatches closer to the 3' end of the spacer (position 20) were generally observed to have no negative impact, and, in some cases, to have a positive impact on nuclease activity. Notably, the gRNAs for CasM.265466 included a PAM sequence immediately 5' of position 1 of the spacer sequence.

Figure 17:
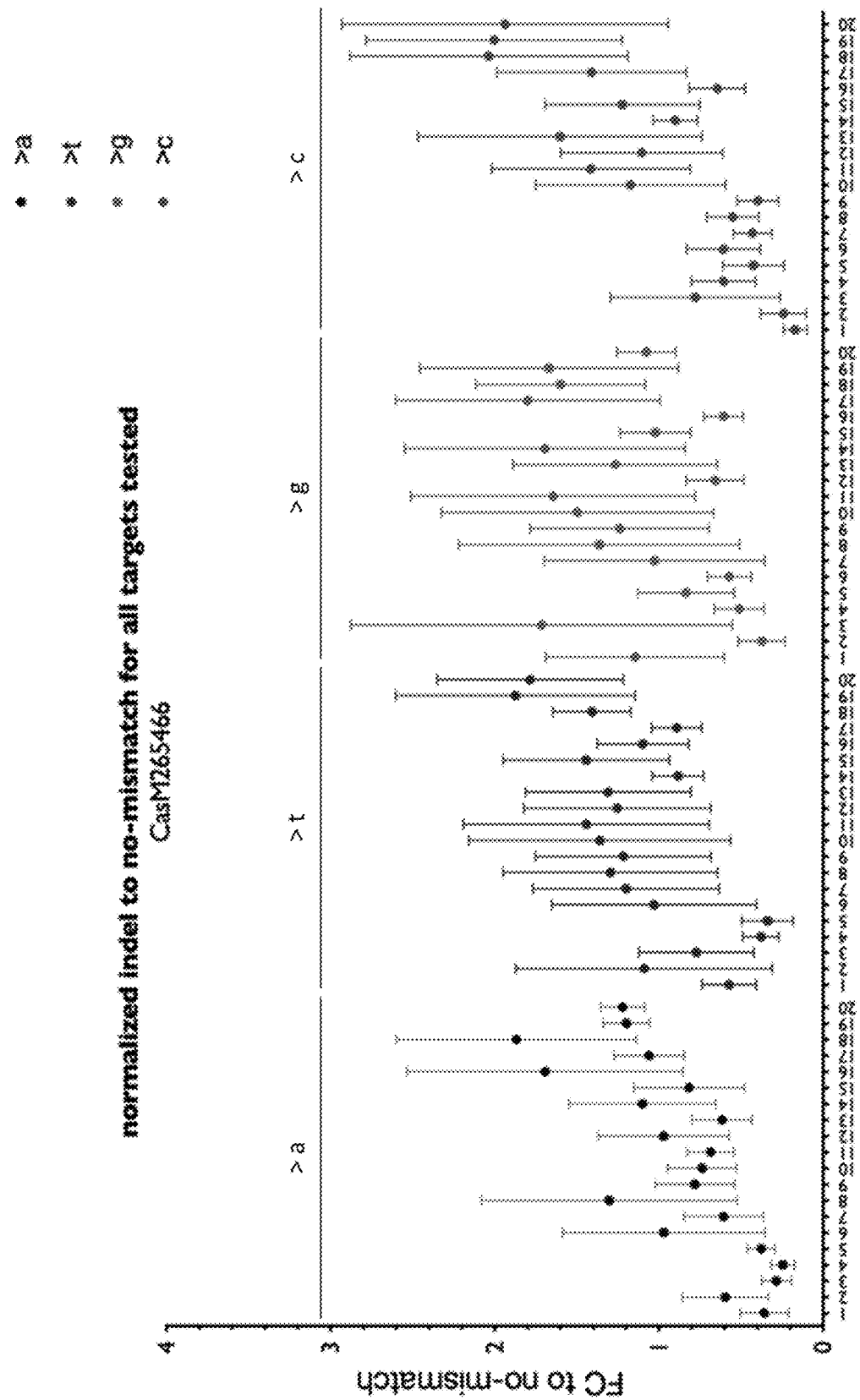
FIG. 17 illustrates the effects of positional gRNA-target sequence mismatches on CasM.265466 nuclease activity stratified by nucleotide identity, in accordance with an embodiment of the present disclosure.

FIG. 17 further illustrates the effect of spacer-target mismatches on nuclease activity, stratified by nucleotide identity of the mismatch (e.g., A, T, G, and C, indicated by the labeled bar above each section of the graph). The results are shown in aggregate over all of the gRNA-target nucleic acid pairs assessed. As described above with reference to FIG. 16, the plot further confirms that mismatch tolerance is generally lower at the 5' end of the spacer sequence but higher at the 3' end of the spacer sequence.

Figure 18:
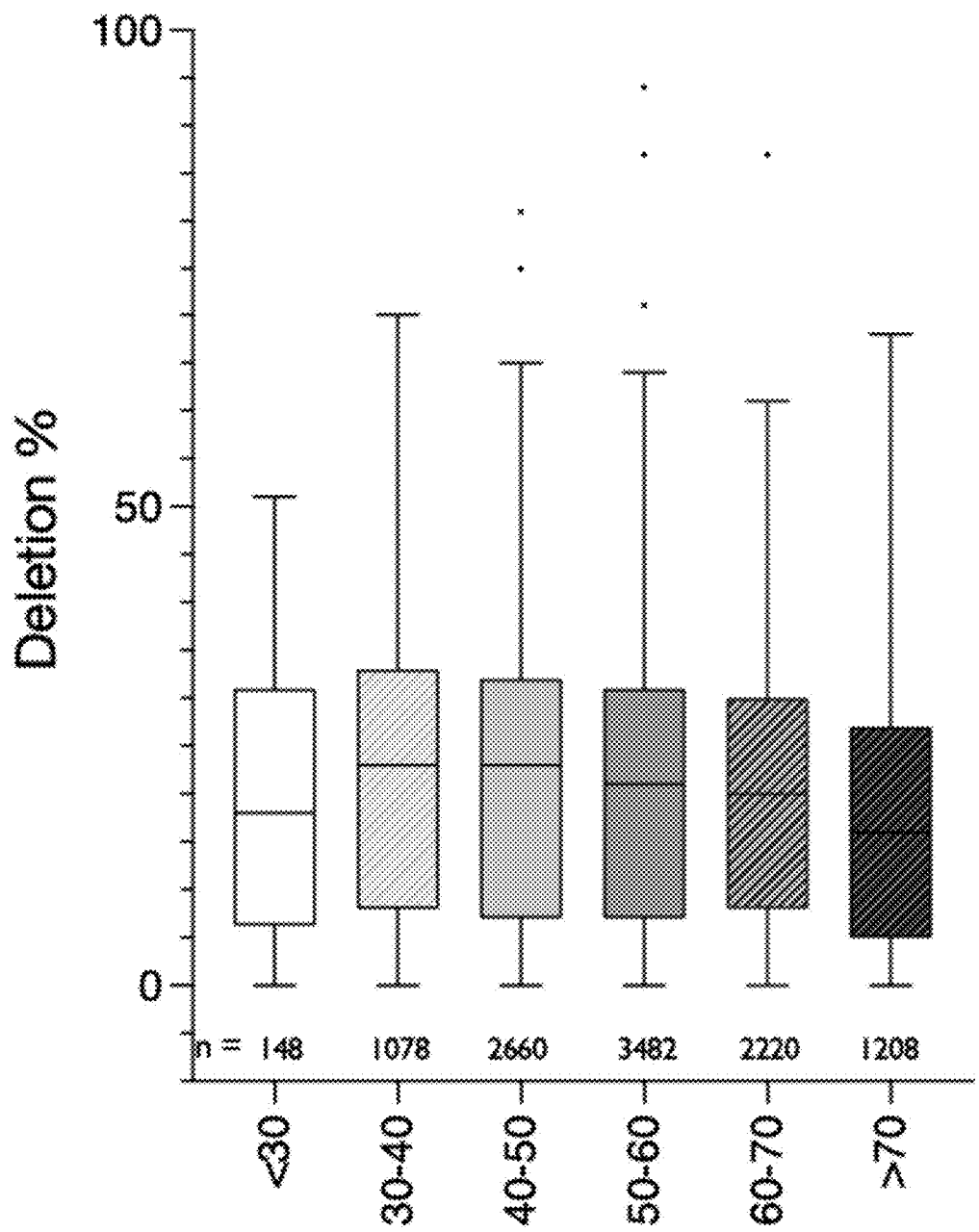
FIG. 18 illustrate the effects of overall GC content in spacer sequences on CasM.265466 nuclease activity, in accordance with an embodiment of the present disclosure.

Overall GC content of gRNA-target variants was determined and evaluated for its effect on CasM.265466 activity. FIG. 18 provides the indel frequencies induced by CasM.265466, over multiple ranges of overall GC content for gRNA-target nucleic acid pairs (e.g., <30%, 30-40%, 40-50%, 50-60%, 60-70%, and >70%). CasM.265466 activity was largely unaffected by overall spacer GC content, although a moderate decline in activity was observed in the extreme cases where the overall GC content was less than 30% or greater than 70%.

Figure 19:
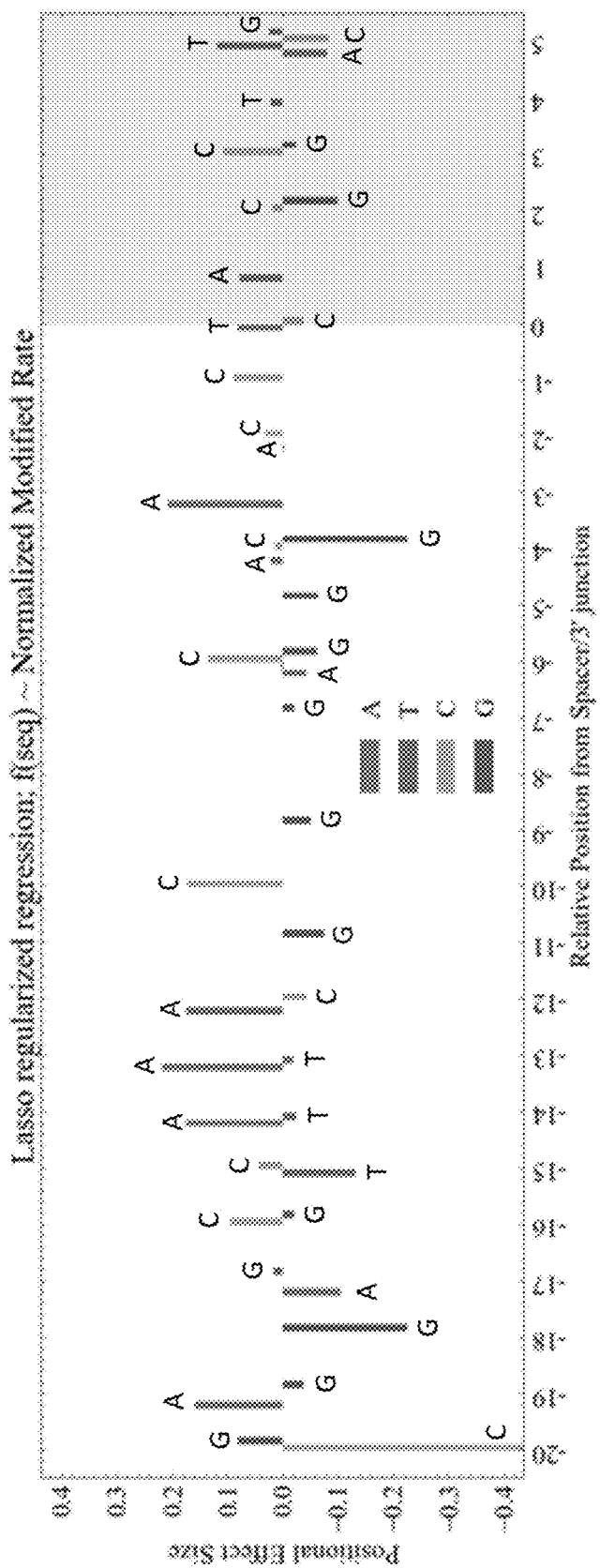
FIG. 19 illustrates the effects of positional spacer sequence nucleotide identity on CasM.265466 nuclease activity, in accordance with an embodiment of the present disclosure.
Figure 20:
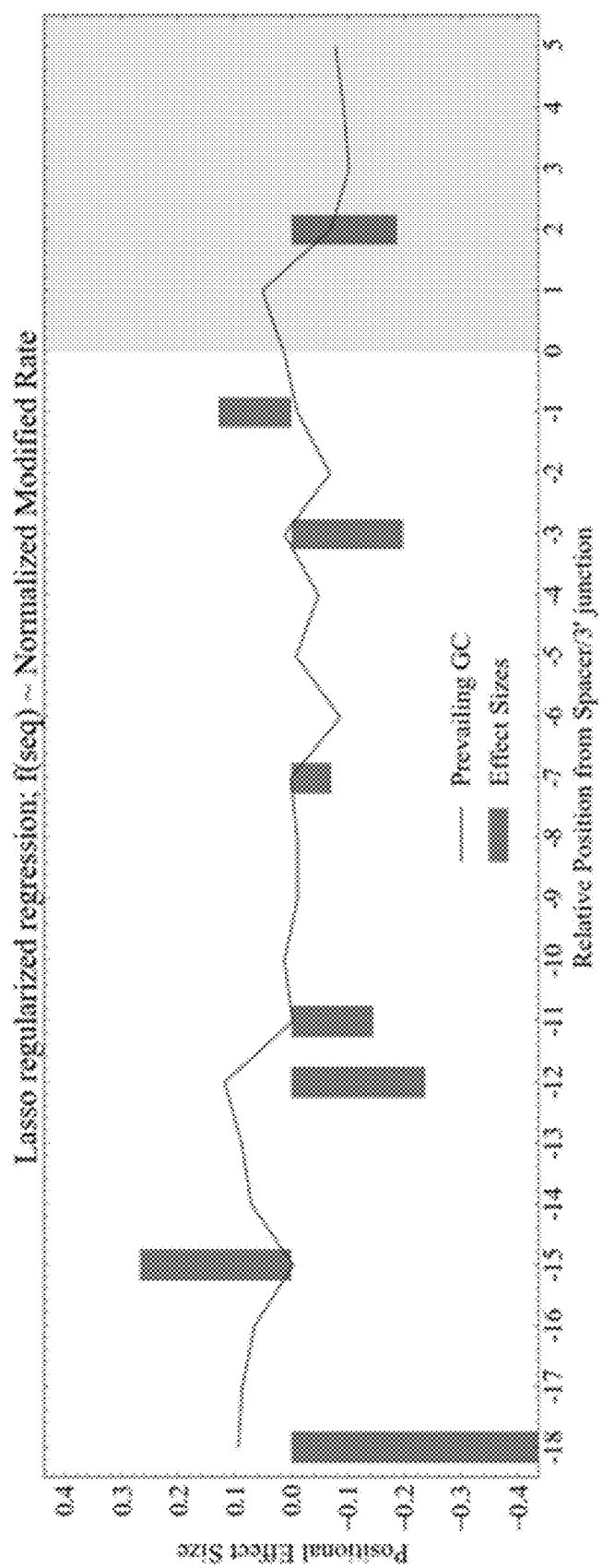
FIG. 20 illustrates the effects of positional GC content in spacer sequences on CasM.265466 nuclease activity, in accordance with an embodiment of the present disclosure.

Positional spacer sequence preferences and positional GC content preferences were also assessed for their effect on CasM.265466 nuclease activity. FIGS. 19 and 20 show Lasso logistic regression plots generated using the Python package seaborn for spacer sequence and GC content, respectively. Results are shown in aggregate over all gRNA-target nucleic acid pairs evaluated in the assay. In both plots, positions are depicted as relative position from the spacer 3' junction, such that the 5'-most position is marked as position −20, and the 3'-most position is marked as position 0.

Accordingly, FIG. 19 illustrates the relative effect of nucleotide identity (labeled above each positional effect size bar) at each position in the spacer sequence on CasM.265466 nuclease activity. For example, a cytosine (C) at the 5'-most position of the spacer sequence strongly reduces nuclease activity, whereas a thymine (T) at the same position induces a moderate relative increase in activity. In FIG. 20, the relative effect of GC content at each position in the spacer sequence on nuclease activity is shown, where GC was determined as a rolling average over a sliding window of 3 nucleotides along the length of the spacer sequence. In contrast to FIG. 18, where overall GC content was shown to have minimal effect on nuclease activity, the plot shows that CasM.265466 activity is moderately sensitive to positional GC content. For instance, a high GC content at the 5'-most end of the spacer sequence (e.g., positions −20, −19, and −18) was shown to have a robustly negative effect on nuclease activity.

Figure 21:
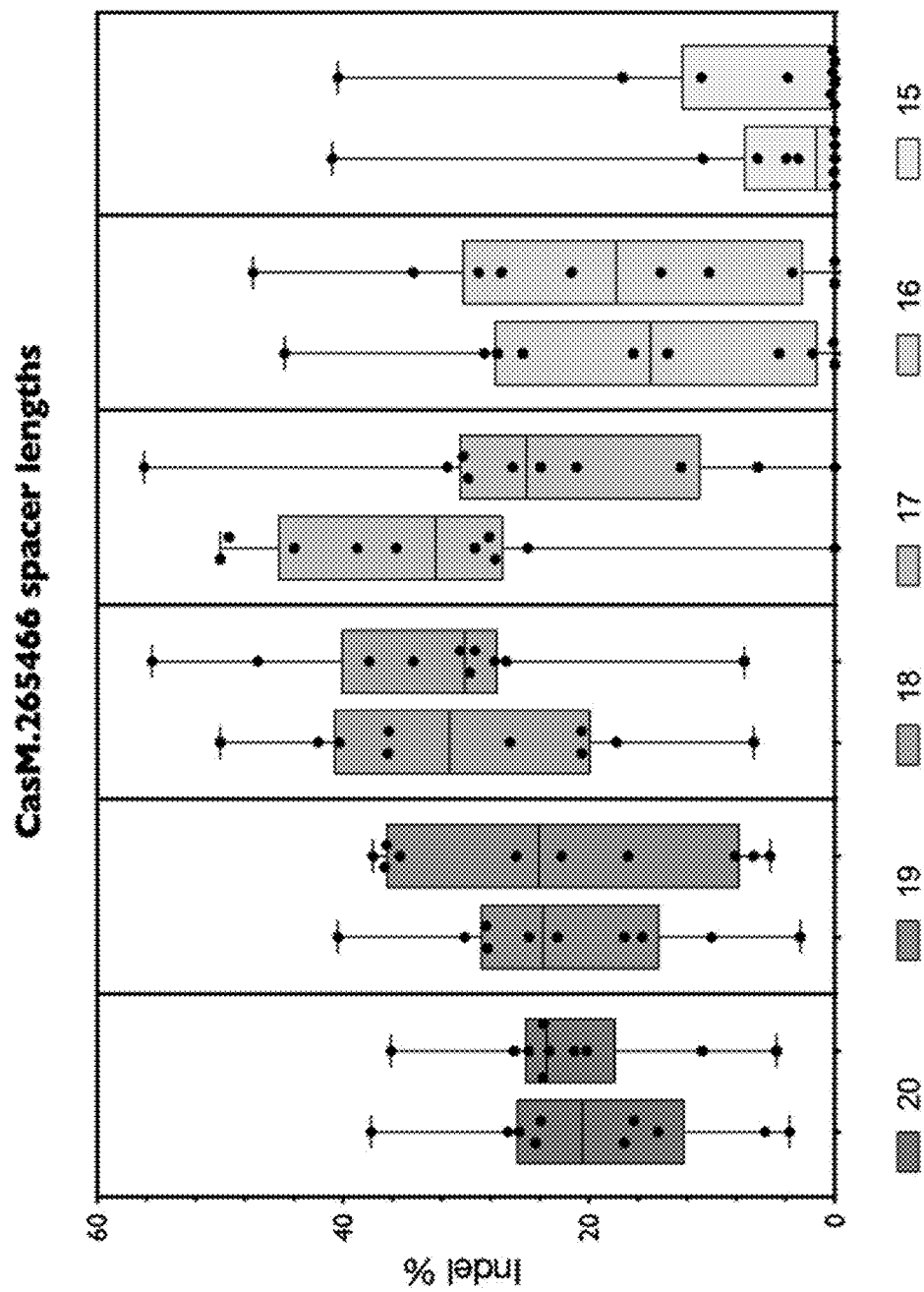
FIG. 21 illustrate the effects of spacer length on CasM.265466 nuclease activity, in accordance with an embodiment of the present disclosure.

FIG. 21 illustrates the relative effects of spacer length on CasM.265466 nuclease activity. Compared to a spacer length of 20 nucleotides (indel frequencies of approximately 20%), spacer lengths of 18 and 17 nucleotides were observed to have a positive effect on nuclease activity (indel frequencies of approximately 30%). In contrast, indel frequencies were reduced drastically for spacers having lengths of 16 and 15 nucleotides (indel frequencies of approximately 15% and 0%, respectively), revealing that, in some instances, nuclease activity is likely negatively impacted when using spacers shorter than 17 nucleotides.

Figure 22A:
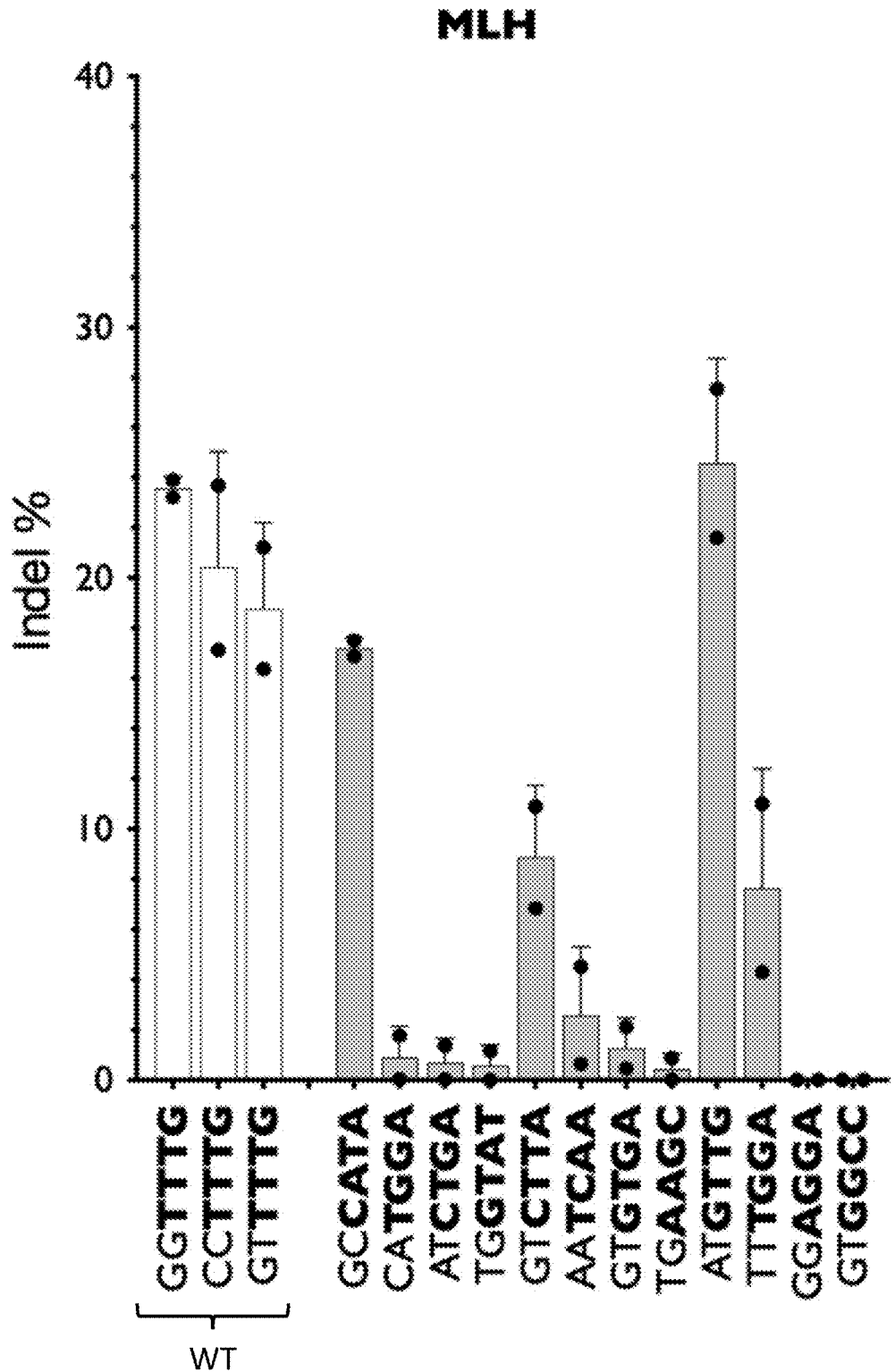
FIGS. 22A-22E illustrate the effects of PAM sequence variation in gRNAs on CasM.265466 nuclease activity for example target sequences, in accordance with an embodiment of the present disclosure.
Figure 22B:
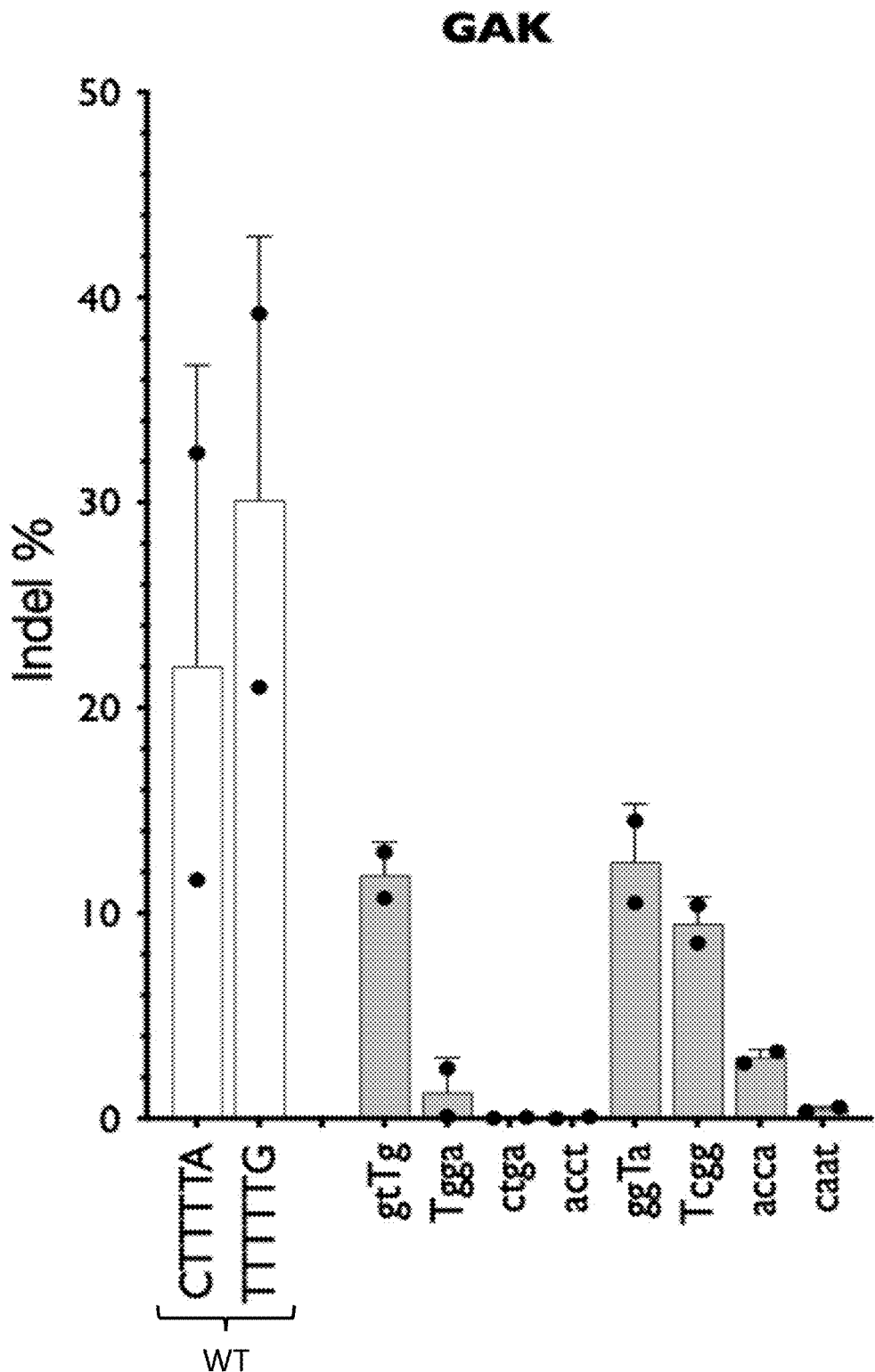
Figure 22C:
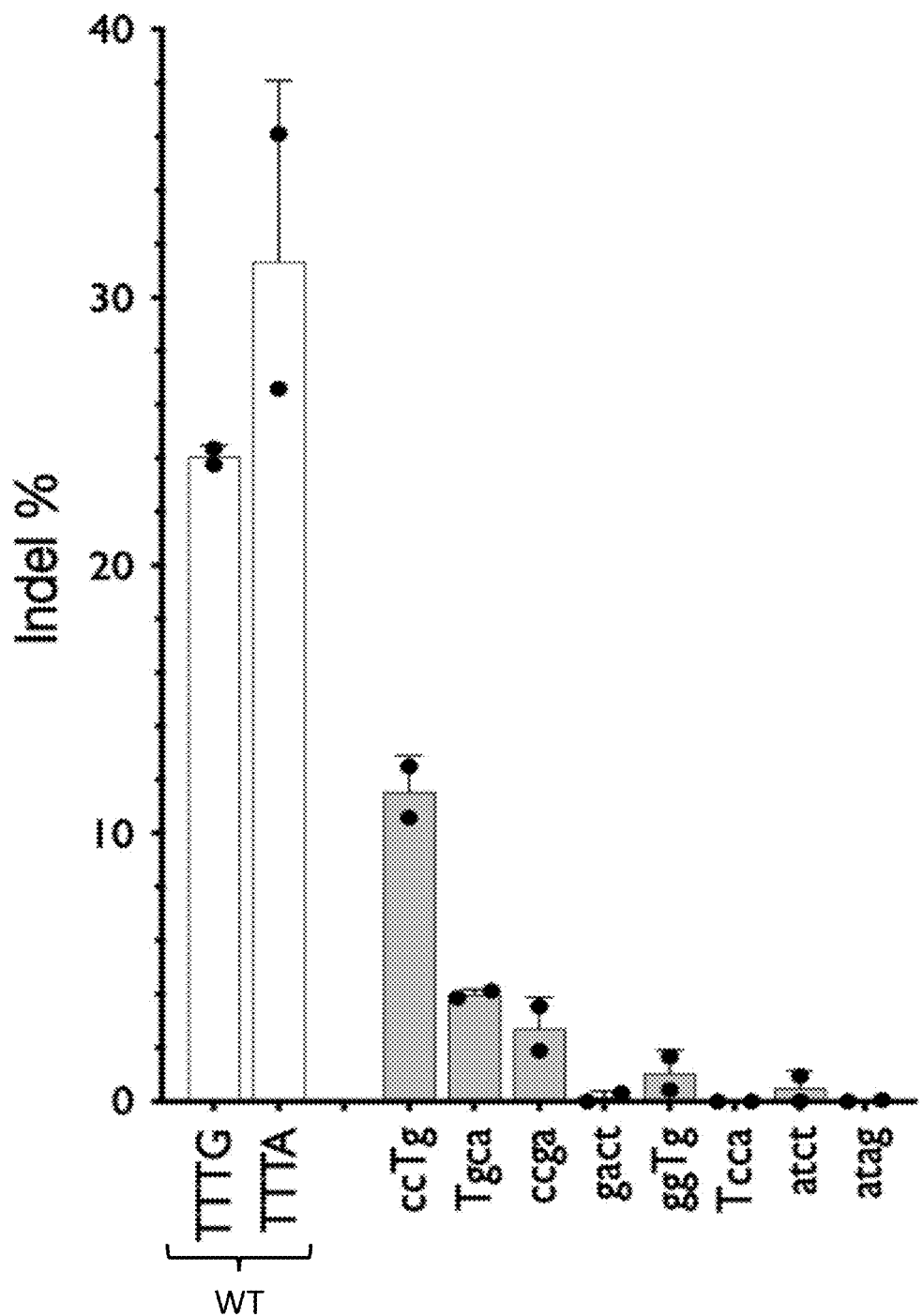
Figure 22D:
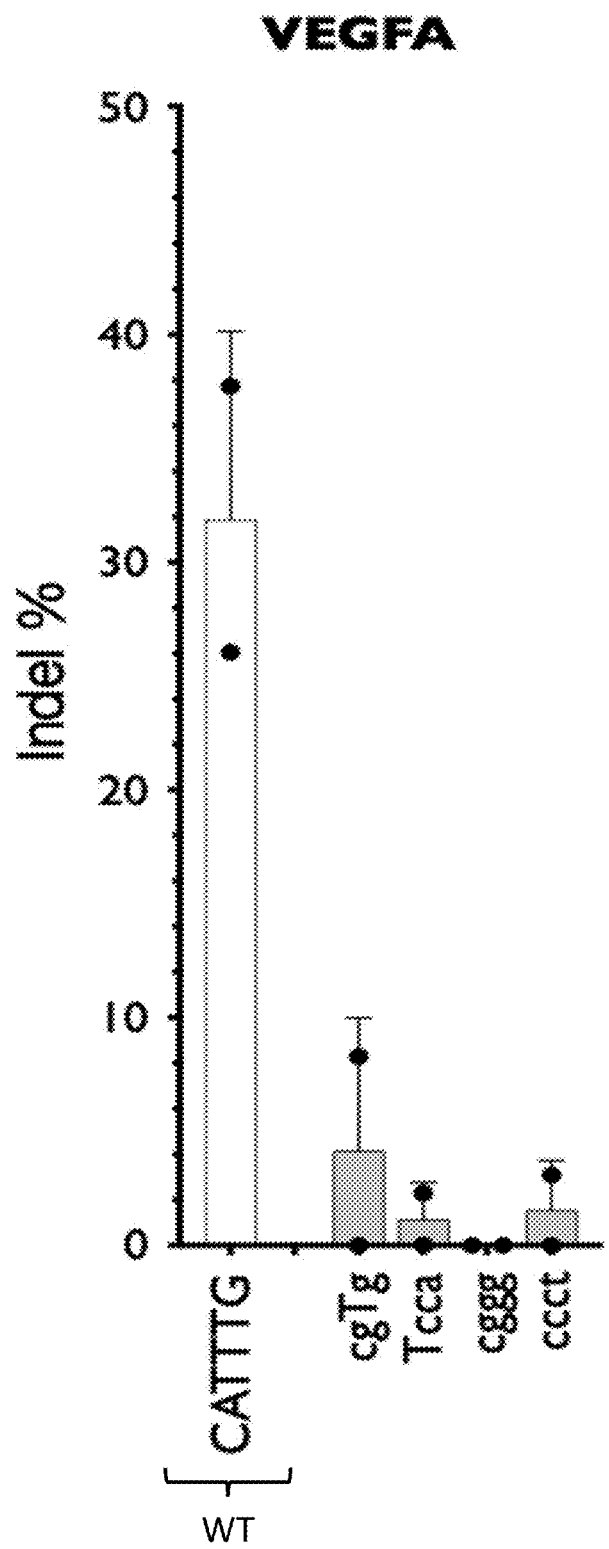
Figure 22E:
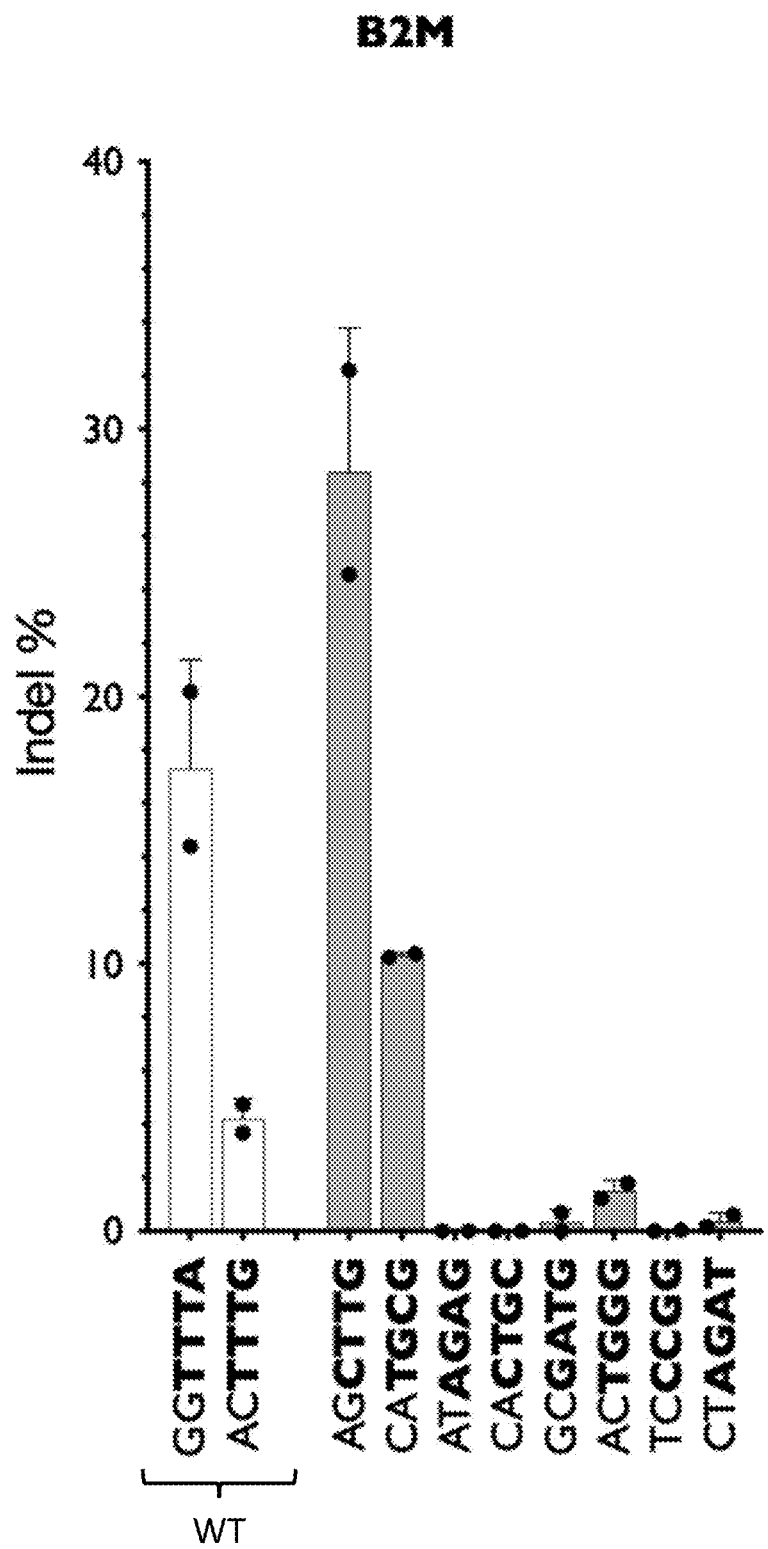

As described above, the library of gRNA-target variants also included variants designed to assess changes in PAM sequences. Accordingly, gRNA-target variants in the high-throughput screen included variants in which randomly generated PAM sequences were appended to spacer sequences for a given target sequence. These variants were evaluated for their relative effect on nuclease activity, compared to wildtype PAM sequences with known activity for the same target sequence. For example, FIG. 22A shows indel frequencies induced by wildtype (WT) PAM sequences on the left (NNTTTG) and variant PAM sequences on the right, aggregated over all gRNA-target variants targeting the MLH gene sequence. Indel frequencies induced by wildtype (WT) PAM sequences and variant PAM sequences in gRNA-target variants are also shown for the GAK gene sequence (FIG. 22B), the APOB gene sequence (FIG. 22C), the VEGFA gene sequence (FIG. 22D), and the B2M gene sequence (FIG. 22E). TABLE 42 summarizes all PAM sequences that have been identified in FIGS. 22A-22E.

TABLE 42

PAM Sequences

| Effector Protein SEQ ID No. | PAM |
|---|---|
| 1 | CATA |
| 1 | TGGA |
| 1 | GTAT |
| 1 | CTTA |
| 1 | TCAA |
| 1 | GTGA |
| 1 | AAGC |
| 1 | GTTG |
| 1 | TGGA |
| 1 | GGTA |
| 1 | TCGG |
| 1 | ACCA |
| 1 | CCTG |
| 1 | TGCA |
| 1 | CCGA |
| 1 | GGTG |
| 1 | ATCT |
| 1 | CGTG |
| 1 | CCCT |
| 1 | CTTG |
| 1 | TGCG |
| 1 | TGGG |

For all targeted gene sequences, the assay identified one or more variant PAM sequences that retained at least partial nuclease activity, and, in some instances, induced comparable or greater than wildtype nuclease activity (e.g., for MLH and B2M gene sequences). These results indicate that, in some cases, comparable nuclease activity can be obtained even with variations in PAM sequences.

Figure 23:
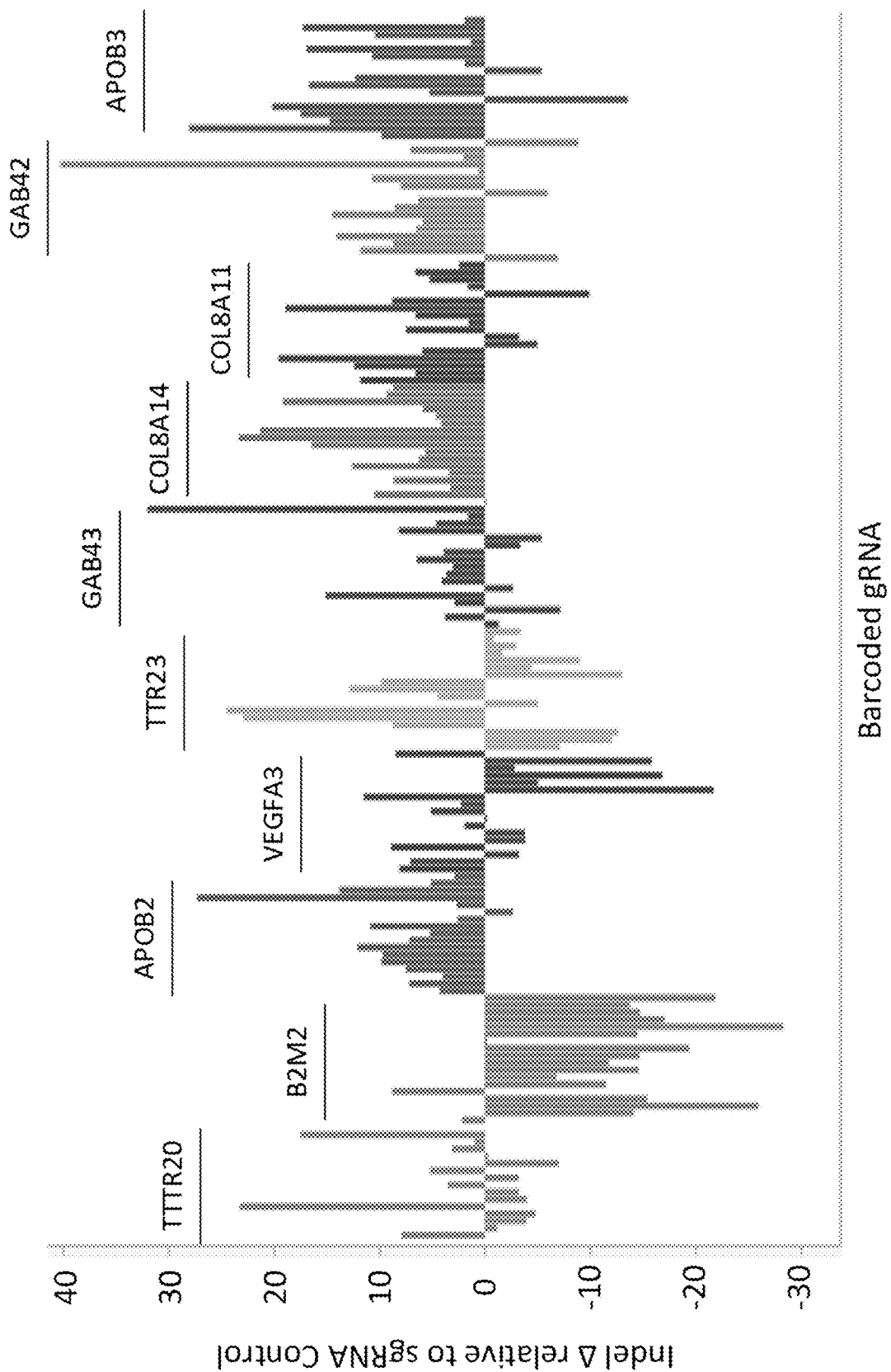
FIG. 23 illustrates the effects of repeat sequence variation in gRNAs on CasM.265466 nuclease activity for example target sequences, in accordance with an embodiment of the present disclosure.

Variations in the handle sequence of the gRNA, particularly in the repeat sequence, provided another means of editing optimization by improving nuclease activity in a target-specific manner. FIG. 23 illustrates increases or decreases in nuclease activity (e.g., indel change relative to control sgRNA) induced by different gRNAs corresponding to different repeat sequence variants, where each respective gRNA variant is represented by a corresponding bar in the plot. Changes in indel frequencies were also dependent on the particular target sequence assayed, as indicated by the labeled bar above each section of the graph.

The high-throughput, pooled gRNA screening assay described herein provides useful data that can be used to establish design rules, optimization criteria, and/or filtering thresholds for the development of Cas nuclease gRNAs, and particularly for CasM.265466. Moreover, such data can be used to train and develop predictive models for designing efficient guides that induce high levels of nuclease activity.

Example 29. Arginine Mutation Scanning of CasM.265466 to Identify Charge Substitution Rules of Effector Protein Activity CasM.265466 arginine mutants were tested for their ability to produce indels in HEK293T cells. A total of 368 arginine mutants were tested. Briefly, a first plasmid encoding a CasM.265466 arginine mutant and a second plasmid encoding a single guide RNA were delivered by lipofection to HEK293T cells. The sgRNA comprised a nucleotide sequence of SEQ ID NO: 52. The sgRNA comprised a spacer sequence that was designed to hybridize to a target sequence adjacent to a PAM of TNTR (e.g., TTTG). For lipofections, 15 ng of the nuclease mutant and 150 ng of the guide RNA encoding plasmid were delivered to ~30,000 HEK293T cells in 200 µl using TransIT-293 lipofection reagent. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence. Sequencing libraries with less than 20% of reads aligning to the reference sequence were excluded from the analysis for quality control purposes. Wildtype CasM.265466 was included as positive control and reference for the mutants.

Figure 24:
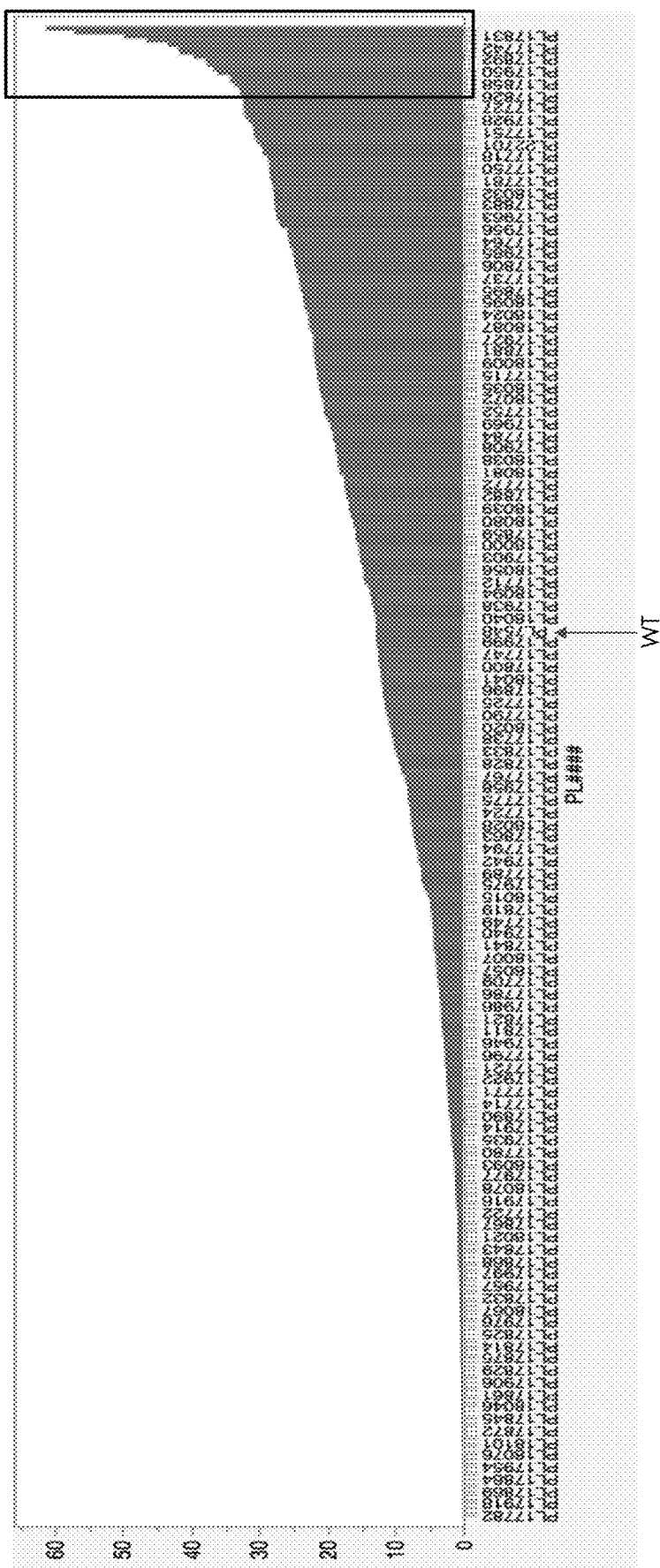
FIG. 24 illustrates the effects of an arginine substitution on CasM.265466 nuclease activity for a target nucleic acid, in accordance with an embodiment of the present disclosure.

The mean indel percentage for each of the arginine mutant is shown in FIG. 24. An analysis of FIG. 24 indicates that positive charge of arginine may strengthen the interaction between the effector protein and the negatively charged DNA backbone. Top 10 arginine mutants that showed increase in indel potency includes I80R, T84R, K105R, G210R, C202R, A218R, D220R, E225R, C246R, and Q360R.

Example 30. CasM.265466 Arginine Mutants and their Potency for Indel Generation The top ten nuclease mutants, each comprising different CasM.265466 arginine mutant, as identified in Example 29 were tested for their ability to produce indels in HEK293T cells over a variety of doses. Briefly, a first plasmid encoding a CasM.265466 mutant and a second plasmid encoding a single guide RNA (sgRNA) were delivered by lipofection to HEK293T cells. The sequence of the sgRNAs included a nucleotide sequence of SEQ ID NO: 52. The sgRNA spacer was designed to hybridize to a target sequence adjacent to a PAM of TNTR (e.g., TTTG). For lipofections, the CasM.265466 mutant and sgRNA were delivered to ~30,000 HEK293T cells in 200 µl using TransIT-293 lipofection reagent. Each of the ten nuclease mutants were tested at a dose ranging from 1.17 ng to 150 ng. The sgRNA encoding plasmid was used at a concentration of 150 ng. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence. Sequencing libraries with less than 20% of reads aligning to the reference sequence were excluded from the analysis for quality control purposes. Wildtype CasM.265466 was included as positive control and reference for the mutants.

Figure 25:
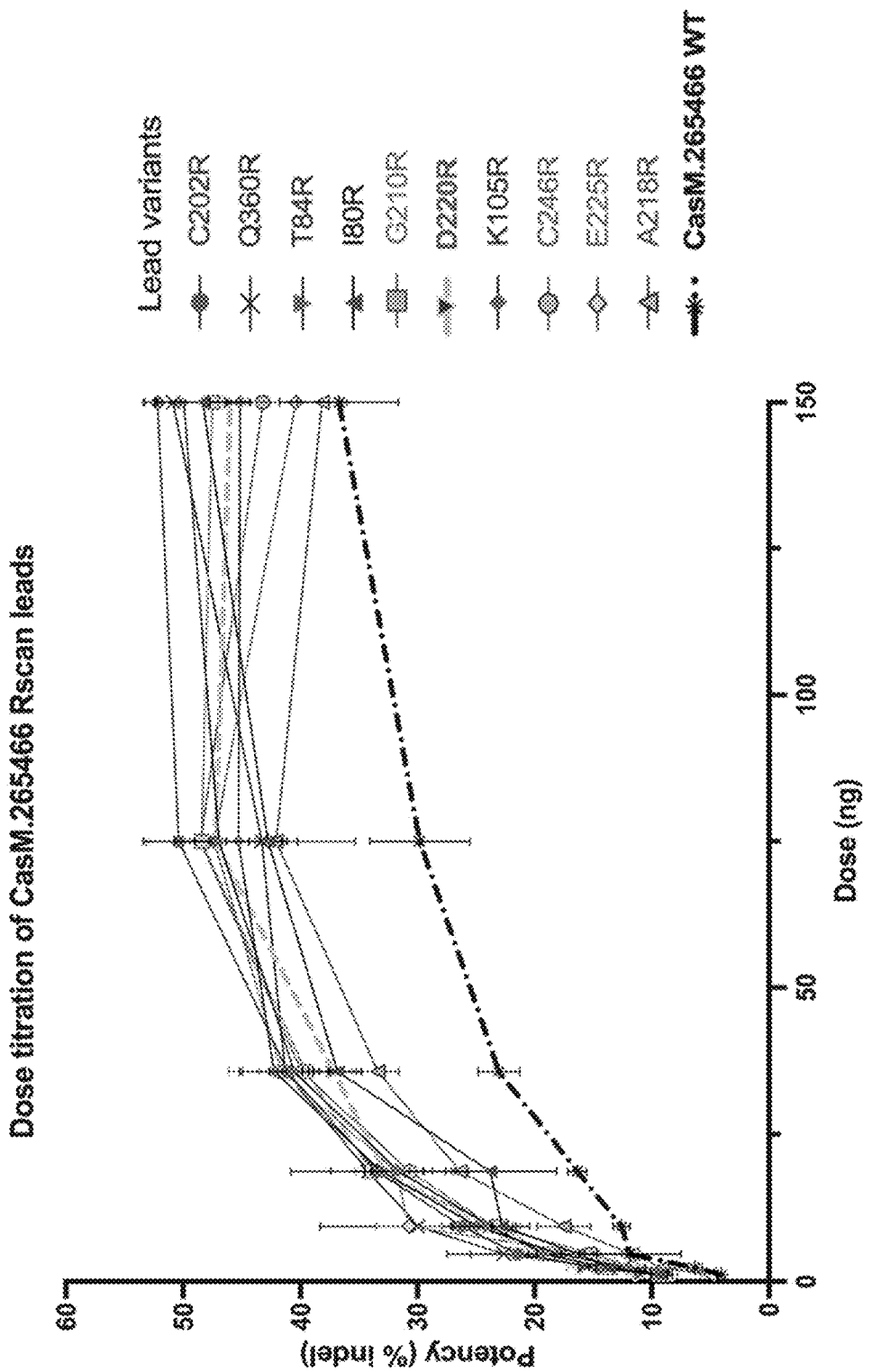
FIG. 25 illustrates the dose titration curves of CasM.265466 arginine mutants, in accordance with an embodiment of the present disclosure.

The mean indel percentage and standard deviation based on three replicates is reported in FIG. 25. An analysis of FIG.

25 indicates that arginine substitution can increase potency of the effector protein in the generation of indels.

Example 31. CasM.265466 Fusion Containing a Single Exonuclease Fusion Partner to Identify Indel Precision Effector proteins, wildtype CasM.265466 protein and sbcB-CasM.265466 fusion protein, and multiple sgRNAs were tested for the ability to produce indels in HEK293T cells. The sbcB-CasM.265466 fusion protein comprised an exonuclease sbcB linked to the effector protein on N-terminus by an XTEN80 linker. Briefly, a first plasmid encoding the effector protein and a second plasmid encoding a single guide RNA (sgRNA) were delivered by lipofection to HEK293T cells. The sequence of the sgRNA included a spacer sequence of AGUCUCCAGGAAGAAAUUAA (SEQ ID NO: 945). The sgRNA spacer was designed to hybridize to a target sequence adjacent to a PAM of TTTG. For lipofections, 15 ng or 150 ng of the effector protein in combination with 150 ng of the guide RNA encoding plasmid were delivered to ~30,000 HEK293T cells in 200 μl using TransIT-293 lipofection reagent. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence. Sequencing libraries with less than 20% of reads aligning to the reference sequence were excluded from the analysis for quality control purposes.

Figures 26A, 26B:
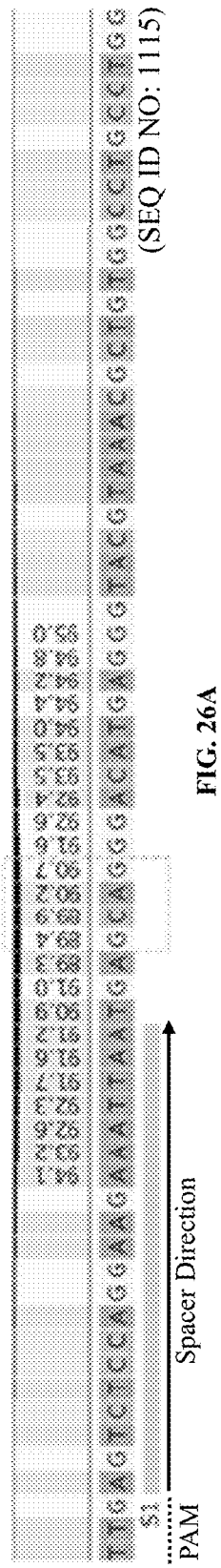
FIGS. 26A-26B illustrate nuclease activity of effector protein on target nucleic acids in accordance with an embodiment of the present disclosure.
Figure 27A:
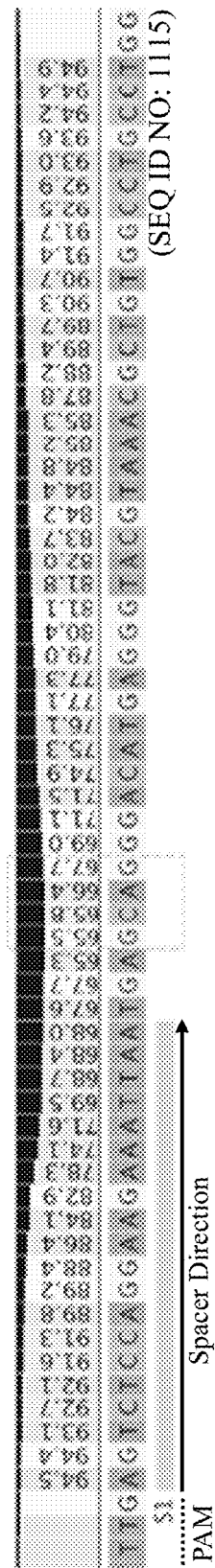
FIGS. 27A-27B illustrate nuclease activity of effector protein on target nucleic acids in accordance with an embodiment of the present disclosure.
Figure 27B:
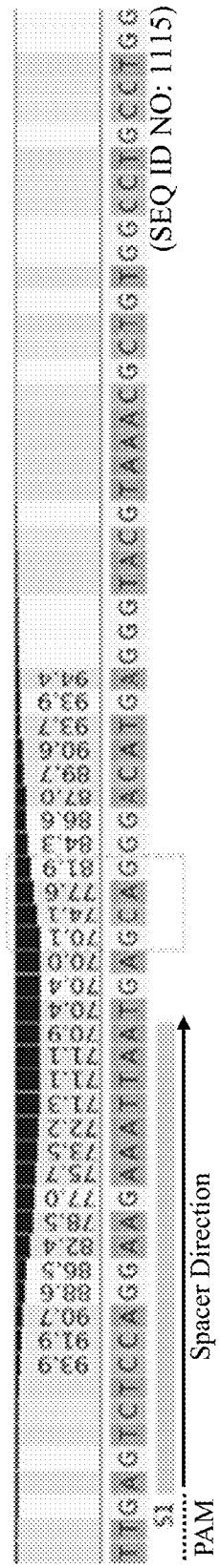

FIG. 26 and FIG. 27 show exemplary indels produced in a target nucleic acid having a nucleotide sequence of TTTT-GAGTCTCCAGGAAGAAATTAATGAGCAGGGACAT-GAGGGTACGTAAACGC TGTGGCCTGCCTG (SEQ ID NO: 870). FIG. 26A and FIG. 26B show an indel activity window at 15 ng dose for wildtype CasM.265466 protein and sbcB-CasM.265466 fusion protein respectively. Similarly, FIG. 27A and FIG. 27B show an indel activity window at 150 ng dose for wildtype CasM.265466 protein and sbcB-CasM.265466 fusion protein respectively. A comparative analysis of FIG. 26A to FIG. 27A, and FIG. 26B to FIG. 27B indicates that the indel activity window (cut site) is narrower at 15 ng dose relative to 150 ng dose of effector protein. Moreover, a comparative analysis of FIG. 26A to FIG. 26B, and FIG. 27A to FIG. 27B indicates that indel activity window is narrower for the sbcB-CasM.265466 fusion protein relative to the wildtype CasM.265466 protein at both a 15 ng and 150 ng dose. At a dose of 150 ng, using a threshold of about 5% indels, indels are detected at about 60 nucleotides within and around the target sequence with wildtype CasM.265466, whereas indels are detected at only about 30 nucleotides within and around the target sequence with sbcB-CasM.265466 fusion protein. Thus, the indel activity window (cut site) is reduced by about 50%.

Figure 28A:
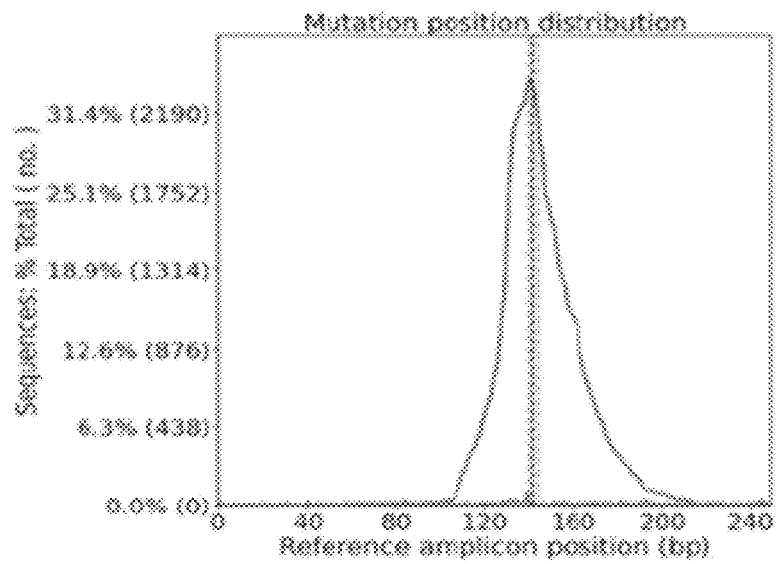
FIGS. 28A and 28B summarizes indel potency and indel precision of wildtype CasM.265466 protein and sbcB-CasM.265466 fusion protein respectively on target nucleic acids in accordance with an embodiment of the present disclosure.
Figure 28B:
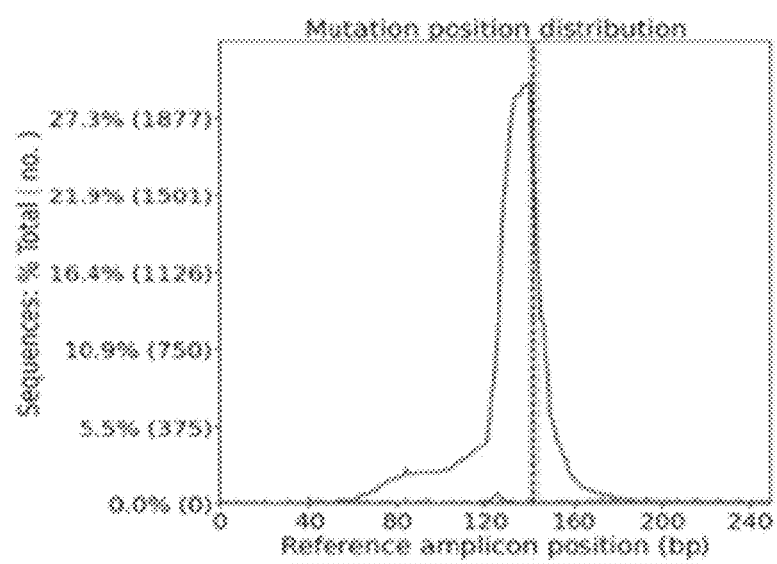

FIG. 28A and FIG. 28B show indel activity windows at 150 ng doses for wildtype CasM.265466 protein, and sbcB-CasM.265466 fusion protein, respectively, by assessing amplicon sizes that span across the activity window. FIG. 28A shows that the majority of amplicons having indels are distributed over about 60 nucleotides (120 bp to 180 bp). FIG. 28B shows that the majority of amplicons having indels are distributed over about 30 nucleotides (120-150 bp). Thus, similar to the results shown in FIG. 27A and FIG. 27B, the indel activity window (cut site) is reduced.

Example 32. sbcB-CasM.265466-recJ Fusion Containing Two Exonuclease Fusion Partners to Identify Indel Precision Effector proteins, wildtype CasM.265466 and sbcB-CasM.265466-recJ fusion protein, and multiple sgRNAs were tested for the ability to produce indels in HEK293T cells. The sbcB-CasM.265466-recJ fusion protein comprised sbcB and recJ fusion partners linked to the CasM.265466 protein on N-terminus and C-terminus respectively. The fusion partners were linked to the effector protein by an XTEN20 linker. Briefly, a first plasmid encoding the effector protein and a second plasmid encoding a single guide RNA (sgRNA) were delivered by lipofection to HEK293T cells. The sequence of the sgRNA included a spacer sequence of AGUCUCCAGGAAGAAAUUAA (SEQ ID NO: 945). The sgRNA spacer was designed to hybridize to a target sequence adjacent to a PAM of TTTG. For lipofections, 150 ng of the effector protein in combination with 150 ng of the guide RNA encoding plasmid were delivered to ~30,000 HEK293T cells in 200 μl using TransIT-293 lipofection reagent. Lipofected cells were grown for ~72 hrs at 37° C. to allow for indel formation. Indels were detected by next generation sequencing of PCR amplicons at the targeted loci and indel percentage was calculated as the fraction of sequencing reads containing insertions or deletions relative to an unedited reference sequence. Sequencing libraries with less than 20% of reads aligning to the reference sequence were excluded from the analysis for quality control purposes.

Figure 29A:
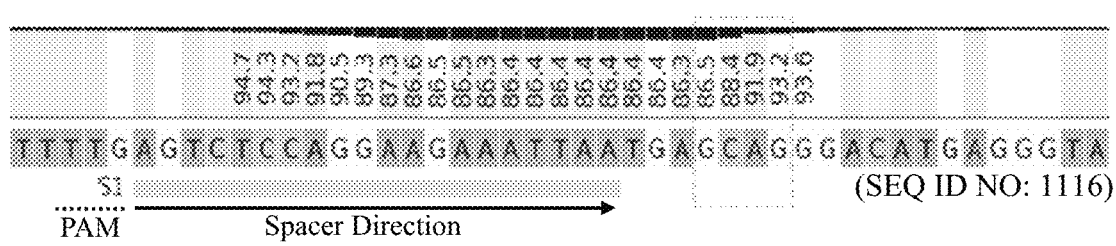
FIGS. 29A-29B illustrate nuclease activity of sbcB-CasM.265466-recJ fusion protein on target nucleic acids in accordance with an embodiment of the present disclosure.

FIG. 27A and FIG. 29A show an exemplary indel activity window produced in a target nucleic acid having a nucleotide sequence of SEQ ID NO: 870 for the wildtype CasM.265466 protein and sbcB-CasM.265466-recJ fusion protein respectively. A comparative analysis of FIG. 27A and FIG. 29A shows that indel activity window is narrower for the sbcB-CasM.265466-recJ fusion protein relative to the wildtype CasM.265466 protein.

Figure 29B:
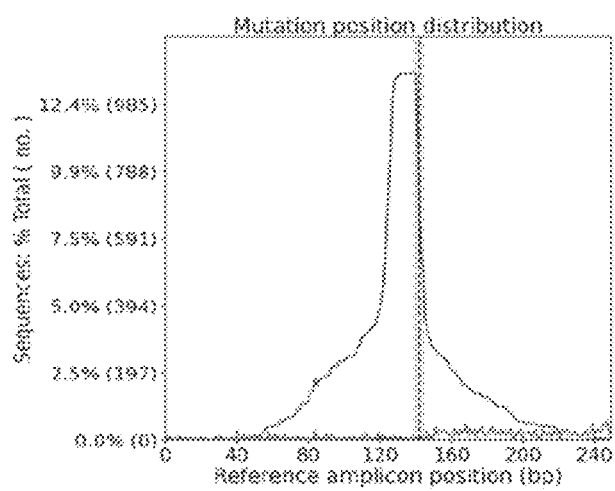

FIG. 28A and FIG. 29B show potency and indel activity window for all the target nucleic acids tested at 150 ng dose of wildtype CasM.265466 protein and sbcB-CasM.265466-recJ fusion protein respectively. An analysis of FIG. 28A and FIG. 29B suggests that fusion partners, sbcB and recJ, when used together, do not increase indel potency of CasM.265466 protein. The analysis also indicates that sbcB-CasM.265466-recJ fusion protein has narrower indel activity window relative to the wildtype CasM.265466 protein. In conclusion, fusion partner can be used to modify the indel activity window of CasM.265466. In other words, the fusion partners can be used to modify indel precision of CasM.265466.

Example 33. CasM.265466 Systems to Identify Effector Proteins that Function Similarly to CasM.265466

To find proteins that may have a similar function and structure to CasM.265466 systems, potential tracrRNAs of CasM.265466 were used as a query sequence for BLAST searching against a proprietary database of potential Cas proteins. In addition, an Infernal hidden Markov model (Infernal-HMM) search consisting of RNA sequences and structural information that are also similar to CasM.265466 potential tracrRNAs was also used to identify similar RNAs in the proprietary database. (An Infernal HMM search involves running an initial filter with an HMM and then applying a covariance model to account for covariation based on a consensus structure). From both of these paradigms of search, a subset of RNA sequences containing conserved sequences and structural motifs similar to those found in the contig associated with CasM.265466. Consensus repeat sequences were identified based on an alignment of all repeats in an array found in a given contig of the proprietary database. After aligning consensus repeat sequences, potential tracrRNA sequences, and nucleases by percent protein identity with that of CasM.265466, protein sequences (SEQ ID NOS: 871-929) that function similarly to CasM.265466 (e.g., bind similar RNA structures) were identified.

Example 34. In Vivo Editing of PCSK9 in a Mammal Using AAV Vector Encoding CasM.265466 and Guide RNA This example demonstrates that genome editing can be performed with an AAV8 vector encoding a CasM.265466 protein (SEQ ID NO: 1) and a guide RNA having a nucleotide sequence of SEQ ID NO: 944 (gRNA1). An AAV8 vector was constructed to contain a transgene between its ITRs. The AAV8 vector was expressed with supporting plasmids to produce an adeno-associated virus.
8-week old male mice were delivered with 2e+13 (vg/kg) of AAV virus by tail vein injection. Each dosing group had three animals. Negative control groups were injected with vehicle only or CasM.265466 system containing gRNA2, wherein a spacer sequence of the gRNA2 was targeting UTR region of PCS9K gene. A positive control group was injected with SaCas9 system. Liver and serum from each mice were harvested 4 weeks post injection.

Figure 30A:
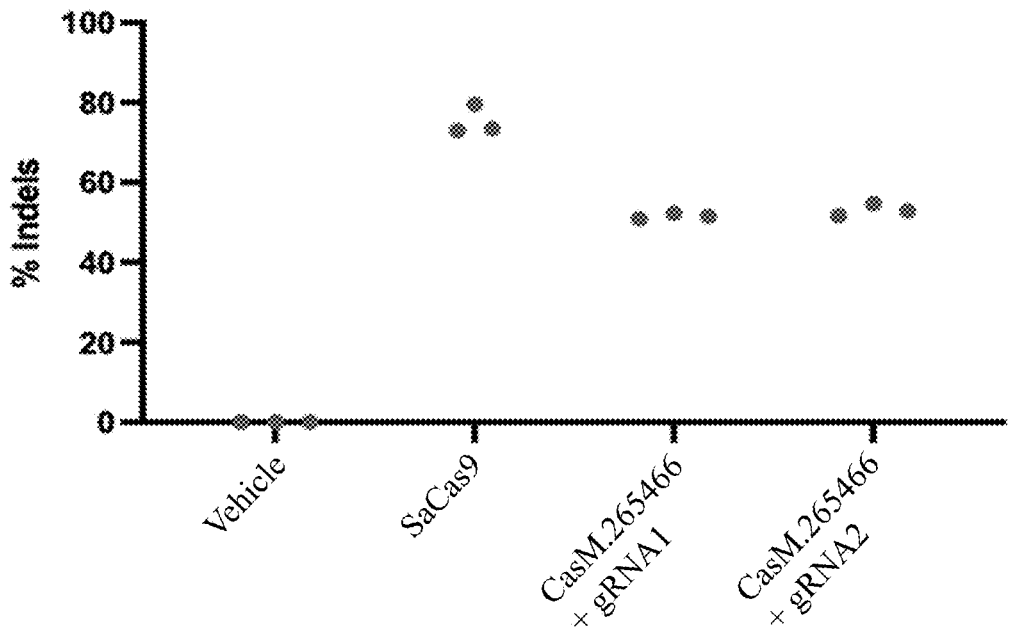
FIGS. 30A-30B shows in vivo effect of CasM.265466 system comprising AAV8 vector encoding CasM.265466 and a guide RNA targeting the PCSK9 gene and serum concentration of PCSK9 protein in mice following treatment.
Figure 30B:
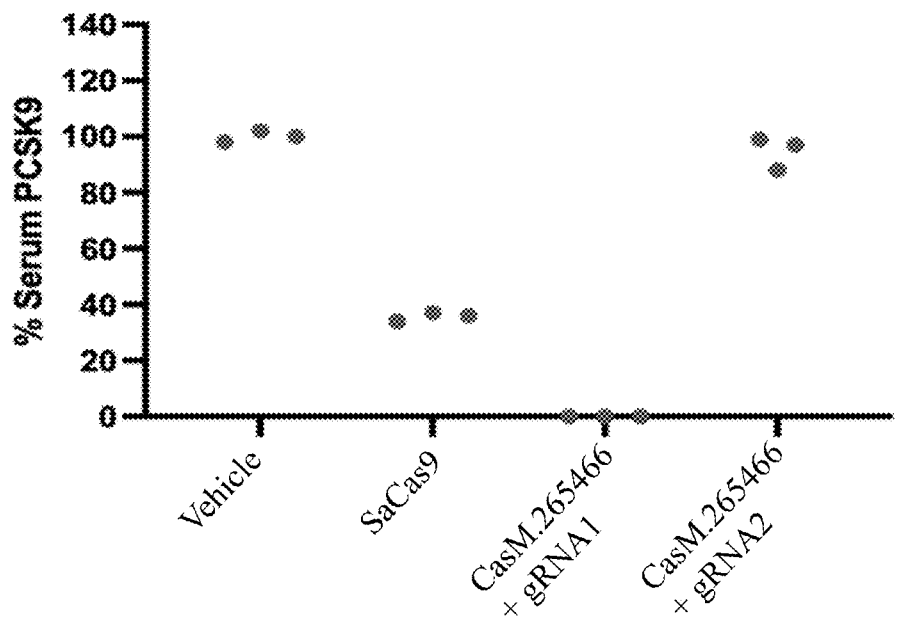

Genomic DNA was extracted from the liver and the frequency of indel mutations was determined using NGS. FIG. 30A illustrates the frequency of CasM.265466 induced indel mutations in mice liver transfected with AAV plasmid. The results depicted in FIG. 30A demonstrate that both CasM.265466 systems introduced about 50% indel mutations in PCSK9 gene. FIG. 30B illustrates that effect of CasM.265466 system on the % serum of PCSK9 protein. In particular, the results depicted in FIG. 30B demonstrate that a group tested with the CasM.265466 system having gRNA1 showed 100% reduction in PCSK9 protein serum concentration. However, a group tested with the CasM.265466 system having gRNA2 showed no substantial reduction of PCSK9 protein serum concentration. This study demonstrates that CasM.265466 system can be used for in vivo genome editing in mice liver.

Example 35: Additional PAM Screening for CasM.265466

Prior in vitro screening as described in Example 1 for D2S effector protein CasM.265466 (SEQ ID NO: 1) PAM recognition demonstrated that the most enriched PAM sequence for CasM.265466 (SEQ ID NO: 1) was a TNTR PAM sequence, but also indicated that the effector protein may tolerate a more flexible PAM sequences beyond TNTR without significantly compromising nuclease activity. Effector protein and flexible PAM group combinations as set forth in TABLE 43 were screened to confirm that chromosomal DNA may be efficiently targeted in mammalian cells (HEK293T) using a more flexible PAM sequence.

Single and double point mutations were made along TNTR.

TABLE 43

PAM SEQUENCES

| SEQ ID NO: | PAM Group* |
|---|---|
| 946 | NNTN |
| 947 | ANTR |
| 1111 | CNTR |
| 948 | GNTR |
| 949 | TNAR |
| 950 | TNCR |
| 951 | TNGR |
| 952 | TNTC |
| 953 | TNTT |
| 954 | VNTY |
| 955 | TNVY |

*wherein each N is any nucleotide, each R is A or G, and each V is A, C or G.

At least six spacers that previously showed >3% indel rate were selected for each PAM group identified in TABLE 43.

Single guide nucleic acids (sgRNA) were generated with the following scaffold sequence: 5'-ACAGCUUAUUUG-GAAGCUGAAAUGUGAGGUUUAUAACACUCACA-AGAAUCCUGAAAAAG GAUGCCAAAC-[SPACER]-3' (SEQ ID NO: 956) wherein "SPACER" represents a 20 nt spacer sequence.

Figure 31:
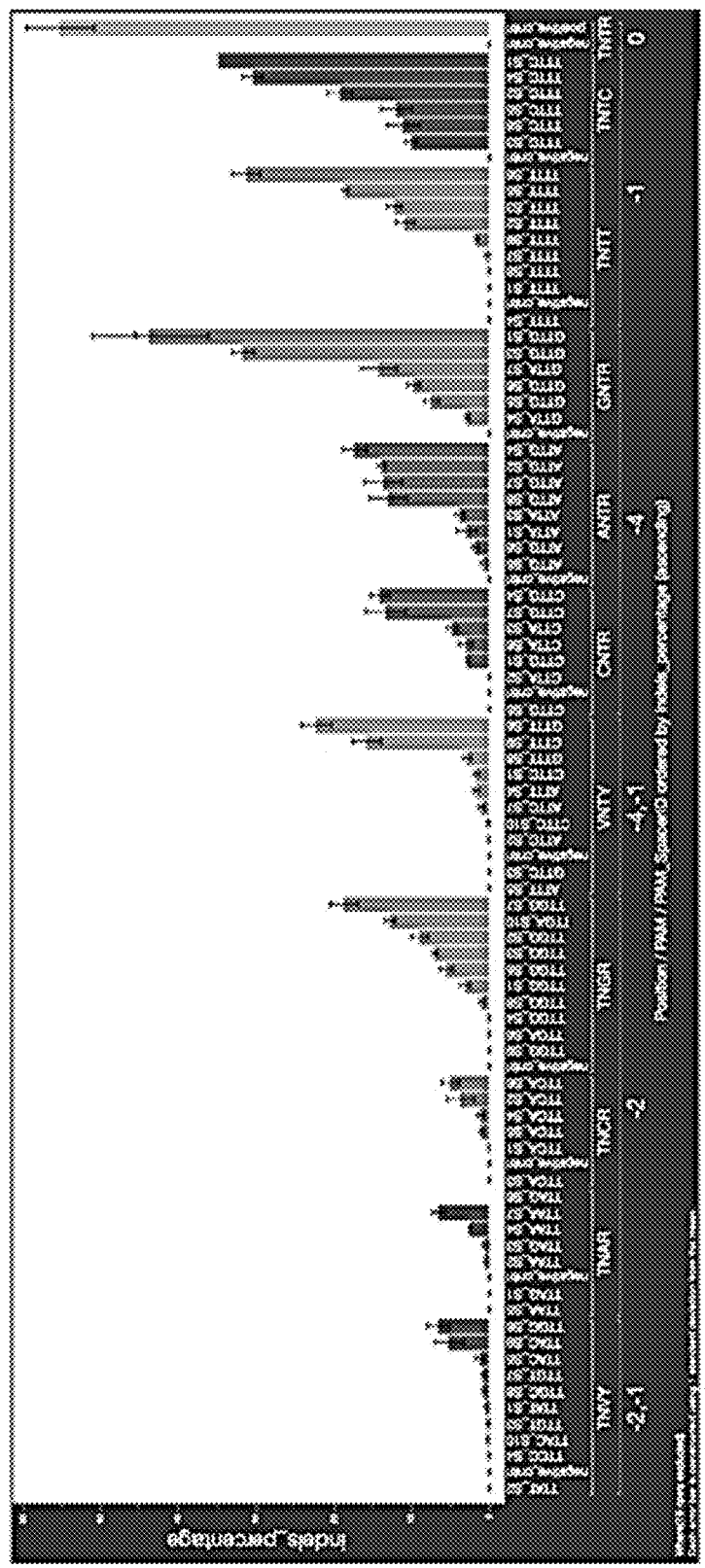
FIG. 31 illustrates the nuclease activity of CasM.265466 with flexible PAM sequences, in accordance with an embodiment of the present disclosure.

Plasmids encoding CasM.265466 effector protein (SEQ ID NO: 1) and plasmids encoding the sgRNAs were delivered via lipofection to HEK293T cells and permitted to grow to allow for indel formation. Cells were lysed and indels were detected by next generation sequencing. Indel percentage was calculated and plotted as shown in FIG. 31.

While the top performing complexes were found to produce up to or greater than 30% indel, the data also demonstrates that single and double point mutations at −4 and −1 were the most permissive for allowing nuclease activity. Furthermore, the CasM.265466 effector protein (SEQ ID NO: 1) complexed with two different sgRNAs having different spacer sequences generated 20% indel at targeted sequences adjacent to an NNTN (SEQ ID NO: 946) PAM. Therefore, these results further confirm the results of Example 1 and demonstrate that the CasM.265466 effector protein (SEQ ID NO: 1) recognizes a flexible NNTN (SEQ ID NO: 946) PAM sequence.

Example 36: Editing Efficiency and Integration Rates of CasM.265466 Effector Protein Variants in HEK293T Cells CasM.265466 effector protein (SEQ ID NO: 1) and CasM.265466 effector protein variants having either a D220R or a E225R substitution was tested for their editing efficiency and ability to integrate double-stranded oligodeoxynucleotide (dsODN) in HEK293T cells as compared to Cas9, empty plasmids and non-targeting (NT) controls.

Briefly, 1 μg of Cas9 and an equivalent amount of the CasM.265466 effector protein or variants thereof (0.63 μg) were complexed with guide nucleic acids (0.37 μg) targeting MLH1, and delivered by nucleofection to HEK293T cells (2.3E+05 cells). Likewise, the controls, empty plasmid, Cas9 and NT controls, were complexed with 2, 1, and 0 μg of guide nucleic acids respectively, and also delivered as described. Guide sequence for CasM.265466 WT and D220R variant is 5'-ACAGCUUAUUUGGAAGCU-GAAAUGUGAGGUUUAUAACACUCACAAGAAUC-CUGAAAAAG GAUGCCAAACagucuccaggaagaaauuaa-3' (SEQ ID NO: 52), wherein 5'-agucuccaggaagaaauuaa-3' (SEQ ID NO: 945) indicates the spacer sequence. Editing efficiency and integration were assessed by NGS.

Figure 32:
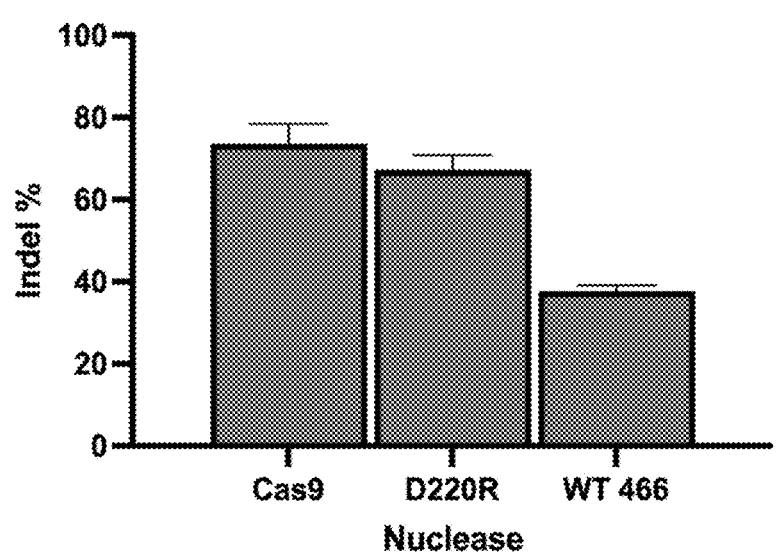
FIG. 32 illustrates % indel generated by D220R effector protein variant of CasM.265466 relative to corresponding wildtype CasM.265466 and Cas9 effector proteins.
Figure 33A:
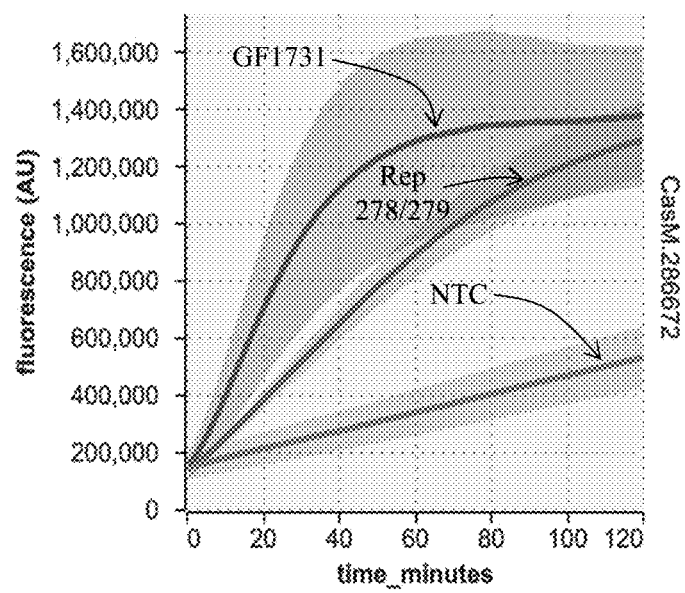
FIGS. 33A-33F show performance of various effector proteins in a trans cleavage DETECTR reaction at 37° C. Three targets, GF1731, Rep278/279 and NTC, were tested. The sgRNA of SEQ ID NO: 27 was used.
Figure 33B:
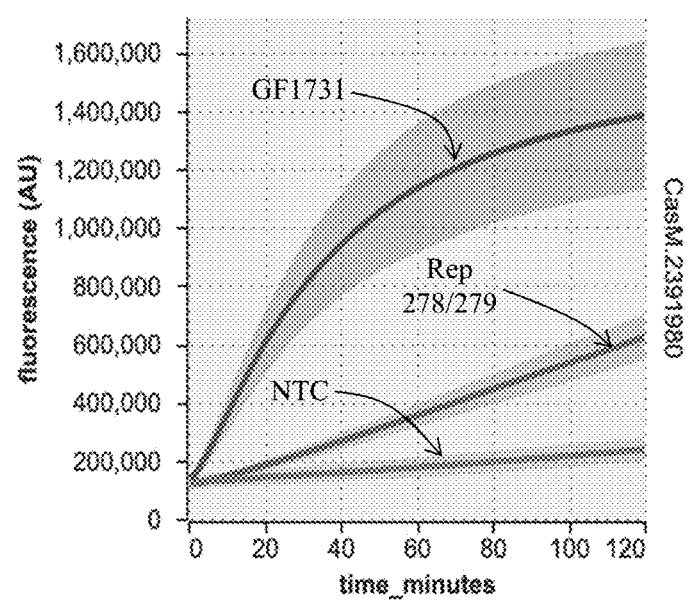
Figure 33C:
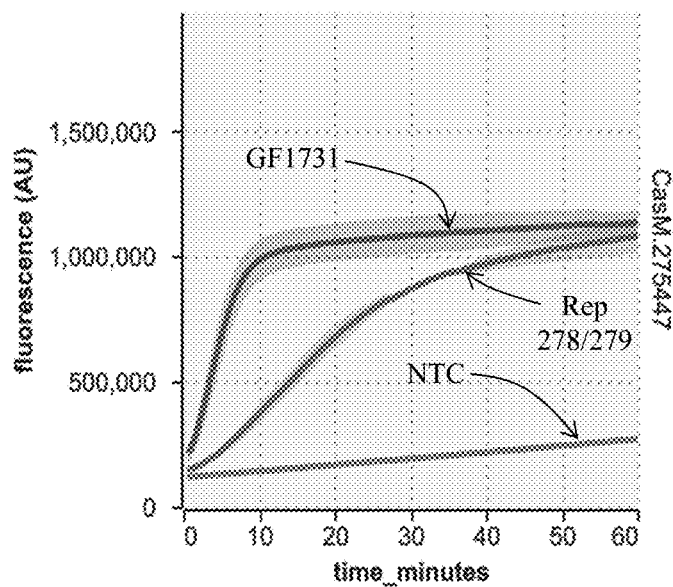
Figure 33D:
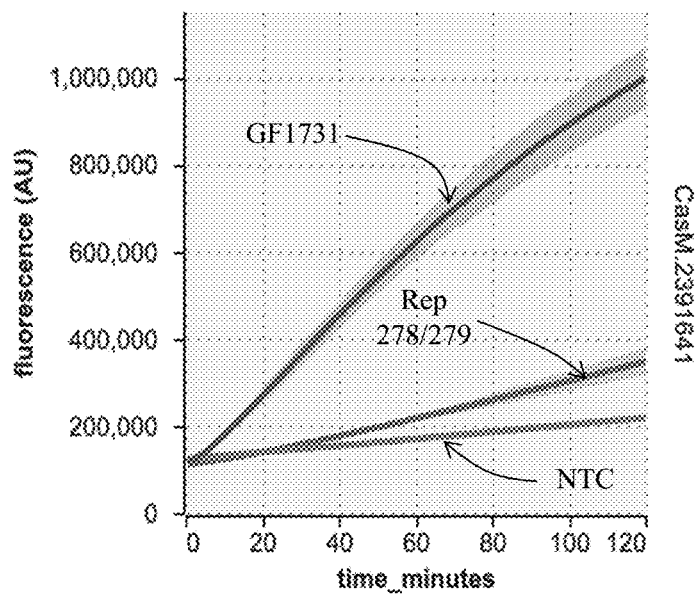
Figure 33E:
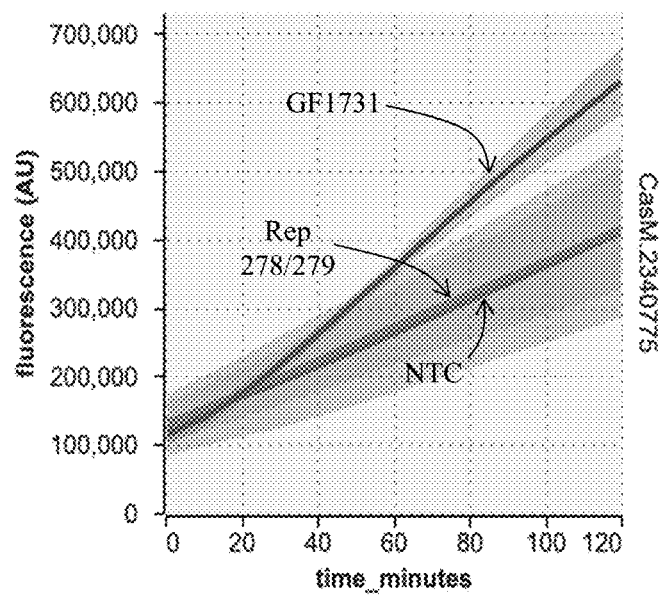
Figure 33F:
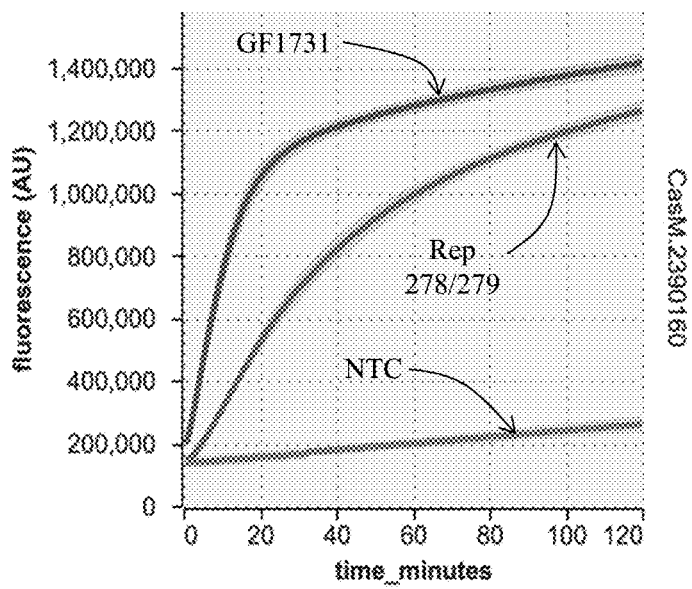

The results confirm the findings from Example 29, namely that the variant effector proteins continue to have an increased editing efficiency as compared to the CasM.265466 effector protein, and had an editing efficiency comparable to Cas9 (FIG. 32). The editing efficiency of the E225R variant was comparable to the editing efficiency of the D220R variant. The D220R and E225R variants were also capable of integrating the dsODN.

Example 37: Trans Cleavage Activity of Effector Proteins at 37° C.

Effector proteins, CasM.286672 (SEQ ID NO: 895), CasM.2391980 (SEQ ID NO: 913), CasM.275447 (SEQ ID NO: 889), CasM.2391641 (SEQ ID NO: 906), CasM.2340775 (SEQ ID NO: 892) and CasM.2390160 (SEQ ID NO: 910), were tested for trans cleavage at 37° C. Briefly, effector proteins were complexed with sgRNA for 15-30 minutes at 37° C. Specifically, effector proteins, CasM.286672 (SEQ ID NO: 895), CasM.275447 (SEQ ID NO: 889) and CasM.2340775 (SEQ ID NO: 892), were complexed with sgRNA of SEQ ID NO: 27. Similarly, effector proteins, CasM.2391980 (SEQ ID NO: 913), CasM.2391641 (SEQ ID NO: 906), and CasM.2390160 (SEQ ID NO: 910), were complexed with sgRNA of SEQ ID NO: 957. A 1× concentration of proteins was 40 nM and the final concentration of sgRNA was 40 nM. 5 μL of these RNPs was combined with a 5 μL mix of the following components for a total volume of 10 μL (listed at final concentration): trans cleavage buffer (20 mM Tricine (pH=9), 15 mM Mg(OAc)$_2$, 0.1 mg/ml BSA, 1 mM TCEP), target dsDNA with TTYG PAM (Rep278/279, 100 nM or 0 nM "NTC") or randomized PAM (GF1731, 100 nM or 0 nM "NTC"), and FQ reporter (/56-FAM/TTTTTTTTTTT (SEQ ID NO: 1064)/3IABkFQ/, 200 nM). Reactions were carried out at 37° C. for up to 120 minutes. Trans cleavage activity was detected by fluorescence signal upon cleavage of a fluorophore-quencher reporter in a DETECTR reaction. FIGS. 33A-33F show performance of various effector proteins in a trans cleavage DETECTR reaction at 37° C.

Example 38: Guide RNA-Dependent Trans Cleavage Activity of Effector Proteins at 37° C.

Figure 34A:
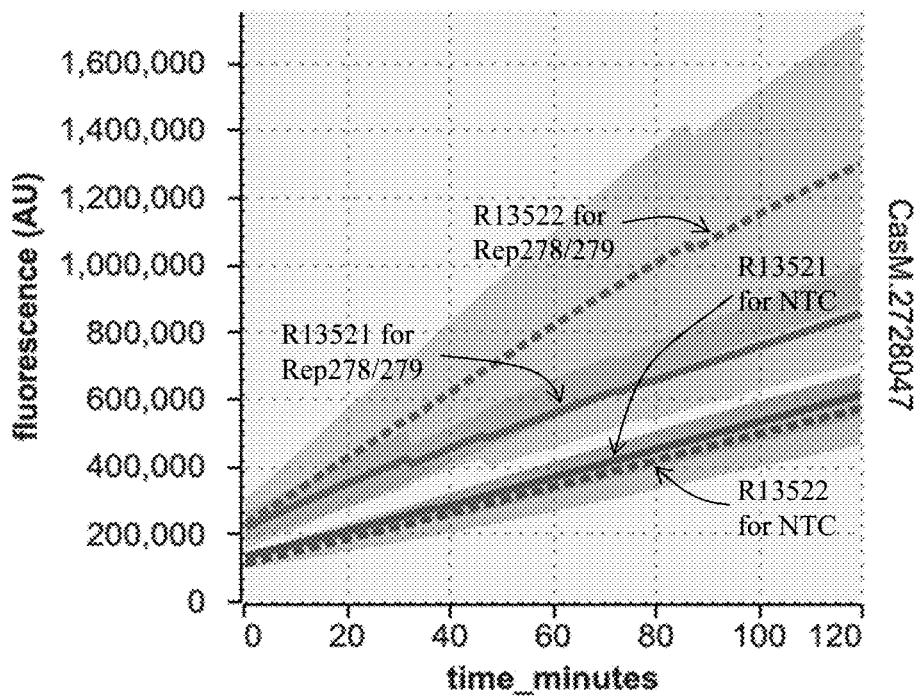
FIGS. 34A-34B show performance of various effector proteins in a trans cleavage DETECTR reaction at 37° C. Two targets, Rep278/279 and NTC, were tested. Each target was tested using two crRNAs, R13521 (SEQ ID NO: 957) and R13522 (SEQ ID NO: 27).
Figure 34B:
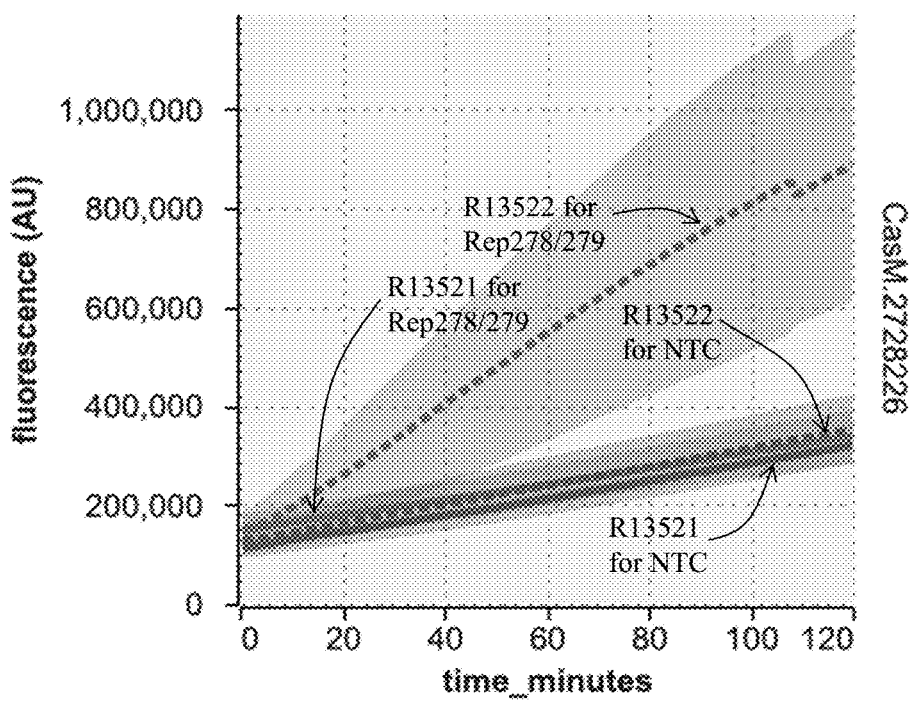

The effects of different sgRNA on trans cleavage was tested for different effector proteins at 37° C. Briefly, effector proteins, CasM.2728047 (SEQ ID NO: 871) and CasM.2728226 (SEQ ID NO: 884), were complexed with R13521 sgRNA (UGGGGCAGUUGGUUGCCCUUAGC-CUGAGGCAUUUAUUGCACUCGGGAAGUAC-CAUUUCU CAGAAAUGGUACAUCCAACuauuaaaua-cucguauugcu (SEQ ID NO: 957)), the handle sequence is in upper case and spacer is in lowercase, or R13522 sgRNA (SEQ ID NO: 27) for 15-30 minutes at 37° C. The 1× concentration of proteins was 40 nM and the final concentration of sgRNA was 40 nM. 5 μL of these RNPs was combined with a 5 μL mix of the following components for a total volume of 10 μL (listed at final concentration): trans cleavage buffer (20 mM Tricine (pH=9), 15 mM Mg(OAc)$_2$, 0.1 mg/ml BSA, 1 mM TCEP), target dsDNA with TTYG PAM (Rep278/279, 100 nM or 0 nM "NTC"), and FQ reporter (/56-FAM/TTTTTTTTTTT (SEQ ID NO: 1064)/3IABkFQ/, 200 nM). Reactions were carried out at 37° C. for up to 120 minutes. Trans cleavage activity was detected by fluorescence signal upon cleavage of a fluorophore-quencher reporter in a DETECTR reaction. FIGS. 34A-34B show performance of various effector proteins in a trans cleavage DETECTR reaction at 37° C. Both effector proteins showed a strong preference for sgRNA R13521 (SEQ ID NO: 957) over R13522 (SEQ ID NO: 27).

Example 39: Thermostability of Effector Proteins

Figure 35A:
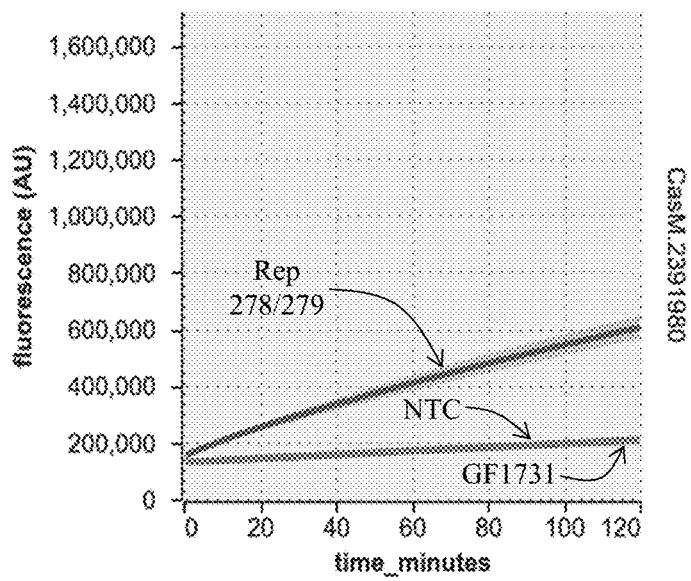
FIGS. 35A-35C show performance of various effector proteins in a trans cleavage DETECTR reaction at 55° C. Three targets, GF1731, Rep278/279 and NTC, were tested. The sgRNA of SEQ ID NO: 27 was used.
Figure 35B:
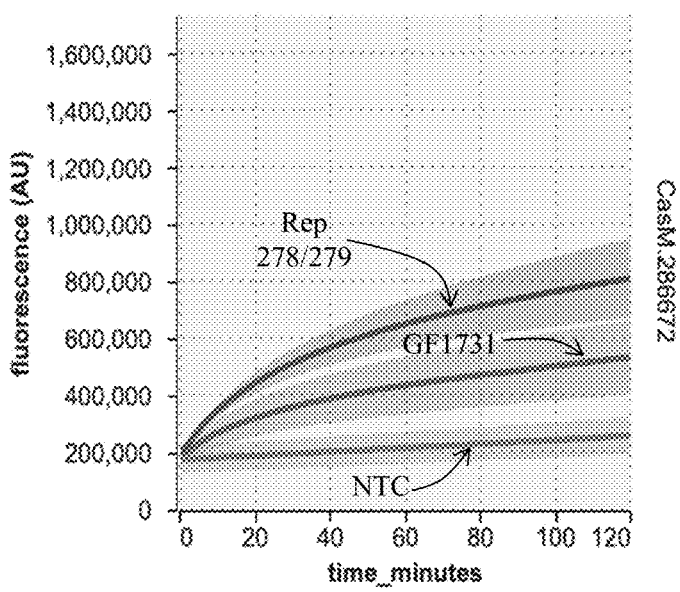
Figure 35C:
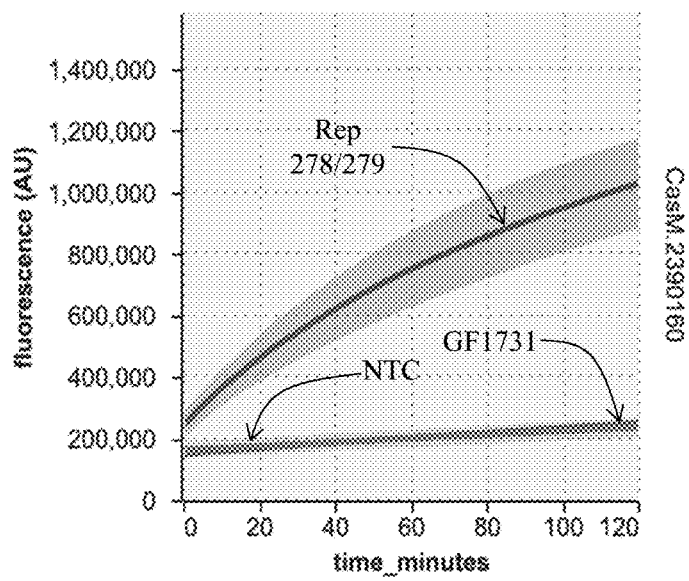

Effector proteins were tested for trans cleavage at 55° C. Briefly, effector proteins, CasM.2391980 (SEQ ID NO: 913), CasM.286672 (SEQ ID NO: 895) and CasM.2390160 (SEQ ID NO: 910), were complexed with sgRNA for 15-30 minutes at 37° C. Specifically, CasM.2391980 (SEQ ID NO: 913) and CasM.2390160 (SEQ ID NO: 910) were complexed with sgRNA of SEQ ID NO: 957. Similarly, CasM.286672 (SEQ ID NO: 895) was complexed with sgRNA of SEQ ID NO: 27. The 1× concentration of proteins was 40 nM and the final concentration of sgRNA was 40 nM. 5 μL of these RNPs was combined with a 5 μL mix of the following components for a total volume of 10 μL (listed at final concentration): trans cleavage buffer (20 mM Tricine (pH=9), 15 mM Mg(OAc)$_2$, 0.1 mg/ml BSA, 1 mM TCEP), target dsDNA with TTYG PAM (Rep278/279, 100 nM) or randomized PAM (GF1731, 100 nM), and FQ reporter (/56-FAM/TTTTTTTTTTT (SEQ ID NO: 1064)/3IABkFQ/, 200 nM). Reactions were carried out at 55° C. for up to 120 minutes. Trans cleavage activity was detected by fluorescence signal upon cleavage of a fluorophore-quencher reporter in a DETECTR reaction. FIGS. 35A-35C show performance of various effector proteins in a trans cleavage DETECTR reaction at 55° C.

Example 40: Engineered Variants of CasM. 265466

A potency assay was performed to evaluate the activity of CasM.265466 protein and engineered variants thereof. The variants were identical to CasM.265466 protein with the exception of the following amino acid substitutions: D220R and A306K. HEK293T cells were transfected with plasmids encoding these proteins and a single guide nucleic acid targeting MLH1. Wildtype CasM.265466 and Cas9 were included as controls. The sequence of the sgRNA used with CasM.265466 and variants thereof is acagcuuauuug-gaagcugaaaugugagguuuauaacacucacaagaauc-cugaaaaaggaugccaaacAGUCUCCAGGA AGAAAUUAA (SEQ ID NO: 958), with the intermediary sequence in bold, repeat sequence italicized and spacer sequence capitalized.

Figure 36:
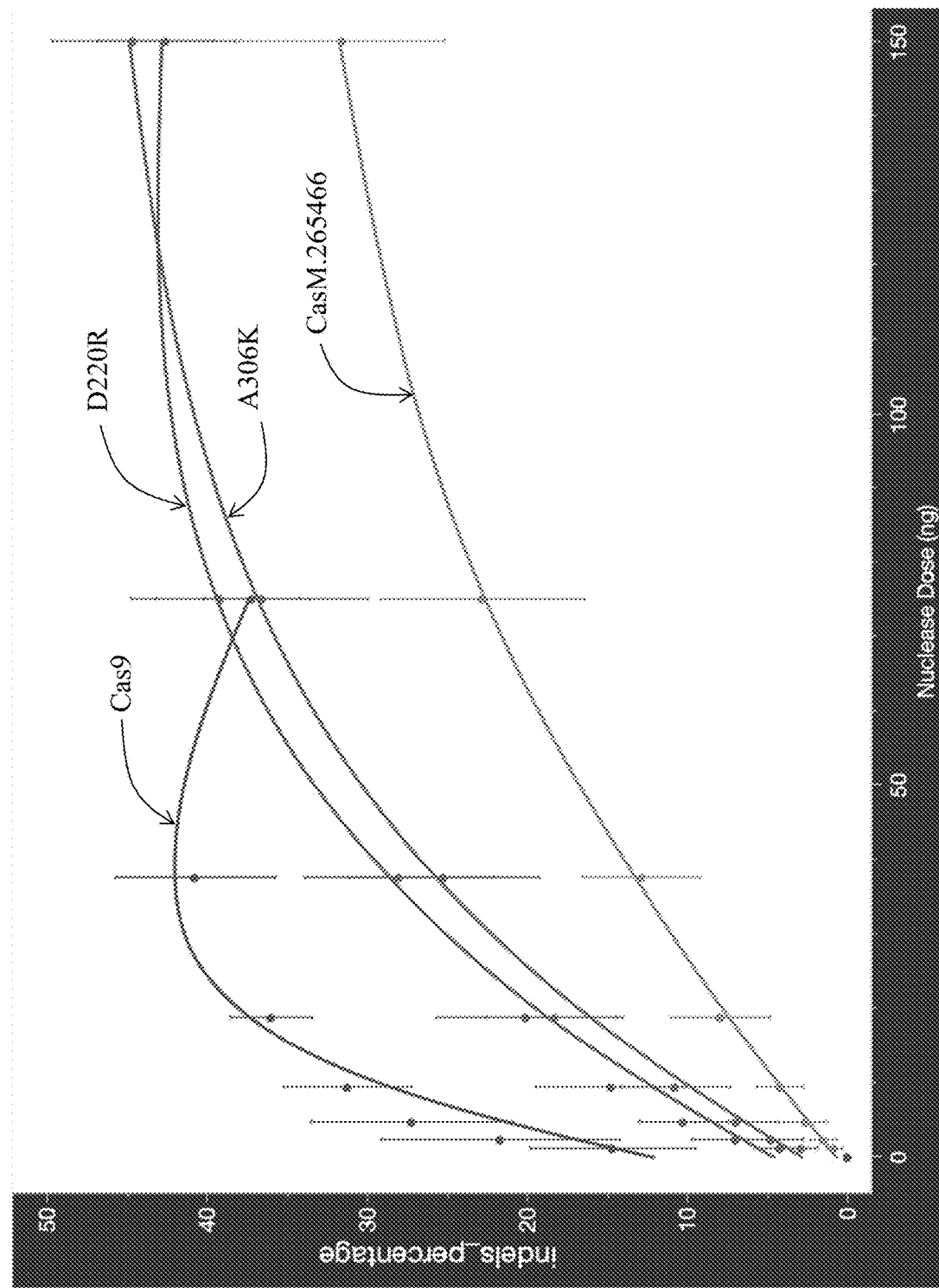
FIG. 36 shows % indel generated at various dose (ng) for D220R and A306K variants relative to CasM.265466 and Cas9 effector proteins.

The percentage of target nucleic acids exhibiting nucleotide insertion(s)/deletion(s) (% indel), indicative of nuclease activity, was assessed with next generation sequencing (NGS). As shown in FIG. 36, D220R and A306K were able to generate higher indel percentage relative to the corresponding wildtype CasM.265466 protein.

Example 41: Rational Engineering of CasM. 265466 Variants

Figure 37:
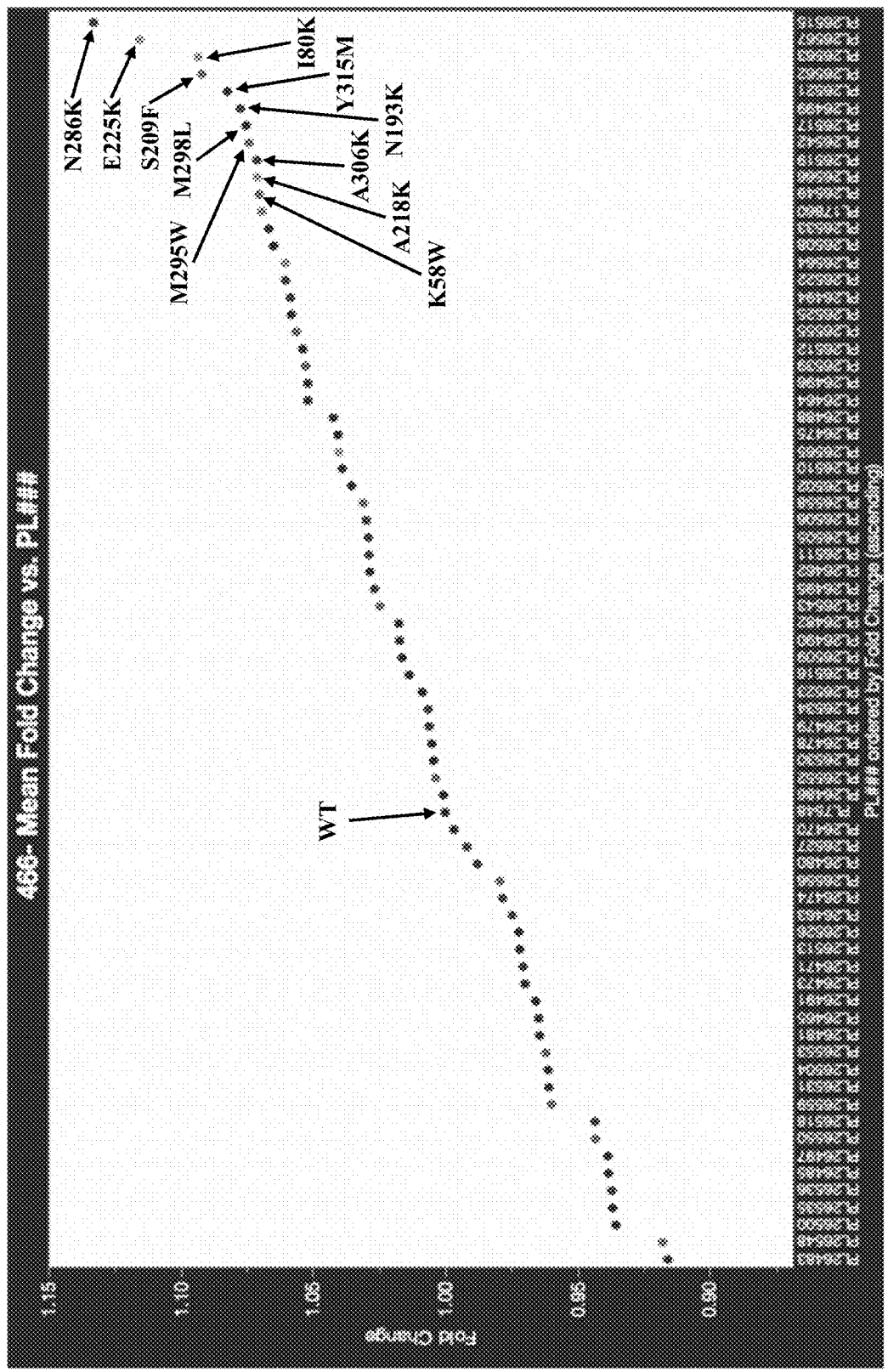
FIG. 37 shows the activity of the engineered variants relative to that of wildtype as fold change.

CasM.265466 protein and engineered variants thereof were tested for their ability to produce indels in a mammalian cell line (e.g., HEK293T cells). Briefly, a plasmid encoding the effector proteins and a guide RNA were delivered by lipofection to the mammalian cells. This was performed with guide RNA (SEQ ID NO: 52) targeting loci adjacent to a PAM of TNTR. Indels in the loci were detected by next generation sequencing of PCR amplicons at the targeted loci and % indel was calculated as the fraction of sequencing reads containing insertions or deletions relative to an unedited reference sequence. FIG. 37 shows the activity of the engineered variants relative to that of wildtype as fold change. TABLE 44 lists CasM.265466 variants that demonstrated increased indel production relative to wildtype CasM.265466 (starting with highest fold change at graph to the left).

TABLE 44

Indel Producing Variants of SEQ ID NO: 1

| PL##### | Amino Acid Substitution Relative to SEQ ID NO: 1 |
|---|---|
| PL26515 | N286K |
| PL26567 | E225K |
| PL26563 | I80K |
| PL26562 | S209F |

TABLE 44-continued

Indel Producing Variants of SEQ ID NO: 1

| PL##### | Amino Acid Substitution Relative to SEQ ID NO: 1 |
|---|---|
| PL26521 | Y315M |
| PL26499 | N193K |
| PL26517 | M298L |
| PL26542 | M295W |
| PL26519 | A306K |
| PL26566 | A218K |
| PL26549 | K58W |

Example 42: Indel Activity of CasM.265466 Fusion Protein

This experiment tested the ability of CasM.265466 to function with a guide nucleic acid (SEQ ID NO: 869) modified to have an MS2 aptamer sequence (ACAUGAGGAUCACCCAUGU (SEQ ID NO: 959)) inserted into the sgRNA sequence. The MS2 aptamer sequence is located 5' or 3' to the spacer sequence. Exonuclease sbcB was fused to an MCP domain that is capable of binding the MS2 aptamer. TABLE 45 lists exemplary modified sgRNA sequences that were tested.

TABLE 45

Aptamer modified sgRNA sequences

| Description | SEQ ID NO | Sequence | Mean (% indels) | Std Dev (% indels) |
|---|---|---|---|---|
| 5-prime--MS2--nolinker--vbbPL7548 | 960 | ACAUGAGGAUCACCCAUGUACAGCUUAUUUGGAAGCUGAAAUGUGAGGUUUAUAACACUCACAAGAAUCCUGAAAAAGGAUGCCAAACACCAAAAAAUAUACGCUAUA | 48.37 | 2.32 |
| 5-prime--MS2-2 bp-linker--vbbPL7548 | 961 | GCACAUGAGGAUCACCCAUGUGCACAGCUUAUUUGGAAGCUGAAAUGUGAGGUUUAUAACACUCACAAGAAUCCUGAAAAAGGAUGCCAAACACCAAAAAAUAUACGCUAUA | 45.82 | 0.36 |
| 5-prime--MS2-5 bp-linker--vbbPL7548 | 962 | GCAGCACAUGAGGAUCACCCAUGUGCUGCACAGCUUAUUUGGAAGCUGAAAUGUGAGGUUUAUAACACUCACAAGAAUCCUGAAAAAGGAUGCCAAACACCAAAAAAUAUACGCUAUA | 41.85 | 3.93 |
| 5-prime--MS2-10 bp-linker--vbbPL7548 | 963 | CGCUAUACGCACAUGAGGAUCACCCAUGUGCGUAUAGCGACAGCUUAUUUGGAAGCUGAAAUGUGAGGUUUAUAACACUCACAAGAAUCCUGAAAAAGGAUGCCAAACACCAAAAAAUAUACGCUAUA | 36.92 | 2.86 |
| 5-prime--MS2-2 bp-2 nt-linker--vbbPL7548 | 964 | GCACAUGAGGAUCACCCAUGUGCAAACAGCUUAUUUGGAAGCUGAAAUGUGAGGUUUAUAACACUCACAAGAAUCCUGAAAAAGGAUGCCAAACACCAAAAAAUAUACGCUAUA | 48.06 | 5.21 |
| 5-prime--MS2-2 bp-5 nt-linker--vbbPL7548 | 965 | GCACAUGAGGAUCACCCAUGUGCAAAAACAGCUUAUUUGGAAGCUGAAAUGUGAGGUUUAUAACACUCACAAGAAUCCUGAAAAAGGAUGCCAAACACCAAAAAAUAUACGCUAUA | 43.22 | 1.66 |

TABLE 45-continued

Aptamer modified sgRNA sequences

| Description | SEQ ID NO | Sequence | Mean (% indels) | Std Dev (% indels) |
|---|---|---|---|---|
| 5-prime--MS2-2 bp-10 nt-linker--vbbPL7548 | 966 | GCACAUGAGGAUCACCCAUGUGCAAAAAAAAAACAGCUUAUUUGGAAGCUGAAAUGUGAGGUUUAUAACACUCACAAGAAUCCUGAAAAAGGAUGCCAAACACCAAAAAAUAUACGCUAUA | 42.42 | 1.80 |
| 5-prime--MS2-2 nt-linker--vbbPL7548 | 967 | ACAUGAGGAUCACCCAUGUAAACAGCUUAUUUGGAAGCUGAAAUGUGAGGUUUAUAACACUCACAAGAAUCCUGAAAAAGGAUGCCAAACACCAAAAAAUAUACGCUAUA | 47.83 | 2.92 |
| 5-prime--MS2-5 nt-linker--vbbPL7548 | 968 | ACAUGAGGAUCACCCAUGUAAAAAACAGCUUAUUUGGAAGCUGAAAUGUGAGGUUUAUAACACUCACAAGAAUCCUGAAAAAGGAUGCCAAACACCAAAAAAUAUACGCUAUA | 40.99 | 1.05 |
| 5-prime--MS2-10 nt-linker--vbbPL7548 | 969 | ACAUGAGGAUCACCCAUGUAAAAAAAAAACAGCUUAUUUGGAAGCUGAAAUGUGAGGUUUAUAACACUCACAAGAAUCCUGAAAAAGGAUGCCAAACACCAAAAAAUAUACGCUAUA | 42.61 | 3.13 |
| Stem2--MS2-nolinker-nobubble--vbbPL7548 | 970 | ACAGCUUAUUUGGAAGCUGAAAUGUGAGGUUACAUGAGGAUCACCCAUGUAACACUCACAAGAAUCCUGAAAAAGGAUGCCAAACACCAAAAAAUAUACGCUAUA | 31.48 | 2.40 |
| Stem2--MS2-nolinker-Midbubble--vbbPL7548 | 971 | ACAGCUUAUUUGGAAGCUGAAAUGUGAGGUUUAACAUGAGGAUCACCCAUGUAUAACACUCACAAGAAUCCUGAAAAAGGAUGCCAAACACCAAAAAAUAUACGCUAUA | 33.55 | 1.80 |
| Stem2--MS2-2 bp-linker-nobubble--vbbPL7548 | 972 | ACAGCUUAUUUGGAAGCUGAAAUGUGAGGUUGCACAUGAGGAUCACCCAUGUGCAACACUCACAAGAAUCCUGAAAAAGGAUGCCAAACACCAAAAAAUAUACGCUAUA | 30.11 | 1.94 |
| Stem2--MS2-5 bp-linker-nobubble--vbbPL7548 | 973 | ACAGCUUAUUUGGAAGCUGAAAUGUGAGGUUGCAGCACAUGAGGAUCACCCAUGUGCUGCAACACUCACAAGAAUCCUGAAAAAGGAUGCCAAACACCAAAAAAUAUACGCUAUA | 25.13 | 1.58 |
| Stem2--MS2-10 bp-linker-nobubble--vbbPL7548 | 974 | ACAGCUUAUUUGGAAGCUGAAAUGUGAGGUUCGCUAUACGCACAUGAGGAUCACCCAUGUGCGUAUAGCGAACACUCACAAGAAUCCUGAAAAGGAUGCCAAACACCAAAAAAUAUACGCUAUA | 20.58 | 1.17 |
| Stem2--MS2-2 bp-linker-MidBubble--vbbPL7548 | 975 | ACAGCUUAUUUGGAAGCUGAAAUGUGAGGUUUAGCACAUGAGGAUCACCCAUGUGCAUAACACUCACAAGAAUCCUGAAAAAGGAUGCCAAACACCAAAAAAUAUACGCUAUA | 32.94 | 2.70 |
| Stem2--MS2-5 bp-linker-MidBubble--vbbPL7548 | 976 | ACAGCUUAUUUGGAAGCUGAAAUGUGAGGUUUAGCAGCACAUGAGGAUCACCCAUGUGCUGCAUAACACUCACAAGAAUCCUGAAAAAGGAUGCCAAACACCAAAAAAUAUACGCUAUA | 30.15 | 1.21 |

TABLE 45-continued

Aptamer modified sgRNA sequences

| Description | SEQ ID NO | Sequence | Mean (% indels) | Std Dev (% indels) |
|---|---|---|---|---|
| Stem2--MS2-10 bp-linker-MidBubble--vbbPL7548 | 977 | ACAGCUUAUUUGGAAGCUGAAAUGUGAGGUUUACGCUAUACGCACAUGGGAUCACCCAUGUGCGUAUAGCGAUAACACUCACAAGAAUCCUGAAAAAGGAUGCCAAACACCAAAAAAUAUACGCUAUA | 25.79 | 2.00 |
| Stem2--MS2-2 bp-linker-MidBubble-T31G-A36C--vbbPL7548 | 978 | ACAGCUUAUUUGGAAGCUGAAAUGUGAGGUGUAGCACAUGAGGAUCACCCAUGUGCAUCACACUCACAAGAAUCCUGAAAAAGGAUGCCAAACACCAAAAAAUAUACGCUAUA | 34.59 | 4.69 |
| Stem2--MS2-2 bp-linker-MidBubble-T31G-A36C-T32A-T34A--vbbPL7548 | 979 | ACAGCUUAUUUGGAAGCUGAAAUGUGAGGUGAAGCACAUGAGGAUCACCCAUGUGCAACACACUCACAAGAAUCCUGAAAAAGGAUGCCAAACACCAAAAAAUAUACGCUAUA | 29.25 | 5.52 |
| Stem3--MS2-nolinker-withT--vbbPL7548 | 980 | ACAGCUUAUUUGGAAGCUGAAAUGUGAGGUUUAUAACACUCACAAGAAUCCUUACAUGAGGAUCACCCAUGUAAGGAUGCCAAACACCAAAAAAUAUACGCUAUA | 36.56 | 1.55 |
| Stem3--MS2-nolinker-Midbubble--vbbPL7548 | 981 | ACAGCUUAUUUGGAAGCUGAAAUGUGAGGUUUAUAACACUCACAAGAAUCCUAAACAUGAGGAUCACCCAUGUAAAGGAUGCCAAACACCAAAAAAUAUACGCUAUA | 37.02 | 3.01 |
| Stem3--MS2-2 bp-linker-nobubble-withT--vbbPL7548 | 982 | ACAGCUUAUUUGGAAGCUGAAAUGUGAGGUUUAUAACACUCACAAGAAUCCUUGCACAUGAGGAUCACCCAUGUGCAAGGAUGCCAAACACCAAAAAAUAUACGCUAUA | 32.80 | 2.22 |
| Stem3--MS2-5 bp-linker-nobubble-withT--vbbPL7548 | 983 | ACAGCUUAUUUGGAAGCUGAAAUGUGAGGUUUAUAACACUCACAAGAAUCCUUGCAGCACAUGAGGAUCACCCAUGUGCUGCAAGGAUGCCAAACACCAAAAAAUAUACGCUAUA | 32.06 | 1.95 |
| Stem3--MS2-10 bp-linker-nobubble-withT--vbbPL7548 | 984 | ACAGCUUAUUUGGAAGCUGAAAUGUGAGGUUUAUAACACUCACAAGAAUCCUUCGCUAUACGCACAUGAGGAUCACCCAUGUGCGUAUAGCGAGGAUGCCAAACACCAAAAAAUAUACGCUAUA | 29.01 | 2.92 |
| Stem3--MS2-2 bp-linker-nobubble-woT--vbbPL7548 | 985 | ACAGCUUAUUUGGAAGCUGAAAUGUGAGGUUUAUAACACUCACAAGAAUCCUGCACAUGAGGAUCACCCAUGUGCAAGGAUGCCAAACACCAAAAAAUAUACGCUAUA | 35.86 | 1.32 |
| Stem3--MS2-5 bp-linker-nobubble-woT--vbbPL7548 | 986 | ACAGCUUAUUUGGAAGCUGAAAUGUGAGGUUUAUAACACUCACAAGAAUCCUGCAGCACAUGAGGAUCACCCAUGUGCUGCAAGGAUGCCAAACACCAAAAAAUAUACGCUAUA | 34.51 | 1.37 |
| Stem3--MS2-5 bp-linker-MidBubble--vbbPL7548 | 987 | ACAGCUUAUUUGGAAGCUGAAAUGUGAGGUUUAUAACACUCACAAGAAUCCUAAGCAGCACAUGAGGAUCACCCAUGUGCUGCAAAGGAUGCCAAACACCAAAAAAUAUACGCUAUA | 32.95 | 3.49 |

TABLE 45-continued

Aptamer modified sgRNA sequences

| Description | SEQ ID NO | Sequence | Mean (% indels) | Std Dev (% indels) |
|---|---|---|---|---|
| Stem3--MS2-10 bp-linker-MidBubble--vbbPL7548 | 988 | ACAGCUUAUUUGGAAGCUGAAAUGUGAGGUUUAUAACACUCACAAGAAUCCUAACGCUAUACGCACAUGAGGAUCACCCAUGUGCGUAUAGCGAAAGGAUGCCAAACACCAAAAAAUAUACGCUAUA | 25.25 | 2.09 |
| Stem3--17 ntRpt-MS2-nobubble--vbbPL7548 | 989 | ACAGCUUAUUUGGAAGCUGAAAUGUGAGGUUUAUAACACUCACAAGAAUCCUUGUAAACAUGAGGAUCACCCAUGUUUACAAGGAUGCCAAACACCAAAAAAUAUACGCUAUA | 25.69 | 2.60 |
| Stem3--17 ntRpt-MS2-Midbubble--vbbPL7548 | 990 | ACAGCUUAUUUGGAAGCUGAAAUGUGAGGUUUAUAACACUCACAAGAAUCCUUGUAAAACAUGAGGAUCACCCAUGUAAUUACAAGGAUGCCAAACACCAAAAAAUAUACGCUAUA | 34.02 | 1.74 |
| Stem3--15 ntRpt-MS2-nobubble--vbbPL7548 | 991 | ACAGCUUAUUUGGAAGCUGAAAUGUGAGGUUUAUAACACUCACAAGAAUCCUUGUACAUGAGGAUCACCCAUGUACAAGGAUGCCAAACACCAAAAAUAUACGCUAUA | 35.78 | 0.92 |
| Stem3--15 ntRpt-MS2-Midbubble--vbbPL7548 | 992 | ACAGCUUAUUUGGAAGCUGAAAUGUGAGGUUUAUAACACUCACAAGAAUCCUUGUAAACAUGAGGAUCACCCAUGUAAACAAGGAUGCCAAACACCAAAAAAUAUACGCUAUA | 36.38 | 4.09 |
| 3prime--MS2-nolinker--vbbPL7548 | 993 | ACAGCUUAUUUGGAAGCUGAAAUGUGAGGUUUAUAACACUCACAAGAAUCCUGAAAAGGAUGCCAAACACCAAAAAAUAUACGCUAUAACAUGAGGAUCACCCAUGU | 35.67 | 3.25 |
| 3prime--MS2-3 nt-2 bp-linker--vbbPL7548 | 994 | ACAGCUUAUUUGGAAGCUGAAAUGUGAGGUUUAUAACACUCACAAGAAUCCUGAAAAGGAUGCCAAACACCAAAAAAUAUACGCUAUAAAAGCACAUGAGGAUCACCCAUGUGC | 16.21 | 1.57 |
| 3prime--MS2-6 nt-2 bp-linker--vbbPL7548 | 995 | ACAGCUUAUUUGGAAGCUGAAAUGUGAGGUUUAUAACACUCACAAGAAUCCUGAAAAGGAUGCCAAACACCAAAAAAUAUACGCUAUAAAAAAAGCACAUGAGGAUCACCCAUGUGC | 34.21 | 3.31 |
| 3prime--MS2-10 nt-2 bp-linker--vbbPL7548 | 996 | ACAGCUUAUUUGGAAGCUGAAAUGUGAGGUUUAUAACACUCACAAGAAUCCUGAAAAGGAUGCCAAACACCAAAAAAUAUACGCUAUAAAAAAAAAAGCACAUGAGGAUCACCCAUGUGC | 40.87 | 2.94 |
| 3prime--MS2-5 nt-5 bp-linker--vbbPL7548 | 997 | ACAGCUUAUUUGGAAGCUGAAAUGUGAGGUUUAUAACACUCACAAGAAUCCUGAAAAGGAUGCCAAACACCAAAAAAUAUACGCUAUAAAAAAGCAGCACAUGAGGAUCACCCAUGUGCUGC | 28.39 | 1.77 |
| Stem0--MS2-nolinker-nobubble--vbbPL7548 | 998 | UAUAUUUACAUGAGGAUCACCCAUGUAAAUAUACAGCUUAUUUGGAAGCUGAAAUGUGAGGUUUAUAACACUCACAAGAAUCCUGAAAAGGAUGCCAAACACCAAAAAAUAUACGCUAUA | 46.94 | 1.30 |

TABLE 45-continued

Aptamer modified sgRNA sequences

| Description | SEQ ID NO | Sequence | Mean (% indels) | Std Dev (% indels) |
|---|---|---|---|---|
| Stem0--MS2-nolinker-Midbubble--vbbPL7548 | 999 | UAUAUUUGAACAUGAGGAUCACC CAUGUAAAAAUAUACAGCUUAUU UGGAAGCUGAAAUGUGAGGUUUA UAACACUCACAAGAAUCCUGAAA AAGGAUGCCAAACACCAAAAAAU AUACGCUAUA | 34.76 | 2.31 |
| Stem0--MS2-2 bp-linker-nobubble--vbbPL7548 | 1000 | UAUAUUUGCACAUGAGGAUCACC CAUGUGCAAAUAUACAGCUUAUU UGGAAGCUGAAAUGUGAGGUUUA UAACACUCACAAGAAUCCUGAAA AAGGAUGCCAAACACCAAAAAAU AUACGCUAUA | 34.27 | 1.71 |
| Stem0--MS2-5 bp-linker-nobubble--vbbPL7548 | 1001 | UAUAUUUGCAGCACAUGAGGAUC ACCCAUGUGCUGCAAAUAUACAGC UUAUUUGGAAGCUGAAAUGUGAG GUUUAUAACACUCACAAGAAUCC UGAAAAGGAUGCCAAACACCAA AAAAUAUACGCUAUA | 33.91 | 2.95 |
| Stem0--MS2-10 bp-linker-nobubble--vbbPL7548 | 1002 | UAUAUUUCGCUAUACGCACAUGA GGAUCACCCAUGUGCGUAUAGCG AAAUAUACAGCUUAUUUGGAAGC UGAAAUGUGAGGUUUAUAACACU CACAAGAAUCCUGAAAAGGAUG CCAAACACCAAAAAAUAUACGCUA UA | 34.02 | 3.36 |
| Stem0--MS2-2 bp-linker-MidBubble--vbbPL7548 | 1003 | UAUAUUUGAGCACAUGAGGAUCA CCCAUGUGCAAAAAUAUACAGCU UAUUUGGAAGCUGAAAUGUGAGG UUUAUAACACUCACAAGAAUCCU GAAAAAGGAUGCCAAACACCAAA AAAUAUACGCUAUA | 35.85 | 2.44 |
| Stem0--MS2-5 bp-linker-MidBubble--vbbPL7548 | 1004 | UAUAUUUGAGCAGCACAUGAGGA UCACCCAUGUGCUGCAAAAAUAU ACAGCUUAUUUGGAAGCUGAAAU GUGAGGUUUAUAACACUCACAAG AAUCCUGAAAAGGAUGCCAAAC ACCAAAAAAUAUACGCUAUA | 26.81 | 1.96 |
| Stem0--MS2-10 bp-linker-MidBubble--vbbPL7548 | 1005 | UAUAUUUGACGCUAUACGCACAU GAGGAUCACCCAUGUGCGUAUAG CGAAAAAUAUACAGCUUAUUUGG AAGCUGAAAUGUGAGGUUUAUAA CACUCACAAGAAUCCUGAAAAAG GAUGCCAAACACCAAAAAAUAUA CGCUAUA | 33.19 | 1.98 |
| NegControl--Original-sgRNA-control--vbbPL7548 | 1006 | ACAGCUUAUUUGGAAGCUGAAAU GUGAGGUUUAUAACACUCACAAG AAUCCUGAAAAGGAUGCCAAAC ACCAAAAAAUAUACGCUAUA | 47.16 | 2.75 |
| NegControl--Original-sgRNAwithT-control--vbbPL7548 | 1007 | ACAGCUUAUUUGGAAGCUGAAAU GUGAGGUUUAUAACACUCACAAG AAUCCUGAAAAGGAUGCCAAA CACCAAAAAAUAUACGCUAUA | 44.99 | 2.61 |
| NegControl--Stem0-sgRNA-control--vbbPL7548 | 1008 | UAUAUUUGAUAAAAAUAUACAGC UUAUUUGGAAGCUGAAAUGUGAG GUUUAUAACACUCACAAGAAUCC UGAAAAGGAUGCCAAACACCAA AAAAUAUACGCUAUA | 32.03 | 2.53 |
| NegControl--Stem0-sgRNAwithT-control--vbbPL7548 | 1009 | UAUAUUUGAUAAAAAUAUACAGC UUAUUUGGAAGCUGAAAUGUGAG GUUUAUAACACUCACAAGAAUCC UUGAAAAGGAUGCCAAACACCA AAAAAUAUACGCUAUA | 31.59 | 2.62 |

TABLE 45-continued

Aptamer modified sgRNA sequences

| Description | SEQ ID NO | Sequence | Mean (% indels) | Std Dev (% indels) |
|---|---|---|---|---|
| NegControl--5-prime-RandomStem--vbbPL7548 | 1010 | GCGCGAGGAUCACCCGCGCACAGCUUAUUUGGAAGCUGAAAUGUGAGGUUUAUAACACUCACAAGAAUCCUGAAAAAGGAUGCCAAACACCAAAAAAUAUACGCUAUA | 47.03 | 2.63 |
| NegControl--Stem2-RandomStem--vbbPL7548 | 1011 | ACAGCUUAUUUGGAAGCUGAAAUGUGAGGUUUAGCGCGAGGAUCACCCGCGCAUAACACUCACAAGAAUCCUGAAAAAGGAUGCCAAACACCAAAAAAUAUACGCUAUA | 26.26 | 1.28 |
| NegControl--Stem3-RandomStem--vbbPL7548 | 1012 | ACAGCUUAUUUGGAAGCUGAAAUGUGAGGUUUAUAACACUCACAAGAAUCCUUGCGCGAGGAUCACCCGCGCAAGGAUGCCAAACACCAAAAAAUAUACGCUAUA | 34.94 | 1.89 |
| NegControl--3prime-RandomStem--vbbPL7548 | 1013 | ACAGCUUAUUUGGAAGCUGAAAUGUGAGGUUUAUAACACUCACAAGAAUCCUGAAAAAGGAUGCCAAACACCAAAAAAUAUACGCUAUAAAAGCGCGAGGAUCACCCGCGC | 22.38 | 1.47 |
| NegControl--Stem0-RandomStem--vbbPL7548 | 1014 | UAUAUUUGAGCGCGAGGAUCACCCGCGCAAAAAUAUACAGCUUAUUUGGAAGCUGAAAUGUGAGGUUUAUAACACUCACAAGAAUCCUGAAAAAGGAUGCCAAACACCAAAAAAUAUACGCUAUA | 37.61 | 1.52 |
| PosControl--Archive-5primeMS2--vbbPL7548 | 1015 | GGACAUGAGGAUCACCCAUGUCCGAACAGCUUAUUUGGAAGCUGAAAUGUGAGGUUUAUAACACUCACAAGAAUCCUGAAAAAGGAUGCCAAACACCAAAAAAUAUACGCUAUA | 49.63 | 2.76 |
| PosControl--Archive-stem2MS2--vbbPL7548 | 1016 | ACAGCUUAUUUGGAAGCUGAAAUGUGAGGUUUGGACAUGAGGAUCACCCAUGUCCAAACACUCACAAGAAUCCUGAAAAAGGAUGCCAAACACCAAAAAAUAUACGCUAUA | 29.47 | 2.17 |
| PosControl--Archive-stem3MS2--vbbPL7548 | 1017 | ACAGCUUAUUUGGAAGCUGAAAUGUGAGGUUUAUAACACUCACAAGAAUCCUGGACAUGAGGAUCACCCAUGUCCAAGGAUGCCAAACACCAAAAAAUAUACGCUAUA | 36.06 | 0.71 |
| PosControl--Archive-3primeMS2--vbbPL7548 | 1018 | ACAGCUUAUUUGGAAGCUGAAAUGUGAGGUUUAUAACACUCACAAGAAUCCUGAAAAAGGAUGCCAAACACCAAAAAAUAUACGCUAUAGGACAUGAGGAUCACCCAUGUCC | 24.59 | 1.99 |

Observance of indels indicated that CasM.265466 was able to function with the modified guide nucleic acid in the presence of an MCP-sbcB fusion protein. Interestingly, fusion of exonuclease sbcB to CasM.265466 significantly decreased indel window size in HEK293T cells.

The result of this experiment indicates that a guide nucleic acid with an aptamer can be useful for recruiting other proteins besides exonucleases, e.g., proteins for precision editing such as deaminases and reverse transcriptases.

Example 43: Cis Cleavage Assay for CasM.265466 Variants

Cell lysates from cells expressing CasM.265466 and variants thereof, and guide RNAs were added to an IVE reaction mix. PAM screening reactions used 10 µl of RNP in 100 µl reactions with 1,000 ng of a 5' PAM library in 1× Cutsmart buffer and were carried out for 15 minutes at 25° C., 45 minutes at 37° C. and 15 minutes at 45° C. Reactions were terminated with 1 µl of proteinase K and 5 µl of 500 mM EDTA for 30 minutes at 37° C. TABLE 46 lists exemplary modified sgRNA sequences that were tested.

TABLE 46

Effector Protein and sgRNA Sequences

| Protein | sgRNA |
|---|---|
| 2390405 (SEQ ID NO: 909) | *UGGGGCAGUUGGUUGCCCUUAGCCUGAGGCAUUUAUUGCACUCGGG AAGUACCA*GAAA*UGGUACAUCCAAC*UAUUAAAUACUCGUAUUGCU (SEQ ID NO: 1019) |
| 2391641 (SEQ ID NO: 906) | *AGGGCGUGUUGGAGCGCCUUAGUUUGAGGUAUCAAGCACUCAAAAA AUCUAC*GAAA*GUGGAUAUCCAAC*UAUUAAAUACUCGUAUUGCU (SEQ ID NO: 1020) |
| 2390217 (SEQ ID NO: 919) | *ACGGGUGGUUGUACACCCGAAGAGUGAGGUCUUAACGGGCACUCGC UAAUCUGAU*GAAA*AGCAGAAUACAAC*UAUUAAAUACUCGUAUUGCU (SEQ ID NO: 1021) |
| 2390160 (SEQ ID NO: 910) | *UGGGCGCGUUGGAGCGCCUUGGUUCGAGGUUCCCUGCACUCGAAA AAUUCAC*GAAA*GUGAAUAUCCAAC*UAUUAAAUACUCGUAUUGCU (SEQ ID NO: 1022) |
| 2391980 (SEQ ID NO: 913) | *UGGGCGUGUUGGAACGCCUUAGUUUGAGGUUUCAAGCACUCAAAAA AUUCAC*GAAA*GUGGAUAUCCAAC*UAUUAAAUACUCGUAUUGCU (SEQ ID NO: 1023) |
| 2390639 (SEQ ID NO: 921) | *CGGGGUGGUUGGACACCCUUAAAUUGAGGUUCAUCGCACUCGAUAA AUACCA*GAAA*AGGUAUAUCCAAC*UAUUAAAUACUCGUAUUGCU (SEQ ID NO: 1024) |
| 2390685 (SEQ ID NO: 922) | *GGGGCUGGUUGUACAGCCUGAAGUUGAGGGAUGAUUCCACUCGACA AAUUGCU*GAAA*AGCAAUAUACAAC*UAUUAAAUACUCGUAUUGCU (SEQ ID NO: 1025) |
| 2391272 (SEQ ID NO: 918) | *CGGGCUGGUUGGACAGCCUUAAACUGAGGUUUAACGCACUCGGUAA AUACCC*GAAA*AGGUAUAUCCAAC*UAUUAAAUACUCGUAUUGCU (SEQ ID NO: 1026) |

Note:
In italics is a handle sequence without a linker or repeat sequence, in bold is a linker, underlined is a repeat sequence, and no formatting is a spacer sequence.

Next generation sequencing was performed on cut sequences to identify enriched PAM sequences for the effector proteins. Results are summarized in FIGS. 38A-38H. Cis cleavage by each complex was confirmed by gel electrophoresis.

Example 44: Cis Cleavage Assay for CasM.265466 Variants

Figure 39:
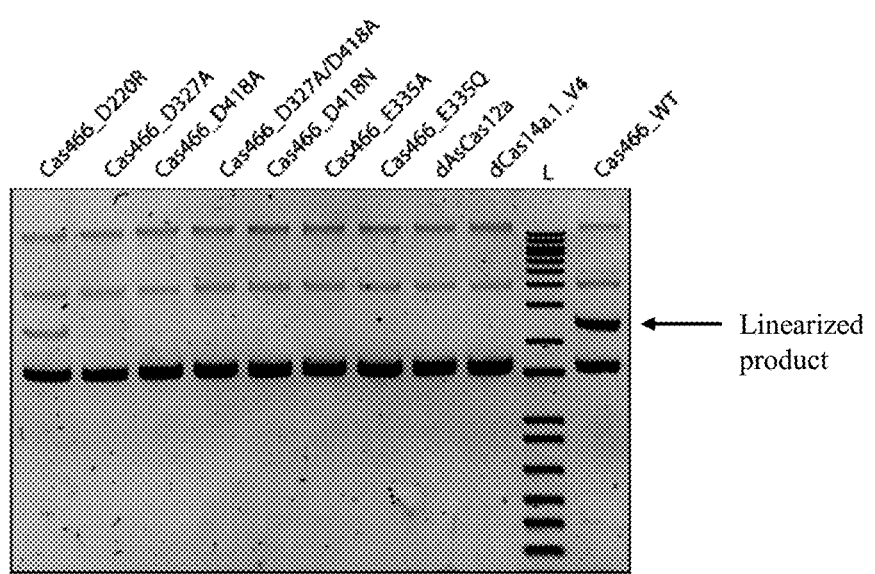
FIG. 39 shows gel electrophoresis analysis of cis cleavage activity by CasM.265466 protein and variants thereof.

This experiment was performed to determine if variants of CasM.265466 can perform cis cleavage. Briefly, effector protein, CasM.265466, was mutated to generate nuclease dead variants using the following substitutions: D237A, D237A & D418A, D418A, D418N, E335A, and E335Q. The variants were then complexed with sgRNA (SEQ ID NO: 27) for 20 minutes at room temperature. The complexes were added to an IVE reaction mix. Cis cleavage assay was carried out with 5 µl of RNP for at least 30 minutes at 37° C. for identifying catalytically dead variants. A plasmid containing TTTG PAM was used as target nucleotide. Wild-type CasM.265466 (Cas466 WT); CasM.265466 variant D220R (Cas466_D220R); dAsCas12a and Cas14a1_D326A/D510A (dCas14a.1) were included as controls. Cis cleavage by each complex was assessed by gel electrophoresis. The results are shown in FIG. 39. An absence of a linearized product indicates a lack of cleavage activity.

Example 45: Binding Affinity of CasM.265466 Variants

Figure 40:
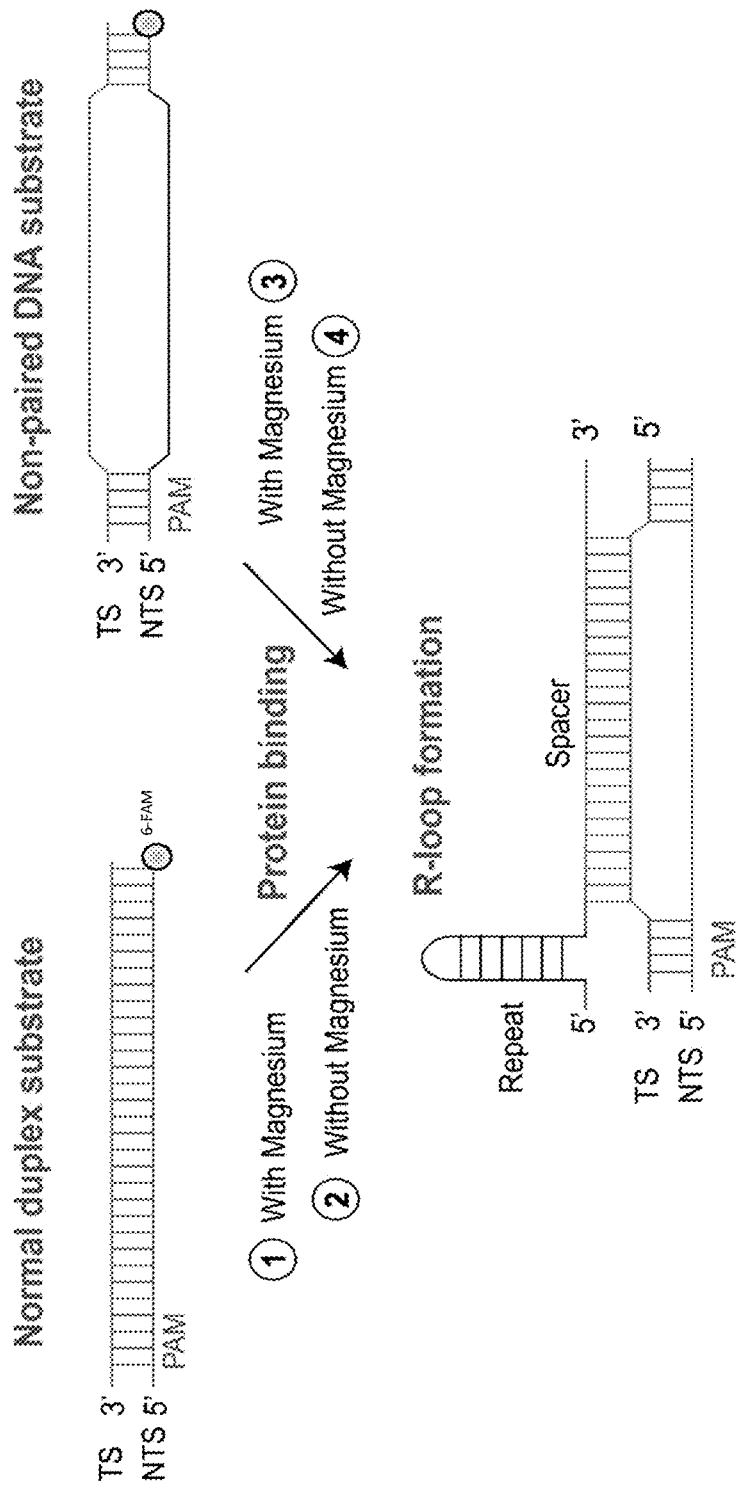
FIG. 40 shows schematics of a fluorescence polarization assay using a duplex substrate and anon-paired DNA substrate.

Fluorescence polarization assays were performed to assess the DNA binding affinity of the RNP complexes comprising CasM.265466 variants and sgRNA (SEQ ID NO: 27) generated in Example 44. Reactions were carried out in both the absence and presence of magnesium, the latter to liken the reaction to cellular conditions. Two different DNA substrates were tested with and without magnesium: double stranded duplex DNA ("normal duplex substrate") and non-paired DNA substrate. These conditions are represented in FIG. 40. Without being bound by theory, non-paired DNA substrate may help mimic an R loop making it easier for an RNP to bind linear DNA. The assay generates different kinds of emissions depending on whether or not a RNP:DNA complex is formed. In the absence of a complex, emissions are depolarized emissions. In the presence of a complex, there are polarized emissions.

The RNP complexes were serially diluted ranging from 500 nM-0.5 nM. Reactions were carried out with the fluorescence polarization assay buffer (20 mM HEPES pH 7.5, 0.2 mg/mL BSA, 1 mM TCEP, 100 mM NaCl, with or without 5 mM Magnesium acetate/EDTA). A 60 bp linear DNA labelled with 6-FAM at the 3' end was used at a concentration of 1 nM for all experiments. DNA only wells and buffer only wells served as controls. The reactions were carried out in black 384-well flat bottom plates and incubated at 37° C. for 30 minutes and read using the Biotek-Synergy H2 plate reader using the fluorescence polarization filter. The reads were adjusted to extended gain and the well height was calibrated before each run. The graphs were interpreted on PRISM using a combination of their $K_D$ values and the maximum polarization value that was recorded at saturating concentrations—referred to as the plateau values.

Figure 41:
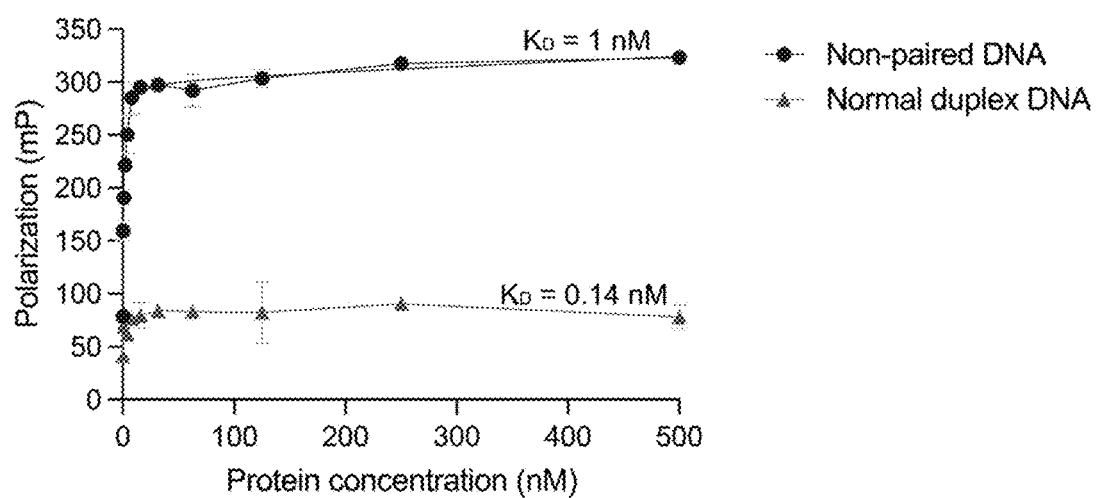
FIG. 41 shows binding affinity curves for the wildtype CasM.265466 protein with non-paired DNA and normal duplex DNA.

FIG. 41 shows results of the fluorescence polarization assay for the RNP comprising wildtype CasM.265466 with non-paired DNA and normal duplex DNA. Apparent $K_D$ value of the RNP comprising wildtype CasM.265466 for non-paired DNA and normal duplex DNA were calculated and are also shown on FIG. 41.

Figures 42A, 42B:
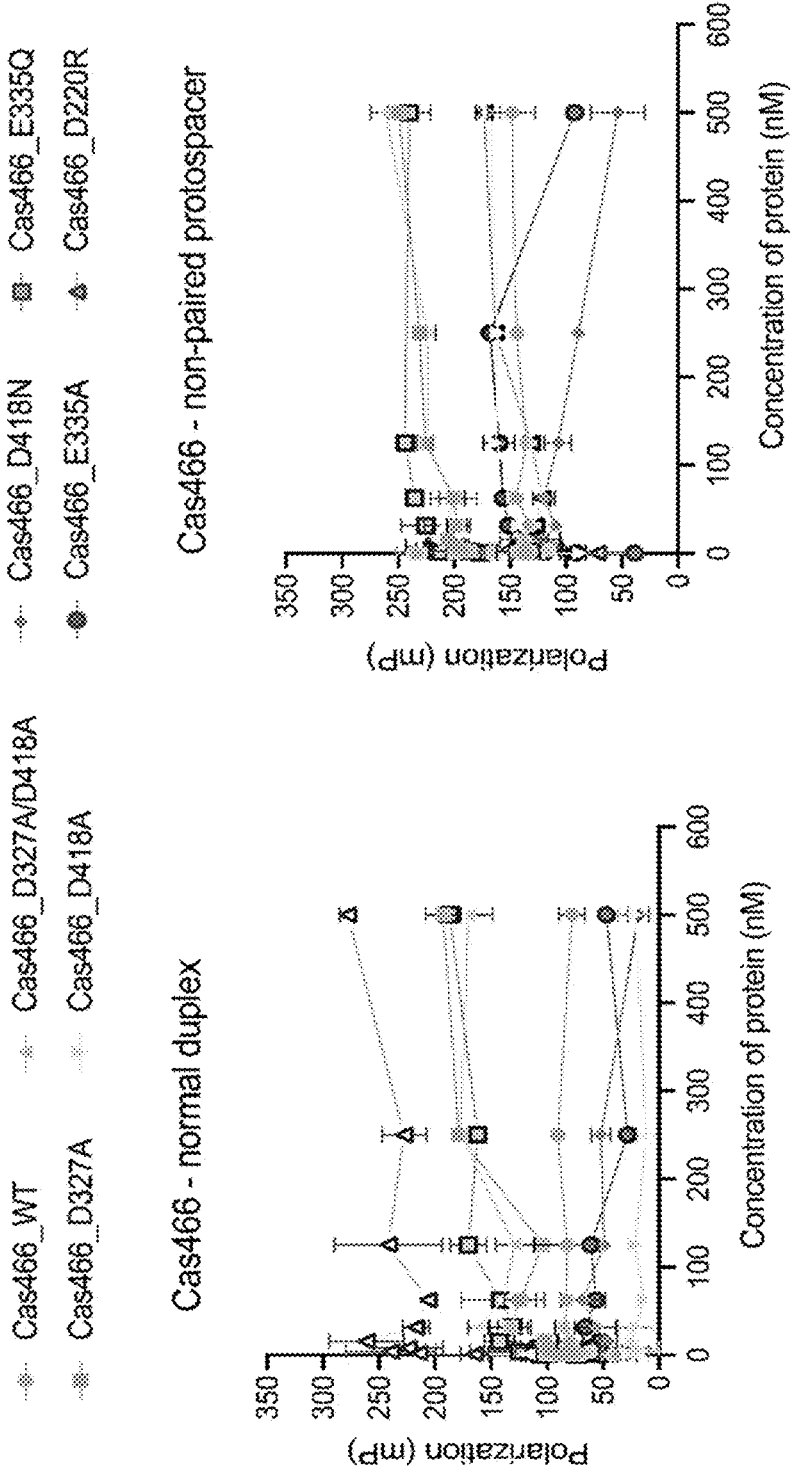
FIGS. 42A-42B show binding affinity curves for the CasM.265466 variant effector proteins relative to corresponding wildtype CasM.265466 effector protein, wherein the polarization (mP) observed is plotted against concentration of the effector protein.

FIGS. 42A-42B shows results of fluorescence polarization assay for the RNPs comprising variants of CasM.265466, relative to corresponding wildtype effector protein. $K_D$ values (nM) for the RNPs comprising variants of CasM.265466 were calculated based on results shown in FIGS. 42A-42B. Calculated $K_D$ values indicated that all variants bind normal duplex substrate and non-paired DNA substrate. In this experiment, the RNP comprising wildtype CasM.265466 demonstrated a higher preference for non-paired DNA substrate than normal duplex substrate.

Figures 43A, 43B:
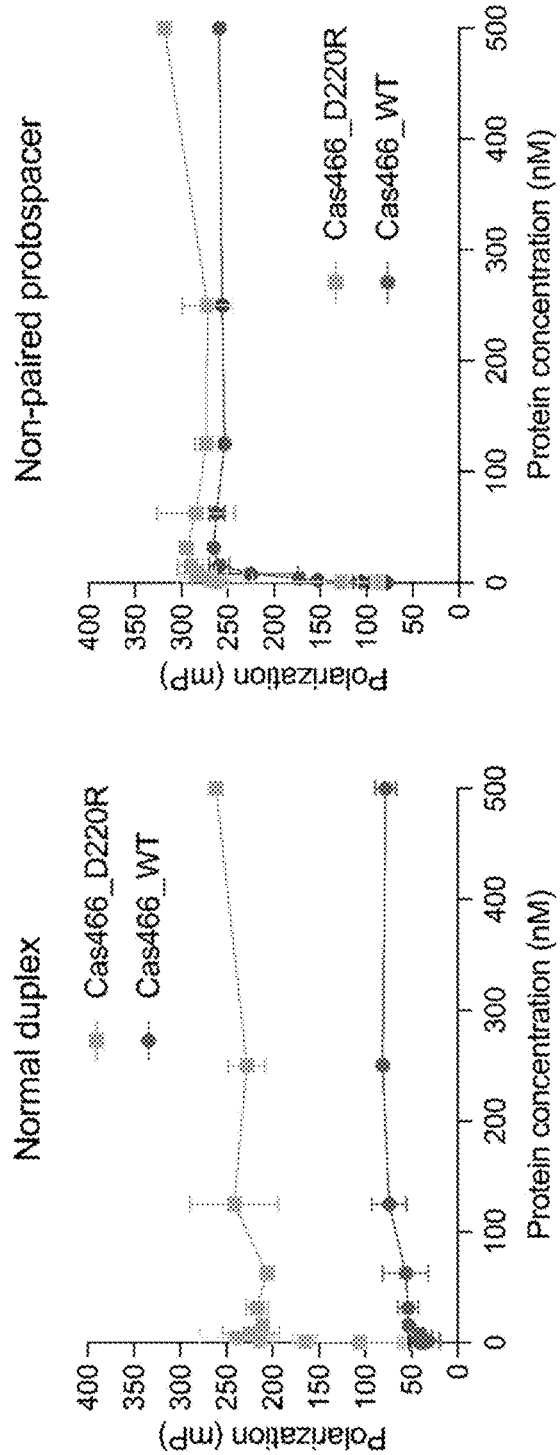
FIGS. 43A-43B show binding affinity curves for the variant D220R, relative to the corresponding wildtype CasM.265466 effector protein, wherein the polarization (mP) observed is plotted against concentration of the effector protein.

FIGS. 43A-43B show results for the RNPs comprising D220R and the wildtype effector protein only. Results indicate that the RNP comprising D220R can bind to both DNA substrates better than the RNP comprising wildtype CasM.265466.

Figures 44A, 44B:
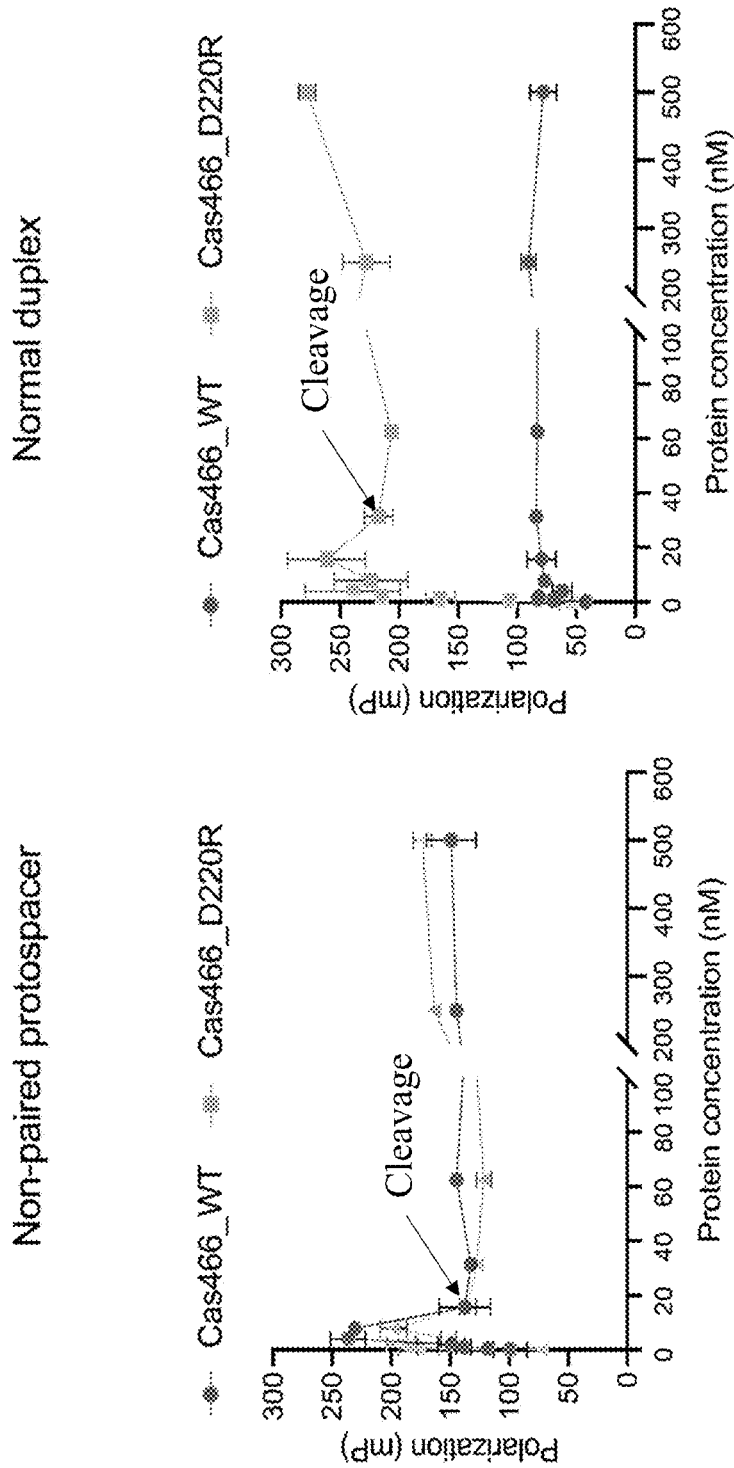
FIGS. 44A-44B show cis cleavage catalytic activity for the variant D220R relative to the wildtype effector protein.
Figure 45:
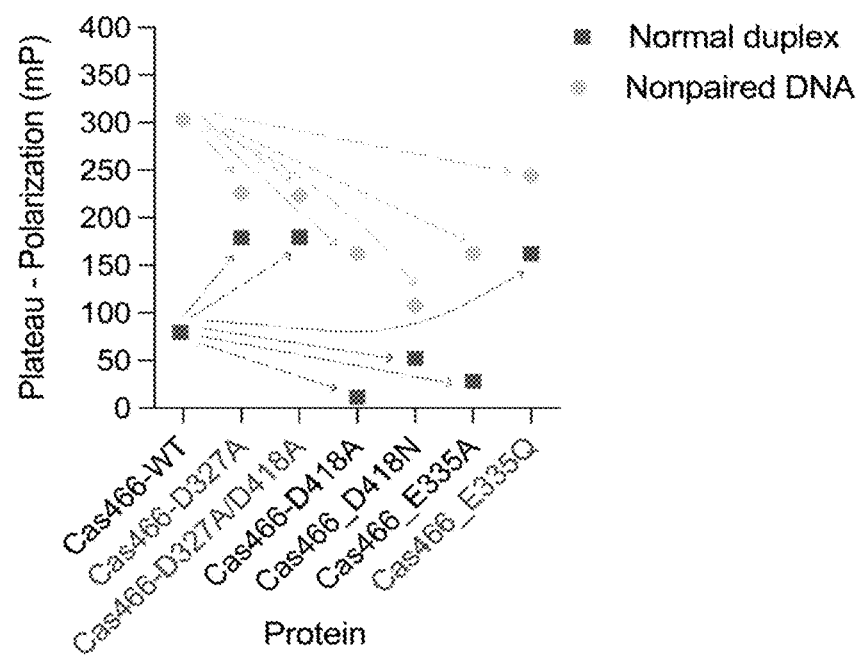
FIG. 45 shows a plateau amplitude curve for the wildtype CasM.265466 protein and variants thereof.
Figure 46:
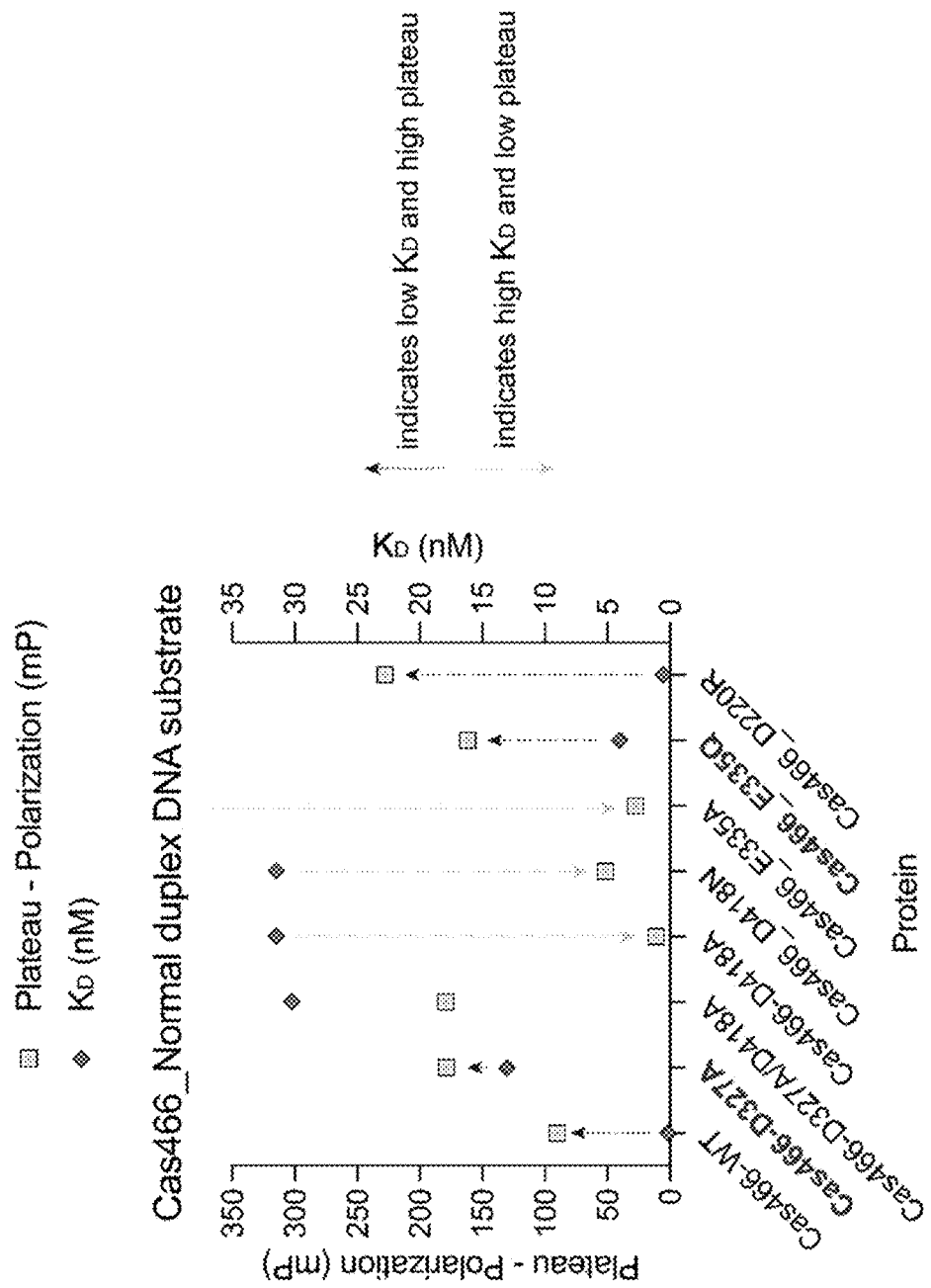
FIG. 46 shows both, $K_D$ and plateau polarization, values for the wildtype CasM.265466 protein and variants thereof using normal duplex DNA substrate.

FIGS. 44A-44B show cis cleavage for catalytically active variant D220R relative to the wildtype effector protein. An analysis of FIGS. 44A-44B show a sharp drop in signal, which can be due to cis cleavage. The results from the fluorescence polarization assay for the RNP comprising D220R variant are consistent with the observations in Example 44. Moreover, the RNPs comprising wildtype CasM.265466 and D220R variant performed cis cleavage in the presence of magnesium.

While preferred embodiments of the present disclosure have been shown and described herein, it will be obvious to those skilled in the art that such embodiments are provided by way of example only. Numerous variations, changes, and substitutions will now occur to those skilled in the art without departing from the disclosure. It should be understood that various alternatives to the embodiments of the disclosure described herein can be employed in practicing the disclosure. It is intended that the following claims define the scope of the disclosure and that methods and structures within the scope of these claims and their equivalents be covered thereby.

What is claimed is:

1. A composition comprising:
 a) an engineered polypeptide or a nucleic acid encoding the engineered polypeptide, wherein the engineered polypeptide comprises an amino acid sequence that is at least 95% identical to SEQ ID NO: 1, and wherein the engineered polypeptide comprises at least one amino acid substitution relative to SEQ ID NO: 1; and
 b) a guide nucleic acid comprising a first sequence and a second sequence,
wherein the engineered polypeptide is capable of binding the first sequence, and wherein the first sequence and the second sequence are heterologous, and
wherein the at least one amino acid substitution is selected from K58W, I80R, T84R, K105R, N193K, C202R, S209F, G210R, A218R, A218K, D220R, E225R, E225K, D237A, C246R, N286K, M298L, A306K, Y315M, E335A, E335Q, Q360R, D418A, and D418N.

2. The composition of claim 1, wherein the at least one amino acid substitution is selected from K58W, I80R, T84R, K105R, N193K, C202R, S209F, G210R, A218R, A218K, D220R, E225R, E225K, C246R, N286K, M298L, A306K, Y315M, Q360R, and a combination thereof.

3. The composition of claim 1, wherein the at least one amino acid substitution comprises D220R.

4. The composition of claim 1, wherein the engineered polypeptide comprises reduced nuclease activity relative to a polypeptide comprising an amino acid sequence consisting of SEQ ID NO: 1.

5. The composition of claim 4, wherein the at least one amino acid substitution is selected from D237A, D418A, D418N, E335A, and E335Q.

6. The composition of claim 1, wherein the at least one amino acid substitution is selected from D237A, D418A, D418N, E335A, and E335Q.

7. The composition of claim 1, wherein the engineered polypeptide is fused to a fusion partner protein.

8. The composition of claim 7, wherein the fusion partner protein is selected from a polymerase, a deaminase, a reverse transcriptase, a transcriptional repressor, an integrase, a recombinase and a transcriptional activator.

9. The composition of claim 7, wherein the fusion partner protein comprises an exonuclease.

10. The composition of claim 1, wherein not more than 10 amino acid substitutions are non-conservative substitutions relative to SEQ ID NO: 1, and any remaining amino acid substitutions relative to SEQ ID NO: 1 are conservative amino acid substitutions.

11. The composition of claim 1, wherein the nucleic acid encoding the engineered polypeptide is a messenger RNA (mRNA).

12. The composition of claim 1, comprising a lipid nanoparticle.

13. The composition of claim 1, wherein the nucleic acid encoding the engineered polypeptide is an adeno-associated viral (AAV) vector.

14. The composition of claim 13, wherein the AAV vector comprises or encodes the guide nucleic acid.

15. The composition of claim 1, wherein the engineered polypeptide comprises nuclease activity.

16. The composition of claim 1, wherein the first sequence comprises a sequence that is at least 80% identical to any one of SEQ ID NOS: 22, 70, 72, 828, 941-943, 1027-1063 and 1065-1097, or a combination thereof.

17. The composition of claim 1, wherein the second sequence is at least 90% complementary to a target sequence, wherein the target sequence is adjacent to a PAM of 5'-NNTN-3'.

18. The composition of claim 1, wherein the second sequence is at least 90% complementary to a eukaryotic sequence.

19. The composition of claim 1 further comprising a donor nucleic acid.

20. The composition of claim 1, wherein the first sequence comprises at least one sequence that is at least 80% identical to any one of SEQ ID NO: 72 and SEQ ID NO: 22.

21. A pharmaceutical composition comprising:
 a) the composition of claim 1; and
 b) a pharmaceutically acceptable excipient.

22. A method of treating a subject for a disease or a symptom thereof by modifying a target nucleic acid associated with a gene or expression of a gene related to the disease comprising administering to the subject the pharmaceutical composition of claim 21.

23. A method of modifying a target nucleic acid, comprising contacting the target nucleic acid with the composition of claim 1, thereby modifying the target nucleic acid.

24. A cell comprising a target nucleic acid, wherein the target nucleic acid is modified by the method of claim 23.

25. An engineered polypeptide comprising an amino acid sequence that is at least 95% identical to SEQ ID NO: 1, wherein the engineered polypeptide comprises at least one amino acid substitution relative to SEQ ID NO: 1, and wherein the at least one amino acid substitution is selected from: K K58W, I80R, T84R, K105R, N193K, C202R, S209F, G210R, A218R, A218K, D220R, E225R, E225K, D237A, C246R, N286K, M298L, A306K, Y315M, E335A, E335Q, Q360R, D418A, and D418N.

26. The engineered polypeptide of claim 25, wherein the at least one amino acid substitution is selected from K58W, I80R, T84R, K105R, N193K, C202R, S209F, G210R, A218R, A218K, D220R, E225R, E225K, C246R, N286K, M298L, A306K, Y315M, Q360R, and a combination thereof.

27. The engineered polypeptide of claim 25, wherein the at least one amino acid substitution is selected from D237A, D418A, D418N, E335A, and E335Q.

28. A nucleic acid encoding the engineered polypeptide of claim 25.

29. The nucleic acid of claim 28, wherein the nucleic acid is an adeno-associated viral (AAV) vector.

30. The nucleic acid of claim 28, wherein the nucleic acid is an mRNA.

* * * * *

SEQUENCE LISTING

```
Sequence total quantity: 1116
SEQ ID NO: 1            moltype = AA  length = 448
FEATURE                 Location/Qualifiers
source                  1..448
                        mol_type = protein
                        organism = synthetic construct
SEQUENCE: 1
MSVLTRKVQL IPVGDKEERD RVYKYLRDGI EAQNRAMNLY MSGLYFAAIN EASKEDRKEL   60
NQLYSRIATS SKGSAYTTDI EFPTGLASTS TLSMAVRQDF TKSLKDGLMY GRVSLPTYRK  120
DNPLFVDVRF VALRGTKQKY NGLYHEYKSH TEFLDNLYSS DLKVYIKFAN DITFQVIFGN  180
PRKSSALRSE FQNIFEEYYK VCQSSIQFSG TKIILNMAMD IPDKEIELDE DVCVGVDLGI  240
AIPAVCALNK NRYSRVSIGS KEDFLRVRTK IRNQRKRLQT NLKSSNGGHG RKKKMKPMDR  300
FRDYEANWVQ NYNHYVSRQV VDFAVKNKAK YINLENLEGI RDDVKNEWLL SNWSYYQLQQ  360
YITYKAKTYG IEVRKINPYH TSQRCSCCGY EDAGNRPKKE KGQAYFKCLK CGEEMNADFN  420
AARNIAMSTE FQSGKKTKKQ KKEQHENK                                    448

SEQ ID NO: 2            moltype = AA  length = 429
FEATURE                 Location/Qualifiers
source                  1..429
                        mol_type = protein
                        organism = synthetic construct
SEQUENCE: 2
MVITRKIALT VVGNKEEKDR VYTYIRDGIK NQNLAMNQYM SALYVANMQD ISKDDRKELN   60
HLYTRISTSK KGSAYSTDIQ FPKGLPCTSS LGQEVRAKFK KACKDGLMYG RVSLPTYRAN  120
NPLLIHVDYV RLRSTNPHND TGLYHNYESH TEFLEHLYKN DCEVFIKFAN NITFQLFFGQ  180
PHKSHELRSV IQKVFEEYYS VCGSSIEISK KGKIMLNMCI EIPVEKKELD ENIVVGVDLG  240
ISTPAMCGLN CNDYVREGIG SKDTLLSKRT QLQRQYRELQ GRMKMTNGGH GRGKKLKKMD  300
DYRNHERHFV QTYNHQVSKK IVDFALKYKA KYINVEDLSG FGNRDTNQWV LRNWSYYELQ  360
QYITYKAQKY GIEVRKVKPY LTSQTCSHCG HYEPGQRLDQ AHFECKNCGL KINADFNASR  420
NIAMSTEFV                                                         429

SEQ ID NO: 3            moltype =     length =
SEQUENCE: 3
000

SEQ ID NO: 4            moltype =     length =
SEQUENCE: 4
000

SEQ ID NO: 5            moltype = AA  length = 20
FEATURE                 Location/Qualifiers
source                  1..20
                        mol_type = protein
                        organism = synthetic construct
VARIANT                 4
                        note = Lys, His, or Arg
VARIANT                 8
                        note = Lys, His, or Arg
VARIANT                 11
                        note = Lys, His, or Arg
VARIANT                 15
```

```
                        note = Lys, His, or Arg
VARIANT                 19
                        note = Lys, His, or Arg
SEQUENCE: 5
GLFXALLXLL XSLWXLLLXA                                                   20

SEQ ID NO: 6            moltype = AA  length = 20
FEATURE                 Location/Qualifiers
source                  1..20
                        mol_type = protein
                        organism = synthetic construct
SEQUENCE: 6
GLFHALLHLL HSLWHLLLHA                                                   20

SEQ ID NO: 7            moltype =   length =
SEQUENCE: 7
000

SEQ ID NO: 8            moltype = AA  length = 5
FEATURE                 Location/Qualifiers
source                  1..5
                        mol_type = protein
                        organism = synthetic construct
SEQUENCE: 8
GSGGS                                                                    5

SEQ ID NO: 9            moltype = AA  length = 6
FEATURE                 Location/Qualifiers
source                  1..6
                        mol_type = protein
                        organism = synthetic construct
SEQUENCE: 9
GGSGGS                                                                   6

SEQ ID NO: 10           moltype = AA  length = 4
FEATURE                 Location/Qualifiers
source                  1..4
                        mol_type = protein
                        organism = synthetic construct
SEQUENCE: 10
GGGS                                                                     4

SEQ ID NO: 11           moltype = AA  length = 4
FEATURE                 Location/Qualifiers
source                  1..4
                        mol_type = protein
                        organism = synthetic construct
SEQUENCE: 11
GGSG                                                                     4

SEQ ID NO: 12           moltype = AA  length = 5
FEATURE                 Location/Qualifiers
source                  1..5
                        mol_type = protein
                        organism = synthetic construct
SEQUENCE: 12
GGSGG                                                                    5

SEQ ID NO: 13           moltype = AA  length = 5
FEATURE                 Location/Qualifiers
source                  1..5
                        mol_type = protein
                        organism = synthetic construct
SEQUENCE: 13
GSGSG                                                                    5

SEQ ID NO: 14           moltype = AA  length = 5
FEATURE                 Location/Qualifiers
source                  1..5
                        mol_type = protein
                        organism = synthetic construct
SEQUENCE: 14
GSGGG                                                                    5

SEQ ID NO: 15           moltype = AA  length = 5
FEATURE                 Location/Qualifiers
source                  1..5
                        mol_type = protein
                        organism = synthetic construct
```

-continued

```
SEQUENCE: 15
GGGSG                                                                    5

SEQ ID NO: 16           moltype = AA   length = 5
FEATURE                 Location/Qualifiers
source                  1..5
                        mol_type = protein
                        organism = synthetic construct
SEQUENCE: 16
GSSSG                                                                    5

SEQ ID NO: 17           moltype = RNA  length = 56
FEATURE                 Location/Qualifiers
source                  1..56
                        mol_type = other RNA
                        organism = synthetic construct
SEQUENCE: 17
gtttgagaac cttatgaaat tacaaggatg ccaaactatt aaatactcgt attgct           56

SEQ ID NO: 18           moltype =      length =
SEQUENCE: 18
000

SEQ ID NO: 19           moltype = RNA  length = 56
FEATURE                 Location/Qualifiers
source                  1..56
                        mol_type = other RNA
                        organism = synthetic construct
SEQUENCE: 19
cttttggaag tatataaatt tacataggta caaaactatt aaatactcgt attgct           56

SEQ ID NO: 20           moltype = RNA  length = 56
FEATURE                 Location/Qualifiers
source                  1..56
                        mol_type = other RNA
                        organism = synthetic construct
SEQUENCE: 20
gtttgagaac catataaatt tacatggtag tcaaactatt aaatactcgt attgct           56

SEQ ID NO: 21           moltype = RNA  length = 56
FEATURE                 Location/Qualifiers
source                  1..56
                        mol_type = other RNA
                        organism = synthetic construct
SEQUENCE: 21
gttttggaat cctataaatt tacataggta caaaactatt aaatactcgt attgct           56

SEQ ID NO: 22           moltype = RNA  length = 52
FEATURE                 Location/Qualifiers
source                  1..52
                        mol_type = other RNA
                        organism = synthetic construct
SEQUENCE: 22
acagcttatt tggaagctga aatgtgaggt ttataacact cacaagaatc ct               52

SEQ ID NO: 23           moltype = RNA  length = 69
FEATURE                 Location/Qualifiers
source                  1..69
                        mol_type = other RNA
                        organism = synthetic construct
SEQUENCE: 23
tatatttgat aaaaatatac agcttatttg gaagctgaaa tgtgaggttt ataacactca       60
caagaatcc                                                               69

SEQ ID NO: 24           moltype = RNA  length = 53
FEATURE                 Location/Qualifiers
source                  1..53
                        mol_type = other RNA
                        organism = synthetic construct
SEQUENCE: 24
tggctgattt tgcagccata aggtgaggaa aattcactca ccaaagccta tgt              53

SEQ ID NO: 25           moltype = RNA  length = 51
FEATURE                 Location/Qualifiers
source                  1..51
                        mol_type = other RNA
                        organism = synthetic construct
SEQUENCE: 25
agggtagatt tgactgccca aggtgagga tgaaatcact caccaaatac t                 51
```

```
SEQ ID NO: 26            moltype = RNA   length = 52
FEATURE                  Location/Qualifiers
source                   1..52
                         mol_type = other RNA
                         organism = synthetic construct
SEQUENCE: 26
acggtggatt ttgccgccga aaggtgaggg aaaatttcca ctcaccaaag cc            52

SEQ ID NO: 27            moltype = RNA   length = 89
FEATURE                  Location/Qualifiers
source                   1..89
                         mol_type = other RNA
                         organism = synthetic construct
SEQUENCE: 27
acagcttatt tggaagctga aatgtgaggt ttataacact cacaagaatc ctgaaaaagg    60
atgccaaact attaaatact cgtattgct                                      89

SEQ ID NO: 28            moltype = RNA   length = 90
FEATURE                  Location/Qualifiers
source                   1..90
                         mol_type = other RNA
                         organism = synthetic construct
SEQUENCE: 28
tggctgattt tgcagccata aggtgaggaa aattcactca ccaaagccta tgtgaaaata    60
ggtacaaaac tattaaatac tcgtattgct                                     90

SEQ ID NO: 29            moltype = RNA   length = 88
FEATURE                  Location/Qualifiers
source                   1..88
                         mol_type = other RNA
                         organism = synthetic construct
SEQUENCE: 29
agggtagatt tgactgccca aaggtgagga tgaaatcact caccaaatac tgaaaatggt    60
agtcaaacta ttaaatactc gtattgct                                       88

SEQ ID NO: 30            moltype = RNA   length = 89
FEATURE                  Location/Qualifiers
source                   1..89
                         mol_type = other RNA
                         organism = synthetic construct
SEQUENCE: 30
acggtggatt ttgccgccga aaggtgaggg aaaatttcca ctcaccaaag ccgaaaatag    60
gtacaaaact attaaatact cgtattgct                                      89

SEQ ID NO: 31            moltype =    length =
SEQUENCE: 31
000

SEQ ID NO: 32            moltype = RNA   length = 70
FEATURE                  Location/Qualifiers
source                   1..70
                         mol_type = other RNA
                         organism = synthetic construct
SEQUENCE: 32
tggctgattt tgcagccata aggtgaggaa aattcactca ccaaagccta tgtgaaaata    60
ggtacaaaac                                                           70

SEQ ID NO: 33            moltype =    length =
SEQUENCE: 33
000

SEQ ID NO: 34            moltype =    length =
SEQUENCE: 34
000

SEQ ID NO: 35            moltype = RNA   length = 68
FEATURE                  Location/Qualifiers
source                   1..68
                         mol_type = other RNA
                         organism = synthetic construct
SEQUENCE: 35
agggtagatt tgactgccca aaggtgagga tgaaatcact caccaaatac tgaaaatggt    60
agtcaaac                                                             68

SEQ ID NO: 36            moltype = RNA   length = 69
FEATURE                  Location/Qualifiers
source                   1..69
                         mol_type = other RNA
```

-continued

```
                        organism = synthetic construct
SEQUENCE: 36
acggtggatt ttgccgccga aaggtgaggg aaaatttcca ctcaccaaag ccgaaaatag  60
gtacaaaac                                                          69

SEQ ID NO: 37           moltype = AA  length = 450
FEATURE                 Location/Qualifiers
source                  1..450
                        mol_type = protein
                        organism = synthetic construct
VARIANT                 2
                        note = Any amino acid
VARIANT                 8
                        note = Any amino acid
VARIANT                 9
                        note = Any amino acid
VARIANT                 11
                        note = Any amino acid
VARIANT                 12
                        note = Any amino acid
VARIANT                 19
                        note = Any amino acid
VARIANT                 24
                        note = Any amino acid
VARIANT                 31
                        note = Any amino acid
VARIANT                 32
                        note = Any amino acid
VARIANT                 35
                        note = Any amino acid
VARIANT                 39
                        note = Any amino acid
VARIANT                 43
                        note = Any amino acid
VARIANT                 46
                        note = Any amino acid
VARIANT                 48
                        note = Any amino acid
VARIANT                 49
                        note = Any amino acid
VARIANT                 50
                        note = Any amino acid
VARIANT                 51
                        note = Any amino acid
VARIANT                 52
                        note = Any amino acid
VARIANT                 55
                        note = Any amino acid
VARIANT                 62
                        note = Any amino acid
VARIANT                 65
                        note = Any amino acid
VARIANT                 68
                        note = Any amino acid
VARIANT                 71
                        note = Any amino acid
VARIANT                 77
                        note = Any amino acid
VARIANT                 84
                        note = Any amino acid
VARIANT                 87
                        note = Any amino acid
VARIANT                 88
                        note = Any amino acid
VARIANT                 91
                        note = Any amino acid
VARIANT                 93
                        note = Any amino acid
VARIANT                 94
                        note = Any amino acid
VARIANT                 95
                        note = Any amino acid
VARIANT                 98
                        note = Any amino acid
VARIANT                 99
                        note = Any amino acid
VARIANT                 101
                        note = Any amino acid
VARIANT                 103
```

| | | |
|---|---|---|
| VARIANT | 104 | note = Any amino acid |
| VARIANT | 120 | note = Any amino acid |
| VARIANT | 125 | note = Any amino acid |
| VARIANT | 126 | note = Any amino acid |
| VARIANT | 127 | note = Any amino acid |
| VARIANT | 129 | note = Any amino acid |
| VARIANT | 130 | note = Any amino acid |
| VARIANT | 132 | note = Any amino acid |
| VARIANT | 135 | note = Any amino acid |
| VARIANT | 137 | note = Any amino acid |
| VARIANT | 138 | note = Any amino acid |
| VARIANT | 139 | note = Any amino acid |
| VARIANT | 140 | note = Any amino acid |
| VARIANT | 141 | note = Any amino acid |
| VARIANT | 142 | note = Any amino acid |
| VARIANT | 147 | note = Any amino acid |
| VARIANT | 149 | note = Any amino acid |
| VARIANT | 156 | note = Any amino acid |
| VARIANT | 157 | note = Any amino acid |
| VARIANT | 160 | note = Any amino acid |
| VARIANT | 161 | note = Any amino acid |
| VARIANT | 163 | note = Any amino acid |
| VARIANT | 164 | note = Any amino acid |
| VARIANT | 166 | note = Any amino acid |
| VARIANT | 177 | note = Any amino acid |
| VARIANT | 178 | note = Any amino acid |
| VARIANT | 181 | note = Any amino acid |
| VARIANT | 183 | note = Any amino acid |
| VARIANT | 186 | note = Any amino acid |
| VARIANT | 187 | note = Any amino acid |
| VARIANT | 191 | note = Any amino acid |
| VARIANT | 192 | note = Any amino acid |
| VARIANT | 194 | note = Any amino acid |
| VARIANT | 195 | note = Any amino acid |
| VARIANT | 201 | note = Any amino acid |
| VARIANT | 204 | note = Any amino acid |
| VARIANT | 209 | note = Any amino acid |
| VARIANT | 211 | note = Any amino acid |
| VARIANT | 212 | note = Any amino acid |

| | |
|---|---|
| VARIANT | 213<br>note = Any amino acid |
| VARIANT | 216<br>note = Any amino acid |
| VARIANT | 220<br>note = Any amino acid |
| VARIANT | 221<br>note = Any amino acid |
| VARIANT | 222<br>note = Any amino acid |
| VARIANT | 225<br>note = Any amino acid |
| VARIANT | 226<br>note = Any amino acid |
| VARIANT | 227<br>note = Any amino acid |
| VARIANT | 228<br>note = Any amino acid |
| VARIANT | 234<br>note = Any amino acid |
| VARIANT | 235<br>note = Any amino acid |
| VARIANT | 243<br>note = Any amino acid |
| VARIANT | 244<br>note = Any amino acid |
| VARIANT | 247<br>note = Any amino acid |
| VARIANT | 249<br>note = Any amino acid |
| VARIANT | 252<br>note = Any amino acid |
| VARIANT | 254<br>note = Any amino acid |
| VARIANT | 256<br>note = Any amino acid |
| VARIANT | 258<br>note = Any amino acid |
| VARIANT | 259<br>note = Any amino acid |
| VARIANT | 264<br>note = Any amino acid |
| VARIANT | 265<br>note = Any amino acid |
| VARIANT | 266<br>note = Any amino acid |
| VARIANT | 268<br>note = Any amino acid |
| VARIANT | 269<br>note = Any amino acid |
| VARIANT | 272<br>note = Any amino acid |
| VARIANT | 274<br>note = Any amino acid |
| VARIANT | 275<br>note = Any amino acid |
| VARIANT | 277<br>note = Any amino acid |
| VARIANT | 278<br>note = Any amino acid |
| VARIANT | 279<br>note = Any amino acid |
| VARIANT | 282<br>note = Any amino acid |
| VARIANT | 283<br>note = Any amino acid |
| VARIANT | 284<br>note = Any amino acid |
| VARIANT | 286<br>note = Any amino acid |
| VARIANT | 287<br>note = Any amino acid |
| VARIANT | 294<br>note = Any amino acid |
| VARIANT | 297<br>note = Any amino acid |
| VARIANT | 299<br>note = Any amino acid |
| VARIANT | 302 |

| | | |
|---|---|---|
| VARIANT | 303 | note = Any amino acid |
| VARIANT | 306 | note = Any amino acid |
| VARIANT | 308 | note = Any amino acid |
| VARIANT | 309 | note = Any amino acid |
| VARIANT | 310 | note = Any amino acid |
| VARIANT | 313 | note = Any amino acid |
| VARIANT | 317 | note = Any amino acid |
| VARIANT | 320 | note = Any amino acid |
| VARIANT | 321 | note = Any amino acid |
| VARIANT | 322 | note = Any amino acid |
| VARIANT | 327 | note = Any amino acid |
| VARIANT | 329 | note = Any amino acid |
| VARIANT | 336 | note = Any amino acid |
| VARIANT | 340 | note = Any amino acid |
| VARIANT | 342 | note = Any amino acid |
| VARIANT | 343 | note = Any amino acid |
| VARIANT | 345 | note = Any amino acid |
| VARIANT | 346 | note = Any amino acid |
| VARIANT | 347 | note = Any amino acid |
| VARIANT | 351 | note = Any amino acid |
| VARIANT | 353 | note = Any amino acid |
| VARIANT | 369 | note = Any amino acid |
| VARIANT | 370 | note = Any amino acid |
| VARIANT | 378 | note = Any amino acid |
| VARIANT | 379 | note = Any amino acid |
| VARIANT | 382 | note = Any amino acid |
| VARIANT | 386 | note = Any amino acid |
| VARIANT | 389 | note = Any amino acid |
| VARIANT | 392 | note = Any amino acid |
| VARIANT | 393 | note = Any amino acid |
| VARIANT | 394 | note = Any amino acid |
| VARIANT | 395 | note = Any amino acid |
| VARIANT | 397 | note = Any amino acid |
| VARIANT | 399 | note = Any amino acid |
| VARIANT | 400 | note = Any amino acid |
| VARIANT | 401 | note = Any amino acid |
| VARIANT | 402 | note = Any amino acid |
| VARIANT | 403 | note = Any amino acid |
| VARIANT | 404 | note = Any amino acid |

| | | |
|---|---|---|
| VARIANT | 407 | |
| | note = Any amino acid | |
| VARIANT | 409 | |
| | note = Any amino acid | |
| VARIANT | 411 | |
| | note = Any amino acid | |
| VARIANT | 412 | |
| | note = Any amino acid | |
| VARIANT | 415 | |
| | note = Any amino acid | |
| VARIANT | 416 | |
| | note = Any amino acid | |
| VARIANT | 417 | |
| | note = Any amino acid | |
| VARIANT | 424 | |
| | note = Any amino acid | |
| VARIANT | 434 | |
| | note = Any amino acid | |

SEQUENCE: 37
```
MXVJTRKXXL XXVGBKEEXD RVYXYJRDGI XXQNXAMNXY MSXLYXAXXX XXSKXDRKEL   60
NXLYXRIXTS XKGSAYXTDI ZFPXGLXXTS XLXXXVRXXF XKXXKDGLMY GRVSLPTYRX  120
BNPLXXXVXX VXLRXTXXXX XXGLYHXYXS HTEFLXXLYX XDXXVXIKFA NBITFQXXFG  180
XPXKSXXLRS XXQXXFEEYY XVCXXSSIZXS XXXKIXLNMX XXIPXXXXEL DEBXXVGVDL  240
GIXXPAXCXL NXNXYXRXXI GSKXXXLXXR TXJXXQXXXL QXXXKXXNGG HGRXKKXKXM  300
DXXRBXEXXX VQXYNHXVSX XXV

```
misc_difference        36
                       note = a, c, t, g, unknown, or other
misc_difference        37
                       note = a, c, t, g, unknown, or other
misc_difference        38
                       note = a, c, t, g, unknown, or other
misc_difference        39
                       note = a, c, t, g, unknown, or other
misc_difference        40
                       note = a, c, t, g, unknown, or other
SEQUENCE: 41
acactctttc cctacacgac gctcttccga tctnnnnnnn cctttcgtct cgcgcgtttc   60
gg                                                                 62

SEQ ID NO: 42          moltype = RNA  length = 89
FEATURE                Location/Qualifiers
source                 1..89
                       mol_type = other RNA
                       organism = synthetic construct
SEQUENCE: 42
acagcttatt tggaagctga aatgtgaggt ttataacact cacaagaatc ctgaaaaagg   60
atgccaaact cacagcccaa gatagttaa                                    89

SEQ ID NO: 43          moltype = RNA  length = 89
FEATURE                Location/Qualifiers
source                 1..89
                       mol_type = other RNA
                       organism = synthetic construct
SEQUENCE: 43
acagcttatt tggaagctga aatgtgaggt ttataacact cacaagaatc ctgaaaaagg   60
atgccaaacc tcacgtcatc cagcagaga                                    89

SEQ ID NO: 44          moltype = RNA  length = 89
FEATURE                Location/Qualifiers
source                 1..89
                       mol_type = other RNA
                       organism = synthetic construct
SEQUENCE: 44
acagcttatt tggaagctga aatgtgaggt ttataacact cacaagaatc ctgaaaaagg   60
atgccaaact tgtgctgtag gaagctcat                                    89

SEQ ID NO: 45          moltype = RNA  length = 89
FEATURE                Location/Qualifiers
source                 1..89
                       mol_type = other RNA
                       organism = synthetic construct
SEQUENCE: 45
acagcttatt tggaagctga aatgtgaggt ttataacact cacaagaatc ctgaaaaagg   60
atgccaaacc gcctttgtct tcgtggccc                                    89

SEQ ID NO: 46          moltype = RNA  length = 89
FEATURE                Location/Qualifiers
source                 1..89
                       mol_type = other RNA
                       organism = synthetic construct
SEQUENCE: 46
acagcttatt tggaagctga aatgtgaggt ttataacact cacaagaatc ctgaaaaagg   60
atgccaaacc tgcagccatg tccaggtaa                                    89

SEQ ID NO: 47          moltype = RNA  length = 89
FEATURE                Location/Qualifiers
source                 1..89
                       mol_type = other RNA
                       organism = synthetic construct
SEQUENCE: 47
acagcttatt tggaagctga aatgtgaggt ttataacact cacaagaatc ctgaaaaagg   60
atgccaaacc ccggagaaag atgaaccta                                    89

SEQ ID NO: 48          moltype = RNA  length = 89
FEATURE                Location/Qualifiers
source                 1..89
                       mol_type = other RNA
                       organism = synthetic construct
SEQUENCE: 48
acagcttatt tggaagctga aatgtgaggt ttataacact cacaagaatc ctgaaaaagg   60
atgccaaacg ccaaaggcat gtgaggtac                                    89

SEQ ID NO: 49          moltype = RNA  length = 89
FEATURE                Location/Qualifiers
```

```
source                          1..89
                                mol_type = other RNA
                                organism = synthetic construct
SEQUENCE: 49
acagcttatt tggaagctga aatgtgaggt ttataacact cacaagaatc ctgaaaaagg    60
atgccaaacc ctttcttggg tacggcttc                                      89

SEQ ID NO: 50                   moltype = RNA   length = 89
FEATURE                         Location/Qualifiers
source                          1..89
                                mol_type = other RNA
                                organism = synthetic construct
SEQUENCE: 50
acagcttatt tggaagctga aatgtgaggt ttataacact cacaagaatc ctgaaaaagg    60
atgccaaacc tcagaggctg cagaaatgc                                      89

SEQ ID NO: 51                   moltype = RNA   length = 89
FEATURE                         Location/Qualifiers
source                          1..89
                                mol_type = other RNA
                                organism = synthetic construct
SEQUENCE: 51
acagcttatt tggaagctga aatgtgaggt ttataacact cacaagaatc ctgaaaaagg    60
atgccaaact tgtatccccc tccaagctc                                      89

SEQ ID NO: 52                   moltype = RNA   length = 89
FEATURE                         Location/Qualifiers
source                          1..89
                                mol_type = other RNA
                                organism = synthetic construct
SEQUENCE: 52
acagcttatt tggaagctga aatgtgaggt ttataacact cacaagaatc ctgaaaaagg    60
atgccaaaca gtctccagga agaaattaa                                      89

SEQ ID NO: 53                   moltype = RNA   length = 89
FEATURE                         Location/Qualifiers
source                          1..89
                                mol_type = other RNA
                                organism = synthetic construct
SEQUENCE: 53
acagcttatt tggaagctga aatgtgaggt ttataacact cacaagaatc ctgaaaaagg    60
atgccaaacg ggcagctggt ggaattttt                                      89

SEQ ID NO: 54                   moltype = RNA   length = 89
FEATURE                         Location/Qualifiers
source                          1..89
                                mol_type = other RNA
                                organism = synthetic construct
SEQUENCE: 54
acagcttatt tggaagctga aatgtgaggt ttataacact cacaagaatc ctgaaaaagg    60
atgccaaaca agaaatgga atctcgagg                                       89

SEQ ID NO: 55                   moltype = RNA   length = 89
FEATURE                         Location/Qualifiers
source                          1..89
                                mol_type = other RNA
                                organism = synthetic construct
SEQUENCE: 55
acagcttatt tggaagctga aatgtgaggt ttataacact cacaagaatc ctgaaaaagg    60
atgccaaacc aggttgagaa cttgttgct                                      89

SEQ ID NO: 56                   moltype = RNA   length = 89
FEATURE                         Location/Qualifiers
source                          1..89
                                mol_type = other RNA
                                organism = synthetic construct
SEQUENCE: 56
acagcttatt tggaagctga aatgtgaggt ttataacact cacaagaatc ctgaaaaagg    60
atgccaaact cccgaccctc ccgtcgccg                                      89

SEQ ID NO: 57                   moltype = RNA   length = 89
FEATURE                         Location/Qualifiers
source                          1..89
                                mol_type = other RNA
                                organism = synthetic construct
SEQUENCE: 57
acagcttatt tggaagctga aatgtgaggt ttataacact cacaagaatc ctgaaaaagg    60
atgccaaacg gacgagccta cccgtcccc                                      89
```

| SEQ ID NO: 58 | moltype = RNA length = 89 |
| --- | --- |
| FEATURE | Location/Qualifiers |
| source | 1..89 |
| | mol_type = other RNA |
| | organism = synthetic construct |

SEQUENCE: 58
acagcttatt tggaagctga aatgtgaggt ttataacact cacaagaatc ctgaaaaagg    60
atgccaaact cgggggggcgg ggggagaa                                     89

| SEQ ID NO: 59 | moltype = RNA length = 89 |
| --- | --- |
| FEATURE | Location/Qualifiers |
| source | 1..89 |
| | mol_type = other RNA |
| | organism = synthetic construct |

SEQUENCE: 59
acagcttatt tggaagctga aatgtgaggt ttataacact cacaagaatc ctgaaaaagg    60
atgccaaacc agactggccc cagagatgc                                     89

| SEQ ID NO: 60 | moltype = AA length = 35 |
| --- | --- |
| FEATURE | Location/Qualifiers |
| source | 1..35 |
| | mol_type = protein |
| | organism = synthetic construct |
| VARIANT | 7 |
| | note = Any amino acid |
| VARIANT | 12 |
| | note = Any amino acid |
| VARIANT | 19 |
| | note = Any amino acid |
| VARIANT | 20 |
| | note = Any amino acid |
| VARIANT | 23 |
| | note = Any amino acid |
| VARIANT | 27 |
| | note = Any amino acid |
| VARIANT | 31 |
| | note = Any amino acid |
| VARIANT | 34 |
| | note = Any amino acid |

SEQUENCE: 60
VGBKEEXDRV YXYJRDGIXX QNXAMNXYMS XLYXA                               35

| SEQ ID NO: 61 | moltype = AA length = 40 |
| --- | --- |
| FEATURE | Location/Qualifiers |
| source | 1..40 |
| | mol_type = protein |
| | organism = synthetic construct |
| VARIANT | 3 |
| | note = Any amino acid |
| VARIANT | 10 |
| | note = Any amino acid |
| VARIANT | 13 |
| | note = Any amino acid |
| VARIANT | 16 |
| | note = Any amino acid |
| VARIANT | 19 |
| | note = Any amino acid |
| VARIANT | 25 |
| | note = Any amino acid |
| VARIANT | 32 |
| | note = Any amino acid |
| VARIANT | 35 |
| | note = Any amino acid |
| VARIANT | 36 |
| | note = Any amino acid |
| VARIANT | 39 |
| | note = Any amino acid |

SEQUENCE: 61
SKXDRKELNX LYXRIXTSXK GSAYXTDIZF PXGLXXTSXL                          40

| SEQ ID NO: 62 | moltype = AA length = 20 |
| --- | --- |
| FEATURE | Location/Qualifiers |
| source | 1..20 |
| | mol_type = protein |
| | organism = synthetic construct |
| VARIANT | 16 |
| | note = Any amino acid |

SEQUENCE: 62
KDGLMYGRVS LPTYRXBNPL                                               20

```
SEQ ID NO: 63          moltype = AA  length = 20
FEATURE                Location/Qualifiers
source                 1..20
                       mol_type = protein
                       organism = synthetic construct
VARIANT                5
                       note = Any amino acid
VARIANT                7
                       note = Any amino acid
VARIANT                14
                       note = Any amino acid
VARIANT                15
                       note = Any amino acid
VARIANT                18
                       note = Any amino acid
VARIANT                19
                       note = Any amino acid
SEQUENCE: 63
GLYHXYXSHT EFLXXLYXXD                                                     20

SEQ ID NO: 64          moltype = AA  length = 14
FEATURE                Location/Qualifiers
source                 1..14
                       mol_type = protein
                       organism = synthetic construct
VARIANT                11
                       note = Any amino acid
VARIANT                12
                       note = Any amino acid
SEQUENCE: 64
IKFANBITFQ XXFG                                                           14

SEQ ID NO: 65          moltype = AA  length = 15
FEATURE                Location/Qualifiers
source                 1..15
                       mol_type = protein
                       organism = synthetic construct
VARIANT                6
                       note = Any amino acid
VARIANT                9
                       note = Any amino acid
VARIANT                14
                       note = Any amino acid
SEQUENCE: 65
FEEYYXVCXS SIZXS                                                          15

SEQ ID NO: 66          moltype = AA  length = 14
FEATURE                Location/Qualifiers
source                 1..14
                       mol_type = protein
                       organism = synthetic construct
VARIANT                6
                       note = Any amino acid
VARIANT                7
                       note = Any amino acid
SEQUENCE: 66
ELDEBXXVGV DLGI                                                           14

SEQ ID NO: 67          moltype = AA  length = 19
FEATURE                Location/Qualifiers
source                 1..19
                       mol_type = protein
                       organism = synthetic construct
VARIANT                5
                       note = Any amino acid
VARIANT                7
                       note = Any amino acid
VARIANT                14
                       note = Any amino acid
VARIANT                18
                       note = Any amino acid
SEQUENCE: 67
VDFAXKXKAK YINXEBLXG                                                      19

SEQ ID NO: 68          moltype = AA  length = 24
FEATURE                Location/Qualifiers
source                 1..24
                       mol_type = protein
```

```
                        organism = synthetic construct
VARIANT                 16
                        note = Any amino acid
VARIANT                 17
                        note = Any amino acid
SEQUENCE: 68
NWSYYZLQQY ITYKAXXYGI EVRK                                          24

SEQ ID NO: 69           moltype = AA   length = 31
FEATURE                 Location/Qualifiers
source                  1..31
                        mol_type = protein
                        organism = synthetic construct
VARIANT                 7
                        note = Any amino acid
VARIANT                 17
                        note = Any amino acid
SEQUENCE: 69
NADFNAXRNI AMSTEFXSGK KTKKQKKEQH E                                  31

SEQ ID NO: 70           moltype = RNA   length = 69
FEATURE                 Location/Qualifiers
source                  1..69
                        mol_type = other RNA
                        organism = synthetic construct
SEQUENCE: 70
acagcttatt tggaagctga aatgtgaggt ttataacact cacaagaatc ctgaaaaagg   60
atgccaaac                                                          69

SEQ ID NO: 71           moltype =   length =
SEQUENCE: 71
000

SEQ ID NO: 72           moltype = RNA   length = 13
FEATURE                 Location/Qualifiers
source                  1..13
                        mol_type = other RNA
                        organism = synthetic construct
SEQUENCE: 72
aaggatgcca aac                                                     13

SEQ ID NO: 73           moltype = RNA   length = 53
FEATURE                 Location/Qualifiers
source                  1..53
                        mol_type = other RNA
                        organism = synthetic construct
SEQUENCE: 73
tggctgattt tgcagccata aggtgaggaa aattcactca ccaaagccta tgt          53

SEQ ID NO: 74           moltype =   length =
SEQUENCE: 74
000

SEQ ID NO: 75           moltype =   length =
SEQUENCE: 75
000

SEQ ID NO: 76           moltype = RNA   length = 13
FEATURE                 Location/Qualifiers
source                  1..13
                        mol_type = other RNA
                        organism = synthetic construct
SEQUENCE: 76
ataggtacaa aac                                                     13

SEQ ID NO: 77           moltype = RNA   length = 13
FEATURE                 Location/Qualifiers
source                  1..13
                        mol_type = other RNA
                        organism = synthetic construct
SEQUENCE: 77
atggtagtca aac                                                     13

SEQ ID NO: 78           moltype = RNA   length = 69
FEATURE                 Location/Qualifiers
source                  1..69
                        mol_type = other RNA
                        organism = synthetic construct
SEQUENCE: 78
```

```
acagcttatt tggaagctga aatgtgaggt ttataacact cacaagaatc ctgaaaaagg    60
atgccaaac                                                            69

SEQ ID NO: 79           moltype =    length =
SEQUENCE: 79
000

SEQ ID NO: 80           moltype =    length =
SEQUENCE: 80
000

SEQ ID NO: 81           moltype = AA   length = 659
FEATURE                 Location/Qualifiers
source                  1..659
                        mol_type = protein
                        organism = synthetic construct
SEQUENCE: 81
MDYKDHDGDY KDHDIDYKDD DDKMAPKKKR KVGIHGVPAA MSVLTRKVQL IPVGDKEERD    60
RVYKYLRDGI EAQNRAMNLY MSGLYFAAIN EASKEDRKEL NQLYSRIATS SKGSAYTTDI   120
EFPTGLASTS TLSMAVRQDF TKSLKDGLMY GRVSLPTYRK DNPLFVDVRF VALRGTKQKY   180
NGLYHEYKSH TEFLDNLYSS DLKVYIKFAN DITFQVIFGN PRKSSALRSE FQNIFEEYYK   240
VCQSSIQFSG TKIILNMAMD IPDKEIELDE DVCVGVDLGI AIPAVCALNK NRYSRVSIGS   300
KEDFLRVRTK IRNQRKRLQT NLKSSNGGHH RKKKMKPMDR FRDYEANWQ NYNHYVSRQV    360
VDFAVKNKAK YINLENLEGI RDDVKNEWLL SNWSYYQLQQ YITYKAKTYG IEVRKINPYH   420
TSQRCSCCGY EDAGNRPKKE KGQAYFKCLK CGEEMNADFN AARNIAMSTE FQSGKKTKKQ   480
KKEQHENKKR PAATKKAGQA KKKKEFGSGE GRGSLLTCGD VEENPGPMAK PLSQEESTLI   540
ERATATINSI PISEDYSVAS AALSSDGRIF TGVNVYHFTG GPCAELVVLG TAAAAAAGNL   600
TCIVAIGNEN RGILSPCGRC RQVLLDLHPG IKAIVKDSDG QPTAVGIREL LPSGYVWEG    659

SEQ ID NO: 82           moltype = AA   length = 23
FEATURE                 Location/Qualifiers
source                  1..23
                        mol_type = protein
                        organism = synthetic construct
SEQUENCE: 82
MDYKDHDGDY KDHDIDYKDD DDK                                            23

SEQ ID NO: 83           moltype = AA   length = 9
FEATURE                 Location/Qualifiers
source                  1..9
                        mol_type = protein
                        organism = synthetic construct
SEQUENCE: 83
MAPKKKRKV                                                             9

SEQ ID NO: 84           moltype = AA   length = 8
FEATURE                 Location/Qualifiers
source                  1..8
                        mol_type = protein
                        organism = synthetic construct
SEQUENCE: 84
GIHGVPAA                                                              8

SEQ ID NO: 85           moltype = AA   length = 16
FEATURE                 Location/Qualifiers
source                  1..16
                        mol_type = protein
                        organism = synthetic construct
SEQUENCE: 85
KRPAATKKAG QAKKKK                                                    16

SEQ ID NO: 86           moltype = AA   length = 23
FEATURE                 Location/Qualifiers
source                  1..23
                        mol_type = protein
                        organism = synthetic construct
SEQUENCE: 86
EFGSGEGRGS LLTCGDVEEN PGP                                            23

SEQ ID NO: 87           moltype = AA   length = 132
FEATURE                 Location/Qualifiers
source                  1..132
                        mol_type = protein
                        organism = synthetic construct
SEQUENCE: 87
MAKPLSQEES TLIERATATI NSIPISEDYS VASAALSSDG RIFTGVNVYH FTGGPCAELV    60
VLGTAAAAAA GNLTCIVAIG NENRGILSPC GRCRQVLLDL HPGIKAIVKD SDGQPTAVGI   120
RELLPSGYVW EG                                                       132
```

```
SEQ ID NO: 88        moltype = RNA    length = 20
FEATURE              Location/Qualifiers
source               1..20
                     mol_type = other RNA
                     organism = synthetic construct
SEQUENCE: 88
aaagaaattc tacccactaa                                                   20

SEQ ID NO: 89        moltype = RNA    length = 20
FEATURE              Location/Qualifiers
source               1..20
                     mol_type = other RNA
                     organism = synthetic construct
SEQUENCE: 89
acagaaaagc atacacatta                                                   20

SEQ ID NO: 90        moltype = RNA    length = 20
FEATURE              Location/Qualifiers
source               1..20
                     mol_type = other RNA
                     organism = synthetic construct
SEQUENCE: 90
gggtggttgg ctaaataat                                                    20

SEQ ID NO: 91        moltype = RNA    length = 20
FEATURE              Location/Qualifiers
source               1..20
                     mol_type = other RNA
                     organism = synthetic construct
SEQUENCE: 91
ttaaagagga agttagaaga                                                   20

SEQ ID NO: 92        moltype = RNA    length = 20
FEATURE              Location/Qualifiers
source               1..20
                     mol_type = other RNA
                     organism = synthetic construct
SEQUENCE: 92
aacaaatagc tagagccaaa                                                   20

SEQ ID NO: 93        moltype = RNA    length = 20
FEATURE              Location/Qualifiers
source               1..20
                     mol_type = other RNA
                     organism = synthetic construct
SEQUENCE: 93
ccgccttcca ctcagagctc                                                   20

SEQ ID NO: 94        moltype = RNA    length = 20
FEATURE              Location/Qualifiers
source               1..20
                     mol_type = other RNA
                     organism = synthetic construct
SEQUENCE: 94
cttacaggct ccaatagtgg                                                   20

SEQ ID NO: 95        moltype = RNA    length = 20
FEATURE              Location/Qualifiers
source               1..20
                     mol_type = other RNA
                     organism = synthetic construct
SEQUENCE: 95
cccactaaag ttaatttaga                                                   20

SEQ ID NO: 96        moltype = RNA    length = 20
FEATURE              Location/Qualifiers
source               1..20
                     mol_type = other RNA
                     organism = synthetic construct
SEQUENCE: 96
acttcctctt taacagaaaa                                                   20

SEQ ID NO: 97        moltype = RNA    length = 20
FEATURE              Location/Qualifiers
source               1..20
                     mol_type = other RNA
                     organism = synthetic construct
SEQUENCE: 97
gctctagcta tttgttcaaa                                                   20
```

```
SEQ ID NO: 98              moltype = RNA   length = 20
FEATURE                    Location/Qualifiers
source                     1..20
                           mol_type = other RNA
                           organism = synthetic construct
SEQUENCE: 98
cttcaagagc tgagggcaaa                                                  20

SEQ ID NO: 99              moltype = RNA   length = 20
FEATURE                    Location/Qualifiers
source                     1..20
                           mol_type = other RNA
                           organism = synthetic construct
SEQUENCE: 99
tcaccagagt aacagtctga                                                  20

SEQ ID NO: 100             moltype = RNA   length = 20
FEATURE                    Location/Qualifiers
source                     1..20
                           mol_type = other RNA
                           organism = synthetic construct
SEQUENCE: 100
gttactaagg aaactgccat                                                  20

SEQ ID NO: 101             moltype = RNA   length = 20
FEATURE                    Location/Qualifiers
source                     1..20
                           mol_type = other RNA
                           organism = synthetic construct
SEQUENCE: 101
gcagatttca accgggcttg                                                  20

SEQ ID NO: 102             moltype = RNA   length = 20
FEATURE                    Location/Qualifiers
source                     1..20
                           mol_type = other RNA
                           organism = synthetic construct
SEQUENCE: 102
gttgaaagaa ttcagaatca                                                  20

SEQ ID NO: 103             moltype = RNA   length = 20
FEATURE                    Location/Qualifiers
source                     1..20
                           mol_type = other RNA
                           organism = synthetic construct
SEQUENCE: 103
gggaccctcc ttccatgact                                                  20

SEQ ID NO: 104             moltype = RNA   length = 20
FEATURE                    Location/Qualifiers
source                     1..20
                           mol_type = other RNA
                           organism = synthetic construct
SEQUENCE: 104
cttctaaatt aactttagtg                                                  20

SEQ ID NO: 105             moltype = RNA   length = 20
FEATURE                    Location/Qualifiers
source                     1..20
                           mol_type = other RNA
                           organism = synthetic construct
SEQUENCE: 105
ttcaccaaat ggattaagat                                                  20

SEQ ID NO: 106             moltype = RNA   length = 20
FEATURE                    Location/Qualifiers
source                     1..20
                           mol_type = other RNA
                           organism = synthetic construct
SEQUENCE: 106
gtgacacaac ctgtggttac                                                  20

SEQ ID NO: 107             moltype = RNA   length = 20
FEATURE                    Location/Qualifiers
source                     1..20
                           mol_type = other RNA
                           organism = synthetic construct
SEQUENCE: 107
```
tagggtggtt ggctaaaata                                                     20

SEQ ID NO: 108         moltype = RNA   length = 20
FEATURE                Location/Qualifiers
source                 1..20
                       mol_type = other RNA
                       organism = synthetic construct
SEQUENCE: 108
gctcctactc agactgttac                                                     20

SEQ ID NO: 109         moltype = RNA   length = 20
FEATURE                Location/Qualifiers
source                 1..20
                       mol_type = other RNA
                       organism = synthetic construct
SEQUENCE: 109
ttctagttga aagaattcag                                                     20

SEQ ID NO: 110         moltype = RNA   length = 20
FEATURE                Location/Qualifiers
source                 1..20
                       mol_type = other RNA
                       organism = synthetic construct
SEQUENCE: 110
ctgtataggg accctccttc                                                     20

SEQ ID NO: 111         moltype = RNA   length = 20
FEATURE                Location/Qualifiers
source                 1..20
                       mol_type = other RNA
                       organism = synthetic construct
SEQUENCE: 111
ccctcagctc ttgaagtaaa                                                     20

SEQ ID NO: 112         moltype = RNA   length = 20
FEATURE                Location/Qualifiers
source                 1..20
                       mol_type = other RNA
                       organism = synthetic construct
SEQUENCE: 112
acatttcatt caactgttgc                                                     20

SEQ ID NO: 113         moltype = RNA   length = 20
FEATURE                Location/Qualifiers
source                 1..20
                       mol_type = other RNA
                       organism = synthetic construct
SEQUENCE: 113
agctctgagt ggaaggcggt                                                     20

SEQ ID NO: 114         moltype = RNA   length = 20
FEATURE                Location/Qualifiers
source                 1..20
                       mol_type = other RNA
                       organism = synthetic construct
SEQUENCE: 114
gccaaccacc ctacaaatat                                                     20

SEQ ID NO: 115         moltype = RNA   length = 20
FEATURE                Location/Qualifiers
source                 1..20
                       mol_type = other RNA
                       organism = synthetic construct
SEQUENCE: 115
tatgcttttc tgttaaagag                                                     20

SEQ ID NO: 116         moltype = RNA   length = 20
FEATURE                Location/Qualifiers
source                 1..20
                       mol_type = other RNA
                       organism = synthetic construct
SEQUENCE: 116
cttttctgtt aaagaggaag                                                     20

SEQ ID NO: 117         moltype = RNA   length = 20
FEATURE                Location/Qualifiers
source                 1..20
                       mol_type = other RNA
                       organism = synthetic construct

```
SEQUENCE: 117
ttgaatcctt taacatttca                                                    20

SEQ ID NO: 118          moltype = RNA   length = 20
FEATURE                 Location/Qualifiers
source                  1..20
                        mol_type = other RNA
                        organism = synthetic construct
SEQUENCE: 118
cttcatccca ctgattctga                                                    20

SEQ ID NO: 119          moltype = RNA   length = 20
FEATURE                 Location/Qualifiers
source                  1..20
                        mol_type = other RNA
                        organism = synthetic construct
SEQUENCE: 119
aattaacttt agtgggtaga                                                    20

SEQ ID NO: 120          moltype = RNA   length = 20
FEATURE                 Location/Qualifiers
source                  1..20
                        mol_type = other RNA
                        organism = synthetic construct
SEQUENCE: 120
gtatcttaca ggaactccag                                                    20

SEQ ID NO: 121          moltype = RNA   length = 20
FEATURE                 Location/Qualifiers
source                  1..20
                        mol_type = other RNA
                        organism = synthetic construct
SEQUENCE: 121
aggattgctg aattatttct                                                    20

SEQ ID NO: 122          moltype = RNA   length = 20
FEATURE                 Location/Qualifiers
source                  1..20
                        mol_type = other RNA
                        organism = synthetic construct
SEQUENCE: 122
tttttgagga ttgctgaatt                                                    20

SEQ ID NO: 123          moltype = RNA   length = 20
FEATURE                 Location/Qualifiers
source                  1..20
                        mol_type = other RNA
                        organism = synthetic construct
SEQUENCE: 123
tgcttttctg ttaaagagga                                                    20

SEQ ID NO: 124          moltype = RNA   length = 20
FEATURE                 Location/Qualifiers
source                  1..20
                        mol_type = other RNA
                        organism = synthetic construct
SEQUENCE: 124
gtgggtagaa tttcttttaa                                                    20

SEQ ID NO: 125          moltype = RNA   length = 89
FEATURE                 Location/Qualifiers
source                  1..89
                        mol_type = other RNA
                        organism = synthetic construct
SEQUENCE: 125
acagcttatt tggaagctga aatgtgaggt ttataacact cacaagaatc ctgaaaaagg        60
atgccaaaca gcgtcatttg acgctgtct                                          89

SEQ ID NO: 126          moltype = RNA   length = 89
FEATURE                 Location/Qualifiers
source                  1..89
                        mol_type = other RNA
                        organism = synthetic construct
SEQUENCE: 126
acagcttatt tggaagctga aatgtgaggt ttataacact cacaagaatc ctgaaaaagg        60
atgccaaaca agagctgatg ctcgccctc                                          89

SEQ ID NO: 127          moltype = RNA   length = 89
FEATURE                 Location/Qualifiers
```

```
source                  1..89
                        mol_type = other RNA
                        organism = synthetic construct
SEQUENCE: 127
acagcttatt tggaagctga aatgtgaggt ttataacact cacaagaatc ctgaaaaagg    60
atgccaaaca ggctagagga ctgagccag                                      89

SEQ ID NO: 128          moltype = RNA   length = 89
FEATURE                 Location/Qualifiers
source                  1..89
                        mol_type = other RNA
                        organism = synthetic construct
SEQUENCE: 128
acagcttatt tggaagctga aatgtgaggt ttataacact cacaagaatc ctgaaaaagg    60
atgccaaacc cccaccggcg ctggtgccc                                      89

SEQ ID NO: 129          moltype = RNA   length = 89
FEATURE                 Location/Qualifiers
source                  1..89
                        mol_type = other RNA
                        organism = synthetic construct
SEQUENCE: 129
acagcttatt tggaagctga aatgtgaggt ttataacact cacaagaatc ctgaaaaagg    60
atgccaaacg ggttttgtcc tcactctga                                      89

SEQ ID NO: 130          moltype = RNA   length = 89
FEATURE                 Location/Qualifiers
source                  1..89
                        mol_type = other RNA
                        organism = synthetic construct
SEQUENCE: 130
acagcttatt tggaagctga aatgtgaggt ttataacact cacaagaatc ctgaaaaagg    60
atgccaaaca cgctgtctgg ggagggcga                                      89

SEQ ID NO: 131          moltype = RNA   length = 89
FEATURE                 Location/Qualifiers
source                  1..89
                        mol_type = other RNA
                        organism = synthetic construct
SEQUENCE: 131
acagcttatt tggaagctga aatgtgaggt ttataacact cacaagaatc ctgaaaaagg    60
atgccaaacg ccaccgccac cttccgccg                                      89

SEQ ID NO: 132          moltype = RNA   length = 89
FEATURE                 Location/Qualifiers
source                  1..89
                        mol_type = other RNA
                        organism = synthetic construct
SEQUENCE: 132
acagcttatt tggaagctga aatgtgaggt ttataacact cacaagaatc ctgaaaaagg    60
atgccaaacc gtggctgcgg tggccgctg                                      89

SEQ ID NO: 133          moltype = RNA   length = 89
FEATURE                 Location/Qualifiers
source                  1..89
                        mol_type = other RNA
                        organism = synthetic construct
SEQUENCE: 133
acagcttatt tggaagctga aatgtgaggt ttataacact cacaagaatc ctgaaaaagg    60
atgccaaacc agcccaatta ggatttggg                                      89

SEQ ID NO: 134          moltype = RNA   length = 89
FEATURE                 Location/Qualifiers
source                  1..89
                        mol_type = other RNA
                        organism = synthetic construct
SEQUENCE: 134
acagcttatt tggaagctga aatgtgaggt ttataacact cacaagaatc ctgaaaaagg    60
atgccaaacg ggagggcgag gccgaaacc                                      89

SEQ ID NO: 135          moltype = RNA   length = 89
FEATURE                 Location/Qualifiers
source                  1..89
                        mol_type = other RNA
                        organism = synthetic construct
SEQUENCE: 135
acagcttatt tggaagctga aatgtgaggt ttataacact cacaagaatc ctgaaaaagg    60
atgccaaact cctcactctg agcgtcatt                                      89
```

```
SEQ ID NO: 136         moltype = RNA   length = 89
FEATURE                Location/Qualifiers
source                 1..89
                       mol_type = other RNA
                       organism = synthetic construct
SEQUENCE: 136
acagcttatt tggaagctga aatgtgaggt ttataacact cacaagaatc ctgaaaaagg   60
atgccaaacg ggagccaagg actggctca                                    89

SEQ ID NO: 137         moltype = RNA   length = 89
FEATURE                Location/Qualifiers
source                 1..89
                       mol_type = other RNA
                       organism = synthetic construct
SEQUENCE: 137
acagcttatt tggaagctga aatgtgaggt ttataacact cacaagaatc ctgaaaaagg   60
atgccaaacg ggtgtgggta ctggacgcc                                    89

SEQ ID NO: 138         moltype = RNA   length = 89
FEATURE                Location/Qualifiers
source                 1..89
                       mol_type = other RNA
                       organism = synthetic construct
SEQUENCE: 138
acagcttatt tggaagctga aatgtgaggt ttataacact cacaagaatc ctgaaaaagg   60
atgccaaacg gtactggacg cctggggc                                     89

SEQ ID NO: 139         moltype = RNA   length = 89
FEATURE                Location/Qualifiers
source                 1..89
                       mol_type = other RNA
                       organism = synthetic construct
SEQUENCE: 139
acagcttatt tggaagctga aatgtgaggt ttataacact cacaagaatc ctgaaaaagg   60
atgccaaaca ttaaacatta acgggcccc                                    89

SEQ ID NO: 140         moltype = RNA   length = 89
FEATURE                Location/Qualifiers
source                 1..89
                       mol_type = other RNA
                       organism = synthetic construct
SEQUENCE: 140
acagcttatt tggaagctga aatgtgaggt ttataacact cacaagaatc ctgaaaaagg   60
atgccaaacc ggcctcatca gccaggcca                                    89

SEQ ID NO: 141         moltype = RNA   length = 89
FEATURE                Location/Qualifiers
source                 1..89
                       mol_type = other RNA
                       organism = synthetic construct
SEQUENCE: 141
acagcttatt tggaagctga aatgtgaggt ttataacact cacaagaatc ctgaaaaagg   60
atgccaaact catcaaggtt ctacatatc                                    89

SEQ ID NO: 142         moltype = RNA   length = 89
FEATURE                Location/Qualifiers
source                 1..89
                       mol_type = other RNA
                       organism = synthetic construct
SEQUENCE: 142
acagcttatt tggaagctga aatgtgaggt ttataacact cacaagaatc ctgaaaaagg   60
atgccaaaca cctcttccct ggcttcttg                                    89

SEQ ID NO: 143         moltype = RNA   length = 89
FEATURE                Location/Qualifiers
source                 1..89
                       mol_type = other RNA
                       organism = synthetic construct
SEQUENCE: 143
acagcttatt tggaagctga aatgtgaggt ttataacact cacaagaatc ctgaaaaagg   60
atgccaaacg tgctgatgga ggagaccca                                    89

SEQ ID NO: 144         moltype = RNA   length = 89
FEATURE                Location/Qualifiers
source                 1..89
                       mol_type = other RNA
                       organism = synthetic construct
SEQUENCE: 144
acagcttatt tggaagctga aatgtgaggt ttataacact cacaagaatc ctgaaaaagg   60
```

```
atgccaaacg gtctcctcca tcagcacca                                      89

SEQ ID NO: 145           moltype = RNA   length = 89
FEATURE                  Location/Qualifiers
source                   1..89
                         mol_type = other RNA
                         organism = synthetic construct
SEQUENCE: 145
acagcttatt tggaagctga aatgtgaggt ttataacact cacaagaatc ctgaaaaagg    60
atgccaaacc aggcggtggg cagtttgtt                                      89

SEQ ID NO: 146           moltype = RNA   length = 89
FEATURE                  Location/Qualifiers
source                   1..89
                         mol_type = other RNA
                         organism = synthetic construct
SEQUENCE: 146
acagcttatt tggaagctga aatgtgaggt ttataacact cacaagaatc ctgaaaaagg    60
atgccaaact agaaccttga tgacatagc                                      89

SEQ ID NO: 147           moltype = RNA   length = 89
FEATURE                  Location/Qualifiers
source                   1..89
                         mol_type = other RNA
                         organism = synthetic construct
SEQUENCE: 147
acagcttatt tggaagctga aatgtgaggt ttataacact cacaagaatc ctgaaaaagg    60
atgccaaact agcctctggg tctcctcca                                      89

SEQ ID NO: 148           moltype = RNA   length = 89
FEATURE                  Location/Qualifiers
source                   1..89
                         mol_type = other RNA
                         organism = synthetic construct
SEQUENCE: 148
acagcttatt tggaagctga aatgtgaggt ttataacact cacaagaatc ctgaaaaagg    60
atgccaaact tcaatctgta gcctctggg                                      89

SEQ ID NO: 149           moltype = RNA   length = 89
FEATURE                  Location/Qualifiers
source                   1..89
                         mol_type = other RNA
                         organism = synthetic construct
SEQUENCE: 149
acagcttatt tggaagctga aatgtgaggt ttataacact cacaagaatc ctgaaaaagg    60
atgccaaact cttcgcccag agcatccca                                      89

SEQ ID NO: 150           moltype = RNA   length = 89
FEATURE                  Location/Qualifiers
source                   1..89
                         mol_type = other RNA
                         organism = synthetic construct
SEQUENCE: 150
acagcttatt tggaagctga aatgtgaggt ttataacact cacaagaatc ctgaaaaagg    60
atgccaaacg agtacattga ggaagactc                                      89

SEQ ID NO: 151           moltype = RNA   length = 89
FEATURE                  Location/Qualifiers
source                   1..89
                         mol_type = other RNA
                         organism = synthetic construct
SEQUENCE: 151
acagcttatt tggaagctga aatgtgaggt ttataacact cacaagaatc ctgaaaaagg    60
atgccaaact ctggtgccat gctgggata                                      89

SEQ ID NO: 152           moltype = RNA   length = 89
FEATURE                  Location/Qualifiers
source                   1..89
                         mol_type = other RNA
                         organism = synthetic construct
SEQUENCE: 152
acagcttatt tggaagctga aatgtgaggt ttataacact cacaagaatc ctgaaaaagg    60
atgccaaacg tgccatgctg ggataattc                                      89

SEQ ID NO: 153           moltype = RNA   length = 89
FEATURE                  Location/Qualifiers
source                   1..89
                         mol_type = other RNA
                         organism = synthetic construct
```

```
SEQUENCE: 153
acagcttatt tggaagctga aatgtgaggt ttataacact cacaagaatc ctgaaaaagg    60
atgccaaacg gcgaagacaa aggagtctt                                      89

SEQ ID NO: 154          moltype = RNA   length = 89
FEATURE                 Location/Qualifiers
source                  1..89
                        mol_type = other RNA
                        organism = synthetic construct
SEQUENCE: 154
acagcttatt tggaagctga aatgtgaggt ttataacact cacaagaatc ctgaaaaagg    60
atgccaaacg aagcgtgtcc catcctcct                                      89

SEQ ID NO: 155          moltype = RNA   length = 89
FEATURE                 Location/Qualifiers
source                  1..89
                        mol_type = other RNA
                        organism = synthetic construct
SEQUENCE: 155
acagcttatt tggaagctga aatgtgaggt ttataacact cacaagaatc ctgaaaaagg    60
atgccaaact ggaagcgtgt cccatcctc                                      89

SEQ ID NO: 156          moltype = RNA   length = 89
FEATURE                 Location/Qualifiers
source                  1..89
                        mol_type = other RNA
                        organism = synthetic construct
SEQUENCE: 156
acagcttatt tggaagctga aatgtgaggt ttataacact cacaagaatc ctgaaaaagg    60
atgccaaaca cagccacggc acccacctg                                      89

SEQ ID NO: 157          moltype = RNA   length = 89
FEATURE                 Location/Qualifiers
source                  1..89
                        mol_type = other RNA
                        organism = synthetic construct
SEQUENCE: 157
acagcttatt tggaagctga aatgtgaggt ttataacact cacaagaatc ctgaaaaagg    60
atgccaaacc tcaactgtca agggaaggg                                      89

SEQ ID NO: 158          moltype = RNA   length = 89
FEATURE                 Location/Qualifiers
source                  1..89
                        mol_type = other RNA
                        organism = synthetic construct
SEQUENCE: 158
acagcttatt tggaagctga aatgtgaggt ttataacact cacaagaatc ctgaaaaagg    60
atgccaaacg ccagggcac cagcctgca                                       89

SEQ ID NO: 159          moltype = RNA   length = 89
FEATURE                 Location/Qualifiers
source                  1..89
                        mol_type = other RNA
                        organism = synthetic construct
SEQUENCE: 159
acagcttatt tggaagctga aatgtgaggt ttataacact cacaagaatc ctgaaaaagg    60
atgccaaacg tcagcggccg ggatgctgg                                      89

SEQ ID NO: 160          moltype = RNA   length = 89
FEATURE                 Location/Qualifiers
source                  1..89
                        mol_type = other RNA
                        organism = synthetic construct
SEQUENCE: 160
acagcttatt tggaagctga aatgtgaggt ttataacact cacaagaatc ctgaaaaagg    60
atgccaaacc aggctggtgc ccttggcca                                      89

SEQ ID NO: 161          moltype = RNA   length = 89
FEATURE                 Location/Qualifiers
source                  1..89
                        mol_type = other RNA
                        organism = synthetic construct
SEQUENCE: 161
acagcttatt tggaagctga aatgtgaggt ttataacact cacaagaatc ctgaaaaagg    60
atgccaaaca gggtgccgct gactgtgcc                                      89

SEQ ID NO: 162          moltype = RNA   length = 89
FEATURE                 Location/Qualifiers
source                  1..89
```

```
                        mol_type = other RNA
                        organism = synthetic construct
SEQUENCE: 162
acagcttatt tggaagctga aatgtgaggt ttataacact cacaagaatc ctgaaaaagg   60
atgccaaacc ccttcccttg acagttgag                                    89

SEQ ID NO: 163          moltype = RNA   length = 89
FEATURE                 Location/Qualifiers
source                  1..89
                        mol_type = other RNA
                        organism = synthetic construct
SEQUENCE: 163
acagcttatt tggaagctga aatgtgaggt ttataacact cacaagaatc ctgaaaaagg   60
atgccaaacc tgcccctggc cggtgggta                                    89

SEQ ID NO: 164          moltype = RNA   length = 89
FEATURE                 Location/Qualifiers
source                  1..89
                        mol_type = other RNA
                        organism = synthetic construct
SEQUENCE: 164
acagcttatt tggaagctga aatgtgaggt ttataacact cacaagaatc ctgaaaaagg   60
atgccaaacg agcagaagct ggggagtag                                    89

SEQ ID NO: 165          moltype = RNA   length = 89
FEATURE                 Location/Qualifiers
source                  1..89
                        mol_type = other RNA
                        organism = synthetic construct
SEQUENCE: 165
acagcttatt tggaagctga aatgtgaggt ttataacact cacaagaatc ctgaaaaagg   60
atgccaaacg atctctttgc ccccgggaa                                    89

SEQ ID NO: 166          moltype = RNA   length = 89
FEATURE                 Location/Qualifiers
source                  1..89
                        mol_type = other RNA
                        organism = synthetic construct
SEQUENCE: 166
acagcttatt tggaagctga aatgtgaggt ttataacact cacaagaatc ctgaaaaagg   60
atgccaaacg ggactaattt tggacgctg                                    89

SEQ ID NO: 167          moltype = RNA   length = 89
FEATURE                 Location/Qualifiers
source                  1..89
                        mol_type = other RNA
                        organism = synthetic construct
SEQUENCE: 167
acagcttatt tggaagctga aatgtgaggt ttataacact cacaagaatc ctgaaaaagg   60
atgccaaact ggatctcttt gcccccggg                                    89

SEQ ID NO: 168          moltype = RNA   length = 89
FEATURE                 Location/Qualifiers
source                  1..89
                        mol_type = other RNA
                        organism = synthetic construct
SEQUENCE: 168
acagcttatt tggaagctga aatgtgaggt ttataacact cacaagaatc ctgaaaaagg   60
atgccaaacc ccccgggaag gacatcatc                                    89

SEQ ID NO: 169          moltype = RNA   length = 89
FEATURE                 Location/Qualifiers
source                  1..89
                        mol_type = other RNA
                        organism = synthetic construct
SEQUENCE: 169
acagcttatt tggaagctga aatgtgaggt ttataacact cacaagaatc ctgaaaaagg   60
atgccaaacg acgctgtgtg gatctctttt                                   89

SEQ ID NO: 170          moltype = RNA   length = 89
FEATURE                 Location/Qualifiers
source                  1..89
                        mol_type = other RNA
                        organism = synthetic construct
SEQUENCE: 170
acagcttatt tggaagctga aatgtgaggt ttataacact cacaagaatc ctgaaaaagg   60
atgccaaaca catgaagcat gtgctgcag                                    89

SEQ ID NO: 171          moltype = RNA   length = 89
```

```
FEATURE                 Location/Qualifiers
source                  1..89
                        mol_type = other RNA
                        organism = synthetic construct
SEQUENCE: 171
acagcttatt tggaagctga aatgtgaggt ttataacact cacaagaatc ctgaaaaagg   60
atgccaaacc tgcagtcact ggacgctcc                                    89

SEQ ID NO: 172          moltype = RNA  length = 89
FEATURE                 Location/Qualifiers
source                  1..89
                        mol_type = other RNA
                        organism = synthetic construct
SEQUENCE: 172
acagcttatt tggaagctga aatgtgaggt ttataacact cacaagaatc ctgaaaaagg   60
atgccaaaca ggtcccactc tgtgacatg                                    89

SEQ ID NO: 173          moltype = RNA  length = 89
FEATURE                 Location/Qualifiers
source                  1..89
                        mol_type = other RNA
                        organism = synthetic construct
SEQUENCE: 173
acagcttatt tggaagctga aatgtgaggt ttataacact cacaagaatc ctgaaaaagg   60
atgccaaact gacatgaagc atgtgctgc                                    89

SEQ ID NO: 174          moltype = RNA  length = 89
FEATURE                 Location/Qualifiers
source                  1..89
                        mol_type = other RNA
                        organism = synthetic construct
SEQUENCE: 174
acagcttatt tggaagctga aatgtgaggt ttataacact cacaagaatc ctgaaaaagg   60
atgccaaacg ctcggatgct gagccggga                                    89

SEQ ID NO: 175          moltype = RNA  length = 89
FEATURE                 Location/Qualifiers
source                  1..89
                        mol_type = other RNA
                        organism = synthetic construct
SEQUENCE: 175
acagcttatt tggaagctga aatgtgaggt ttataacact cacaagaatc ctgaaaaagg   60
atgccaaacg tagagaagtg gatcagcct                                    89

SEQ ID NO: 176          moltype = RNA  length = 89
FEATURE                 Location/Qualifiers
source                  1..89
                        mol_type = other RNA
                        organism = synthetic construct
SEQUENCE: 176
acagcttatt tggaagctga aatgtgaggt ttataacact cacaagaatc ctgaaaaagg   60
atgccaaacg ccaccaggtt gggggtcag                                    89

SEQ ID NO: 177          moltype = RNA  length = 89
FEATURE                 Location/Qualifiers
source                  1..89
                        mol_type = other RNA
                        organism = synthetic construct
SEQUENCE: 177
acagcttatt tggaagctga aatgtgaggt ttataacact cacaagaatc ctgaaaaagg   60
atgccaaacg gctcccggct cagcatccg                                    89

SEQ ID NO: 178          moltype = RNA  length = 89
FEATURE                 Location/Qualifiers
source                  1..89
                        mol_type = other RNA
                        organism = synthetic construct
SEQUENCE: 178
acagcttatt tggaagctga aatgtgaggt ttataacact cacaagaatc ctgaaaaagg   60
atgccaaacc cgcagctcgg ccagggtaa                                    89

SEQ ID NO: 179          moltype = RNA  length = 89
FEATURE                 Location/Qualifiers
source                  1..89
                        mol_type = other RNA
                        organism = synthetic construct
SEQUENCE: 179
acagcttatt tggaagctga aatgtgaggt ttataacact cacaagaatc ctgaaaaagg   60
atgccaaacc cccagaagag gagctgctg                                    89
```

```
SEQ ID NO: 180          moltype = RNA   length = 89
FEATURE                 Location/Qualifiers
source                  1..89
                        mol_type = other RNA
                        organism = synthetic construct
SEQUENCE: 180
acagcttatt tggaagctga aatgtgaggt ttataacact cacaagaatc ctgaaaaagg    60
atgccaaact aggacggtgt ggtcggcac                                     89

SEQ ID NO: 181          moltype = RNA   length = 89
FEATURE                 Location/Qualifiers
source                  1..89
                        mol_type = other RNA
                        organism = synthetic construct
SEQUENCE: 181
acagcttatt tggaagctga aatgtgaggt ttataacact cacaagaatc ctgaaaaagg    60
atgccaaacg tcggcacact cggggccca                                     89

SEQ ID NO: 182          moltype = RNA   length = 89
FEATURE                 Location/Qualifiers
source                  1..89
                        mol_type = other RNA
                        organism = synthetic construct
SEQUENCE: 182
acagcttatt tggaagctga aatgtgaggt ttataacact cacaagaatc ctgaaaaagg    60
atgccaaacc cgaccacacc gtcctacag                                     89

SEQ ID NO: 183          moltype = RNA   length = 89
FEATURE                 Location/Qualifiers
source                  1..89
                        mol_type = other RNA
                        organism = synthetic construct
SEQUENCE: 183
acagcttatt tggaagctga aatgtgaggt ttataacact cacaagaatc ctgaaaaagg    60
atgccaaacg ggcacagcgg gctgtagct                                     89

SEQ ID NO: 184          moltype = RNA   length = 89
FEATURE                 Location/Qualifiers
source                  1..89
                        mol_type = other RNA
                        organism = synthetic construct
SEQUENCE: 184
acagcttatt tggaagctga aatgtgaggt ttataacact cacaagaatc ctgaaaaagg    60
atgccaaacc aaggccctca atgcatttg                                     89

SEQ ID NO: 185          moltype = RNA   length = 89
FEATURE                 Location/Qualifiers
source                  1..89
                        mol_type = other RNA
                        organism = synthetic construct
SEQUENCE: 185
acagcttatt tggaagctga aatgtgaggt ttataacact cacaagaatc ctgaaaaagg    60
atgccaaacc cgtcgcgaga tgctgcctg                                     89

SEQ ID NO: 186          moltype = RNA   length = 89
FEATURE                 Location/Qualifiers
source                  1..89
                        mol_type = other RNA
                        organism = synthetic construct
SEQUENCE: 186
acagcttatt tggaagctga aatgtgaggt ttataacact cacaagaatc ctgaaaaagg    60
atgccaaacg gggtgagggt gtctatgcc                                     89

SEQ ID NO: 187          moltype = RNA   length = 89
FEATURE                 Location/Qualifiers
source                  1..89
                        mol_type = other RNA
                        organism = synthetic construct
SEQUENCE: 187
acagcttatt tggaagctga aatgtgaggt ttataacact cacaagaatc ctgaaaaagg    60
atgccaaacg ctgcaggggt gttgtggat                                     89

SEQ ID NO: 188          moltype = RNA   length = 89
FEATURE                 Location/Qualifiers
source                  1..89
                        mol_type = other RNA
                        organism = synthetic construct
SEQUENCE: 188
```

```
acagcttatt tggaagctga aatgtgaggt ttataacact cacaagaatc ctgaaaaagg    60
atgccaaaca gaacatggtc cttctggtg                                      89

SEQ ID NO: 189          moltype = RNA   length = 89
FEATURE                 Location/Qualifiers
source                  1..89
                        mol_type = other RNA
                        organism = synthetic construct
SEQUENCE: 189
acagcttatt tggaagctga aatgtgaggt ttataacact cacaagaatc ctgaaaaagg    60
atgccaaacg tggcagtgga catgggtct                                      89

SEQ ID NO: 190          moltype = RNA   length = 89
FEATURE                 Location/Qualifiers
source                  1..89
                        mol_type = other RNA
                        organism = synthetic construct
SEQUENCE: 190
acagcttatt tggaagctga aatgtgaggt ttataacact cacaagaatc ctgaaaaagg    60
atgccaaacg atgctgcagt tggcacggg                                      89

SEQ ID NO: 191          moltype = RNA   length = 89
FEATURE                 Location/Qualifiers
source                  1..89
                        mol_type = other RNA
                        organism = synthetic construct
SEQUENCE: 191
acagcttatt tggaagctga aatgtgaggt ttataacact cacaagaatc ctgaaaaagg    60
atgccaaacc ttcctgctgc catgcccca                                      89

SEQ ID NO: 192          moltype = RNA   length = 89
FEATURE                 Location/Qualifiers
source                  1..89
                        mol_type = other RNA
                        organism = synthetic construct
SEQUENCE: 192
acagcttatt tggaagctga aatgtgaggt ttataacact cacaagaatc ctgaaaaagg    60
atgccaaacc attccagccc tggggcatg                                      89

SEQ ID NO: 193          moltype = RNA   length = 89
FEATURE                 Location/Qualifiers
source                  1..89
                        mol_type = other RNA
                        organism = synthetic construct
SEQUENCE: 193
acagcttatt tggaagctga aatgtgaggt ttataacact cacaagaatc ctgaaaaagg    60
atgccaaaca aggacctgag atcccatgc                                      89

SEQ ID NO: 194          moltype = RNA   length = 89
FEATURE                 Location/Qualifiers
source                  1..89
                        mol_type = other RNA
                        organism = synthetic construct
SEQUENCE: 194
acagcttatt tggaagctga aatgtgaggt ttataacact cacaagaatc ctgaaaaagg    60
atgccaaacg acctcagcgc aggctgcct                                      89

SEQ ID NO: 195          moltype = RNA   length = 89
FEATURE                 Location/Qualifiers
source                  1..89
                        mol_type = other RNA
                        organism = synthetic construct
SEQUENCE: 195
acagcttatt tggaagctga aatgtgaggt ttataacact cacaagaatc ctgaaaaagg    60
atgccaaaca aagccacaag gacagtcaa                                      89

SEQ ID NO: 196          moltype = RNA   length = 89
FEATURE                 Location/Qualifiers
source                  1..89
                        mol_type = other RNA
                        organism = synthetic construct
SEQUENCE: 196
acagcttatt tggaagctga aatgtgaggt ttataacact cacaagaatc ctgaaaaagg    60
atgccaaacg aagcacctcc ttcacggtc                                      89

SEQ ID NO: 197          moltype = RNA   length = 89
FEATURE                 Location/Qualifiers
source                  1..89
                        mol_type = other RNA
```

```
                        organism = synthetic construct
SEQUENCE: 197
acagcttatt tggaagctga aatgtgaggt ttataacact cacaagaatc ctgaaaaagg    60
atgccaaacg ccagctgctc cagtgtacc                                     89

SEQ ID NO: 198          moltype = RNA  length = 89
FEATURE                 Location/Qualifiers
source                  1..89
                        mol_type = other RNA
                        organism = synthetic construct
SEQUENCE: 198
acagcttatt tggaagctga aatgtgaggt ttataacact cacaagaatc ctgaaaaagg    60
atgccaaaca gctcttctgt ctttttata                                     89

SEQ ID NO: 199          moltype = RNA  length = 89
FEATURE                 Location/Qualifiers
source                  1..89
                        mol_type = other RNA
                        organism = synthetic construct
SEQUENCE: 199
acagcttatt tggaagctga aatgtgaggt ttataacact cacaagaatc ctgaaaaagg    60
atgccaaacg cctgcgaagc aggatggac                                     89

SEQ ID NO: 200          moltype = RNA  length = 89
FEATURE                 Location/Qualifiers
source                  1..89
                        mol_type = other RNA
                        organism = synthetic construct
SEQUENCE: 200
acagcttatt tggaagctga aatgtgaggt ttataacact cacaagaatc ctgaaaaagg    60
atgccaaact agtgactttt cagaataaa                                     89

SEQ ID NO: 201          moltype = RNA  length = 89
FEATURE                 Location/Qualifiers
source                  1..89
                        mol_type = other RNA
                        organism = synthetic construct
SEQUENCE: 201
acagcttatt tggaagctga aatgtgaggt ttataacact cacaagaatc ctgaaaaagg    60
atgccaaact ggcaagagtc catgacact                                     89

SEQ ID NO: 202          moltype = RNA  length = 89
FEATURE                 Location/Qualifiers
source                  1..89
                        mol_type = other RNA
                        organism = synthetic construct
SEQUENCE: 202
acagcttatt tggaagctga aatgtgaggt ttataacact cacaagaatc ctgaaaaagg    60
atgccaaact gtggcaagag tccatgaca                                     89

SEQ ID NO: 203          moltype = RNA  length = 89
FEATURE                 Location/Qualifiers
source                  1..89
                        mol_type = other RNA
                        organism = synthetic construct
SEQUENCE: 203
acagcttatt tggaagctga aatgtgaggt ttataacact cacaagaatc ctgaaaaagg    60
atgccaaacc tgccggagcc ggccttcag                                     89

SEQ ID NO: 204          moltype = RNA  length = 89
FEATURE                 Location/Qualifiers
source                  1..89
                        mol_type = other RNA
                        organism = synthetic construct
SEQUENCE: 204
acagcttatt tggaagctga aatgtgaggt ttataacact cacaagaatc ctgaaaaagg    60
atgccaaacg cttgctcctg gacctatac                                     89

SEQ ID NO: 205          moltype = RNA  length = 89
FEATURE                 Location/Qualifiers
source                  1..89
                        mol_type = other RNA
                        organism = synthetic construct
SEQUENCE: 205
acagcttatt tggaagctga aatgtgaggt ttataacact cacaagaatc ctgaaaaagg    60
atgccaaacc ttggctttct gccatcaga                                     89

SEQ ID NO: 206          moltype = RNA  length = 89
FEATURE                 Location/Qualifiers
```

```
source                  1..89
                        mol_type = other RNA
                        organism = synthetic construct
SEQUENCE: 206
acagcttatt tggaagctga aatgtgaggt ttataacact cacaagaatc ctgaaaaagg    60
atgccaaacg gagcctacag cgtggacaa                                      89

SEQ ID NO: 207          moltype = RNA   length = 89
FEATURE                 Location/Qualifiers
source                  1..89
                        mol_type = other RNA
                        organism = synthetic construct
SEQUENCE: 207
acagcttatt tggaagctga aatgtgaggt ttataacact cacaagaatc ctgaaaaagg    60
atgccaaacc catcagacat taagctgta                                      89

SEQ ID NO: 208          moltype = RNA   length = 89
FEATURE                 Location/Qualifiers
source                  1..89
                        mol_type = other RNA
                        organism = synthetic construct
SEQUENCE: 208
acagcttatt tggaagctga aatgtgaggt ttataacact cacaagaatc ctgaaaaagg    60
atgccaaacc acacctccag gggtggatc                                      89

SEQ ID NO: 209          moltype = RNA   length = 89
FEATURE                 Location/Qualifiers
source                  1..89
                        mol_type = other RNA
                        organism = synthetic construct
SEQUENCE: 209
acagcttatt tggaagctga aatgtgaggt ttataacact cacaagaatc ctgaaaaagg    60
atgccaaacc ctgcatggct ctcttgtag                                      89

SEQ ID NO: 210          moltype = RNA   length = 89
FEATURE                 Location/Qualifiers
source                  1..89
                        mol_type = other RNA
                        organism = synthetic construct
SEQUENCE: 210
acagcttatt tggaagctga aatgtgaggt ttataacact cacaagaatc ctgaaaaagg    60
atgccaaacc agggttttgt agttttat                                       89

SEQ ID NO: 211          moltype = RNA   length = 89
FEATURE                 Location/Qualifiers
source                  1..89
                        mol_type = other RNA
                        organism = synthetic construct
SEQUENCE: 211
acagcttatt tggaagctga aatgtgaggt ttataacact cacaagaatc ctgaaaaagg    60
atgccaaact actggagaac catacagga                                      89

SEQ ID NO: 212          moltype = RNA   length = 89
FEATURE                 Location/Qualifiers
source                  1..89
                        mol_type = other RNA
                        organism = synthetic construct
SEQUENCE: 212
acagcttatt tggaagctga aatgtgaggt ttataacact cacaagaatc ctgaaaaagg    60
atgccaaact tgcttttgta acttgatat                                      89

SEQ ID NO: 213          moltype = RNA   length = 89
FEATURE                 Location/Qualifiers
source                  1..89
                        mol_type = other RNA
                        organism = synthetic construct
SEQUENCE: 213
acagcttatt tggaagctga aatgtgaggt ttataacact cacaagaatc ctgaaaaagg    60
atgccaaaca gccctcatct gactctcag                                      89

SEQ ID NO: 214          moltype = RNA   length = 89
FEATURE                 Location/Qualifiers
source                  1..89
                        mol_type = other RNA
                        organism = synthetic construct
SEQUENCE: 214
acagcttatt tggaagctga aatgtgaggt ttataacact cacaagaatc ctgaaaaagg    60
atgccaaacc tccctggggc atccctcac                                      89
```

```
SEQ ID NO: 215           moltype = RNA   length = 89
FEATURE                  Location/Qualifiers
source                   1..89
                         mol_type = other RNA
                         organism = synthetic construct
SEQUENCE: 215
acagcttatt tggaagctga aatgtgaggt ttataacact cacaagaatc ctgaaaaagg   60
atgccaaact ctttcaggaa gatcataat                                    89

SEQ ID NO: 216           moltype = RNA   length = 89
FEATURE                  Location/Qualifiers
source                   1..89
                         mol_type = other RNA
                         organism = synthetic construct
SEQUENCE: 216
acagcttatt tggaagctga aatgtgaggt ttataacact cacaagaatc ctgaaaaagg   60
atgccaaact cttttatag taagcttcc                                     89

SEQ ID NO: 217           moltype = RNA   length = 89
FEATURE                  Location/Qualifiers
source                   1..89
                         mol_type = other RNA
                         organism = synthetic construct
SEQUENCE: 217
acagcttatt tggaagctga aatgtgaggt ttataacact cacaagaatc ctgaaaaagg   60
atgccaaacc tgcagggctt tggccctgc                                    89

SEQ ID NO: 218           moltype = RNA   length = 89
FEATURE                  Location/Qualifiers
source                   1..89
                         mol_type = other RNA
                         organism = synthetic construct
SEQUENCE: 218
acagcttatt tggaagctga aatgtgaggt ttataacact cacaagaatc ctgaaaaagg   60
atgccaaacc tatgagccct catctgact                                    89

SEQ ID NO: 219           moltype = RNA   length = 89
FEATURE                  Location/Qualifiers
source                   1..89
                         mol_type = other RNA
                         organism = synthetic construct
SEQUENCE: 219
acagcttatt tggaagctga aatgtgaggt ttataacact cacaagaatc ctgaaaaagg   60
atgccaaaca ctctcagttt gtactggag                                    89

SEQ ID NO: 220           moltype = RNA   length = 89
FEATURE                  Location/Qualifiers
source                   1..89
                         mol_type = other RNA
                         organism = synthetic construct
SEQUENCE: 220
acagcttatt tggaagctga aatgtgaggt ttataacact cacaagaatc ctgaaaaagg   60
atgccaaacc gtgggagaac ttggtgtct                                    89

SEQ ID NO: 221           moltype = RNA   length = 89
FEATURE                  Location/Qualifiers
source                   1..89
                         mol_type = other RNA
                         organism = synthetic construct
SEQUENCE: 221
acagcttatt tggaagctga aatgtgaggt ttataacact cacaagaatc ctgaaaaagg   60
atgccaaacg caagagtcca tgacactgc                                    89

SEQ ID NO: 222           moltype = RNA   length = 89
FEATURE                  Location/Qualifiers
source                   1..89
                         mol_type = other RNA
                         organism = synthetic construct
SEQUENCE: 222
acagcttatt tggaagctga aatgtgaggt ttataacact cacaagaatc ctgaaaaagg   60
atgccaaacc actgactggc ctcattttA                                    89

SEQ ID NO: 223           moltype = RNA   length = 89
FEATURE                  Location/Qualifiers
source                   1..89
                         mol_type = other RNA
                         organism = synthetic construct
SEQUENCE: 223
acagcttatt tggaagctga aatgtgaggt ttataacact cacaagaatc ctgaaaaagg   60
```

```
atgccaaaca aggaagagac aggaccaga                                             89

SEQ ID NO: 224          moltype = RNA   length = 89
FEATURE                 Location/Qualifiers
source                  1..89
                        mol_type = other RNA
                        organism = synthetic construct
SEQUENCE: 224
acagcttatt tggaagctga aatgtgaggt ttataacact cacaagaatc ctgaaaaagg           60
atgccaaact aacttgatat ttatgcagg                                             89

SEQ ID NO: 225          moltype = RNA   length = 89
FEATURE                 Location/Qualifiers
source                  1..89
                        mol_type = other RNA
                        organism = synthetic construct
SEQUENCE: 225
acagcttatt tggaagctga aatgtgaggt ttataacact cacaagaatc ctgaaaaagg           60
atgccaaacg gctccctgat taaatgcag                                             89

SEQ ID NO: 226          moltype = RNA   length = 89
FEATURE                 Location/Qualifiers
source                  1..89
                        mol_type = other RNA
                        organism = synthetic construct
SEQUENCE: 226
acagcttatt tggaagctga aatgtgaggt ttataacact cacaagaatc ctgaaaaagg           60
atgccaaacg ccctgctcag gataatgtg                                             89

SEQ ID NO: 227          moltype = RNA   length = 89
FEATURE                 Location/Qualifiers
source                  1..89
                        mol_type = other RNA
                        organism = synthetic construct
SEQUENCE: 227
acagcttatt tggaagctga aatgtgaggt ttataacact cacaagaatc ctgaaaaagg           60
atgccaaaca acctccaagg atctctgtc                                             89

SEQ ID NO: 228          moltype = RNA   length = 89
FEATURE                 Location/Qualifiers
source                  1..89
                        mol_type = other RNA
                        organism = synthetic construct
SEQUENCE: 228
acagcttatt tggaagctga aatgtgaggt ttataacact cacaagaatc ctgaaaaagg           60
atgccaaacc tgaaggccgg ctccggcag                                             89

SEQ ID NO: 229          moltype = RNA   length = 89
FEATURE                 Location/Qualifiers
source                  1..89
                        mol_type = other RNA
                        organism = synthetic construct
SEQUENCE: 229
acagcttatt tggaagctga aatgtgaggt ttataacact cacaagaatc ctgaaaaagg           60
atgccaaaca atttatgtcc tgacatcac                                             89

SEQ ID NO: 230          moltype = RNA   length = 89
FEATURE                 Location/Qualifiers
source                  1..89
                        mol_type = other RNA
                        organism = synthetic construct
SEQUENCE: 230
acagcttatt tggaagctga aatgtgaggt ttataacact cacaagaatc ctgaaaaagg           60
atgccaaaca gttgactgtc cttgtggct                                             89

SEQ ID NO: 231          moltype = RNA   length = 89
FEATURE                 Location/Qualifiers
source                  1..89
                        mol_type = other RNA
                        organism = synthetic construct
SEQUENCE: 231
acagcttatt tggaagctga aatgtgaggt ttataacact cacaagaatc ctgaaaaagg           60
atgccaaact gggactgggg ctaagggag                                             89

SEQ ID NO: 232          moltype = RNA   length = 89
FEATURE                 Location/Qualifiers
source                  1..89
                        mol_type = other RNA
                        organism = synthetic construct
```

```
SEQUENCE: 232
acagcttatt tggaagctga aatgtgaggt ttataacact cacaagaatc ctgaaaaagg      60
atgccaaacg aagatatagg tatggcctt                                       89

SEQ ID NO: 233          moltype = RNA   length = 89
FEATURE                 Location/Qualifiers
source                  1..89
                        mol_type = other RNA
                        organism = synthetic construct
SEQUENCE: 233
acagcttatt tggaagctga aatgtgaggt ttataacact cacaagaatc ctgaaaaagg      60
atgccaaaca catcgcctct ctggtcctg                                       89

SEQ ID NO: 234          moltype = RNA   length = 89
FEATURE                 Location/Qualifiers
source                  1..89
                        mol_type = other RNA
                        organism = synthetic construct
SEQUENCE: 234
acagcttatt tggaagctga aatgtgaggt ttataacact cacaagaatc ctgaaaaagg      60
atgccaaacg ttctccagta caaactgag                                       89

SEQ ID NO: 235          moltype = RNA   length = 89
FEATURE                 Location/Qualifiers
source                  1..89
                        mol_type = other RNA
                        organism = synthetic construct
SEQUENCE: 235
acagcttatt tggaagctga aatgtgaggt ttataacact cacaagaatc ctgaaaaagg      60
atgccaaacg tcctgtctct tccttcata                                       89

SEQ ID NO: 236          moltype = RNA   length = 89
FEATURE                 Location/Qualifiers
source                  1..89
                        mol_type = other RNA
                        organism = synthetic construct
SEQUENCE: 236
acagcttatt tggaagctga aatgtgaggt ttataacact cacaagaatc ctgaaaaagg      60
atgccaaacg ccttggtaca gtcgccctc                                       89

SEQ ID NO: 237          moltype = RNA   length = 89
FEATURE                 Location/Qualifiers
source                  1..89
                        mol_type = other RNA
                        organism = synthetic construct
SEQUENCE: 237
acagcttatt tggaagctga aatgtgaggt ttataacact cacaagaatc ctgaaaaagg      60
atgccaaacg ctacaagaga gccatgcag                                       89

SEQ ID NO: 238          moltype = RNA   length = 89
FEATURE                 Location/Qualifiers
source                  1..89
                        mol_type = other RNA
                        organism = synthetic construct
SEQUENCE: 238
acagcttatt tggaagctga aatgtgaggt ttataacact cacaagaatc ctgaaaaagg      60
atgccaaacc tctggcagtg tcatggact                                       89

SEQ ID NO: 239          moltype = RNA   length = 89
FEATURE                 Location/Qualifiers
source                  1..89
                        mol_type = other RNA
                        organism = synthetic construct
SEQUENCE: 239
acagcttatt tggaagctga aatgtgaggt ttataacact cacaagaatc ctgaaaaagg      60
atgccaaacg cttctccact ggtcctgtc                                       89

SEQ ID NO: 240          moltype = RNA   length = 89
FEATURE                 Location/Qualifiers
source                  1..89
                        mol_type = other RNA
                        organism = synthetic construct
SEQUENCE: 240
acagcttatt tggaagctga aatgtgaggt ttataacact cacaagaatc ctgaaaaagg      60
atgccaaacc atttaatcag ggagcccaa                                       89

SEQ ID NO: 241          moltype = RNA   length = 89
FEATURE                 Location/Qualifiers
source                  1..89
```

```
                        mol_type = other RNA
                        organism = synthetic construct
SEQUENCE: 241
acagcttatt tggaagctga aatgtgaggt ttataacact cacaagaatc ctgaaaaagg     60
atgccaaact ccattatgat cttcctgaa                                       89

SEQ ID NO: 242          moltype = RNA   length = 89
FEATURE                 Location/Qualifiers
source                  1..89
                        mol_type = other RNA
                        organism = synthetic construct
SEQUENCE: 242
acagcttatt tggaagctga aatgtgaggt ttataacact cacaagaatc ctgaaaaagg     60
atgccaaaca gctggctgtg agttgactg                                       89

SEQ ID NO: 243          moltype = RNA   length = 89
FEATURE                 Location/Qualifiers
source                  1..89
                        mol_type = other RNA
                        organism = synthetic construct
SEQUENCE: 243
acagcttatt tggaagctga aatgtgaggt ttataacact cacaagaatc ctgaaaaagg     60
atgccaaacc agaactgatc tgcatttaa                                       89

SEQ ID NO: 244          moltype = RNA   length = 89
FEATURE                 Location/Qualifiers
source                  1..89
                        mol_type = other RNA
                        organism = synthetic construct
SEQUENCE: 244
acagcttatt tggaagctga aatgtgaggt ttataacact cacaagaatc ctgaaaaagg     60
atgccaaacg ccttacagct ggatccacc                                       89

SEQ ID NO: 245          moltype = RNA   length = 89
FEATURE                 Location/Qualifiers
source                  1..89
                        mol_type = other RNA
                        organism = synthetic construct
SEQUENCE: 245
acagcttatt tggaagctga aatgtgaggt ttataacact cacaagaatc ctgaaaaagg     60
atgccaaacg cagtgtcatg gactcttgc                                       89

SEQ ID NO: 246          moltype = RNA   length = 89
FEATURE                 Location/Qualifiers
source                  1..89
                        mol_type = other RNA
                        organism = synthetic construct
SEQUENCE: 246
acagcttatt tggaagctga aatgtgaggt ttataacact cacaagaatc ctgaaaaagg     60
atgccaaacc aatgtgagct ggctgtgag                                       89

SEQ ID NO: 247          moltype = RNA   length = 89
FEATURE                 Location/Qualifiers
source                  1..89
                        mol_type = other RNA
                        organism = synthetic construct
SEQUENCE: 247
acagcttatt tggaagctga aatgtgaggt ttataacact cacaagaatc ctgaaaaagg     60
atgccaaacg gactggggct aagggagta                                       89

SEQ ID NO: 248          moltype = RNA   length = 89
FEATURE                 Location/Qualifiers
source                  1..89
                        mol_type = other RNA
                        organism = synthetic construct
SEQUENCE: 248
acagcttatt tggaagctga aatgtgaggt ttataacact cacaagaatc ctgaaaaagg     60
atgccaaacg tacttggtct ttgaacctc                                       89

SEQ ID NO: 249          moltype = RNA   length = 89
FEATURE                 Location/Qualifiers
source                  1..89
                        mol_type = other RNA
                        organism = synthetic construct
SEQUENCE: 249
acagcttatt tggaagctga aatgtgaggt ttataacact cacaagaatc ctgaaaaagg     60
atgccaaact cctgacatca ctggctgtg                                       89

SEQ ID NO: 250          moltype = RNA   length = 89
```

```
FEATURE                 Location/Qualifiers
source                  1..89
                        mol_type = other RNA
                        organism = synthetic construct
SEQUENCE: 250
acagcttatt tggaagctga aatgtgaggt ttataacact cacaagaatc ctgaaaaagg    60
atgccaaact cactccagtc tccacctga                                      89

SEQ ID NO: 251          moltype = RNA  length = 89
FEATURE                 Location/Qualifiers
source                  1..89
                        mol_type = other RNA
                        organism = synthetic construct
SEQUENCE: 251
acagcttatt tggaagctga aatgtgaggt ttataacact cacaagaatc ctgaaaaagg    60
atgccaaacg ctttcagact caattttcc                                      89

SEQ ID NO: 252          moltype = RNA  length = 89
FEATURE                 Location/Qualifiers
source                  1..89
                        mol_type = other RNA
                        organism = synthetic construct
SEQUENCE: 252
acagcttatt tggaagctga aatgtgaggt ttataacact cacaagaatc ctgaaaaagg    60
atgccaaaca tggcagaaag ccaagcaca                                      89

SEQ ID NO: 253          moltype = RNA  length = 89
FEATURE                 Location/Qualifiers
source                  1..89
                        mol_type = other RNA
                        organism = synthetic construct
SEQUENCE: 253
acagcttatt tggaagctga aatgtgaggt ttataacact cacaagaatc ctgaaaaagg    60
atgccaaact gacatcgcct ctctggtcc                                      89

SEQ ID NO: 254          moltype = RNA  length = 89
FEATURE                 Location/Qualifiers
source                  1..89
                        mol_type = other RNA
                        organism = synthetic construct
SEQUENCE: 254
acagcttatt tggaagctga aatgtgaggt ttataacact cacaagaatc ctgaaaaagg    60
atgccaaacc tggtcagctg gtgtggcct                                      89

SEQ ID NO: 255          moltype = RNA  length = 89
FEATURE                 Location/Qualifiers
source                  1..89
                        mol_type = other RNA
                        organism = synthetic construct
SEQUENCE: 255
acagcttatt tggaagctga aatgtgaggt ttataacact cacaagaatc ctgaaaaagg    60
atgccaaaca tcttcctgaa agacaaata                                      89

SEQ ID NO: 256          moltype = RNA  length = 89
FEATURE                 Location/Qualifiers
source                  1..89
                        mol_type = other RNA
                        organism = synthetic construct
SEQUENCE: 256
acagcttatt tggaagctga aatgtgaggt ttataacact cacaagaatc ctgaaaaagg    60
atgccaaacc acccagcctc aagcaccat                                      89

SEQ ID NO: 257          moltype = RNA  length = 89
FEATURE                 Location/Qualifiers
source                  1..89
                        mol_type = other RNA
                        organism = synthetic construct
SEQUENCE: 257
acagcttatt tggaagctga aatgtgaggt ttataacact cacaagaatc ctgaaaaagg    60
atgccaaacg tacactggag cagctggcc                                      89

SEQ ID NO: 258          moltype =   length =
SEQUENCE: 258
000

SEQ ID NO: 259          moltype = RNA  length = 17
FEATURE                 Location/Qualifiers
source                  1..17
                        mol_type = other RNA
```

```
                           organism = synthetic construct
SEQUENCE: 259
gaaaaaggat gccaaac                                                          17

SEQ ID NO: 260         moltype = RNA   length = 89
FEATURE                Location/Qualifiers
source                 1..89
                       mol_type = other RNA
                       organism = synthetic construct
SEQUENCE: 260
acagcttatt tggaagctga aatgtgaggt ttataacact cacaagaatc ctgaaaaagg           60
atgccaaact tcactagcaa cctcaaaca                                             89

SEQ ID NO: 261         moltype = RNA   length = 89
FEATURE                Location/Qualifiers
source                 1..89
                       mol_type = other RNA
                       organism = synthetic construct
SEQUENCE: 261
acagcttatt tggaagctga aatgtgaggt ttataacact cacaagaatc ctgaaaaagg           60
atgccaaaca ctcctgagga gaagtctgc                                             89

SEQ ID NO: 262         moltype = RNA   length = 89
FEATURE                Location/Qualifiers
source                 1..89
                       mol_type = other RNA
                       organism = synthetic construct
SEQUENCE: 262
acagcttatt tggaagctga aatgtgaggt ttataacact cacaagaatc ctgaaaaagg           60
atgccaaaca agctagtcta gtgcaagct                                             89

SEQ ID NO: 263         moltype = RNA   length = 89
FEATURE                Location/Qualifiers
source                 1..89
                       mol_type = other RNA
                       organism = synthetic construct
SEQUENCE: 263
acagcttatt tggaagctga aatgtgaggt ttataacact cacaagaatc ctgaaaaagg           60
atgccaaacg tgcaagctaa cagttgctt                                             89

SEQ ID NO: 264         moltype = RNA   length = 89
FEATURE                Location/Qualifiers
source                 1..89
                       mol_type = other RNA
                       organism = synthetic construct
SEQUENCE: 264
acagcttatt tggaagctga aatgtgaggt ttataacact cacaagaatc ctgaaaaagg           60
atgccaaacc cttgtcaagg ctattggtc                                             89

SEQ ID NO: 265         moltype = RNA   length = 89
FEATURE                Location/Qualifiers
source                 1..89
                       mol_type = other RNA
                       organism = synthetic construct
SEQUENCE: 265
acagcttatt tggaagctga aatgtgaggt ttataacact cacaagaatc ctgaaaaagg           60
atgccaaacc attgagatag tgtggggaa                                             89

SEQ ID NO: 266         moltype = RNA   length = 89
FEATURE                Location/Qualifiers
source                 1..89
                       mol_type = other RNA
                       organism = synthetic construct
SEQUENCE: 266
acagcttatt tggaagctga aatgtgaggt ttataacact cacaagaatc ctgaaaaagg           60
atgccaaacc tcgcgctact ctctctttc                                             89

SEQ ID NO: 267         moltype = RNA   length = 89
FEATURE                Location/Qualifiers
source                 1..89
                       mol_type = other RNA
                       organism = synthetic construct
SEQUENCE: 267
acagcttatt tggaagctga aatgtgaggt ttataacact cacaagaatc ctgaaaaagg           60
atgccaaacg gtttcatcca tccgacatt                                             89

SEQ ID NO: 268         moltype = RNA   length = 89
FEATURE                Location/Qualifiers
source                 1..89
```

```
                       mol_type = other RNA
                       organism = synthetic construct
SEQUENCE: 268
acagcttatt tggaagctga aatgtgaggt ttataacact cacaagaatc ctgaaaaagg    60
atgccaaact ctcttgtact acactgaat                                     89

SEQ ID NO: 269         moltype =    length =
SEQUENCE: 269
000

SEQ ID NO: 270         moltype = RNA   length = 89
FEATURE                Location/Qualifiers
source                 1..89
                       mol_type = other RNA
                       organism = synthetic construct
SEQUENCE: 270
acagcttatt tggaagctga aatgtgaggt ttataacact cacaagaatc ctgaaaaagg    60
atgccaaacc ctgccgtgtg aaccatgtg                                     89

SEQ ID NO: 271         moltype =    length =
SEQUENCE: 271
000

SEQ ID NO: 272         moltype = RNA   length = 89
FEATURE                Location/Qualifiers
source                 1..89
                       mol_type = other RNA
                       organism = synthetic construct
SEQUENCE: 272
acagcttatt tggaagctga aatgtgaggt ttataacact cacaagaatc ctgaaaaagg    60
atgccaaaca ctttgtcaca gcccaagat                                     89

SEQ ID NO: 273         moltype = RNA   length = 89
FEATURE                Location/Qualifiers
source                 1..89
                       mol_type = other RNA
                       organism = synthetic construct
SEQUENCE: 273
acagcttatt tggaagctga aatgtgaggt ttataacact cacaagaatc ctgaaaaagg    60
atgccaaact ctgggtttca tccatccga                                     89

SEQ ID NO: 274         moltype = RNA   length = 89
FEATURE                Location/Qualifiers
source                 1..89
                       mol_type = other RNA
                       organism = synthetic construct
SEQUENCE: 274
acagcttatt tggaagctga aatgtgaggt ttataacact cacaagaatc ctgaaaaagg    60
atgccaaaca accatgtgac tttgtcaca                                     89

SEQ ID NO: 275         moltype = RNA   length = 89
FEATURE                Location/Qualifiers
source                 1..89
                       mol_type = other RNA
                       organism = synthetic construct
SEQUENCE: 275
acagcttatt tggaagctga aatgtgaggt ttataacact cacaagaatc ctgaaaaagg    60
atgccaaaca atgctccact ttttcaatt                                     89

SEQ ID NO: 276         moltype = RNA   length = 89
FEATURE                Location/Qualifiers
source                 1..89
                       mol_type = other RNA
                       organism = synthetic construct
SEQUENCE: 276
acagcttatt tggaagctga aatgtgaggt ttataacact cacaagaatc ctgaaaaagg    60
atgccaaaca ctttccattc tctgctgga                                     89

SEQ ID NO: 277         moltype = RNA   length = 89
FEATURE                Location/Qualifiers
source                 1..89
                       mol_type = other RNA
                       organism = synthetic construct
SEQUENCE: 277
acagcttatt tggaagctga aatgtgaggt ttataacact cacaagaatc ctgaaaaagg    60
atgccaaaca caaagtcaca tggttcaca                                     89

SEQ ID NO: 278         moltype = RNA   length = 89
FEATURE                Location/Qualifiers
```

```
                                  source          1..89
                                                  mol_type = other RNA
                                                  organism = synthetic construct
SEQUENCE: 278
acagcttatt tggaagctga aatgtgaggt ttataacact cacaagaatc ctgaaaaagg    60
atgccaaacg tacaagagat agaaagacc                                      89

SEQ ID NO: 279            moltype = RNA   length = 89
FEATURE                   Location/Qualifiers
source                    1..89
                          mol_type = other RNA
                          organism = synthetic construct
SEQUENCE: 279
acagcttatt tggaagctga aatgtgaggt ttataacact cacaagaatc ctgaaaaagg    60
atgccaaacc tggatgacgt gagtaaacc                                      89

SEQ ID NO: 280            moltype =   length =
SEQUENCE: 280
000

SEQ ID NO: 281            moltype =   length =
SEQUENCE: 281
000

SEQ ID NO: 282            moltype =   length =
SEQUENCE: 282
000

SEQ ID NO: 283            moltype =   length =
SEQUENCE: 283
000

SEQ ID NO: 284            moltype =   length =
SEQUENCE: 284
000

SEQ ID NO: 285            moltype =   length =
SEQUENCE: 285
000

SEQ ID NO: 286            moltype =   length =
SEQUENCE: 286
000

SEQ ID NO: 287            moltype =   length =
SEQUENCE: 287
000

SEQ ID NO: 288            moltype =   length =
SEQUENCE: 288
000

SEQ ID NO: 289            moltype =   length =
SEQUENCE: 289
000

SEQ ID NO: 290            moltype =   length =
SEQUENCE: 290
000

SEQ ID NO: 291            moltype =   length =
SEQUENCE: 291
000

SEQ ID NO: 292            moltype =   length =
SEQUENCE: 292
000

SEQ ID NO: 293            moltype =   length =
SEQUENCE: 293
000

SEQ ID NO: 294            moltype =   length =
SEQUENCE: 294
000

SEQ ID NO: 295            moltype =   length =
SEQUENCE: 295
000
```

| | | |
|---|---|---|
| SEQ ID NO: 296 | moltype = length = | |
| SEQUENCE: 296 | | |
| 000 | | |
| | | |
| SEQ ID NO: 297 | moltype = length = | |
| SEQUENCE: 297 | | |
| 000 | | |
| | | |
| SEQ ID NO: 298 | moltype = length = | |
| SEQUENCE: 298 | | |
| 000 | | |
| | | |
| SEQ ID NO: 299 | moltype = length = | |
| SEQUENCE: 299 | | |
| 000 | | |
| | | |
| SEQ ID NO: 300 | moltype = length = | |
| SEQUENCE: 300 | | |
| 000 | | |
| | | |
| SEQ ID NO: 301 | moltype = RNA length = 20 | |
| FEATURE | Location/Qualifiers | |
| source | 1..20 | |
| | mol_type = other RNA | |
| | organism = synthetic construct | |
| SEQUENCE: 301 | | |
| tcacagccca agatagttaa | | 20 |
| | | |
| SEQ ID NO: 302 | moltype = RNA length = 20 | |
| FEATURE | Location/Qualifiers | |
| source | 1..20 | |
| | mol_type = other RNA | |
| | organism = synthetic construct | |
| SEQUENCE: 302 | | |
| ctcacgtcat ccagcagaga | | 20 |
| | | |
| SEQ ID NO: 303 | moltype = length = | |
| SEQUENCE: 303 | | |
| 000 | | |
| | | |
| SEQ ID NO: 304 | moltype = length = | |
| SEQUENCE: 304 | | |
| 000 | | |
| | | |
| SEQ ID NO: 305 | moltype = length = | |
| SEQUENCE: 305 | | |
| 000 | | |
| | | |
| SEQ ID NO: 306 | moltype = length = | |
| SEQUENCE: 306 | | |
| 000 | | |
| | | |
| SEQ ID NO: 307 | moltype = length = | |
| SEQUENCE: 307 | | |
| 000 | | |
| | | |
| SEQ ID NO: 308 | moltype = length = | |
| SEQUENCE: 308 | | |
| 000 | | |
| | | |
| SEQ ID NO: 309 | moltype = length = | |
| SEQUENCE: 309 | | |
| 000 | | |
| | | |
| SEQ ID NO: 310 | moltype = length = | |
| SEQUENCE: 310 | | |
| 000 | | |
| | | |
| SEQ ID NO: 311 | moltype = length = | |
| SEQUENCE: 311 | | |
| 000 | | |
| | | |
| SEQ ID NO: 312 | moltype = length = | |
| SEQUENCE: 312 | | |
| 000 | | |
| | | |
| SEQ ID NO: 313 | moltype = length = | |
| SEQUENCE: 313 | | |

```
SEQ ID NO: 314          moltype =    length =
SEQUENCE: 314
000

SEQ ID NO: 315          moltype =    length =
SEQUENCE: 315
000

SEQ ID NO: 316          moltype =    length =
SEQUENCE: 316
000

SEQ ID NO: 317          moltype =    length =
SEQUENCE: 317
000

SEQ ID NO: 318          moltype =    length =
SEQUENCE: 318
000

SEQ ID NO: 319          moltype =    length =
SEQUENCE: 319
000

SEQ ID NO: 320          moltype =    length =
SEQUENCE: 320
000

SEQ ID NO: 321          moltype =    length =
SEQUENCE: 321
000

SEQ ID NO: 322          moltype =    length =
SEQUENCE: 322
000

SEQ ID NO: 323          moltype =    length =
SEQUENCE: 323
000

SEQ ID NO: 324          moltype =    length =
SEQUENCE: 324
000

SEQ ID NO: 325          moltype = RNA  length = 20
FEATURE                 Location/Qualifiers
source                  1..20
                        mol_type = other RNA
                        organism = synthetic construct
SEQUENCE: 325
ctcgcgctac tctctctttc                                               20

SEQ ID NO: 326          moltype = RNA  length = 20
FEATURE                 Location/Qualifiers
source                  1..20
                        mol_type = other RNA
                        organism = synthetic construct
SEQUENCE: 326
ggtttcatcc atccgacatt                                               20

SEQ ID NO: 327          moltype = RNA  length = 20
FEATURE                 Location/Qualifiers
source                  1..20
                        mol_type = other RNA
                        organism = synthetic construct
SEQUENCE: 327
tctcttgtac tacactgaat                                               20

SEQ ID NO: 328          moltype =    length =
SEQUENCE: 328
000

SEQ ID NO: 329          moltype = RNA  length = 20
FEATURE                 Location/Qualifiers
source                  1..20
                        mol_type = other RNA
                        organism = synthetic construct
```

```
SEQUENCE: 329
cctgccgtgt gaaccatgtg                                                    20

SEQ ID NO: 331          moltype = RNA  length = 20
FEATURE                 Location/Qualifiers
source                  1..20
                        mol_type = other RNA
                        organism = synthetic construct
SEQUENCE: 331
actttgtcac agcccaagat                                                    20

SEQ ID NO: 332          moltype = RNA  length = 20
FEATURE                 Location/Qualifiers
source                  1..20
                        mol_type = other RNA
                        organism = synthetic construct
SEQUENCE: 332
tctgggtttc atccatccga                                                    20

SEQ ID NO: 333          moltype = RNA  length = 20
FEATURE                 Location/Qualifiers
source                  1..20
                        mol_type = other RNA
                        organism = synthetic construct
SEQUENCE: 333
aaccatgtga ctttgtcaca                                                    20

SEQ ID NO: 334          moltype = RNA  length = 20
FEATURE                 Location/Qualifiers
source                  1..20
                        mol_type = other RNA
                        organism = synthetic construct
SEQUENCE: 334
aatgctccac tttttcaatt                                                    20

SEQ ID NO: 335          moltype = RNA  length = 20
FEATURE                 Location/Qualifiers
source                  1..20
                        mol_type = other RNA
                        organism = synthetic construct
SEQUENCE: 335
actttccatt ctctgctgga                                                    20

SEQ ID NO: 336          moltype = RNA  length = 20
FEATURE                 Location/Qualifiers
source                  1..20
                        mol_type = other RNA
                        organism = synthetic construct
SEQUENCE: 336
acaaagtcac atggttcaca                                                    20

SEQ ID NO: 337          moltype = RNA  length = 20
FEATURE                 Location/Qualifiers
source                  1..20
                        mol_type = other RNA
                        organism = synthetic construct
SEQUENCE: 337
gtacaagaga tagaaagacc                                                    20

SEQ ID NO: 338          moltype = RNA  length = 20
FEATURE                 Location/Qualifiers
source                  1..20
                        mol_type = other RNA
                        organism = synthetic construct
SEQUENCE: 338
ctggatgacg tgagtaaacc                                                    20

SEQ ID NO: 339          moltype =      length =
SEQUENCE: 339
000

SEQ ID NO: 340          moltype =      length =
SEQUENCE: 340
000
```

Note: SEQ ID NO: 330 appears before SEQ ID NO: 331 with moltype = length = and SEQUENCE: 330 000.

| | | |
|---|---|---|
| SEQ ID NO: 341<br>SEQUENCE: 341<br>000 | moltype = | length = |
| SEQ ID NO: 342<br>SEQUENCE: 342<br>000 | moltype = | length = |
| SEQ ID NO: 343<br>SEQUENCE: 343<br>000 | moltype = | length = |
| SEQ ID NO: 344<br>SEQUENCE: 344<br>000 | moltype = | length = |
| SEQ ID NO: 345<br>SEQUENCE: 345<br>000 | moltype = | length = |
| SEQ ID NO: 346<br>SEQUENCE: 346<br>000 | moltype = | length = |
| SEQ ID NO: 347<br>SEQUENCE: 347<br>000 | moltype = | length = |
| SEQ ID NO: 348<br>SEQUENCE: 348<br>000 | moltype = | length = |
| SEQ ID NO: 349<br>SEQUENCE: 349<br>000 | moltype = | length = |
| SEQ ID NO: 350<br>SEQUENCE: 350<br>000 | moltype = | length = |
| SEQ ID NO: 351<br>SEQUENCE: 351<br>000 | moltype = | length = |
| SEQ ID NO: 352<br>SEQUENCE: 352<br>000 | moltype = | length = |
| SEQ ID NO: 353<br>SEQUENCE: 353<br>000 | moltype = | length = |
| SEQ ID NO: 354<br>SEQUENCE: 354<br>000 | moltype = | length = |
| SEQ ID NO: 355<br>SEQUENCE: 355<br>000 | moltype = | length = |
| SEQ ID NO: 356<br>SEQUENCE: 356<br>000 | moltype = | length = |
| SEQ ID NO: 357<br>SEQUENCE: 357<br>000 | moltype = | length = |
| SEQ ID NO: 358<br>SEQUENCE: 358<br>000 | moltype = | length = |
| SEQ ID NO: 359<br>SEQUENCE: 359<br>000 | moltype = | length = |
| SEQ ID NO: 360<br>SEQUENCE: 360<br>000 | moltype = | length = |

| | | |
|---|---|---|
| SEQ ID NO: 361 SEQUENCE: 361 | moltype = | length = 000 |
| SEQ ID NO: 362 SEQUENCE: 362 | moltype = | length = 000 |
| SEQ ID NO: 363 SEQUENCE: 363 | moltype = | length = 000 |
| SEQ ID NO: 364 SEQUENCE: 364 | moltype = | length = 000 |
| SEQ ID NO: 365 SEQUENCE: 365 | moltype = | length = 000 |
| SEQ ID NO: 366 SEQUENCE: 366 | moltype = | length = 000 |
| SEQ ID NO: 367 SEQUENCE: 367 | moltype = | length = 000 |
| SEQ ID NO: 368 SEQUENCE: 368 | moltype = | length = 000 |
| SEQ ID NO: 369 SEQUENCE: 369 | moltype = | length = 000 |
| SEQ ID NO: 370 SEQUENCE: 370 | moltype = | length = 000 |
| SEQ ID NO: 371 SEQUENCE: 371 | moltype = | length = 000 |
| SEQ ID NO: 372 SEQUENCE: 372 | moltype = | length = 000 |
| SEQ ID NO: 373 SEQUENCE: 373 | moltype = | length = 000 |
| SEQ ID NO: 374 SEQUENCE: 374 | moltype = | length = 000 |
| SEQ ID NO: 375 SEQUENCE: 375 | moltype = | length = 000 |
| SEQ ID NO: 376 SEQUENCE: 376 | moltype = | length = 000 |
| SEQ ID NO: 377 SEQUENCE: 377 | moltype = | length = 000 |
| SEQ ID NO: 378 SEQUENCE: 378 | moltype = | length = 000 |
| SEQ ID NO: 379 SEQUENCE: 379 | moltype = | length = 000 |
| SEQ ID NO: 380 SEQUENCE: 380 | moltype = | length = |

000

SEQ ID NO: 381         moltype =    length =
SEQUENCE: 381
000

SEQ ID NO: 382         moltype =    length =
SEQUENCE: 382
000

SEQ ID NO: 383         moltype =    length =
SEQUENCE: 383
000

SEQ ID NO: 384         moltype =    length =
SEQUENCE: 384
000

SEQ ID NO: 385         moltype =    length =
SEQUENCE: 385
000

SEQ ID NO: 386         moltype =    length =
SEQUENCE: 386
000

SEQ ID NO: 387         moltype =    length =
SEQUENCE: 387
000

SEQ ID NO: 388         moltype =    length =
SEQUENCE: 388
000

SEQ ID NO: 389         moltype =    length =
SEQUENCE: 389
000

SEQ ID NO: 390         moltype =    length =
SEQUENCE: 390
000

SEQ ID NO: 391         moltype =    length =
SEQUENCE: 391
000

SEQ ID NO: 392         moltype =    length =
SEQUENCE: 392
000

SEQ ID NO: 393         moltype =    length =
SEQUENCE: 393
000

SEQ ID NO: 394         moltype =    length =
SEQUENCE: 394
000

SEQ ID NO: 395         moltype =    length =
SEQUENCE: 395
000

SEQ ID NO: 396         moltype =    length =
SEQUENCE: 396
000

SEQ ID NO: 397         moltype =    length =
SEQUENCE: 397
000

SEQ ID NO: 398         moltype =    length =
SEQUENCE: 398
000

SEQ ID NO: 399         moltype =    length =
SEQUENCE: 399
000

SEQ ID NO: 400         moltype =    length =

| | | |
|---|---|---|
| SEQUENCE: 400 000 | | |
| SEQ ID NO: 401 SEQUENCE: 401 000 | moltype = | length = |
| SEQ ID NO: 402 SEQUENCE: 402 000 | moltype = | length = |
| SEQ ID NO: 403 SEQUENCE: 403 000 | moltype = | length = |
| SEQ ID NO: 404 SEQUENCE: 404 000 | moltype = | length = |
| SEQ ID NO: 405 SEQUENCE: 405 000 | moltype = | length = |
| SEQ ID NO: 406 SEQUENCE: 406 000 | moltype = | length = |
| SEQ ID NO: 407 SEQUENCE: 407 000 | moltype = | length = |
| SEQ ID NO: 408 SEQUENCE: 408 000 | moltype = | length = |
| SEQ ID NO: 409 SEQUENCE: 409 000 | moltype = | length = |
| SEQ ID NO: 410 SEQUENCE: 410 000 | moltype = | length = |
| SEQ ID NO: 411 SEQUENCE: 411 000 | moltype = | length = |
| SEQ ID NO: 412 SEQUENCE: 412 000 | moltype = | length = |
| SEQ ID NO: 413 SEQUENCE: 413 000 | moltype = | length = |
| SEQ ID NO: 414 SEQUENCE: 414 000 | moltype = | length = |
| SEQ ID NO: 415 SEQUENCE: 415 000 | moltype = | length = |
| SEQ ID NO: 416 SEQUENCE: 416 000 | moltype = | length = |
| SEQ ID NO: 417 SEQUENCE: 417 000 | moltype = | length = |
| SEQ ID NO: 418 SEQUENCE: 418 000 | moltype = | length = |
| SEQ ID NO: 419 SEQUENCE: 419 000 | moltype = | length = |

| | | |
|---|---|---|
| SEQ ID NO: 420
SEQUENCE: 420
000 | moltype = | length = |
| SEQ ID NO: 421
SEQUENCE: 421
000 | moltype = | length = |
| SEQ ID NO: 422
SEQUENCE: 422
000 | moltype = | length = |
| SEQ ID NO: 423
SEQUENCE: 423
000 | moltype = | length = |
| SEQ ID NO: 424
SEQUENCE: 424
000 | moltype = | length = |
| SEQ ID NO: 425
SEQUENCE: 425
000 | moltype = | length = |
| SEQ ID NO: 426
SEQUENCE: 426
000 | moltype = | length = |
| SEQ ID NO: 427
SEQUENCE: 427
000 | moltype = | length = |
| SEQ ID NO: 428
SEQUENCE: 428
000 | moltype = | length = |
| SEQ ID NO: 429
SEQUENCE: 429
000 | moltype = | length = |
| SEQ ID NO: 430
SEQUENCE: 430
000 | moltype = | length = |
| SEQ ID NO: 431
SEQUENCE: 431
000 | moltype = | length = |
| SEQ ID NO: 432
SEQUENCE: 432
000 | moltype = | length = |
| SEQ ID NO: 433
SEQUENCE: 433
000 | moltype = | length = |
| SEQ ID NO: 434
SEQUENCE: 434
000 | moltype = | length = |
| SEQ ID NO: 435
SEQUENCE: 435
000 | moltype = | length = |
| SEQ ID NO: 436
SEQUENCE: 436
000 | moltype = | length = |
| SEQ ID NO: 437
SEQUENCE: 437
000 | moltype = | length = |
| SEQ ID NO: 438
SEQUENCE: 438
000 | moltype = | length = |
| SEQ ID NO: 439
SEQUENCE: 439
000 | moltype = | length = |

SEQ ID NO: 440      moltype =     length =
SEQUENCE: 440
000

SEQ ID NO: 441      moltype =     length =
SEQUENCE: 441
000

SEQ ID NO: 442      moltype =     length =
SEQUENCE: 442
000

SEQ ID NO: 443      moltype =     length =
SEQUENCE: 443
000

SEQ ID NO: 444      moltype =     length =
SEQUENCE: 444
000

SEQ ID NO: 445      moltype =     length =
SEQUENCE: 445
000

SEQ ID NO: 446      moltype =     length =
SEQUENCE: 446
000

SEQ ID NO: 447      moltype =     length =
SEQUENCE: 447
000

SEQ ID NO: 448      moltype =     length =
SEQUENCE: 448
000

SEQ ID NO: 449      moltype =     length =
SEQUENCE: 449
000

SEQ ID NO: 450      moltype =     length =
SEQUENCE: 450
000

SEQ ID NO: 451      moltype =     length =
SEQUENCE: 451
000

SEQ ID NO: 452      moltype =     length =
SEQUENCE: 452
000

SEQ ID NO: 453      moltype =     length =
SEQUENCE: 453
000

SEQ ID NO: 454      moltype =     length =
SEQUENCE: 454
000

SEQ ID NO: 455      moltype =     length =
SEQUENCE: 455
000

SEQ ID NO: 456      moltype =     length =
SEQUENCE: 456
000

SEQ ID NO: 457      moltype =     length =
SEQUENCE: 457
000

SEQ ID NO: 458      moltype =     length =
SEQUENCE: 458
000

SEQ ID NO: 459      moltype =     length =
SEQUENCE: 459

```
SEQ ID NO: 460          moltype =    length =
SEQUENCE: 460
000

SEQ ID NO: 461          moltype =    length =
SEQUENCE: 461
000

SEQ ID NO: 462          moltype =    length =
SEQUENCE: 462
000

SEQ ID NO: 463          moltype =    length =
SEQUENCE: 463
000

SEQ ID NO: 464          moltype =    length =
SEQUENCE: 464
000

SEQ ID NO: 465          moltype =    length =
SEQUENCE: 465
000

SEQ ID NO: 466          moltype =    length =
SEQUENCE: 466
000

SEQ ID NO: 467          moltype =    length =
SEQUENCE: 467
000

SEQ ID NO: 468          moltype =    length =
SEQUENCE: 468
000

SEQ ID NO: 469          moltype =    length =
SEQUENCE: 469
000

SEQ ID NO: 470          moltype =    length =
SEQUENCE: 470
000

SEQ ID NO: 471          moltype =    length =
SEQUENCE: 471
000

SEQ ID NO: 472          moltype =    length =
SEQUENCE: 472
000

SEQ ID NO: 473          moltype =    length =
SEQUENCE: 473
000

SEQ ID NO: 474          moltype = RNA  length = 20
FEATURE                 Location/Qualifiers
source                  1..20
                        mol_type = other RNA
                        organism = synthetic construct
SEQUENCE: 474
ctacactgaa ttcaccccca                                                   20

SEQ ID NO: 475          moltype =    length =
SEQUENCE: 475
000

SEQ ID NO: 476          moltype =    length =
SEQUENCE: 476
000

SEQ ID NO: 477          moltype = RNA  length = 20
FEATURE                 Location/Qualifiers
source                  1..20
                        mol_type = other RNA
                        organism = synthetic construct
```

| | | |
|---|---|---|
| SEQUENCE: 477 | | |
| tgtctgggtt tcatccatcc | | 20 |
| SEQ ID NO: 478 SEQUENCE: 478 000 | moltype = length = | |
| SEQ ID NO: 479 SEQUENCE: 479 000 | moltype = length = | |
| SEQ ID NO: 480 SEQUENCE: 480 000 | moltype = length = | |
| SEQ ID NO: 481 SEQUENCE: 481 000 | moltype = length = | |
| SEQ ID NO: 482 SEQUENCE: 482 000 | moltype = length = | |
| SEQ ID NO: 483 SEQUENCE: 483 000 | moltype = length = | |
| SEQ ID NO: 484 SEQUENCE: 484 000 | moltype = length = | |
| SEQ ID NO: 485 SEQUENCE: 485 000 | moltype = length = | |
| SEQ ID NO: 486 SEQUENCE: 486 000 | moltype = length = | |
| SEQ ID NO: 487 SEQUENCE: 487 000 | moltype = length = | |
| SEQ ID NO: 488 FEATURE source | moltype = RNA length = 20 Location/Qualifiers 1..20 mol_type = other RNA organism = synthetic construct | |
| SEQUENCE: 488 | | |
| gtttattttt gttccacaag | | 20 |
| SEQ ID NO: 489 FEATURE source | moltype = RNA length = 20 Location/Qualifiers 1..20 mol_type = other RNA organism = synthetic construct | |
| SEQUENCE: 489 | | |
| cacaaaatgt agggttataa | | 20 |
| SEQ ID NO: 490 FEATURE source | moltype = RNA length = 20 Location/Qualifiers 1..20 mol_type = other RNA organism = synthetic construct | |
| SEQUENCE: 490 | | |
| ggggaaaatt tagaaatata | | 20 |
| SEQ ID NO: 491 FEATURE source | moltype = RNA length = 20 Location/Qualifiers 1..20 mol_type = other RNA organism = synthetic construct | |
| SEQUENCE: 491 | | |
| cttgcttgct ttttaatatt | | 20 |
| SEQ ID NO: 492 FEATURE source | moltype = RNA length = 20 Location/Qualifiers 1..20 mol_type = other RNA | |

-continued

```
SEQUENCE: 492
ctttgagtgc tgtctccatg                                              20

SEQ ID NO: 493         moltype = RNA   length = 20
FEATURE                Location/Qualifiers
source                 1..20
                       mol_type = other RNA
                       organism = synthetic construct
SEQUENCE: 493
ataaagtaag gcatggttgt                                              20

SEQ ID NO: 494         moltype = RNA   length = 20
FEATURE                Location/Qualifiers
source                 1..20
                       mol_type = other RNA
                       organism = synthetic construct
SEQUENCE: 494
gttaatctgg tttattttg                                               20

SEQ ID NO: 495         moltype = RNA   length = 20
FEATURE                Location/Qualifiers
source                 1..20
                       mol_type = other RNA
                       organism = synthetic construct
SEQUENCE: 495
atgtatctga gcaggttgct                                              20

SEQ ID NO: 496         moltype = RNA   length = 20
FEATURE                Location/Qualifiers
source                 1..20
                       mol_type = other RNA
                       organism = synthetic construct
SEQUENCE: 496
cttagaattt gggggaaaat                                              20

SEQ ID NO: 497         moltype = RNA   length = 20
FEATURE                Location/Qualifiers
source                 1..20
                       mol_type = other RNA
                       organism = synthetic construct
SEQUENCE: 497
gattggatga attccaaatt                                              20

SEQ ID NO: 498         moltype = RNA   length = 20
FEATURE                Location/Qualifiers
source                 1..20
                       mol_type = other RNA
                       organism = synthetic construct
SEQUENCE: 498
tgcacaaaat gtagggttat                                              20

SEQ ID NO: 499         moltype = RNA   length = 20
FEATURE                Location/Qualifiers
source                 1..20
                       mol_type = other RNA
                       organism = synthetic construct
SEQUENCE: 499
gaaatataat tgacaggatt                                              20

SEQ ID NO: 500         moltype = RNA   length = 20
FEATURE                Location/Qualifiers
source                 1..20
                       mol_type = other RNA
                       organism = synthetic construct
SEQUENCE: 500
agtgctgtct ccatgtttga                                              20

SEQ ID NO: 501         moltype = RNA   length = 20
FEATURE                Location/Qualifiers
source                 1..20
                       mol_type = other RNA
                       organism = synthetic construct
SEQUENCE: 501
ggagggctgg caacttagag                                              20

SEQ ID NO: 502         moltype = RNA   length = 20
FEATURE                Location/Qualifiers
source                 1..20
```

```
                              -continued mol_type = other RNA
                         organism = synthetic construct
SEQUENCE: 502
aactcttcaa tctcttgcac                                                 20

SEQ ID NO: 503           moltype = RNA  length = 20
FEATURE                  Location/Qualifiers
source                   1..20
                         mol_type = other RNA
                         organism = synthetic construct
SEQUENCE: 503
ataatgttaa catggacatg                                                 20

SEQ ID NO: 504           moltype = RNA  length = 20
FEATURE                  Location/Qualifiers
source                   1..20
                         mol_type = other RNA
                         organism = synthetic construct
SEQUENCE: 504
cttatacact tacactttat                                                 20

SEQ ID NO: 505           moltype = RNA  length = 20
FEATURE                  Location/Qualifiers
source                   1..20
                         mol_type = other RNA
                         organism = synthetic construct
SEQUENCE: 505
atattgatat gcttatacac                                                 20

SEQ ID NO: 506           moltype = RNA  length = 20
FEATURE                  Location/Qualifiers
source                   1..20
                         mol_type = other RNA
                         organism = synthetic construct
SEQUENCE: 506
gggttataat aatgttaaca                                                 20

SEQ ID NO: 507           moltype = RNA  length = 20
FEATURE                  Location/Qualifiers
source                   1..20
                         mol_type = other RNA
                         organism = synthetic construct
SEQUENCE: 507
catttgataa agtaaggcat                                                 20

SEQ ID NO: 508           moltype = RNA  length = 20
FEATURE                  Location/Qualifiers
source                   1..20
                         mol_type = other RNA
                         organism = synthetic construct
SEQUENCE: 508
tttttgttcc acaagttaaa                                                 20

SEQ ID NO: 509           moltype = RNA  length = 20
FEATURE                  Location/Qualifiers
source                   1..20
                         mol_type = other RNA
                         organism = synthetic construct
SEQUENCE: 509
ttccacaagt taaataaatc                                                 20

SEQ ID NO: 510           moltype = RNA  length = 20
FEATURE                  Location/Qualifiers
source                   1..20
                         mol_type = other RNA
                         organism = synthetic construct
SEQUENCE: 510
tctgagcagg ttgctccaca                                                 20

SEQ ID NO: 511           moltype = RNA  length = 20
FEATURE                  Location/Qualifiers
source                   1..20
                         mol_type = other RNA
                         organism = synthetic construct
SEQUENCE: 511
attctacttt gagtgctgtc                                                 20

SEQ ID NO: 512           moltype = RNA  length = 20
FEATURE                  Location/Qualifiers
```

```
source                      1..20
                            mol_type = other RNA
                            organism = synthetic construct
SEQUENCE: 512
agcaggttgc tccacaggta                                                    20

SEQ ID NO: 513              moltype = RNA  length = 20
FEATURE                     Location/Qualifiers
source                      1..20
                            mol_type = other RNA
                            organism = synthetic construct
SEQUENCE: 513
attgacagga ttattggaaa                                                    20

SEQ ID NO: 514              moltype = RNA  length = 20
FEATURE                     Location/Qualifiers
source                      1..20
                            mol_type = other RNA
                            organism = synthetic construct
SEQUENCE: 514
aagatgccgc atttggattg                                                    20

SEQ ID NO: 515              moltype = RNA  length = 20
FEATURE                     Location/Qualifiers
source                      1..20
                            mol_type = other RNA
                            organism = synthetic construct
SEQUENCE: 515
atgaatgaaa cattttgtca                                                    20

SEQ ID NO: 516              moltype = RNA  length = 20
FEATURE                     Location/Qualifiers
source                      1..20
                            mol_type = other RNA
                            organism = synthetic construct
SEQUENCE: 516
catactctgc ttagaatttg                                                    20

SEQ ID NO: 517              moltype = RNA  length = 20
FEATURE                     Location/Qualifiers
source                      1..20
                            mol_type = other RNA
                            organism = synthetic construct
SEQUENCE: 517
taattctact ttgagtgctg                                                    20

SEQ ID NO: 518              moltype = RNA  length = 20
FEATURE                     Location/Qualifiers
source                      1..20
                            mol_type = other RNA
                            organism = synthetic construct
SEQUENCE: 518
cacttacact ttatgcacaa                                                    20

SEQ ID NO: 519              moltype = RNA  length = 20
FEATURE                     Location/Qualifiers
source                      1..20
                            mol_type = other RNA
                            organism = synthetic construct
SEQUENCE: 519
accaagatgt tgatgttgga                                                    20

SEQ ID NO: 520              moltype = RNA  length = 20
FEATURE                     Location/Qualifiers
source                      1..20
                            mol_type = other RNA
                            organism = synthetic construct
SEQUENCE: 520
cataaagtgt aagtgtataa                                                    20

SEQ ID NO: 521              moltype = RNA  length = 20
FEATURE                     Location/Qualifiers
source                      1..20
                            mol_type = other RNA
                            organism = synthetic construct
SEQUENCE: 521
gaacaaaaat aaaccagatt                                                    20

SEQ ID NO: 522              moltype = RNA  length = 20
```

```
FEATURE                 Location/Qualifiers
source                  1..20
                        mol_type = other RNA
                        organism = synthetic construct
SEQUENCE: 522
ctccccacct ctaagttgcc                                                    20

SEQ ID NO: 523          moltype = RNA   length = 20
FEATURE                 Location/Qualifiers
source                  1..20
                        mol_type = other RNA
                        organism = synthetic construct
SEQUENCE: 523
agttgccagc cctcctagag                                                    20

SEQ ID NO: 524          moltype = RNA   length = 20
FEATURE                 Location/Qualifiers
source                  1..20
                        mol_type = other RNA
                        organism = synthetic construct
SEQUENCE: 524
aattggaagt taacttatgc                                                    20

SEQ ID NO: 525          moltype = RNA   length = 20
FEATURE                 Location/Qualifiers
source                  1..20
                        mol_type = other RNA
                        organism = synthetic construct
SEQUENCE: 525
agcagagtat gtaaattgga                                                    20

SEQ ID NO: 526          moltype = RNA   length = 20
FEATURE                 Location/Qualifiers
source                  1..20
                        mol_type = other RNA
                        organism = synthetic construct
SEQUENCE: 526
acaaatttcc aataatcctg                                                    20

SEQ ID NO: 527          moltype = RNA   length = 20
FEATURE                 Location/Qualifiers
source                  1..20
                        mol_type = other RNA
                        organism = synthetic construct
SEQUENCE: 527
cacgcttaac tatcttaaca                                                    20

SEQ ID NO: 528          moltype = RNA   length = 20
FEATURE                 Location/Qualifiers
source                  1..20
                        mol_type = other RNA
                        organism = synthetic construct
SEQUENCE: 528
tttaacttgt ggaacaaaaa                                                    20

SEQ ID NO: 529          moltype = RNA   length = 20
FEATURE                 Location/Qualifiers
source                  1..20
                        mol_type = other RNA
                        organism = synthetic construct
SEQUENCE: 529
tgatttattt aacttgtgga                                                    20

SEQ ID NO: 530          moltype = RNA   length = 20
FEATURE                 Location/Qualifiers
source                  1..20
                        mol_type = other RNA
                        organism = synthetic construct
SEQUENCE: 530
gagcaacctg ctcagataca                                                    20

SEQ ID NO: 531          moltype = RNA   length = 20
FEATURE                 Location/Qualifiers
source                  1..20
                        mol_type = other RNA
                        organism = synthetic construct
SEQUENCE: 531
acttgtggaa caaaaataaa                                                    20
```

-continued

SEQ ID NO: 532            moltype = RNA   length = 20
FEATURE                   Location/Qualifiers
source                    1..20
                          mol_type = other RNA
                          organism = synthetic construct
SEQUENCE: 532
agtgcaagag attgaagagt                                                       20

SEQ ID NO: 533            moltype = RNA   length = 20
FEATURE                   Location/Qualifiers
source                    1..20
                          mol_type = other RNA
                          organism = synthetic construct
SEQUENCE: 533
agtgtataag catatcaata                                                       20

SEQ ID NO: 534            moltype = RNA   length = 20
FEATURE                   Location/Qualifiers
source                    1..20
                          mol_type = other RNA
                          organism = synthetic construct
SEQUENCE: 534
atttatttaa cttgtggaac                                                       20

SEQ ID NO: 535            moltype = RNA   length = 20
FEATURE                   Location/Qualifiers
source                    1..20
                          mol_type = other RNA
                          organism = synthetic construct
SEQUENCE: 535
tgacaaaatg tttcattcat                                                       20

SEQ ID NO: 536            moltype = RNA   length = 20
FEATURE                   Location/Qualifiers
source                    1..20
                          mol_type = other RNA
                          organism = synthetic construct
SEQUENCE: 536
tgcataaagt gtaagtgtat                                                       20

SEQ ID NO: 537            moltype = RNA   length = 20
FEATURE                   Location/Qualifiers
source                    1..20
                          mol_type = other RNA
                          organism = synthetic construct
SEQUENCE: 537
aagaagatca tgtccatgtt                                                       20

SEQ ID NO: 538            moltype = RNA   length = 20
FEATURE                   Location/Qualifiers
source                    1..20
                          mol_type = other RNA
                          organism = synthetic construct
SEQUENCE: 538
aattttcccc caaattctaa                                                       20

SEQ ID NO: 539            moltype = RNA   length = 20
FEATURE                   Location/Qualifiers
source                    1..20
                          mol_type = other RNA
                          organism = synthetic construct
SEQUENCE: 539
gaattcatcc aatccaaatg                                                       20

SEQ ID NO: 540            moltype = RNA   length = 20
FEATURE                   Location/Qualifiers
source                    1..20
                          mol_type = other RNA
                          organism = synthetic construct
SEQUENCE: 540
tttctaaatt ttcccccaaa                                                       20

SEQ ID NO: 541            moltype = RNA   length = 20
FEATURE                   Location/Qualifiers
source                    1..20
                          mol_type = other RNA
                          organism = synthetic construct
SEQUENCE: 541
accctacatt ttgtgcataa                                                       20

```
SEQ ID NO: 542           moltype = RNA  length = 20
FEATURE                  Location/Qualifiers
source                   1..20
                         mol_type = other RNA
                         organism = synthetic construct
modified_base            18
                         mod_base = OTHER
                         note = 2'O-methyluridine phosphorothioate
modified_base            19
                         mod_base = OTHER
                         note = 2'O-methyluridine phosphorothioate
modified_base            20
                         mod_base = OTHER
                         note = 2'O-methylcytidine
SEQUENCE: 542
ctcgcgctac tctctctttc                                                  20

SEQ ID NO: 543           moltype = RNA  length = 20
FEATURE                  Location/Qualifiers
source                   1..20
                         mol_type = other RNA
                         organism = synthetic construct
modified_base            18
                         mod_base = OTHER
                         note = 2'O-methyladenosine phosphorothioate
modified_base            19
                         mod_base = OTHER
                         note = 2'O-methyluridine phosphorothioate
modified_base            20
                         mod_base = OTHER
                         note = 2'O-methyluridine
SEQUENCE: 543
ggtttcatcc atccgacatt                                                  20

SEQ ID NO: 544           moltype = RNA  length = 20
FEATURE                  Location/Qualifiers
source                   1..20
                         mol_type = other RNA
                         organism = synthetic construct
modified_base            18
                         mod_base = OTHER
                         note = 2'O-methylcytidine phosphorothioate
modified_base            19
                         mod_base = OTHER
                         note = 2'O-methylcytidine phosphorothioate
modified_base            20
                         mod_base = OTHER
                         note = 2'O-methyladenosine
SEQUENCE: 544
ctacactgaa ttcaccccca                                                  20

SEQ ID NO: 545           moltype = RNA  length = 20
FEATURE                  Location/Qualifiers
source                   1..20
                         mol_type = other RNA
                         organism = synthetic construct
modified_base            18
                         mod_base = OTHER
                         note = 2'O-methyladenosine phosphorothioate
modified_base            19
                         mod_base = OTHER
                         note = 2'O-methyladenosine phosphorothioate
modified_base            20
                         mod_base = OTHER
                         note = 2'O-methyluridine
SEQUENCE: 545
tctcttgtac tacactgaat                                                  20

SEQ ID NO: 546           moltype = RNA  length = 20
FEATURE                  Location/Qualifiers
source                   1..20
                         mol_type = other RNA
                         organism = synthetic construct
modified_base            18
                         mod_base = OTHER
                         note = 2'O-methyladenosine phosphorothioate
modified_base            19
                         mod_base = OTHER
```

|                 |                                                              |    |
|-----------------|--------------------------------------------------------------|----|
|                 | note = 2′O-methylguanosine phosphorothioate                  |    |
| modified_base   | 20                                                           |    |
|                 | mod_base = OTHER                                             |    |
|                 | note = 2′O-methyladenosine                                   |    |
| SEQUENCE: 546   |                                                              |    |
| ctcacgtcat ccagcagaga |                                                        | 20 |
|                 |                                                              |    |
| SEQ ID NO: 547  | moltype = RNA   length = 20                                  |    |
| FEATURE         | Location/Qualifiers                                          |    |
| source          | 1..20                                                        |    |
|                 | mol_type = other RNA                                         |    |
|                 | organism = synthetic construct                               |    |
| modified_base   | 18                                                           |    |
|                 | mod_base = OTHER                                             |    |
|                 | note = 2′O-methyluridine phosphorothioate                    |    |
| modified_base   | 19                                                           |    |
|                 | mod_base = OTHER                                             |    |
|                 | note = 2′O-methylcytidine phosphorothioate                   |    |
| modified_base   | 20                                                           |    |
|                 | mod_base = OTHER                                             |    |
|                 | note = 2′O-methylcytidine                                    |    |
| SEQUENCE: 547   |                                                              |    |
| tgtctgggtt tcatccatcc |                                                        | 20 |
|                 |                                                              |    |
| SEQ ID NO: 548  | moltype = RNA   length = 20                                  |    |
| FEATURE         | Location/Qualifiers                                          |    |
| source          | 1..20                                                        |    |
|                 | mol_type = other RNA                                         |    |
|                 | organism = synthetic construct                               |    |
| modified_base   | 18                                                           |    |
|                 | mod_base = OTHER                                             |    |
|                 | note = 2′O-methylguanosine phosphorothioate                  |    |
| modified_base   | 19                                                           |    |
|                 | mod_base = OTHER                                             |    |
|                 | note = 2′O-methyluridine phosphorothioate                    |    |
| modified_base   | 20                                                           |    |
|                 | mod_base = OTHER                                             |    |
|                 | note = 2′O-methylguanosine                                   |    |
| SEQUENCE: 548   |                                                              |    |
| cctgccgtgt gaaccatgtg |                                                        | 20 |
|                 |                                                              |    |
| SEQ ID NO: 549  | moltype = RNA   length = 20                                  |    |
| FEATURE         | Location/Qualifiers                                          |    |
| source          | 1..20                                                        |    |
|                 | mol_type = other RNA                                         |    |
|                 | organism = synthetic construct                               |    |
| modified_base   | 18                                                           |    |
|                 | mod_base = OTHER                                             |    |
|                 | note = 2′O-methyluridine phosphorothioate                    |    |
| modified_base   | 19                                                           |    |
|                 | mod_base = OTHER                                             |    |
|                 | note = 2′O-methyladenosine phosphorothioate                  |    |
| modified_base   | 20                                                           |    |
|                 | mod_base = OTHER                                             |    |
|                 | note = 2′O-methyladenosine                                   |    |
| SEQUENCE: 549   |                                                              |    |
| tcacagccca agatagttaa |                                                        | 20 |
|                 |                                                              |    |
| SEQ ID NO: 550  | moltype = RNA   length = 20                                  |    |
| FEATURE         | Location/Qualifiers                                          |    |
| source          | 1..20                                                        |    |
|                 | mol_type = other RNA                                         |    |
|                 | organism = synthetic construct                               |    |
| modified_base   | 18                                                           |    |
|                 | mod_base = OTHER                                             |    |
|                 | note = 2′O-methylguanosine phosphorothioate                  |    |
| modified_base   | 19                                                           |    |
|                 | mod_base = OTHER                                             |    |
|                 | note = 2′O-methyladenosine phosphorothioate                  |    |
| modified_base   | 20                                                           |    |
|                 | mod_base = OTHER                                             |    |
|                 | note = 2′O-methyluridine                                     |    |
| SEQUENCE: 550   |                                                              |    |
| actttgtcac agcccaagat |                                                        | 20 |
|                 |                                                              |    |
| SEQ ID NO: 551  | moltype = RNA   length = 20                                  |    |
| FEATURE         | Location/Qualifiers                                          |    |
| source          | 1..20                                                        |    |
|                 | mol_type = other RNA                                         |    |

```
                        organism = synthetic construct
modified_base           18
                        mod_base = OTHER
                        note = 2'O-methylcytidine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 551
tctgggtttc atccatccga                                                        20

SEQ ID NO: 552          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 552
aaccatgtga ctttgtcaca                                                        20

SEQ ID NO: 553          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methyluridine
SEQUENCE: 553
aatgctccac tttttcaatt                                                        20

SEQ ID NO: 554          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 554
actttccatt ctctgctgga                                                        20

SEQ ID NO: 555          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 555
```
acaaagtcac atggttcaca                                                    20

```
SEQ ID NO: 556          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methylcytidine phosphorothioate
modified_base           20
                        mod_base = OTHER
                        note = 2'O-methylcytidine
SEQUENCE: 556
```
gtacaagaga tagaaagacc                                                    20

```
SEQ ID NO: 557          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methylcytidine phosphorothioate
modified_base           20
                        mod_base = OTHER
                        note = 2'O-methylcytidine
SEQUENCE: 557
```
ctggatgacg tgagtaaacc                                                    20

```
SEQ ID NO: 558          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methylguanosine
SEQUENCE: 558
```
gtttattttt gttccacaag                                                    20

```
SEQ ID NO: 559          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 559
```
cacaaaatgt agggttataa                                                    20

```
SEQ ID NO: 560          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
```

|                    |                                                       |    |
|--------------------|-------------------------------------------------------|----|
|                    | mod_base = OTHER                                      |    |
|                    | note = 2'O-methyluridine phosphorothioate             |    |
| modified_base      | 20                                                    |    |
|                    | mod_base = OTHER                                      |    |
|                    | note = 2'O-methyladenosine                            |    |
| SEQUENCE: 560      |                                                       |    |
| ggggaaaatt tagaaatata |                                                     | 20 |
|                    |                                                       |    |
| SEQ ID NO: 561     | moltype = RNA   length = 20                           |    |
| FEATURE            | Location/Qualifiers                                   |    |
| source             | 1..20                                                 |    |
|                    | mol_type = other RNA                                  |    |
|                    | organism = synthetic construct                        |    |
| modified_base      | 18                                                    |    |
|                    | mod_base = OTHER                                      |    |
|                    | note = 2'O-methyladenosine phosphorothioate           |    |
| modified_base      | 19                                                    |    |
|                    | mod_base = OTHER                                      |    |
|                    | note = 2'O-methyluridine phosphorothioate             |    |
| modified_base      | 20                                                    |    |
|                    | mod_base = OTHER                                      |    |
|                    | note = 2'O-methyluridine                              |    |
| SEQUENCE: 561      |                                                       |    |
| cttgcttgct ttttaatatt |                                                     | 20 |
|                    |                                                       |    |
| SEQ ID NO: 562     | moltype = RNA   length = 20                           |    |
| FEATURE            | Location/Qualifiers                                   |    |
| source             | 1..20                                                 |    |
|                    | mol_type = other RNA                                  |    |
|                    | organism = synthetic construct                        |    |
| modified_base      | 18                                                    |    |
|                    | mod_base = OTHER                                      |    |
|                    | note = 2'O-methyladenosine phosphorothioate           |    |
| modified_base      | 19                                                    |    |
|                    | mod_base = OTHER                                      |    |
|                    | note = 2'O-methyluridine phosphorothioate             |    |
| modified_base      | 20                                                    |    |
|                    | mod_base = OTHER                                      |    |
|                    | note = 2'O-methylguanosine                            |    |
| SEQUENCE: 562      |                                                       |    |
| ctttgagtgc tgtctccatg |                                                     | 20 |
|                    |                                                       |    |
| SEQ ID NO: 563     | moltype = RNA   length = 20                           |    |
| FEATURE            | Location/Qualifiers                                   |    |
| source             | 1..20                                                 |    |
|                    | mol_type = other RNA                                  |    |
|                    | organism = synthetic construct                        |    |
| modified_base      | 18                                                    |    |
|                    | mod_base = OTHER                                      |    |
|                    | note = 2'O-methyluridine phosphorothioate             |    |
| modified_base      | 19                                                    |    |
|                    | mod_base = OTHER                                      |    |
|                    | note = 2'O-methylguanosine phosphorothioate           |    |
| modified_base      | 20                                                    |    |
|                    | mod_base = OTHER                                      |    |
|                    | note = 2'O-methyluridine                              |    |
| SEQUENCE: 563      |                                                       |    |
| ataaagtaag gcatggttgt |                                                     | 20 |
|                    |                                                       |    |
| SEQ ID NO: 564     | moltype = RNA   length = 20                           |    |
| FEATURE            | Location/Qualifiers                                   |    |
| source             | 1..20                                                 |    |
|                    | mol_type = other RNA                                  |    |
|                    | organism = synthetic construct                        |    |
| modified_base      | 18                                                    |    |
|                    | mod_base = OTHER                                      |    |
|                    | note = 2'O-methyluridine phosphorothioate             |    |
| modified_base      | 19                                                    |    |
|                    | mod_base = OTHER                                      |    |
|                    | note = 2'O-methyluridine phosphorothioate             |    |
| modified_base      | 20                                                    |    |
|                    | mod_base = OTHER                                      |    |
|                    | note = 2'O-methylguanosine                            |    |
| SEQUENCE: 564      |                                                       |    |
| gttaatctgg tttatttttg |                                                     | 20 |
|                    |                                                       |    |
| SEQ ID NO: 565     | moltype = RNA   length = 20                           |    |
| FEATURE            | Location/Qualifiers                                   |    |
| source             | 1..20                                                 |    |

```
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylcytidine phosphorothioate
modified_base           20
                        mod_base = OTHER
                        note = 2'O-methyluridine
SEQUENCE: 565
atgtatctga gcaggttgct                                                    20

SEQ ID NO: 566          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 566
cttagaattt gggggaaaat                                                    20

SEQ ID NO: 567          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methyluridine
SEQUENCE: 567
gattggatga attccaaatt                                                    20

SEQ ID NO: 568          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 568
tgcacaaaat gtagggttat                                                    20

SEQ ID NO: 569          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methyluridine
```

```
SEQUENCE: 569
gaaatataat tgacaggatt                                               20

SEQ ID NO: 570          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 570
agtgctgtct ccatgtttga                                               20

SEQ ID NO: 571          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methyladenosine phosphorothioate
modified_base           20
                        mod_base = OTHER
                        note = 2'O-methylguanosine
SEQUENCE: 571
ggagggctgg caacttagag                                               20

SEQ ID NO: 572          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methyladenosine phosphorothioate
modified_base           20
                        mod_base = OTHER
                        note = 2'O-methylcytidine
SEQUENCE: 572
aactcttcaa tctcttgcac                                               20

SEQ ID NO: 573          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 573
ataatgttaa catggacatg                                               20

SEQ ID NO: 574          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
```

```
modified_base          19
                       mod_base = OTHER
                       note = 2'O-methyladenosine phosphorothioate
modified_base          20
                       mod_base = OTHER
                       note = 2'O-methyluridine
SEQUENCE: 574
cttatacact tacactttat                                                        20

SEQ ID NO: 575         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methylcytidine phosphorothioate
modified_base          19
                       mod_base = OTHER
                       note = 2'O-methyladenosine phosphorothioate
modified_base          20
                       mod_base = OTHER
                       note = 2'O-methylcytidine
SEQUENCE: 575
atattgatat gcttatacac                                                        20

SEQ ID NO: 576         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methyladenosine phosphorothioate
modified_base          19
                       mod_base = OTHER
                       note = 2'O-methylcytidine phosphorothioate
modified_base          20
                       mod_base = OTHER
                       note = 2'O-methyladenosine
SEQUENCE: 576
gggttataat aatgttaaca                                                        20

SEQ ID NO: 577         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methylcytidine phosphorothioate
modified_base          19
                       mod_base = OTHER
                       note = 2'O-methyladenosine phosphorothioate
modified_base          20
                       mod_base = OTHER
                       note = 2'O-methyluridine
SEQUENCE: 577
catttgataa agtaaggcat                                                        20

SEQ ID NO: 578         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methyladenosine phosphorothioate
modified_base          19
                       mod_base = OTHER
                       note = 2'O-methyladenosine phosphorothioate
modified_base          20
                       mod_base = OTHER
                       note = 2'O-methyladenosine
SEQUENCE: 578
tttttgttcc acaagttaaa                                                        20

SEQ ID NO: 579         moltype = RNA   length = 20
FEATURE                Location/Qualifiers
```

```
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methyluridine phosphorothioate
modified_base             20
                          mod_base = OTHER
                          note = 2'O-methylcytidine
SEQUENCE: 579
ttccacaagt taaataaatc                                                       20

SEQ ID NO: 580            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methylcytidine phosphorothioate
modified_base             20
                          mod_base = OTHER
                          note = 2'O-methyladenosine
SEQUENCE: 580
tctgagcagg ttgctccaca                                                       20

SEQ ID NO: 581            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylguanosine phosphorothioate
modified_base             19
                          mod_base = OTHER
                          note = 2'O-methyluridine phosphorothioate
modified_base             20
                          mod_base = OTHER
                          note = 2'O-methylcytidine
SEQUENCE: 581
attctacttt gagtgctgtc                                                       20

SEQ ID NO: 582            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylguanosine phosphorothioate
modified_base             19
                          mod_base = OTHER
                          note = 2'O-methyluridine phosphorothioate
modified_base             20
                          mod_base = OTHER
                          note = 2'O-methyladenosine
SEQUENCE: 582
agcaggttgc tccacaggta                                                       20

SEQ ID NO: 583            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methyladenosine phosphorothioate
modified_base             20
                          mod_base = OTHER
```

```
                    note = 2'O-methyladenosine
SEQUENCE: 583
attgacagga ttattggaaa                                              20

SEQ ID NO: 584          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 584
aagatgccgc atttggattg                                              20

SEQ ID NO: 585          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 585
atgaatgaaa cattttgtca                                              20

SEQ ID NO: 586          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 586
catactctgc ttagaatttg                                              20

SEQ ID NO: 587          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 587
taattctact ttgagtgctg                                              20

SEQ ID NO: 588          moltype = RNA   length = 20
FEATURE                 Location/Qualifiers
source                  1..20
                        mol_type = other RNA
                        organism = synthetic construct
modified_base           18
                        mod_base = OTHER
```

```
                        note = 2'O-methylcytidine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 588
cacttacact ttatgcacaa                                                           20

SEQ ID NO: 589          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 589
accaagatgt tgatgttgga                                                           20

SEQ ID NO: 590          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 590
cataaagtgt aagtgtataa                                                           20

SEQ ID NO: 591          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methyluridine
SEQUENCE: 591
gaacaaaaat aaaccagatt                                                           20

SEQ ID NO: 592          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylcytidine phosphorothioate
modified_base           20
                        mod_base = OTHER
                        note = 2'O-methylcytidine
SEQUENCE: 592
ctcccccacct ctaagttgcc                                                          20

SEQ ID NO: 593          moltype = RNA   length = 20
```

```
FEATURE              Location/Qualifiers
source               1..20
                     mol_type = other RNA
                     organism = synthetic construct
modified_base        18
                     mod_base = OTHER
                     note = 2'O-methylguanosine phosphorothioate
modified_base        19
                     mod_base = OTHER
                     note = 2'O-methyladenosine phosphorothioate
modified_base        20
                     mod_base = OTHER
                     note = 2'O-methylguanosine
SEQUENCE: 593
agttgccagc cctcctagag                                               20

SEQ ID NO: 594       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyluridine phosphorothioate
modified_base        19
                     mod_base = OTHER
                     note = 2'O-methylguanosine phosphorothioate
modified_base        20
                     mod_base = OTHER
                     note = 2'O-methylcytidine
SEQUENCE: 594
aattggaagt taacttatgc                                               20

SEQ ID NO: 595       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylguanosine phosphorothioate
modified_base        19
                     mod_base = OTHER
                     note = 2'O-methylguanosine phosphorothioate
modified_base        20
                     mod_base = OTHER
                     note = 2'O-methyladenosine
SEQUENCE: 595
agcagagtat gtaaattgga                                               20

SEQ ID NO: 596       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylcytidine phosphorothioate
modified_base        19
                     mod_base = OTHER
                     note = 2'O-methyluridine phosphorothioate
modified_base        20
                     mod_base = OTHER
                     note = 2'O-methylguanosine
SEQUENCE: 596
acaaatttcc aataatcctg                                               20

SEQ ID NO: 597       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyladenosine phosphorothioate
modified_base        19
                     mod_base = OTHER
                     note = 2'O-methylcytidine phosphorothioate
modified_base        20
```

```
                        mod_base = OTHER
                        note = 2'O-methyladenosine
SEQUENCE: 597
cacgcttaac tatcttaaca                                                    20

SEQ ID NO: 598          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 598
tttaacttgt ggaacaaaaa                                                    20

SEQ ID NO: 599          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 599
tgatttattt aacttgtgga                                                    20

SEQ ID NO: 600          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 600
gagcaacctg ctcagataca                                                    20

SEQ ID NO: 601          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 601
acttgtggaa caaaataaa                                                     20

SEQ ID NO: 602          moltype = RNA   length = 20
FEATURE                 Location/Qualifiers
source                  1..20
                        mol_type = other RNA
                        organism = synthetic construct
modified_base           18
```

```
                        mod_base = OTHER
                        note = 2'O-methyladenosine phosphorothioate
modified_base           19
                        mod_base = OTHER
                        note = 2'O-methylguanosine phosphorothioate
modified_base           20
                        mod_base = OTHER
                        note = 2'O-methyluridine
SEQUENCE: 602
agtgcaagag attgaagagt                                                  20

SEQ ID NO: 603          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methyladenosine
SEQUENCE: 603
agtgtataag catatcaata                                                  20

SEQ ID NO: 604          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methylcytidine
SEQUENCE: 604
atttatttaa cttgtggaac                                                  20

SEQ ID NO: 605          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 605
tgacaaaatg tttcattcat                                                  20

SEQ ID NO: 606          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 606
tgcataaagt gtaagtgtat                                                  20
```

```
SEQ ID NO: 607          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methyluridine phosphorothioate
modified_base           20
                        mod_base = OTHER
                        note = 2'O-methyluridine
SEQUENCE: 607
aagaagatca tgtccatgtt                                                       20

SEQ ID NO: 608          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 608
aattttcccc caaattctaa                                                       20

SEQ ID NO: 609          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 609
gaattcatcc aatccaaatg                                                       20

SEQ ID NO: 610          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methyladenosine
SEQUENCE: 610
tttctaaatt ttcccccaaa                                                       20

SEQ ID NO: 611          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyladenosine phosphorothioate
```

```
modified_base        20
                     mod_base = OTHER
                     note = 2'O-methyladenosine
SEQUENCE: 611
accctacatt ttgtgcataa                                                    20

SEQ ID NO: 612       moltype = RNA   length = 20
FEATURE              Location/Qualifiers
source               1..20
                     mol_type = other RNA
                     organism = synthetic construct
SEQUENCE: 612
tcacaaagta aggattctga                                                    20

SEQ ID NO: 613       moltype = RNA   length = 20
FEATURE              Location/Qualifiers
source               1..20
                     mol_type = other RNA
                     organism = synthetic construct
SEQUENCE: 613
tggacttcaa gagcaacagt                                                    20

SEQ ID NO: 614       moltype = RNA   length = 20
FEATURE              Location/Qualifiers
source               1..20
                     mol_type = other RNA
                     organism = synthetic construct
SEQUENCE: 614
attctcaaac aaatgtgtca                                                    20

SEQ ID NO: 615       moltype = RNA   length = 20
FEATURE              Location/Qualifiers
source               1..20
                     mol_type = other RNA
                     organism = synthetic construct
SEQUENCE: 615
actttgcatg tgcaaacgcc                                                    20

SEQ ID NO: 616       moltype = RNA   length = 20
FEATURE              Location/Qualifiers
source               1..20
                     mol_type = other RNA
                     organism = synthetic construct
SEQUENCE: 616
caaacgcctt caacaacagc                                                    20

SEQ ID NO: 617       moltype = RNA   length = 20
FEATURE              Location/Qualifiers
source               1..20
                     mol_type = other RNA
                     organism = synthetic construct
SEQUENCE: 617
tatatcacag acaaaactgt                                                    20

SEQ ID NO: 618       moltype = RNA   length = 20
FEATURE              Location/Qualifiers
source               1..20
                     mol_type = other RNA
                     organism = synthetic construct
SEQUENCE: 618
aatccagtga caagtctgtc                                                    20

SEQ ID NO: 619       moltype = RNA   length = 20
FEATURE              Location/Qualifiers
source               1..20
                     mol_type = other RNA
                     organism = synthetic construct
SEQUENCE: 619
atgtgtatat cacagacaaa                                                    20

SEQ ID NO: 620       moltype = RNA   length = 20
FEATURE              Location/Qualifiers
source               1..20
                     mol_type = other RNA
                     organism = synthetic construct
SEQUENCE: 620
catgtgcaaa cgccttcaac                                                    20

SEQ ID NO: 621       moltype = RNA   length = 20
```

```
FEATURE                 Location/Qualifiers
source                  1..20
                        mol_type = other RNA
                        organism = synthetic construct
SEQUENCE: 621
tcacagacaa aactgtgcta                                                    20

SEQ ID NO: 622          moltype = RNA   length = 20
FEATURE                 Location/Qualifiers
source                  1..20
                        mol_type = other RNA
                        organism = synthetic construct
SEQUENCE: 622
tatcacagac aaaactgtgc                                                    20

SEQ ID NO: 623          moltype = RNA   length = 20
FEATURE                 Location/Qualifiers
source                  1..20
                        mol_type = other RNA
                        organism = synthetic construct
SEQUENCE: 623
tctgcctatt caccgatttt                                                    20

SEQ ID NO: 624          moltype = RNA   length = 20
FEATURE                 Location/Qualifiers
source                  1..20
                        mol_type = other RNA
                        organism = synthetic construct
SEQUENCE: 624
gcctggagca acaaatctga                                                    20

SEQ ID NO: 625          moltype = RNA   length = 20
FEATURE                 Location/Qualifiers
source                  1..20
                        mol_type = other RNA
                        organism = synthetic construct
SEQUENCE: 625
ccagctgaga gactctaaat                                                    20

SEQ ID NO: 626          moltype = RNA   length = 20
FEATURE                 Location/Qualifiers
source                  1..20
                        mol_type = other RNA
                        organism = synthetic construct
SEQUENCE: 626
cctattcacc gattttgatt                                                    20

SEQ ID NO: 627          moltype = RNA   length = 20
FEATURE                 Location/Qualifiers
source                  1..20
                        mol_type = other RNA
                        organism = synthetic construct
SEQUENCE: 627
ctagacatga ggtctatgga                                                    20

SEQ ID NO: 628          moltype = RNA   length = 20
FEATURE                 Location/Qualifiers
source                  1..20
                        mol_type = other RNA
                        organism = synthetic construct
SEQUENCE: 628
gacttcaaga gcaacagtgc                                                    20

SEQ ID NO: 629          moltype = RNA   length = 20
FEATURE                 Location/Qualifiers
source                  1..20
                        mol_type = other RNA
                        organism = synthetic construct
SEQUENCE: 629
gcacagtttt gtctgtgata                                                    20

SEQ ID NO: 630          moltype = RNA   length = 20
FEATURE                 Location/Qualifiers
source                  1..20
                        mol_type = other RNA
                        organism = synthetic construct
SEQUENCE: 630
agaatcaaaa tcggtgaata                                                    20
```

| | | |
|---|---|---|
| SEQ ID NO: 631<br>FEATURE<br>source | moltype = RNA   length = 20<br>Location/Qualifiers<br>1..20<br>mol_type = other RNA<br>organism = synthetic construct | |
| SEQUENCE: 631<br>cacatcagaa tccttacttt | | 20 |
| SEQ ID NO: 632<br>FEATURE<br>source | moltype = RNA   length = 20<br>Location/Qualifiers<br>1..20<br>mol_type = other RNA<br>organism = synthetic construct | |
| SEQUENCE: 632<br>tgatatacac atcagaatcc | | 20 |
| SEQ ID NO: 633<br>FEATURE<br>source | moltype = RNA   length = 20<br>Location/Qualifiers<br>1..20<br>mol_type = other RNA<br>organism = synthetic construct | |
| SEQUENCE: 633<br>acacatttgt ttgagaatca | | 20 |
| SEQ ID NO: 634<br>FEATURE<br>source | moltype = RNA   length = 20<br>Location/Qualifiers<br>1..20<br>mol_type = other RNA<br>organism = synthetic construct | |
| SEQUENCE: 634<br>tgacacattt gtttgagaat | | 20 |
| SEQ ID NO: 635<br>FEATURE<br>source | moltype = RNA   length = 20<br>Location/Qualifiers<br>1..20<br>mol_type = other RNA<br>organism = synthetic construct | |
| SEQUENCE: 635<br>gagtctctca gctggtacac | | 20 |
| SEQ ID NO: 636<br>FEATURE<br>source | moltype = RNA   length = 20<br>Location/Qualifiers<br>1..20<br>mol_type = other RNA<br>organism = synthetic construct | |
| SEQUENCE: 636<br>ttgctccagg ccacagcact | | 20 |
| SEQ ID NO: 637<br>FEATURE<br>source | moltype = RNA   length = 20<br>Location/Qualifiers<br>1..20<br>mol_type = other RNA<br>organism = synthetic construct | |
| SEQUENCE: 637<br>cacatgcaaa gtcagatttg | | 20 |
| SEQ ID NO: 638<br>FEATURE<br>source | moltype = RNA   length = 20<br>Location/Qualifiers<br>1..20<br>mol_type = other RNA<br>organism = synthetic construct | |
| SEQUENCE: 638<br>tttgagaatc aaaatcggtg | | 20 |
| SEQ ID NO: 639<br>FEATURE<br>source | moltype = RNA   length = 20<br>Location/Qualifiers<br>1..20<br>mol_type = other RNA<br>organism = synthetic construct | |
| SEQUENCE: 639<br>atatacacat cagaatcctt | | 20 |
| SEQ ID NO: 640<br>FEATURE<br>source | moltype = RNA   length = 20<br>Location/Qualifiers<br>1..20<br>mol_type = other RNA<br>organism = synthetic construct | |
| SEQUENCE: 640<br>gaataatgct gttgttgaag | | 20 |

| SEQ ID NO: 641 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 641 | | |
| tctgtgatat acacatcaga | | 20 |

| SEQ ID NO: 642 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 642 | | |
| atgtcaagct ggtcgagaaa | | 20 |

| SEQ ID NO: 643 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 643 | | |
| ctcatgacgc tgcggctgtg | | 20 |

| SEQ ID NO: 644 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 644 | | |
| atctgctcat gacgctgcgg | | 20 |

| SEQ ID NO: 645 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 645 | | |
| ctccctcgct ccttcctctg | | 20 |

| SEQ ID NO: 646 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 646 | | |
| ggcgtgttgt atgtcctgct | | 20 |

| SEQ ID NO: 647 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 647 | | |
| cacattccct cctgctcccc | | 20 |

| SEQ ID NO: 648 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 648 | | |
| caagattgta agacagcctg | | 20 |

| SEQ ID NO: 649 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 649 | | |
| cattgcccct cttctccctc | | 20 |

| SEQ ID NO: 650 | moltype = RNA length = 20 | |
|---|---|---|
| FEATURE | Location/Qualifiers | |
| source | 1..20 | |
| | mol_type = other RNA | |
| | organism = synthetic construct | |
| SEQUENCE: 650 | | | tatctgggcg tgttgtatgt                                              20

SEQ ID NO: 651          moltype = RNA   length = 20
FEATURE                 Location/Qualifiers
source                  1..20
                        mol_type = other RNA
                        organism = synthetic construct SEQUENCE: 651
tgtcctgctg ccgatgcctt                                              20

SEQ ID NO: 652          moltype = RNA   length = 20
FEATURE                 Location/Qualifiers
source                  1..20
                        mol_type = other RNA
                        organism = synthetic construct SEQUENCE: 652
agacagcctg tgctccctcg                                              20

SEQ ID NO: 653          moltype = RNA   length = 20
FEATURE                 Location/Qualifiers
source                  1..20
                        mol_type = other RNA
                        organism = synthetic construct SEQUENCE: 653
ttcccttatt gctgcttgtc                                              20

SEQ ID NO: 654          moltype = RNA   length = 20
FEATURE                 Location/Qualifiers
source                  1..20
                        mol_type = other RNA
                        organism = synthetic construct SEQUENCE: 654
attaagattg ctgaagagct                                              20

SEQ ID NO: 655          moltype = RNA   length = 20
FEATURE                 Location/Qualifiers
source                  1..20
                        mol_type = other RNA
                        organism = synthetic construct SEQUENCE: 655
ccccccggc aatgccacca                                               20

SEQ ID NO: 656          moltype = RNA   length = 20
FEATURE                 Location/Qualifiers
source                  1..20
                        mol_type = other RNA
                        organism = synthetic construct SEQUENCE: 656
tctgggcgtg ttgtatgtcc                                              20

SEQ ID NO: 657          moltype = RNA   length = 20
FEATURE                 Location/Qualifiers
source                  1..20
                        mol_type = other RNA
                        organism = synthetic construct SEQUENCE: 657
tgattaagat tgctgaagag                                              20

SEQ ID NO: 658          moltype = RNA   length = 20
FEATURE                 Location/Qualifiers
source                  1..20
                        mol_type = other RNA
                        organism = synthetic construct SEQUENCE: 658
ggtcctgcag aatgttgtga                                              20

SEQ ID NO: 659          moltype = RNA   length = 20
FEATURE                 Location/Qualifiers
source                  1..20
                        mol_type = other RNA
                        organism = synthetic construct SEQUENCE: 659
tgccccccg gcaatgccac                                               20

SEQ ID NO: 660          moltype = RNA   length = 20
FEATURE                 Location/Qualifiers
source                  1..20
                        mol_type = other RNA
                        organism = synthetic construct

| | | |
|---|---|---|
| SEQUENCE: 660 ctgtgtatct gggcgtgttg | | 20 |
| SEQ ID NO: 661<br>FEATURE<br>source<br><br>SEQUENCE: 661<br>tttggagagg gagaagaggg | moltype = RNA   length = 20<br>Location/Qualifiers<br>1..20<br>mol_type = other RNA<br>organism = synthetic construct | <br><br><br><br><br>20 |
| SEQ ID NO: 662<br>FEATURE<br>source<br><br>SEQUENCE: 662<br>caggacctag agcccaagag | moltype = RNA   length = 20<br>Location/Qualifiers<br>1..20<br>mol_type = other RNA<br>organism = synthetic construct | <br><br><br><br><br>20 |
| SEQ ID NO: 663<br>FEATURE<br>source<br><br>SEQUENCE: 663<br>ccgtgaatgt caggcagtga | moltype = RNA   length = 20<br>Location/Qualifiers<br>1..20<br>mol_type = other RNA<br>organism = synthetic construct | <br><br><br><br><br>20 |
| SEQ ID NO: 664<br>FEATURE<br>source<br><br>SEQUENCE: 664<br>gagagggaga agaggggcaa | moltype = RNA   length = 20<br>Location/Qualifiers<br>1..20<br>mol_type = other RNA<br>organism = synthetic construct | <br><br><br><br><br>20 |
| SEQ ID NO: 665<br>FEATURE<br>source<br><br>SEQUENCE: 665<br>gggagcagga gggaatgtgc | moltype = RNA   length = 20<br>Location/Qualifiers<br>1..20<br>mol_type = other RNA<br>organism = synthetic construct | <br><br><br><br><br>20 |
| SEQ ID NO: 666<br>FEATURE<br>source<br><br>SEQUENCE: 666<br>cacagccagg ggaggctgca | moltype = RNA   length = 20<br>Location/Qualifiers<br>1..20<br>mol_type = other RNA<br>organism = synthetic construct | <br><br><br><br><br>20 |
| SEQ ID NO: 667<br>FEATURE<br>source<br><br>SEQUENCE: 667<br>ggatggcgga ggcagtctct | moltype = RNA   length = 20<br>Location/Qualifiers<br>1..20<br>mol_type = other RNA<br>organism = synthetic construct | <br><br><br><br><br>20 |
| SEQ ID NO: 668<br>FEATURE<br>source<br><br>SEQUENCE: 668<br>tgggatggcg gaggcagtct | moltype = RNA   length = 20<br>Location/Qualifiers<br>1..20<br>mol_type = other RNA<br>organism = synthetic construct | <br><br><br><br><br>20 |
| SEQ ID NO: 669<br>FEATURE<br>source<br><br>SEQUENCE: 669<br>gcagctcttc agcaatctta | moltype = RNA   length = 20<br>Location/Qualifiers<br>1..20<br>mol_type = other RNA<br>organism = synthetic construct | <br><br><br><br><br>20 |
| SEQ ID NO: 670<br>FEATURE<br>source | moltype = RNA   length = 20<br>Location/Qualifiers<br>1..20<br>mol_type = other RNA | |

-continued

```
                         organism = synthetic construct
modified_base            18
                         mod_base = OTHER
                         note = 2'O-methyluridine phosphorothioate
modified_base            19
                         mod_base = OTHER
                         note = 2'O-methylguanosine phosphorothioate
modified_base            20
                         mod_base = OTHER
                         note = 2'O-methyladenosine
SEQUENCE: 670
tcacaaagta aggattctga                                                     20

SEQ ID NO: 671           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methyladenosine phosphorothioate
modified_base            19
                         mod_base = OTHER
                         note = 2'O-methylguanosine phosphorothioate
modified_base            20
                         mod_base = OTHER
                         note = 2'O-methyluridine
SEQUENCE: 671
tggacttcaa gagcaacagt                                                     20

SEQ ID NO: 672           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methyluridine phosphorothioate
modified_base            19
                         mod_base = OTHER
                         note = 2'O-methylcytidine phosphorothioate
modified_base            20
                         mod_base = OTHER
                         note = 2'O-methyladenosine
SEQUENCE: 672
attctcaaac aaatgtgtca                                                     20

SEQ ID NO: 673           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methylguanosine phosphorothioate
modified_base            19
                         mod_base = OTHER
                         note = 2'O-methylcytidine phosphorothioate
modified_base            20
                         mod_base = OTHER
                         note = 2'O-methylcytidine
SEQUENCE: 673
actttgcatg tgcaaacgcc                                                     20

SEQ ID NO: 674           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methyladenosine phosphorothioate
modified_base            19
                         mod_base = OTHER
                         note = 2'O-methylguanosine phosphorothioate
modified_base            20
                         mod_base = OTHER
                         note = 2'O-methylcytidine
SEQUENCE: 674
```

```
caaacgcctt caacaacagc                                                  20

SEQ ID NO: 675         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methyluridine phosphorothioate
modified_base          19
                       mod_base = OTHER
                       note = 2'O-methylguanosine phosphorothioate
modified_base          20
                       mod_base = OTHER
                       note = 2'O-methyluridine
SEQUENCE: 675
tatatcacag acaaaactgt                                                  20

SEQ ID NO: 676         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methylguanosine phosphorothioate
modified_base          19
                       mod_base = OTHER
                       note = 2'O-methyluridine phosphorothioate
modified_base          20
                       mod_base = OTHER
                       note = 2'O-methylcytidine
SEQUENCE: 676
aatccagtga caagtctgtc                                                  20

SEQ ID NO: 677         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methyladenosine phosphorothioate
modified_base          19
                       mod_base = OTHER
                       note = 2'O-methyladenosine phosphorothioate
modified_base          20
                       mod_base = OTHER
                       note = 2'O-methyladenosine
SEQUENCE: 677
atgtgtatat cacagacaaa                                                  20

SEQ ID NO: 678         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methyladenosine phosphorothioate
modified_base          19
                       mod_base = OTHER
                       note = 2'O-methyladenosine phosphorothioate
modified_base          20
                       mod_base = OTHER
                       note = 2'O-methylcytidine
SEQUENCE: 678
catgtgcaaa cgccttcaac                                                  20

SEQ ID NO: 679         moltype = RNA   length = 20
FEATURE                Location/Qualifiers
source                 1..20
                       mol_type = other RNA
                       organism = synthetic construct
modified_base          18
                       mod_base = OTHER
                       note = 2'O-methylcytidine phosphorothioate
modified_base          19
```

```
                            mod_base = OTHER
                            note = 2'O-methyluridine phosphorothioate
modified_base               20
                            mod_base = OTHER
                            note = 2'O-methyladenosine
SEQUENCE: 679
tcacagacaa aactgtgcta                                                         20

SEQ ID NO: 680              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methylguanosine phosphorothioate
modified_base               20
                            mod_base = OTHER
                            note = 2'O-methylcytidine
SEQUENCE: 680
tatcacagac aaaactgtgc                                                         20

SEQ ID NO: 681              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methyluridine phosphorothioate
modified_base               20
                            mod_base = OTHER
                            note = 2'O-methyluridine
SEQUENCE: 681
tctgcctatt caccgattttt                                                        20

SEQ ID NO: 682              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methylguanosine phosphorothioate
modified_base               20
                            mod_base = OTHER
                            note = 2'O-methyladenosine
SEQUENCE: 682
gcctggagca acaaatctga                                                         20

SEQ ID NO: 683              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methyladenosine phosphorothioate
modified_base               19
                            mod_base = OTHER
                            note = 2'O-methyladenosine phosphorothioate
modified_base               20
                            mod_base = OTHER
                            note = 2'O-methyluridine
SEQUENCE: 683
ccagctgaga gactctaaat                                                         20

SEQ ID NO: 684              moltype = RNA  length = 20
FEATURE                     Location/Qualifiers
source                      1..20
```

```
                            -continued mol_type = other RNA
                            organism = synthetic construct
modified_base               18
                            mod_base = OTHER
                            note = 2'O-methyladenosine phosphorothioate
modified_base               19
                            mod_base = OTHER
                            note = 2'O-methyluridine phosphorothioate
modified_base               20
                            mod_base = OTHER
                            note = 2'O-methyluridine
SEQUENCE: 684
cctattcacc gattttgatt                                                    20

SEQ ID NO: 685              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methylguanosine phosphorothioate
modified_base               19
                            mod_base = OTHER
                            note = 2'O-methylguanosine phosphorothioate
modified_base               20
                            mod_base = OTHER
                            note = 2'O-methyladenosine
SEQUENCE: 685
ctagacatga ggtctatgga                                                    20

SEQ ID NO: 686              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methylguanosine phosphorothioate
modified_base               20
                            mod_base = OTHER
                            note = 2'O-methylcytidine
SEQUENCE: 686
gacttcaaga gcaacagtgc                                                    20

SEQ ID NO: 687              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methyladenosine phosphorothioate
modified_base               19
                            mod_base = OTHER
                            note = 2'O-methyluridine phosphorothioate
modified_base               20
                            mod_base = OTHER
                            note = 2'O-methyladenosine
SEQUENCE: 687
gcacagtttt gtctgtgata                                                    20

SEQ ID NO: 688              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methyladenosine phosphorothioate
modified_base               19
                            mod_base = OTHER
                            note = 2'O-methyluridine phosphorothioate
modified_base               20
                            mod_base = OTHER
                            note = 2'O-methyladenosine
```

```
SEQUENCE: 688
agaatcaaaa tcggtgaata                                             20

SEQ ID NO: 689          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyluridine phosphorothioate
modified_base           20
                        mod_base = OTHER
                        note = 2'O-methyluridine
SEQUENCE: 689
cacatcagaa tccttacttt                                             20

SEQ ID NO: 690          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methylcytidine phosphorothioate
modified_base           20
                        mod_base = OTHER
                        note = 2'O-methylcytidine
SEQUENCE: 690
tgatatacac atcagaatcc                                             20

SEQ ID NO: 691          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 691
acacatttgt ttgagaatca                                             20

SEQ ID NO: 692          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methyladenosine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 692
tgacacattt gtttgagaat                                             20

SEQ ID NO: 693          moltype = RNA  length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
```

```
modified_base        19
                     mod_base = OTHER
                     note = 2'O-methyladenosine phosphorothioate
modified_base        20
                     mod_base = OTHER
                     note = 2'O-methylcytidine
SEQUENCE: 693
gagtctctca gctggtacac                                             20

SEQ ID NO: 694       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyladenosine phosphorothioate
modified_base        19
                     mod_base = OTHER
                     note = 2'O-methylcytidine phosphorothioate
modified_base        20
                     mod_base = OTHER
                     note = 2'O-methyluridine
SEQUENCE: 694
ttgctccagg ccacagcact                                             20

SEQ ID NO: 695       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyluridine phosphorothioate
modified_base        19
                     mod_base = OTHER
                     note = 2'O-methyluridine phosphorothioate
modified_base        20
                     mod_base = OTHER
                     note = 2'O-methylguanosine
SEQUENCE: 695
cacatgcaaa gtcagatttg                                             20

SEQ ID NO: 696       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylguanosine phosphorothioate
modified_base        19
                     mod_base = OTHER
                     note = 2'O-methyluridine phosphorothioate
modified_base        20
                     mod_base = OTHER
                     note = 2'O-methylguanosine
SEQUENCE: 696
tttgagaatc aaaatcggtg                                             20

SEQ ID NO: 697       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylcytidine phosphorothioate
modified_base        19
                     mod_base = OTHER
                     note = 2'O-methyluridine phosphorothioate
modified_base        20
                     mod_base = OTHER
                     note = 2'O-methyluridine
SEQUENCE: 697
atatacacat cagaatcctt                                             20

SEQ ID NO: 698       moltype = RNA   length = 20
FEATURE              Location/Qualifiers
```

-continued

```
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methyladenosine phosphorothioate
modified_base             20
                          mod_base = OTHER
                          note = 2'O-methylguanosine
SEQUENCE: 698
gaataatgct gttgttgaag                                                    20

SEQ ID NO: 699            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methylguanosine phosphorothioate
modified_base             20
                          mod_base = OTHER
                          note = 2'O-methyladenosine
SEQUENCE: 699
tctgtgatat acacatcaga                                                    20

SEQ ID NO: 700            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methyladenosine phosphorothioate
modified_base             19
                          mod_base = OTHER
                          note = 2'O-methyladenosine phosphorothioate
modified_base             20
                          mod_base = OTHER
                          note = 2'O-methyladenosine
SEQUENCE: 700
atgtcaagct ggtcgagaaa                                                    20

SEQ ID NO: 701            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylguanosine phosphorothioate
modified_base             19
                          mod_base = OTHER
                          note = 2'O-methyluridine phosphorothioate
modified_base             20
                          mod_base = OTHER
                          note = 2'O-methylguanosine
SEQUENCE: 701
ctcatgacgc tgcggctgtg                                                    20

SEQ ID NO: 702            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methylguanosine phosphorothioate
modified_base             20
                          mod_base = OTHER
```

```
                          note = 2'O-methylguanosine
SEQUENCE: 702
atctgctcat gacgctgcgg                                                    20

SEQ ID NO: 703            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methyluridine phosphorothioate
modified_base             20
                          mod_base = OTHER
                          note = 2'O-methylguanosine
SEQUENCE: 703
ctccctcgct ccttcctctg                                                    20

SEQ ID NO: 704            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylguanosine phosphorothioate
modified_base             19
                          mod_base = OTHER
                          note = 2'O-methylcytidine phosphorothioate
modified_base             20
                          mod_base = OTHER
                          note = 2'O-methyluridine
SEQUENCE: 704
ggcgtgttgt atgtcctgct                                                    20

SEQ ID NO: 705            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methylcytidine phosphorothioate
modified_base             20
                          mod_base = OTHER
                          note = 2'O-methylcytidine
SEQUENCE: 705
cacattccct cctgctcccc                                                    20

SEQ ID NO: 706            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methyluridine phosphorothioate
modified_base             20
                          mod_base = OTHER
                          note = 2'O-methylguanosine
SEQUENCE: 706
caagattgta agacagcctg                                                    20

SEQ ID NO: 707            moltype = RNA   length = 20
FEATURE                   Location/Qualifiers
source                    1..20
                          mol_type = other RNA
                          organism = synthetic construct
modified_base             18
                          mod_base = OTHER
```

```
                            note = 2'O-methylcytidine phosphorothioate
modified_base               19
                            mod_base = OTHER
                            note = 2'O-methyluridine phosphorothioate
modified_base               20
                            mod_base = OTHER
                            note = 2'O-methylcytidine
SEQUENCE: 707
cattgcccct cttctccctc                                                           20

SEQ ID NO: 708              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methylguanosine phosphorothioate
modified_base               20
                            mod_base = OTHER
                            note = 2'O-methyluridine
SEQUENCE: 708
tatctgggcg tgttgtatgt                                                           20

SEQ ID NO: 709              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methylcytidine phosphorothioate
modified_base               19
                            mod_base = OTHER
                            note = 2'O-methyluridine phosphorothioate
modified_base               20
                            mod_base = OTHER
                            note = 2'O-methyluridine
SEQUENCE: 709
tgtcctgctg ccgatgcctt                                                           20

SEQ ID NO: 710              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methyluridine phosphorothioate
modified_base               19
                            mod_base = OTHER
                            note = 2'O-methylcytidine phosphorothioate
modified_base               20
                            mod_base = OTHER
                            note = 2'O-methylguanosine
SEQUENCE: 710
agacagcctg tgctccctcg                                                           20

SEQ ID NO: 711              moltype = RNA   length = 20
FEATURE                     Location/Qualifiers
source                      1..20
                            mol_type = other RNA
                            organism = synthetic construct
modified_base               18
                            mod_base = OTHER
                            note = 2'O-methylguanosine phosphorothioate
modified_base               19
                            mod_base = OTHER
                            note = 2'O-methyluridine phosphorothioate
modified_base               20
                            mod_base = OTHER
                            note = 2'O-methylcytidine
SEQUENCE: 711
ttcccttatt gctgcttgtc                                                           20

SEQ ID NO: 712              moltype = RNA   length = 20
```

```
FEATURE              Location/Qualifiers
source               1..20
                     mol_type = other RNA
                     organism = synthetic construct
modified_base        18
                     mod_base = OTHER
                     note = 2'O-methylguanosine phosphorothioate
modified_base        19
                     mod_base = OTHER
                     note = 2'O-methylcytidine phosphorothioate
modified_base        20
                     mod_base = OTHER
                     note = 2'O-methyluridine
SEQUENCE: 712
attaagattg ctgaagagct                                              20

SEQ ID NO: 713       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylcytidine phosphorothioate
modified_base        19
                     mod_base = OTHER
                     note = 2'O-methylcytidine phosphorothioate
modified_base        20
                     mod_base = OTHER
                     note = 2'O-methyladenosine
SEQUENCE: 713
ccccccggc aatgccacca                                               20

SEQ ID NO: 714       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyluridine phosphorothioate
modified_base        19
                     mod_base = OTHER
                     note = 2'O-methylcytidine phosphorothioate
modified_base        20
                     mod_base = OTHER
                     note = 2'O-methylcytidine
SEQUENCE: 714
tctgggcgtg ttgtatgtcc                                              20

SEQ ID NO: 715       moltype = RNA   length = 20
FEATURE              Location/Qualifiers
source               1..20
                     mol_type = other RNA
                     organism = synthetic construct
modified_base        18
                     mod_base = OTHER
                     note = 2'O-methylguanosine phosphorothioate
modified_base        19
                     mod_base = OTHER
                     note = 2'O-methyladenosine phosphorothioate
modified_base        20
                     mod_base = OTHER
                     note = 2'O-methylguanosine
SEQUENCE: 715
tgattaagat tgctgaagag                                              20

SEQ ID NO: 716       moltype = RNA   length = 20
FEATURE              Location/Qualifiers
source               1..20
                     mol_type = other RNA
                     organism = synthetic construct
modified_base        18
                     mod_base = OTHER
                     note = 2'O-methyluridine phosphorothioate
modified_base        19
                     mod_base = OTHER
                     note = 2'O-methylguanosine phosphorothioate
modified_base        20
```

```
                        mod_base = OTHER
                        note = 2'O-methyladenosine
SEQUENCE: 716
ggtcctgcag aatgttgtga                                               20

SEQ ID NO: 717          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methyladenosine phosphorothioate
modified_base           20
                        mod_base = OTHER
                        note = 2'O-methylcytidine
SEQUENCE: 717
tgcccccccg gcaatgccac                                               20

SEQ ID NO: 718          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methyluridine phosphorothioate
modified_base           20
                        mod_base = OTHER
                        note = 2'O-methylguanosine
SEQUENCE: 718
ctgtgtatct gggcgtgttg                                               20

SEQ ID NO: 719          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylguanosine phosphorothioate
modified_base           20
                        mod_base = OTHER
                        note = 2'O-methylguanosine
SEQUENCE: 719
tttggagagg gagaagaggg                                               20

SEQ ID NO: 720          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methyladenosine phosphorothioate
modified_base           20
                        mod_base = OTHER
                        note = 2'O-methylguanosine
SEQUENCE: 720
caggacctag agcccaagag                                               20

SEQ ID NO: 721          moltype = RNA   length = 20
FEATURE                 Location/Qualifiers
source                  1..20
                        mol_type = other RNA
                        organism = synthetic construct
modified_base           18
```

|                | mod_base = OTHER |
|                | note = 2'O-methyluridine phosphorothioate |
| modified_base  | 19 |
|                | mod_base = OTHER |
|                | note = 2'O-methylguanosine phosphorothioate |
| modified_base  | 20 |
|                | mod_base = OTHER |
|                | note = 2'O-methyladenosine |
| SEQUENCE: 721  | |
| ccgtgaatgt caggcagtga | 20 |
| | |
| SEQ ID NO: 722 | moltype = RNA   length = 20 |
| FEATURE        | Location/Qualifiers |
| source         | 1..20 |
|                | mol_type = other RNA |
|                | organism = synthetic construct |
| modified_base  | 18 |
|                | mod_base = OTHER |
|                | note = 2'O-methylcytidine phosphorothioate |
| modified_base  | 19 |
|                | mod_base = OTHER |
|                | note = 2'O-methyladenosine phosphorothioate |
| modified_base  | 20 |
|                | mod_base = OTHER |
|                | note = 2'O-methyladenosine |
| SEQUENCE: 722  | |
| gagagggaga agaggggcaa | 20 |
| | |
| SEQ ID NO: 723 | moltype = RNA   length = 20 |
| FEATURE        | Location/Qualifiers |
| source         | 1..20 |
|                | mol_type = other RNA |
|                | organism = synthetic construct |
| modified_base  | 18 |
|                | mod_base = OTHER |
|                | note = 2'O-methyluridine phosphorothioate |
| modified_base  | 19 |
|                | mod_base = OTHER |
|                | note = 2'O-methylguanosine phosphorothioate |
| modified_base  | 20 |
|                | mod_base = OTHER |
|                | note = 2'O-methylcytidine |
| SEQUENCE: 723  | |
| gggagcagga gggaatgtgc | 20 |
| | |
| SEQ ID NO: 724 | moltype = RNA   length = 20 |
| FEATURE        | Location/Qualifiers |
| source         | 1..20 |
|                | mol_type = other RNA |
|                | organism = synthetic construct |
| modified_base  | 18 |
|                | mod_base = OTHER |
|                | note = 2'O-methylguanosine phosphorothioate |
| modified_base  | 19 |
|                | mod_base = OTHER |
|                | note = 2'O-methylcytidine phosphorothioate |
| modified_base  | 20 |
|                | mod_base = OTHER |
|                | note = 2'O-methyladenosine |
| SEQUENCE: 724  | |
| cacagccagg ggaggctgca | 20 |
| | |
| SEQ ID NO: 725 | moltype = RNA   length = 20 |
| FEATURE        | Location/Qualifiers |
| source         | 1..20 |
|                | mol_type = other RNA |
|                | organism = synthetic construct |
| modified_base  | 18 |
|                | mod_base = OTHER |
|                | note = 2'O-methyluridine phosphorothioate |
| modified_base  | 19 |
|                | mod_base = OTHER |
|                | note = 2'O-methylcytidine phosphorothioate |
| modified_base  | 20 |
|                | mod_base = OTHER |
|                | note = 2'O-methyluridine |
| SEQUENCE: 725  | |
| ggatggcgga ggcagtctct | 20 |

```
SEQ ID NO: 726           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methyluridine phosphorothioate
modified_base            19
                         mod_base = OTHER
                         note = 2'O-methylcytidine phosphorothioate
modified_base            20
                         mod_base = OTHER
                         note = 2'O-methyluridine
SEQUENCE: 726
tgggatggcg gaggcagtct                                                    20

SEQ ID NO: 727           moltype = RNA   length = 20
FEATURE                  Location/Qualifiers
source                   1..20
                         mol_type = other RNA
                         organism = synthetic construct
modified_base            18
                         mod_base = OTHER
                         note = 2'O-methyluridine phosphorothioate
modified_base            19
                         mod_base = OTHER
                         note = 2'O-methyluridine phosphorothioate
modified_base            20
                         mod_base = OTHER
                         note = 2'O-methyladenosine
SEQUENCE: 727
gcagctcttc agcaatctta                                                    20

SEQ ID NO: 728           moltype = RNA   length = 20
FEATURE                  Location/Qualifiers
source                   1..20
                         mol_type = other RNA
                         organism = synthetic construct
SEQUENCE: 728
tgcttctgag ctgggcatcc                                                    20

SEQ ID NO: 729           moltype = RNA   length = 20
FEATURE                  Location/Qualifiers
source                   1..20
                         mol_type = other RNA
                         organism = synthetic construct
SEQUENCE: 729
agctgggcat ccgaaggcat                                                    20

SEQ ID NO: 730           moltype = RNA   length = 20
FEATURE                  Location/Qualifiers
source                   1..20
                         mol_type = other RNA
                         organism = synthetic construct
SEQUENCE: 730
cttctgagct gggcatccga                                                    20

SEQ ID NO: 731           moltype = RNA   length = 20
FEATURE                  Location/Qualifiers
source                   1..20
                         mol_type = other RNA
                         organism = synthetic construct
SEQUENCE: 731
ggaatcccag ccaggcagca                                                    20

SEQ ID NO: 732           moltype = RNA   length = 20
FEATURE                  Location/Qualifiers
source                   1..20
                         mol_type = other RNA
                         organism = synthetic construct
SEQUENCE: 732
taggaatccc agccaggcag                                                    20

SEQ ID NO: 733           moltype = RNA   length = 20
FEATURE                  Location/Qualifiers
source                   1..20
                         mol_type = other RNA
                         organism = synthetic construct
```

-continued

```
SEQUENCE: 733
gcagcccctc ctcgtgccct                                                    20

SEQ ID NO: 734          moltype = RNA  length = 20
FEATURE                 Location/Qualifiers
source                  1..20
                        mol_type = other RNA
                        organism = synthetic construct
SEQUENCE: 734
acaggtagga cccagcaggg                                                    20

SEQ ID NO: 735          moltype = RNA  length = 20
FEATURE                 Location/Qualifiers
source                  1..20
                        mol_type = other RNA
                        organism = synthetic construct
SEQUENCE: 735
tgaccagatg gacctggctg                                                    20

SEQ ID NO: 736          moltype = RNA  length = 20
FEATURE                 Location/Qualifiers
source                  1..20
                        mol_type = other RNA
                        organism = synthetic construct
SEQUENCE: 736
ccacttctat gaccagatgg                                                    20

SEQ ID NO: 737          moltype = RNA  length = 20
FEATURE                 Location/Qualifiers
source                  1..20
                        mol_type = other RNA
                        organism = synthetic construct
SEQUENCE: 737
accagatgga cctggctgga                                                    20

SEQ ID NO: 738          moltype = RNA  length = 20
FEATURE                 Location/Qualifiers
source                  1..20
                        mol_type = other RNA
                        organism = synthetic construct
SEQUENCE: 738
ccaccatgga gttggggccc                                                    20

SEQ ID NO: 739          moltype = RNA  length = 20
FEATURE                 Location/Qualifiers
source                  1..20
                        mol_type = other RNA
                        organism = synthetic construct
SEQUENCE: 739
cctctaccac ttctatgacc                                                    20

SEQ ID NO: 740          moltype = RNA  length = 20
FEATURE                 Location/Qualifiers
source                  1..20
                        mol_type = other RNA
                        organism = synthetic construct
SEQUENCE: 740
ggggccccaa ctccatggtg                                                    20

SEQ ID NO: 741          moltype = RNA  length = 20
FEATURE                 Location/Qualifiers
source                  1..20
                        mol_type = other RNA
                        organism = synthetic construct
SEQUENCE: 741
gtcatagaag tggtagaggc                                                    20

SEQ ID NO: 742          moltype = RNA  length = 20
FEATURE                 Location/Qualifiers
source                  1..20
                        mol_type = other RNA
                        organism = synthetic construct
SEQUENCE: 742
acatggaagg tgatgaagag                                                    20

SEQ ID NO: 743          moltype = RNA  length = 20
FEATURE                 Location/Qualifiers
source                  1..20
                        mol_type = other RNA
```

```
                        organism = synthetic construct
SEQUENCE: 743
tgacatggaa ggtgatgaag                                                  20

SEQ ID NO: 744          moltype = RNA   length = 20
FEATURE                 Location/Qualifiers
source                  1..20
                        mol_type = other RNA
                        organism = synthetic construct
SEQUENCE: 744
tcttccagga ctcccagctg                                                  20

SEQ ID NO: 745          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methyluridine phosphorothioate
modified_base           19
                        mod_base = OTHER
                        note = 2'O-methylcytidine phosphorothioate
modified_base           20
                        mod_base = OTHER
                        note = 2'O-methylcytidine
SEQUENCE: 745
tgcttctgag ctgggcatcc                                                  20

SEQ ID NO: 746          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methyladenosine phosphorothioate
modified_base           20
                        mod_base = OTHER
                        note = 2'O-methyluridine
SEQUENCE: 746
agctgggcat ccgaaggcat                                                  20

SEQ ID NO: 747          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylcytidine phosphorothioate
modified_base           19
                        mod_base = OTHER
                        note = 2'O-methylguanosine phosphorothioate
modified_base           20
                        mod_base = OTHER
                        note = 2'O-methyladenosine
SEQUENCE: 747
cttctgagct gggcatccga                                                  20

SEQ ID NO: 748          moltype = RNA   length = 20
FEATURE                 Location/Qualifiers
source                  1..20
                        mol_type = other RNA
                        organism = synthetic construct
modified_base           18
                        mod_base = OTHER
                        note = 2'O-methylguanosine phosphorothioate
modified_base           19
                        mod_base = OTHER
                        note = 2'O-methylcytidine phosphorothioate
modified_base           20
                        mod_base = OTHER
                        note = 2'O-methyladenosine
SEQUENCE: 748
ggaatcccag ccaggcagca                                                  20
```

```
SEQ ID NO: 749            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methyladenosine phosphorothioate
modified_base             20
                          mod_base = OTHER
                          note = 2'O-methylguanosine
SEQUENCE: 749
taggaatccc agccaggcag                                                       20

SEQ ID NO: 750            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methylcytidine phosphorothioate
modified_base             20
                          mod_base = OTHER
                          note = 2'O-methyluridine
SEQUENCE: 750
gcagcccctc ctcgtgccct                                                       20

SEQ ID NO: 751            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylguanosine phosphorothioate
modified_base             19
                          mod_base = OTHER
                          note = 2'O-methylguanosine phosphorothioate
modified_base             20
                          mod_base = OTHER
                          note = 2'O-methylguanosine
SEQUENCE: 751
acaggtagga cccagcaggg                                                       20

SEQ ID NO: 752            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methylcytidine phosphorothioate
modified_base             19
                          mod_base = OTHER
                          note = 2'O-methyluridine phosphorothioate
modified_base             20
                          mod_base = OTHER
                          note = 2'O-methylguanosine
SEQUENCE: 752
tgaccagatg gacctggctg                                                       20

SEQ ID NO: 753            moltype = RNA   length = 20
FEATURE                   Location/Qualifiers
source                    1..20
                          mol_type = other RNA
                          organism = synthetic construct
modified_base             18
                          mod_base = OTHER
                          note = 2'O-methyluridine phosphorothioate
modified_base             19
                          mod_base = OTHER
```

```
                           note = 2'O-methylguanosine phosphorothioate
modified_base              20
                           mod_base = OTHER
                           note = 2'O-methylguanosine
SEQUENCE: 753
ccacttctat gaccagatgg                                                         20

SEQ ID NO: 754             moltype = RNA   length = 20
FEATURE                    Location/Qualifiers
source                     1..20
                           mol_type = other RNA
                           organism = synthetic construct
modified_base              18
                           mod_base = OTHER
                           note = 2'O-methylguanosine phosphorothioate
modified_base              19
                           mod_base = OTHER
                           note = 2'O-methylguanosine phosphorothioate
modified_base              20
                           mod_base = OTHER
                           note = 2'O-methyladenosine
SEQUENCE: 754
accagatgga cctggctgga                                                         20

SEQ ID NO: 755             moltype = RNA   length = 20
FEATURE                    Location/Qualifiers
source                     1..20
                           mol_type = other RNA
                           organism = synthetic construct
modified_base              18
                           mod_base = OTHER
                           note = 2'O-methylcytidine phosphorothioate
modified_base              19
                           mod_base = OTHER
                           note = 2'O-methylcytidine phosphorothioate
modified_base              20
                           mod_base = OTHER
                           note = 2'O-methylcytidine
SEQUENCE: 755
ccaccatgga gttggggccc                                                         20

SEQ ID NO: 756             moltype = RNA   length = 20
FEATURE                    Location/Qualifiers
source                     1..20
                           mol_type = other RNA
                           organism = synthetic construct
modified_base              18
                           mod_base = OTHER
                           note = 2'O-methyladenosine phosphorothioate
modified_base              19
                           mod_base = OTHER
                           note = 2'O-methylcytidine phosphorothioate
modified_base              20
                           mod_base = OTHER
                           note = 2'O-methylcytidine
SEQUENCE: 756
cctctaccac ttctatgacc                                                         20

SEQ ID NO: 757             moltype = RNA   length = 20
FEATURE                    Location/Qualifiers
source                     1..20
                           mol_type = other RNA
                           organism = synthetic construct
modified_base              18
                           mod_base = OTHER
                           note = 2'O-methylguanosine phosphorothioate
modified_base              19
                           mod_base = OTHER
                           note = 2'O-methyluridine phosphorothioate
modified_base              20
                           mod_base = OTHER
                           note = 2'O-methylguanosine
SEQUENCE: 757
ggggccccaa ctccatggtg                                                         20

SEQ ID NO: 758             moltype = RNA   length = 20
FEATURE                    Location/Qualifiers
source                     1..20
                           mol_type = other RNA
```

```
                            organism = synthetic construct
modified_base               18
                            mod_base = OTHER
                            note = 2'O-methylguanosine phosphorothioate
modified_base               19
                            mod_base = OTHER
                            note = 2'O-methylguanosine phosphorothioate
modified_base               20
                            mod_base = OTHER
                            note = 2'O-methylcytidine
SEQUENCE: 758
gtcatagaag tggtagaggc                                                    20

SEQ ID NO: 759              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methylguanosine phosphorothioate
modified_base               19
                            mod_base = OTHER
                            note = 2'O-methyladenosine phosphorothioate
modified_base               20
                            mod_base = OTHER
                            note = 2'O-methylguanosine
SEQUENCE: 759
acatggaagg tgatgaagag                                                    20

SEQ ID NO: 760              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methyladenosine phosphorothioate
modified_base               19
                            mod_base = OTHER
                            note = 2'O-methyladenosine phosphorothioate
modified_base               20
                            mod_base = OTHER
                            note = 2'O-methylguanosine
SEQUENCE: 760
tgacatggaa ggtgatgaag                                                    20

SEQ ID NO: 761              moltype = RNA  length = 20
FEATURE                     Location/Qualifiers
source                      1..20
                            mol_type = other RNA
                            organism = synthetic construct
modified_base               18
                            mod_base = OTHER
                            note = 2'O-methylcytidine phosphorothioate
modified_base               19
                            mod_base = OTHER
                            note = 2'O-methyluridine phosphorothioate
modified_base               20
                            mod_base = OTHER
                            note = 2'O-methylguanosine
SEQUENCE: 761
tcttccagga ctcccagctg                                                    20

SEQ ID NO: 762              moltype = RNA  length = 89
FEATURE                     Location/Qualifiers
source                      1..89
                            mol_type = other RNA
                            organism = synthetic construct
modified_base               1
                            mod_base = OTHER
                            note = 2'O-methyladenosine phosphorothioate
modified_base               2
                            mod_base = OTHER
                            note = 2'O-methylcytidine phosphorothioate
modified_base               3
                            mod_base = OTHER
                            note = 2'O-methyladenosine phosphorothioate
modified_base               87
```

```
                        mod_base = OTHER
                        note = 2'O-methyluridine phosphorothioate
modified_base           88
                        mod_base = OTHER
                        note = 2'O-methyluridine phosphorothioate
modified_base           89
                        mod_base = OTHER
                        note = 2'O-methylcytidine
SEQUENCE: 762
acagcttatt tggaagctga aatgtgaggt ttataacact cacaagaatc ctgaaaaagg     60
atgccaaacc tcgcgctact ctctctttc                                       89

SEQ ID NO: 763          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyluridine phosphorothioate
modified_base           89
                        mod_base = OTHER
                        note = 2'O-methyluridine
SEQUENCE: 763
acagcttatt tggaagctga aatgtgaggt ttataacact cacaagaatc ctgaaaaagg     60
atgccaaacg gtttcatcca tccgacatt                                       89

SEQ ID NO: 764          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methylcytidine phosphorothioate
modified_base           89
                        mod_base = OTHER
                        note = 2'O-methyladenosine
SEQUENCE: 764
acagcttatt tggaagctga aatgtgaggt ttataacact cacaagaatc ctgaaaaagg     60
atgccaaacc tacactgaat tcaccccca                                       89

SEQ ID NO: 765          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
```

```
                          note = 2'O-methyladenosine phosphorothioate
modified_base             87
                          mod_base = OTHER
                          note = 2'O-methyladenosine phosphorothioate
modified_base             88
                          mod_base = OTHER
                          note = 2'O-methyladenosine phosphorothioate
modified_base             89
                          mod_base = OTHER
                          note = 2'O-methyluridine
SEQUENCE: 765
acagcttatt tggaagctga aatgtgaggt ttataacact cacaagaatc ctgaaaaagg   60
atgccaaact ctcttgtact acactgaat                                    89

SEQ ID NO: 766            moltype = RNA   length = 89
FEATURE                   Location/Qualifiers
source                    1..89
                          mol_type = other RNA
                          organism = synthetic construct
modified_base             1
                          mod_base = OTHER
                          note = 2'O-methyladenosine phosphorothioate
modified_base             2
                          mod_base = OTHER
                          note = 2'O-methylcytidine phosphorothioate
modified_base             3
                          mod_base = OTHER
                          note = 2'O-methyladenosine phosphorothioate
modified_base             87
                          mod_base = OTHER
                          note = 2'O-methyladenosine phosphorothioate
modified_base             88
                          mod_base = OTHER
                          note = 2'O-methylguanosine phosphorothioate
modified_base             89
                          mod_base = OTHER
                          note = 2'O-methyladenosine
SEQUENCE: 766
acagcttatt tggaagctga aatgtgaggt ttataacact cacaagaatc ctgaaaaagg   60
atgccaaacc tcacgtcatc cagcagaga                                    89

SEQ ID NO: 767            moltype = RNA   length = 89
FEATURE                   Location/Qualifiers
source                    1..89
                          mol_type = other RNA
                          organism = synthetic construct
modified_base             1
                          mod_base = OTHER
                          note = 2'O-methyladenosine phosphorothioate
modified_base             2
                          mod_base = OTHER
                          note = 2'O-methylcytidine phosphorothioate
modified_base             3
                          mod_base = OTHER
                          note = 2'O-methyladenosine phosphorothioate
modified_base             87
                          mod_base = OTHER
                          note = 2'O-methyluridine phosphorothioate
modified_base             88
                          mod_base = OTHER
                          note = 2'O-methylcytidine phosphorothioate
modified_base             89
                          mod_base = OTHER
                          note = 2'O-methylcytidine
SEQUENCE: 767
acagcttatt tggaagctga aatgtgaggt ttataacact cacaagaatc ctgaaaaagg   60
atgccaaact gtctgggttt catccatcc                                    89

SEQ ID NO: 768            moltype = RNA   length = 89
FEATURE                   Location/Qualifiers
source                    1..89
                          mol_type = other RNA
                          organism = synthetic construct
modified_base             1
                          mod_base = OTHER
                          note = 2'O-methyladenosine phosphorothioate
modified_base             2
                          mod_base = OTHER
                          note = 2'O-methylcytidine phosphorothioate
```

```
modified_base         3
                      mod_base = OTHER
                      note = 2'O-methyladenosine phosphorothioate
modified_base         87
                      mod_base = OTHER
                      note = 2'O-methylguanosine phosphorothioate
modified_base         88
                      mod_base = OTHER
                      note = 2'O-methyluridine phosphorothioate
modified_base         89
                      mod_base = OTHER
                      note = 2'O-methylguanosine
SEQUENCE: 768
acagcttatt tggaagctga aatgtgaggt ttataacact cacaagaatc ctgaaaaagg   60
atgccaaacc ctgccgtgtg aaccatgtg                                    89

SEQ ID NO: 769        moltype = RNA  length = 89
FEATURE               Location/Qualifiers
source                1..89
                      mol_type = other RNA
                      organism = synthetic construct
modified_base         1
                      mod_base = OTHER
                      note = 2'O-methyladenosine phosphorothioate
modified_base         2
                      mod_base = OTHER
                      note = 2'O-methylcytidine phosphorothioate
modified_base         3
                      mod_base = OTHER
                      note = 2'O-methyladenosine phosphorothioate
modified_base         87
                      mod_base = OTHER
                      note = 2'O-methyluridine phosphorothioate
modified_base         88
                      mod_base = OTHER
                      note = 2'O-methyladenosine phosphorothioate
modified_base         89
                      mod_base = OTHER
                      note = 2'O-methyladenosine
SEQUENCE: 769
acagcttatt tggaagctga aatgtgaggt ttataacact cacaagaatc ctgaaaaagg   60
atgccaaact cacagcccaa gatagttaa                                    89

SEQ ID NO: 770        moltype = RNA  length = 89
FEATURE               Location/Qualifiers
source                1..89
                      mol_type = other RNA
                      organism = synthetic construct
modified_base         1
                      mod_base = OTHER
                      note = 2'O-methyladenosine phosphorothioate
modified_base         2
                      mod_base = OTHER
                      note = 2'O-methylcytidine phosphorothioate
modified_base         3
                      mod_base = OTHER
                      note = 2'O-methyladenosine phosphorothioate
modified_base         87
                      mod_base = OTHER
                      note = 2'O-methylguanosine phosphorothioate
modified_base         88
                      mod_base = OTHER
                      note = 2'O-methyladenosine phosphorothioate
modified_base         89
                      mod_base = OTHER
                      note = 2'O-methyluridine
SEQUENCE: 770
acagcttatt tggaagctga aatgtgaggt ttataacact cacaagaatc ctgaaaaagg   60
atgccaaaca ctttgtcaca gcccaagat                                    89

SEQ ID NO: 771        moltype = RNA  length = 89
FEATURE               Location/Qualifiers
source                1..89
                      mol_type = other RNA
                      organism = synthetic construct
modified_base         1
                      mod_base = OTHER
                      note = 2'O-methyladenosine phosphorothioate
modified_base         2
```

```
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methylguanosine phosphorothioate
modified_base           89
                        mod_base = OTHER
                        note = 2'O-methyladenosine
SEQUENCE: 771
acagcttatt tggaagctga aatgtgaggt ttataacact cacaagaatc ctgaaaaagg    60
atgccaaact ctgggtttca tccatccga                                     89

SEQ ID NO: 772          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methylcytidine phosphorothioate
modified_base           89
                        mod_base = OTHER
                        note = 2'O-methyladenosine
SEQUENCE: 772
acagcttatt tggaagctga aatgtgaggt ttataacact cacaagaatc ctgaaaaagg    60
atgccaaaca accatgtgac tttgtcaca                                     89

SEQ ID NO: 773          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyluridine phosphorothioate
modified_base           89
                        mod_base = OTHER
                        note = 2'O-methyluridine
SEQUENCE: 773
acagcttatt tggaagctga aatgtgaggt ttataacact cacaagaatc ctgaaaaagg    60
atgccaaaca atgctccact ttttcaatt                                     89

SEQ ID NO: 774          moltype = RNA   length = 89
FEATURE                 Location/Qualifiers
source                  1..89
                        mol_type = other RNA
                        organism = synthetic construct
modified_base           1
                        mod_base = OTHER
```

```
                              note = 2'O-methyladenosine phosphorothioate
modified_base                 2
                              mod_base = OTHER
                              note = 2'O-methylcytidine phosphorothioate
modified_base                 3
                              mod_base = OTHER
                              note = 2'O-methyladenosine phosphorothioate
modified_base                 87
                              mod_base = OTHER
                              note = 2'O-methylguanosine phosphorothioate
modified_base                 88
                              mod_base = OTHER
                              note = 2'O-methylguanosine phosphorothioate
modified_base                 89
                              mod_base = OTHER
                              note = 2'O-methyladenosine
SEQUENCE: 774
acagcttatt tggaagctga aatgtgaggt ttataacact cacaagaatc ctgaaaaagg    60
atgccaaaca ctttccattc tctgctgga                                     89

SEQ ID NO: 775                moltype = RNA   length = 89
FEATURE                       Location/Qualifiers
source                        1..89
                              mol_type = other RNA
                              organism = synthetic construct
modified_base                 1
                              mod_base = OTHER
                              note = 2'O-methyladenosine phosphorothioate
modified_base                 2
                              mod_base = OTHER
                              note = 2'O-methylcytidine phosphorothioate
modified_base                 3
                              mod_base = OTHER
                              note = 2'O-methyladenosine phosphorothioate
modified_base                 87
                              mod_base = OTHER
                              note = 2'O-methyladenosine phosphorothioate
modified_base                 88
                              mod_base = OTHER
                              note = 2'O-methylcytidine phosphorothioate
modified_base                 89
                              mod_base = OTHER
                              note = 2'O-methyladenosine
SEQUENCE: 775
acagcttatt tggaagctga aatgtgaggt ttataacact cacaagaatc ctgaaaaagg    60
atgccaaaca caaagtcaca tggttcaca                                     89

SEQ ID NO: 776                moltype = RNA   length = 89
FEATURE                       Location/Qualifiers
source                        1..89
                              mol_type = other RNA
                              organism = synthetic construct
modified_base                 1
                              mod_base = OTHER
                              note = 2'O-methyladenosine phosphorothioate
modified_base                 2
                              mod_base = OTHER
                              note = 2'O-methylcytidine phosphorothioate
modified_base                 3
                              mod_base = OTHER
                              note = 2'O-methyladenosine phosphorothioate
modified_base                 87
                              mod_base = OTHER
                              note = 2'O-methyladenosine phosphorothioate
modified_base                 88
                              mod_base = OTHER
                              note = 2'O-methylcytidine phosphorothioate
modified_base                 89
                              mod_base = OTHER
                              note = 2'O-methylcytidine
SEQUENCE: 776
acagcttatt tggaagctga aatgtgaggt ttataacact cacaagaatc ctgaaaaagg    60
atgccaaacg tacaagagat agaaagacc                                     89

SEQ ID NO: 777                moltype = RNA   length = 89
FEATURE                       Location/Qualifiers
source                        1..89
                              mol_type = other RNA
                              organism = synthetic construct
```

```
modified_base         1
                      mod_base = OTHER
                      note = 2'O-methyladenosine phosphorothioate
modified_base         2
                      mod_base = OTHER
                      note = 2'O-methylcytidine phosphorothioate
modified_base         3
                      mod_base = OTHER
                      note = 2'O-methyladenosine phosphorothioate
modified_base         87
                      mod_base = OTHER
                      note = 2'O-methyladenosine phosphorothioate
modified_base         88
                      mod_base = OTHER
                      note = 2'O-methylcytidine phosphorothioate
modified_base         89
                      mod_base = OTHER
                      note = 2'O-methylcytidine
SEQUENCE: 777
acagcttatt tggaagctga aatgtgaggt ttataacact cacaagaatc ctgaaaaagg    60
atgccaaacc tggatgacgt gagtaaacc                                      89

SEQ ID NO: 778        moltype = RNA   length = 89
FEATURE               Location/Qualifiers
source                1..89
                      mol_type = other RNA
                      organism = synthetic construct
modified_base         1
                      mod_base = OTHER
                      note = 2'O-methyladenosine phosphorothioate
modified_base         2
                      mod_base = OTHER
                      note = 2'O-methylcytidine phosphorothioate
modified_base         3
                      mod_base = OTHER
                      note = 2'O-methyladenosine phosphorothioate
modified_base         87
                      mod_base = OTHER
                      note = 2'O-methyluridine phosphorothioate
modified_base         88
                      mod_base = OTHER
                      note = 2'O-methylguanosine phosphorothioate
modified_base         89
                      mod_base = OTHER
                      note = 2'O-methyladenosine
SEQUENCE: 778
acagcttatt tggaagctga aatgtgaggt ttataacact cacaagaatc ctgaaaaagg    60
atgccaaact cacaaagtaa ggattctga                                      89

SEQ ID NO: 779        moltype = RNA   length = 89
FEATURE               Location/Qualifiers
source                1..89
                      mol_type = other RNA
                      organism = synthetic construct
modified_base         1
                      mod_base = OTHER
                      note = 2'O-methyladenosine phosphorothioate
modified_base         2
                      mod_base = OTHER
                      note = 2'O-methylcytidine phosphorothioate
modified_base         3
                      mod_base = OTHER
                      note = 2'O-methyladenosine phosphorothioate
modified_base         87
                      mod_base = OTHER
                      note = 2'O-methyladenosine phosphorothioate
modified_base         88
                      mod_base = OTHER
                      note = 2'O-methylguanosine phosphorothioate
modified_base         89
                      mod_base = OTHER
                      note = 2'O-methyluridine
SEQUENCE: 779
acagcttatt tggaagctga aatgtgaggt ttataacact cacaagaatc ctgaaaaagg    60
atgccaaact ggacttcaag agcaacagt                                      89

SEQ ID NO: 780        moltype = RNA   length = 89
FEATURE               Location/Qualifiers
source                1..89
```

```
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylcytidine phosphorothioate
modified_base           89
                        mod_base = OTHER
                        note = 2'O-methyladenosine
SEQUENCE: 780
acagcttatt tggaagctga aatgtgaggt ttataacact cacaagaatc ctgaaaaagg   60
atgccaaaca ttctcaaaca aatgtgtca                                    89

SEQ ID NO: 781          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylguanosine phosphorothioate
modified_base           88
                        mod_base = OTHER
                        note = 2'O-methylcytidine phosphorothioate
modified_base           89
                        mod_base = OTHER
                        note = 2'O-methylcytidine
SEQUENCE: 781
acagcttatt tggaagctga aatgtgaggt ttataacact cacaagaatc ctgaaaaagg   60
atgccaaaca ctttgcatgt gcaaacgcc                                    89

SEQ ID NO: 782          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methylguanosine phosphorothioate
modified_base           89
                        mod_base = OTHER
                        note = 2'O-methylcytidine
SEQUENCE: 782
acagcttatt tggaagctga aatgtgaggt ttataacact cacaagaatc ctgaaaaagg   60
atgccaaacc aaacgccttc aacaacagc                                    89

SEQ ID NO: 783          moltype = RNA  length = 89
```

```
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylguanosine phosphorothioate
modified_base           89
                        mod_base = OTHER
                        note = 2'O-methyluridine
SEQUENCE: 783
acagcttatt tggaagctga aatgtgaggt ttataacact cacaagaatc ctgaaaaagg    60
atgccaaact atatcacaga caaaactgt                                      89

SEQ ID NO: 784          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylguanosine phosphorothioate
modified_base           88
                        mod_base = OTHER
                        note = 2'O-methyluridine phosphorothioate
modified_base           89
                        mod_base = OTHER
                        note = 2'O-methylcytidine
SEQUENCE: 784
acagcttatt tggaagctga aatgtgaggt ttataacact cacaagaatc ctgaaaaagg    60
atgccaaaca atccagtgac aagtctgtc                                      89

SEQ ID NO: 785          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyladenosine phosphorothioate
modified_base           89
                        mod_base = OTHER
                        note = 2'O-methyladenosine
SEQUENCE: 785
acagcttatt tggaagctga aatgtgaggt ttataacact cacaagaatc ctgaaaaagg    60
atgccaaaca tgtgtatatc acagacaaa                                      89
```

```
SEQ ID NO: 786          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyladenosine phosphorothioate
modified_base           89
                        mod_base = OTHER
                        note = 2'O-methylcytidine
SEQUENCE: 786
acagcttatt tggaagctga aatgtgaggt ttataacact cacaagaatc ctgaaaaagg    60
atgccaaacc atgtgcaaac gccttcaac                                     89

SEQ ID NO: 787          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methyluridine phosphorothioate
modified_base           89
                        mod_base = OTHER
                        note = 2'O-methyladenosine
SEQUENCE: 787
acagcttatt tggaagctga aatgtgaggt ttataacact cacaagaatc ctgaaaaagg    60
atgccaaact cacagacaaa actgtgcta                                     89

SEQ ID NO: 788          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylguanosine phosphorothioate
modified_base           89
                        mod_base = OTHER
                        note = 2'O-methylcytidine
SEQUENCE: 788
```
acagcttatt tggaagctga aatgtgaggt ttataacact cacaagaatc ctgaaaaagg   60
atgccaaact atcacagaca aaactgtgc                                    89

```
SEQ ID NO: 789           moltype = RNA   length = 89
FEATURE                  Location/Qualifiers
source                   1..89
                         mol_type = other RNA
                         organism = synthetic construct
modified_base            1
                         mod_base = OTHER
                         note = 2'O-methyladenosine phosphorothioate
modified_base            2
                         mod_base = OTHER
                         note = 2'O-methylcytidine phosphorothioate
modified_base            3
                         mod_base = OTHER
                         note = 2'O-methyladenosine phosphorothioate
modified_base            87
                         mod_base = OTHER
                         note = 2'O-methyluridine phosphorothioate
modified_base            88
                         mod_base = OTHER
                         note = 2'O-methyluridine phosphorothioate
modified_base            89
                         mod_base = OTHER
                         note = 2'O-methyluridine
SEQUENCE: 789
```
acagcttatt tggaagctga aatgtgaggt ttataacact cacaagaatc ctgaaaaagg   60
atgccaaact ctgcctattc accgatttt                                    89

```
SEQ ID NO: 790           moltype = RNA   length = 89
FEATURE                  Location/Qualifiers
source                   1..89
                         mol_type = other RNA
                         organism = synthetic construct
modified_base            1
                         mod_base = OTHER
                         note = 2'O-methyladenosine phosphorothioate
modified_base            2
                         mod_base = OTHER
                         note = 2'O-methylcytidine phosphorothioate
modified_base            3
                         mod_base = OTHER
                         note = 2'O-methyladenosine phosphorothioate
modified_base            87
                         mod_base = OTHER
                         note = 2'O-methyluridine phosphorothioate
modified_base            88
                         mod_base = OTHER
                         note = 2'O-methylguanosine phosphorothioate
modified_base            89
                         mod_base = OTHER
                         note = 2'O-methyladenosine
SEQUENCE: 790
```
acagcttatt tggaagctga aatgtgaggt ttataacact cacaagaatc ctgaaaaagg   60
atgccaaacg cctggagcaa caaatctga                                    89

```
SEQ ID NO: 791           moltype = RNA   length = 89
FEATURE                  Location/Qualifiers
source                   1..89
                         mol_type = other RNA
                         organism = synthetic construct
modified_base            1
                         mod_base = OTHER
                         note = 2'O-methyladenosine phosphorothioate
modified_base            2
                         mod_base = OTHER
                         note = 2'O-methylcytidine phosphorothioate
modified_base            3
                         mod_base = OTHER
                         note = 2'O-methyladenosine phosphorothioate
modified_base            87
                         mod_base = OTHER
                         note = 2'O-methyladenosine phosphorothioate
modified_base            88
                         mod_base = OTHER
                         note = 2'O-methyladenosine phosphorothioate
modified_base            89
                         mod_base = OTHER
```

```
                           note = 2'O-methyluridine
SEQUENCE: 791
acagcttatt tggaagctga aatgtgaggt ttataacact cacaagaatc ctgaaaaagg    60
atgccaaacc cagctgagag actctaaat                                      89

SEQ ID NO: 792         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
                       mod_base = OTHER
                       note = 2'O-methyladenosine phosphorothioate
modified_base          87
                       mod_base = OTHER
                       note = 2'O-methyladenosine phosphorothioate
modified_base          88
                       mod_base = OTHER
                       note = 2'O-methyluridine phosphorothioate
modified_base          89
                       mod_base = OTHER
                       note = 2'O-methyluridine
SEQUENCE: 792
acagcttatt tggaagctga aatgtgaggt ttataacact cacaagaatc ctgaaaaagg    60
atgccaaacc ctattcaccg attttgatt                                      89

SEQ ID NO: 793         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
                       mod_base = OTHER
                       note = 2'O-methyladenosine phosphorothioate
modified_base          87
                       mod_base = OTHER
                       note = 2'O-methylguanosine phosphorothioate
modified_base          88
                       mod_base = OTHER
                       note = 2'O-methylguanosine phosphorothioate
modified_base          89
                       mod_base = OTHER
                       note = 2'O-methyladenosine
SEQUENCE: 793
acagcttatt tggaagctga aatgtgaggt ttataacact cacaagaatc ctgaaaaagg    60
atgccaaacc tagacatgag gtctatgga                                      89

SEQ ID NO: 794         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
                       mod_base = OTHER
                       note = 2'O-methyladenosine phosphorothioate
modified_base          87
                       mod_base = OTHER
                       note = 2'O-methyluridine phosphorothioate
modified_base          88
                       mod_base = OTHER
                       note = 2'O-methylguanosine phosphorothioate
```

-continued

```
modified_base        89
                     mod_base = OTHER
                     note = 2'O-methylcytidine
SEQUENCE: 794
acagcttatt tggaagctga aatgtgaggt ttataacact cacaagaatc ctgaaaaagg    60
atgccaaacg acttcaagag caacagtgc                                      89

SEQ ID NO: 795       moltype = RNA   length = 89
FEATURE              Location/Qualifiers
source               1..89
                     mol_type = other RNA
                     organism = synthetic construct
modified_base        1
                     mod_base = OTHER
                     note = 2'O-methyladenosine phosphorothioate
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methyladenosine phosphorothioate
modified_base        88
                     mod_base = OTHER
                     note = 2'O-methyluridine phosphorothioate
modified_base        89
                     mod_base = OTHER
                     note = 2'O-methyladenosine
SEQUENCE: 795
acagcttatt tggaagctga aatgtgaggt ttataacact cacaagaatc ctgaaaaagg    60
atgccaaacg cacagttttg tctgtgata                                      89

SEQ ID NO: 796       moltype = RNA   length = 89
FEATURE              Location/Qualifiers
source               1..89
                     mol_type = other RNA
                     organism = synthetic construct
modified_base        1
                     mod_base = OTHER
                     note = 2'O-methyladenosine phosphorothioate
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methyladenosine phosphorothioate
modified_base        88
                     mod_base = OTHER
                     note = 2'O-methyluridine phosphorothioate
modified_base        89
                     mod_base = OTHER
                     note = 2'O-methyladenosine
SEQUENCE: 796
acagcttatt tggaagctga aatgtgaggt ttataacact cacaagaatc ctgaaaaagg    60
atgccaaaca gaatcaaaat cggtgaata                                      89

SEQ ID NO: 797       moltype = RNA   length = 89
FEATURE              Location/Qualifiers
source               1..89
                     mol_type = other RNA
                     organism = synthetic construct
modified_base        1
                     mod_base = OTHER
                     note = 2'O-methyladenosine phosphorothioate
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methyluridine phosphorothioate
modified_base        88
```

```
                        mod_base = OTHER
                        note = 2'O-methyluridine phosphorothioate
modified_base           89
                        mod_base = OTHER
                        note = 2'O-methyluridine
SEQUENCE: 797
acagcttatt tggaagctga aatgtgaggt ttataacact cacaagaatc ctgaaaaagg    60
atgccaaacc acatcagaat ccttactttt                                    89

SEQ ID NO: 798          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylcytidine phosphorothioate
modified_base           89
                        mod_base = OTHER
                        note = 2'O-methylcytidine
SEQUENCE: 798
acagcttatt tggaagctga aatgtgaggt ttataacact cacaagaatc ctgaaaaagg    60
atgccaaact gatatacaca tcagaatcc                                     89

SEQ ID NO: 799          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylcytidine phosphorothioate
modified_base           89
                        mod_base = OTHER
                        note = 2'O-methyladenosine
SEQUENCE: 799
acagcttatt tggaagctga aatgtgaggt ttataacact cacaagaatc ctgaaaaagg    60
atgccaaaca cacatttgtt tgagaatca                                     89

SEQ ID NO: 800          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
```

```
                    note = 2'O-methyladenosine phosphorothioate
modified_base       88
                    mod_base = OTHER
                    note = 2'O-methyladenosine phosphorothioate
modified_base       89
                    mod_base = OTHER
                    note = 2'O-methyluridine
SEQUENCE: 800
acagcttatt tggaagctga aatgtgaggt ttataacact cacaagaatc ctgaaaaagg    60
atgccaaact gacacatttg tttgagaat                                     89

SEQ ID NO: 801      moltype = RNA   length = 89
FEATURE             Location/Qualifiers
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
modified_base       87
                    mod_base = OTHER
                    note = 2'O-methylcytidine phosphorothioate
modified_base       88
                    mod_base = OTHER
                    note = 2'O-methyladenosine phosphorothioate
modified_base       89
                    mod_base = OTHER
                    note = 2'O-methylcytidine
SEQUENCE: 801
acagcttatt tggaagctga aatgtgaggt ttataacact cacaagaatc ctgaaaaagg    60
atgccaaacg agtctctcag ctggtacac                                     89

SEQ ID NO: 802      moltype = RNA   length = 89
FEATURE             Location/Qualifiers
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
modified_base       87
                    mod_base = OTHER
                    note = 2'O-methyladenosine phosphorothioate
modified_base       88
                    mod_base = OTHER
                    note = 2'O-methylcytidine phosphorothioate
modified_base       89
                    mod_base = OTHER
                    note = 2'O-methyluridine
SEQUENCE: 802
acagcttatt tggaagctga aatgtgaggt ttataacact cacaagaatc ctgaaaaagg    60
atgccaaact tgctccaggc cacagcact                                     89

SEQ ID NO: 803      moltype = RNA   length = 89
FEATURE             Location/Qualifiers
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
```

```
modified_base          87
                       mod_base = OTHER
                       note = 2'O-methyluridine phosphorothioate
modified_base          88
                       mod_base = OTHER
                       note = 2'O-methyluridine phosphorothioate
modified_base          89
                       mod_base = OTHER
                       note = 2'O-methylguanosine
SEQUENCE: 803
acagcttatt tggaagctga aatgtgaggt ttataacact cacaagaatc ctgaaaaagg    60
atgccaaacc acatgcaaag tcagatttg                                     89

SEQ ID NO: 804         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
                       mod_base = OTHER
                       note = 2'O-methyladenosine phosphorothioate
modified_base          87
                       mod_base = OTHER
                       note = 2'O-methylguanosine phosphorothioate
modified_base          88
                       mod_base = OTHER
                       note = 2'O-methyluridine phosphorothioate
modified_base          89
                       mod_base = OTHER
                       note = 2'O-methylguanosine
SEQUENCE: 804
acagcttatt tggaagctga aatgtgaggt ttataacact cacaagaatc ctgaaaaagg    60
atgccaaact tgagaatca aaatcggtg                                      89

SEQ ID NO: 805         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
                       mod_base = OTHER
                       note = 2'O-methyladenosine phosphorothioate
modified_base          87
                       mod_base = OTHER
                       note = 2'O-methylcytidine phosphorothioate
modified_base          88
                       mod_base = OTHER
                       note = 2'O-methyluridine phosphorothioate
modified_base          89
                       mod_base = OTHER
                       note = 2'O-methyluridine
SEQUENCE: 805
acagcttatt tggaagctga aatgtgaggt ttataacact cacaagaatc ctgaaaaagg    60
atgccaaaca tatacacatc agaatcctt                                     89

SEQ ID NO: 806         moltype = RNA   length = 89
FEATURE                Location/Qualifiers
source                 1..89
                       mol_type = other RNA
                       organism = synthetic construct
modified_base          1
                       mod_base = OTHER
                       note = 2'O-methyladenosine phosphorothioate
modified_base          2
                       mod_base = OTHER
                       note = 2'O-methylcytidine phosphorothioate
modified_base          3
```

```
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyladenosine phosphorothioate
modified_base           89
                        mod_base = OTHER
                        note = 2'O-methylguanosine
SEQUENCE: 806
acagcttatt tggaagctga aatgtgaggt ttataacact cacaagaatc ctgaaaaagg    60
atgccaaacg aataatgctg ttgttgaag                                      89

SEQ ID NO: 807          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methylguanosine phosphorothioate
modified_base           89
                        mod_base = OTHER
                        note = 2'O-methyladenosine
SEQUENCE: 807
acagcttatt tggaagctga aatgtgaggt ttataacact cacaagaatc ctgaaaaagg    60
atgccaaact ctgtgatata cacatcaga                                      89

SEQ ID NO: 808          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyladenosine phosphorothioate
modified_base           88
                        mod_base = OTHER
                        note = 2'O-methyladenosine phosphorothioate
modified_base           89
                        mod_base = OTHER
                        note = 2'O-methyladenosine
SEQUENCE: 808
acagcttatt tggaagctga aatgtgaggt ttataacact cacaagaatc ctgaaaaagg    60
atgccaaaca tgtcaagctg gtcgagaaa                                      89

SEQ ID NO: 809          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
```

```
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylguanosine phosphorothioate
modified_base           88
                        mod_base = OTHER
                        note = 2'O-methyluridine phosphorothioate
modified_base           89
                        mod_base = OTHER
                        note = 2'O-methylguanosine
SEQUENCE: 809
acagcttatt tggaagctga aatgtgaggt ttataacact cacaagaatc ctgaaaaagg   60
atgccaaacc tcatgacgct gcggctgtg                                    89

SEQ ID NO: 810          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methylguanosine phosphorothioate
modified_base           89
                        mod_base = OTHER
                        note = 2'O-methylguanosine
SEQUENCE: 810
acagcttatt tggaagctga aatgtgaggt ttataacact cacaagaatc ctgaaaaagg   60
atgccaaaca tctgctcatg acgctgcgg                                    89

SEQ ID NO: 811          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylcytidine phosphorothioate
modified_base           89
                        mod_base = OTHER
                        note = 2'O-methylcytidine
SEQUENCE: 811
acagcttatt tggaagctga aatgtgaggt ttataacact cacaagaatc ctgaaaaagg   60
atgccaaact gcttctgagc tgggcatcc                                    89

SEQ ID NO: 812          moltype = RNA  length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
```

-continued

```
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methylcytidine phosphorothioate
modified_base        88
                     mod_base = OTHER
                     note = 2'O-methyladenosine phosphorothioate
modified_base        89
                     mod_base = OTHER
                     note = 2'O-methyluridine
SEQUENCE: 812
acagcttatt tggaagctga aatgtgaggt ttataacact cacaagaatc ctgaaaaagg    60
atgccaaaca gctgggcatc cgaaggcat                                      89

SEQ ID NO: 813       moltype = RNA   length = 89
FEATURE              Location/Qualifiers
source               1..89
                     mol_type = other RNA
                     organism = synthetic construct
modified_base        1
                     mod_base = OTHER
                     note = 2'O-methyladenosine phosphorothioate
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methylcytidine phosphorothioate
modified_base        88
                     mod_base = OTHER
                     note = 2'O-methylguanosine phosphorothioate
modified_base        89
                     mod_base = OTHER
                     note = 2'O-methyladenosine
SEQUENCE: 813
acagcttatt tggaagctga aatgtgaggt ttataacact cacaagaatc ctgaaaaagg    60
atgccaaacc ttctgagctg ggcatccga                                      89

SEQ ID NO: 814       moltype = RNA   length = 89
FEATURE              Location/Qualifiers
source               1..89
                     mol_type = other RNA
                     organism = synthetic construct
modified_base        1
                     mod_base = OTHER
                     note = 2'O-methyladenosine phosphorothioate
modified_base        2
                     mod_base = OTHER
                     note = 2'O-methylcytidine phosphorothioate
modified_base        3
                     mod_base = OTHER
                     note = 2'O-methyladenosine phosphorothioate
modified_base        87
                     mod_base = OTHER
                     note = 2'O-methylguanosine phosphorothioate
modified_base        88
                     mod_base = OTHER
                     note = 2'O-methylcytidine phosphorothioate
modified_base        89
                     mod_base = OTHER
                     note = 2'O-methyladenosine
SEQUENCE: 814
acagcttatt tggaagctga aatgtgaggt ttataacact cacaagaatc ctgaaaaagg    60
atgccaaacg gaatcccagc caggcagca                                      89

SEQ ID NO: 815       moltype = RNA   length = 89
FEATURE              Location/Qualifiers
source               1..89
                     mol_type = other RNA
                     organism = synthetic construct
modified_base        1
```

```
                           mod_base = OTHER
                           note = 2'O-methyladenosine phosphorothioate
modified_base              2
                           mod_base = OTHER
                           note = 2'O-methylcytidine phosphorothioate
modified_base              3
                           mod_base = OTHER
                           note = 2'O-methyladenosine phosphorothioate
modified_base              87
                           mod_base = OTHER
                           note = 2'O-methylcytidine phosphorothioate
modified_base              88
                           mod_base = OTHER
                           note = 2'O-methyladenosine phosphorothioate
modified_base              89
                           mod_base = OTHER
                           note = 2'O-methylguanosine
SEQUENCE: 815
acagcttatt tggaagctga aatgtgaggt ttataacact cacaagaatc ctgaaaaagg    60
atgccaaact aggaatccca gccaggcag                                      89

SEQ ID NO: 816             moltype = RNA  length = 89
FEATURE                    Location/Qualifiers
source                     1..89
                           mol_type = other RNA
                           organism = synthetic construct
modified_base              1
                           mod_base = OTHER
                           note = 2'O-methyladenosine phosphorothioate
modified_base              2
                           mod_base = OTHER
                           note = 2'O-methylcytidine phosphorothioate
modified_base              3
                           mod_base = OTHER
                           note = 2'O-methyladenosine phosphorothioate
modified_base              87
                           mod_base = OTHER
                           note = 2'O-methylcytidine phosphorothioate
modified_base              88
                           mod_base = OTHER
                           note = 2'O-methylcytidine phosphorothioate
modified_base              89
                           mod_base = OTHER
                           note = 2'O-methyluridine
SEQUENCE: 816
acagcttatt tggaagctga aatgtgaggt ttataacact cacaagaatc ctgaaaaagg    60
atgccaaacg cagcccctcc tcgtgccct                                      89

SEQ ID NO: 817             moltype = RNA  length = 89
FEATURE                    Location/Qualifiers
source                     1..89
                           mol_type = other RNA
                           organism = synthetic construct
modified_base              1
                           mod_base = OTHER
                           note = 2'O-methyladenosine phosphorothioate
modified_base              2
                           mod_base = OTHER
                           note = 2'O-methylcytidine phosphorothioate
modified_base              3
                           mod_base = OTHER
                           note = 2'O-methyladenosine phosphorothioate
modified_base              87
                           mod_base = OTHER
                           note = 2'O-methylguanosine phosphorothioate
modified_base              88
                           mod_base = OTHER
                           note = 2'O-methylguanosine phosphorothioate
modified_base              89
                           mod_base = OTHER
                           note = 2'O-methylguanosine
SEQUENCE: 817
acagcttatt tggaagctga aatgtgaggt ttataacact cacaagaatc ctgaaaaagg    60
atgccaaaca caggtaggac ccagcaggg                                      89

SEQ ID NO: 818             moltype = RNA  length = 89
FEATURE                    Location/Qualifiers
source                     1..89
                           mol_type = other RNA
```

```
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methyluridine phosphorothioate
modified_base           89
                        mod_base = OTHER
                        note = 2'O-methylguanosine
SEQUENCE: 818
acagcttatt tggaagctga aatgtgaggt ttataacact cacaagaatc ctgaaaaagg    60
atgccaaact gaccagatgg acctggctg                                     89

SEQ ID NO: 819          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methyluridine phosphorothioate
modified_base           88
                        mod_base = OTHER
                        note = 2'O-methylguanosine phosphorothioate
modified_base           89
                        mod_base = OTHER
                        note = 2'O-methylguanosine
SEQUENCE: 819
acagcttatt tggaagctga aatgtgaggt ttataacact cacaagaatc ctgaaaaagg    60
atgccaaacc cacttctatg accagatgg                                     89

SEQ ID NO: 820          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylguanosine phosphorothioate
modified_base           88
                        mod_base = OTHER
                        note = 2'O-methylguanosine phosphorothioate
modified_base           89
                        mod_base = OTHER
                        note = 2'O-methyladenosine
SEQUENCE: 820
acagcttatt tggaagctga aatgtgaggt ttataacact cacaagaatc ctgaaaaagg    60
atgccaaaca ccagatggac ctggctgga                                     89

SEQ ID NO: 821          moltype = RNA   length = 89
FEATURE                 Location/Qualifiers
```

```
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
modified_base       87
                    mod_base = OTHER
                    note = 2'O-methylcytidine phosphorothioate
modified_base       88
                    mod_base = OTHER
                    note = 2'O-methylcytidine phosphorothioate
modified_base       89
                    mod_base = OTHER
                    note = 2'O-methylcytidine
SEQUENCE: 821
acagcttatt tggaagctga aatgtgaggt ttataacact cacaagaatc ctgaaaaagg    60
atgccaaacc caccatggag ttggggccc                                     89

SEQ ID NO: 822      moltype = RNA   length = 89
FEATURE             Location/Qualifiers
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
modified_base       87
                    mod_base = OTHER
                    note = 2'O-methyladenosine phosphorothioate
modified_base       88
                    mod_base = OTHER
                    note = 2'O-methylcytidine phosphorothioate
modified_base       89
                    mod_base = OTHER
                    note = 2'O-methylcytidine
SEQUENCE: 822
acagcttatt tggaagctga aatgtgaggt ttataacact cacaagaatc ctgaaaaagg    60
atgccaaacc ctctaccact tctatgacc                                     89

SEQ ID NO: 823      moltype = RNA   length = 89
FEATURE             Location/Qualifiers
source              1..89
                    mol_type = other RNA
                    organism = synthetic construct
modified_base       1
                    mod_base = OTHER
                    note = 2'O-methyladenosine phosphorothioate
modified_base       2
                    mod_base = OTHER
                    note = 2'O-methylcytidine phosphorothioate
modified_base       3
                    mod_base = OTHER
                    note = 2'O-methyladenosine phosphorothioate
modified_base       87
                    mod_base = OTHER
                    note = 2'O-methylguanosine phosphorothioate
modified_base       88
                    mod_base = OTHER
                    note = 2'O-methyluridine phosphorothioate
modified_base       89
                    mod_base = OTHER
                    note = 2'O-methylguanosine
SEQUENCE: 823
acagcttatt tggaagctga aatgtgaggt ttataacact cacaagaatc ctgaaaaagg    60
atgccaaacg gggcccaac tccatggtg                                      89
```

| | | |
|---|---|---|
| SEQ ID NO: 824 | moltype = RNA length = 89 | |
| FEATURE | Location/Qualifiers | |
| source | 1..89 | |
| | mol_type = other RNA | |
| | organism = synthetic construct | |
| modified_base | 1 | |
| | mod_base = OTHER | |
| | note = 2'O-methyladenosine phosphorothioate | |
| modified_base | 2 | |
| | mod_base = OTHER | |
| | note = 2'O-methylcytidine phosphorothioate | |
| modified_base | 3 | |
| | mod_base = OTHER | |
| | note = 2'O-methyladenosine phosphorothioate | |
| modified_base | 87 | |
| | mod_base = OTHER | |
| | note = 2'O-methylguanosine phosphorothioate | |
| modified_base | 88 | |
| | mod_base = OTHER | |
| | note = 2'O-methylguanosine phosphorothioate | |
| modified_base | 89 | |
| | mod_base = OTHER | |
| | note = 2'O-methylcytidine | |
| SEQUENCE: 824 | | |
| acagcttatt tggaagctga aatgtgaggt ttataacact cacaagaatc ctgaaaaagg | | 60 |
| atgccaaacg tcatagaagt ggtagaggc | | 89 |
| | | |
| SEQ ID NO: 825 | moltype = RNA length = 89 | |
| FEATURE | Location/Qualifiers | |
| source | 1..89 | |
| | mol_type = other RNA | |
| | organism = synthetic construct | |
| modified_base | 1 | |
| | mod_base = OTHER | |
| | note = 2'O-methyladenosine phosphorothioate | |
| modified_base | 2 | |
| | mod_base = OTHER | |
| | note = 2'O-methylcytidine phosphorothioate | |
| modified_base | 3 | |
| | mod_base = OTHER | |
| | note = 2'O-methyladenosine phosphorothioate | |
| modified_base | 87 | |
| | mod_base = OTHER | |
| | note = 2'O-methylguanosine phosphorothioate | |
| modified_base | 88 | |
| | mod_base = OTHER | |
| | note = 2'O-methyladenosine phosphorothioate | |
| modified_base | 89 | |
| | mod_base = OTHER | |
| | note = 2'O-methylguanosine | |
| SEQUENCE: 825 | | |
| acagcttatt tggaagctga aatgtgaggt ttataacact cacaagaatc ctgaaaaagg | | 60 |
| atgccaaaca catggaaggt gatgaagag | | 89 |
| | | |
| SEQ ID NO: 826 | moltype = RNA length = 89 | |
| FEATURE | Location/Qualifiers | |
| source | 1..89 | |
| | mol_type = other RNA | |
| | organism = synthetic construct | |
| modified_base | 1 | |
| | mod_base = OTHER | |
| | note = 2'O-methyladenosine phosphorothioate | |
| modified_base | 2 | |
| | mod_base = OTHER | |
| | note = 2'O-methylcytidine phosphorothioate | |
| modified_base | 3 | |
| | mod_base = OTHER | |
| | note = 2'O-methyladenosine phosphorothioate | |
| modified_base | 87 | |
| | mod_base = OTHER | |
| | note = 2'O-methyladenosine phosphorothioate | |
| modified_base | 88 | |
| | mod_base = OTHER | |
| | note = 2'O-methyladenosine phosphorothioate | |
| modified_base | 89 | |
| | mod_base = OTHER | |
| | note = 2'O-methylguanosine | |
| SEQUENCE: 826 | | |
| acagcttatt tggaagctga aatgtgaggt ttataacact cacaagaatc ctgaaaaagg | | 60 |

```
atgccaaact gacatggaag gtgatgaag                                       89

SEQ ID NO: 827          moltype = RNA   length = 89
FEATURE                 Location/Qualifiers
source                  1..89
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
modified_base           87
                        mod_base = OTHER
                        note = 2'O-methylcytidine phosphorothioate
modified_base           88
                        mod_base = OTHER
                        note = 2'O-methyluridine phosphorothioate
modified_base           89
                        mod_base = OTHER
                        note = 2'O-methylguanosine
SEQUENCE: 827
acagcttatt tggaagctga aatgtgaggt ttataacact cacaagaatc tgaaaaagg       60
atgccaaact cttccaggac tcccagctg                                       89

SEQ ID NO: 828          moltype = RNA   length = 56
FEATURE                 Location/Qualifiers
source                  1..56
                        mol_type = other RNA
                        organism = synthetic construct
SEQUENCE: 828
acagcttatt tggaagctga aatgtgaggt ttataacact cacaagaatc ctgaaa         56

SEQ ID NO: 829          moltype = RNA   length = 57
FEATURE                 Location/Qualifiers
source                  1..57
                        mol_type = other RNA
                        organism = synthetic construct
SEQUENCE: 829
tggctgattt tgcagccata aggtgaggaa aattcactca ccaaagccta tgtgaaa        57

SEQ ID NO: 830          moltype = RNA   length = 55
FEATURE                 Location/Qualifiers
source                  1..55
                        mol_type = other RNA
                        organism = synthetic construct
SEQUENCE: 830
agggtagatt tgactgccca aaggtgagga tgaaatcact caccaaatac tgaaa          55

SEQ ID NO: 831          moltype = RNA   length = 56
FEATURE                 Location/Qualifiers
source                  1..56
                        mol_type = other RNA
                        organism = synthetic construct
SEQUENCE: 831
acggtggatt ttgccgccga aaggtgaggg aaaatttcca ctcaccaaag ccgaaa         56

SEQ ID NO: 832          moltype =   length =
SEQUENCE: 832
000

SEQ ID NO: 833          moltype = RNA   length = 69
FEATURE                 Location/Qualifiers
source                  1..69
                        mol_type = other RNA
                        organism = synthetic construct
modified_base           1
                        mod_base = OTHER
                        note = 2'O-methyladenosine phosphorothioate
modified_base           2
                        mod_base = OTHER
                        note = 2'O-methylcytidine phosphorothioate
modified_base           3
                        mod_base = OTHER
                        note = 2'O-methyladenosine phosphorothioate
```

```
SEQUENCE: 833
acagcttatt tggaagctga aatgtgaggt ttataacact cacaagaatc ctgaaaaagg    60
atgccaaac                                                            69

SEQ ID NO: 834          moltype = RNA   length = 20
FEATURE                 Location/Qualifiers
source                  1..20
                        mol_type = other RNA
                        organism = synthetic construct
SEQUENCE: 834
catctttaaa gaattatttt                                                20

SEQ ID NO: 835          moltype = RNA   length = 20
FEATURE                 Location/Qualifiers
source                  1..20
                        mol_type = other RNA
                        organism = synthetic construct
SEQUENCE: 835
ccattttaga aataaatgcc                                                20

SEQ ID NO: 836          moltype = RNA   length = 20
FEATURE                 Location/Qualifiers
source                  1..20
                        mol_type = other RNA
                        organism = synthetic construct
SEQUENCE: 836
gcatttattt ctaaaatggc                                                20

SEQ ID NO: 837          moltype = RNA   length = 20
FEATURE                 Location/Qualifiers
source                  1..20
                        mol_type = other RNA
                        organism = synthetic construct
SEQUENCE: 837
tatttgtgaa gtcttacaag                                                20

SEQ ID NO: 838          moltype = RNA   length = 20
FEATURE                 Location/Qualifiers
source                  1..20
                        mol_type = other RNA
                        organism = synthetic construct
SEQUENCE: 838
aattttatta ataagataac                                                20

SEQ ID NO: 839          moltype = RNA   length = 20
FEATURE                 Location/Qualifiers
source                  1..20
                        mol_type = other RNA
                        organism = synthetic construct
SEQUENCE: 839
tgaagtctta caaggttatc                                                20

SEQ ID NO: 840          moltype = RNA   length = 20
FEATURE                 Location/Qualifiers
source                  1..20
                        mol_type = other RNA
                        organism = synthetic construct
SEQUENCE: 840
aagtcttaca aggttatctt                                                20

SEQ ID NO: 841          moltype = RNA   length = 20
FEATURE                 Location/Qualifiers
source                  1..20
                        mol_type = other RNA
                        organism = synthetic construct
SEQUENCE: 841
acctttttt tttttttacct                                                20

SEQ ID NO: 842          moltype = RNA   length = 20
FEATURE                 Location/Qualifiers
source                  1..20
                        mol_type = other RNA
                        organism = synthetic construct
SEQUENCE: 842
cactttcctt agtgcgcaaa                                                20

SEQ ID NO: 843          moltype = RNA   length = 20
FEATURE                 Location/Qualifiers
source                  1..20
```

```
                    mol_type = other RNA
                    organism = synthetic construct
SEQUENCE: 843
cgcactaagg aaagtgcaaa                                               20

SEQ ID NO: 844      moltype = RNA  length = 20
FEATURE             Location/Qualifiers
source              1..20
                    mol_type = other RNA
                    organism = synthetic construct
SEQUENCE: 844
aagtttcagt cactctaagt                                               20

SEQ ID NO: 845      moltype = RNA  length = 20
FEATURE             Location/Qualifiers
source              1..20
                    mol_type = other RNA
                    organism = synthetic construct
SEQUENCE: 845
tgaagtttca gtcactctaa                                               20

SEQ ID NO: 846      moltype = RNA  length = 20
FEATURE             Location/Qualifiers
source              1..20
                    mol_type = other RNA
                    organism = synthetic construct
SEQUENCE: 846
aattcaatct tcaaccctat                                               20

SEQ ID NO: 847      moltype = RNA  length = 20
FEATURE             Location/Qualifiers
source              1..20
                    mol_type = other RNA
                    organism = synthetic construct
SEQUENCE: 847
ggatagttat gaattcaatc                                               20

SEQ ID NO: 848      moltype = RNA  length = 20
FEATURE             Location/Qualifiers
source              1..20
                    mol_type = other RNA
                    organism = synthetic construct
SEQUENCE: 848
gtttttaaat aaagcatagt                                               20

SEQ ID NO: 849      moltype = RNA  length = 20
FEATURE             Location/Qualifiers
source              1..20
                    mol_type = other RNA
                    organism = synthetic construct
SEQUENCE: 849
tggtttttaa ataaagcata                                               20

SEQ ID NO: 850      moltype = RNA  length = 20
FEATURE             Location/Qualifiers
source              1..20
                    mol_type = other RNA
                    organism = synthetic construct
SEQUENCE: 850
agatcaacag cacaggtttt                                               20

SEQ ID NO: 851      moltype = RNA  length = 20
FEATURE             Location/Qualifiers
source              1..20
                    mol_type = other RNA
                    organism = synthetic construct
SEQUENCE: 851
ctttatttaa aaaccacaaa                                               20

SEQ ID NO: 852      moltype = RNA  length = 20
FEATURE             Location/Qualifiers
source              1..20
                    mol_type = other RNA
                    organism = synthetic construct
SEQUENCE: 852
ctgttgatct cataaataga                                               20

SEQ ID NO: 853      moltype = RNA  length = 20
FEATURE             Location/Qualifiers
```

```
source                  1..20
                        mol_type = other RNA
                        organism = synthetic construct
SEQUENCE: 853
tcttcttggt tgctgttgat                                                   20

SEQ ID NO: 854          moltype = RNA  length = 20
FEATURE                 Location/Qualifiers
source                  1..20
                        mol_type = other RNA
                        organism = synthetic construct
SEQUENCE: 854
aatataaggc tataaatatt                                                   20

SEQ ID NO: 855          moltype = RNA  length = 20
FEATURE                 Location/Qualifiers
source                  1..20
                        mol_type = other RNA
                        organism = synthetic construct
SEQUENCE: 855
cctttaaaca gaagaataat                                                   20

SEQ ID NO: 856          moltype = RNA  length = 20
FEATURE                 Location/Qualifiers
source                  1..20
                        mol_type = other RNA
                        organism = synthetic construct
SEQUENCE: 856
tttaaaggca gaagaaataa                                                   20

SEQ ID NO: 857          moltype = RNA  length = 20
FEATURE                 Location/Qualifiers
source                  1..20
                        mol_type = other RNA
                        organism = synthetic construct
SEQUENCE: 857
attcctacag aaaaactcag                                                   20

SEQ ID NO: 858          moltype = RNA  length = 20
FEATURE                 Location/Qualifiers
source                  1..20
                        mol_type = other RNA
                        organism = synthetic construct
SEQUENCE: 858
tttcaaaata ttgggctctg                                                   20

SEQ ID NO: 859          moltype = RNA  length = 20
FEATURE                 Location/Qualifiers
source                  1..20
                        mol_type = other RNA
                        organism = synthetic construct
SEQUENCE: 859
catttgtttc aaaatattgg                                                   20

SEQ ID NO: 860          moltype = RNA  length = 20
FEATURE                 Location/Qualifiers
source                  1..20
                        mol_type = other RNA
                        organism = synthetic construct
SEQUENCE: 860
taggaatcag agcccaatat                                                   20

SEQ ID NO: 861          moltype = RNA  length = 20
FEATURE                 Location/Qualifiers
source                  1..20
                        mol_type = other RNA
                        organism = synthetic construct
SEQUENCE: 861
acttagatta tgcatttgtt                                                   20

SEQ ID NO: 862          moltype = RNA  length = 20
FEATURE                 Location/Qualifiers
source                  1..20
                        mol_type = other RNA
                        organism = synthetic construct
SEQUENCE: 862
aaacaaatgc ataatctaag                                                   20

SEQ ID NO: 863          moltype =    length =
```

```
SEQUENCE: 863
000

SEQ ID NO: 864         moltype =    length =
SEQUENCE: 864
000

SEQ ID NO: 865         moltype = AA   length = 8
FEATURE                Location/Qualifiers
source                 1..8
                       mol_type = protein
                       organism = synthetic construct
VARIANT                3
                       note = Any naturally occurring amino acid
VARIANT                4
                       note = Trp, Phe, or Tyr
VARIANT                5
                       note = Any naturally occurring amino acid
VARIANT                6
                       note = Any naturally occurring amino acid
SEQUENCE: 865
KRXXXXAF                                                                  8

SEQ ID NO: 866         moltype =    length =
SEQUENCE: 866
000

SEQ ID NO: 867         moltype = AA   length = 6
FEATURE                Location/Qualifiers
source                 1..6
                       mol_type = protein
                       organism = synthetic construct
VARIANT                5
                       note = Lys or Arg
VARIANT                6
                       note = Trp, Phe, or Tyr
SEQUENCE: 867
LGKRXX                                                                    6

SEQ ID NO: 868         moltype =    length =
SEQUENCE: 868
000

SEQ ID NO: 869         moltype = RNA  length = 89
FEATURE                Location/Qualifiers
source                 1..89
                       mol_type = other RNA
                       organism = synthetic construct
SEQUENCE: 869
acagcttatt tggaagctga aatgtgaggt ttataacact cacaagaatc ctgaaaaagg    60
atgccaaaca ccaaaaaata tacgctata                                       89

SEQ ID NO: 870         moltype = DNA  length = 67
FEATURE                Location/Qualifiers
source                 1..67
                       mol_type = other DNA
                       organism = synthetic construct
SEQUENCE: 870
ttttgagtct ccaggaagaa attaatgagc agggacatga gggtacgtaa acgctgtggc    60
ctgccctg                                                              67

SEQ ID NO: 871         moltype = AA   length = 435
FEATURE                Location/Qualifiers
source                 1..435
                       mol_type = protein
                       organism = synthetic construct
SEQUENCE: 871
MILTRKIQLI PVGDKEEVNR VYSYLRDGIF NQNRAMNQYI SALYTATMQG VSKEDRQELN    60
RLYSRMPTSK LGSAYTEDIV FPKGLGTPSS LTLKVKQDFS KQCKDGLLYG KVSLITYKKD   120
NPLLVESEYV KLRKYSKRQN GIYHNYSSHQ EFLDKLYSND LDIFIKFANG ITFKMVFGNP   180
HKSAGLRSEI QQIFEEHYKV CGSSIQIDGK KIILNLSMEI PKKEIELNSD TVVGVDLGIA   240
IPAVCALNNN DYIRQSIGSK EDFLRVRTQL QSQRRRLQKA LKSTSGGHGR TKKLKALDKL   300
KTRERNFVKT YNHYVSKQVI DFAVKNKAKY INLEDLTGPD SSKFILRNWS YYELQQFITY   360
KAAQYGIEVR KVNPYHTSQI CSKCGHWEEG QRIDQAHFVC RNCGAELNAD FNAARNIAMS   420
ADFIDKKTTK SNKAA                                                     435

SEQ ID NO: 872         moltype = AA   length = 297
FEATURE                Location/Qualifiers
source                 1..297
```

```
                        mol_type = protein
                        organism = synthetic construct
SEQUENCE: 872
MILTRKIQII PLGEKEEIDR VYKYLRDGIF YQNKAMNQYM SALYIAAIKD ISKEDRKELN    60
RLYSRVSNSK KGSAYDKSIE FAKNMNLGYV VKQVKQDFAN SCKNGLLCGK VSLPTYRKNN   120
PLLVHVNFVR LRSTNYHQDN GMYHNYESHT DFLDHLYSKD LEVFIKFANN ITFKMIFGNP   180
HKSASLRSEI QQIFEENYKV CGSSIQIDGK KIILNLSMDI PKQELELDEN IVVGVDLGLA   240
IPAVCGLNTN DYIRQSIGSK DDFLRIRTQL QSQRRRLQKS LASTSGGHGR QKKLKPL      297

SEQ ID NO: 873          moltype = AA  length = 433
FEATURE                 Location/Qualifiers
source                  1..433
                        mol_type = protein
                        organism = synthetic construct
SEQUENCE: 873
MILTRKIQLL IVGNNDEVNR VFNYIREGMI SQNKAMNEYM SALYLAELNK ASKEDRKELN    60
QLYGRISNSK KGSAYSQDIV FPKGLPVASS LSMKVKQDFK QSCKNGLMYG KVSLPTYRSD   120
NPLLIHVDYV RLRSNNPHRD SGLYHNYKNH AEFLEHLDNK NITFKLILGN             180
VKKSASLRHE IQMIFEEYYK VCSSSIEIDG RKIILNLSMD IPKEKRELDE NVVVGVDVGI   240
AIPAVCGLNI NDYSRKYIGS VNDFMRVKTK IQHQKSRLQT NLKMTKGGHG RKRKLKTMDK   300
FTDYERNWVQ SYNHYISKQV IDFALKNKAK YINIEDLSGI TKGKNVNKFL KGWSYYQLQS   360
FITYKANKYG IEVRKIDPHY TSQTCSCCGY VDEKNRPKNE KGQSYFRCLK CGHEENADFN   420
AAKNIAKSVN FVK                                                     433

SEQ ID NO: 874          moltype = AA  length = 433
FEATURE                 Location/Qualifiers
source                  1..433
                        mol_type = protein
                        organism = synthetic construct
SEQUENCE: 874
MIQNRRQNRL ILTRKIQIIP LGEKEEIDRV YKYLRDGIFY QNKAMNQYMS ALYIAAIKDI    60
SKEDRKELNR LYSRVSNSKK GSAYDKSIEF AKNMNLGYVV KQVKQDFANS CKNGLLCGKV   120
SLPTYRKNNP LLVHVNFVRL RSTNYHQDNG MYHNYESHTD FLDHLYSKDL EVFIKFANNI   180
TFKMIFGNPH KSAYLRSEIQ QIFEENYKVC GSSIQIDGKK IILNLSMDIP KQELELDENI   240
VVGVDLGLAI PAMCGLNTND YIRQSIGSKD DFLRIRTQLQ SQRRRLQKSL ASTSGGHGRQ   300
KKLKPLEKLK DRERNPVKTY NHYVSKNVVD FAVKNKAKYI NVEDLSGFDS NQFILRNWSF   360
YELQQFITYK AAKYGIEVRK INPYHTSQIC SCCGHWEEGQ RIDQAHFKCK SCGAELNADF   420
NASRNIAMST DFV                                                     433

SEQ ID NO: 875          moltype = AA  length = 453
FEATURE                 Location/Qualifiers
source                  1..453
                        mol_type = protein
                        organism = synthetic construct
SEQUENCE: 875
MILTRKIQLI PVGDKEEIDR VYSYLRDGIF NQNKAMNQYL SALYTATIQE ASKEDRQELD    60
RLYTRIATSK KGSAYQTDIE FPKGLPIGAF GIKVRQDFAK QCKDGLLYGK VSLATYKKDN   120
PLLVHVDYVR LRKTNPHLDN GMYHNYESHQ EFLDHLYSND LEVFIKFANK ITFKLIFGNP   180
RRSAVLRSEI KEIFEEYYKV CGSSIQIDGK KIILNLSMEI PKEEAELDED TVVGVDLGIA   240
VPAMCALNNN MYVRAAIGNK DDFLRIRTKI QAQRRRLQHS LKYTSGGHGR NKKLKALEKL   300
KKSEAHFVET YNHMVSRRIV DFAVKNHAKY INVENLTGYN TSKFILRNWS FYQLQQYITY   360
KAARYGIEVR KINPCYTSQV CSVCGHWEEG QRKSQSVFEC ANPDCESYTK YEYGFNADFN   420
AARNIAMSTL FMEKGEVTEK SKQEAREYYG IIS                                453

SEQ ID NO: 876          moltype = AA  length = 424
FEATURE                 Location/Qualifiers
source                  1..424
                        mol_type = protein
                        organism = synthetic construct
SEQUENCE: 876
MILTRKIQLY PIGDKEEVKR VYKYLSDGIF NQNKAMNQYI SALYMSTIQE ASKEDKQELN    60
RLYTRISTSK KGSAYDKDIE FAKGLPIGSL GQKVKQDFQK SIKDGLLYGK VSLPTYRKDN   120
PLLIHVDYVR LRKTNPHRDN GIYHNYFNHQ DFLDLNYSKD LEILIKFANN ITFKMILGQP   180
HKSATLREEI KQIFEENYKV CGSSIQIDGT KIILNLSMDV PKKEVELDEN TVVGVDLGIA   240
IPAVCGLNNN EYIKQSIGNK EDFLRIRTQM QSERRRVQSN LKLSKGGHGR KKKLKHLDNL   300
SDRERNFVKT YNHYVSKQVV DFALKNKAKY INVEDLSGFD SSQFILRNWS YYELQQFITY   360
KANKYGIEVK KINPYHTSQI CSCCGYWEEG QRDSQSHFKC KSCGYETNAD FNASRNIAKS   420
VDFR                                                               424

SEQ ID NO: 877          moltype = AA  length = 433
FEATURE                 Location/Qualifiers
source                  1..433
                        mol_type = protein
                        organism = synthetic construct
SEQUENCE: 877
MILTRKIQLL VVGNNDEVNR VFDYIREGMI SQNKAMNQYM SALYLAELDK ISKEDRKELN    60
QLYGRISNSK KGSAYSQDIV FPKGLPTASS LSMKVKQDFK QSCKNGLMYG RVSLPTYRSD   120
NPLLIHVDWV RLRSSNPHND FGLYYNYKNH AEFLEHLDDK DLEVFIKFAN NITFKLILGN   180
VKKSASLRHE IQMIFEKYYK VCNSSIEIDG RKIILNLSMD IPEQKIELDE NVIVGVDIGI   240
```

```
AIPAVCGLNT NDYSRKYIGS VNDFMRIKIK IQHQKNRLQT NLKMAKGGHG RKRKLKAMDK   300
FTDYERNWVQ SYNHYVSKQI INFALKNKAK YINIEDLSGI TKGKNVNKFL KGWSYYQLQS   360
FITYKANKYG IEVRKIDPHY TSQTCSCCGY VDEKNRSKNE KGQSYFKCLK CGHEENADFN   420
AAKNIAKSVN FVK                                                     433

SEQ ID NO: 878          moltype = AA  length = 437
FEATURE                 Location/Qualifiers
source                  1..437
                        mol_type = protein
                        organism = synthetic construct
SEQUENCE: 878
MSMLTRKIQL IPIGDKEEIN RVYSYLRDGI FNQNKAMNQY ISALYTAAMQ DASKDDRQEL   60
NRLYSRMPSS KLGSAYTDTI EFPKGLGTPS SLTMKVKQDF SKQCKDGLLY GKVSLITYRM   120
DNPLLVEAEY IKLRKHSKKQ CGIYHNYSSH QEFLDHLYSN DLDIFIKFAN KITFKMVLGN   180
PRKSASLRSE LQQIFEEYYQ VCGSSIQIDG KKIILNLSME IPKKEIKLKE DTVIGVDLGI   240
AIPAMCALNN NEYIRKSIGS KDEFLRIRTH LQSQRRRLQK SLASTSGGHG RKKKLKALDK   300
LKARERNFVK TYNHYISKQV VDFAVKNEAK YINIEDLSGF NGSDFILRNW SYYELQQFIT   360
YKAAQYGIEV RKINPYYTSQ VCSKCGHWEE GQRIDQAHFI CKECGNEMNA DLNAARNIAL   420
STNFAETKKT KKDKKVA                                                 437

SEQ ID NO: 879          moltype = AA  length = 441
FEATURE                 Location/Qualifiers
source                  1..441
                        mol_type = protein
                        organism = synthetic construct
SEQUENCE: 879
MSNTYIITRK IQVVPVGDKE EINRVYTYLR EGIAQNMAM NQYMSALYST MMMDISKEDR    60
KELNKLYARV SSSKLGSAYD KSIEFAKGLP MGGSIQQKVK QDFDNAMKKG LQYGKLSLPS   120
YREDNPLLIH VDYVRLRSTN PHIDNGLYHN YESHQDFLDH LFKSDLELFI KFANKITFKV   180
IVGQPHKSAE IRSVFKNIFE DYYHIKGSSI EFSGTKIILN MSIEIPKQQK ELDENVVVGV   240
DLGIAIPAVC ALNTNDYVRK SIGSKDDFLR VRTQIQNQRR RLQSNLKMSN GGHGRKKKMK   300
PMDKFTKYEK HWVQTYNHQI SKQIIDFALK NNAKYINLED LSSFNQKRLR DNFLLANWSY   360
YQLQQYIKYK AEKYGIVVRF INPYHTSQNC SCCGHYEDGQ RVKQSEFICK NPECKNFGIK   420
INADFNAARN IAMSTDFIKN K                                            441

SEQ ID NO: 880          moltype = AA  length = 426
FEATURE                 Location/Qualifiers
source                  1..426
                        mol_type = protein
                        organism = synthetic construct
SEQUENCE: 880
MILTRKIQLY PVGDKEEVNR VYQYIRDGIF NQNKAMNQYM TALYVSTIQD ISKEDRQELN   60
RLYTRIATSK KGSAYDLDVE FAKGLPTTSS LGQKVRQDFS KACKDGLLYG KVSLPTYRKD   120
NPLLVHVDYV RLRETNPHKD NGIYHNYESY DEFISKLYDK DLEIFIRFAN GITFKMILGQ   180
PHKSIYLREE IKKIFDGEYN VCGSSIQFND KKIILNMSMD IPKISRELDE NTVVGVDLGI   240
AVPAVCGLNN SNVKKQFIGS KEDFLRIRTQ LQARKRLQK NVKITNGGHG RNKKLKALDK    300
LSNKERNFVK TYNHYVSKQV IDFALKNNAK YINMEDLSGF NTNKFILRNW SFYELQQFIT   360
YKAQRYGIEV RKINPYHTSQ ICSKCGHWEE GQRDTQDHFK CKACGYEDNA DFNASKNIAK   420
SIDFRK                                                             426

SEQ ID NO: 881          moltype = AA  length = 441
FEATURE                 Location/Qualifiers
source                  1..441
                        mol_type = protein
                        organism = synthetic construct
SEQUENCE: 881
MNNILSRKIQ LFPIGDKEEI NRVYKYLRDG MKAQNLAMNQ YMSALYISMQ NEATKEDRKE   60
LRNLYGRIST SKKGSAYNLS IEFAKGLPSA SSVTQKVEKD FKNAMKKGLA YGKISLPTYR   120
DTNPLIIHPD YVRLRTKSKC DNGFYHNYEN HFEFLSHLYN KDLELFLKFA NGITFKVILG   180
NPHKSVEIRN VFGNIFEENY SINQSTIEID GTKIILNLSL SMPQCEIKLD ENICVGVDVG   240
LAIPAVCALN TNDVYKKFIG SKDDFLRVRT KIQNQYKRLQ KSIAQSNGGH GRKKKLQAMD   300
RFKEYESNWT KTYNHWVSKQ VVDFAVKNKA KYINIEDLSG IGNGNKNQFV LRNWSYYQLQ   360
QFITYKANKY GIIVRNVNPY HTSQVCSCCG HWEKGQRISQ SEFICKNPEC DNFGKKINAD   420
FNAARNIAMS TDFVDDKKKA V                                            441

SEQ ID NO: 882          moltype = AA  length = 432
FEATURE                 Location/Qualifiers
source                  1..432
                        mol_type = protein
                        organism = synthetic construct
SEQUENCE: 882
MNETCVITRK VKLFPVGNKE EVNRVYKYLR DGIESQNKAM NQYMTALYVA MIQEASSEER   60
KELKNLYQRI STSKKGSAYD KTIEFAKGLP MGGSITTKVK SDFDNAMKKG LKYGRISLPS   120
YRDKNPLLIH RDYVRLLETN PHLNNGIYHN YKNSDEFKEH LYKDDFEMFI KFANDITFKV   180
IFGNPHKSE LRSVFGNIVD GIYNVGGSSI GIDGNKIILN LSIEIPKKKV ELSEDIVCGV    240
DLGIAVPAMC ALNTDDYKRM SIGSANDFIR VRTKIQAQYK RLQMSLKNTS GGHGRKKKLS   300
PLNKFKEYEK NWVNNYNHMV SRRVVDFAIK NGAKYINIEN LEGFGKSKHT YILRNWSYYQ   360
LQQDIIYKAN MVGIEVRKVN PYHTSQNCSC CGHWEEGQRL DQAHFVCGSC GATLNADFNA   420
ARNIAMSTDF IE                                                      432
```

```
SEQ ID NO: 883          moltype = AA   length = 432
FEATURE                 Location/Qualifiers
source                  1..432
                        mol_type = protein
                        organism = synthetic construct
SEQUENCE: 883
MNETCVITRK VKLFPVGNKE EVNRVYKYLR DGIESQNKAM NQYMTALYVA MIQEASSEER    60
KELKNLYQRI STSKKGSAYD KTIEFAKGLP MGGSITTKVK SDFDNAMKKG LKYGRISLPS   120
YRDKNPLLIH RDYVRLLETN PHLNNGIYHN YKNSDEFKEH LYKDDFEMFI KFANDITFKV   180
IFGNPHKSKE LRSVFGNIVD GIYNVGGSSI GIDGNKIILN LSIEIPKKKV ELSEDIVCGV   240
DLGIAVPAMC ALNADDYKRM SIGSANDFIR VRTKIQAQYK RLQMSLKNTS GGHGRKKKLS   300
PLNKFKEYEK NWVNNYNHMV SRRVVDFAIK NGAKYINIEN LEGFGKSKHT YILRNWSYYQ   360
LQQDIIYKAN MVGIEVRKVN PYHTSQNCSC CGHWEEGQRL DQAHFVCGSC GATLNADFNA   420
ARNIAMSTDF IE                                                      432

SEQ ID NO: 884          moltype = AA   length = 432
FEATURE                 Location/Qualifiers
source                  1..432
                        mol_type = protein
                        organism = synthetic construct
SEQUENCE: 884
MNETCTIVRK IKLFPVGDNE EINRVYTYLR EGIESQNRAM NQYMSALYMA MMQDVSKEDR    60
KELNALYQRI STSKKGSAYD DTIEFAKGLL MGGSITQKVK ADFDNAMKKG LKYGRISLPT   120
YRDKNPLLVH RDYVRLLETN PHLKNGIYHN YETMDEFKEH LYKDDFEMFI KFANDITFKI   180
IFGNPHKSRE LRSVFENIVD GTYDVQGSTI GIEGKSIILN LSIKIPKKKI ELLEDVVVGV   240
DLGVAIPAVC ALNTNDYVRL SIGSADDFIR VRTKIQAQRK RLQKDLAKSN GGHGRKKKMA   300
AIERFEQYES NWVRSYNHMV SRRIVDFAIK NQAKYINIEC LDGFAEAGHT YILRNWSYYQ   360
LQQDIVYKAN MVGIEVRKVN PYHTSQICSC CGHWEEGQRK DQAHFVCGSC GAKLNADFNA   420
ARNIAMSTAF VK                                                      432

SEQ ID NO: 885          moltype = AA   length = 426
FEATURE                 Location/Qualifiers
source                  1..426
                        mol_type = protein
                        organism = synthetic construct
SEQUENCE: 885
MILTRKIQLY PVGDKEEVNR VYQYIRDGIF NQNKAMNQYM TALYVSTIQD ISKEDRQELN    60
RLYTRIATSK KGSAYDLDVE FAKGLPTASS LGQKVKQDFS KACDGLLYG KVSLPTYRKD   120
NPLLVHDYV RLRETNPHKD NGIYHNYESY DEFISKLYDK DLEIFIRFAN GITFKMILGQ   180
PHKSIYLREE IKKIFDGEYN VCGSSIQFND KKIILNMSMD IPKISRELDE NTVVGVDLGI   240
AVPAVCGLNN SNVKKQFIGS KEDFLRIRTQ LQAQRKRLQK NVKITNGGHG RNKKLKALDK   300
LSNKERNFVK TYNHYVSKQV IDFALKNNAK YINMEDLSGF NTNKFILRNW SFYELQQFIT   360
YKAQRYGIEV RKINPYHTSQ ICSKCGHWEE GQRDTQDHFK CKACGYEDNA DFNASKNIAK   420
SIDFRK                                                             426

SEQ ID NO: 886          moltype = AA   length = 452
FEATURE                 Location/Qualifiers
source                  1..452
                        mol_type = protein
                        organism = synthetic construct
SEQUENCE: 886
MTETQIITRK IQLIPVGDKE EINRVYTYLQ DGIKSQNMAM NQYMSALYSS MVVEISKDDR    60
KELNKLFGRI STSNLGSAYD KTIEFAKGLP MGGAIQQKVK RDFDNAMKKG LKYGKLSLPT   120
YRENNPLLVH VDYVRLRTTN PHSDNGLYHN YESHEDFLNS LYSKDLELFI KFANKITFQI   180
VLGNPHKSAE IRSVFKNIFE DYYHIKGSSI QIDGKKIILN MSIEIPKQKV ELDENVVVGV   240
DLGLAIPAMC ALNTNDYVRL RIGSRDDFLR VRTQIKSQRR RLYSNLKPAH GGHGRSKKMQ   300
ATDRFTNYEK NWVQTYNHMV SKRVVDFALK HKAKYINLEC LDGFSKKQLR DNYLLANWSY   360
YQLQQYIKYK AEKYGIVVRF VNPYHTSQNC SCCGHWEEGQ RVKQAEFICK NPECKNYGKK   420
INADFNAARN IAMSTDFVEK EEKKKKTKK AA                                 452

SEQ ID NO: 887          moltype = AA   length = 301
FEATURE                 Location/Qualifiers
source                  1..301
                        mol_type = protein
                        organism = synthetic construct
SEQUENCE: 887
MKFVNGIWFE VKFGQPHKSK ELRSVFQNIF NGTYKTMGSS IEISRNNKII MNLTLQMPKQ    60
EVELDPNVVV GVDLGVAIPA YCALNTNDYV KKACGNADDF LRVSTQIKAE RRRLQKPLKY   120
NSGGHGRKKK LAPMDRFTDY ESNWAKTYNH KISNDIVDFA VKNHAKYINI ENLQGFGSVE   180
SADEVRAERE PKSKNFLLGN WRYYQLQQFI TYKAEKYNIE VRKVNPYYTS RRCSCCGNED   240
ANNRKSQAEF VCTKCGAKMN ADFNVARNIA MSTDFSDGKT SKETKKRQHK EYIAKNQKAI   300
A                                                                  301

SEQ ID NO: 888          moltype = AA   length = 437
FEATURE                 Location/Qualifiers
source                  1..437
                        mol_type = protein
                        organism = synthetic construct
```

```
SEQUENCE: 888
MAKDTFTITR KIQLVPVGDK TEVNRVYNYI REGMKAQNLA MNQYISALYL GMQNDVSKDD    60
RKELNNLFSR ISTSKKGSAY DESIQFAKGL PIGSMTRKVK SDFDTAMKKG LKYGKLSLPT   120
YKDSNPLLVH VDYVRLRSTN PHQDSGLYHN YTNHTEFLEH LYKSDFELFI KFANYITFKI   180
ILGNPHKSAE IRDVFKNIFE ECYAIQGSSI GIYNNKIICN LSISIPKKQL CLDENIVVGV   240
DLGLAVPAVC ALNTVPYIHK SLGNYDDFVR ERTKMQSQRK RLQKSLNYAN GGHGRKKKLQ   300
SLERLKKRER NWVQTYNHKI SKQIVDFAIK NKAQYINIED LSGFDSSQFV LRNWSYFELQ   360
QFIEYKANKY GIIVRKINPY HTSQTCSFCG HWEEGQRISQ SEFICKNPEC VNHNKSINAD   420
YNAARNIAMS TDFVKNN                                                 437

SEQ ID NO: 889         moltype = AA  length = 455
FEATURE                Location/Qualifiers
source                 1..455
                       mol_type = protein
                       organism = synthetic construct
SEQUENCE: 889
MPTITRKYQL KVVGDKEETD RVYTYLRNGI EAQNKALNEA ISALYAAKIL EMSTDDNKEL    60
TKLFQRVTHG KNETGFTDDI TFPVGLPTAG GVGRKAKQDL DNAFKKGLRY GRVSLPSYKA   120
DNPLMIHVDY VRLRSTNPHK DNGIYHEYET PIDLIEALEK ENNPKVFLKF VNGIVFRFVF   180
GNPWKGREQR KVFEKIFSEE YKVCGSSIEV DGKKIILNLC MDVPKAEHKL DKNVTVGVDL   240
GLAIPAVCAL NNNEYERLFI GNIDDFLRVR TQLQSQRRRL QKNMRNGSGG HGRSKKLKAM   300
DRLRDRERNF VQTYNHMVSR RVVDFAVKNN AAYINIEDLS GFGKDRNGDI HKDKEIVLRN   360
WSYYELQNYI TYKAQMHGIE VRKVKPEYTS QICSYCGKRG IRREQAKFVC INPECRSHKI   420
YDKGFVNADF NAARNIAMSA NFVEDTETKQ TRKGA                             455

SEQ ID NO: 890         moltype = AA  length = 442
FEATURE                Location/Qualifiers
source                 1..442
                       mol_type = protein
                       organism = synthetic construct
SEQUENCE: 890
MPNLTRKYKL IPVGDKEEVN RVYTYLREGM EMQNKAMNQY MTALYVAQMR EASKEDRKEL    60
SKLFSRVSTS KKGSAYTDDI VFPKGLGTPS MIKRKVNEDF GNAMKKGLMY GRISLPTYRQ   120
DNPLLIHPDY VRLRSLSTRD NGIYHKYDSP MDLINGLEKD TNPEVYIKFA NGITFKIVFG   180
NPHKGREQRK VFENIFSETY KVCGSSIGID KNRKIILNLC LEVPKQEHNL DGNVIVGVDV   240
GIAINAMCAL NNNYHIREAI GDESNLLRVK EQMNAERKRL QEGLKFSKGG HGRKKKLKAL   300
DRLKDRERNF TQTYNHKVSN KVVEFALRHN ASQINIEDLS GFGKDRKGNV KDDKDILRS    360
WCYYELQNYI TYKAQLHGII VRKVNKDYTS QTCSCCGQRG IRLSQSEFMC QNPDCKCHTL   420
YGKYINADFN AARNIAMSTD YK                                           442

SEQ ID NO: 891         moltype = AA  length = 417
FEATURE                Location/Qualifiers
source                 1..417
                       mol_type = protein
                       organism = synthetic construct
SEQUENCE: 891
VDAQTITRKI QLYPVGDNEE VDRVYKFIRD GMYAQYQASN LLMGQLASEY FKSNRDFKSE    60
SFKTAQKEIL KAVNPLLQEI SFPKGNDTIS IVIQKVKQDF STSLKNGLAR GERAITNYKR   120
TNPLLIRSRN LEFYNEYKSY NDFLDKLFTD ELEVFIKWVN HIKFKVVFGN PHKSHELRCV   180
VQNIFEEIYK VKGSSIQFDN TEKKIILNLS LSIPKKIMEL DENTVVGVDL GIAVPAVCAL   240
NNDEVTREFI GSKDDFIRVR TKIQAQKRRL QKSLKYTNGG HGRNKKLKPL NKFEEYEKNF   300
VQTYSHMVSK NVVEFAIKNK AKYINIEDLE GYNSNGFILR NWSYSKLEEY IIYKARLHGI   360
EVRKVNPYHT SQVCSCCGHW EEEQRIDQSH FKCKLCGAEL NADFNAARNI AKSNNFR     417

SEQ ID NO: 892         moltype = AA  length = 442
FEATURE                Location/Qualifiers
source                 1..442
                       mol_type = protein
                       organism = synthetic construct
SEQUENCE: 892
MPKITRKYQL KVIGDKEEID RVYKYIREGT EAQNKALNEA MSALYAANLL DMSKDDKKEL    60
SKLFSRVTNG KNESGFTDDI CFATGLGTTS SIKQKVKQDF NNACKKGLMY GRVSLPSYKT   120
DNPLLVSKSY VQLLSESDKN FGIYNAYETP MDLVDALEKE TNPEVYLKFA NNILFKFVFG   180
NPWRGREQRK VFERIFSGEY KICGSSIGID GKKIILNLCM DIPKQKHNLD ENIIVGVDLG   240
LAIPAMCALN NDDYKRLSIG SIDDLLRVRI QLQNERKRIQ GNLKNSKGGH GRQRKLKALE   300
NLKDRERNFV QTYNHMVSKR VVDFAVKNNA RYINMEDLSG FGKTRYGKSK SEDEKVLRNW   360
SYYELQNYIT YKAQLHGITV RKVRAEYTSQ TCSYCGSKGI RKEQKKFVCV NPDCKCHKIY   420
DGYINADFNA ARNIAMSNDF VE                                           442

SEQ ID NO: 893         moltype = AA  length = 532
FEATURE                Location/Qualifiers
source                 1..532
                       mol_type = protein
                       organism = synthetic construct
SEQUENCE: 893
MANKSSKKPL IITRKYALIP IESPSPIWTK SVISFLNKDY ISKIEYKKQL IEIENKKGKK    60
KDNNKIEKWE KEIANIESKI ELVDNGDFTS GIVNDYTYNL IRKCCEEQSI IKNHTMFAMG   120
AAYKDCIIKG IDEKERTEIV TDVFNSWSRV PNSSKGSMLD KMNIDLSIGS YELAYVNALK   180
NKFWECVKDG FAYARQTLPY YKSDCPMDIA SKEMSFTHDY ESFEELCEHI NEKPNLYFNY   240
```

```
GGNGKPHIFR FKINTGHGKN NDELMATLMK VYAKEYKVCG SSIQIQKSGN DKKDKIILNL      300
SLEIPKVKRE LDKNICVGVD LGIAIPAMCA LNTNDYVRQS IGSKDDFLRV RTKISNQRSR      360
LQASLKMSNG GHGRKKKMKP MDRFEDYEAN WVQNYNHFVS KQVVDFAIKN KAKYINIENL      420
EGFDANNYLL AKWSYYQLQQ YISYKAKING IEVRKINPYH TSQRCSCCGY EDKGNRPKGK      480
KKQAYFKCLK CGKEMNADFN AARNIAMSTE WSDGKTTKEQ KKKQHEEYIK KE             532

SEQ ID NO: 894            moltype = AA   length = 426
FEATURE                   Location/Qualifiers
source                    1..426
                          mol_type = protein
                          organism = synthetic construct
SEQUENCE: 894
LILTRKIQLI PCTEGMTTDE AKVEVNRIYQ LLRDGIYAQN KAYNIFISRM YTAILLGASK       60
EELKEIRLKG ERTPKESDSD YSLYDFDKIK FIKGLPQASA LGEQALKALK KQQKDGLYKG      120
KVSLACRKLD APMWIKTKFS FFHKYNDYQE FLDHLYCDDL KIYMKFVQGI VFEVVLGNPH      180
KSETIRTEFQ QIFEGHYKLC SSSLQIKDKK IMLNLAIDIP EKGIELNDET VVGVDIGIAI      240
PAVCALNNRE YVHKSIGSAE ELLRIRTQLQ SQKRRLQKNL KNTTGGHGRS HKLAPLDKLA      300
KRERNFVQTY NHMISKTVVE FAVKNKAKYI NLEDLSNYKD NGSEFILRNW SYFELQSQIE      360
YKAKMHGIIV RKINPYHTSQ ICSKCGHWEE GQRISQSKFK CKSCGYESNA DFNAARNIAL      420
STDFIE                                                                 426

SEQ ID NO: 895            moltype = AA   length = 470
FEATURE                   Location/Qualifiers
source                    1..470
                          mol_type = protein
                          organism = synthetic construct
SEQUENCE: 895
MPTLTRKVEL YVVGDKEEVS RVYDYIRLAM NATYKCFNEC MTALYIAQVK EDTKEDRKEL       60
NHLYSRQTYT KKETAFTNDI VFPEGLALAA YVNRMAQQKF VTSLKNGLMY GCVSLPTFKK      120
DCAVPLHVKF VSLAGEKGTN TGFYHEYADV NDLVNALEYD NSPKVFLRFP NNITFGVVFG      180
NPYRGREQRS VFSKIFLGEY KIQGSSIQIN SRGKIILNLS MEVPKKKMEH IEGRVVGVDV      240
GLAIPAMCAI NDDDYTRSAI GNIDDFLKVR TQIQSQRRRL QKSLKNTSSG HGRTKKLKPL      300
ERIAEKERNF ANTYNHMVSK RVVDFAVKNG ASQINIEDLS GFAKDKNGKS VEDDNMKRVL      360
SNWSYFELQQ QIRYKAEQYD IKVRTVNPAY TSQTCSYCGQ IGKRETQSKF VCTNPDCKCH      420
KMYKKDWFNA DFNAARNIAL STDYTDDEDG KKTKKKKSAK KKPEKKTEEA                 470

SEQ ID NO: 896            moltype = AA   length = 474
FEATURE                   Location/Qualifiers
source                    1..474
                          mol_type = protein
                          organism = synthetic construct
SEQUENCE: 896
MPKLTRKYRL QVVGDDQERS RVYKYIRNAM DATYKCYNEY MSARYIAELK SETGEEKKEL       60
TKLVNKLYSR QTGTKLESAF TSNIEFPKGL ALAATIENSA SKKFEDIKYD VINGRVSLPT      120
YKKDGAVPLH VRYVSLKGEK GSGHGFHHGY DTLEQLYYGL EKDLEPKVFL RFPDKIEFRV      180
CFGNPYKSSE QRKVFMRIFS GEYKSQGSSI QINSKGKIIL NLVMEVPKKE MKHIDGVVVG      240
VDLGMAIPAM CALNNDLYDK CDIGNINDFL RVRTAIAARR RRLQKSLTTT NGGHGRTKKL      300
QALDRFAETE RNFVQTYNHM VSRNVVDYAV KHGAVQINVE DLSGFGRDKN GKSLDDERKK      360
KVLRNWSYFE LQQQITYKAA QYGIEVRKVN PAYTSQTCSY CGTMGERPKQ AVFICSNPDC      420
KCHEIYQKNK DHCFNADFNA ARNIAMSTDY TDVNSDGEKK KTVKKKKKAD KKED            474

SEQ ID NO: 897            moltype = AA   length = 474
FEATURE                   Location/Qualifiers
source                    1..474
                          mol_type = protein
                          organism = synthetic construct
SEQUENCE: 897
MSKDYNVTTR KFNLKVVGDQ KEKDRVNKYL SDGMYAQNAA YNILISKVYS KLHEKGSTFA       60
DVDEILKKGS RKPKENDPDH SLSEYEGLHF PTGLSVPGCL GREVNADIKK NGLMKMDSSL      120
PTRKIGCPLY VTYQNGKIFS FYHNYDSYDD LVDNLYNNKN VKIFMKFANN ITFEVVFGNI      180
NKSRELRSVF EHIFDGTYGI GDSKIAIENP KSIYAENINN ETNDTKKPKR QAKDKEITFY      240
LSVKMPKKYI DLDENVVAGV DLGIKVPAMC ALNTNSYIKE SIGDIEDFLR VRTKINAERS      300
RLQHSLKYSN GGHGRYKKMK AMDAFKNYEK NFATTYNHKV SKDVVDFAIK NKAKYINIEN      360
LEGFGNSDSG VEEKEYRKKS FFLRYWSYYQ LQQFITYKAE QNGIIVRKVN PYYTSRRCSC      420
CGNEDKNNRK SQENFVCTKC GKKMNADFNA ARNIAMSTDF SDGKKTKKEN KKTA            474

SEQ ID NO: 898            moltype = AA   length = 457
FEATURE                   Location/Qualifiers
source                    1..457
                          mol_type = protein
                          organism = synthetic construct
SEQUENCE: 898
MTICRKIKLF PVGDKDEINR VYDFIRNGQY AQYQACNLLM GQLMSEYYKY NRDIKNEEFK       60
ARQKEIMTNS NIILKDIDFA TGVDTPSAVT QKVKQDFSTA LKNGLAKGER TVTNYKRTNP      120
LITRGRNLTF YHEYETYHDF LDKINDFDLA VYVKWVNKIV FKVVFGNPHR SLELRSVQQN      180
ILEENYKVQG SSIEIDGKSI ILNLSISIPK QLRELDENTV VGVDLGIAVP AMCALNNNLY      240
ERLAIGNADD FLRIRTKMQA QRRRLQKSLR NTSGGHGRAK KLKALERLQK TEAHFVETYC      300
HMISKRVVDF ALKHNAKYIN IENLTGYDTS DFILRNWNYY KLQDYITYKA AKYGIEVRKI      360
NPCYTSQVCS VCGNWEFGQR KSQSVFECAN ENCDSHKKYE KTGFNADFNA ARNIAMSTLW      420
```

```
MEGGQVTEKS KQEAREYYDI SEKYEQNKND SENNKVA                              457

SEQ ID NO: 899         moltype = AA  length = 540
FEATURE                Location/Qualifiers
source                 1..540
                       mol_type = protein
                       organism = synthetic construct
SEQUENCE: 899
VNTFISTKKI IISPIEEDKY KKNDIYSYLR KAITAQNRAF NLLLTKTASA ILDNKSSKTI      60
EDIYYSYSHQ KPDVSLETEK LLYEVLALAP ITEEVIESKI AELKEFLKSK GKSEKSIKTS    120
CDKKEKSYRK FLGKSKEDIQ RDIVRLQNYC AYPEDIYNDF ANGLSTPSYV MQQVKKYWKT    180
NKNNVIKGEG VRTMSLTNPL ILPPNIFYNN NGNLQGITHG YSSDEEFYNN LYGDKKLKVY    240
FSMPYRKGED KILFQLILGN PYKSHELRYV LENIFIGTYK IRGSSIGFIK NRETGKMTDL    300
CLYLVVEHQQ KEHVLDENVT CGVDLGQAVP AVCAVSNNKY DRLYIGSAAD FLRQRTKIQD    360
QYKRLKKSLK NTSGGHGRKK KLKALDRFED YEKNFVSSYN HMVSKRVVDF ALKHNAKYIN    420
LEYLKGYDTS KFILRNWSYY QLQTYIEQKA AKYGIVVRYI NPCYTSQVCS ECGHWEENQR    480
KSQADFVCGD GCFSNDKYKK INADVNAARN ISNSTLFLDR TEDYEKEDLI KQARAYYGIE    540

SEQ ID NO: 900         moltype = AA  length = 478
FEATURE                Location/Qualifiers
source                 1..478
                       mol_type = protein
                       organism = synthetic construct
SEQUENCE: 900
MPILTRTIEL IPIGDKEERD RCYKWIRDFM EEQSKMMNQY MSALYIAAVE EVSKDDRKEL      60
NNLYNRIATS KKGSAFSKEE CNLPKGLGAN YGQRVRSDFD TACENGLLHG RVSLPTYKKN    120
FPIILAPIYV NLQKNNIEEK GKSAGFYHNY ASYNELYDAL KEENKPEIIW NFVQKMQYQI    180
KFGNPYKSAF LRDEILHFLE GEYKAVGSQL SINSRGKIIL NLSLDVPQKK VKLDENIVVG    240
IDIGLAVPVM CAINNDYYKR LAVGDFEAFT RMREKLYSQK CKLQRQLKYT SGGHGRKKKL    300
ASLNAIRDRE HRFVHTMNHK YSSEVINFAL KNNAKYINME DLTGFGKDNK GNAIDDYQFV    360
LRNWSYFELQ KMIQDKAQKY GIVVRKVESA YTSQLCSCCG EMGERVSQSV FRCLNPNCIS    420
HNKYEKQRKS GVGNYHFNAD FNAARNISMS TNYTKKKRKT KAEKVEERKK NAIEKTAG      478

SEQ ID NO: 901         moltype = AA  length = 449
FEATURE                Location/Qualifiers
source                 1..449
                       mol_type = protein
                       organism = synthetic construct
SEQUENCE: 901
MNNDRITICR KIKLTPLGDK EERNRVFQYI RNGQYAQYQA CNLLMGQLIS EYYKYDRDIK      60
NEDFKARQKE IMKNSNPLFH EIEFAIGNDT PSAVTQKVKA DFNTALKNGL AKGERSVTNY    120
KRTNPLITRG RSIQFYHNYG TYQEFLDNIN STDLEIYLKK VNKIKFKVIL GNPYRSAELR    180
SVIKNIIEEN YGIQGSSIYI DEKDIILNLS LSIPKKIQKL DENTVVGVNL GLIVPAMCAL    240
NNNEYKRLAI GNTDDFVRMR IKLQEQRKRI QKGLRSAAGG HGRSKKLKGL SKLKKREQKF    300
VETYCHMISR RIVDFALINN AKYINLEYLQ GYDTNEFVLR NWSYYKIQQY CKYKASIYGI    360
EVRFVNPCYN AQVCSFCGHW SETQRISREV FKCENPNCIS HKLYKDGYLN ADFNNARNVA    420
LSSLFVNDGN ITDDKFKEAR EYYDIDISR                                      449

SEQ ID NO: 902         moltype = AA  length = 511
FEATURE                Location/Qualifiers
source                 1..511
                       mol_type = protein
                       organism = synthetic construct
SEQUENCE: 902
MDTMMITRKF VLLPVASCKK EWVKKITTYI ISDTDKKLDY FNEKLKKTEK EMKKANGSEQ      60
LSKEYNKLKS KKAEYESLLK DAKEGIFSPK AINNYTYHLV REAMESEARR KNYILSWAFS    120
EMIANGVPYM ETYKEKCKFI NEMIKPAYRT KGSKKGSLFD ESEIQNILGG YGISFSQELT    180
QKLKDCVKDG LLEGKVVLPN YKLNSPFTVA KTHISLSHDF ETYEELCEHI GKKDGKIYLN    240
YGGYGEPTIA RFAIDTGSNK NKEELNTTLL RLISGEYEVC ASSIGLCKDE KKIVLNLSMK    300
IPKKELELDE NTVVGVDLGL VVPACCALNN NMYVKKAIGS VAEFLRVRTQ LQSQYRRMQK    360
QVATNNGGHG RKKKMQPLDK FREKERNFVK TYNHYVSKEV VDFAVKNNAK YINMEDLSGF    420
KGDNRILRNW SYYELQQFIE YKAAKYGIVV RYINPYHTSQ VCSCCGHWEE GQRMDQAHFV    480
CKKCGTELNA DYNAARNISM STEFKKQKLS V                                   511

SEQ ID NO: 903         moltype = AA  length = 543
FEATURE                Location/Qualifiers
source                 1..543
                       mol_type = protein
                       organism = synthetic construct
SEQUENCE: 903
MDNTITITRK YTLIPTFSDT KEWTKKVMEY TKTSYIEKIK YYEEKIKKTK KDKEEREKY       60
ENRLSQLKEQ QLDFEENGTL LQTNVNDYTY DLVREAMASE SDRKNMIISY VCGELINRDA    120
KDMDFKERNK LISELCNYGY RVKGSKKGSL FDHLDINNPL GGYGVSFCQD LTKKIKELIN    180
NKRWLDGKAS TLHYKDDSPF SIAKATMGFA YDCDTFEELC EHIREKNCNL YFNYGNNGKA    240
TIARFKINLG ANRKNKDELI STILRVYSGE YQYCGSSIGI EGTKIILNLS MKIPKQEKEL    300
DENTVVGVDL GIAVPAVCAL NNNVYARKFV GNKDDFFKAR KQLNAQYKRV QSALKRASGG    360
HGRKKKLKAL ERLRKKEAHF VETYCHMVSK AVVDFALKYN AKYINLENLT GYDTDDIVLR    420
NWSYYKLQQY ITYKASKYGI EVRKINPCYT SQICSECGNY HPENRPKGDK GQAYFNCHNE    480
ECITHGKKSP YQYGINADFN AARNIAKSTL WMEKGKITEE SKKKAREYYG IEEEYEELNK    540
```

```
EVA                                                                              543

SEQ ID NO: 904              moltype = AA  length = 549
FEATURE                     Location/Qualifiers
source                      1..549
                            mol_type = protein
                            organism = synthetic construct
SEQUENCE: 904
MINKDKNENT VTITRKYALI PVSSDKTQWY KKVYDFTIED LTRKIEYYKE KLKKEKDKEK  60
KEQIKTKIKN FEEGLESIYN GGDFTQKMIN DYTYNLVRTA MEEEARRKNY ILSWIFSEMR 120
LNRVDQMESL KDKFKFISDT LNYAYRKKGS NKGSLFDDTE INSILNAYGI AWNQELTKEI 180
KDLVKNGALE GKVSLTNYKL DSPFTIAKAH FSFDHDYDSF EELCEHIDDS DCKMYMNYGG 240
DNKKDGTNPA SLARFRINLG QGKNRNELKS TLLKVYSGEY QYCGSSIQIS KNKIILNLSM 300
KIPKIETELD ENTVCGVDLG IAVPAMCALN NDMYKRLAIG SADDFLRVRT KHQEQRRRLQ 360
KSLKNSNGGH GRKKKLKPLE RMNKAEAHFV ETYCHMVSKR VVEFAVKNRA KYINIENLNG 420
YDSSEFILRN WSFYKLQQYI TYKAARYGIV VRRINPCYTS QICSVCGNWE PDQRKTQAKF 480
ECANEECASY DKYKYGFNAD FNAARNIAMS TLFMETGEVT EKKKEEARKY YGIEEKYQAS 540
LKEKDDKVA                                                        549

SEQ ID NO: 905              moltype = AA  length = 484
FEATURE                     Location/Qualifiers
source                      1..484
                            mol_type = protein
                            organism = synthetic construct
SEQUENCE: 905
MATEYTCITR KIEVHLHRHG EDEDAVQRYK NEFQIWNEIN NNLYKVANFI SSHLFFNDAF  60
VDRLRVQSNE YRDLLDLISK TTDAKEIKAL ENRKKALDAE FKRQQKIFLK GGSEDEKGSE 120
KTAIRRIAVE TFPNIPYSII NSLNDQISKT YNSSRFDVSI GKRTVPNYKK GIPVPFLMAN 180
GSGKIALRER EDGSPYVLFP RGLEWDLHFG KDSSNNREIV KRVFNGEYKA CDSSLQQAKN 240
KKIFLSLVVK IPKKNHNLNP DRIVGVDLGI NIPLYAALND NDYGGMGIGS REQFLKVRMR 300
MSAQKRELQR NLRQSTNGGH GRAQKLQALE RLEGKERNWV HLQNHIFSKS IIEYALKNNA 360
GAIQMERLTG FGRDKNDEVD SNFKPILRYW SFYELQTMIE YKANAAGIEV RYVDPYHTSQ 420
TCSFCGHYEK GQRLNQSTFV CKNPDCEKGK GKKLSDGTYQ GINADWNAAR NIALSDKIVD 480
RKKK                                                             484

SEQ ID NO: 906              moltype = AA  length = 488
FEATURE                     Location/Qualifiers
source                      1..488
                            mol_type = protein
                            organism = synthetic construct
SEQUENCE: 906
MANEFTCITR KIEVHLHKHG DSDEAIQRYK EEYRMWDDIN NNLYKAANRI VSHCFFNDTY  60
EYRLKLHSPR FQEIEKLLSN PKRNKLSDDD IKELKAERKL LFSDFKSQRQ TFLRGGIETG 120
TNPEQNSTYK VISNEFIDCI PSEVLTNLNQ NISSTYREYT LDVERGIRTI PNFKKGIPVP 180
FSIKQHGEIA LKKRDDGTIY VRFPKGLEWD LNFGRDRSNN REIVERVLSG QYGVGNSSIQ 240
ESKNKKQFLL LVVKIPKENR VLDKERIVGV DLGVNTPLYA ALNDNEYGGM GIGSREQFLK 300
VRERMNAQKR ELQRNLRHST NGGHGRSQKL QALDRLEGKE RNWVHLQNHI FSKSIIEYAL 360
KNDAGVIQME RLTGFGRDNN EEVQNEYKYI LRYWSYFELQ TMIEYKAKAA GIEVRYINPY 420
HTSQTCSFCG HYEKGQRINQ PTFICKNPDC TKGKGKQKSN GAYEGINADW NAARNIARSN 480
EFVEKKKK                                                         488

SEQ ID NO: 907              moltype = AA  length = 445
FEATURE                     Location/Qualifiers
source                      1..445
                            mol_type = protein
                            organism = synthetic construct
SEQUENCE: 907
MGENITEVVT KKTKKDVKKI MSNRKITIFI DEEDKELKKE YYKKLNDWFY HARHYANDVV  60
NILQCVVVME NINKSIEGDL HLKLTDYLDC KSQSINYKLL TQKYKELLPS YVRGAVGNNV 120
YKNYCENIKS ILKGEKTVST YNVGFPLYFM SIGFKFDKSD KNNFTFKLFG IPFKTKLGRD 180
RSNNEEIIYR IISGEYTISD SSLKKDGSDL YLLLSFRLPK KENKLDKDKV VGVDLGITTP 240
AYVSVCGKSN VRKSIGDREG FLKQRLSIQV QRRSLQGSLK YTTGGRGRNN KLSKLESIKD 300
RERNFVKNMN HKYSKEIIDF ALVNGCGSIN IEDLSGIGSM ERNEFILRNW SYFELQSMIK 360
YKAEREGIIV NVINPRYSSQ RCSVCGHIHT DNRITQSKFE CLSCGNKDNA DYNASKNISI 420
AHTESYIEEI TQHKKRMDKE KNKNI                                      445

SEQ ID NO: 908              moltype = AA  length = 496
FEATURE                     Location/Qualifiers
source                      1..496
                            mol_type = protein
                            organism = synthetic construct
SEQUENCE: 908
MENINIKDDN NNRMTITRKY AIIPTSSPYK EWKKKVYNFT VEDLEFRIKY NEEKLKSIKN  60
KEEKQKIGLY IDELKKSLQN VKDGNDFTQK MINDYTYHLV RESMESESAR KNYILSWMRD 120
QLRLNHVAQF PSLAEKKKFV SDTINCAYRV KGSKKGSLFD DTIKNALGS YGIAFCQNLT 180
EIIKGQIEDG LLEGKCNPVE FKCDSPFTVA KTAMGFSHNY KDICDLQAHI DDKDCKLYFD 240
FGGNGNPTIA RFRINLGSWK NRDELKATLL KVYTGEYQYC GSSIQISKNK IILNLSLSIP 300
KKEMELDENT VVGVDLGIKI PAVCALNNNP YARSYIGSVD DFIRVKTQLQ AQKRRLSIAL 360
KNTSGGHGRK KKLKPLDRFN KRELHFTESY CHKVSREVVD FAVKHRAKYI NVENLTGYDT 420
```

```
SDFVLRNWNY YRLQNYITYK AAKYGIIVRK INPCYTSQVC SVCGNWHEEN RPKGDKGQAY   480
FNCHNEDCLT HDKKKF                                                  496

SEQ ID NO: 909            moltype = AA  length = 468
FEATURE                   Location/Qualifiers
source                    1..468
                          mol_type = protein
                          organism = synthetic construct
SEQUENCE: 909
MPTITRKIEL TLCTDGLSDE ERKAQWGLLY HINDNLYKAA NNISSKLYLD EHVSSMVRLK    60
HAEYLSLQKE LAKAERQKMP DVDVIEELRE RLSAAEQEMS DQELAICKYA TEMSTNTLAY   120
RFATEIETNI FGQILARLEN NAQAVFLTDA PDVKRGERAI RNYKKGMPIP FPWNNSIKIE   180
CEGGEFYLRW YSGLRFHFNF GKDRSGNRLI VQRCLKLDKE YDGEYKLCNS SIQMVKRDGS   240
TKFFLLMVVN IPQEYVELNK HIVVGVDLGI NVPAYVATNI TPERKAIGDR EHFLNTRMAF   300
QRRYKSLQRL KTTAGGKGRT KKLEPLERLR QAEHNWVHTQ NHLFSREVVN FALQTHAATI   360
HLEDLSGFGK DSDGNADERK EFVLRNWSYY ELQNMITYKA AKYGIRVEKI RPAFTSRTCS   420
CCGHEGFREG VTFICENPEC QQFGEKVHAD YNAARNIANS KDIIKKNE               468

SEQ ID NO: 910            moltype = AA  length = 492
FEATURE                   Location/Qualifiers
source                    1..492
                          mol_type = protein
                          organism = synthetic construct
SEQUENCE: 910
MATEFTCITR KIEVHLHRHG DSEEAKQRFN EEYRIWNEIN DNLYKAANRI VSHCFFNDAY    60
EYRLKIQSPR YNEIQKLLRY SKRNKLTDDD IKSLKAERKN LFDEFKKQRM TFLRGGESEG   120
ANPEQNSTYK VVSNEFLDII PSTILTCLNQ NVSSTYKCYS KEVEFGNRTI PNFKKGMPVP   180
FSIKTHKTLM LKRREDGSIF VYFPKGLEWD LSFGRDRSNN REIVERILSG QYDVGNSSLQ   240
ESKNGKIFLL LVVKIPKRST ALDPNRVVGI DLGINIPLYA ALNDNEYGGM SIGSREQFLK   300
MRMRMTAQKR ELQSNLRYST NGGHGRSHKL QALERLEGKE RNWVHLQNHI FSKSIIEFAV   360
KNNAGVIQME RLTGFGHDKN DEVDEGFKFI LRYWSFFELQ QLIEYKAEAA GIEVRYIDPY   420
HTSQTCSFCG HYEKGQRINQ STFVCKNPEC EKGKGKKHAD GTYAGINADW NAARNIALSD   480
KFVDKKKSDL KY                                                      492

SEQ ID NO: 911            moltype = AA  length = 517
FEATURE                   Location/Qualifiers
source                    1..517
                          mol_type = protein
                          organism = synthetic construct
SEQUENCE: 911
MDNTITITRK YALIPEFSDR KEWKKRVYDF TINDLEQKID YRNKKKQDAS ELESQLEYIK    60
NGGDFTRNMV NNYTYSLVRT AMEEEARRKN YILSWIFSEM RANRVDQMES LKDKFKFVSD   120
TINYAYRKAG SNKGSLFDET EIHCILKSYG IAFSQELTKE IKELVKNGVL EGKVVIPTYK   180
LDSPFTIAKS HFSFEHDYDS FEELCEHISD SDCKMYMNYG GDNRKDGINP ASIAKFKISI   240
GHGKNKDELK STLLKVYSGE YQYCGSSIQI AKNKIILNLT MKIPKIETKL DENTVVGVDL   300
GIAIPAMCAL NNNMYERLAI GSADDFLRTR TKLQSQRRRL QKSLKNSNGG HGRNKKLKVL   360
ERLGKSETHF VETYCHMVSK RVVEFAVKNR AKYINIENLN GYDTSQFILR NWSYYKLQQY   420
ITYKAERYGI LVRKINPCYT SQVCSVCGNW EEGQRKTQSS FECANPECKS HEKYKYGFNA   480
DFNAARNIAM STLFMETGNV TEKSKEEARK YYGIEKD                           517

SEQ ID NO: 912            moltype = AA  length = 431
FEATURE                   Location/Qualifiers
source                    1..431
                          mol_type = protein
                          organism = synthetic construct
SEQUENCE: 912
MKTTIVTRKI EFYVNESDKD LKKQFYQTLR DFSYYTFKHA NELVDTNRMV DVIKRGFGNS    60
KNEITSEEMT EQLSGMFGCK PVSVPYKFSN QEFRDKLPSN IRVALSATIN ALYAKDRSDV   120
ARGNRTIRSY KNGMPVPFTK TSIRQFKFDV ERKNFTFIFN GIPLITRLGR DRSNNKSILE   180
SIIEGKYQLC DSSFQIKDGK FFLLLVHKVP VEKYKLNEKR VLGIDLGINV PLYGAINDKK   240
DRIALGDRDS FLNQRLKFQK RKRQLQRDLK LTKGGKGRGK KLKALESLST KERNFAKNYN   300
HNLSREVINF ALKHKCGIIN LEDLSGFKKN TNDFILRNWS FYELQTMIEQ KAKKVGITVN   360
KVKAKYTSQR CNNCGYIDKE SRKSQSEFEC TSCGHEESAD YNAAKNISMA HTKEFQKEIE   420
KHASSLKLCE A                                                       431

SEQ ID NO: 913            moltype = AA  length = 488
FEATURE                   Location/Qualifiers
source                    1..488
                          mol_type = protein
                          organism = synthetic construct
SEQUENCE: 913
MATEYTCITR KIEVHLHKHG DSEEALQRLN EECRIWDEIN NNLYKAANRI ISHCFFNDTY    60
EYRLKLQSPR LQEIEKLLSN PKRNKLSDED IKQLKAERKQ LFANFKKQRQ VFLRGGVEEG   120
ANPEQNSTYR VVSNEFIDVI PSEVLTNLNQ NISSTYREYS LDVERGSRTI PNYKKGIPVP   180
FSIKRSGELM LKKREDGSIY VRFPKCLEWD LFFGRDRSNN REIVERVLNG QYDVGISTIQ   240
ETKNKKRFLL LVVKIPKESK KLNPNRVVGV DLGINIPLYA ALNDNEYGGL GIGSREQFLK   300
VRMRMVAQKR ALQRNLRHTT NGGHGRAQKL QALDQLEGKE RNWVHLQNHI FSKSIIEYAL   360
KNGAGVIQME RLAGFGRDKN EEVENEFKFI LRYWSFFELQ TMIEYKANVA GIEVRYIDPY   420
HTSQTCSFCG HYEKGQRINQ STFVCKNPDC VKGKGKQHAD GSYDGINADW NAARNIALST   480
```

```
TVVDKKKK                                                                    488

SEQ ID NO: 914           moltype = AA  length = 479
FEATURE                  Location/Qualifiers
source                   1..479
                         mol_type = protein
                         organism = synthetic construct
SEQUENCE: 914
MYITRKIELW VKEDDKNLRN EIWRTIRDYE HMVFKSANLI VTNQLFNQTF TDRIVLTDEE            60
LSVKREKIER DIDKLNEKLK DEKDDTKKDK LKENRNKLYR QINQLTIEAR KMAEEFYTTS           120
EKNTTYQLIR KEFPTLPSHI SASLNDMVTK NYSNEIFDVR LGKRSLRTYR KGMPIPFMKL           180
SLKLKKVDDE ICLKWVNNIE FTLHFGRDKS NNQIIVERIL KGDYKVGDSS IQLKKGKIFL           240
LLVVDVPEEE NKLNDDVYVG VDLGLSIPAV CSLNVGDERL FIGSYNDPIR VRTQLQSRKR           300
RLQRSLTLTK GGKGRGKKLK AFDRLKTKER NFVKTYNHTL TNRIVKFAKD NLASTIKLEF           360
LEGYGEDETN SFVLRNWSYY ELQTQLQYKA EREGMEVVFI DPYHTSQMCS FCNHYEEGQR           420
LKQSEFLCKN VDCSNKDKKG ENKIINADWN ASRNIAKSEK FVTKKSDCEY FKRKKDEKN            479

SEQ ID NO: 915           moltype = AA  length = 479
FEATURE                  Location/Qualifiers
source                   1..479
                         mol_type = protein
                         organism = synthetic construct
SEQUENCE: 915
MYITRKIELW VKEDDKNLRN EIWRTIRDYE HMVFKSANLI VTNQLFNQTF TDRIVLTDEE            60
LSVKREKIER DIDKLNEKLK DEKDDTKKDK LKENRNKLYR QINQLSTEAR KMAEEFYTTS           120
EKNTTYQLIR KEFPTLPSHI SASLNDMVTK NYSNEIFDVR LGKRSLRTYR KGMPIPFMKL           180
SLKLKKVDDE ICLKWVNNIE FTLHFGRDKS NNQIIVERIL KGDYKVGDSS IQLKKGKIFL           240
LLVVDIPKEE NQLNDEVSVG VDLGLSIPAV CSLNVGDERL FIGSYNDPIR VRTQLQSRKR           300
RLQRSLTLTK GGKGRGKKLK AFDRLKTKER NFVKTYNHTL TNRIVKFAKD NLASTIKLEF           360
LEGYGEDETN SFVLRNWSYY ELQTQLQYKA EREGMEVVFI DPYHTSQMCS FCNHYEEGQR           420
LKQSEFLCKN VDCSNKDKKG ENKIINADWN ASMNIAKSEK FVTKKSDCEY FKRKKDEKN            479

SEQ ID NO: 916           moltype = AA  length = 479
FEATURE                  Location/Qualifiers
source                   1..479
                         mol_type = protein
                         organism = synthetic construct
SEQUENCE: 916
MITVRKLKIV CKDKEFYDFF KWEQREQNKA LNIAIGLIHS STVLRSIDSG AEVQLKKSIE            60
KLTQNNEKLE KELEKEKITD KKKEKLLKAI KTNKELIASK EKELKAGQKF RCGIDKKFDE           120
LYMNKTTLYH VLDSICDFKY KRTIELVRQK VKQDYSNSFI DIVTGKVSIQ NYKSTFPLMI           180
DGSCISILKE VDEVGIVNGY KIKIMLGYEL NIVLGKRKNE MTMELQKTLE KCISGEYKIC           240
ASSIQRDKNN NIIFNLTLDI PIDKGYKPVK GRVCGVDLGI KYPAYMCLSD DTYKKEAVGS           300
INNFLRIRKQ MQERRKKLQK ELLLTNGGKG RTKKIQALEK LRENEKNFVK TYNHAISKRI           360
VGFAKKNKCE YINLEKLTKE GFGDSILRNW SYFELQKMIE YKAKRESIEV RYIDPHFTSQ           420
KCSKCGYIDK ENRDIQNTNE DIIAFESQSN KNDEKIFGTF DFDIKAIKNI GSKNFFPKE            479

SEQ ID NO: 917           moltype = AA  length = 443
FEATURE                  Location/Qualifiers
source                   1..443
                         mol_type = protein
                         organism = synthetic construct
SEQUENCE: 917
NYTYGLVRIS MQEEAERKNY IVEYVRMILT AEHAYTLSPV ERNKRIKEIL KYAYRKKGSK            60
SGSLFDEVEI GNILGSYGLA FNQMLTKKIQ DCCNKGALVG RAGYPFFKMD SPFTIAKADM           120
GFTHEYDTFE ELCEHVNDCK LYFSYGGNGN PHIARFRIDL GHGKNRRELM STILKVYSGE           180
YPYCGSSIQL EKNKIVLNLT MQVPKQTKEL DENTVVGVNL GMVVPAMCAL NNDKYKRLAI           240
GDENDFIRMR TKLQQQRSRL QAGLRNTAGG HGREKKLKAL ERLKKQEAHY NETYSHMVSR           300
RIVEFALNNN AKYINLENFT GMDKDNVVLK NFIYYKIEQY TTYKAEHYGI IVRKINPCYN           360
GQVCSIDGNW APGQRISRNV FKCANPDCES HIIYKKSGFD ADFNNARNNA MSTLFMTKGQ           420
VSGKSMEEAR EYYGFEEEYK KFL                                                  443

SEQ ID NO: 918           moltype = AA  length = 429
FEATURE                  Location/Qualifiers
source                   1..429
                         mol_type = protein
                         organism = synthetic construct
SEQUENCE: 918
MSVITRKIEV FVSESNTELK KEFYKTLRDW SNTSRNYAND IMNLLQSTYF LDSINKDIDP            60
SNKKSLNEYL ETSKRNLGYK VFAQKYRETL PSSYRSCINS YVFSNFGNSI KDVLKGESSI           120
ISYKKDFPLL FMSKSIRGLQ MDDSGASFEF FSIPFRMKFG RDRSNNREIV DKVISGQYKM           180
CDSSFKFYDN KLFMLVVDI PQTKVNLIED NVLGVDLGIT HPAYVSVNTN KKFRQAIGCS            240
ESFLQVRLAI QKQRKNISKN LKYTNGGKGR TKKMQKLDSL GIKERNFAKT MNHTISKEII           300
NAAIKNNCAI INIENLKGIG KDEKNSFILR NWSYHELQTM IKYKAKKYGI TVNLINPRYS           360
SQRCSNCGHI HEDNRISQSK FKCQNCDFED NADFNASKNI SIAHTKDYIK QIEKYSKNKE           420
KKETELLKV                                                                  429

SEQ ID NO: 919           moltype = AA  length = 456
FEATURE                  Location/Qualifiers
```

| | | |
|---|---|---|
| source | 1..456 | |
| | mol_type = protein | |
| | organism = synthetic construct | |

SEQUENCE: 919
```
MYITRKIELH ISEPDLEKRK EHWKFLRMID AELYRAANLI VTNQLFNDYY ENRVINKDGT   60
LTHIDSKIRS LYRNKEKNAE EINLLKEKKK ELWEQAKKFY DTSKQNVTYQ ITSRDFPAIP  120
SSIVTALNAT IIKTLKQEWN EVKRGSRSLR TYKKGMPIPF NFGTSKQWFE KSGEEIYLNW  180
FGNIQFHLFF GRDKSNNRII VNRCLTGEYK YADSSIQLKD RKIFLLLVLD IPVSDNTVDE  240
NISVGVDLGV TVPAYCALSD GLKRLSIGSK DDLLRVRLQF QNRKRSLQKR LKMVSGGKGR  300
EKKLKTFNDL TDKEKRYVTT YNHMISHSVV KFAKDNKAAT IKMEMLEGFG EDEKNKFILR  360
NWSYYQLQTM TEYKAKKENI KVVFVDPYHT SQTCSLCGNY EEGQREKQDE FICKNKECKN  420
FNEKVNADYN AAVNIAKSDK IVTSKEECEY FKKEEI                           456
```

| SEQ ID NO: 920 | moltype = AA length = 479 |
|---|---|
| FEATURE | Location/Qualifiers |
| source | 1..479 |
| | mol_type = protein |
| | organism = synthetic construct |

SEQUENCE: 920
```
MILTRKIELL IAEDDQDKRL DIWKYLRSVE MDTFKAANLI ISHQYFNDTF KERILLTKNE   60
LKERHQKIEN KIEKLTEKLK AEKDKEKKKK LTADRKGLYT QRDKLKPEAR EEMVSVYTTS  120
EKNSTYQLIS KHFPHMSSYI SASLNDMVTK NFSNELFDVK RGDRSLRSYR KGMPIPFMKS  180
GMSFESTDEG IHMNWVNNIK FYLRFGRDAS NNRAVMERVL AGEYKMSDSQ IQIKKNKIFL  240
LLVVDIPNKT VKLDKKLSVG VDLGINNPAY CALSKGPARF AIGSREDFFR VRVQMQSRRR  300
RLQKNLKLTK GGKGRQKKLK ALERLRDKER NFVRTYNHTV THQIVKFARD NHAGVINMEL  360
LEGFMEEEKS NFILRNWSYY ELQQMLSYKS KREGMEVRFV DPYHTSQDCG ECGHYEEGQR  420
LDQAKFLCGN PDCTRKDKKG NNEEVNADYN AALNIAKSKK FVTRKEECEY FKKSQSESG   479
```

| SEQ ID NO: 921 | moltype = AA length = 422 |
|---|---|
| FEATURE | Location/Qualifiers |
| source | 1..422 |
| | mol_type = protein |
| | organism = synthetic construct |

SEQUENCE: 921
```
MSVVTRKIEI FVFETDTDKR KEYYKQLRDW SYISRNYAND VMNVLQSARV LDNLMKDTAE   60
ENAKGLSDYI ETSKRNLGYK MLANKYKETL PSTYRTCINS YVFSNFNNTI KEVLRGDRAI  120
NSYKKDFPLL FMSKSIRNLS LDDLGGSFEF YSIPFRINFG RDKSNNRSIV EKVLTGQYKM  180
CDSSIKFDGT KLFLFLVVNI PDKKMELDEN KVMGVDLGIQ YPAYVSINSD KNFRQSIGNA  240
ETFLNVRLSL QKQRRSLQAN LKYAKGGRGR NNKLAKLNDI RDKERNFAKT MNHTFSKEII  300
DLAIKNNCGT INIEDLKGFG KNDKNGFVLR NWSFFELQSF IQYKADKFGI KLNVVNPKYS  360
SQRCSKCGHI HEDNRQTQSK FECTSCGFTE NADYNASKNI SVAHTKEYKK EIETHIKNKE  420
KK                                                                422
```

| SEQ ID NO: 922 | moltype = AA length = 433 |
|---|---|
| FEATURE | Location/Qualifiers |
| source | 1..433 |
| | mol_type = protein |
| | organism = synthetic construct |

SEQUENCE: 922
```
MNIATRKIQI VVNESDPVKR KEYYEQLREI SYNSYRYANE IVNINYFNHV LKKGMGNAKN   60
TLTPKEISEK VSDMYGCSEL NSTYKFASEE FKAKLPSYVT ATLSNTVSKN FKSDLKDVMR  120
GDKTVRNYRR NMPVPFHNKA LRKLSKDGVD FTFNLFSIPL KTHLGRDRSN NRHILDSIIS  180
GEYGLSDSSF KFVKNKLFVY LVFKSPDDKV NLSKENVIGV DLGINIPLYA SINNQKSVVL  240
RMGDRESFLN ARLSLQKRKR NLQSALKFTK GGRGRTKKLK ALDSLRTKER NFVKNYNHKL  300
SKGLIDFALK NDCGVINIEN LSKINKDGYD FILRNWSYFE LQNFIKTKAE KYGIVVNVID  360
ATYSSQRCSS CGHISKENRL DQQKFKCVSC GEEMNADKNA SKNISIANTK EYIKQIEEHK  420
KAKNDQVLQE EVL                                                    433
```

| SEQ ID NO: 923 | moltype = AA length = 413 |
|---|---|
| FEATURE | Location/Qualifiers |
| source | 1..413 |
| | mol_type = protein |
| | organism = synthetic construct |

SEQUENCE: 923
```
MRILRLSLSV DSSNLYDDKQ KIWDRLYQII NDSWKSANHI ATGQYMNDNF IRHVYARKQI   60
DPKNIEQVTE IENLIFSKDG FFETKRQATT ERDIKEVFPN IPPSVTNPLN QIVYASYIKE  120
KKDMLMGNRS LRSYKQNMPI PIRLSMNFN KNFQFIWNLQ RNETITFNIY FGKDRANYKS   180
TIAKILNNEI STTASSIQLK DKKLYLLLGV KDPINKIKLD PNKAIGVDCG ITIPAFCATN  240
FNDDKLPIGN IESFANVRVQ MQCRYKRIQK SVIMAKSQHG RKRKTKALET LREKERNFAQ  300
SYNHMISKKV VDFAIKNSAS KIIMEKLSFD KNFASTLRNW SYFELQSMIK YKAKKFGIEF  360
QQIPSAYTST TCSKCGHNDK NNRIEQSMFQ CVKCGYKENA DYNAAKNIAC FAK         413
```

| SEQ ID NO: 924 | moltype = AA length = 439 |
|---|---|
| FEATURE | Location/Qualifiers |
| source | 1..439 |
| | mol_type = protein |
| | organism = synthetic construct |

SEQUENCE: 924
```
MSQNTLTTRK IEIYVSESDK DLRKEYYKTL RNWSYISRNY ANDTINALQS SFFLDNITKD   60
```

```
SNEENKKALT EYLGIKKMGM GYKILANKYK EHLPSYFRSA INSFVYKNFS ESIRDVLRGD    120
SSVTSFKKDF PLLFDSRSIR NLSIDDKGGS FEFSAIPFRF VFGRDKSNNK SIVEKITTGE    180
YKMSNSSFKF IDNKLFFFLT VSIPKEKFEL DENKTLGVDL GIANPAYVSI NNDKHFKQAI    240
GSTDAFLHTR LAIQKSRKSL QKNLTHTKGG RGRNHKLDKL NDIGSKERNF AKTMNHSWSK    300
QIIEAAVKNK CGTINIEDLK GIGRDEKNSF VLRNWSYFEL QTMIQYKADR AGIKVNMVNP    360
KYSSQRCSSC GFIHEDNRIS QSKFICLECK TEMNADYNAS KNISIAHTKE YVKEIENHSK    420
AIEKLKKLNK EEKNVEEML                                                 439

SEQ ID NO: 925          moltype = AA   length = 458
FEATURE                 Location/Qualifiers
source                  1..458
                        mol_type = protein
                        organism = synthetic construct
SEQUENCE: 925
MLITRKIEIY FNPETTKEEY DEYWIKLRDL ERDTFKAANF IVNNQFFNEI IDERLLFMDD    60
KTSQKKLDIG EKISDIFKKK SLSEEESKKQ RDKLYKELNE LTKESRIFAK DFYLKSKQNS    120
TYELITKEFP NLGSYVASSL NQSIVSVFNN DMKEIRTGKR TVRNYKKGMP IPFMKTGIIF    180
QKIEDKYHIK WIGKFNFIIK FGRDRSNNKA IIDKVLSAEY SFSDSSVQIK DNKIFLLLIV    240
NIPDSVVVLD KNICVGVDLG LNIPVYLALN NGFERQALGD RESFLKFRVR MQQVRRRLQQ    300
SLKLAAGGKG RDKKMKALDN SKANEKKFAT TYNHQITAEI IKFALKHNAG IIKMENLKGI    360
AQDEKNSFIL RNWSYFQLQQ FVEYKAKRNN IEIKYINPKY TSQMCSYCEN REDGQRLSQS    420
EFLCKNPDCT NKDDKNENLK INADFNAARN IAKSEKYS                            458

SEQ ID NO: 926          moltype = AA   length = 500
FEATURE                 Location/Qualifiers
source                  1..500
                        mol_type = protein
                        organism = synthetic construct
SEQUENCE: 926
MAKKTKSETI SLTRTLRAEI VCSPDMAWAE LGPRLRAWRS LVSHMVNEAV FRCREAERDQ    60
VAARAADVDK DDMPPGPATA AYQACADAQA DFQAWARRAK GLSDAERGRL STVAFGGASQ    120
SCIGQEAFGY FKKWKKERNS IPSAGRGQPI PCRAAETKFY EDDSGKLILD ARIGPNEVPR    180
SRFVLAVSRG WHWEQLRKIV SGECRHGQVD IVLDERAVRK NGGKGKWYAL ISYSFAKPER    240
PEKCDPDGML VMHRGMHNAL QFLGSDGEGS GKTTIRGNKL QAYKRRCKAI RRSMGSVSAP    300
ERGDGAKGRG IARRYEHAQK LLDDAEARHVR TFCQQSAARA IELAIQWRKG VIVIEDYGGI    360
EPSDDRGERR FFDRPYYQL KQAIVCAAEG AGLEVREVPA AYISQTCPRC GNQDASQRLH    420
RTGMPHCAVC EFDRTADMVA AIHMLRLAGP KNNGWDGKLR KEHEAAKRLR KPDAGQSEEE    480
TEKVRELPKA KKRKPPEDAE                                                500

SEQ ID NO: 927          moltype = AA   length = 448
FEATURE                 Location/Qualifiers
source                  1..448
                        mol_type = protein
                        organism = synthetic construct
SEQUENCE: 927
MKKEKESKEA ARVTITRKIE LVLHCEDEQL RKDQFKQLLE WKYQVFRAAN MVINHQHFTY    60
LLRRKIKDTV SENEKQGWKE AKQMVETLYD TSLLNDTYRM VSEEFPDLPS SIRTCINMQV    120
AQKYNNDLKE VLRGERTIAN YKYGMPIPFA ISAKDNLERI PTEHGEDIIL KFFKGIKFRL    180
NFGRDKSNNQ VMIDRAIAGE YKLCNSSIIL EKKQNKYSIY LLAVIQHDRL KTSLDYDKVA    240
ATNLGMNCPI FLTTSEGHEM PIGSKDEFLR VRLQFQARRR KLQKDLDMAK AGHGRERKLK    300
ALEHLKKVEA NYANTYNHKL SKKIVMFCYN NGIGTIKTEN LLGGAETLEK TFVLRNWSYF    360
QLQADLEYKA AMYNIKVIKV APQYITRKCN CCGNIAEEAV NLQDRTYICV NDACKLFGVK    420
VDIDKNASLN VLDTEESKVE KTELIEVV                                       448

SEQ ID NO: 928          moltype = AA   length = 365
FEATURE                 Location/Qualifiers
source                  1..365
                        mol_type = protein
                        organism = synthetic construct
SEQUENCE: 928
MLKAYKYRIY PNKEQKLYLS KTFGCTRFIY NQMLANRIDI YETHKDNLTS KEMSKLYPTP    60
AQYKKEFEWL KEVDSLALAN AQLNLDKAYK NFFRDKSIGF PKFKSKKSNY HSYTTNNQKG    120
TIYIENSRIK IPKLKTMIKI KQHRQFNGLI KSCTISQIPS GKYYISILVD TENIQLPKTD    180
KKVGIDVGLK EFAITSDGEF FGNPKWLRKS EKRLKKLQKN LSRKKKGSNN RRKARLKVAK    240
LCEKIVNQRK DFLHKLSMQI ISENQAIVIE DLKVSNMLKN HRLAKAISEI SWYEFRRMLE    300
YKADWYGRKI IVAPPNYASS QLCSSCGNKS NQTKDLSCRT YICPVCGMIM GRDLNASKNL    360
LKLAI                                                                365

SEQ ID NO: 929          moltype = AA   length = 541
FEATURE                 Location/Qualifiers
source                  1..541
                        mol_type = protein
                        organism = synthetic construct
SEQUENCE: 929
MKKCLFSTYI KTDDMDIIKE EIELFNAMKR IAFSNVRILG GDKTVKENLS IHMFLKSQFH    60
VSDYFINSAR QEAKAVYRSA MEVLTLQKEN LESRIKQMEK KIKEINTRLA HLEKEKQSLI    120
KRSKTGKGKF VSYRGGRESE PSPGVFQVRY KKKTVRYENQ YLFEVLYLTP EIKKLKARLR    180
MISQRITSNR CRLQKVEGKI ENHLPAVCFG SKKLFQQQNT IYQNQHEDWK RAMYKGRNPG    240
MTISGRKDAL QGNFLFKYDV KTKNLTYRTT TGEIIVLKNV TFPYGQELVE QAVNATANER    300
```

```
NAIAWRLEVH GSCVLVKCMV KVFNRQKNYD FSEGCVAFDT NVDHLAYTEL DGHGNLLSHN    360
IIPFTLRGLS TGQREQVLSK VLEEIFQYAR NAAKPIIMER LEDIKQKPMY QHKRLNEVLS    420
SFAYTKVTML AESKSNKYSI GLVKVNPAFT SQIGKFKYMR HYGISVHEAA AFVIGRRGLG    480
YQDKVPKPMR HLIPKGKKNR HHWSHWSYLM TQLKNYASGV FYQPIDYAAI STMKELKQQL    540
N                                                                   541

SEQ ID NO: 930          moltype = AA   length = 585
FEATURE                 Location/Qualifiers
source                  1..585
                        mol_type = protein
                        organism = synthetic construct
SEQUENCE: 930
MLGRALINKY GFLIHPRRFV HLNDKSLDGT FILPSKKNHM YDVPTNDPSG ILNASDIDRI    60
NNLPFFDNTS PTKETNTKEG ALLSEKLASV KELFGEDPEN PSFINYRFPR GLENPYFDIQ    120
VNQLKKKRLS VTQLCTTQNW CELRNFYDFY SQNLSNQLLN LKFQVQKGKK IHKSLEDETH    180
PELNQYKSFT HNFLALTKLS MDIDNDMDAL LDNWFNSINR LVSLFTKGDG HAREIVCHGF    240
INLEDGKLVE HLLNSDSKTK ENVIISGVID HLTLRNRHNH QVQKGAAHLD TEYQSWGNIL    300
TNLLSNLKEL KSNNEIVISD IKTRSVPKIP SIESVIESSK LQTMYYKFFF SHLSQDMTQT    360
YHSFLINAQR RGLDVDAPIN PTKILTFILT NPLFANDVKN LLYGLPINHS AFDNDAKGSN    420
TFDMTAFNDL LDRGPTSFNV PIEQDEDSSE STKCVSLRDY GHFYTKWKTP LTLKYFAARL    480
SQIYFIVGNL VSNDLMIEYY YHNDNFHNII FPYDPLKLGT HAHDSAMVWF GGRDMHPIEP    540
TQKNFNTYCK FCDYRHVCSW KNKNELKLID LGKELKKIIL ESSMK                   585

SEQ ID NO: 931          moltype = AA   length = 702
FEATURE                 Location/Qualifiers
source                  1..702
                        mol_type = protein
                        organism = synthetic construct
SEQUENCE: 931
MGIQGLLPQL KPIQNPVSLR RYEGEVLAID GYAWLHRAAC SCAYELAMGK PTDKYLQFFI    60
KRFSLLKTFK VEPYLVFDGD AIPVKKSTES KRRDKRKENK AIAAERLWACG EKKNAMDYFQ   120
KCVDITPEMA KCIICYCKLN GIRYIVAPPE ADSQMVYLEQ KNIVQGIISE DSDLLVFPGCR  180
RLITKLNDYG ECLEICRDNF IKLPKKFPLG SLTNEEIITM VCLSGCDYTN GIPKVGLITA   240
MKLVRRFNTI ERIILSIQRE GKLMIPDTYI NEYEAAVLAF QFQRVFCPIR KKIVSLNEIP   300
LYLKDTESKR KRLYACIGFV IHRETQKKQI VHFDDDIDHH LHLKIAQGDL NPYDFHQPLA   360
NREHKLQLAS KSNIEFGKTN TTNSEAKVKP IESFFQKMTK LDHNPKVANN IHSLRQAEDK   420
LTMAIKRRKL SNANVVQETL KDTRSKFFNK PSMTVVENFK EKGDSIQDFK EDTNSQSLEE   480
PVSESQLSTQ IPSSFITTNL EDDDNLSEEV SEVVSDIEED RKNSEGKTIG NEIYNTDDDG   540
DGDTSEDYSE TAESRVPTSS TTSFPGSSQR SISGCTKVLQ KFRYSSSFSG VNANRQPLFP   600
RHVNQKSRGM VYVNQNRDDD CDDNDGKNQI TQRPSLRKSL IGARSQRIVI DMKSVDERKS   660
FNSSPILHEE SKKRDIETTK SSQARPAVRS ISLLSQFVYK GK                      702

SEQ ID NO: 932          moltype = AA   length = 291
FEATURE                 Location/Qualifiers
source                  1..291
                        mol_type = protein
                        organism = synthetic construct
SEQUENCE: 932
MSKSWGKFIE EEEAEMASRR NLMIVDGTNL GFRFKHNNSK KPFASSYVST IQSLAKSYSA    60
RTTIVLGDKG KSVFRLEHLP EYKGNRDEKY AQRTEEEKAL DEQFFEYLKD AFELCKTTFP   120
TFTIRGVEAD DMAAYIVKLI GHLYDHVWLI STDGDWDTLL TDKVSRFSFT TRREYHLRDN   180
YEHHNVDDVE QFISLKAIMG DLGDNIRGVE GIGAKRGYNI IREFGNVLDI IDQLPLPGKQ   240
KYIQNLNASE ELLFRNLILV DLPTYCVDAI AAVGQDVLDK FTKDILEIAE Q           291

SEQ ID NO: 933          moltype = AA   length = 319
FEATURE                 Location/Qualifiers
source                  1..319
                        mol_type = protein
                        organism = synthetic construct
SEQUENCE: 933
MTAPILLLDG ASMWFRSYFG VPSSIKAPDG RPVNAVRGFI DAISTLVTRE KPRRLVVCRD    60
DDWRPQWRVD LIPSYKAHRV AEPEPDGVPD IEEVPDDLTP QVNMILELLD AFGIPTAGAA   120
GFEADDVLGT LSAREERDPV VVVSGDRDLL QLVRDEPAPQ VRVLYLGRGL AKATKWGPAE   180
VAEQYGVPLD RAGTAYAELA LLRGDPSDGL PGVAGIGEKT AASLLAKHGS LQNILDAAHD   240
PKSGLSKAHR TKLLGAVDYI AAAETVVRVA TDAPVTFSTP TDTLPLAAGD PARVAELAAA   300
YGVSSSISRL QTALDQLPD                                               319

SEQ ID NO: 934          moltype = AA   length = 332
FEATURE                 Location/Qualifiers
source                  1..332
                        mol_type = protein
                        organism = synthetic construct
SEQUENCE: 934
MIDKAYEELI KMKEKIMRDS YTIHKELSES VESILNELWI NYSPESVEHS KKLLAIDGGM    60
WVKETRQGVI FIVNAKAIVF EGINEINSEG KVLVHIFSPG NYAKERIELL MQLLELQLAL   120
KLVENVDYVL LDGSFSKKLG RHKSELKVDL LDDIVSIDKI LSLEEKDEDN MLRFLIAENQ   180
LVLSELVSRY KDKLLFISKN SKSSDLFKQA YSDITILELF TQNCGYSKIL EKKIDENYIL   240
SRKASKLLSG LNYYFTNLRL EPSERLFRLD FFNADKIFEY LKVLKPVSLK GYPYPLIKVH   300
KDVRVGKEDR ERIYSILEMK RKDISWWPSQ FY                                332
```

```
SEQ ID NO: 935           moltype = AA   length = 575
FEATURE                  Location/Qualifiers
source                   1..575
                         mol_type = protein
                         organism = synthetic construct
SEQUENCE: 935
MKKLIKRREI PIGNSVSNHP LLDRLYRARH IQNTKELDRT LKSMLNPNQL YGIEQAVNLL    60
VEAYQPQQKI VIVGDFDADG ATSTALSVLA LRQLGFSDVD YLVPNRFEQG YGLSIPVAEM   120
AIEKGVQLLM TVDNGVSSFD GVAFLKEKGI RVLVTDHHLP PETLPPADAI VNPNLSQCGF   180
PSKSLAGVGV AFYLMLAVRA KFRELGIFTA ETQPNFTDLL DLVALGTIAD VVPLDQNNRI   240
LAYQGLMRIR ARHCRLGIIA LAEVANRNVE QFTSSDLGFC IGPRLNAAGR LDNMSIGVEL   300
LLANEMSKAR ELALDLDQLN QTRKEIEAGM KLEAIKICQN LTALFKELPY GITLYQPDWH   360
QGVLGIVSSR IKDQYHRPVI AFAQDSEGIL KGSARSIEGL HMRDVLERIH SQHPNMILKF   420
GGHAMAAGLS IREEHFADFQ HIFNQTVADW LDEEHLQGVI WTDGELNSNE FNLETAELIK   480
SVGTWGQGFP EPCFDGEFKI LDQRAIGQNK NHLKMLLEPK QGGVLLDAIA FNINTRLYPD   540
LSIKQARLAY KLEINEFRGN RSLQLLVDYI EPIDE                             575

SEQ ID NO: 936           moltype = AA   length = 475
FEATURE                  Location/Qualifiers
source                   1..475
                         mol_type = protein
                         organism = synthetic construct
SEQUENCE: 936
MMNDGKQQST FLFHDYETFG THPALDRPAQ FAAIRTDSEF NVIGEPEVFY CKPADDYLPQ    60
PGAVLITGIT PQEARAKGEN EAAFAARIHS LFTVPKTCIL GYNNVRFDDE VTRNIFYRNF   120
YDPYAWSWQH DNSRWDLLDV MRACYALRPE GINWPENDDG LPSFRLEHLT KANGIEHSNA   180
HDAMADVYAT IAMAKLVKTR QPRLFDYLFT HRNKHKLMAL IDVPQMKPLV HVSGMFGAWR   240
GNTSWVAPLA WHPENRNAVI MVDLAGDISP LLELDSDTLR ERLYTAKTDL GDNAAVPVKL   300
VHINKCPVLA QANTLRPEDA DRLGINRQHC LDNLKILREN PQVREKVVAI FAEAEPFTPS   360
DNVDAQLYNG FFSDADRAAM KIVLETEPRN LPALDITFVD KRIEKLLFNY RARNFPGTLD   420
YAEQQRWLEH RRQVFTPEFL QGYADELQML VQQYADDKEK VALLKALWQY AEEIV        475

SEQ ID NO: 937           moltype = AA   length = 661
FEATURE                  Location/Qualifiers
source                   1..661
                         mol_type = protein
                         organism = synthetic construct
SEQUENCE: 937
MSRKSIVQIR RSEVKRKRSS TASSTSEGKT LHKNTHTSSK RQRTLTEFNI PTSSNLPVRS    60
SSYSFSRFSC STSNKNTEPV IINDDDHNSI CLEDTAKVEI TIDTDEEELV SLHDNEVSAI   120
ENRTEDRIVT ELEEQVNVKV STEVIQCPIC LENLSHLEYL ERETHCDTCI GSDPSNMGTP   180
KKNIRSFISN PSSPAKTKRD IATSKKPTRV KLVLPSFKII KFNNGHEIVV DGFNYKASET   240
ISQYFLSHFH SDHYIGLKKS WNNPDENPIK KTLYCSKITA ILVNLKFKIP MDEIQILPMN   300
KRFWITDTIS VVTLDANHCP GAIIMLFQEF LANSYDKPIR QILHTGDFRS NAKMIETIQK   360
WLAETANETI DQVYLDTTYM TMGYNFPSQH SVCETVADFT LRLIKHGKNK TFGDSQRNLF   420
HPQRKKTLTT HRYRVLFLVG TYTIGKEKLA IKICEFLKTK KFVMPNSVKF SMMLTVLQNN   480
ENQNDMWDES LLTSNLHESS VHLVPIRVLK SQETIEAYLK SLKELETEDYV KDIEDVVGFI   540
PTGWSHNFGL KYQKKNDDDE NEMSGNTEYC LELMKNDRDN DDENGFEISS ILRQYKKYNK   600
FQVFNVPYSE HSSFNDLVKF GCKLKCSEVI PTVNLNNLWK VRYMTNWFQC WENVRKTRAA   660
K                                                                  661

SEQ ID NO: 938           moltype = AA   length = 260
FEATURE                  Location/Qualifiers
source                   1..260
                         mol_type = protein
                         organism = synthetic construct
SEQUENCE: 938
MFDIGVNLTS SQFVKDRDDV VTRALAAGVS GMLLTGTNLH ESQQAQKLAQ RYACCWSTAG    60
VHPHDSSQWQ SETEDAIVAL ARQPDVVAIG ECGLDFNRNF STPQEQERAF QAQLRIAAEL   120
QMPVFMHCRD AHARFLALLE PWLDKLPGAV LHCFTGTREE MQECIDRGLY IGITGWVCDE   180
RRGLELRELL PFIPAEKLLI ETDAPYLLPR DLTPKPASRR NEPAHLAHIL ARVAHWRGED   240
PQWLAATTDA NVKTLFGIAF                                              260

SEQ ID NO: 939           moltype = AA   length = 314
FEATURE                  Location/Qualifiers
source                   1..314
                         mol_type = protein
                         organism = synthetic construct
SEQUENCE: 939
MGSQALPPGP MQTLIFFDME ATGLPFSQPK VTELCLLAVH RCALESPPTS QGPPPTVPPP    60
PRVVDKLSLC VAPGKACSPA ASEITGLSTA VLAAHGRQCF DDNLANLLLA FLRRQPQPWC   120
LVAHNGDRYD FPLLQAELAM LGLTSALDGA FCVDSITALK ALERASSPSE HGPRKSYSLG   180
SIYTRLYGQS PPDSHTAEGD VLALLSICQW RPQALLRWVD AHARPFGTIR PMYGVTASAR   240
TKPRPSAVTT TAHLATTRNT SPSLGESRGT KDLPPVKDPG ALSREGLLAP LGLLAILTLA   300
VATLYGLSLA TPGE                                                    314

SEQ ID NO: 940           moltype = AA   length = 26
FEATURE                  Location/Qualifiers
```

```
source                  1..26
                        mol_type = protein
                        organism = synthetic construct
SEQUENCE: 940
GSGGSPAGSP TSTEEGTSES ATPGSG                                         26

SEQ ID NO: 941          moltype = RNA   length = 70
FEATURE                 Location/Qualifiers
source                  1..70
                        mol_type = other RNA
                        organism = synthetic construct
SEQUENCE: 941
gacagcttat ttggaagctg aaatgtgagg tttataacac tcacaagaat cctgaaaaag    60
gatgccaaac                                                           70

SEQ ID NO: 942          moltype = RNA   length = 57
FEATURE                 Location/Qualifiers
source                  1..57
                        mol_type = other RNA
                        organism = synthetic construct
SEQUENCE: 942
gacagcttat ttggaagctg aaatgtgagg tttataacac tcacaagaat cctgaaa       57

SEQ ID NO: 943          moltype = RNA   length = 53
FEATURE                 Location/Qualifiers
source                  1..53
                        mol_type = other RNA
                        organism = synthetic construct
SEQUENCE: 943
gacagcttat ttggaagctg aaatgtgagg tttataacac tcacaagaat cct           53

SEQ ID NO: 944          moltype = RNA   length = 90
FEATURE                 Location/Qualifiers
source                  1..90
                        mol_type = other RNA
                        organism = synthetic construct
SEQUENCE: 944
gacagcttat ttggaagctg aaatgtgagg tttataacac tcacaagaat cctgaaaaag    60
gatgccaaac atcttggaac tactgtatcg                                     90

SEQ ID NO: 945          moltype = RNA   length = 20
FEATURE                 Location/Qualifiers
source                  1..20
                        mol_type = other RNA
                        organism = synthetic construct
SEQUENCE: 945
agtctccagg aagaaattaa                                                20

SEQ ID NO: 946          moltype =   length =
SEQUENCE: 946
000

SEQ ID NO: 947          moltype =   length =
SEQUENCE: 947
000

SEQ ID NO: 948          moltype =   length =
SEQUENCE: 948
000

SEQ ID NO: 949          moltype =   length =
SEQUENCE: 949
000

SEQ ID NO: 950          moltype =   length =
SEQUENCE: 950
000

SEQ ID NO: 951          moltype =   length =
SEQUENCE: 951
000

SEQ ID NO: 952          moltype =   length =
SEQUENCE: 952
000

SEQ ID NO: 953          moltype =   length =
SEQUENCE: 953
000
```

```
SEQ ID NO: 954            moltype =    length =
SEQUENCE: 954
000

SEQ ID NO: 955            moltype =    length =
SEQUENCE: 955
000

SEQ ID NO: 956            moltype = RNA   length = 70
FEATURE                   Location/Qualifiers
source                    1..70
                          mol_type = other RNA
                          organism = synthetic construct
misc_feature              70
                          note = n can be repeated 20 times
SEQUENCE: 956
acagcttatt tggaagctga aatgtgaggt ttataacact cacaagaatc ctgaaaaagg    60
atgccaaacn                                                          70

SEQ ID NO: 957            moltype = RNA   length = 98
FEATURE                   Location/Qualifiers
source                    1..98
                          mol_type = other RNA
                          organism = synthetic construct
SEQUENCE: 957
tggggcagtt ggttgccctt agcctgaggc atttattgca ctcgggaagt accatttctc    60
agaaatggta catccaacta ttaaatactc gtattgct                            98

SEQ ID NO: 958            moltype = RNA   length = 89
FEATURE                   Location/Qualifiers
source                    1..89
                          mol_type = other RNA
                          organism = synthetic construct
SEQUENCE: 958
acagcttatt tggaagctga aatgtgaggt ttataacact cacaagaatc ctgaaaaagg    60
atgccaaaca gtctccagga agaaattaa                                      89

SEQ ID NO: 959            moltype = RNA   length = 19
FEATURE                   Location/Qualifiers
source                    1..19
                          mol_type = other RNA
                          organism = synthetic construct
SEQUENCE: 959
acatgaggat cacccatgt                                                 19

SEQ ID NO: 960            moltype = RNA   length = 108
FEATURE                   Location/Qualifiers
source                    1..108
                          mol_type = other RNA
                          organism = synthetic construct
SEQUENCE: 960
acatgaggat cacccatgta cagcttattt ggaagctgaa atgtgaggtt tataacactc    60
acaagaatcc tgaaaaagga tgccaaacac caaaaaatat acgctata                108

SEQ ID NO: 961            moltype = RNA   length = 112
FEATURE                   Location/Qualifiers
source                    1..112
                          mol_type = other RNA
                          organism = synthetic construct
SEQUENCE: 961
gcacatgagg atcacccatg tgcacagctt atttggaagc tgaaatgtga ggtttataac    60
actcacaaga atcctgaaaa aggatgccaa acaccaaaaa atatacgcta ta           112

SEQ ID NO: 962            moltype = RNA   length = 118
FEATURE                   Location/Qualifiers
source                    1..118
                          mol_type = other RNA
                          organism = synthetic construct
SEQUENCE: 962
gcagcacatg aggatcaccc atgtgctgca cagcttattt ggaagctgaa atgtgaggtt    60
tataacactc acaagaatcc tgaaaaagga tgccaaacac caaaaaatat acgctata    118

SEQ ID NO: 963            moltype = RNA   length = 128
FEATURE                   Location/Qualifiers
source                    1..128
                          mol_type = other RNA
                          organism = synthetic construct
SEQUENCE: 963
```

```
cgctatacgc acatgaggat cacccatgtg cgtatagcga cagcttattt ggaagctgaa    60
atgtgaggtt tataacactc acaagaatcc tgaaaaagga tgccaaacac caaaaaatat   120
acgctata                                                            128

SEQ ID NO: 964          moltype = RNA   length = 114
FEATURE                 Location/Qualifiers
source                  1..114
                        mol_type = other RNA
                        organism = synthetic construct
SEQUENCE: 964
gcacatgagg atcacccatg tgcaaacagc ttatttggaa gctgaaatgt gaggtttata    60
acactcacaa gaatcctgaa aaaggatgcc aaacaccaaa aaatatacgc tata         114

SEQ ID NO: 965          moltype = RNA   length = 117
FEATURE                 Location/Qualifiers
source                  1..117
                        mol_type = other RNA
                        organism = synthetic construct
SEQUENCE: 965
gcacatgagg atcacccatg tgcaaaaaac agcttatttg gaagctgaaa tgtgaggttt    60
ataacactca caagaatcct gaaaaggat gccaaacacc aaaaaatata cgctata       117
```

```
SEQ ID NO: 966          moltype = RNA   length = 122
FEATURE                 Location/Qualifiers
source                  1..122
                        mol_type = other RNA
                        organism = synthetic construct
SEQUENCE: 966
gcacatgagg atcacccatg tgcaaaaaaa aaaacagctt atttggaagc tgaaatgtga    60
ggtttataac actcacaaga atcctgaaaa aggatgccaa acaccaaaaa atatacgcta   120
ta                                                                  122

SEQ ID NO: 967          moltype = RNA   length = 110
FEATURE                 Location/Qualifiers
source                  1..110
                        mol_type = other RNA
                        organism = synthetic construct
SEQUENCE: 967
acatgaggat cacccatgta aacagcttat ttggaagctg aaatgtgagg tttataacac    60
tcacaagaat cctgaaaaag gatgccaaac accaaaaaat atacgctata              110

SEQ ID NO: 968          moltype = RNA   length = 113
FEATURE                 Location/Qualifiers
source                  1..113
                        mol_type = other RNA
                        organism = synthetic construct
SEQUENCE: 968
acatgaggat cacccatgta aaaacagct tatttggaag ctgaaatgtg aggtttataa     60
cactcacaag aatcctgaaa aaggatgcca acaccaaaa aatatacgct ata           113

SEQ ID NO: 969          moltype = RNA   length = 118
FEATURE                 Location/Qualifiers
source                  1..118
                        mol_type = other RNA
                        organism = synthetic construct
SEQUENCE: 969
acatgaggat cacccatgta aaaaaaaaa cagcttattt ggaagctgaa atgtgaggtt     60
tataacactc acaagaatcc tgaaaaagga tgccaaacac caaaaaatat acgctata    118

SEQ ID NO: 970          moltype = RNA   length = 105
FEATURE                 Location/Qualifiers
source                  1..105
                        mol_type = other RNA
                        organism = synthetic construct
SEQUENCE: 970
acagcttatt tggaagctga aatgtgaggt tacatgagga tcacccatgt aacactcaca    60
agaatcctga aaaggatgc caaacaccaa aaaatatacg ctata                   105

SEQ ID NO: 971          moltype = RNA   length = 109
FEATURE                 Location/Qualifiers
source                  1..109
                        mol_type = other RNA
                        organism = synthetic construct
SEQUENCE: 971
acagcttatt tggaagctga aatgtgaggt ttaacatgag gatcacccat gtataacact    60
cacaagaatc ctgaaaaagg atgccaaaca ccaaaaaata tacgctata              109

SEQ ID NO: 972          moltype = RNA   length = 109
FEATURE                 Location/Qualifiers
```

```
source                  1..109
                        mol_type = other RNA
                        organism = synthetic construct
SEQUENCE: 972
acagcttatt tggaagctga aatgtgaggt tgcacatgag gatcacccat gtgcaacact    60
cacaagaatc ctgaaaaagg atgccaaaca ccaaaaaata tacgctata             109

SEQ ID NO: 973          moltype = RNA   length = 115
FEATURE                 Location/Qualifiers
source                  1..115
                        mol_type = other RNA
                        organism = synthetic construct
SEQUENCE: 973
acagcttatt tggaagctga aatgtgaggt tgcagcacat gaggatcacc catgtgctgc    60
aacactcaca agaatcctga aaaggatgc caaacaccaa aaatatacg ctata          115

SEQ ID NO: 974          moltype = RNA   length = 125
FEATURE                 Location/Qualifiers
source                  1..125
                        mol_type = other RNA
                        organism = synthetic construct
SEQUENCE: 974
acagcttatt tggaagctga aatgtgaggt tcgctatacg cacatgagga tcacccatgt    60
gcgtatagcg aacactcaca agaatcctga aaaggatgc caaacaccaa aaatatacg    120
ctata                                                               125

SEQ ID NO: 975          moltype = RNA   length = 113
FEATURE                 Location/Qualifiers
source                  1..113
                        mol_type = other RNA
                        organism = synthetic construct
SEQUENCE: 975
acagcttatt tggaagctga aatgtgaggt ttagcacatg aggatcaccc atgtgcataa    60
cactcacaag aatcctgaaa aaggatgcca acaccaaaa atatacgct ata            113

SEQ ID NO: 976          moltype = RNA   length = 119
FEATURE                 Location/Qualifiers
source                  1..119
                        mol_type = other RNA
                        organism = synthetic construct
SEQUENCE: 976
acagcttatt tggaagctga aatgtgaggt ttagcagcac atgaggatca cccatgtgct    60
gcataacact cacaagaatc ctgaaaaagg atgccaaaca ccaaaaaata tacgctata   119

SEQ ID NO: 977          moltype = RNA   length = 129
FEATURE                 Location/Qualifiers
source                  1..129
                        mol_type = other RNA
                        organism = synthetic construct
SEQUENCE: 977
acagcttatt tggaagctga aatgtgaggt ttacgctata cgcacatgag gatcacccat    60
gtgcgtatag cgataacact cacaagaatc ctgaaaaagg atgccaaaca ccaaaaaata  120
tacgctata                                                          129

SEQ ID NO: 978          moltype = RNA   length = 113
FEATURE                 Location/Qualifiers
source                  1..113
                        mol_type = other RNA
                        organism = synthetic construct
SEQUENCE: 978
acagcttatt tggaagctga aatgtgaggt gtagcacatg aggatcaccc atgtgcatca    60
cactcacaag aatcctgaaa aaggatgcca acaccaaaa atatacgct ata            113

SEQ ID NO: 979          moltype = RNA   length = 113
FEATURE                 Location/Qualifiers
source                  1..113
                        mol_type = other RNA
                        organism = synthetic construct
SEQUENCE: 979
acagcttatt tggaagctga aatgtgaggt gaagcacatg aggatcaccc atgtgcaaca    60
cactcacaag aatcctgaaa aaggatgcca acaccaaaa atatacgct ata            113

SEQ ID NO: 980          moltype = RNA   length = 105
FEATURE                 Location/Qualifiers
source                  1..105
                        mol_type = other RNA
                        organism = synthetic construct
SEQUENCE: 980
acagcttatt tggaagctga aatgtgaggt ttataacact cacaagaatc cttacatgag    60
```

```
gatcacccat gtaaggatgc caaacaccaa aaaatatacg ctata              105

SEQ ID NO: 981           moltype = RNA   length = 107
FEATURE                  Location/Qualifiers
source                   1..107
                         mol_type = other RNA
                         organism = synthetic construct
SEQUENCE: 981
acagcttatt tggaagctga aatgtgaggt ttataacact cacaagaatc ctaaacatga  60
ggatcaccca tgtaaaggat gccaaacacc aaaaaatata cgctata              107

SEQ ID NO: 982           moltype = RNA   length = 109
FEATURE                  Location/Qualifiers
source                   1..109
                         mol_type = other RNA
                         organism = synthetic construct
SEQUENCE: 982
acagcttatt tggaagctga aatgtgaggt ttataacact cacaagaatc cttgcacatg  60
aggatcaccc atgtgcaagg atgccaaaca ccaaaaaata tacgctata             109

SEQ ID NO: 983           moltype = RNA   length = 115
FEATURE                  Location/Qualifiers
source                   1..115
                         mol_type = other RNA
                         organism = synthetic construct
SEQUENCE: 983
acagcttatt tggaagctga aatgtgaggt ttataacact cacaagaatc cttgcagcac  60
atgaggatca cccatgtgct gcaaggatgc caaacaccaa aaatatacg ctata       115

SEQ ID NO: 984           moltype = RNA   length = 125
FEATURE                  Location/Qualifiers
source                   1..125
                         mol_type = other RNA
                         organism = synthetic construct
SEQUENCE: 984
acagcttatt tggaagctga aatgtgaggt ttataacact cacaagaatc cttcgctata  60
cgcacatgag gatcacccat gtgcgtatag cgaaggatgc caaacaccaa aaatatacg 120
ctata                                                            125

SEQ ID NO: 985           moltype = RNA   length = 108
FEATURE                  Location/Qualifiers
source                   1..108
                         mol_type = other RNA
                         organism = synthetic construct
SEQUENCE: 985
acagcttatt tggaagctga aatgtgaggt ttataacact cacaagaatc ctgcacatga  60
ggatcaccca tgtgcaagga tgccaaacac caaaaaatat acgctata             108

SEQ ID NO: 986           moltype = RNA   length = 114
FEATURE                  Location/Qualifiers
source                   1..114
                         mol_type = other RNA
                         organism = synthetic construct
SEQUENCE: 986
acagcttatt tggaagctga aatgtgaggt ttataacact cacaagaatc ctgcagcaca  60
tgaggatcac ccatgtgctg caaggatgcc aaacaccaaa aatatacgc tata        114

SEQ ID NO: 987           moltype = RNA   length = 117
FEATURE                  Location/Qualifiers
source                   1..117
                         mol_type = other RNA
                         organism = synthetic construct
SEQUENCE: 987
acagcttatt tggaagctga aatgtgaggt ttataacact cacaagaatc ctaagcagca  60
catgaggatc acccatgtgc tgcaaaggat gccaaacacc aaaaaatata cgctata    117

SEQ ID NO: 988           moltype = RNA   length = 127
FEATURE                  Location/Qualifiers
source                   1..127
                         mol_type = other RNA
                         organism = synthetic construct
SEQUENCE: 988
acagcttatt tggaagctga aatgtgaggt ttataacact cacaagaatc ctaacgctat  60
acgcacatga ggatcaccca tgtgcgtata gcgaaaggat gccaaacacc aaaaaatata 120
cgctata                                                          127

SEQ ID NO: 989           moltype = RNA   length = 113
FEATURE                  Location/Qualifiers
source                   1..113
```

```
                          mol_type = other RNA
                          organism = synthetic construct
SEQUENCE: 989
acagcttatt tggaagctga aatgtgaggt ttataacact cacaagaatc cttgtaaaca    60
tgaggatcac ccatgtttac aaggatgcca acaccaaaa aatatacgct ata           113

SEQ ID NO: 990           moltype = RNA   length = 117
FEATURE                  Location/Qualifiers
source                   1..117
                         mol_type = other RNA
                         organism = synthetic construct
SEQUENCE: 990
acagcttatt tggaagctga aatgtgaggt ttataacact cacaagaatc cttgtaaaaa    60
catgaggatc acccatgtaa ttacaaggat gccaaacacc aaaaaatata cgctata     117

SEQ ID NO: 991           moltype = RNA   length = 109
FEATURE                  Location/Qualifiers
source                   1..109
                         mol_type = other RNA
                         organism = synthetic construct
SEQUENCE: 991
acagcttatt tggaagctga aatgtgaggt ttataacact cacaagaatc cttgtacatg    60
aggatcaccc atgtacaagg atgccaaaca ccaaaaaata tacgctata             109

SEQ ID NO: 992           moltype = RNA   length = 113
FEATURE                  Location/Qualifiers
source                   1..113
                         mol_type = other RNA
                         organism = synthetic construct
SEQUENCE: 992
acagcttatt tggaagctga aatgtgaggt ttataacact cacaagaatc cttgtaaaca    60
tgaggatcac ccatgtaaac aaggatgcca acaccaaaa aatatacgct ata           113

SEQ ID NO: 993           moltype = RNA   length = 108
FEATURE                  Location/Qualifiers
source                   1..108
                         mol_type = other RNA
                         organism = synthetic construct
SEQUENCE: 993
acagcttatt tggaagctga aatgtgaggt ttataacact cacaagaatc ctgaaaaagg    60
atgccaaaca ccaaaaaata tacgctataa catgaggatc acccatgt              108

SEQ ID NO: 994           moltype = RNA   length = 115
FEATURE                  Location/Qualifiers
source                   1..115
                         mol_type = other RNA
                         organism = synthetic construct
SEQUENCE: 994
acagcttatt tggaagctga aatgtgaggt ttataacact cacaagaatc ctgaaaaagg    60
atgccaaaca ccaaaaaata tacgctataa agcacatga ggatcaccca tgtgc         115

SEQ ID NO: 995           moltype = RNA   length = 118
FEATURE                  Location/Qualifiers
source                   1..118
                         mol_type = other RNA
                         organism = synthetic construct
SEQUENCE: 995
acagcttatt tggaagctga aatgtgaggt ttataacact cacaagaatc ctgaaaaagg    60
atgccaaaca ccaaaaaata tacgctataa aaaaagcaca tgaggatcac ccatgtgc    118

SEQ ID NO: 996           moltype = RNA   length = 122
FEATURE                  Location/Qualifiers
source                   1..122
                         mol_type = other RNA
                         organism = synthetic construct
SEQUENCE: 996
acagcttatt tggaagctga aatgtgaggt ttataacact cacaagaatc ctgaaaaagg    60
atgccaaaca ccaaaaaata tacgctataa aaaaaaaag cacatgagga tcacccatgt   120
gc                                                                 122

SEQ ID NO: 997           moltype = RNA   length = 123
FEATURE                  Location/Qualifiers
source                   1..123
                         mol_type = other RNA
                         organism = synthetic construct
SEQUENCE: 997
acagcttatt tggaagctga aatgtgaggt ttataacact cacaagaatc ctgaaaaagg    60
atgccaaaca ccaaaaaata tacgctataa aaaagcagca catgaggatc acccatgtgc   120
tgc                                                                123
```

-continued

```
SEQ ID NO: 998            moltype = RNA   length = 121
FEATURE                   Location/Qualifiers
source                    1..121
                          mol_type = other RNA
                          organism = synthetic construct
SEQUENCE: 998
tatatttaca tgaggatcac ccatgtaaat atacagctta tttggaagct gaaatgtgag   60
gtttataaca ctcacaagaa tcctgaaaaa ggatgccaaa caccaaaaaa tatacgctat  120
a                                                                  121

SEQ ID NO: 999            moltype = RNA   length = 125
FEATURE                   Location/Qualifiers
source                    1..125
                          mol_type = other RNA
                          organism = synthetic construct
SEQUENCE: 999
tatatttgaa catgaggatc acccatgtaa aaatatacag cttatttgga agctgaaatg   60
tgaggtttat aacactcaca agaatcctga aaaggatgc caaacaccaa aaatatacg   120
ctata                                                              125

SEQ ID NO: 1000           moltype = RNA   length = 125
FEATURE                   Location/Qualifiers
source                    1..125
                          mol_type = other RNA
                          organism = synthetic construct
SEQUENCE: 1000
tatatttgca catgaggatc acccatgtgc aaatatacag cttatttgga agctgaaatg   60
tgaggtttat aacactcaca agaatcctga aaaggatgcc caaacaccaa aaatatacg  120
ctata                                                              125

SEQ ID NO: 1001           moltype = RNA   length = 131
FEATURE                   Location/Qualifiers
source                    1..131
                          mol_type = other RNA
                          organism = synthetic construct
SEQUENCE: 1001
tatatttgca gcacatgagg atcacccatg tgctgcaaat atacagctta tttggaagct   60
gaaatgtgag gtttataaca ctcacaagaa tcctgaaaaa ggatgccaaa caccaaaaaa  120
tatacgctat a                                                       131

SEQ ID NO: 1002           moltype = RNA   length = 141
FEATURE                   Location/Qualifiers
source                    1..141
                          mol_type = other RNA
                          organism = synthetic construct
SEQUENCE: 1002
tatatttcgc tatacgcaca tgaggatcac ccatgtgcgt atagcgaaat atacagctta   60
tttggaagct gaaatgtgag gtttataaca ctcacaagaa tcctgaaaaa ggatgccaaa  120
caccaaaaaa tatacgctat a                                            141

SEQ ID NO: 1003           moltype = RNA   length = 129
FEATURE                   Location/Qualifiers
source                    1..129
                          mol_type = other RNA
                          organism = synthetic construct
SEQUENCE: 1003
tatatttgag cacatgagga tcacccatgt gcaaaatat acagcttatt tggaagctga    60
aatgtgaggt ttataacact cacaagaatc tgaaaaagg atgccaaaca ccaaaaaata   120
tacgctata                                                          129

SEQ ID NO: 1004           moltype = RNA   length = 135
FEATURE                   Location/Qualifiers
source                    1..135
                          mol_type = other RNA
                          organism = synthetic construct
SEQUENCE: 1004
tatatttgag cagcacatga ggatcaccca tgtgctgcaa aatatacag cttatttgga    60
agctgaaatg tgaggtttat aacactcaca agaatcctga aaaggatgc caaacaccaa   120
aaatatacg ctata                                                    135

SEQ ID NO: 1005           moltype = RNA   length = 145
FEATURE                   Location/Qualifiers
source                    1..145
                          mol_type = other RNA
                          organism = synthetic construct
SEQUENCE: 1005
tatatttgac gctatacgca catgaggatc acccatgtgc gtatagcgaa aatatacag    60
cttatttgga agctgaaatg tgaggtttat aacactcaca agaatcctga aaaggatgc   120
```

```
caaacaccaa aaaatatacg ctata                                              145

SEQ ID NO: 1006         moltype = RNA   length = 89
FEATURE                 Location/Qualifiers
source                  1..89
                        mol_type = other RNA
                        organism = synthetic construct
SEQUENCE: 1006
acagcttatt tggaagctga aatgtgaggt ttataacact cacaagaatc ctgaaaaagg          60
atgccaaaca ccaaaaaata tacgctata                                           89

SEQ ID NO: 1007         moltype = RNA   length = 90
FEATURE                 Location/Qualifiers
source                  1..90
                        mol_type = other RNA
                        organism = synthetic construct
SEQUENCE: 1007
acagcttatt tggaagctga aatgtgaggt ttataacact cacaagaatc cttgaaaaag          60
gatgccaaac accaaaaaat atacgctata                                          90

SEQ ID NO: 1008         moltype = RNA   length = 107
FEATURE                 Location/Qualifiers
source                  1..107
                        mol_type = other RNA
                        organism = synthetic construct
SEQUENCE: 1008
tatatttgat aaaatatac agcttatttg gaagctgaaa tgtgaggttt ataacactca           60
caagaatcct gaaaaaggat gccaaacacc aaaaaatata cgctata                      107

SEQ ID NO: 1009         moltype = RNA   length = 108
FEATURE                 Location/Qualifiers
source                  1..108
                        mol_type = other RNA
                        organism = synthetic construct
SEQUENCE: 1009
tatatttgat aaaatatac agcttatttg gaagctgaaa tgtgaggttt ataacactca           60
caagaatcct gaaaaagga tgccaaacac caaaaaatat acgctata                      108

SEQ ID NO: 1010         moltype = RNA   length = 108
FEATURE                 Location/Qualifiers
source                  1..108
                        mol_type = other RNA
                        organism = synthetic construct
SEQUENCE: 1010
gcgcgaggat cacccgcgca cagcttattt ggaagctgaa atgtgaggtt tataacactc          60
acaagaatcc tgaaaaagga tgccaaacac caaaaaatat acgctata                     108

SEQ ID NO: 1011         moltype = RNA   length = 109
FEATURE                 Location/Qualifiers
source                  1..109
                        mol_type = other RNA
                        organism = synthetic construct
SEQUENCE: 1011
acagcttatt tggaagctga aatgtgaggt ttagcgcgag gatcacccgc gcataacact          60
cacaagaatc ctgaaaaagg atgccaaaca ccaaaaaata tacgctata                    109

SEQ ID NO: 1012         moltype = RNA   length = 105
FEATURE                 Location/Qualifiers
source                  1..105
                        mol_type = other RNA
                        organism = synthetic construct
SEQUENCE: 1012
acagcttatt tggaagctga aatgtgaggt ttataacact cacaagaatc cttgcgcgag          60
gatcacccgc gcaaggatgc caaacaccaa aaaatatacg ctata                        105

SEQ ID NO: 1013         moltype = RNA   length = 111
FEATURE                 Location/Qualifiers
source                  1..111
                        mol_type = other RNA
                        organism = synthetic construct
SEQUENCE: 1013
acagcttatt tggaagctga aatgtgaggt ttataacact cacaagaatc ctgaaaaagg          60
atgccaaaca ccaaaaaata tacgctataa aagcgcgagg atcacccgcg c                 111

SEQ ID NO: 1014         moltype = RNA   length = 125
FEATURE                 Location/Qualifiers
source                  1..125
                        mol_type = other RNA
                        organism = synthetic construct
```

```
SEQUENCE: 1014
tatatttgag cgcgaggatc acccgcgcaa aaatatacag cttatttgga agctgaaatg    60
tgaggtttat aacactcaca agaatcctga aaaaggatgc caaacaccaa aaaatatacg   120
ctata                                                              125

SEQ ID NO: 1015         moltype = RNA   length = 114
FEATURE                 Location/Qualifiers
source                  1..114
                        mol_type = other RNA
                        organism = synthetic construct
SEQUENCE: 1015
ggacatgagg atcacccatg tccgaacagc ttatttggaa gctgaaatgt gaggtttata    60
acactcacaa gaatcctgaa aaaggatgcc aaacaccaaa aatatacgc tata          114

SEQ ID NO: 1016         moltype = RNA   length = 111
FEATURE                 Location/Qualifiers
source                  1..111
                        mol_type = other RNA
                        organism = synthetic construct
SEQUENCE: 1016
acagcttatt tggaagctga aatgtgaggt ttggacatga ggatcaccca tgtccaaaca    60
ctcacaagaa tcctgaaaaa ggatgccaaa caccaaaaaa tatacgctat a            111

SEQ ID NO: 1017         moltype = RNA   length = 108
FEATURE                 Location/Qualifiers
source                  1..108
                        mol_type = other RNA
                        organism = synthetic construct
SEQUENCE: 1017
acagcttatt tggaagctga aatgtgaggt ttataacact cacaagaatc ctggacatga    60
ggatcaccca tgtccaagga tgccaaacac caaaaaatat acgctata               108

SEQ ID NO: 1018         moltype = RNA   length = 112
FEATURE                 Location/Qualifiers
source                  1..112
                        mol_type = other RNA
                        organism = synthetic construct
SEQUENCE: 1018
acagcttatt tggaagctga aatgtgaggt ttataacact cacaagaatc ctgaaaaagg    60
atgccaaaca ccaaaaaata tacgctatag gacatgagga tcacccatgt cc           112

SEQ ID NO: 1019         moltype = RNA   length = 91
FEATURE                 Location/Qualifiers
source                  1..91
                        mol_type = other RNA
                        organism = synthetic construct
SEQUENCE: 1019
tgggcagtt ggttgccctt agcctgaggc atttattgca ctcgggaagt accagaaatg     60
gtacatccaa ctattaaata ctcgtattgc t                                  91

SEQ ID NO: 1020         moltype = RNA   length = 89
FEATURE                 Location/Qualifiers
source                  1..89
                        mol_type = other RNA
                        organism = synthetic construct
SEQUENCE: 1020
agggcgtgtt ggagcgcctt agtttgaggt atcaagcact caaaaaatct acgaaagtgg    60
atatccaact attaaatact cgtattgct                                     89

SEQ ID NO: 1021         moltype = RNA   length = 92
FEATURE                 Location/Qualifiers
source                  1..92
                        mol_type = other RNA
                        organism = synthetic construct
SEQUENCE: 1021
acgggtggtt gtacacccga agagtgaggt cttaacgggc actcgctaat ctgatgaaaa    60
gcagaataca actattaaat actcgtattg ct                                 92

SEQ ID NO: 1022         moltype = RNA   length = 89
FEATURE                 Location/Qualifiers
source                  1..89
                        mol_type = other RNA
                        organism = synthetic construct
SEQUENCE: 1022
tgggcgcgtt ggagcgcctt ggttcgaggt tccctgcact cgaaaaattc acgaaagtga    60
atatccaact attaaatact cgtattgct                                     89

SEQ ID NO: 1023         moltype = RNA   length = 89
FEATURE                 Location/Qualifiers
```

```
source                      1..89
                            mol_type = other RNA
                            organism = synthetic construct
SEQUENCE: 1023
tgggcgtgtt ggaacgcctt agtttgaggt ttcaagcact caaaaaattc acgaaagtgg    60
atatccaact attaaatact cgtattgct                                      89

SEQ ID NO: 1024             moltype = RNA  length = 89
FEATURE                     Location/Qualifiers
source                      1..89
                            mol_type = other RNA
                            organism = synthetic construct
SEQUENCE: 1024
cggggtggtt ggacaccctt aaattgaggt tcatcgcact cgataaatac cagaaaaggt    60
atatccaact attaaatact cgtattgct                                      89

SEQ ID NO: 1025             moltype = RNA  length = 90
FEATURE                     Location/Qualifiers
source                      1..90
                            mol_type = other RNA
                            organism = synthetic construct
SEQUENCE: 1025
ggggctggtt gtacagcctg aagttgaggg atgattccac tcgacaaatt gctgaaaagc    60
aatatacaac tattaaatac tcgtattgct                                     90

SEQ ID NO: 1026             moltype = RNA  length = 89
FEATURE                     Location/Qualifiers
source                      1..89
                            mol_type = other RNA
                            organism = synthetic construct
SEQUENCE: 1026
cgggctggtt ggacagcctt aaactgaggt ttaacgcact cggtaaatac ccgaaaaggt    60
atatccaact attaaatact cgtattgct                                      89

SEQ ID NO: 1027             moltype = RNA  length = 13
FEATURE                     Location/Qualifiers
source                      1..13
                            mol_type = other RNA
                            organism = synthetic construct
SEQUENCE: 1027
tggtacatcc aac                                                       13

SEQ ID NO: 1028             moltype = RNA  length = 13
FEATURE                     Location/Qualifiers
source                      1..13
                            mol_type = other RNA
                            organism = synthetic construct
SEQUENCE: 1028
aaggatgcca aac                                                       13

SEQ ID NO: 1029             moltype = RNA  length = 13
FEATURE                     Location/Qualifiers
source                      1..13
                            mol_type = other RNA
                            organism = synthetic construct
SEQUENCE: 1029
gtggatatcc aac                                                       13

SEQ ID NO: 1030             moltype = RNA  length = 13
FEATURE                     Location/Qualifiers
source                      1..13
                            mol_type = other RNA
                            organism = synthetic construct
SEQUENCE: 1030
agcagaatac aac                                                       13

SEQ ID NO: 1031             moltype = RNA  length = 13
FEATURE                     Location/Qualifiers
source                      1..13
                            mol_type = other RNA
                            organism = synthetic construct
SEQUENCE: 1031
gtgaatatcc aac                                                       13

SEQ ID NO: 1032             moltype = RNA  length = 13
FEATURE                     Location/Qualifiers
source                      1..13
                            mol_type = other RNA
                            organism = synthetic construct
```

```
SEQUENCE: 1032
aggtatatcc aac                                                          13

SEQ ID NO: 1033         moltype = RNA  length = 13
FEATURE                 Location/Qualifiers
source                  1..13
                        mol_type = other RNA
                        organism = synthetic construct
SEQUENCE: 1033
agcaatatac aac                                                          13

SEQ ID NO: 1034         moltype = RNA  length = 78
FEATURE                 Location/Qualifiers
source                  1..78
                        mol_type = other RNA
                        organism = synthetic construct
SEQUENCE: 1034
tggggcagtt ggttgccctt agcctgaggc atttattgca ctcgggaagt accatttctc       60
agaaatggta catccaac                                                     78

SEQ ID NO: 1035         moltype = RNA  length = 65
FEATURE                 Location/Qualifiers
source                  1..65
                        mol_type = other RNA
                        organism = synthetic construct
SEQUENCE: 1035
tggggcagtt ggttgccctt agcctgaggc atttattgca ctcgggaagt accatttctc       60
agaaa                                                                   65

SEQ ID NO: 1036         moltype = RNA  length = 61
FEATURE                 Location/Qualifiers
source                  1..61
                        mol_type = other RNA
                        organism = synthetic construct
SEQUENCE: 1036
tggggcagtt ggttgccctt agcctgaggc atttattgca ctcgggaagt accatttctc       60
a                                                                       61

SEQ ID NO: 1037         moltype = RNA  length = 69
FEATURE                 Location/Qualifiers
source                  1..69
                        mol_type = other RNA
                        organism = synthetic construct
SEQUENCE: 1037
acagcttatt tggaagctga aatgtgaggt ttataacact cacaagaatc ctgaaaagg        60
atgccaaac                                                               69

SEQ ID NO: 1038         moltype = RNA  length = 56
FEATURE                 Location/Qualifiers
source                  1..56
                        mol_type = other RNA
                        organism = synthetic construct
SEQUENCE: 1038
acagcttatt tggaagctga aatgtgaggt ttataacact cacaagaatc ctgaaa           56

SEQ ID NO: 1039         moltype = RNA  length = 52
FEATURE                 Location/Qualifiers
source                  1..52
                        mol_type = other RNA
                        organism = synthetic construct
SEQUENCE: 1039
acagcttatt tggaagctga aatgtgaggt ttataacact cacaagaatc ct               52

SEQ ID NO: 1040         moltype = RNA  length = 71
FEATURE                 Location/Qualifiers
source                  1..71
                        mol_type = other RNA
                        organism = synthetic construct
SEQUENCE: 1040
tggggcagtt ggttgccctt agcctgaggc atttattgca ctcgggaagt accagaaatg       60
gtacatccaa c                                                            71

SEQ ID NO: 1041         moltype = RNA  length = 58
FEATURE                 Location/Qualifiers
source                  1..58
                        mol_type = other RNA
                        organism = synthetic construct
SEQUENCE: 1041
tggggcagtt ggttgccctt agcctgaggc atttattgca ctcgggaagt accagaaa         58
```

```
SEQ ID NO: 1042         moltype = RNA   length = 54
FEATURE                 Location/Qualifiers
source                  1..54
                        mol_type = other RNA
                        organism = synthetic construct
SEQUENCE: 1042
tggggcagtt ggttgccctt agcctgaggc atttattgca ctcgggaagt acca           54

SEQ ID NO: 1043         moltype = RNA   length = 69
FEATURE                 Location/Qualifiers
source                  1..69
                        mol_type = other RNA
                        organism = synthetic construct
SEQUENCE: 1043
agggcgtgtt ggagcgcctt agtttgaggt atcaagcact caaaaaatct acgaaagtgg     60
atatccaac                                                             69

SEQ ID NO: 1044         moltype = RNA   length = 56
FEATURE                 Location/Qualifiers
source                  1..56
                        mol_type = other RNA
                        organism = synthetic construct
SEQUENCE: 1044
agggcgtgtt ggagcgcctt agtttgaggt atcaagcact caaaaaatct acgaaa         56

SEQ ID NO: 1045         moltype = RNA   length = 52
FEATURE                 Location/Qualifiers
source                  1..52
                        mol_type = other RNA
                        organism = synthetic construct
SEQUENCE: 1045
agggcgtgtt ggagcgcctt agtttgaggt atcaagcact caaaaaatct ac             52

SEQ ID NO: 1046         moltype = RNA   length = 72
FEATURE                 Location/Qualifiers
source                  1..72
                        mol_type = other RNA
                        organism = synthetic construct
SEQUENCE: 1046
acgggtggtt gtacacccga agagtgaggt cttaacgggc actcgctaat ctgatgaaaa     60
gcagaataca ac                                                         72

SEQ ID NO: 1047         moltype = RNA   length = 59
FEATURE                 Location/Qualifiers
source                  1..59
                        mol_type = other RNA
                        organism = synthetic construct
SEQUENCE: 1047
acgggtggtt gtacacccga agagtgaggt cttaacgggc actcgctaat ctgatgaaa      59

SEQ ID NO: 1048         moltype = RNA   length = 55
FEATURE                 Location/Qualifiers
source                  1..55
                        mol_type = other RNA
                        organism = synthetic construct
SEQUENCE: 1048
acgggtggtt gtacacccga agagtgaggt cttaacgggc actcgctaat ctgat          55

SEQ ID NO: 1049         moltype = RNA   length = 69
FEATURE                 Location/Qualifiers
source                  1..69
                        mol_type = other RNA
                        organism = synthetic construct
SEQUENCE: 1049
tgggcgcgtt ggagcgcctt ggttcgaggt tccctgcact cgaaaaattc acgaaagtga     60
atatccaac                                                             69

SEQ ID NO: 1050         moltype = RNA   length = 56
FEATURE                 Location/Qualifiers
source                  1..56
                        mol_type = other RNA
                        organism = synthetic construct
SEQUENCE: 1050
tgggcgcgtt ggagcgcctt ggttcgaggt tccctgcact cgaaaaattc acgaaa         56

SEQ ID NO: 1051         moltype = RNA   length = 52
FEATURE                 Location/Qualifiers
source                  1..52
```

```
                         mol_type = other RNA
                         organism = synthetic construct
SEQUENCE: 1051
tgggcgcgtt ggagcgcctt ggttcgaggt tccctgcact cgaaaaattc ac          52

SEQ ID NO: 1052          moltype = RNA  length = 69
FEATURE                  Location/Qualifiers
source                   1..69
                         mol_type = other RNA
                         organism = synthetic construct
SEQUENCE: 1052
tgggcgtgtt ggaacgcctt agtttgaggt ttcaagcact caaaaaattc acgaaagtgg  60
atatccaac                                                          69

SEQ ID NO: 1053          moltype = RNA  length = 56
FEATURE                  Location/Qualifiers
source                   1..56
                         mol_type = other RNA
                         organism = synthetic construct
SEQUENCE: 1053
tgggcgtgtt ggaacgcctt agtttgaggt ttcaagcact caaaaaattc acgaaa      56

SEQ ID NO: 1054          moltype = RNA  length = 52
FEATURE                  Location/Qualifiers
source                   1..52
                         mol_type = other RNA
                         organism = synthetic construct
SEQUENCE: 1054
tgggcgtgtt ggaacgcctt agtttgaggt ttcaagcact caaaaaattc ac          52

SEQ ID NO: 1055          moltype = RNA  length = 69
FEATURE                  Location/Qualifiers
source                   1..69
                         mol_type = other RNA
                         organism = synthetic construct
SEQUENCE: 1055
cggggtggtt ggacaccctt aaattgaggt tcatcgcact cgataaatac cagaaaaggt  60
atatccaac                                                          69

SEQ ID NO: 1056          moltype = RNA  length = 56
FEATURE                  Location/Qualifiers
source                   1..56
                         mol_type = other RNA
                         organism = synthetic construct
SEQUENCE: 1056
cggggtggtt ggacaccctt aaattgaggt tcatcgcact cgataaatac cagaaa      56

SEQ ID NO: 1057          moltype = RNA  length = 52
FEATURE                  Location/Qualifiers
source                   1..52
                         mol_type = other RNA
                         organism = synthetic construct
SEQUENCE: 1057
cggggtggtt ggacaccctt aaattgaggt tcatcgcact cgataaatac ca          52

SEQ ID NO: 1058          moltype = RNA  length = 70
FEATURE                  Location/Qualifiers
source                   1..70
                         mol_type = other RNA
                         organism = synthetic construct
SEQUENCE: 1058
ggggctggtt gtacagcctg aagttgaggg atgattccac tcgacaaatt gctgaaaagc  60
aatatacaac                                                         70

SEQ ID NO: 1059          moltype = RNA  length = 57
FEATURE                  Location/Qualifiers
source                   1..57
                         mol_type = other RNA
                         organism = synthetic construct
SEQUENCE: 1059
ggggctggtt gtacagcctg aagttgaggg atgattccac tcgacaaatt gctgaaa     57

SEQ ID NO: 1060          moltype = RNA  length = 53
FEATURE                  Location/Qualifiers
source                   1..53
                         mol_type = other RNA
                         organism = synthetic construct
SEQUENCE: 1060
ggggctggtt gtacagcctg aagttgaggg atgattccac tcgacaaatt gct         53
```

```
SEQ ID NO: 1061       moltype = RNA   length = 69
FEATURE               Location/Qualifiers
source                1..69
                      mol_type = other RNA
                      organism = synthetic construct
SEQUENCE: 1061
cgggctggtt ggacagcctt aaactgaggt ttaacgcact cggtaaatac ccgaaaaggt    60
atatccaac                                                            69

SEQ ID NO: 1062       moltype = RNA   length = 56
FEATURE               Location/Qualifiers
source                1..56
                      mol_type = other RNA
                      organism = synthetic construct
SEQUENCE: 1062
cgggctggtt ggacagcctt aaactgaggt ttaacgcact cggtaaatac ccgaaa        56

SEQ ID NO: 1063       moltype = RNA   length = 52
FEATURE               Location/Qualifiers
source                1..52
                      mol_type = other RNA
                      organism = synthetic construct
SEQUENCE: 1063
cgggctggtt ggacagcctt aaactgaggt ttaacgcact cggtaaatac cc            52

SEQ ID NO: 1064       moltype = DNA   length = 12
FEATURE               Location/Qualifiers
source                1..12
                      mol_type = other DNA
                      organism = synthetic construct
SEQUENCE: 1064
tttttttttt tt                                                        12

SEQ ID NO: 1065       moltype = RNA   length = 88
FEATURE               Location/Qualifiers
source                1..88
                      mol_type = other RNA
                      organism = synthetic construct
SEQUENCE: 1065
acatgaggat cacccatgta cagcttattt ggaagctgaa atgtgaggtt tataacactc    60
acaagaatcc tgaaaaagga tgccaaac                                       88

SEQ ID NO: 1066       moltype = RNA   length = 92
FEATURE               Location/Qualifiers
source                1..92
                      mol_type = other RNA
                      organism = synthetic construct
SEQUENCE: 1066
gcacatgagg atcacccatg tgcacagctt atttggaagc tgaaatgtga ggtttataac    60
actcacaaga atcctgaaaa aggatgccaa ac                                  92

SEQ ID NO: 1067       moltype = RNA   length = 98
FEATURE               Location/Qualifiers
source                1..98
                      mol_type = other RNA
                      organism = synthetic construct
SEQUENCE: 1067
gcagcacatg aggatcaccc atgtgctgca cagcttattt ggaagctgaa atgtgaggtt    60
tataacactc acaagaatcc tgaaaaagga tgccaaac                            98

SEQ ID NO: 1068       moltype = RNA   length = 108
FEATURE               Location/Qualifiers
source                1..108
                      mol_type = other RNA
                      organism = synthetic construct
SEQUENCE: 1068
cgctatacgc acatgaggat cacccatgtg cgtatagcga cagcttattt ggaagctgaa    60
atgtgaggtt tataacactc acaagaatcc tgaaaaagga tgccaaac                108

SEQ ID NO: 1069       moltype = RNA   length = 94
FEATURE               Location/Qualifiers
source                1..94
                      mol_type = other RNA
                      organism = synthetic construct
SEQUENCE: 1069
gcacatgagg atcacccatg tgcaaacagc ttatttggaa gctgaatgt gaggtttata     60
acactcacaa gaatcctgaa aaggatgcc aaac                                 94
```

| SEQ ID NO: 1070 | moltype = RNA length = 97 |
| --- | --- |
| FEATURE | Location/Qualifiers |
| source | 1..97 |
| | mol_type = other RNA |
| | organism = synthetic construct |

SEQUENCE: 1070
gcacatgagg atcacccatg tgcaaaaaac agcttatttg gaagctgaaa tgtgaggttt   60
ataacactca caagaatcct gaaaaaggat gccaaac                           97

| SEQ ID NO: 1071 | moltype = RNA length = 102 |
| --- | --- |
| FEATURE | Location/Qualifiers |
| source | 1..102 |
| | mol_type = other RNA |
| | organism = synthetic construct |

SEQUENCE: 1071
gcacatgagg atcacccatg tgcaaaaaaa aaaacagctt atttggaagc tgaaatgtga   60
ggtttataac actcacaaga atcctgaaaa aggatgccaa ac                    102

| SEQ ID NO: 1072 | moltype = RNA length = 90 |
| --- | --- |
| FEATURE | Location/Qualifiers |
| source | 1..90 |
| | mol_type = other RNA |
| | organism = synthetic construct |

SEQUENCE: 1072
acatgaggat cacccatgta aacagcttat ttggaagctg aaatgtgagg tttataacac   60
tcacaagaat cctgaaaaag gatgccaaac                                   90

| SEQ ID NO: 1073 | moltype = RNA length = 93 |
| --- | --- |
| FEATURE | Location/Qualifiers |
| source | 1..93 |
| | mol_type = other RNA |
| | organism = synthetic construct |

SEQUENCE: 1073
acatgaggat cacccatgta aaaacagct tatttggaag ctgaaatgtg aggtttataa   60
cactcacaag aatcctgaaa aggatgcca aac                                93

| SEQ ID NO: 1074 | moltype = RNA length = 98 |
| --- | --- |
| FEATURE | Location/Qualifiers |
| source | 1..98 |
| | mol_type = other RNA |
| | organism = synthetic construct |

SEQUENCE: 1074
acatgaggat cacccatgta aaaaaaaaaa cagcttattt ggaagctgaa atgtgaggtt   60
tataacactc acaagaatcc tgaaaaagga tgccaaac                          98

| SEQ ID NO: 1075 | moltype = RNA length = 85 |
| --- | --- |
| FEATURE | Location/Qualifiers |
| source | 1..85 |
| | mol_type = other RNA |
| | organism = synthetic construct |

SEQUENCE: 1075
acagcttatt tggaagctga aatgtgaggt tacatgagga tcacccatgt aacactcaca   60
agaatcctga aaaggatgc caaac                                         85

| SEQ ID NO: 1076 | moltype = RNA length = 89 |
| --- | --- |
| FEATURE | Location/Qualifiers |
| source | 1..89 |
| | mol_type = other RNA |
| | organism = synthetic construct |

SEQUENCE: 1076
acagcttatt tggaagctga aatgtgaggt ttaacatgag gatcacccat gtataacact   60
cacaagaatc ctgaaaaagg atgccaaac                                    89

| SEQ ID NO: 1077 | moltype = RNA length = 89 |
| --- | --- |
| FEATURE | Location/Qualifiers |
| source | 1..89 |
| | mol_type = other RNA |
| | organism = synthetic construct |

SEQUENCE: 1077
acagcttatt tggaagctga aatgtgaggt tgcacatgag gatcacccat gtgcaacact   60
cacaagaatc ctgaaaaagg atgccaaac                                    89

| SEQ ID NO: 1078 | moltype = RNA length = 95 |
| --- | --- |
| FEATURE | Location/Qualifiers |
| source | 1..95 |
| | mol_type = other RNA |
| | organism = synthetic construct |

SEQUENCE: 1078
acagcttatt tggaagctga aatgtgaggt tgcagcacat gaggatcacc catgtgctgc   60

```
aacactcaca agaatcctga aaaaggatgc caaac                                  95

SEQ ID NO: 1079         moltype = RNA   length = 105
FEATURE                 Location/Qualifiers
source                  1..105
                        mol_type = other RNA
                        organism = synthetic construct
SEQUENCE: 1079
acagcttatt tggaagctga aatgtgaggt tcgctatacg cacatgagga tcacccatgt       60
gcgtatagcg aacactcaca agaatcctga aaaaggatgc caaac                      105

SEQ ID NO: 1080         moltype = RNA   length = 93
FEATURE                 Location/Qualifiers
source                  1..93
                        mol_type = other RNA
                        organism = synthetic construct
SEQUENCE: 1080
acagcttatt tggaagctga aatgtgaggt ttagcacatg aggatcaccc atgtgcataa       60
cactcacaag aatcctgaaa aaggatgcca aac                                   93

SEQ ID NO: 1081         moltype = RNA   length = 99
FEATURE                 Location/Qualifiers
source                  1..99
                        mol_type = other RNA
                        organism = synthetic construct
SEQUENCE: 1081
acagcttatt tggaagctga aatgtgaggt ttagcagcac atgaggatca cccatgtgct       60
gcataacact cacaagaatc ctgaaaaagg atgccaaac                             99

SEQ ID NO: 1082         moltype = RNA   length = 109
FEATURE                 Location/Qualifiers
source                  1..109
                        mol_type = other RNA
                        organism = synthetic construct
SEQUENCE: 1082
acagcttatt tggaagctga aatgtgaggt ttacgctata cgcacatgag gatcacccat       60
gtgcgtatag cgataacact cacaagaatc ctgaaaaagg atgccaaac                  109

SEQ ID NO: 1083         moltype = RNA   length = 93
FEATURE                 Location/Qualifiers
source                  1..93
                        mol_type = other RNA
                        organism = synthetic construct
SEQUENCE: 1083
acagcttatt tggaagctga aatgtgaggt gtagcacatg aggatcaccc atgtgcatca       60
cactcacaag aatcctgaaa aaggatgcca aac                                   93

SEQ ID NO: 1084         moltype = RNA   length = 93
FEATURE                 Location/Qualifiers
source                  1..93
                        mol_type = other RNA
                        organism = synthetic construct
SEQUENCE: 1084
acagcttatt tggaagctga aatgtgaggt gaagcacatg aggatcaccc atgtgcaaca       60
cactcacaag aatcctgaaa aaggatgcca aac                                   93

SEQ ID NO: 1085         moltype = RNA   length = 85
FEATURE                 Location/Qualifiers
source                  1..85
                        mol_type = other RNA
                        organism = synthetic construct
SEQUENCE: 1085
acagcttatt tggaagctga aatgtgaggt ttataacact cacaagaatc cttacatgag       60
gatcacccat gtaaggatgc caaac                                            85

SEQ ID NO: 1086         moltype = RNA   length = 87
FEATURE                 Location/Qualifiers
source                  1..87
                        mol_type = other RNA
                        organism = synthetic construct
SEQUENCE: 1086
acagcttatt tggaagctga aatgtgaggt ttataacact cacaagaatc ctaaacatga      60
ggatcaccca tgtaaaggat gccaaac                                          87

SEQ ID NO: 1087         moltype = RNA   length = 89
FEATURE                 Location/Qualifiers
source                  1..89
                        mol_type = other RNA
                        organism = synthetic construct
```

SEQUENCE: 1087
acagcttatt tggaagctga aatgtgaggt ttataacact cacaagaatc cttgcacatg    60
aggatcaccc atgtgcaagg atgccaaac                                      89

SEQ ID NO: 1088         moltype = RNA   length = 95
FEATURE                 Location/Qualifiers
source                  1..95
                        mol_type = other RNA
                        organism = synthetic construct
SEQUENCE: 1088
acagcttatt tggaagctga aatgtgaggt ttataacact cacaagaatc cttgcagcac    60
atgaggatca cccatgtgct gcaaggatgc caaac                               95

SEQ ID NO: 1089         moltype = RNA   length = 105
FEATURE                 Location/Qualifiers
source                  1..105
                        mol_type = other RNA
                        organism = synthetic construct
SEQUENCE: 1089
acagcttatt tggaagctga aatgtgaggt ttataacact cacaagaatc cttcgctata    60
cgcacatgag gatcacccat gtgcgtatag cgaaggatgc caaac                   105

SEQ ID NO: 1090         moltype = RNA   length = 88
FEATURE                 Location/Qualifiers
source                  1..88
                        mol_type = other RNA
                        organism = synthetic construct
SEQUENCE: 1090
acagcttatt tggaagctga aatgtgaggt ttataacact cacaagaatc ctgcacatga    60
ggatcaccca tgtgcaagga tgccaaac                                       88

SEQ ID NO: 1091         moltype = RNA   length = 94
FEATURE                 Location/Qualifiers
source                  1..94
                        mol_type = other RNA
                        organism = synthetic construct
SEQUENCE: 1091
acagcttatt tggaagctga aatgtgaggt ttataacact cacaagaatc ctgcagcaca    60
tgaggatcac ccatgtgctg caaggatgcc aaac                                94

SEQ ID NO: 1092         moltype = RNA   length = 97
FEATURE                 Location/Qualifiers
source                  1..97
                        mol_type = other RNA
                        organism = synthetic construct
SEQUENCE: 1092
acagcttatt tggaagctga aatgtgaggt ttataacact cacaagaatc ctaagcagca    60
catgaggatc acccatgtgc tgcaaaggat gccaaac                             97

SEQ ID NO: 1093         moltype = RNA   length = 107
FEATURE                 Location/Qualifiers
source                  1..107
                        mol_type = other RNA
                        organism = synthetic construct
SEQUENCE: 1093
acagcttatt tggaagctga aatgtgaggt ttataacact cacaagaatc ctaacgctat    60
acgcacatga ggatcaccca tgtgcgtata gcgaaaggat gccaaac                 107

SEQ ID NO: 1094         moltype = RNA   length = 93
FEATURE                 Location/Qualifiers
source                  1..93
                        mol_type = other RNA
                        organism = synthetic construct
SEQUENCE: 1094
acagcttatt tggaagctga aatgtgaggt ttataacact cacaagaatc cttgtaaaca    60
tgaggatcac ccatgtttac aaggatgcca aac                                 93

SEQ ID NO: 1095         moltype = RNA   length = 97
FEATURE                 Location/Qualifiers
source                  1..97
                        mol_type = other RNA
                        organism = synthetic construct
SEQUENCE: 1095
acagcttatt tggaagctga aatgtgaggt ttataacact cacaagaatc cttgtaaaaa    60
catgaggatc acccatgtaa ttacaaggat gccaaac                             97

SEQ ID NO: 1096         moltype = RNA   length = 89
FEATURE                 Location/Qualifiers
source                  1..89

```
                                mol_type = other RNA
                                organism = synthetic construct
SEQUENCE: 1096
acagcttatt tggaagctga aatgtgaggt ttataacact cacaagaatc cttgtacatg    60
aggatcaccc atgtacaagg atgccaaac                                      89

SEQ ID NO: 1097          moltype = RNA   length = 93
FEATURE                  Location/Qualifiers
source                   1..93
                                mol_type = other RNA
                                organism = synthetic construct
SEQUENCE: 1097
acagcttatt tggaagctga aatgtgaggt ttataacact cacaagaatc cttgtaaaca    60
tgaggatcac ccatgtaaac aaggatgcca aac                                 93

SEQ ID NO: 1098          moltype = AA   length = 130
FEATURE                  Location/Qualifiers
source                   1..130
                                mol_type = protein
                                organism = synthetic construct
SEQUENCE: 1098
MASNFTQFVL VDNGGTGDVT VAPSNFANGV AEWISSNSRS QAYKVTCSVR QSSAQKRKYT    60
IKVEVPKVAT QTVGGVELPV AAWRSYLNME LTIPIFATNS DCELIVKAMQ GLLKDGNPIP   120
SAIAANSGIY                                                          130

SEQ ID NO: 1099          moltype = AA   length = 475
FEATURE                  Location/Qualifiers
source                   1..475
                                mol_type = protein
                                organism = synthetic construct
SEQUENCE: 1099
MMNDGKQQST FLFHDYETFG THPALDRPAQ FAAIRTDSEF NVIGEPEVFY CKPADDYLPQ    60
PGAVLITGIT PQEARAKGEN EAAFAARIHS LFTVPKTCIL GYNNVRFDDE VTRNIFYRNF   120
YDPYAWSWQH DNSRWDLLDV MRACYALRPE GINWPENDDG LPSFRLEHLT KANGIEHSNA   180
HDAMADVYAT IAMAKLVKTR QPRLFDYLFT HRNKHKLMAL IDVPQMKPLV HVSGMFGAWR   240
GNTSWVAPLA WHPENRNAVI MVDLAGDISP LLELDSDTLR ERLYTAKTDL GDNAAVPVKL   300
VHINKCPVLA QANTLRPEDA DRLGINRQHC LDNLKILREN PQVREKVVAI FAEAEPFTPS   360
DNVDAQLYNG FFSDADRAAM KIVLETEPRN LPALDITFVD KRIEKLLFNY RARNFPGTLD   420
YAEQQRWLEH RRQVFTPEFL QGYADELQML VQQYADDKEK VALLKALWQY AEEIV        475

SEQ ID NO: 1100          moltype = RNA   length = 89
FEATURE                  Location/Qualifiers
source                   1..89
                                mol_type = other RNA
                                organism = synthetic construct
misc_feature             70
                                note = n can be repeated 15 to 28 times
SEQUENCE: 1100
acagcttatt tggaagctga aatgtgaggt ttataacact cacaagaatc ctgaaaaagg    60
atgccaaacn acatgaggat cacccatgt                                      89

SEQ ID NO: 1101          moltype = RNA   length = 96
FEATURE                  Location/Qualifiers
source                   1..96
                                mol_type = other RNA
                                organism = synthetic construct
misc_feature             70
                                note = n can be repeated 15 to 28 times
SEQUENCE: 1101
acagcttatt tggaagctga aatgtgaggt ttataacact cacaagaatc ctgaaaaagg    60
atgccaaacn aaagcacatg aggatcaccc atgtgc                              96

SEQ ID NO: 1102          moltype = RNA   length = 99
FEATURE                  Location/Qualifiers
source                   1..99
                                mol_type = other RNA
                                organism = synthetic construct
misc_feature             70
                                note = n can be repeated 15 to 28 times
SEQUENCE: 1102
acagcttatt tggaagctga aatgtgaggt ttataacact cacaagaatc ctgaaaaagg    60
atgccaaacn aaaaaagcac atgaggatca cccatgtgc                           99

SEQ ID NO: 1103          moltype = RNA   length = 103
FEATURE                  Location/Qualifiers
source                   1..103
                                mol_type = other RNA
                                organism = synthetic construct
misc_feature             70
```

```
                    note = n can be repeated 15 to 28 times
SEQUENCE: 1103
acagcttatt tggaagctga aatgtgaggt ttataacact cacaagaatc ctgaaaaagg    60
atgccaaacn aaaaaaaaaa gcacatgagg atcacccatg tgc                     103

SEQ ID NO: 1104         moltype = RNA  length = 104
FEATURE                 Location/Qualifiers
source                  1..104
                        mol_type = other RNA
                        organism = synthetic construct
misc_feature            70
                        note = n can be repeated 15 to 28 times
SEQUENCE: 1104
acagcttatt tggaagctga aatgtgaggt ttataacact cacaagaatc ctgaaaaagg    60
atgccaaacn aaaaagcagc acatgaggat cacccatgtg ctgc                    104

SEQ ID NO: 1105         moltype =   length =
SEQUENCE: 1105
000

SEQ ID NO: 1106         moltype =   length =
SEQUENCE: 1106
000

SEQ ID NO: 1107         moltype = AA  length = 18
FEATURE                 Location/Qualifiers
source                  1..18
                        mol_type = protein
                        organism = synthetic construct
SEQUENCE: 1107
KRPAATKKAG QAKKKKEF                                                  18

SEQ ID NO: 1108         moltype = AA  length = 7
FEATURE                 Location/Qualifiers
source                  1..7
                        mol_type = protein
                        organism = synthetic construct
SEQUENCE: 1108
PKKKRKV                                                              7

SEQ ID NO: 1109         moltype = AA  length = 9
FEATURE                 Location/Qualifiers
source                  1..9
                        mol_type = protein
                        organism = synthetic construct
SEQUENCE: 1109
PAAKRVKLD                                                            9

SEQ ID NO: 1110         moltype = AA  length = 15
FEATURE                 Location/Qualifiers
source                  1..15
                        mol_type = protein
                        organism = synthetic construct
SEQUENCE: 1110
PKKKRKVGIH GVPAA                                                     15

SEQ ID NO: 1111         moltype =   length =
SEQUENCE: 1111
000

SEQ ID NO: 1112         moltype = DNA  length = 46
FEATURE                 Location/Qualifiers
source                  1..46
                        mol_type = other DNA
                        organism = synthetic construct
SEQUENCE: 1112
gtttatatta aatactcgta ttgctgttcg attatgaccg aattcc                   46

SEQ ID NO: 1113         moltype = DNA  length = 16
FEATURE                 Location/Qualifiers
source                  1..16
                        mol_type = other DNA
                        organism = synthetic construct
SEQUENCE: 1113
ntatgaccga attccc                                                    16

SEQ ID NO: 1114         moltype = DNA  length = 29
FEATURE                 Location/Qualifiers
source                  1..29
```

```
                        mol_type = other DNA
                        organism = synthetic construct
SEQUENCE: 1114
gtttatatta aatactcgta ttgctgtta                                          29

SEQ ID NO: 1115         moltype = DNA   length = 66
FEATURE                 Location/Qualifiers
source                  1..66
                        mol_type = other DNA
                        organism = synthetic construct
SEQUENCE: 1115
ttgagtctcc aggaagaaat taatgagcag ggacatgagg gtacgtaaac gctgtggcct        60
gcctgg                                                                   66

SEQ ID NO: 1116         moltype = DNA   length = 45
FEATURE                 Location/Qualifiers
source                  1..45
                        mol_type = other DNA
                        organism = synthetic construct
SEQUENCE: 1116
ttttgagtct ccaggaagaa attaatgagc agggacatga gggta                        45
```

UNITED STATES PATENT AND TRADEMARK OFFICE
CERTIFICATE OF CORRECTION

PATENT NO. : 12,077,775 B2
APPLICATION NO. : 18/333467
DATED : September 3, 2024
INVENTOR(S) : Aaron Deloughery et al.

Page 1 of 1

It is certified that error appears in the above-identified patent and that said Letters Patent is hereby corrected as shown below:

In the Claims

Column 617, Line 6, Claim 25, delete "from: K K58W, I80R, T84R, K105R, N193K, C202R," and replace with --from: K58W, I80R, T84R, K105R, N193K, C202R,--

Signed and Sealed this
Fifteenth Day of October, 2024

Katherine Kelly Vidal
*Director of the United States Patent and Trademark Office*